United States Patent
Chesworth et al.

(10) Patent No.: US 9,598,374 B2
(45) Date of Patent: Mar. 21, 2017

(54) ARGININE METHYLTRANSFERASE INHIBITORS AND USES THEREOF

(71) Applicant: Epizyme, Inc., Cambridge, MA (US)

(72) Inventors: Richard Chesworth, Concord, MA (US); Lorna Helen Mitchell, Cambridge, MA (US); Gideon Shapiro, Gainesville, FL (US); Kerren Kalai Swinger, Lexington, MA (US)

(73) Assignee: Epizyme, Inc., Cambridge, MA (US)

( * ) Notice: Subject to any disclaimer, the term of this patent is extended or adjusted under 35 U.S.C. 154(b) by 0 days.

(21) Appl. No.: 14/775,794

(22) PCT Filed: Mar. 14, 2014

(86) PCT No.: PCT/US2014/029710
§ 371 (c)(1),
(2) Date: Sep. 14, 2015

(87) PCT Pub. No.: WO2014/153226
PCT Pub. Date: Sep. 25, 2014

(65) Prior Publication Data
US 2016/0024016 A1    Jan. 28, 2016

Related U.S. Application Data

(60) Provisional application No. 61/876,034, filed on Sep. 10, 2013, provisional application No. 61/781,051, filed on Mar. 14, 2013.

(51) Int. Cl.
| | |
|---|---|
| *C07D 231/12* | (2006.01) |
| *A61K 31/415* | (2006.01) |
| *A61K 31/4155* | (2006.01) |
| *C07D 401/04* | (2006.01) |
| *C07D 403/08* | (2006.01) |
| *C07D 405/04* | (2006.01) |
| *C07D 405/08* | (2006.01) |
| *C07D 405/12* | (2006.01) |
| *C07D 493/10* | (2006.01) |
| *C07D 403/04* | (2006.01) |

(52) U.S. Cl.
CPC .......... *C07D 231/12* (2013.01); *A61K 31/415* (2013.01); *A61K 31/4155* (2013.01); *C07D 401/04* (2013.01); *C07D 403/04* (2013.01); *C07D 403/08* (2013.01); *C07D 405/04* (2013.01); *C07D 405/08* (2013.01); *C07D 405/12* (2013.01); *C07D 493/10* (2013.01)

(58) Field of Classification Search
None
See application file for complete search history.

(56) References Cited

U.S. PATENT DOCUMENTS

| | | |
|---|---|---|
| 5,011,849 A | 4/1991 | Gassner et al. |
| 5,204,482 A | 4/1993 | Gassner et al. |
| 5,932,737 A | 8/1999 | Itoh et al. |
| 6,566,376 B1 | 5/2003 | Baxter et al. |
| 6,914,160 B1 | 7/2005 | Armour et al. |
| 7,485,722 B2 | 2/2009 | Egle et al. |
| 7,629,294 B2 | 12/2009 | Gebauer et al. |
| 7,632,855 B2 | 12/2009 | Barrilalonso et al. |
| 7,759,336 B2 | 7/2010 | Habashita et al. |
| 8,063,071 B2 | 11/2011 | Kerns et al. |
| 8,097,708 B2 | 1/2012 | Sugimoto et al. |
| 8,133,904 B2 | 3/2012 | McElroy et al. |
| 8,153,625 B2 | 4/2012 | Habashita et al. |
| 8,338,437 B2 | 12/2012 | Wahhab et al. |
| 8,952,026 B2 | 2/2015 | Mitchell et al. |
| 9,023,883 B2 | 5/2015 | Kuntz et al. |
| 9,045,455 B2 | 6/2015 | Mitchell et al. |
| 9,120,757 B2 | 9/2015 | Chesworth et al. |
| 9,133,189 B2 | 9/2015 | Chesworth et al. |
| 9,346,761 B2 | 5/2016 | Chesworth et al. |
| 9,346,802 B2 | 5/2016 | Chesworth et al. |
| 9,365,519 B2 | 6/2016 | Duncan et al. |
| 9,365,527 B2 | 6/2016 | Chesworth et al. |

(Continued)

FOREIGN PATENT DOCUMENTS

| | | |
|---|---|---|
| DE | 10149370 A1 | 4/2003 |
| EP | 1 571 146 A1 | 9/2005 |

(Continued)

OTHER PUBLICATIONS

CAS Registry Files RN 1179596-03-2 and RN 1179823-36-9, STN Entry Date: Sep. 3, 2009.

(Continued)

*Primary Examiner* — Samantha Shterengarts
(74) *Attorney, Agent, or Firm* — Wolf, Greenfield & Sacks, P.C.

(57) ABSTRACT

Described herein are compounds of Formula (I), pharmaceutically acceptable salts thereof, and pharmaceutical compositions thereof. Compounds described herein are useful for inhibiting arginine methyltransferase activity. Methods of using the compounds for treating arginine methyltransferase-mediated disorders are also described.

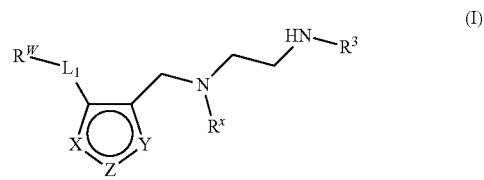

9 Claims, No Drawings

(56) References Cited

U.S. PATENT DOCUMENTS

| | | |
|---|---|---|
| 9,365,555 B2 | 6/2016 | Duncan et al. |
| 9,394,258 B2 | 7/2016 | Chesworth et al. |
| 9,440,950 B2 | 9/2016 | Mitchell et al. |
| 9,447,079 B2 | 9/2016 | Mitchell et al. |
| 2002/0090627 A1 | 7/2002 | Meyers |
| 2004/0176325 A1 | 9/2004 | Munson et al. |
| 2005/0032794 A1 | 2/2005 | Padia et al. |
| 2005/0187224 A1 | 8/2005 | Gebauer et al. |
| 2006/0128724 A1 | 6/2006 | Cui et al. |
| 2006/0235037 A1 | 10/2006 | Purandare et al. |
| 2006/0239990 A1 | 10/2006 | Nabel et al. |
| 2006/0264419 A1 | 11/2006 | Schiemann et al. |
| 2007/0060589 A1 | 3/2007 | Purandare et al. |
| 2008/0214615 A1 | 9/2008 | Muller et al. |
| 2008/0214654 A1 | 9/2008 | Lampe et al. |
| 2008/0280925 A1 | 11/2008 | Wahhab et al. |
| 2008/0312298 A1 | 12/2008 | Foreman et al. |
| 2009/0012031 A1 | 1/2009 | Chinnaiyan et al. |
| 2009/0036435 A1 | 2/2009 | Curry et al. |
| 2009/0143372 A1 | 6/2009 | Deng et al. |
| 2009/0298910 A1 | 12/2009 | Griffey et al. |
| 2009/0306201 A1 | 12/2009 | Reinberg et al. |
| 2010/0151506 A1 | 6/2010 | Thompson et al. |
| 2011/0003784 A1 | 1/2011 | Garvey et al. |
| 2011/0021362 A1 | 1/2011 | Trojer et al. |
| 2011/0065681 A1 | 3/2011 | Wei et al. |
| 2011/0160293 A1 | 6/2011 | Nakamura et al. |
| 2011/0251216 A1 | 10/2011 | Chinnaiyan et al. |
| 2011/0269770 A1 | 11/2011 | Gross et al. |
| 2012/0071418 A1 | 3/2012 | Copeland et al. |
| 2012/0142625 A1 | 6/2012 | Olhava et al. |
| 2012/0156219 A1 | 6/2012 | Habashita et al. |
| 2012/0264734 A1 | 10/2012 | Kuntz et al. |
| 2013/0345268 A1 | 12/2013 | Ratner et al. |
| 2014/0288105 A1 | 9/2014 | Chesworth et al. |
| 2014/0288124 A1 | 9/2014 | Chesworth et al. |
| 2014/0288128 A1 | 9/2014 | Mitchell et al. |
| 2014/0288129 A1 | 9/2014 | Mitchell et al. |
| 2014/0288140 A1 | 9/2014 | Mitchell et al. |
| 2014/0288141 A1 | 9/2014 | Kuntz et al. |
| 2014/0315904 A1 | 10/2014 | Chesworth et al. |
| 2014/0315961 A1 | 10/2014 | Chesworth et al. |
| 2014/0323537 A1 | 10/2014 | Chesworth et al. |
| 2015/0259322 A1 | 9/2015 | Kita et al. |
| 2015/0284334 A1 | 10/2015 | Kuntz et al. |
| 2016/0024017 A1 | 1/2016 | Chesworth et al. |
| 2016/0031839 A1 | 2/2016 | Chesworth et al. |
| 2016/0039767 A1 | 2/2016 | Mitchell et al. |
| 2016/0108018 A1 | 4/2016 | Mitchell et al. |
| 2016/0137609 A1 | 5/2016 | Chesworth et al. |
| 2016/0137631 A1 | 5/2016 | Duncan et al. |
| 2016/0184267 A1 | 6/2016 | Chesworth et al. |
| 2016/0185772 A1 | 6/2016 | Chesworth et al. |
| 2016/0214985 A1 | 7/2016 | Duncan et al. |

FOREIGN PATENT DOCUMENTS

| | | | |
|---|---|---|---|
| EP | 2 221 053 A1 | 8/2010 | |
| EP | 2 226 315 A1 | 9/2010 | |
| JP | 2009-179616 A | 8/2009 | |
| WO | WO 96/16981 A2 | 6/1996 | |
| WO | WO 03/031435 A1 | 4/2003 | |
| WO | WO 2004/020414 A1 | 3/2004 | |
| WO | WO 2004/052862 A1 | 6/2004 | |
| WO | WO 2004/089931 A1 | 10/2004 | |
| WO | WO 2004/096212 A1 | 11/2004 | |
| WO | WO 2006/025832 A1 | 3/2006 | |
| WO | WO 2006/033995 A2 | 3/2006 | |
| WO | WO 2006/040136 A1 | 4/2006 | |
| WO | WO 2006/069155 A2 | 6/2006 | |
| WO | WO 2007/091393 A1 | 8/2007 | |
| WO | WO 2008/001076 A1 | 1/2008 | |
| WO | WO 2008/008286 A2 | 1/2008 | |
| WO | WO 2008/104077 A1 | 9/2008 | |
| WO | WO 2008/137834 A2 | 11/2008 | |
| WO | WO 2009/033125 A1 | 3/2009 | |
| WO | WO 2009/126537 A1 | 10/2009 | |
| WO | WO 2010/034737 A1 | 4/2010 | |
| WO | WO 2010/094009 A2 | 8/2010 | |
| WO | WO 2010/094609 A1 | 8/2010 | |
| WO | WO 2011/079236 A1 | 6/2011 | |
| WO | WO 2011/082098 A1 | 7/2011 | |
| WO | WO 2011/096210 A1 | 8/2011 | |
| WO | WO 2011/096211 A1 | 8/2011 | |
| WO | WO 2011/140324 A1 | 11/2011 | |
| WO | WO 2012/005805 A1 | 1/2012 | |
| WO | WO 2012/060760 A1 | 5/2012 | |
| WO | WO 2012/068589 A2 | 5/2012 | |
| WO | WO 2012/075080 A1 | 6/2012 | |
| WO | WO 2012/075492 A2 | 6/2012 | |
| WO | WO 2012/075500 A2 | 6/2012 | |
| WO | WO 2012/082436 A2 | 6/2012 | |
| WO | WO 2012/118812 A2 | 9/2012 | |
| WO | WO 2012/142513 A1 | 10/2012 | |
| WO | WO 2013/174947 A1 | 11/2013 | |
| WO | WO 2014/034750 A1 | 3/2014 | |
| WO | WO 2014/100695 A1 | 6/2014 | |
| WO | WO 2014/100716 A1 | 6/2014 | |
| WO | WO 2014/100719 A1 | 6/2014 | |
| WO | WO 2014/100730 A1 | 6/2014 | |
| WO | WO 2014/100734 A1 | 6/2014 | |
| WO | WO 2014/100764 A1 | 6/2014 | |
| WO | WO 2014/144169 A1 | 9/2014 | |
| WO | WO 2014/144455 A1 | 9/2014 | |
| WO | WO 2014/144659 A1 | 9/2014 | |
| WO | WO 2014/153090 A1 | 9/2014 | |
| WO | WO 2014/153100 A1 | 9/2014 | |
| WO | WO 2014/153172 A1 | 9/2014 | |
| WO | WO 2014/153208 A1 | 9/2014 | |
| WO | WO 2014/153214 A1 | 9/2014 | |
| WO | WO 2014/153235 A1 | 9/2014 | |
| WO | WO 2014/178954 A1 | 11/2014 | |
| WO | WO 2015/200677 A1 | 12/2015 | |
| WO | WO 2015/200680 A1 | 12/2015 | |
| WO | WO 2016/022605 A1 | 2/2016 | |
| WO | WO 2016/044556 A2 | 3/2016 | |
| WO | WO 2016/044569 A1 | 3/2016 | |
| WO | WO 2016/044576 A1 | 3/2016 | |
| WO | WO 2016/044585 A1 | 3/2016 | |
| WO | WO 2016/044604 A1 | 3/2016 | |
| WO | WO 2016/044626 A1 | 3/2016 | |
| WO | WO 2016/044641 A2 | 3/2016 | |
| WO | WO 2016/044650 A1 | 3/2016 | |

OTHER PUBLICATIONS

Ito et al., A medium-term rat liver bioassay for rapid in vivo detection of carcinogenic potential of chemicals. Cancer Sci. Jan. 2003;94(1):3-8. Review.
International Search Report and Written Opinion for International Application No. PCT/US2014/029009 mailed May 28, 2014.
International Search Report and Written Opinion for International Application No. PCT/US2014/029160 mailed May 28, 2014.
International Search Report and Written Opinion for International Application No. PCT/US2014/029583 mailed Jul. 29, 2014.
International Search Report and Written Opinion for International Application No. PCT/US2014/029605 mailed Jul. 23, 2014.
International Search Report and Written Opinion for International Application No. PCT/US2014/029665 mailed Jul. 23, 2014.
International Search Report and Written Opinion for International Application No. PCT/US2014/029710 mailed Jul. 15, 2014.
International Search Report and Written Opinion for International Application No. PCT/US2014/029062 mailed Sep. 17, 2014.
International Search Report and Written Opinion for International Application No. PCT/US2014/029750 mailed Oct. 2, 2014.
International Search Report and Written Opinion for International Application No. PCT/US2014/029408 mailed Jun. 17, 2014.
International Search Report and Written Opinion for International Application No. PCT/US2015/050659 mailed Dec. 21, 2015.
Invitation to Pay Additional Fees, and Where Applicable, Protest Fee for International Application No. PCT/US2015/050750 mailed Nov. 19, 2015.

(56) References Cited

OTHER PUBLICATIONS

International Search Report and Written Opinion for International Application No. PCT/US2015/050750 mailed Feb. 3, 2016.
International Search Report and Written Opinion for International Application No. PCT/US2015/050675 mailed Dec. 17, 2015.
Al-Dhaheri et al., CARM1 is an important determinant of ERα-dependent breast cancer cell differentiation and proliferation in breast cancer cells. Cancer Res. Mar. 15, 2011;71(6):2118-28. doi: 10.1158/0008-5472.CAN-10-2426. Epub Jan. 31, 2011.
Blanchet et al., CD28 costimulatory signal induces protein arginine methylation in T cells. J Exp Med. Aug. 1, 2005;202(3):371-7.
Boger, Asymmetric dimethylarginine (ADMA): a novel risk marker in cardiovascular medicine and beyond. Ann Med. 2006;38(2):126-36.
Bratenko et al., Synthesis and antimicrobial activities of 1,3-bis(4-pyrazolylmethyl)-2-(4-nitrophenyl) imidazolidines and hexahydropyrimidines. Farmatsevtichnii Zhurnal. 2007;5:66-70.
CAS Registry Accession No. 1340581-60-3. Nov. 3, 2011.
CAS Registry Accession No. 1342545-59-8. Nov. 8, 2011.
CAS Registry File RN 1524901-21-0, STN Entry Date: Oct. 10, 2013.
CAS Registry File RN 1547978-57-3, STN Entry Date: Jul. 3, 2013.
CAS Registry File RN 1551294-59-7, STN Entry Date: Oct. 10, 2013.
CAS Registry File RN 1564967-49-2, STN Entry Date: Oct. 10, 2013.
CAS Registry File RN 1564977-15-6, STN Entry Date: Oct. 10, 2013.
CAS Registry File RN 1565645-75-1. Dated Mar. 10, 2014.
CAS Registry File RN 1566071-28-0, STN Entry Date: Oct. 10, 2013.
CAS Registry File RN 1566350-70-6, STN Entry Date: Oct. 10, 2013.
Chen et al., Expression of nitric oxide related enzymes in coronary heart disease. Basic Res Cardiol. Jul. 2006;101(4):346-53. Epub May 16, 2006.
Cheung et al., Protein arginine-methyltransferase-dependent oncogenesis. Nat Cell Biol. Oct. 2007;9(10):1208-15. Epub Sep. 23, 2007.
Choi et al., Protein arginine methyltransferase 1 regulates hepatic glucose production in a FoxO1-dependent manner. Hepatology. Oct. 2012;56(4):1546-56. doi: 10.1002/hep.25809.
Copeland, Protein methyltransferase inhibitors as personalized cancer therapeutics. Drug Discov Today Ther Strateg. 2012;9:e83-e90.
Covic et al., Arginine methyltransferase CARM1 is a promoter-specific regulator of NF-kappaB-dependent gene expression. EMBO J. Jan. 12, 2005;24(1):85-96. Epub Dec. 16, 2004.
Davies et al., Oculopharyngeal muscular dystrophy: potential therapies for an aggregate-associated disorder. Int J Biochem Cell Biol. 2006;38(9):1457-62. Epub Feb. 28, 2006.
Engelmann et al., The dark side of E2F1: in transit beyond apoptosis. Cancer Res. Feb. 1, 2012;72(3):571-5. doi: 10.1158/0008-5472.CAN-11-2575.
Forbes et al., COSMIC: mining complete cancer genomes in the Catalogue of Somatic Mutations in Cancer. Nucleic Acids Res. Jan. 2011;39(Database issue):D945-50. doi: 10.1093/nar/gkq929. Epub Oct. 15, 2010.
Frietze et al., CARM1 regulates estrogen-stimulated breast cancer growth through up-regulation of E2F1. Cancer Res. Jan. 1, 2008;68(1):301-6. doi: 10.1158/0008-5472.CAN-07-1983.
Fuchi et al., A library synthesis of pyrazoles by azomethine imine cycloaddition to the polymer-supported vinylsulfone. Chem Lett. 2005;34(3):438-9.
Hong et al., Aberrant expression of CARM1, a transcriptional coactivator of androgen receptor, in the development of prostate carcinoma and androgen-independent status. Cancer. Jul. 1, 2004;101(1):83-9.
Jacobi et al., Asymmetrical dimethylarginine in renal disease: limits of variation or variation limits? A systematic review. Am J Nephrol. 2008;28(2):224-37. Epub Oct. 24, 2007.
Kleinschmidt et al., Cell cycle regulation by the PRMT6 arginine methyltransferase through repression of cyclin-dependent kinase inhibitors. PLoS One. 2012;7(8):e41446. doi: 10.1371/journal.pone.0041446. Epub Aug. 20, 2012.
Le Romancer et al., Methylation, a key step for nongenomic estrogen signaling in breast tumors. Steroids. Aug.-Sep. 2010;75(8-9):560-4. doi: 10.1016/j.steroids.2010.01.013. Epub Jan. 29, 2010.
Le Romancer et al., Regulation of estrogen rapid signaling through arginine methylation by PRMT1. Mol Cell. Jul. 25, 2008;31(2):212-21. doi: 10.1016/j.molcel.2008.05.025.
Leovac et al., Copper(II) complexes with reduced Schiff base: Synthesis, spectroscopic, thermal, X-ray, and cytotoxic studies of novel copper(II) complexes with an arylpyrazole ligand. Austrailian J Chem. 2007;60(8):615-20.
Majumder et al., Involvement of arginine methyltransferase CARM1 in androgen receptor function and prostate cancer cell viability. Prostate. Sep. 1, 2006;66(12):1292-301.
Michaud-Levesque et al., Thrombospondin-1 is a transcriptional repression target of PRMT6. J Biol Chem. Aug. 7, 2009;284(32):21338-46. doi: 10.1074/jbc.M109.005322. Epub Jun. 9, 2009.
Nagahata et al., Expression profiling to predict postoperative prognosis for estrogen receptor-negative breast cancers by analysis of 25,344 genes on a cDNA microarray. Cancer Sci. Mar. 2004;95(3):218-25.
Perreault et al., Regulation of the nuclear poly(A)-binding protein by arginine methylation in fission yeast. J Biol Chem. Mar. 9, 2007;282(10):7552-62. Epub Jan. 9, 2007.
PUBCHEM Submission; NIH/NCBI, Compound Identifier 1170606. Jul. 10, 2005. 10 pages.
PUBCHEM Submission; NIH/NCBI, Compound Identifier 46961966. Nov 25, 2010. 9 pages.
PUBCHEM Submission; NIH/NCBI, Compound Identifier 51623447. May 20, 2011. 10 pages.
PUBCHEM Submission; NIH/NCBI, Compound Identifier 62687207. Oct. 22, 2012. 9 pages.
PUBCHEM Submission; NIH/NCBI, Compound Identifier 65237285. Oct. 23, 2012. 9 pages.
PUBCHEM Submission; NIH/NCBI, Compound Identifier 72853360. Feb 28, 2014. 10 pages.
PUBCHEM Submission; NIH/NCBI, Substance Identifier 107215563. Akos Consulting & Solutions. Feb 22, 2011. 6 pages.
PUBCHEM Submission; NIH/NCBI, Substance Identifier 151630580. Akos Consulting & Solutions. Oct 24, 2012. 10 pages.
Rappsilber et al., Detection of arginine dimethylated peptides by parallel precursor ion scanning mass spectrometry in positive ion mode. Anal Chem. 2003 Jul. 1, 2003;75(13):3107-14.
Richard et al., Arginine methylation regulates IL-2 gene expression: a role for protein arginine methyltransferase 5 (PRMT5). Biochem J. May 15, 2005;388(Pt 1):379-86.
Seligson et al., Global histone modification patterns predict risk of prostate cancer recurrence. Nature. Jun. 30, 2005;435(7046):1262-6.
Shia et al., PRMT1 interacts with AML1-ETO to promote its transcriptional activation and progenitor cell proliferative potential. Blood. May 24, 2012;119(21):4953-62. doi: 10.1182/blood-2011-04-347476. Epub Apr. 12, 2012.
Singh et al., DAL-1/4.1B tumor suppressor interacts with protein arginine N-methyltransferase 3 (PRMT3) and inhibits its ability to methylate substrates in vitro and in vivo. Oncogene. Oct. 14, 2004;23(47):7761-71.
Sydow et al., Insulin resistance: potential role of the endogenous nitric oxide synthase inhibitor ADMA. Vasc Med. Jul. 2005;10 Suppl 1:S35-43.
Therrien et al., 1,2-Diamines as inhibitors of co-activator associated arginine methyltransferase 1 (CARM1). Bioorg Med Chem Lett. Dec. 1, 2009;19(23):6725-32. doi: 10.1016/j.bmcl.2009.09.110. Epub Oct. 2, 2009.
Vallance et al., Accumulation of an endogenous inhibitor of nitric oxide synthesis in chronic renal failure. Lancet. Mar. 7, 1992;339(8793):572-5.

(56) References Cited

OTHER PUBLICATIONS

Vallance et al., Endogenous dimethylarginine as an inhibitor of nitric oxide synthesis. J Cardiovasc Pharmacol. 1992;20 Suppl 12:S60-2.

Wan et al., Benzo[d]imidazole inhibitors of Coactivator Associated Arginine Methyltransferase 1 (CARM1)—Hit to Lead studies. Bioorg Med Chem Lett. Sep. 1, 2009;19(17):5063-6. doi: 10.1016/j.bmcl.2009.07.040. Epub Jul. 10, 2009.

Wang et al., CARM1/PRMT4 is necessary for the glycogen gene expression programme in skeletal muscle cells. Biochem J. Jun. 1, 2012;444(2):323-31. doi: 10.1042/BJ20112033.

Yoshimatsu et al., Dysregulation of PRMT1 and PRMT6, Type I arginine methyltransferases, is involved in various types of human cancers. Int J Cancer. Feb. 1, 2011;128(3):562-73. doi: 10.1002/ijc.25366.

Zakrzewicz et al., From arginine methylation to ADMA: a novel mechanism with therapeutic potential in chronic lung diseases. BMC Pulm Med. Jan. 29, 2009;9:5. doi: 10.1186/1471-2466-9-5.

SEQUENCE LISTING

```
<160> NUMBER OF SEQ ID NOS: 17

<210> SEQ ID NO 1
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Acp

<400> SEQUENCE: 1

Xaa Arg Leu Ala Arg Arg Gly Gly Val Lys Arg Ile Ser Gly Leu Ile
1               5                   10                  15
```

```
<210> SEQ ID NO 2
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 2

Asp Tyr Lys Asp Asp Asp Asp Lys
1               5

<210> SEQ ID NO 3
<211> LENGTH: 230
<212> TYPE: PRT
<213> ORGANISM: Artificial Sequence
<220> FEATURE:
<223> OTHER INFORMATION: Synthetic Polypeptide

<400> SEQUENCE: 3

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Glu Asn Leu Tyr
    210                 215                 220

Phe Gln Gly Gly Asn Ser
225                 230

<210> SEQ ID NO 4
<211> LENGTH: 609
<212> TYPE: PRT
<213> ORGANISM: Artificial Sequence
<220> FEATURE:
<223> OTHER INFORMATION: Synthetic Polypeptide

<400> SEQUENCE: 4

Met Ser Pro Ile Leu Gly Tyr Trp Lys Ile Lys Gly Leu Val Gln Pro
1               5                   10                  15
```

-continued

Thr Arg Leu Leu Leu Glu Tyr Leu Glu Glu Lys Tyr Glu Glu His Leu
        20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Ile Asp Gly Asp Val Lys
 50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
                115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Glu Asn Leu Tyr
    210                 215                 220

Phe Gln Gly Gly Asn Ser Asp Tyr Lys Asp Asp Asp Lys Met Ala
225                 230                 235                 240

Ala Ala Glu Ala Ala Asn Cys Ile Met Glu Asn Phe Val Ala Thr Leu
            245                 250                 255

Ala Asn Gly Met Ser Leu Gln Pro Pro Leu Glu Glu Val Ser Cys Gly
        260                 265                 270

Gln Ala Glu Ser Ser Glu Lys Pro Asn Ala Glu Asp Met Thr Ser Lys
        275                 280                 285

Asp Tyr Tyr Phe Asp Ser Tyr Ala His Phe Gly Ile His Glu Glu Met
    290                 295                 300

Leu Lys Asp Glu Val Arg Thr Leu Thr Tyr Arg Asn Ser Met Phe His
305                 310                 315                 320

Asn Arg His Leu Phe Lys Asp Lys Val Val Leu Asp Val Gly Ser Gly
                325                 330                 335

Thr Gly Ile Leu Cys Met Phe Ala Ala Lys Ala Gly Ala Arg Lys Val
            340                 345                 350

Ile Gly Ile Glu Cys Ser Ser Ile Ser Asp Tyr Ala Val Lys Ile Val
        355                 360                 365

Lys Ala Asn Lys Leu Asp His Val Val Thr Ile Ile Lys Gly Lys Val
    370                 375                 380

Glu Glu Val Glu Leu Pro Val Glu Lys Val Asp Ile Ile Ser Glu
385                 390                 395                 400

Trp Met Gly Tyr Cys Leu Phe Tyr Glu Ser Met Leu Asn Thr Val Leu
                405                 410                 415

Tyr Ala Arg Asp Lys Trp Leu Ala Pro Asp Gly Leu Ile Phe Pro Asp
            420                 425                 430

```
Arg Ala Thr Leu Tyr Val Thr Ala Ile Glu Asp Arg Gln Tyr Lys Asp
            435                 440                 445

Tyr Lys Ile His Trp Trp Glu Asn Val Tyr Gly Phe Asp Met Ser Cys
    450                 455                 460

Ile Lys Asp Val Ala Ile Lys Glu Pro Leu Val Asp Val Val Asp Pro
465                 470                 475                 480

Lys Gln Leu Val Thr Asn Ala Cys Leu Ile Lys Glu Val Asp Ile Tyr
                485                 490                 495

Thr Val Lys Val Glu Asp Leu Thr Phe Thr Ser Pro Phe Cys Leu Gln
            500                 505                 510

Val Lys Arg Asn Asp Tyr Val His Ala Leu Val Ala Tyr Phe Asn Ile
        515                 520                 525

Glu Phe Thr Arg Cys His Lys Arg Thr Gly Phe Ser Thr Ser Pro Glu
530                 535                 540

Ser Pro Tyr Thr His Trp Lys Gln Thr Val Phe Tyr Met Glu Asp Tyr
545                 550                 555                 560

Leu Thr Val Lys Thr Gly Glu Glu Ile Phe Gly Thr Ile Gly Met Arg
                565                 570                 575

Pro Asn Ala Lys Asn Asn Arg Asp Leu Asp Phe Thr Ile Asp Leu Asp
            580                 585                 590

Phe Lys Gly Gln Leu Cys Glu Leu Ser Cys Ser Thr Asp Tyr Arg Met
        595                 600                 605

Arg

<210> SEQ ID NO 5
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Acp

<400> SEQUENCE: 5

Xaa Arg Leu Ala Arg Arg Gly Gly Val Lys Arg Ile Ser Gly Leu Ile
1               5                   10                  15

<210> SEQ ID NO 6
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 6

Met Asp Tyr Lys Asp Asp Asp Asp Lys
1               5

<210> SEQ ID NO 7
<211> LENGTH: 389
<212> TYPE: PRT
<213> ORGANISM: Artificial Sequence
<220> FEATURE:
<223> OTHER INFORMATION: Synthetic Polypeptide

<400> SEQUENCE: 7

Met Asp Tyr Lys Asp Asp Asp Asp Lys Ser Gln Pro Lys Lys Arg Lys
1               5                   10                  15

Leu Glu Ser Gly Gly Gly Gly Glu Gly Gly Glu Gly Thr Glu Glu Glu
```

```
                20              25              30
Asp Gly Ala Glu Arg Glu Ala Ala Leu Glu Arg Pro Arg Arg Thr Lys
            35                  40                  45

Arg Glu Arg Asp Gln Leu Tyr Tyr Glu Cys Tyr Ser Asp Val Ser Val
        50                  55                  60

His Glu Glu Met Ile Ala Asp Arg Val Arg Thr Asp Ala Tyr Arg Leu
65                  70                  75                  80

Gly Ile Leu Arg Asn Trp Ala Ala Leu Arg Gly Lys Thr Val Leu Asp
                85                  90                  95

Val Gly Ala Gly Thr Gly Ile Leu Ser Ile Phe Cys Ala Gln Ala Gly
            100                 105                 110

Ala Arg Arg Val Tyr Ala Val Glu Ala Ser Ala Ile Trp Gln Gln Ala
        115                 120                 125

Arg Glu Val Val Arg Phe Asn Gly Leu Glu Asp Arg Val His Val Leu
    130                 135                 140

Pro Gly Pro Val Glu Thr Val Glu Leu Pro Glu Gln Val Asp Ala Ile
145                 150                 155                 160

Val Ser Glu Trp Met Gly Tyr Gly Leu Leu His Glu Ser Met Leu Ser
                165                 170                 175

Ser Val Leu His Ala Arg Thr Lys Trp Leu Lys Glu Gly Gly Leu Leu
            180                 185                 190

Leu Pro Ala Ser Ala Glu Leu Phe Ile Ala Pro Ile Ser Asp Gln Met
        195                 200                 205

Leu Glu Trp Arg Leu Gly Phe Trp Ser Gln Val Lys Gln His Tyr Gly
    210                 215                 220

Val Asp Met Ser Cys Leu Glu Gly Phe Ala Thr Arg Cys Leu Met Gly
225                 230                 235                 240

His Ser Glu Ile Val Val Gln Gly Leu Ser Gly Glu Asp Val Leu Ala
                245                 250                 255

Arg Pro Gln Arg Phe Ala Gln Leu Glu Leu Ser Arg Ala Gly Leu Glu
            260                 265                 270

Gln Glu Leu Glu Ala Gly Val Gly Gly Arg Phe Arg Cys Ser Cys Tyr
        275                 280                 285

Gly Ser Ala Pro Met His Gly Phe Ala Ile Trp Phe Gln Val Thr Phe
    290                 295                 300

Pro Gly Gly Glu Ser Glu Lys Pro Leu Val Leu Ser Thr Ser Pro Phe
305                 310                 315                 320

His Pro Ala Thr His Trp Lys Gln Ala Leu Leu Tyr Leu Asn Glu Pro
                325                 330                 335

Val Gln Val Glu Gln Asp Thr Asp Val Ser Gly Glu Ile Thr Leu Leu
            340                 345                 350

Pro Ser Arg Asp Asn Pro Arg Arg Leu Arg Val Leu Leu Arg Tyr Lys
        355                 360                 365

Val Gly Asp Gln Glu Glu Lys Thr Lys Asp Phe Ala Met Glu Asp His
    370                 375                 380

His His His His
385

<210> SEQ ID NO 8
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
```

```
<221> NAME/KEY: misc_feature
<222> LOCATION: (1)..(1)
<223> OTHER INFORMATION: Xaa is Acp

<400> SEQUENCE: 8

Xaa Lys Pro Ala Ile Arg Arg Leu Ala Arg Arg Gly Gly Val Lys Arg
1               5                   10                  15

<210> SEQ ID NO 9
<211> LENGTH: 229
<212> TYPE: PRT
<213> ORGANISM: Artificial Sequence
<220> FEATURE:
<223> OTHER INFORMATION: Synthetic Polypeptide

<400> SEQUENCE: 9

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Glu Phe
225

<210> SEQ ID NO 10
<211> LENGTH: 623
<212> TYPE: PRT
<213> ORGANISM: Artificial Sequence
<220> FEATURE:
<223> OTHER INFORMATION: Synthetic Polypeptide

<400> SEQUENCE: 10

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30
```

```
Tyr Glu Arg Asp Glu Gly Asp Lys Trp Arg Asn Lys Lys Phe Glu Leu
         35                  40                  45
Gly Leu Glu Phe Pro Asn Leu Pro Tyr Tyr Ile Asp Gly Asp Val Lys
 50                  55                  60
Leu Thr Gln Ser Met Ala Ile Ile Arg Tyr Ile Ala Asp Lys His Asn
 65                  70                  75                  80
Met Leu Gly Gly Cys Pro Lys Glu Arg Ala Glu Ile Ser Met Leu Glu
                 85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
         115                 120                 125
Met Leu Lys Met Phe Glu Asp Arg Leu Cys His Lys Thr Tyr Leu Asn
 130                 135                 140
Gly Asp His Val Thr His Pro Asp Phe Met Leu Tyr Asp Ala Leu Asp
 145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
                180                 185                 190
Leu Lys Ser Ser Lys Tyr Ile Ala Trp Pro Leu Gln Gly Trp Gln Ala
         195                 200                 205
Thr Phe Gly Gly Gly Asp His Pro Pro Lys Ser Asp Leu Val Pro Arg
 210                 215                 220
Gly Ser Pro Glu Phe Met Gly Met Lys His Ser Ser Arg Cys Leu Leu
225                 230                 235                 240
Leu Arg Arg Lys Met Ala Glu Asn Ala Ala Glu Ser Thr Glu Val Asn
                245                 250                 255
Ser Pro Pro Ser Gln Pro Pro Gln Pro Val Val Pro Ala Lys Pro Val
                260                 265                 270
Gln Cys Val His His Val Ser Thr Gln Pro Ser Cys Pro Gly Arg Gly
         275                 280                 285
Lys Met Ser Lys Leu Leu Asn Pro Glu Glu Met Thr Ser Arg Asp Tyr
 290                 295                 300
Tyr Phe Asp Ser Tyr Ala His Phe Gly Ile His Glu Glu Met Leu Lys
305                 310                 315                 320
Asp Glu Val Arg Thr Leu Thr Tyr Arg Asn Ser Met Tyr His Asn Lys
                325                 330                 335
His Val Phe Lys Asp Lys Val Val Leu Asp Val Gly Ser Gly Thr Gly
                340                 345                 350
Ile Leu Ser Met Phe Ala Ala Lys Ala Gly Ala Lys Lys Val Phe Gly
         355                 360                 365
Ile Glu Cys Ser Ser Ile Ser Asp Tyr Ser Glu Lys Ile Ile Lys Ala
 370                 375                 380
Asn His Leu Asp Asn Ile Ile Thr Ile Phe Lys Gly Lys Val Glu Glu
385                 390                 395                 400
Val Glu Leu Pro Val Glu Lys Val Asp Ile Ile Ser Glu Trp Met
                405                 410                 415
Gly Tyr Cys Leu Phe Tyr Glu Ser Met Leu Asn Thr Val Ile Phe Ala
                420                 425                 430
Arg Asp Lys Trp Leu Lys Pro Gly Gly Leu Met Phe Pro Asp Arg Ala
         435                 440                 445
```

```
Ala Leu Tyr Val Val Ala Ile Glu Asp Arg Gln Tyr Lys Asp Phe Lys
            450                 455                 460

Ile His Trp Trp Glu Asn Val Tyr Gly Phe Asp Met Thr Cys Ile Arg
465                 470                 475                 480

Asp Val Ala Met Lys Glu Pro Leu Val Asp Ile Val Asp Pro Lys Gln
                485                 490                 495

Val Val Thr Asn Ala Cys Leu Ile Lys Glu Val Asp Ile Tyr Thr Val
            500                 505                 510

Lys Thr Glu Glu Leu Ser Phe Thr Ser Ala Phe Cys Leu Gln Ile Gln
        515                 520                 525

Arg Asn Asp Tyr Val His Ala Leu Val Thr Tyr Phe Asn Ile Glu Phe
530                 535                 540

Thr Lys Cys His Lys Lys Met Gly Phe Ser Thr Ala Pro Asp Ala Pro
545                 550                 555                 560

Tyr Thr His Trp Lys Gln Thr Val Phe Tyr Leu Glu Asp Tyr Leu Thr
                565                 570                 575

Val Arg Arg Gly Glu Glu Ile Tyr Gly Thr Ile Ser Met Lys Pro Asn
            580                 585                 590

Ala Lys Asn Val Arg Asp Leu Asp Phe Thr Val Asp Leu Asp Phe Lys
        595                 600                 605

Gly Gln Leu Cys Glu Thr Ser Val Ser Asn Asp Tyr Lys Met Arg
610                 615                 620

<210> SEQ ID NO 11
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Acp

<400> SEQUENCE: 11

Xaa Gly Gly Arg Gly Gly Phe Gly Gly Arg Gly Gly Phe Gly Gly Arg
1               5                   10                  15

Gly Gly Phe Gly
            20

<210> SEQ ID NO 12
<211> LENGTH: 226
<212> TYPE: PRT
<213> ORGANISM: Artificial Sequence
<220> FEATURE:
<223> OTHER INFORMATION: Synthetic Polypeptide

<400> SEQUENCE: 12

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
```

```
                    85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
            115                 120                 125
Met Leu Lys Met Phe Glu Asp Arg Leu Cys His Lys Thr Tyr Leu Asn
        130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
                180                 185                 190
Leu Lys Ser Ser Lys Tyr Ile Ala Trp Pro Leu Gln Gly Trp Gln Ala
            195                 200                 205
Thr Phe Gly Gly Gly Asp His Pro Pro Lys Ser Asp Leu Val Pro Arg
        210                 215                 220
Gly Ser
225

<210> SEQ ID NO 13
<211> LENGTH: 756
<212> TYPE: PRT
<213> ORGANISM: Artificial Sequence
<220> FEATURE:
<223> OTHER INFORMATION: Synthetic Polypeptide

<400> SEQUENCE: 13

Met Ser Pro Ile Leu Gly Tyr Trp Lys Ile Lys Gly Leu Val Gln Pro
1               5                   10                  15
Thr Arg Leu Leu Leu Glu Tyr Leu Glu Glu Lys Tyr Glu Glu His Leu
                20                  25                  30
Tyr Glu Arg Asp Glu Gly Asp Lys Trp Arg Asn Lys Lys Phe Glu Leu
            35                  40                  45
Gly Leu Glu Phe Pro Asn Leu Pro Tyr Tyr Ile Asp Gly Asp Val Lys
        50                  55                  60
Leu Thr Gln Ser Met Ala Ile Ile Arg Tyr Ile Ala Asp Lys His Asn
65                  70                  75                  80
Met Leu Gly Gly Cys Pro Lys Glu Arg Ala Glu Ile Ser Met Leu Glu
                85                  90                  95
Gly Ala Val Leu Asp Ile Arg Tyr Gly Val Ser Arg Ile Ala Tyr Ser
                100                 105                 110
Lys Asp Phe Glu Thr Leu Lys Val Asp Phe Leu Ser Lys Leu Pro Glu
            115                 120                 125
Met Leu Lys Met Phe Glu Asp Arg Leu Cys His Lys Thr Tyr Leu Asn
        130                 135                 140
Gly Asp His Val Thr His Pro Asp Phe Met Leu Tyr Asp Ala Leu Asp
145                 150                 155                 160
Val Val Leu Tyr Met Asp Pro Met Cys Leu Asp Ala Phe Pro Lys Leu
                165                 170                 175
```

-continued

```
Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
    210                 215                 220

Gly Ser Cys Ser Leu Ala Ser Gly Ala Thr Gly Arg Gly Ala Val
225                 230                 235                 240

Glu Asn Glu Glu Asp Leu Pro Glu Leu Ser Asp Ser Gly Asp Glu Ala
                245                 250                 255

Ala Trp Glu Asp Glu Asp Ala Asp Leu Pro His Gly Lys Gln Gln
            260                 265                 270

Thr Pro Cys Leu Phe Cys Asn Arg Leu Phe Thr Ser Ala Glu Glu Thr
    275                 280                 285

Phe Ser His Cys Lys Ser Glu His Gln Phe Asn Ile Asp Ser Met Val
    290                 295                 300

His Lys His Gly Leu Glu Phe Tyr Gly Tyr Ile Lys Leu Ile Asn Phe
305                 310                 315                 320

Ile Arg Leu Lys Asn Pro Thr Val Glu Tyr Met Asn Ser Ile Tyr Asn
                325                 330                 335

Pro Val Pro Trp Glu Lys Glu Tyr Leu Lys Pro Val Leu Glu Asp
            340                 345                 350

Asp Leu Leu Leu Gln Phe Asp Val Glu Asp Leu Tyr Glu Pro Val Ser
            355                 360                 365

Val Pro Phe Ser Tyr Pro Asn Gly Leu Ser Glu Asn Thr Ser Val Val
    370                 375                 380

Glu Lys Leu Lys His Met Glu Ala Arg Ala Leu Ser Ala Glu Ala Ala
385                 390                 395                 400

Leu Ala Arg Ala Arg Glu Asp Leu Gln Lys Met Lys Gln Phe Ala Gln
                405                 410                 415

Asp Phe Val Met His Thr Asp Val Arg Thr Cys Ser Ser Ser Thr Ser
            420                 425                 430

Val Ile Ala Asp Leu Gln Glu Asp Glu Asp Gly Val Tyr Phe Ser Ser
            435                 440                 445

Tyr Gly His Tyr Gly Ile His Glu Glu Met Leu Lys Asp Lys Ile Arg
    450                 455                 460

Thr Glu Ser Tyr Arg Asp Phe Ile Tyr Gln Asn Pro His Ile Phe Lys
465                 470                 475                 480

Asp Lys Val Val Leu Asp Val Gly Cys Gly Thr Gly Ile Leu Ser Met
                485                 490                 495

Phe Ala Ala Lys Ala Gly Ala Lys Lys Val Leu Gly Val Asp Gln Ser
            500                 505                 510

Glu Ile Leu Tyr Gln Ala Met Asp Ile Ile Arg Leu Asn Lys Leu Glu
            515                 520                 525

Asp Thr Ile Thr Leu Ile Lys Gly Lys Ile Glu Glu Val His Leu Pro
    530                 535                 540
```

Val Glu Lys Val Asp Val Ile Ile Ser Glu Trp Met Gly Tyr Phe Leu
545                 550                 555                 560

Leu Phe Glu Ser Met Leu Asp Ser Val Leu Tyr Ala Lys Asn Lys Tyr
                565                 570                 575

Leu Ala Lys Gly Gly Ser Val Tyr Pro Asp Ile Cys Thr Ile Ser Leu
            580                 585                 590

Val Ala Val Ser Asp Val Asn Lys His Ala Asp Arg Ile Ala Phe Trp
        595                 600                 605

Asp Asp Val Tyr Gly Phe Lys Met Ser Cys Met Lys Lys Ala Val Ile
    610                 615                 620

Pro Glu Ala Val Val Glu Val Leu Asp Pro Lys Thr Leu Ile Ser Glu
625                 630                 635                 640

Pro Cys Gly Ile Lys His Ile Asp Cys His Thr Thr Ser Ile Ser Asp
                645                 650                 655

Leu Glu Phe Ser Ser Asp Phe Thr Leu Lys Ile Thr Arg Thr Ser Met
            660                 665                 670

Cys Thr Ala Ile Ala Gly Tyr Phe Asp Ile Tyr Phe Glu Lys Asn Cys
        675                 680                 685

His Asn Arg Val Val Phe Ser Thr Gly Pro Gln Ser Thr Lys Thr His
    690                 695                 700

Trp Lys Gln Thr Val Phe Leu Leu Glu Lys Pro Phe Ser Val Lys Ala
705                 710                 715                 720

Gly Glu Ala Leu Lys Gly Lys Val Thr Val His Lys Asn Lys Lys Asp
                725                 730                 735

Pro Arg Ser Leu Thr Val Thr Leu Thr Leu Asn Asn Ser Thr Gln Thr
            740                 745                 750

Tyr Gly Leu Gln
        755

<210> SEQ ID NO 14
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa is Acp

<400> SEQUENCE: 14

Xaa Pro Arg Lys Gln Leu Ala Thr Lys Ala Arg Lys Ser Ala Pro
1               5                   10                  15

<210> SEQ ID NO 15
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 15

Glu Gly His His His His His His
1               5

<210> SEQ ID NO 16
<211> LENGTH: 601
<212> TYPE: PRT
<213> ORGANISM: Artificial Sequence
<220> FEATURE:

<223> OTHER INFORMATION: Synthetic Polypeptide

<400> SEQUENCE: 16

```
Met Asp Tyr Lys Asp Asp Asp Lys Ala Ala Ala Ala Ala Ala Ala Val
1               5                   10                  15
Gly Pro Gly Ala Gly Ala Gly Ser Ala Val Pro Gly Gly Ala Gly
            20                  25                  30
Pro Cys Ala Thr Val Ser Val Phe Pro Gly Ala Arg Leu Leu Thr Ile
            35                  40                  45
Gly Asp Ala Asn Gly Glu Ile Gln Arg His Ala Glu Gln Gln Ala Leu
        50                  55                  60
Arg Leu Glu Val Arg Ala Gly Pro Asp Ser Ala Gly Ile Ala Leu Tyr
65                  70                  75                  80
Ser His Glu Asp Val Cys Val Phe Lys Cys Ser Val Ser Arg Glu Thr
                85                  90                  95
Glu Cys Ser Arg Val Gly Lys Gln Ser Phe Ile Ile Thr Leu Gly Cys
            100                 105                 110
Asn Ser Val Leu Ile Gln Phe Ala Thr Pro Asn Asp Phe Cys Ser Phe
        115                 120                 125
Tyr Asn Ile Leu Lys Thr Cys Arg Gly His Thr Leu Glu Arg Ser Val
    130                 135                 140
Phe Ser Glu Arg Thr Glu Glu Ser Ser Ala Val Gln Tyr Phe Gln Phe
145                 150                 155                 160
Tyr Gly Tyr Leu Ser Gln Gln Gln Asn Met Met Gln Asp Tyr Val Arg
                165                 170                 175
Thr Gly Thr Tyr Gln Arg Ala Ile Leu Gln Asn His Thr Asp Phe Lys
            180                 185                 190
Asp Lys Ile Val Leu Asp Val Gly Cys Gly Ser Gly Ile Leu Ser Phe
        195                 200                 205
Phe Ala Ala Gln Ala Gly Ala Arg Lys Ile Tyr Ala Val Glu Ala Ser
    210                 215                 220
Thr Met Ala Gln His Ala Glu Val Leu Val Lys Ser Asn Asn Leu Thr
225                 230                 235                 240
Asp Arg Ile Val Val Ile Pro Gly Lys Val Glu Glu Val Ser Leu Pro
                245                 250                 255
Glu Gln Val Asp Ile Ile Ile Ser Glu Pro Met Gly Tyr Met Leu Phe
            260                 265                 270
Asn Glu Arg Met Leu Glu Ser Tyr Leu His Ala Lys Lys Tyr Leu Lys
        275                 280                 285
Pro Ser Gly Asn Met Phe Pro Thr Ile Gly Asp Val His Leu Ala Pro
    290                 295                 300
Phe Thr Asp Glu Gln Leu Tyr Met Glu Gln Phe Thr Lys Ala Asn Phe
305                 310                 315                 320
Trp Tyr Gln Pro Ser Phe His Gly Val Asp Leu Ser Ala Leu Arg Gly
                325                 330                 335
Ala Ala Val Asp Glu Tyr Phe Arg Gln Pro Val Val Asp Thr Phe Asp
            340                 345                 350
Ile Arg Ile Leu Met Ala Lys Ser Val Lys Tyr Thr Val Asn Phe Leu
        355                 360                 365
Glu Ala Lys Glu Gly Asp Leu His Arg Ile Glu Ile Pro Phe Lys Phe
    370                 375                 380
His Met Leu His Ser Gly Leu Val His Gly Leu Ala Phe Trp Phe Asp
385                 390                 395                 400
```

```
Val Ala Phe Ile Gly Ser Ile Met Thr Val Trp Leu Ser Thr Ala Pro
                405                 410                 415

Thr Glu Pro Leu Thr His Trp Tyr Gln Val Arg Cys Leu Phe Gln Ser
            420                 425                 430

Pro Leu Phe Ala Lys Ala Gly Asp Thr Leu Ser Gly Thr Cys Leu Leu
            435                 440                 445

Ile Ala Asn Lys Arg Gln Ser Tyr Asp Ile Ser Ile Val Ala Gln Val
    450                 455                 460

Asp Gln Thr Gly Ser Lys Ser Ser Asn Leu Leu Asp Leu Lys Asn Pro
465                 470                 475                 480

Phe Phe Arg Tyr Thr Gly Thr Thr Pro Ser Pro Pro Gly Ser His
                485                 490                 495

Tyr Thr Ser Pro Ser Glu Asn Met Trp Asn Thr Gly Ser Thr Tyr Asn
            500                 505                 510

Leu Ser Ser Gly Met Ala Val Ala Gly Met Pro Thr Ala Tyr Asp Leu
            515                 520                 525

Ser Ser Val Ile Ala Ser Gly Ser Ser Val Gly His Asn Asn Leu Ile
530                 535                 540

Pro Leu Gly Ser Ser Gly Ala Gln Gly Ser Gly Gly Ser Thr Ser
545                 550                 555                 560

Ala His Tyr Ala Val Asn Ser Gln Phe Thr Met Gly Gly Pro Ala Ile
            565                 570                 575

Ser Met Ala Ser Pro Met Ser Ile Pro Thr Asn Thr Met His Tyr Gly
            580                 585                 590

Ser Glu Gly His His His His His His
        595                 600

<210> SEQ ID NO 17
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 17

His His His His His His
1               5
```

ARGININE METHYLTRANSFERASE INHIBITORS AND USES THEREOF

RELATED APPLICATIONS

The present application is a national stage filing under 35 U.S.C. §371 of International PCT application PCT/US2014/029710, filed Mar. 14, 2014 which claims priority under 35 U.S.C. §119(e) to U.S. provisional patent applications, U.S. Ser. No. 61/781,051, filed Mar. 14, 2013, and U.S. Ser. No. 61/876,034 filed Sep. 10, 2013, the entire contents of each of which is incorporated herein by reference.

BACKGROUND OF THE INVENTION

Epigenetic regulation of gene expression is an important biological determinant of protein production and cellular differentiation and plays a significant pathogenic role in a number of human diseases.

Epigenetic regulation involves heritable modification of genetic material without changing its nucleotide sequence. Typically, epigenetic regulation is mediated by selective and reversible modification (e.g., methylation) of DNA and proteins (e.g., histones) that control the conformational transition between transcriptionally active and inactive states of chromatin. These covalent modifications can be controlled by enzymes such as methyltransferases (e.g., arginine methyltransferases), many of which are associated with specific genetic alterations that can cause human disease.

Disease-associated chromatin-modifying enzymes (e.g., arginine methyltransferases) play a role in diseases such as proliferative disorders, autoimmune disorders, muscular disorders, vascular disorders, metabolic disorders, and neurological disorders. Thus, there is a need for the development of small molecules that are capable of inhibiting the activity of arginine methyltransferases.

DETAILED DESCRIPTION OF CERTAIN EMBODIMENTS

Arginine methyltransferases are attractive targets for modulation given their role in the regulation of diverse biological processes. It has now been found that compounds described herein, and pharmaceutically acceptable salts and compositions thereof, are effective as inhibitors of arginine methyltransferases. Such compounds have the general Formula (I):

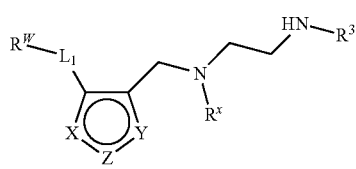

or a pharmaceutically acceptable salt thereof, wherein X, Y, Z, $L_1$, $R^W$, $R^3$, and $R^x$ are as defined herein.

In some embodiments, pharmaceutical compositions are provided which comprise a compound described herein (e.g., a compound of Formula (I)), or a pharmaceutically acceptable salt thereof, and optionally a pharmaceutically acceptable excipient.

In certain embodiments, compounds described herein inhibit activity of an arginine methyltransferase (RMT) (e.g., PRMT1, PRMT3, CARM1, PRMT6, and/or PRMT8). In certain embodiments, methods of inhibiting an arginine methyltransferase are provided which comprise contacting the arginine methyltransferase with an effective amount of a compound of Formula (I), or a pharmaceutically acceptable salt thereof. The RMT may be purified or crude, and may be present in a cell, tissue, or a subject. Thus, such methods encompass inhibition of RMT activity both in vitro and in vivo. In certain embodiments, the RMT is wild-type. In certain embodiments, the RMT is overexpressed. In certain embodiments, the RMT is a mutant. In certain embodiments, the RMT is in a cell. In some embodiments, the RMT is expressed at normal levels in a subject, but the subject would benefit from RMT inhibition (e.g., because the subject has one or more mutations in an RMT substrate that causes an increase in methylation of the substrate with normal levels of RMT). In some embodiments, the RMT is in a subject known or identified as having abnormal RMT activity (e.g., overexpression).

In certain embodiments, methods of modulating gene expression in a cell are provided which comprise contacting a cell with an effective amount of a compound of Formula (I), or a pharmaceutically acceptable salt thereof, or a pharmaceutical composition thereof. In certain embodiments, the cell is in culture in vitro. In certain embodiments, cell is in an animal, e.g., a human.

In certain embodiments, methods of modulating transcription in a cell are provided which comprise contacting a cell with an effective amount of a compound of Formula (I), or a pharmaceutically acceptable salt thereof, or a pharmaceutical composition thereof. In certain embodiments, the cell in culture in vitro. In certain embodiments, the cell is in an animal, e.g., a human.

In some embodiments, methods of treating an RMT-mediated disorder (e.g., a PRMT1-, PRMT3-, CARM1-, PRMT6-, or PRMT8-mediated disorder) are provided which comprise administering to a subject suffering from an RMT-mediated disorder an effective amount of a compound described herein (e.g., a compound of Formula (I)), or a pharmaceutically acceptable salt thereof, or a pharmaceutical composition thereof. In certain embodiments, the RMT-mediated disorder is a proliferative disorder. In certain embodiments, compounds described herein are useful for treating cancer. In certain embodiments, compounds described herein are useful for treating breast cancer, prostate cancer, lung cancer, colon cancer, bladder cancer, or leukemia. In certain embodiments, the RMT-mediated disorder is a muscular disorder. In certain embodiments, the RMT-mediated disorder is an autoimmune disorder. In certain embodiments, the RMT-mediated disorder is a neurological disorder. In certain embodiments, the RMT-mediated disorder is a vascular disorder. In certain embodiments, the RMT-mediated disorder is a metabolic disorder.

Compounds described herein are also useful for the study of arginine methyltransferases in biological and pathological phenomena, the study of intracellular signal transduction pathways mediated by arginine methyltransferases, and the comparative evaluation of new RMT inhibitors.

This application refers to various issued patent, published patent applications, journal articles, and other publications, all of which are incorporated herein by reference.

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The present disclosure additionally encompasses compounds described herein as individual isomers substantially free of other isomers, and alternatively, as mixtures of various isomers.

It is to be understood that the compounds of the present invention may be depicted as different tautomers. It should also be understood that when compounds have tautomeric forms, all tautomeric forms are intended to be included in the scope of the present invention, and the naming of any compound described herein does not exclude any tautomer form.

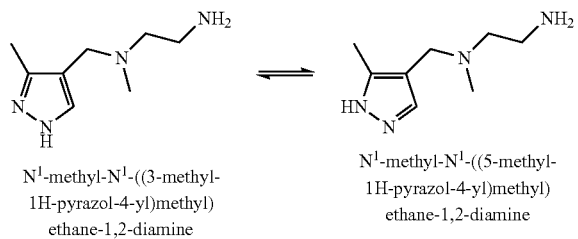

$N^1$-methyl-$N^1$-((3-methyl-1H-pyrazol-4-yl)methyl)ethane-1,2-diamine $N^1$-methyl-$N^1$-((5-methyl-1H-pyrazol-4-yl)methyl)ethane-1,2-diamine Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of a carbon by a $^{13}C$- or $^{14}C$-enriched carbon are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Radical" refers to a point of attachment on a particular group. Radical includes divalent radicals of a particular group.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. In certain embodiments, each instance of an alkyl group is independently optionally substituted, e.g., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

In some embodiments, an alkyl group is substituted with one or more halogens. "Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

"Alkenyl" refers to a radical of a straight-chain or branched hydrocarbon group having from 2 to 20 carbon atoms and one or more carbon-carbon double bonds (e.g., 1, 2, 3, or 4 double bonds), and optionally one or more triple bonds (e.g., 1, 2, 3, or 4 triple bonds) ("$C_{2-20}$ alkenyl"). In certain embodiments, alkenyl does not comprise triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. In certain embodiments, each instance of an alkenyl group is independently optionally substituted, e.g., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms and one or more carbon-carbon triple bonds (e.g., 1, 2, 3, or 4 triple bonds), and optionally one or more double bonds (e.g., 1, 2, 3, or 4 double bonds) ("$C_{2-20}$ alkynyl"). In certain embodiments, alkynyl does not comprise double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. In certain embodiments, each instance of an alkynyl group is independently optionally substituted, e.g., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Fused" or "ortho-fused" are used interchangeably herein, and refer to two rings that have two atoms and one bond in common, e.g.,

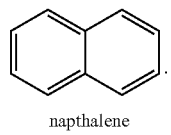

napthalene

"Bridged" refers to a ring system containing (1) a bridgehead atom or group of atoms which connect two or more non-adjacent positions of the same ring; or (2) a bridgehead atom or group of atoms which connect two or more positions of different rings of a ring system and does not thereby form an ortho-fused ring, e.g.,

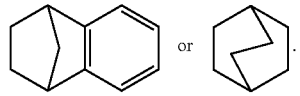

"Spiro" or "Spiro-fused" refers to a group of atoms which connect to the same atom of a carbocyclic or heterocyclic ring system (geminal attachment), thereby forming a ring, e.g.,

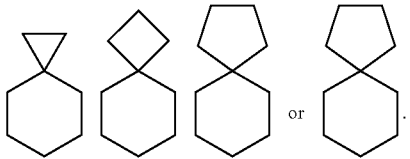

Spiro-fusion at a bridgehead atom is also contemplated.

"Carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In certain embodiments, a carbocyclyl group refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or is a fused, bridged or spiro-fused ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. In certain embodiments, each instance of a carbocyclyl group is independently optionally substituted, e.g., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). In certain embodiments, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In certain embodiments, heterocyclyl or heterocyclic refers to a radical of a 3-10 membered non-aromatic ring system having ring carbon atoms and 1-4 ring heteroatoms, wherein each heteroatom is independently selected from nitrogen, oxygen, and sulfur ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro-fused ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. In certain embodiments, each instance of heterocyclyl is independently optionally substituted, e.g., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms independently selected from nitrogen, oxygen, and sulfur. In some embodiments, the 5-6 membered heterocyclyl has 1-2 ring heteroatoms independently selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing three heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. In certain embodiments, each instance of an aryl group is independently optionally substituted, e.g., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-14 membered monocyclic or polycyclic (e.g., bicyclic or tricyclic) 4n+2 aromatic ring system (e.g., having 6 or 10 it electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In certain embodiments, heteroaryl refers to a radical of a 5-10 membered monocyclic or bicyclic 4n+2 aromatic ring system having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl).

In some embodiments, a heteroaryl group is a 5-14 membered aromatic ring system having ring carbon atoms and 1-4 ring heteroatoms provided in the aromatic ring system, wherein each heteroatom is independently selected from nitrogen, oxygen, and sulfur ("5-14 membered heteroaryl"). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms independently selected from nitrogen, oxygen, and sulfur. In some embodiments, the 5-6 membered heteroaryl has 1-2 ring heteroatoms independently selected from nitrogen, oxygen, and sulfur. In some embodiments, the 5-6 membered heteroaryl has 1 ring heteroatom selected from nitrogen, oxygen, and sulfur. In certain embodiments, each instance of a heteroaryl group is independently optionally substituted, e.g., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary 5,6-bicyclic heteroaryl groups include, without limitation, any one of the following formulae:

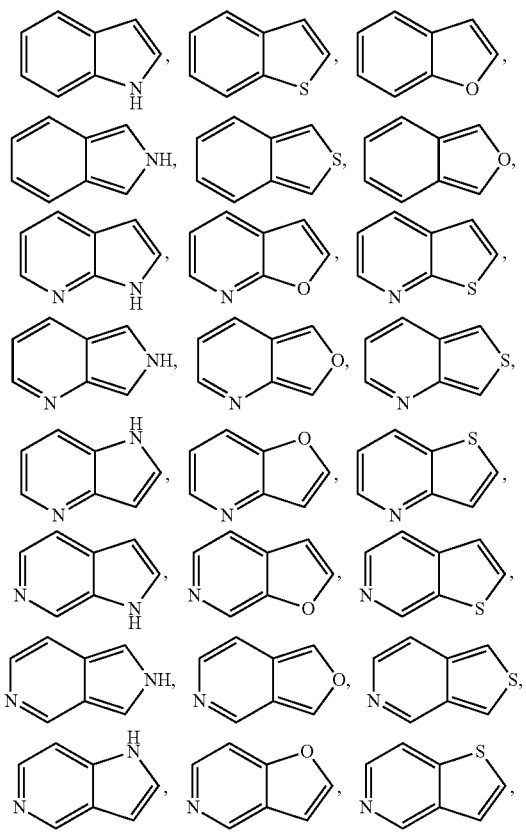

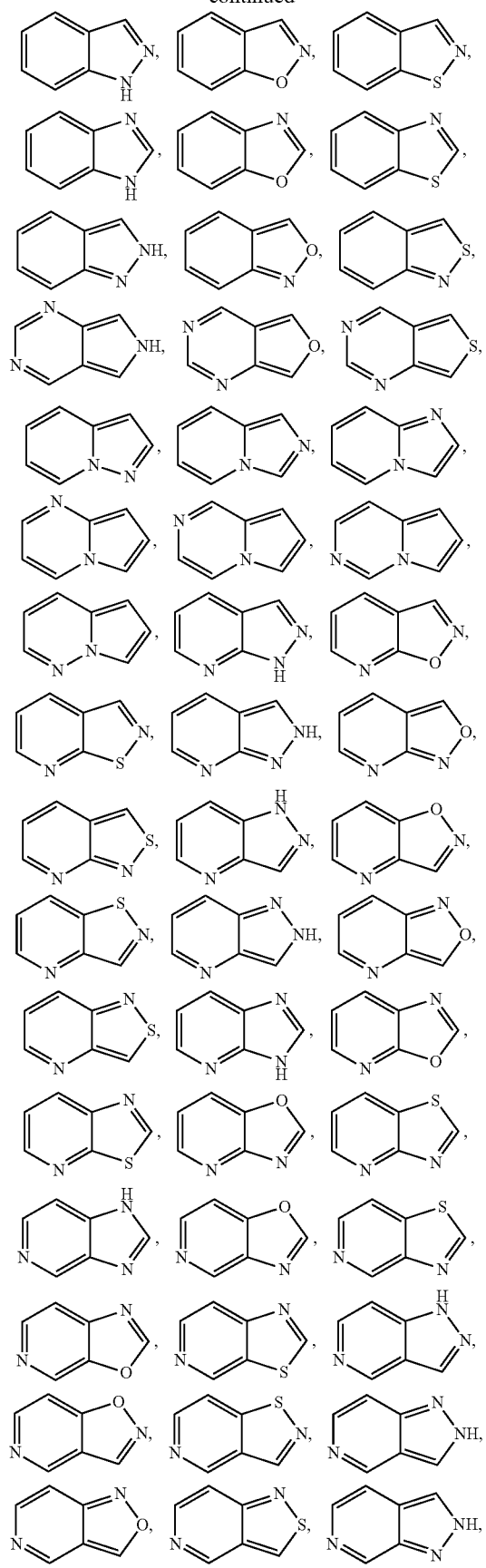
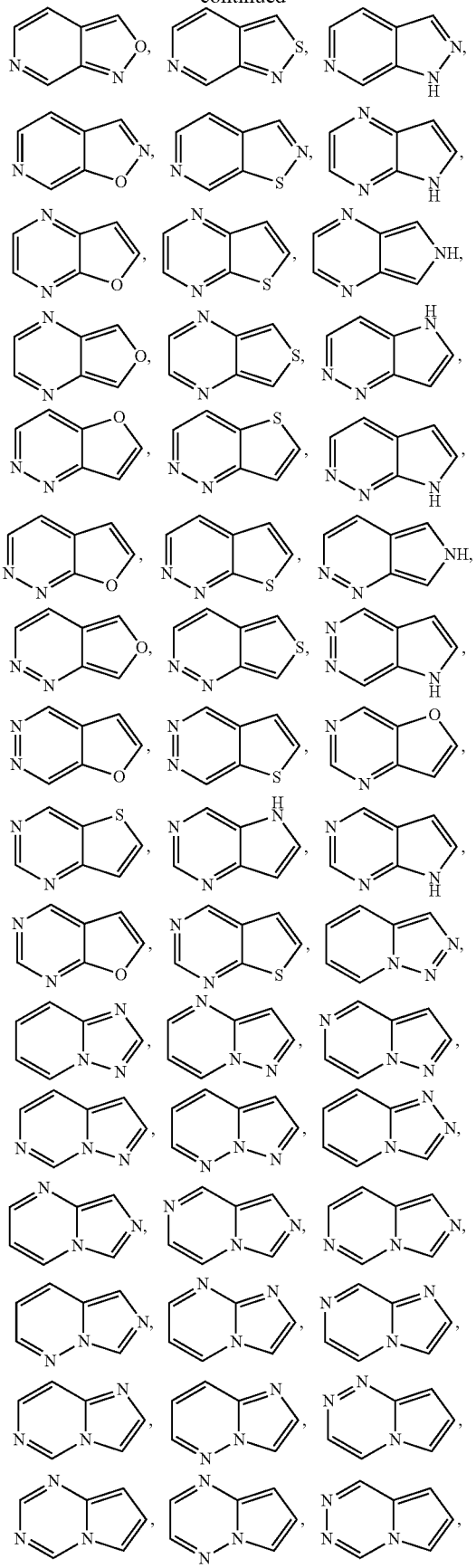

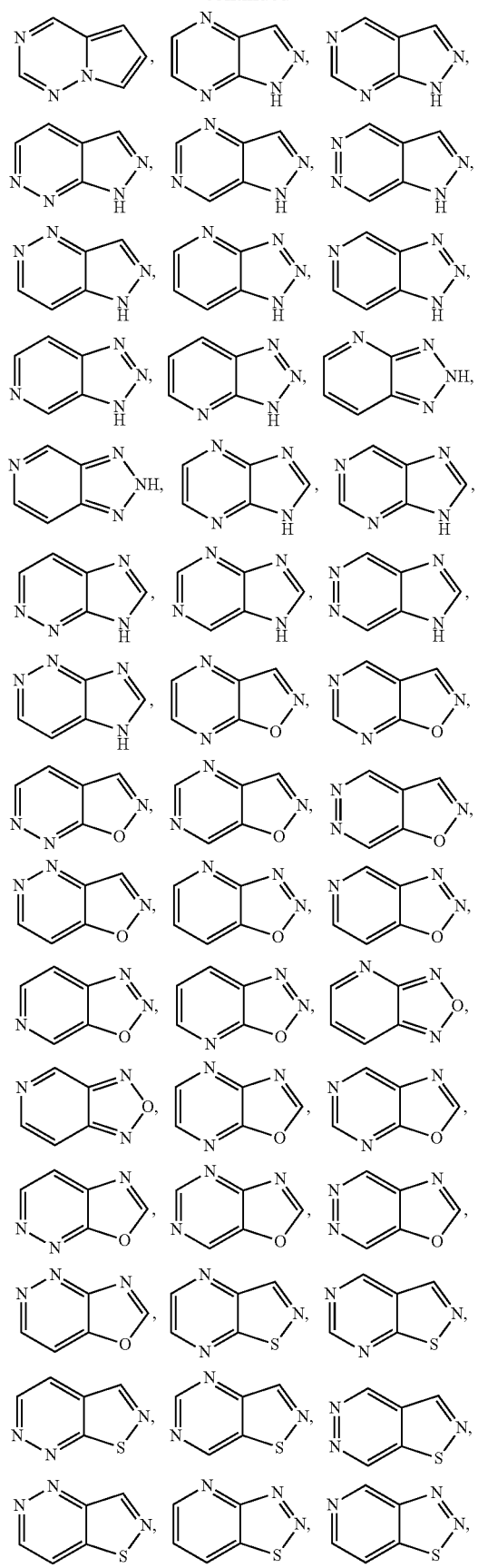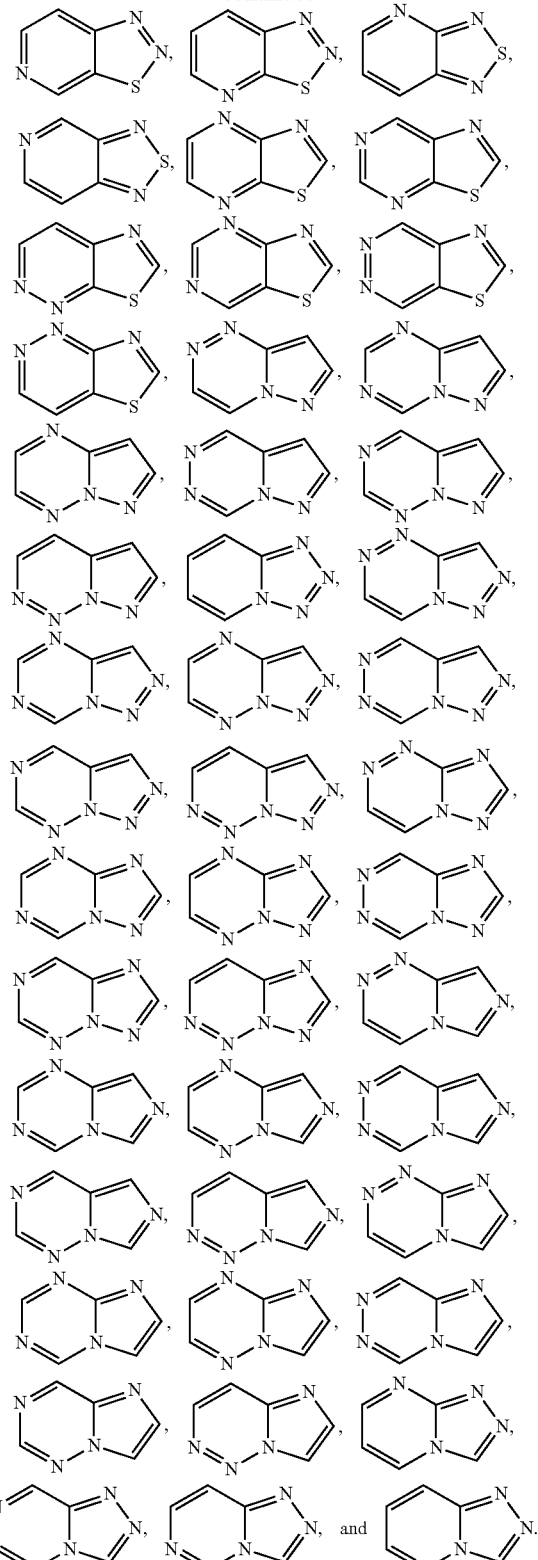
In any of the monocyclic or bicyclic heteroaryl groups, the point of attachment can be any carbon or nitrogen atom, as valency permits.
"Partially unsaturated" refers to a group that includes at least one double or triple bond. The term "partially unsaturated" is intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

In some embodiments, alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, including any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_1$ alkyl, —OSO$_2$C$_{1-6}$ alkyl, —SOC$_{1-6}$ alkyl, —Si(C$_{1-4}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$-alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Amide nitrogen protecting groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine, o-nitrobenzamide, and o-(benzoyloxymethyl)benzamide.

Carbamate nitrogen protecting groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Sulfonamide nitrogen protecting groups (e.g., —S(═O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), J3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(═O)SR$^{aa}$, —C(═O)R$^{aa}$, —CO$_2$R$^{aa}$, —C(═O)N(R$^{bb}$)$_2$, —C(═NR$^{bb}$)R$^{aa}$, —C(═NR$^{bb}$)OR$^{aa}$, —C(═NR$^{bb}$)N(R$^{bb}$)$_2$, —S(═O)R$^{aa}$, —SO$_2$R$^{aa}$, —Si(R$^{aa}$)$_3$, —P(R$^{cc}$)$_2$, —P(R$^{cc}$)$_3$, —P(═O)$_2$R$^{aa}$, —P(═O)(R$^{aa}$)$_2$, —P(═O)(OR$^{cc}$)$_2$, —P(═O)$_2$N(R$^{bb}$)$_2$, and —P(═O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), t-butyl carbonate (BOC), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate, alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

These and other exemplary substituents are described in more detail in the Detailed Description, Examples, and claims. The present disclosure is not intended to be limited in any manner by the above exemplary listing of substituents.

"Pharmaceutically acceptable salt" refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences* (1977) 66:1-19. Pharmaceutically acceptable salts of the compounds describe herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, quaternary salts.

A "subject" to which administration is contemplated includes, but is not limited to, humans (e.g., a male or female of any age group, e.g., a pediatric subject (e.g, infant, child, adolescent) or adult subject (e.g., young adult, middle-aged adult or senior adult)) and/or other non-human animals, for example, non-human mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), rodents (e.g., rats and/or mice), reptiles, amphibians, and fish. In certain embodiments, the non-human animal is a mammal. The non-human animal may be a male or female at any stage of development. A non-human animal may be a transgenic animal.

"Condition," "disease," and "disorder" are used interchangeably herein.

"Treat," "treating" and "treatment" encompasses an action that occurs while a subject is suffering from a condition which reduces the severity of the condition or retards or slows the progression of the condition ("therapeutic treatment"). "Treat," "treating" and "treatment" also encompasses an action that occurs before a subject begins to suffer from the condition and which inhibits or reduces the severity of the condition ("prophylactic treatment").

An "effective amount" of a compound refers to an amount sufficient to elicit the desired biological response, e.g., treat the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, the term "methyltransferase" represents transferase class enzymes that are able to transfer a methyl group from a donor molecule to an acceptor molecule, e.g., an amino acid residue of a protein or a nucleic base of a DNA molecule. Methytransferases typically use a reactive methyl group bound to sulfur in S-adenosyl methionine (SAM) as the methyl donor. In some embodiments, a methyltransferase described herein is a protein methyltransferase. In some embodiments, a methyltransferase described herein is a histone methyltransferase. Histone methyltransferases (HMT) are histone-modifying enzymes, (including histone-lysine N-methyltransferase and histone-arginine N-methyltransferase), that catalyze the transfer of one or more methyl groups to lysine and arginine residues of histone proteins. In certain embodiments, a methyltransferase described herein is a histone-arginine N-methyltransferase.

As generally described above, provided herein are compounds useful as arginine methyltransferase (RMT) inhibitors. In some embodiments, the present disclosure provides a compound of Formula (I):

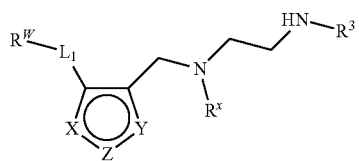

or a pharmaceutically acceptable salt thereof,
wherein:
X is N, Z is $NR^4$, and Y is $CR^5$; or
X is $NR^4$, Z is N, and Y is $CR^5$; or
X is $CR^5$, Z is $NR^4$, and Y is N; or
X is $CR^5$, Z is N, and Y is $NR^4$;
$R^x$ is optionally substituted $C_{1-4}$ alkyl or optionally substituted $C_{3-4}$ cycloalkyl;
$L_1$ is a bond, —O—, —N($R^B$)—, —S—, —C(O)—, —C(O)O—, —C(O)S—, —C(O)N($R^B$)—, —C(O)N($R^B$)N($R^B$)—, —OC(O)—, —OC(O)N($R^B$)—, —$NR^B$C(O)—, —$NR^B$C(O)N($R^B$)—, —$NR^B$C(O)N($R^B$)N($R^B$)—, —$NR^B$C(O)O—, —SC(O)—, —C(=$NR^B$)—, —C(=$NNR^B$)—, —C(=$NOR^A$)—, —C(=$NR^B$)N($R^B$)—, —$NR^B$C(=$NR^B$)—, —C(S)—, —C(S)N($R^B$)—, —$NR^B$C(S)—, —S(O)—, —OS(O)$_2$—, —S(O)$_2$O—, —SO$_2$—, —N($R^B$)SO$_2$—, —SO$_2$N($R^B$)—, or an optionally substituted $C_{1-6}$ saturated or unsaturated hydrocarbon chain, wherein one or more methylene units of the hydrocarbon chain is optionally and independently replaced with —O—, —N($R^B$)—, —S—, —C(O)—, —C(O)O—, —C(O)S—, —C(O)N ($R^B$)—, —C(O)N($R^B$)N($R^B$)—, —OC(O)—, —OC(O)N ($R^B$)—, —$NR^B$C(O)—, —$NR^B$C(O)N($R^B$)—, —$NR^B$C(O) N($R^B$)N($R^B$)—, —$NR^B$C(O)O—, —SC(O)—, —C(=$NR^B$)—, —C(=$NNR^B$)—, —C(=$NOR^A$)—, —C(=$NR^B$)N($R^B$)—, —$NR^B$C(=$NR^B$)—, —C(S)—, —C(S)N($R^B$)—, —$NR^B$C(S)—, —S(O)—, —OS(O)$_2$—, —S(O)$_2$O—, —SO$_2$—, —N($R^B$)SO$_2$—, or —SO$_2$N($R^B$)—;
each $R^A$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom;
each $R^B$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group, or an $R^B$ and $R^W$ on the same nitrogen atom may be taken together with the intervening nitrogen to form an optionally substituted heterocyclic ring;
$R^W$ is hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, provided that when $L_1$ is a bond, $R^W$ is not optionally substituted aryl or optionally substituted heteroaryl;
$R^3$ is hydrogen, $C_{1-4}$ alkyl, or $C_{3-4}$ cycloalkyl;
$R^4$ is hydrogen, optionally substituted $C_{1-6}$ alkyl, optionally substituted $C_{2-6}$ alkenyl, optionally substituted $C_{2-6}$ alkynyl, optionally substituted carbocyclyl, optionally substituted heterocyclyl; or optionally substituted $C_{1-4}$ alkyl-Cy;
Cy is optionally substituted $C_{3-7}$ cycloalkyl, optionally substituted 4- to 7-membered heterocyclyl, optionally substituted aryl, or optionally substituted heteroaryl; and
$R^5$ is hydrogen, halo, —CN, optionally substituted $C_{1-4}$ alkyl, or optionally substituted $C_{3-4}$ cycloalkyl.

In certain embodiments, $R^4$ is hydrogen, optionally substituted $C_{1-6}$ alkyl, optionally substituted $C_{2-6}$ alkenyl, optionally substituted $C_{2-6}$ alkynyl, optionally substituted $C_{3-7}$ cycloalkyl, optionally substituted 4- to 7-membered heterocyclyl; or optionally substituted $C_{1-4}$ alkyl-Cy.

In certain embodiments, when $L_1$ is a bond, then $R^W$ is not hydrogen. In certain embodiments, when $L_1$ is a bond, $R^W$ is not hydrogen, optionally substituted aryl, or optionally substituted heteroaryl.

However, in certain embodiments, $L_1$ is a bond and $R^W$ is hydrogen, halogen, or optionally substituted $C_{1-6}$alkyl. In certain embodiments, $L_1$ is a bond, $R^W$ is hydrogen, halogen, or optionally substituted $C_{1-6}$alkyl, X is $CR^5$, Z is N, and Y is $NR^4$, wherein $R^4$ is optionally substituted carbocyclyl or optionally substituted heterocyclyl, and in such instances $R^4$ is also referred to as Ring A.

As generally described herein, $R^W$ may also be referred to as Ring A, wherein Ring A is optionally substituted carbocyclyl, optionally substituted heterocyclyl, optionally substituted aryl, or optionally substituted heteroaryl, provided that when $L_1$ is a bond, $R^W$ is not optionally substituted aryl or optionally substituted heteroaryl. $R^W$ and Ring A are thus used interchangeably herein when $R^W$ is describes a cyclic moiety. Furthermore, as described above, in certain embodiments, Ring A and $R^4$ are used interchangeably herein when $R^4$ encompass an optionally substituted carbocyclyl or optionally substituted heterocyclyl group.

In certain embodiments, a provided compound is of Formula (II):

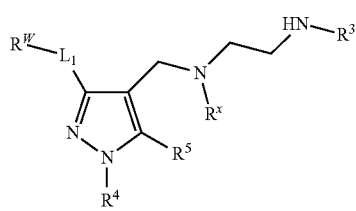

or a pharmaceutically acceptable salt thereof, wherein $R^W$, $L_1$, $R^3$, $R^4$, $R^5$, and $R^x$ are as described herein. In certain embodiments, $R^x$ is optionally substituted $C_{1-4}$ alkyl (e.g., methyl). In certain embodiments, $R^3$ is hydrogen or $C_{1-4}$ alkyl (e.g., methyl). In certain embodiments, $R^4$ is hydrogen or optionally substituted $C_{1-6}$ alkyl (e.g., methyl). In certain embodiments, $R^5$ is hydrogen. In certain embodiments, $L_1$ is a bond and $R^W$ is optionally substituted $C_{3-6}$ carbocyclyl or optionally substituted 5-6 membered heterocyclyl. In certain embodiments, $L_1$ is a bond and $R^W$ is an optionally substituted bicyclic carbocyclyl (e.g., an optionally substituted spiro-fused bicyclic carbocyclyl) or optionally substituted bicyclic heterocyclyl (e.g., optionally substituted spiro-fused bicyclic heterocyclyl). In certain embodiments, $L_1$ is an optionally substituted $C_{2-6}$alkylene, optionally substituted $C_{2-6}$alkenylene, or optionally substituted $C_{2-6}$alkynylene chain, and $R^W$ is optionally substituted aryl or optionally substituted heteroaryl.

In certain embodiments, a provided compound is of Formula (III):

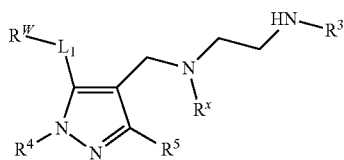

III or a pharmaceutically acceptable salt thereof, wherein $R^W$, $L_1$, $R^3$, $R^4$, $R^5$, and $R^x$ are as described herein. In certain embodiments, $R^x$ is optionally substituted $C_{1-4}$ alkyl (e.g., methyl). In certain embodiments, $R^3$ is hydrogen or $C_{1-4}$ alkyl (e.g., methyl). In certain embodiments, $R^4$ is hydrogen or optionally substituted $C_{1-6}$ alkyl (e.g., methyl). In certain embodiments, $R^5$ is hydrogen. In certain embodiments, $L_1$ is a bond and $R^W$ is optionally substituted $C_{3-6}$ carbocyclyl or optionally substituted 5-6 membered heterocyclyl. In certain embodiments, $L_1$ is a bond and $R^W$ is an optionally substituted bicyclic carbocyclyl (e.g., an optionally substituted spiro-fused bicyclic carbocyclyl) or optionally substituted bicyclic heterocyclyl (e.g., optionally substituted spiro-fused bicyclic heterocyclyl). In certain embodiments, $L_1$ is an optionally substituted $C_{2-6}$alkylene, optionally substituted $C_{2-6}$alkenylene, or optionally substituted $C_{2-6}$alkynylene chain, and $R^W$ is optionally substituted aryl or optionally substituted heteroaryl.

In certain embodiments, a provided compound is of Formula (IV):

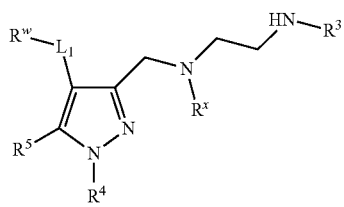

IV or a pharmaceutically acceptable salt thereof, wherein $R^W$, $L_1$, $R^3$, $R^4$, $R^5$, and $R^x$ are as described herein. In certain embodiments, $R^x$ is optionally substituted $C_{1-4}$ alkyl (e.g., methyl). In certain embodiments, $R^3$ is hydrogen or $C_{1-4}$ alkyl (e.g., methyl). In certain embodiments, $R^4$ is hydrogen or optionally substituted $C_{1-6}$ alkyl (e.g., methyl). In certain embodiments, $R^5$ is hydrogen. In certain embodiments, $L_1$ is a bond and $R^W$ is optionally substituted $C_{3-6}$ carbocyclyl or optionally substituted 5-6 membered heterocyclyl. In certain embodiments, $L_1$ is a bond and $R^W$ is an optionally substituted bicyclic carbocyclyl (e.g., an optionally substituted spiro-fused bicyclic carbocyclyl) or optionally substituted bicyclic heterocyclyl (e.g., optionally substituted spiro-fused bicyclic heterocyclyl). In certain embodiments, $L_1$ is an optionally substituted $C_{2-6}$alkylene, optionally substituted $C_{2-6}$alkenylene, or optionally substituted $C_{2-6}$alkynylene chain, and $R^W$ is optionally substituted aryl or optionally substituted heteroaryl.

In certain embodiments, a provided compound is of Formula (V):

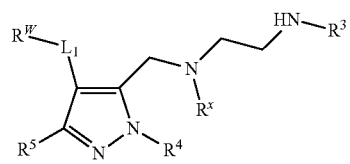

V or a pharmaceutically acceptable salt thereof, wherein $R^W$, $L_1$, $R^3$, $R^4$, $R^5$, and $R^x$ are as described herein. In certain embodiments, $R^x$ is optionally substituted $C_{1-4}$ alkyl (e.g., methyl). In certain embodiments, $R^3$ is hydrogen or $C_{1-4}$ alkyl (e.g., methyl). In certain embodiments, $R^4$ is hydrogen or optionally substituted $C_{1-6}$ alkyl (e.g., methyl). In certain embodiments, $R^5$ is hydrogen. In certain embodiments, $L_1$ is a bond and $R^W$ is optionally substituted $C_{3-6}$ carbocyclyl or optionally substituted 5-6 membered heterocyclyl. In certain embodiments, $L_1$ is a bond and $R^W$ is an optionally substituted bicyclic carbocyclyl (e.g., an optionally substituted spiro-fused bicyclic carbocyclyl) or optionally substituted bicyclic heterocyclyl (e.g., optionally substituted spiro-fused bicyclic heterocyclyl). In certain embodiments, $L_1$ is an optionally substituted $C_{2-6}$alkylene, optionally substituted $C_{2-6}$alkenylene, or optionally substituted $C_{2-6}$alkynylene chain, and $R^W$ is optionally substituted aryl or optionally substituted heteroaryl. In certain embodiments, $L_1$ is a bond, $R^W$ is hydrogen, and $R^4$ is an optionally substituted carbocyclyl (e.g., an optionally substituted spiro-fused bicyclic carbocyclyl) or optionally substituted heterocyclyl (e.g., optionally substituted spiro-fused bicyclic heterocyclyl).

In certain embodiments, when $R^4$ is Ring A, wherein Ring A is an optionally substituted carbocyclyl or optionally substituted heterocyclyl, a provided compound is of Formula (XII-a5):

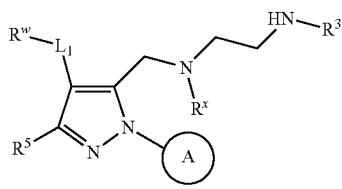

XII-a5 or a pharmaceutically acceptable salt thereof, wherein $R^W$, $L_1$, $R^3$, $R^5$, $R^x$, and Ring A are as described herein. In certain embodiments, $R^x$ is optionally substituted $C_{1-4}$ alkyl (e.g., methyl). In certain embodiments, $R^3$ is hydrogen or $C_{1-4}$ alkyl (e.g., methyl). In certain embodiments, $R^5$ is hydrogen. In certain embodiments, $L_1$ is a bond, $R^W$ is hydrogen, halogen, or optionally substituted $C_{1-4}$alkyl. In certain embodiments, L₁ is a bond and $R^W$ is hydrogen. In certain embodiments, L₁ is a bond, $R^W$ is hydrogen, and $R^5$ is hydrogen. In certain embodiments, L₁ is a bond and $R^W$ is halogen, e.g., fluoro, chloro, bromo, or iodo. In certain embodiments, L₁ is a bond and $R^W$ is optionally substituted $C_{1-6}$alkyl, e.g., unsubstituted $C_{1-4}$alkyl, e.g., methyl, ethyl, propyl, butyl, isopropyl, isobutyl, or isoamyl. In certain embodiments, Ring A is an optionally substituted bicyclic carbocyclyl (e.g., an optionally substituted spiro-fused bicyclic carbocyclyl) or optionally substituted bicyclic heterocyclyl (e.g., optionally substituted spiro-fused bicyclic heterocyclyl).

In certain embodiments, a provided compound is of Formula (VI):

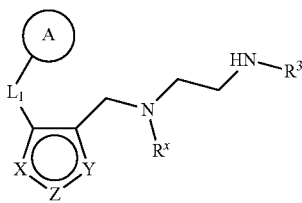

VI or a pharmaceutically acceptable salt thereof, wherein L₁, Ring A, $R^3$, $R^4$, $R^5$, and $R^x$ are as described herein. In certain embodiments, $R^x$ is optionally substituted $C_{1-4}$ alkyl (e.g., methyl). In certain embodiments, $R^3$ is hydrogen or $C_{1-4}$ alkyl (e.g., methyl). In certain embodiments, $R^4$ is hydrogen or optionally substituted $C_{1-6}$ alkyl (e.g., methyl). In certain embodiments, $R^5$ is hydrogen. In certain embodiments, L₁ is a bond and $R^W$ is optionally substituted $C_{3-6}$ carbocyclyl or optionally substituted 5-6 membered heterocyclyl. In certain embodiments, L₁ is a bond and $R^W$ is an optionally substituted bicyclic carbocyclyl (e.g., an optionally substituted spiro-fused bicyclic carbocyclyl) or optionally substituted bicyclic heterocyclyl (e.g., optionally substituted spiro-fused bicyclic heterocyclyl). In certain embodiments, L₁ is an optionally substituted $C_{2-6}$alkylene, optionally substituted $C_{2-6}$alkenylene, or optionally substituted $C_{2-6}$alkynylene chain, and Ring A (a subset of $R^W$) is optionally substituted aryl or optionally substituted heteroaryl.

In certain embodiments, a provided compound is of Formula (VI-a):

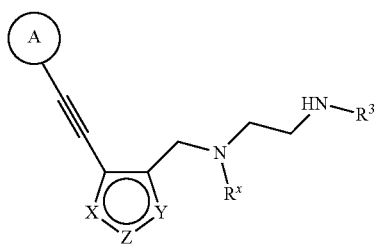

VI-a or a pharmaceutically acceptable salt thereof, wherein Ring A, $R^3$, $R^4$, $R^5$, and $R^x$ are as described herein. In certain embodiments, $R^x$ is optionally substituted $C_{1-4}$ alkyl (e.g., methyl). In certain embodiments, $R^3$ is hydrogen or $C_{1-4}$ alkyl (e.g., methyl). In certain embodiments, X is N, Z is NR⁴, and Y is CR⁵. In certain embodiments, X is NR⁴, Z is N, and Y is CR⁵. In certain embodiments, X is CR⁵, Z is NR⁴, and Y is N. In certain embodiments, X is CR⁵, Z is N, and Y is NR⁴. In certain embodiments, $R^4$ is hydrogen or optionally substituted $C_{1-6}$ alkyl (e.g., methyl). In certain embodiments, $R^5$ is hydrogen. In certain embodiments, Ring A (a subset of $R^W$) is optionally substituted aryl or optionally substituted heteroaryl. In certain embodiments, Ring A (a subset of $R^W$) is optionally substituted $C_{3-6}$ carbocyclyl or optionally substituted 5-6 membered heterocyclyl. In certain embodiments, Ring A (a subset of $R^W$) is an optionally substituted bicyclic carbocyclyl (e.g., an optionally substituted spiro-fused bicyclic carbocyclyl) or optionally substituted bicyclic heterocyclyl (e.g., optionally substituted spiro-fused bicyclic heterocyclyl).

In certain embodiments, a provided compound is of Formula (VI-b):

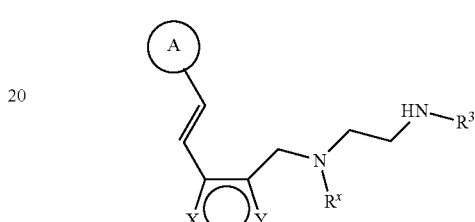

VI-b or a pharmaceutically acceptable salt thereof, wherein Ring A, $R^3$, $R^4$, $R^5$, and $R^x$ are as described herein. In certain embodiments, $R^x$ is optionally substituted $C_{1-4}$ alkyl (e.g., methyl). In certain embodiments, $R^3$ is hydrogen or $C_{1-4}$ alkyl (e.g., methyl). In certain embodiments, X is N, Z is NR⁴, and Y is CR⁵. In certain embodiments, X is NR⁴, Z is N, and Y is CR⁵. In certain embodiments, X is CR⁵, Z is NR⁴, and Y is N. In certain embodiments, X is CR⁵, Z is N, and Y is NR⁴. In certain embodiments, $R^4$ is hydrogen or optionally substituted $C_{1-6}$ alkyl (e.g., methyl). In certain embodiments, $R^5$ is hydrogen. In certain embodiments, Ring A (a subset of $R^W$) is optionally substituted aryl or optionally substituted heteroaryl. In certain embodiments, Ring A (a subset of $R^W$) is optionally substituted $C_{3-6}$ carbocyclyl or optionally substituted 5-6 membered heterocyclyl. In certain embodiments, Ring A (a subset of $R^W$) is an optionally substituted bicyclic carbocyclyl (e.g., an optionally substituted spiro-fused bicyclic carbocyclyl) or optionally substituted bicyclic heterocyclyl (e.g., optionally substituted spiro-fused bicyclic heterocyclyl).

In certain embodiments, a provided compound is of Formula (VI-c) or (VI-c'):

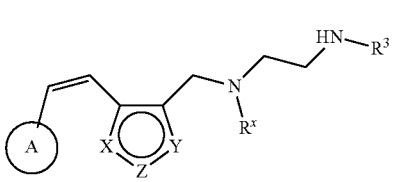

VI-c

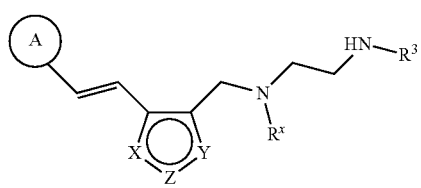

VI-c' or a pharmaceutically acceptable salt thereof, wherein Ring A, $R^3$, $R^4$, $R^5$, and $R^x$ are as described herein. In certain embodiments, $R^x$ is optionally substituted $C_{1-4}$ alkyl (e.g., methyl). In certain embodiments, $R^3$ is hydrogen or $C_{1-4}$ alkyl (e.g., methyl). In certain embodiments, X is N, Z is $NR^4$, and Y is $CR^5$. In certain embodiments, X is $NR^4$, Z is N, and Y is $CR^5$. In certain embodiments, X is $CR^5$, Z is $NR^4$, and Y is N. In certain embodiments, X is $CR^5$, Z is N, and Y is $NR^4$. In certain embodiments, $R^4$ is hydrogen or optionally substituted $C_{1-6}$ alkyl (e.g., methyl). In certain embodiments, $R^5$ is hydrogen. In certain embodiments, Ring A (a subset of $R^W$) is optionally substituted aryl or optionally substituted heteroaryl. In certain embodiments, Ring A (a subset of $R^W$) is optionally substituted $C_{3-6}$ carbocyclyl or optionally substituted 5-6 membered heterocyclyl. In certain embodiments, Ring A (a subset of $R^W$) is an optionally substituted bicyclic carbocyclyl (e.g., an optionally substituted spiro-fused bicyclic carbocyclyl) or optionally substituted bicyclic heterocyclyl (e.g., optionally substituted spiro-fused bicyclic heterocyclyl).

In certain embodiments, a provided compound is of Formula (VI-d):

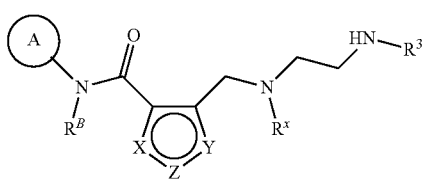

VI-d or a pharmaceutically acceptable salt thereof, wherein Ring A, $R^B$, $R^3$, $R^4$, $R^5$, and $R^x$ are as described herein. In certain embodiments, $R^x$ is optionally substituted $C_{1-4}$ alkyl (e.g., methyl). In certain embodiments, $R^3$ is hydrogen or $C_{1-4}$ alkyl (e.g., methyl). In certain embodiments, X is N, Z is $NR^4$, and Y is $CR^5$. In certain embodiments, X is $NR^4$, Z is N, and Y is $CR^5$. In certain embodiments, X is $CR^5$, Z is $NR^4$, and Y is N. In certain embodiments, X is $CR^5$, Z is N, and Y is $NR^4$. In certain embodiments, $R^4$ is hydrogen or optionally substituted $C_{1-6}$ alkyl (e.g., methyl). In certain embodiments, $R^5$ is hydrogen. In certain embodiments, Ring A (a subset of $R^W$) is optionally substituted aryl or optionally substituted heteroaryl. In certain embodiments, Ring A (a subset of $R^W$) is optionally substituted $C_{3-6}$ carbocyclyl or optionally substituted 5-6 membered heterocyclyl. In certain embodiments, Ring A (a subset of $R^W$) is an optionally substituted bicyclic carbocyclyl (e.g., an optionally substituted spiro-fused bicyclic carbocyclyl) or optionally substituted bicyclic heterocyclyl (e.g., optionally substituted spiro-fused bicyclic heterocyclyl).

In certain embodiments, a provided compound is of Formula (VI-e):

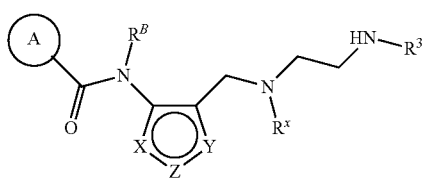

VI-e or a pharmaceutically acceptable salt thereof, wherein Ring A, $R^B$, $R^3$, $R^4$, $R^5$, and $R^x$ are as described herein. In certain embodiments, $R^x$ is optionally substituted $C_{1-4}$ alkyl (e.g., methyl). In certain embodiments, $R^3$ is hydrogen or $C_{1-4}$ alkyl (e.g., methyl). In certain embodiments, X is N, Z is $NR^4$, and Y is $CR^5$. In certain embodiments, X is $NR^4$, Z is N, and Y is $CR^5$. In certain embodiments, X is $CR^5$, Z is $NR^4$, and Y is N. In certain embodiments, X is $CR^5$, Z is N, and Y is $NR^4$. In certain embodiments, $R^4$ is hydrogen or optionally substituted $C_{1-6}$ alkyl (e.g., methyl). In certain embodiments, $R^5$ is hydrogen. In certain embodiments, Ring A (a subset of $R^W$) is optionally substituted aryl or optionally substituted heteroaryl. In certain embodiments, Ring A (a subset of $R^W$) is optionally substituted $C_{3-6}$ carbocyclyl or optionally substituted 5-6 membered heterocyclyl. In certain embodiments, Ring A (a subset of $R^W$) is an optionally substituted bicyclic carbocyclyl (e.g., an optionally substituted spiro-fused bicyclic carbocyclyl) or optionally substituted bicyclic heterocyclyl (e.g., optionally substituted spiro-fused bicyclic heterocyclyl).

In certain embodiments, a provided compound is of Formula (VI-f):

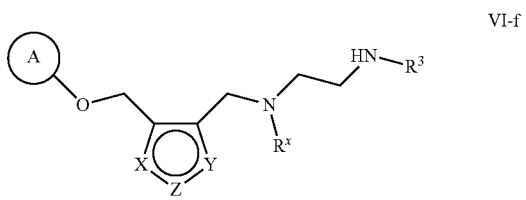

VI-f or a pharmaceutically acceptable salt thereof, wherein Ring A, $R^3$, $R^4$, $R^5$, and $R^x$ are as described herein. In certain embodiments, $R^x$ is optionally substituted $C_{1-4}$ alkyl (e.g., methyl). In certain embodiments, $R^3$ is hydrogen or $C_{1-4}$ alkyl (e.g., methyl). In certain embodiments, X is N, Z is $NR^4$, and Y is $CR^5$. In certain embodiments, X is $NR^4$, Z is N, and Y is $CR^5$. In certain embodiments, X is $CR^5$, Z is $NR^4$, and Y is N. In certain embodiments, X is $CR^5$, Z is N, and Y is $NR^4$. In certain embodiments, $R^4$ is hydrogen or optionally substituted $C_{1-6}$ alkyl (e.g., methyl). In certain embodiments, $R^5$ is hydrogen. In certain embodiments, Ring A (a subset of $R^W$) is optionally substituted aryl or optionally substituted heteroaryl. In certain embodiments, Ring A (a subset of $R^W$) is optionally substituted $C_{3-6}$ carbocyclyl or optionally substituted 5-6 membered heterocyclyl. In certain embodiments, Ring A (a subset of $R^W$) is an optionally substituted bicyclic carbocyclyl (e.g., an optionally substituted spiro-fused bicyclic carbocyclyl) or optionally substituted bicyclic heterocyclyl (e.g., optionally substituted spiro-fused bicyclic heterocyclyl).

In certain embodiments, a provided compound is of Formula (VI-g):

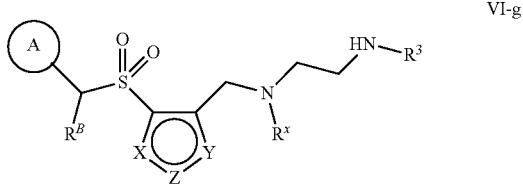

VI-g or a pharmaceutically acceptable salt thereof, wherein Ring A, $R^B$, $R^3$, $R^4$, $R^5$, and $R^x$ are as described herein. In certain embodiments, $R^x$ is optionally substituted $C_{1-4}$ alkyl (e.g., methyl). In certain embodiments, $R^3$ is hydrogen or $C_{1-4}$ alkyl (e.g., methyl). In certain embodiments, X is N, Z is NR⁴, and Y is CR⁵. In certain embodiments, X is NR⁴, Z is N, and Y is CR⁵. In certain embodiments, X is CR⁵, Z is NR⁴, and Y is N. In certain embodiments, X is CR⁵, Z is N, and Y is NR⁴. In certain embodiments, R⁴ is hydrogen or optionally substituted $C_{1-6}$ alkyl (e.g., methyl). In certain embodiments, R⁵ is hydrogen. In certain embodiments, Ring A (a subset of $R^W$) is optionally substituted aryl or optionally substituted heteroaryl. In certain embodiments, Ring A (a subset of $R^W$) is optionally substituted $C_{3-6}$ carbocyclyl or optionally substituted 5-6 membered heterocyclyl. In certain embodiments, Ring A (a subset of $R^W$) is an optionally substituted bicyclic carbocyclyl (e.g., an optionally substituted spiro-fused bicyclic carbocyclyl) or optionally substituted bicyclic heterocyclyl (e.g., optionally substituted spiro-fused bicyclic heterocyclyl).

In certain embodiments, a provided compound is of Formula (VI-h):

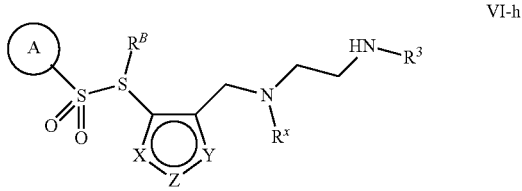

VI-h or a pharmaceutically acceptable salt thereof, wherein Ring A, $R^B$, R³, R⁴, R⁵, and $R^x$ are as described herein. In certain embodiments, $R^x$ is optionally substituted $C_{1-4}$ alkyl (e.g., methyl). In certain embodiments, R³ is hydrogen or $C_{1-4}$ alkyl (e.g., methyl). In certain embodiments, X is N, Z is NR⁴, and Y is CR⁵. In certain embodiments, X is NR⁴, Z is N, and Y is CR⁵. In certain embodiments, X is CR⁵, Z is NR⁴, and Y is N. In certain embodiments, X is CR⁵, Z is N, and Y is NR⁴. In certain embodiments, R⁴ is hydrogen or optionally substituted $C_{1-6}$ alkyl (e.g., methyl). In certain embodiments, R⁵ is hydrogen. In certain embodiments, Ring A (a subset of $R^W$) is optionally substituted aryl or optionally substituted heteroaryl. In certain embodiments, Ring A (a subset of $R^W$) is optionally substituted $C_{3-6}$ carbocyclyl or optionally substituted 5-6 membered heterocyclyl. In certain embodiments, Ring A (a subset of $R^W$) is an optionally substituted bicyclic carbocyclyl (e.g., an optionally substituted spiro-fused bicyclic carbocyclyl) or optionally substituted bicyclic heterocyclyl (e.g., optionally substituted spiro-fused bicyclic heterocyclyl).

In certain embodiments, a provided compound is of Formula (VI-i):

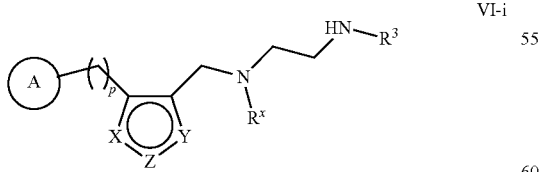

VI-i or a pharmaceutically acceptable salt thereof, wherein Ring A, R³, R⁴, R⁵, and $R^x$ are as described herein, and p is 1, 2, 3, 4, 5, or 6. In certain embodiments, $R^x$ is optionally substituted $C_{1-4}$ alkyl (e.g., methyl). In certain embodiments, R³ is hydrogen or $C_{1-4}$ alkyl (e.g., methyl). In certain embodiments, X is N, Z is NR⁴, and Y is CR⁵. In certain embodiments, X is NR⁴, Z is N, and Y is CR⁵. In certain embodiments, X is CR⁵, Z is NR⁴, and Y is N. In certain embodiments, X is CR⁵, Z is N, and Y is NR⁴. In certain embodiments, R⁴ is hydrogen or optionally substituted $C_{1-6}$ alkyl (e.g., methyl). In certain embodiments, R⁵ is hydrogen. In certain embodiments, Ring A (a subset of $R^W$) is optionally substituted aryl or optionally substituted heteroaryl. In certain embodiments, Ring A (a subset of $R^W$) is optionally substituted $C_{3-6}$ carbocyclyl or optionally substituted 5-6 membered heterocyclyl. In certain embodiments, Ring A (a subset of $R^W$) is an optionally substituted bicyclic carbocyclyl (e.g., an optionally substituted spiro-fused bicyclic carbocyclyl) or optionally substituted bicyclic heterocyclyl (e.g., optionally substituted spiro-fused bicyclic heterocyclyl). In certain embodiments, p is 1, 2, or 3.

In certain embodiments, a provided compound is of Formula (VI-j):

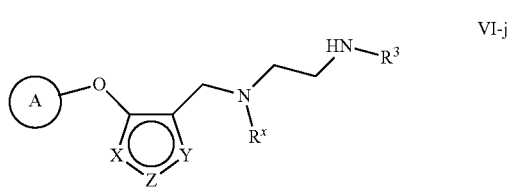

VI-j or a pharmaceutically acceptable salt thereof, wherein Ring A, R³, R⁴, R⁵, and $R^x$ are as described herein. In certain embodiments, $R^x$ is optionally substituted $C_{1-4}$ alkyl (e.g., methyl). In certain embodiments, R³ is hydrogen or $C_{1-4}$ alkyl (e.g., methyl). In certain embodiments, X is N, Z is NR⁴, and Y is CR⁵. In certain embodiments, X is NR⁴, Z is N, and Y is CR⁵. In certain embodiments, X is CR⁵, Z is NR⁴, and Y is N. In certain embodiments, X is CR⁵, Z is N, and Y is NR⁴. In certain embodiments, R⁴ is hydrogen or optionally substituted $C_{1-6}$ alkyl (e.g., methyl). In certain embodiments, R⁵ is hydrogen. In certain embodiments, Ring A (a subset of $R^W$) is optionally substituted aryl or optionally substituted heteroaryl. In certain embodiments, Ring A (a subset of $R^W$) is optionally substituted $C_{3-6}$ carbocyclyl or optionally substituted 5-6 membered heterocyclyl In certain embodiments, Ring A (a subset of $R^W$) is an optionally substituted bicyclic carbocyclyl (e.g., an optionally substituted spiro-fused bicyclic carbocyclyl) or optionally substituted bicyclic heterocyclyl (e.g., optionally substituted spiro-fused bicyclic heterocyclyl).

In certain embodiments, a provided compound is of Formula (VI-k):

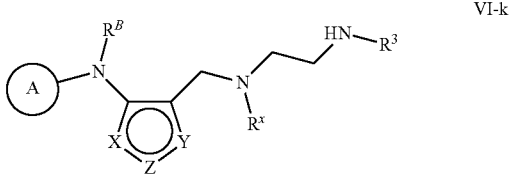

VI-k or a pharmaceutically acceptable salt thereof, wherein Ring A, $R^B$, R³, R⁴, R⁵, and $R^x$ are as described herein. In certain embodiments, $R^x$ is optionally substituted $C_{1-4}$ alkyl (e.g., methyl). In certain embodiments, R³ is hydrogen or $C_{1-4}$ alkyl (e.g., methyl). In certain embodiments, X is N, Z is NR⁴, and Y is CR⁵. In certain embodiments, X is NR⁴, Z is N, and Y is CR⁵. In certain embodiments, X is CR⁵, Z is $NR^4$, and Y is N. In certain embodiments, X is $CR^5$, Z is N, and Y is $NR^4$. In certain embodiments, $R^4$ is hydrogen or optionally substituted $C_{1-6}$ alkyl (e.g., methyl). In certain embodiments, $R^5$ is hydrogen. In certain embodiments, Ring A (a subset of $R^W$) is optionally substituted aryl or optionally substituted heteroaryl. In certain embodiments, Ring A (a subset of $R^W$) is optionally substituted $C_{3-6}$ carbocyclyl or optionally substituted 5-6 membered heterocyclyl. In certain embodiments, Ring A (a subset of $R^W$) is an optionally substituted bicyclic carbocyclyl (e.g., an optionally substituted spiro-fused bicyclic carbocyclyl) or optionally substituted bicyclic heterocyclyl (e.g., optionally substituted spiro-fused bicyclic heterocyclyl).

In certain embodiments, a provided compound is of Formula (VI-l):

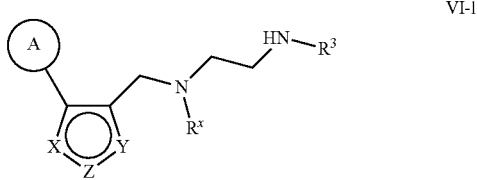

VI-1 or a pharmaceutically acceptable salt thereof, wherein Ring A, $R^B$, $R^3$, $R^4$, $R^5$, and $R^x$ are as described herein. In certain embodiments, $R^x$ is optionally substituted $C_{1-4}$ alkyl (e.g., methyl). In certain embodiments, $R^3$ is hydrogen or $C_{1-4}$ alkyl (e.g., methyl). In certain embodiments, X is N, Z is $NR^4$, and Y is $CR^5$. In certain embodiments, X is $NR^4$, Z is N, and Y is $CR^5$. In certain embodiments, X is $CR^5$, Z is $NR^4$, and Y is N. In certain embodiments, X is $CR^5$, Z is N, and Y is $NR^4$. In certain embodiments, $R^4$ is hydrogen or optionally substituted $C_{1-6}$ alkyl (e.g., methyl). In certain embodiments, $R^5$ is hydrogen. In certain embodiments, Ring A (a subset of $R^W$) is optionally substituted aryl or optionally substituted heteroaryl. In certain embodiments, Ring A (a subset of $R^W$) is optionally substituted $C_{3-6}$ carbocyclyl or optionally substituted 5-6 membered heterocyclyl. In certain embodiments, Ring A (a subset of $R^W$) is an optionally substituted bicyclic carbocyclyl (e.g., an optionally substituted spiro-fused bicyclic carbocyclyl) or optionally substituted bicyclic heterocyclyl (e.g., optionally substituted spiro-fused bicyclic heterocyclyl).

As defined generally above, $L_1$ is a bond, —O—, —N($R^B$)—, —S—, —C(O)—, —C(O)O—, —C(O)S—, —C(O)N($R^B$)—, —C(O)N($R^B$)N($R^B$)—, —OC(O)—, —OC(O)N($R^B$)—, —$NR^B$C(O)—, —$NR^B$C(O)N($R^B$)—, —$NR^B$C(O)N($R^B$)N($R^B$)—, —$NR^B$C(O)O—, —SC(O)—, —C(=$NR^B$)—, —C(=NN$R^B$)—, —C(=$NOR^A$)—, —C(=$NR^B$)N($R^B$)—, —$NR^B$C(=$NR^B$)—, —C(S)—, —C(S)N($R^B$)—, —$NR^B$C(S)—, —S(O)—, —OS(O)$_2$—, —S(O)$_2$O—, —SO$_2$—, —N($R^B$)SO$_2$—, —SO$_2$N($R^B$)—, or an optionally substituted $C_{1-6}$ saturated or unsaturated hydrocarbon chain, wherein one or more methylene units of the hydrocarbon chain is optionally and independently replaced with —O—, —N($R^B$)—, —S—, —C(O)—, —C(O)O—, —C(O)S—, —C(O)N($R^B$)—, —C(O)N($R^B$)N($R^B$)—, —OC(O)—, —OC(O)N($R^B$)—, —$NR^B$C(O)—, —$NR^B$C(O)N($R^B$)—, —$NR^B$C(O)N($R^B$)N($R^B$)—, —$NR^B$C(O)O—, —SC(O)—, —C(=$NR^B$)—, —C(=NN$R^B$)—, —C(=$NOR^A$)—, —C(=$NR^B$)N($R^B$)—, —$NR^B$C(=$NR^B$)—, —C(S)—, —C(S)N($R^B$)—, —$NR^B$C(S)—, —S(O)—, —OS(O)$_2$—, —S(O)$_2$O—, —SO$_2$—, —N($R^B$)SO$_2$—, or —SO$_2$N($R^B$)—. In some embodiments, $L_1$ is a bond. In some embodiments, $L_1$ is —O—, —N($R^B$)—, —S—. In some embodiments, $L_1$ is —O—. In some embodiments, $L_1$ is —N($R^B$)—. In some embodiments, $L_1$ is —NH—. In some embodiments, $L_1$ is —C(O)—. In some embodiments, $L_1$ is —C(O)N($R^B$)— or —$NR^B$C(O)—. In some embodiments, $L_1$ is —C(O)NH—. In some embodiments, $L_1$ is —NHC(O)—. In some embodiments, $L_1$ is —N($R^B$)SO$_2$— or —SO$_2$N($R^B$)—. In some embodiments, $L_1$ is —NHSO$_2$—. In some embodiments, $L_1$ is —SO$_2$NH—.

In some embodiments, $L_1$ is an optionally substituted $C_{1-6}$ saturated or unsaturated hydrocarbon chain, wherein one or more methylene units of the hydrocarbon chain is optionally and independently replaced with —O—, —N($R^B$)—, —S—, —C(O)—, —C(O)O—, —C(O)S—, —C(O)N($R^B$)—, —C(O)N($R^B$)N($R^B$)—, —OC(O)—, —OC(O)N($R^B$)—, —$NR^B$C(O)—, —$NR^B$C(O)N($R^B$)—, —$NR^B$C(O)N($R^B$)N($R^B$)—, —$NR^B$C(O)O—, —SC(O)—, —C(=$NR^B$)—, —C(=NN$R^B$)—, —C(=$NOR^A$)—, —C(=$NR^B$)N($R^B$)—, —$NR^B$C(=$NR^B$)—, —C(S)—, —C(S)N($R^B$)—, —$NR^B$C(S)—, —S(O)—, —OS(O)$_2$—, —S(O)$_2$O—, —SO$_2$—, —N($R^B$)SO$_2$—, or —SO$_2$N($R^B$)—. In some embodiments, $L_1$ is an optionally substituted $C_{1-6}$ saturated or unsaturated hydrocarbon chain. In some embodiments, $L_1$ is an optionally substituted $C_{1-6}$ alkylene chain. In some embodiments, $L_1$ is an unsubstituted $C_{1-6}$ alkylene chain. In some embodiments, $L_1$ is an optionally substituted $C_{2-6}$ alkenylene chain. In some embodiments, $L_1$ is an unsubstituted $C_{2-6}$ alkenylene chain. In some embodiments, $L_1$ is —CH=CH—. In some embodiments, $L_1$ is an optionally substituted $C_{2-6}$ alkynylene chain. In some embodiments, $L_1$ is an unsubstituted $C_{2-6}$ alkynylene chain. In some embodiments, $L_1$ is —C≡C—. In some embodiments, $L_1$ is an optionally substituted $C_{1-6}$ saturated or unsaturated hydrocarbon chain, wherein one methylene unit of the hydrocarbon chain is optionally and independently replaced with —O—, —N($R^B$)—, —S—, —C(O)—, —C(O)O—, —C(O)S—, —C(O)N($R^B$)—, —C(O)N($R^B$)N($R^B$)—, —OC(O)—, —OC(O)N($R^B$)—, —$NR^B$C(O)—, —$NR^B$C(O)N($R^B$)—, —$NR^B$C(O)N($R^B$)N($R^B$)—, —$NR^B$C(O)O—, —SC(O)—, —C(=$NR^B$)—, —C(=NN$R^B$)—, —C(=$NOR^A$) —C(=$NR^B$)N($R^B$)—, —$NR^B$C(=$NR^B$)—, —C(S)—, —C(S)N($R^B$)—, —$NR^B$C(S)—, —S(O)—, —OS(O)$_2$—, —S(O)$_2$O—, —SO$_2$—, —N($R^B$)SO$_2$—, or —SO$_2$N($R^B$)—. In some embodiments, $L_1$ is an optionally substituted $C_{1-6}$ saturated or unsaturated hydrocarbon chain, wherein two methylene units of the hydrocarbon chain is optionally and independently replaced with —O—, —N($R^B$)—, —S—, —C(O)—, —C(O)O—, —C(O)S—, —C(O)N($R^B$)—, —C(O)N($R^B$)N($R^B$)—, —OC(O)—, —OC(O)N($R^B$)—, —$NR^B$C(O)—, —$NR^B$C(O)N($R^B$)—, —$NR^B$C(O)N($R^B$)N($R^B$)—, —$NR^B$C(O)O—, —SC(O)—, —C(=$NR^B$)—, —C(=NN$R^B$)—, —C(=$NOR^A$)—, —C(=$NR^B$)N($R^B$)—, —$NR^B$C(=$NR^B$)—, —C(S)—, —C(S)N($R^B$)—, —$NR^B$C(S)—, —S(O)—, —OS(O)$_2$—, —S(O)$_2$O—, —SO$_2$—, —N($R^B$)SO$_2$—, or —SO$_2$N($R^B$)—. In some embodiments, $L_1$ is an optionally substituted $C_{1-6}$ saturated or unsaturated hydrocarbon chain, wherein three methylene units of the hydrocarbon chain is optionally and independently replaced with —O—, —N($R^B$)—, —S—, —C(O)—, —C(O)O—, —C(O)S—, —C(O)N($R^B$)—, —C(O)N($R^B$)N($R^B$)—, —OC(O)—, —OC(O)N($R^B$)—, —$NR^B$C(O)—, —$NR^B$C(O)N($R^B$)—, —$NR^B$C(O)N($R^B$)N($R^B$)—, —$NR^B$C(O)O—, —SC(O)—, —C(=$NR^B$)—, —C(=NN$R^B$)—, —C(=$NOR^A$)—, —C(=$NR^B$)N($R^B$)—, —$NR^B$C(=$NR^B$)—, —C(S)—, —C(S)N($R^B$)—, —$NR^B$C(S)—, —S(O)—, —OS(O)$_2$—, —S(O)$_2$O—, —SO$_2$—, —N(R$^B$)SO$_2$—, or —SO$_2$N(R$^B$)—. In some embodiments, L$_1$ is an optionally substituted C$_{1-6}$ saturated or unsaturated hydrocarbon chain, wherein one or more methylene units of the hydrocarbon chain is optionally and independently replaced with —O—, —N(R$^B$)—, —S—, —C(O)—, —C(O)N(R$^B$)—, —NR$^B$C(O)—, —SO$_2$—, —N(R$^B$)SO$_2$—, or —SO$_2$N(R$^B$)—. In some embodiments, L$_1$ is —CH$_2$O— or —OCH$_2$—.

As defined generally above, R$^W$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; provided that when L$_1$ is a bond, R$^W$ is not optionally substituted aryl or optionally substituted heteroaryl. In certain embodiments, when L$_1$ is a bond, then R$^W$ is not hydrogen. In some embodiments, when L$_1$ is a bond, R$^W$ is not hydrogen, optionally substituted aryl, or optionally substituted heteroaryl.

In certain embodiments, L$_1$ is a bond, and R$^W$ is hydrogen, halogen, or optionally substituted C$_{1-6}$alkyl. In certain embodiments, L$_1$ is a bond and R$^W$ is hydrogen. In certain embodiments, L$_1$ is a bond and R$^W$ is halogen, e.g., fluoro, chloro, bromo, or iodo. In certain embodiments, L$_1$ is a bond and R$^W$ is optionally substituted C$_{1-6}$alkyl, e.g., unsubstituted C$_{1-6}$alkyl, e.g., methyl, ethyl, propyl, butyl, isopropyl, isobutyl, or isoamyl. In certain embodiments, L$_1$ is a bond, R$^W$ is hydrogen, halogen, or optionally substituted C$_{1-6}$alkyl, X is CR$^5$, Z is N, and Y is NR$^4$, and R$^4$ is optionally substituted carbocyclyl or optionally substituted heterocyclyl (in such instances, R$^4$ may also be referred to as Ring A).

In some embodiments, R$^W$ is hydrogen.

In some embodiments, R$^W$ is halogen, e.g., fluoro, chloro, bromo, or iodo.

In some embodiments, R$^W$ is optionally substituted C$_{1-6}$ alkyl. In some embodiments, R$^W$ is unsubstituted C$_{1-6}$ alkyl. In some embodiments, R$^W$ is methyl, ethyl, propyl, or butyl. In some embodiments, R$^W$ is isopropyl, isobutyl, or isoamyl. In some embodiments, R$^W$ is optionally substituted C$_{2-6}$ alkenyl. In some embodiments, R$^W$ is C$_{2-6}$ alkynyl.

In some embodiments, R$^W$ is optionally substituted carbocyclyl. In some embodiments, R$^W$ is optionally substituted C$_{3-6}$ carbocyclyl. In some embodiments, R$^W$ is unsubstituted cyclopropyl. In some embodiments, R$^W$ is substituted cyclopropyl. In some embodiments, R$^W$ is unsubstituted cyclobutyl. In some embodiments, R$^W$ is substituted cyclobutyl. In some embodiments, R$^W$ is unsubstituted cyclopentyl. In some embodiments, R$^W$ is substituted cyclopentyl. In some embodiments, R$^W$ is unsubstituted cyclohexyl. In some embodiments, R$^W$ is substituted cyclohexyl. In some embodiments, R$^W$ is optionally substituted cyclopentenyl or optionally substituted cyclohexenyl.

In some embodiments, R$^W$ is optionally substituted heterocyclyl. In some embodiments, R$^W$ is an optionally substituted 4- to 7-membered heterocyclyl ring having 1-2 heteroatoms independently selected from nitrogen, oxygen, and sulfur. In some embodiments, R$^W$ is azetidinyl or oxetanyl. In some embodiments, R$^W$ is optionally substituted tetrahydrofuranyl, optionally substituted pyrrolidinyl, optionally substituted dihydropyrrolyl, or optionally substituted pyrrolyl-2,5-dione. In some embodiments, R$^W$ is optionally substituted piperidinyl, optionally substituted tetrahydropyranyl, optionally substituted dihydropyranyl, optionally substituted dihydropyridinyl, and optionally substituted thianyl. In certain embodiments, R$^W$ is optionally substituted piperidinyl. In some embodiments, R$^W$ is optionally substituted piperazinyl, optionally substituted morpholinyl, optionally substituted dithianyl, and optionally substituted dioxanyl. In some embodiments, R$^W$ is a 5- or 6-membered heterocyclyl group fused to a C$_6$ aryl ring. In some embodiments, R$^W$ is optionally substituted indolinyl, optionally substituted isoindolinyl, optionally substituted dihydrobenzofuranyl, optionally substituted dihydrobenzothienyl, or optionally substituted benzoxazolinonyl. In some embodiments, R$^W$ is optionally substituted tetrahydroquinolinyl or optionally substituted tetrahydroisoquinolinyl.

In some embodiments, R$^W$ is optionally substituted aryl. In some embodiments, R$^W$ is optionally substituted phenyl. In some embodiments, R$^W$ is unsubstituted phenyl. In some embodiments, R$^W$ is substituted phenyl. In some embodiments, R$^W$ is monosubstituted phenyl. In some embodiments, R$^W$ is disubstituted phenyl. In some embodiments, R$^W$ is trisubstituted phenyl. In some embodiments, R$^W$ is optionally substituted naphthyl. In some embodiments, R$^W$ is unsubstituted naphthyl.

In some embodiments, R$^W$ is optionally substituted heteroaryl. In some embodiments, R$^W$ is an optionally substituted 5- to 10-membered heteroaryl having 1-4 heteroatoms independently selected from nitrogen, oxygen, and sulfur. In some embodiments, R$^W$ is an optionally substituted 5- to 8-membered heteroaryl having 1-4 heteroatoms independently selected from nitrogen, oxygen, and sulfur. In some embodiments, R$^W$ is an optionally substituted 5- to 6-membered heteroaryl having 1-4 heteroatoms independently selected from nitrogen, oxygen, and sulfur. In some embodiments, R$^W$ is an optionally substituted 5- to 6-membered heteroaryl having 1-3 heteroatoms independently selected from nitrogen, oxygen, and sulfur. In some embodiments, R$^W$ is an optionally substituted 5- to 6-membered heteroaryl having 1-2 heteroatoms independently selected from nitrogen, oxygen, and sulfur. In some embodiments, R$^W$ is an optionally substituted 5- to 6-membered heteroaryl having 1 heteroatom selected from nitrogen, oxygen, and sulfur. In some embodiments, R$^W$ is an optionally substituted 8- to 10-membered bicyclic heteroaryl having 1-4 heteroatoms independently selected from nitrogen, oxygen, and sulfur. In some embodiments, R$^W$ is an optionally substituted 9- to 10-membered bicyclic heteroaryl having 1-4 heteroatoms independently selected from nitrogen, oxygen, and sulfur. In some embodiments, R$^W$ is an optionally substituted 9-membered bicyclic heteroaryl having 1-4 heteroatoms independently selected from nitrogen, oxygen, and sulfur. In some embodiments, R$^W$ is an optionally substituted 9-membered bicyclic heteroaryl having 1-3 heteroatoms independently selected from nitrogen, oxygen, and sulfur. In some embodiments, R$^W$ is an optionally substituted 9-membered bicyclic heteroaryl having 1-2 heteroatoms independently selected from nitrogen, oxygen, and sulfur. In some embodiments, R$^W$ is an optionally substituted 9-membered bicyclic heteroaryl having 1 heteroatom selected from nitrogen, oxygen, and sulfur. In some embodiments, R$^W$ is an optionally substituted 10-membered bicyclic heteroaryl having 1-4 heteroatoms independently selected from nitrogen, oxygen, and sulfur. In some embodiments, R$^W$ is an optionally substituted 10-membered bicyclic heteroaryl having 1-3 heteroatoms independently selected from nitrogen, oxygen, and sulfur. In some embodiments, R$^W$ is an optionally substituted 10-membered bicyclic heteroaryl having 1-2 heteroatoms independently selected from nitrogen, oxygen, and sulfur. In some embodiments, R$^W$ is an optionally substituted 10-membered bicyclic heteroaryl having 1 heteroatom selected from nitrogen, oxygen, and sulfur.

In some embodiments, $R^W$ is substituted or unsubstituted pyrrolyl, substituted or unsubstituted furanyl, substituted or unsubstituted thienyl, substituted or unsubstituted imidazolyl, substituted or unsubstituted pyrazolyl, substituted or unsubstituted oxazolyl, substituted or unsubstituted thiazolyl, substituted or unsubstituted isothiazolyl, substituted or unsubstituted triazolyl, substituted or unsubstituted thiadiazolyl, substituted or unsubstituted thiadiazolyl, substituted or unsubstituted tetrazolyl, substituted or unsubstituted pyridyl, substituted or unsubstituted pyrimidyl, substituted or unsubstituted pyrazinyl, substituted or unsubstituted pyridazinyl, substituted or unsubstituted triazinyl, substituted or unsubstituted indolyl, substituted or unsubstituted isoindolyl, substituted or unsubstituted indazolyl, substituted or unsubstituted benzotriazolyl, substituted or unsubstituted benzothiophenyl, substituted or unsubstituted isobenzothiophenyl, substituted or unsubstituted benzofuranyl, substituted or unsubstituted benzoisofuranyl, substituted or unsubstituted benzimidazolyl, substituted or unsubstituted benzoxazolyl, substituted or unsubstituted benzoxadiazolyl, substituted or unsubstituted benzisoxazolyl, substituted or unsubstituted benzthiazolyl, substituted or unsubstituted benzisothiazolyl, substituted or unsubstituted benzthiadiazolyl, substituted or unsubstituted indolizinyl, substituted or unsubstituted purinyl, substituted or unsubstituted pyrrolopyridinyl, substituted or unsubstituted triazolopyridinyl, substituted or unsubstituted naphthyridinyl, substituted or unsubstituted pteridinyl, substituted or unsubstituted quinolinyl, substituted or unsubstituted isoquinolinyl, substituted or unsubstituted cinnolinyl, substituted or unsubstituted quinoxalinyl, substituted or unsubstituted quinazolinyl, or substituted or unsubstituted phthalazinyl.

As generally described herein, $R^W$ may also be referred to as Ring A, wherein Ring A is optionally substituted carbocyclyl, optionally substituted heterocyclyl, optionally substituted aryl, or optionally substituted heteroaryl, provided that when $L_1$ is a bond, $R^W$ is not optionally substituted aryl or optionally substituted heteroaryl. $R^W$ and Ring A are thus used interchangeably herein when $R^W$ is describes a cyclic moiety. Furthermore, as described above, in certain embodiments, Ring A and $R^4$ are used interchangeably herein when $R^4$ encompass an optionally substituted carbocyclyl or optionally substituted heterocyclyl group.

In some embodiments, Ring A (corresponding to $R^W$ or $R^4$) is optionally substituted carbocyclyl. In some embodiments, Ring A is optionally substituted $C_{3-6}$ carbocyclyl. In some embodiments, Ring A is optionally substituted $C_3$-8 carbocyclyl. In some embodiments, Ring A is optionally substituted $C_3$ carbocyclyl, $C_4$ carbocyclyl, $C_5$ carbocyclyl, $C_6$ carbocyclyl, $C_7$ carbocyclyl, or $C_8$ carbocyclyl. In some embodiments, Ring A is unsubstituted cyclopropyl. In some embodiments, Ring A is substituted cyclopropyl. In some embodiments, Ring A is unsubstituted cyclobutyl. In some embodiments, Ring A is substituted cyclobutyl. In some embodiments, Ring A is unsubstituted cyclopentyl. In some embodiments, Ring A is substituted cyclopentyl. In some embodiments, Ring A is unsubstituted cyclohexyl. In some embodiments, Ring A is substituted cyclohexyl. In some embodiments, Ring A is optionally substituted cyclopentenyl or optionally substituted cyclohexenyl.

In some embodiments, Ring A (corresponding to $R^W$ or $R^4$) is optionally substituted bicyclic carbocyclyl. In certain embodiments, Ring A is a fused bicyclic carbocyclyl, e.g., Ring A is an optionally substituted $C_{3-10}$ carbocyclyl radical comprising an optionally substituted $C_{3-10}$ carbocyclyl, optionally substituted aryl, or optionally substituted heteroaryl ring fused thereto. In certain embodiments, Ring A is a bridged bicyclic carbocyclyl, e.g., an optionally substituted $C_{3-10}$ carbocyclyl radical bridged by a group comprising 1, 2, 3, 4, or 5 linear atoms. In certain embodiments, Ring A is a spiro-fused bicyclic carbocyclyl, e.g., an optionally substituted $C_{3-10}$ carbocyclyl radical comprising an optionally substituted $C_{3-10}$ carbocyclyl ring spiro-fused thereto.

In some embodiments, Ring A (corresponding to $R^W$ or $R^4$) is optionally substituted heterocyclyl. In some embodiments, Ring A is an optionally substituted 4- to 7-membered heterocyclyl ring having 1-2 heteroatoms independently selected from nitrogen, oxygen, and sulfur. In some embodiments, Ring A is azetidinyl or oxetanyl. In some embodiments, Ring A is optionally substituted tetrahydrofuranyl, optionally substituted pyrrolidinyl, optionally substituted dihydropyrrolyl, or optionally substituted pyrrolyl-2,5-dione. In some embodiments, Ring A is optionally substituted piperidinyl, optionally substituted tetrahydropyranyl, optionally substituted dihydropyranyl, optionally substituted dihydropyridinyl, and optionally substituted thianyl. In certain embodiments, Ring A is optionally substituted piperidinyl. In some embodiments, Ring A is optionally substituted piperazinyl, optionally substituted morpholinyl, optionally substituted dithianyl, and optionally substituted dioxanyl. In some embodiments, Ring A is a 5- or 6-membered heterocyclyl group fused to a $C_6$ aryl ring. In some embodiments, Ring A is optionally substituted indolinyl, optionally substituted isoindolinyl, optionally substituted dihydrobenzofuranyl, optionally substituted dihydrobenzothienyl, or optionally substituted benzoxazolinonyl. In some embodiments, Ring A is optionally substituted tetrahydroquinolinyl or optionally substituted tetrahydroisoquinolinyl.

In some embodiments, Ring A (corresponding to $R^W$ or $R^4$) is optionally substituted bicyclic heterocyclyl. In certain embodiments, Ring A is a fused bicyclic heterocyclyl, e.g., Ring A is an optionally substituted 3- to 10-membered heterocyclyl radical comprising an optionally substituted $C_{3-10}$ carbocyclyl, optionally substituted 3- to 10-membered heterocyclyl, optionally substituted aryl, or optionally substituted heteroaryl ring fused thereto. In certain embodiments, Ring A is a bridged bicyclic heterocyclyl, e.g., an optionally substituted 3- to 10-membered heterocyclyl radical bridged by a group comprising 1, 2, 3, 4, or 5 linear atoms. In certain embodiments, Ring A is a spiro-fused bicyclic heterocyclyl, e.g., an optionally substituted 3- to 10-membered heterocyclyl radical comprising an optionally substituted $C_{3-10}$ carbocyclyl ring or optionally substituted 3- to 10-membered heterocyclyl ring spiro-fused thereto.

In some embodiments, Ring A (corresponding to $R^W$) is optionally substituted aryl. In some embodiments, Ring A is optionally substituted phenyl. In some embodiments, Ring A is unsubstituted phenyl. In some embodiments, Ring A is substituted phenyl. In some embodiments, Ring A is monosubstituted phenyl. In some embodiments, Ring A is disubstituted phenyl. In some embodiments, Ring A is trisubstituted phenyl. In some embodiments, Ring A is optionally substituted naphthyl. In some embodiments, Ring A is unsubstituted naphthyl.

In some embodiments, Ring A (corresponding to $R^W$) is optionally substituted heteroaryl. In some embodiments, Ring A is an optionally substituted 5- to 10-membered heteroaryl having 1-4 heteroatoms independently selected from nitrogen, oxygen, and sulfur. In some embodiments, Ring A is an optionally substituted 5- to 8-membered heteroaryl having 1-4 heteroatoms independently selected from nitrogen, oxygen, and sulfur. In some embodiments, Ring A is an optionally substituted 5- to 6-membered heteroaryl having 1-4 heteroatoms independently selected from nitrogen, oxygen, and sulfur. In some embodiments, Ring A is an optionally substituted 5- to 6-membered heteroaryl having 1-3 heteroatoms independently selected from nitrogen, oxygen, and sulfur. In some embodiments, Ring A is an optionally substituted 5- to 6-membered heteroaryl having 1-2 heteroatoms independently selected from nitrogen, oxygen, and sulfur. In some embodiments, Ring A is an optionally substituted 5- to 6-membered heteroaryl having 1 heteroatom selected from nitrogen, oxygen, and sulfur. In some embodiments, Ring A is an optionally substituted 8- to 10-membered bicyclic heteroaryl having 1-4 heteroatoms independently selected from nitrogen, oxygen, and sulfur. In some embodiments, Ring A is an optionally substituted 9- to 10-membered bicyclic heteroaryl having 1-4 heteroatoms independently selected from nitrogen, oxygen, and sulfur. In some embodiments, Ring A is an optionally substituted 9-membered bicyclic heteroaryl having 1-4 heteroatoms independently selected from nitrogen, oxygen, and sulfur. In some embodiments, Ring A is an optionally substituted 9-membered bicyclic heteroaryl having 1-3 heteroatoms independently selected from nitrogen, oxygen, and sulfur. In some embodiments, Ring A is an optionally substituted 9-membered bicyclic heteroaryl having 1-2 heteroatoms independently selected from nitrogen, oxygen, and sulfur. In some embodiments, Ring A is an optionally substituted 9-membered bicyclic heteroaryl having 1 heteroatom selected from nitrogen, oxygen, and sulfur. In some embodiments, Ring A is an optionally substituted 10-membered bicyclic heteroaryl having 1-4 heteroatoms independently selected from nitrogen, oxygen, and sulfur. In some embodiments, Ring A is an optionally substituted 10-membered bicyclic heteroaryl having 1-3 heteroatoms independently selected from nitrogen, oxygen, and sulfur. In some embodiments, Ring A is an optionally substituted 10-membered bicyclic heteroaryl having 1-2 heteroatoms independently selected from nitrogen, oxygen, and sulfur. In some embodiments, Ring A is an optionally substituted 10-membered bicyclic heteroaryl having 1 heteroatom selected from nitrogen, oxygen, and sulfur.

In some embodiments, Ring A (corresponding to $R^W$) is substituted or unsubstituted pyrrolyl, substituted or unsubstituted furanyl, substituted or unsubstituted thienyl, substituted or unsubstituted imidazolyl, substituted or unsubstituted pyrazolyl, substituted or unsubstituted oxazolyl, substituted or unsubstituted thiazolyl, substituted or unsubstituted isothiazolyl, substituted or unsubstituted triazolyl, substituted or unsubstituted thiadiazolyl, substituted or unsubstituted thiadiazolyl, substituted or unsubstituted tetrazolyl, substituted or unsubstituted pyridyl, substituted or unsubstituted pyrimidyl, substituted or unsubstituted pyrazinyl, substituted or unsubstituted pyridazinyl, substituted or unsubstituted triazinyl, substituted or unsubstituted indolyl, substituted or unsubstituted isoindolyl, substituted or unsubstituted indazolyl, substituted or unsubstituted benzotriazolyl, substituted or unsubstituted benzothiophenyl, substituted or unsubstituted isobenzothiophenyl, substituted or unsubstituted benzofuranyl, substituted or unsubstituted benzoisofuranyl, substituted or unsubstituted benzimidazolyl, substituted or unsubstituted benzoxazolyl, substituted or unsubstituted benzoxadiazolyl, substituted or unsubstituted benzisoxazolyl, substituted or unsubstituted benzthiazolyl, substituted or unsubstituted benzisothiazolyl, substituted or unsubstituted benzthiadiazolyl, substituted or unsubstituted indolizinyl, substituted or unsubstituted purinyl, substituted or unsubstituted pyrrolopyridinyl, substituted or unsubstituted triazolopyridinyl, substituted or unsubstituted naphthyridinyl, substituted or unsubstituted pteridinyl, substituted or unsubstituted quinolinyl, substituted or unsubstituted isoquinolinyl, substituted or unsubstituted cinnolinyl, substituted or unsubstituted quinoxalinyl, substituted or unsubstituted quinazolinyl, or substituted or unsubstituted phthalazinyl.

In certain embodiments, $R^W$ (or Ring A) is of Formula (q-1):

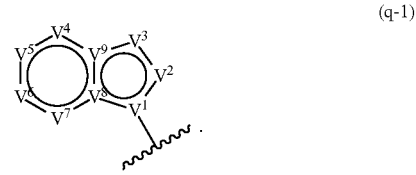

In certain embodiments, $R^W$ (or Ring A) is of Formula (q-2):

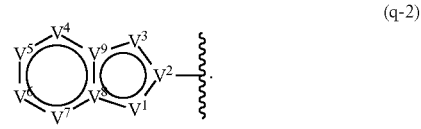

In certain embodiments, $R^W$ (or Ring A) is of Formula (q-3):

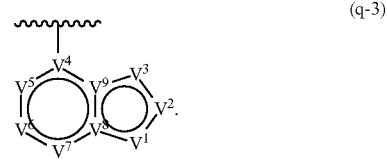

In certain embodiments, $R^W$ (or Ring A) is of Formula (q-4):

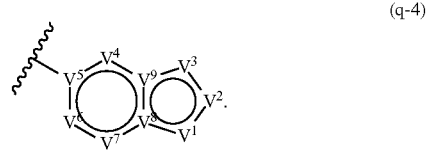

As used herein, each instance of $V^1$, $V^2$, $V^3$, $V^4$, $V^5$, $V^6$, $V^7$, $V^8$, and $V^9$ may independently be O, S, N, $NR^N$, C, or $CR^C$, as valency permits, wherein at least one of $V^1$, $V^2$, $V^3$, $V^4$, $V^5$, $V^6$, $V^7$, $V^8$, and $V^9$ is O, S, N, $NR^N$, and wherein:

each instance of $R^C$ is independently selected from the group consisting of hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(O)OR$^A$, —C(O)SR$^A$, —C(O)N(R$^B$)$_2$, —C(O)N(R$^B$)N(R$^B$)$_2$, —OC(O)R$^A$, —OC(O)N(R$^B$)$_2$, —NR$^B$C(O)R$^A$, —NR$^B$C(O)N(R$^B$)$_2$, —NR$^B$C(O)N(R$^B$)N(R$^B$)$_2$, —NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(O)R$^A$, —OS(O)$_2$R$^A$, —SO$_2$R$^A$, —NR$^B$SO$_2$R$^A$, or —SO$_2$N(R$^B$)$_2$; and each instance of R$^N$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)R$^A$, —C(=O)OR$^A$, —C(=O)SR$^A$, —C(=O)N(R$^B$)$_2$, —C(=NR$^B$)R$^A$, —C(=NNR$^B$)R$^A$, —C(=NOR$^A$)R$^A$, —C(=NR$^B$)N(R$^B$)$_2$, —C(=S)R$^A$, —C(=S)N(R$^B$)$_2$, —S(=O)R$^A$, —SO$_2$R$^A$, —SO$_2$N(R$^B$)$_2$, and a nitrogen protecting group.

In certain embodiments, V$^1$ is O, S, N or NR$^N$. In certain embodiments, V$^1$ is N or NR$^N$. In certain embodiments, V$^1$ is O. In certain embodiments, V$^1$ is S. In certain embodiments, only one of V$^1$, V$^2$, V$^3$, V$^4$, V$^5$, V$^6$, V$^7$, V$^8$, and V$^9$ is selected from the group consisting of O, S, N, and NR$^N$. In certain embodiments, only one of V$^1$, V$^2$, V$^3$, V$^4$, V$^5$, V$^6$, V$^7$, V$^8$, and V$^9$ is selected from the group consisting of N and NR$^N$. In certain embodiments, only one of V$^1$, V$^2$, V$^3$, V$^4$, V$^5$, V$^6$, V$^7$, V$^8$, and V$^9$ is O. In certain embodiments, only one of V$^1$, V$^2$, V$^3$, V$^4$, V$^5$, V$^6$, V$^7$, V$^8$, and V$^9$ is S. In certain embodiments, only two of V$^1$, V$^2$, V$^3$, V$^4$, V$^5$, V$^6$, V$^7$, V$^8$, and V$^9$ are each independently selected from the group consisting of O, S, N, and NR$^N$. In certain embodiments, only two of V$^1$, V$^2$, V$^3$, V$^4$, V$^5$, V$^6$, V$^7$, V$^5$, and V$^9$ are each independently selected from the group consisting of N and NR$^N$. In certain embodiments, only two of V$^1$, V$^2$, V$^3$, V$^4$, V$^5$, V$^6$, V$^7$, V$^8$, and V$^9$ are each independently selected from the group consisting of O, N and NR$^N$. In certain embodiments, only two of V$^1$, V$^2$, V$^3$, V$^4$, V$^5$, V$^6$, V$^7$, V$^8$, and V$^9$ are each independently selected from the group consisting of S, N and NR$^N$. In certain embodiments, only three of V$^1$, V$^2$, V$^3$, V$^4$, V$^5$, V$^6$, V$^7$, V$^5$, and V$^9$ are each independently selected from the group consisting of O, S, N, and NR$^N$. In certain embodiments, only three of V$^1$, V$^2$, V$^3$, V$^4$, V$^5$, V$^6$, V$^7$, V$^8$, and V$^9$ are each independently selected from the group consisting of N and NR$^N$. In certain embodiments, only three of V$^1$, V$^2$, V$^3$, V$^4$, V$^5$, V$^6$, V$^7$, V$^8$, and V$^9$ are each independently selected from the group consisting of O, N and NR$^N$. In certain embodiments, only three of V$^1$, V$^2$, V$^3$, V$^4$, V$^5$, V$^6$, V$^7$, V$^5$, and V$^9$ are each independently selected from the group consisting of S, N and NR$^N$. In certain embodiments, only four of V$^1$, V$^2$, V$^3$, V$^4$, V$^5$, V$^6$, V$^7$, V$^8$, and V$^9$ are each independently selected from the group consisting of O, S, N, and NR$^N$. In certain embodiments, only four of V$^1$, V$^2$, V$^3$, V$^4$, V$^5$, V$^6$, V$^7$, V$^8$, and V$^9$ are each independently selected from the group consisting of N and NR$^N$. In certain embodiments, only four of V$^1$, V$^2$, V$^3$, V$^4$, V$^5$, V$^6$, V$^7$, V$^8$, and V$^9$ are each independently selected from the group consisting of O, N and NR$^N$. In certain embodiments, only four of V$^1$, V$^2$, V$^3$, V$^4$, V$^5$, V$^6$, V$^7$, V$^8$, and V$^9$ are each independently selected from the group consisting of S, N and NR$^N$. In certain embodiments, only five of V$^1$, V$^2$, V$^3$, V$^4$, V$^5$, V$^6$, V$^7$, V$^8$, and V$^9$ are each independently selected from the group consisting of O, S, N, and NR$^N$. In certain embodiments, only five of V$^1$, V$^2$, V$^3$, V$^4$, V$^5$, V$^6$, V$^7$, V$^8$, and V$^9$ are each independently selected from the group consisting of N and NR$^N$.

In certain embodiments, R$^W$ (or Ring A) is an optionally substituted 5-membered heteroaryl ring. In certain embodiments, R$^W$ (or Ring A) is of Formula (q-5):

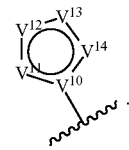

(q-5)

As used herein, each instance of V$^{10}$, V$^{11}$, V$^{12}$, V$^{13}$, and V$^{14}$ may independently be O, S, N, NR$^N$, C, or CR$^C$, as valency permits, wherein R$^N$ and R$^C$ are as defined herein, and wherein at least one of V$^{10}$, V$^{11}$, V$^{12}$, V$^{13}$, and V$^{14}$ is O, S, N, or NR$^N$. In certain embodiments, only one of V$^{10}$, V$^{11}$, V$^{12}$, V$^{13}$, and V$^{14}$ is selected from the group consisting of O, S, N, and NR$^N$. In certain embodiments, only two of V$^{10}$, V$^{11}$, V$^{12}$, V$^{13}$, and V$^{14}$ are selected from the group consisting of O, S, N, and NR$^N$. In certain embodiments, only three of V$^{10}$, V$^{11}$, V$^{12}$, V$^{13}$, and V$^{14}$ are selected from the group consisting of O, S, N, and NR$^N$. In certain embodiments, only four of V$^{10}$, V$^{11}$, V$^{12}$, V$^{13}$, and V$^{14}$ are selected from the group consisting of O, S, N, and NR$^N$.

In certain embodiments, R$^W$ (or Ring A) is an optionally substituted 6-membered heteroaryl ring. In certain embodiments, R$^W$ (or Ring A) is of Formula (q-6):

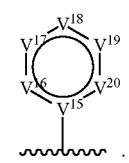

(q-6)

In compounds of Formula (q-6), V$^{15}$, V$^{16}$, V$^{17}$, V$^{18}$, V$^{19}$, and V$^{20}$ are each independently selected from the group consisting of N or CR$^C$, wherein at least one of V$^{15}$, V$^{16}$, V$^{17}$, V$^{18}$, V$^{19}$, and V$^{20}$ is N. In certain embodiments, only one of V$^5$, V$^6$, V$^7$, V$^{18}$, V$^{19}$ and V$^{20}$ is N. In certain embodiments, only two of V$^{15}$, V$^{16}$, V$^{17}$, V$^{18}$, V$^{19}$, and V$^{20}$ are N. In certain embodiments, only three of V$^{15}$, V$^{16}$, V$^{17}$, V$^{18}$, V$^{19}$, and V$^{20}$ are N.

In certain embodiments, Ring A (corresponding to R$^W$ or R$^4$) is an optionally substituted carbocyclyl or optionally substituted heterocyclyl, e.g., an optionally substituted C$_6$ carbocyclyl, optionally substituted 6-membered heterocyclyl, optionally substituted C$_6$ carbocyclyl radical comprising an optionally substituted C$_{3-10}$ carbocyclyl ring or optionally substituted 3- to 10-membered heterocyclyl ring spiro-fused thereto, or an optionally substituted 6-membered heterocyclyl radical comprising an optionally substituted C$_{3-10}$ carbocyclyl ring or optionally substituted 3- to 10-membered heterocyclyl ring spiro-fused thereto. Furthermore, in certain embodiments, L$_1$ is a bond, R$^W$ is hydrogen, halogen, or optionally substituted C$_{1-6}$alkyl, X is CR$^5$, Z is N, and Y is NR$^4$, and R$^4$ is optionally substituted carbocyclyl or optionally substituted heterocyclyl, e.g., an optionally substituted C$_6$ carbocyclyl, optionally substituted 6-membered heterocyclyl, optionally substituted C$_6$ carbocyclyl radical comprising an optionally substituted C$_{3-10}$ carbocyclyl ring or optionally substituted 3- to 10-membered heterocyclyl ring spiro-fused thereto, or an optionally substituted 6-membered heterocyclyl radical comprising an optionally substituted C$_{3-10}$ carbocyclyl ring or optionally substituted 3- to 10-membered heterocyclyl ring spiro-fused thereto.

In certain embodiments, Ring A ($R^W$ or $R^4$) is of Formula (q-7)-(q-17):

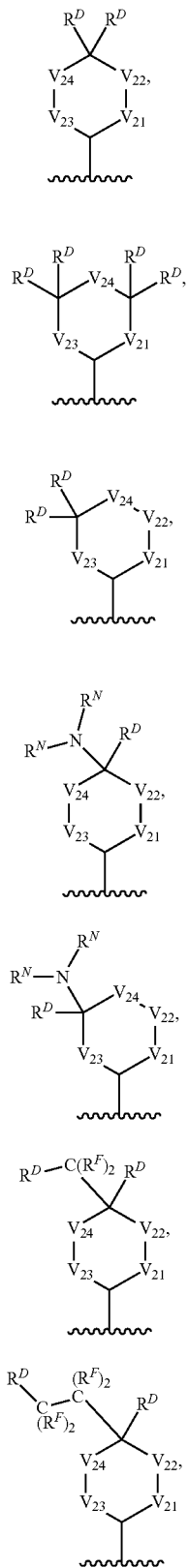

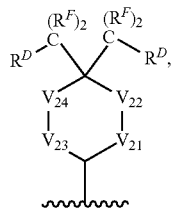

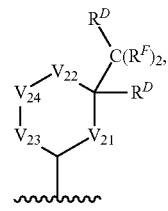

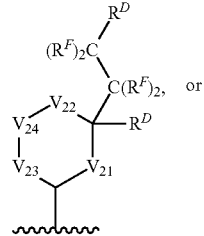

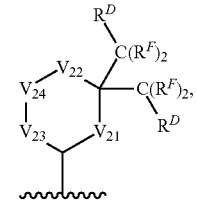

wherein:

$V^{21}$, $V^{22}$, $V^{23}$, and $V^{24}$ are each independently O, S, $NR^N$, C=O, or $C(R^C)_2$ as valency permits, provided no more than two of $V^{21}$, $V^{22}$, $V^{23}$, and $V^{24}$ is a heteroatom O, S, and $NR^N$, alternatively wherein one of $V^{21}$, $V^{22}$, $V^{23}$, and $V^{24}$ and another of $V^{21}$, $V^{22}$, $V^{23}$, and $V^{24}$ adjacent to each other are joined to form an $N=C(R^C)$ or $C(R^C)=C(R^C)$ group provided the ring thus formed is not an aromatic ring;

each instance of $R^C$ is independently hydrogen, halo, —CN, —$NO_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, —$SR^A$, —C(=O)$R^A$, —C(O)$OR^A$, —C(O)$SR^A$, —C(O)N($R^B$)$_2$, —C(O)N($R^B$)N($R^B$)$_2$, —OC(O)$R^A$, —OC(O)N($R^B$)$_2$, —$NR^B$C(O)$R^A$, —$NR^B$C(O)N($R^B$)$_2$, —$NR^B$C(O)N($R^B$)N($R^B$)$_2$, —$NR^B$C(O)$OR^A$, —SC(O)$R^A$, —C(=$NR^B$)$R^A$, —C(=$NNR^B$)$R^A$, —C(=$NOR^A$)$R^A$, —C(=$NR^B$)N($R^B$)$_2$, —$NR^B$C(=$NR^B$)$R^B$, —C(=S)$R^A$, —C(=S)N($R^B$)$_2$, —$NR^B$C(=S)$R^A$, —S(O)$R^A$, —OS(O)$_2R^A$, —$SO_2R^A$, —$NR^B$$SO_2R^A$, or —$SO_2$N($R^B$)$_2$;

each instance of $R^N$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)R$^A$, —C(=O)OR$^A$, —C(=O)SR$^A$, —C(=O)N(R$^B$)$_2$, —C(=NR$^B$)R$^A$, —C(=NNR$^B$)R$^A$, —C(=NOR$^A$)R$^A$, —C(=NR$^B$)N(R$^B$)$_2$, —C(=S)R$^A$, —C(=S)N(R$^B$)$_2$, —S(=O)R$^A$, —SO$_2$R$^A$, —SO$_2$N(R$^B$)$_2$, or a nitrogen protecting group, or two R$^N$ groups are joined to form an optionally substituted heterocyclic ring, or one R$^N$ group and one R$^D$ group are joined to form an optionally substituted heterocyclic ring;

each instance of R$^F$ is independently hydrogen or halo; and each instance of R$^D$ is independently hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(O)OR$^A$, —C(O)SR$^A$, —C(O)N(R$^B$)$_2$, —C(O)N(R$^B$)N(R$^B$)$_2$, —OC(O)R$^A$, —OC(O)N(R$^B$)$_2$, —NR$^B$C(O)R$^A$, —NR$^B$C(O)N(R$^B$)$_2$, —NR$^B$C(O)N(R$^B$)N(R$^B$)$_2$, —NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(O)R$^A$, —OS(O)$_2$R$^A$, —SO$_2$R$^A$, —NR$^B$SO$_2$R$^A$, or —SO$_2$N(R$^B$)$_2$; or two R$^D$ groups are joined to form an optionally substituted carbocyclic or optionally substituted heterocyclic ring.

In certain embodiments, each instance of V$^{21}$, V$^{22}$, V$^{23}$, and V$^{24}$ is C(R$^C$)$_2$. In certain embodiments, one instance of V$^{21}$, V$^{22}$, V$^{23}$, and V$^{24}$ is O. In certain embodiments, one instance of V$^{21}$, V$^{22}$, V$^{23}$, and V$^{24}$ is S. In certain embodiments, one instance of V$^{21}$, V$^{22}$, V$^{23}$, and V$^{24}$ is NR$^N$. In certain embodiments, only one of V$^{21}$, V$^{22}$, V$^{23}$, and V$^{24}$ is a heteroatom selected from O, S, and NR$^N$. In certain embodiments, two of V$^{21}$, V$^{22}$, V$^{23}$, and V$^{24}$ is a heteroatom selected from O, S, and NR$^N$.

In certain embodiments, V$^{21}$ is a heteroatom selected from O, S, and NR$^N$. In certain embodiments, V$^{21}$ is O. In certain embodiments, V$^{21}$ is NR$^N$. For example, in certain embodiments, wherein V$^{21}$ is O or NR$^N$, provided is an Ring A (R$^W$ or R$^4$) group of Formula:

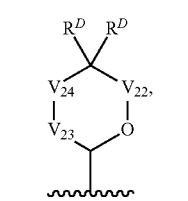
(q-7-V$^{210}$)

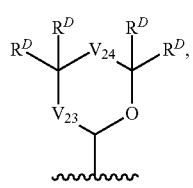
(q-8-V$^{210}$)

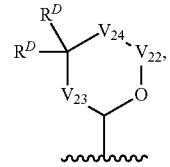
(q-9-V$^{210}$)

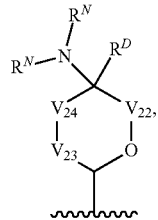
(q-10-V$^{210}$)

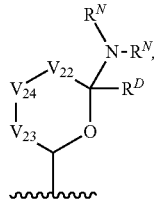
(q-11-V$^{210}$)

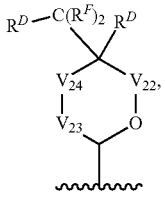
(q-12-V$^{210}$)

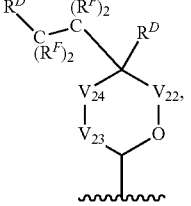
(q-13-V$^{210}$)

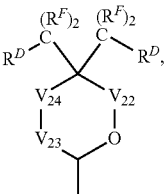
(q-14-V$^{210}$)

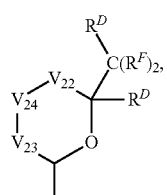
(q-15-V$^{21)}$)

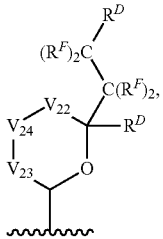
(q-16-V$^{210}$)

(q-17-V²¹ᴼ) 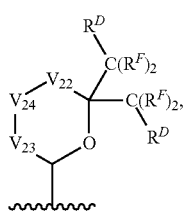
(q-7-V²¹ᴺ) 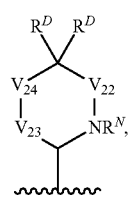
(q-8-V²¹ᴺ) 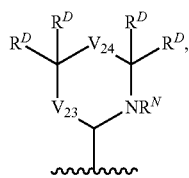
(q-9-V²¹ᴺ) 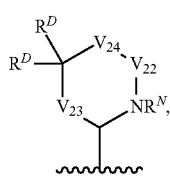
(q-10-V²¹ᴺ) 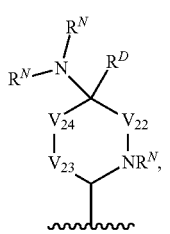
(q-11-V²¹ᴺ) 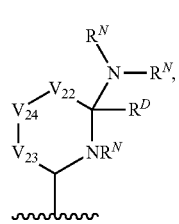
(q-12-V²¹ᴺ) 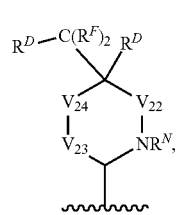
(q-13-V²¹ᴺ) 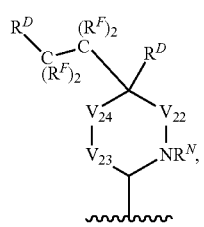
(q-14-V²¹ᴺ) 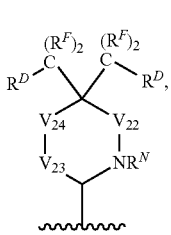
(q-15-V²¹ᴺ) 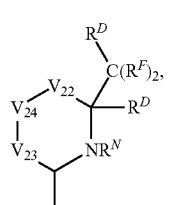
(q-16-V²¹ᴺ), or 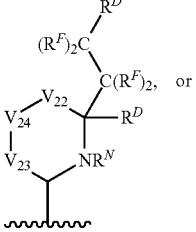
(q-17-V²¹ᴺ) 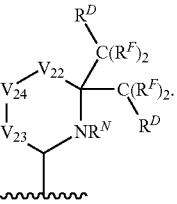
In certain embodiments, $V^{22}$ is a heteroatom selected from O, S, and $NR^N$. In certain embodiments, $V^2$ is O. In certain embodiments, $V^2$ is $NR^N$. For example, in certain embodiments, wherein $V^{22}$ is O or $NR^N$, provided is an Ring A ($R^W$ or $R^4$) group of Formula:
(q-7-V²²ᴼ) 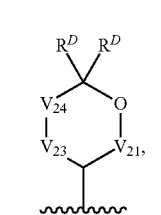

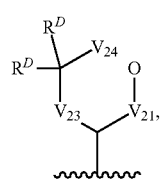
(q-9-V²²ᴼ)
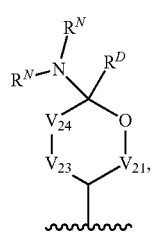
(q-10-V²²ᴼ)
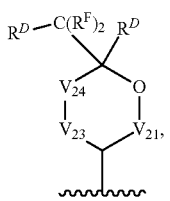
(q-12-V²²ᴼ)
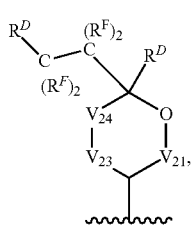
(q-13-V²²ᴼ)
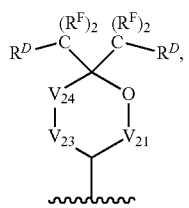
(q-14-V²²ᴼ)
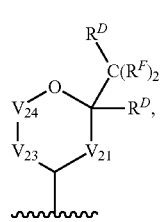
(q-15-V²²ᴼ)
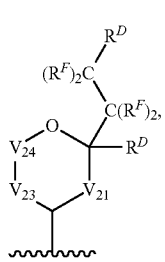
(q-16-V²²ᴼ)
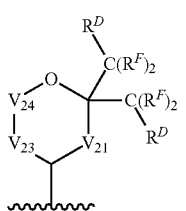
(q-17-V²²ᴼ)
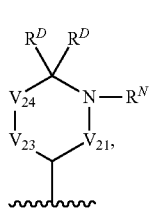
(q-7-V²²ᴼ)
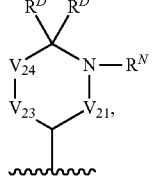
(q-9-V²²ᴼ)
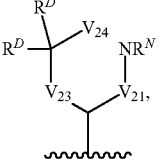
(q-10-V²²ᴼ)
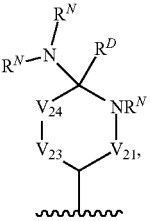
(q-12-V²²ᴼ)
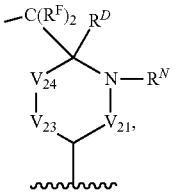
(q-13-V²²ᴼ)
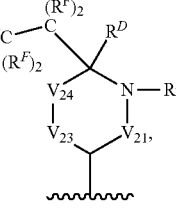
(q-14-V²²ᴼ)

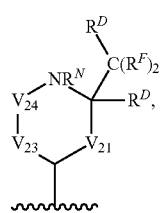 (q-15-$V^{22O}$)
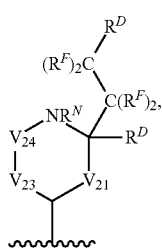 (q-16-$V^{22N}$)
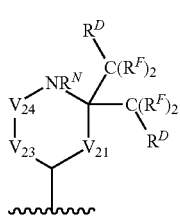 (q-17-$V^{22N}$)
In certain embodiments, $V^{23}$ is a heteroatom selected from O, S, and $NR^N$. In certain embodiments, $V^{23}$ is O. In certain embodiments, $V^{23}$ is $NR^N$. For example, in certain embodiments, wherein $V^{23}$ is O or $NR^N$, provided is an Ring A ($R^W$ or $R^4$) group of Formula:
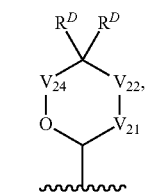 (q-7-$V^{230}$)
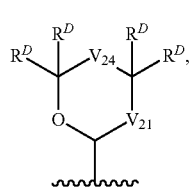 (q-8-$V^{230}$)
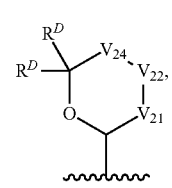 (q-9-$V^{230}$)
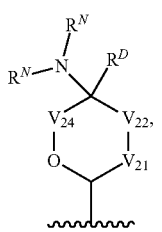 (q-10-$V^{230}$)
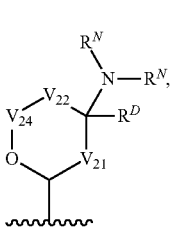 (q-11-$V^{230}$)
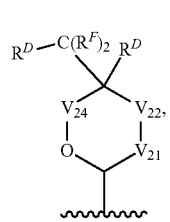 (q-12-$V^{230}$)
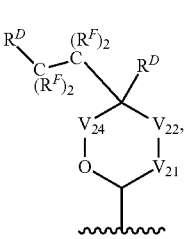 (q-13-$V^{230}$)
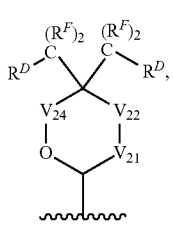 (q-14-$V^{230}$)
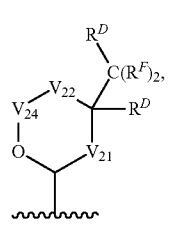 (q-15-$V^{230}$)
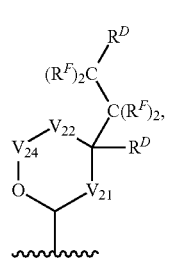 (q-16-$V^{230}$)

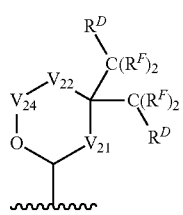 (q-17-V²³⁰)
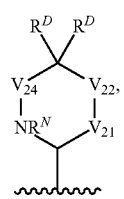 (q-7-V²³ᴺ)
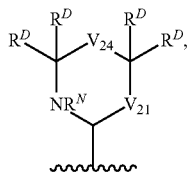 (q-8-V²³ᴺ)
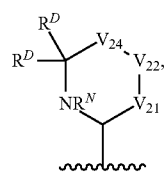 (q-9-V²³ᴺ)
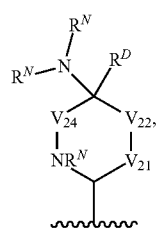 (q-10-V²³ᴺ)
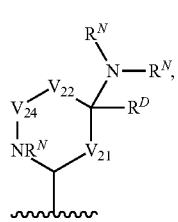 (q-11-V²³ᴺ)
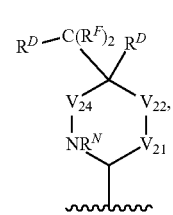 (q-12-V²³ᴺ)
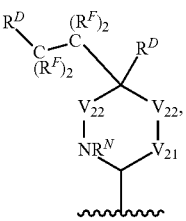 (q-13-V²³ᴺ)
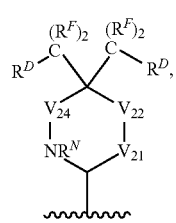 (q-14-V²³ᴺ)
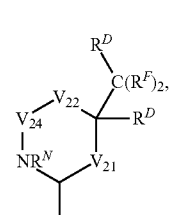 (q-15-V²³ᴺ)
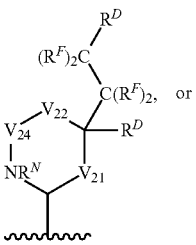 (q-16-V²³ᴺ), or
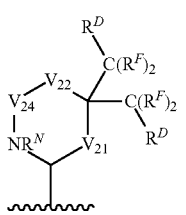 (1-17-V²³ᴺ)
In certain embodiments, $V^{24}$ is a heteroatom selected from O, S, and $NR^N$. In certain embodiments, $V^{24}$ is O. In certain embodiments, $V^{24}$ is $NR^N$. For example, in certain embodiments, wherein $V^{24}$ is O or $NR^N$, provided is Ring A ($R^W$ or $R^4$) group of Formula:
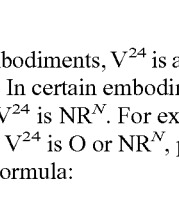 (q-7-V²⁴⁰)

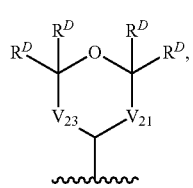 (q-8-V²⁴⁰)
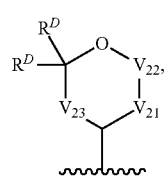 (q-9-V²⁴⁰)
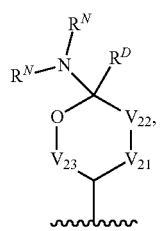 (q-10-V²⁴⁰)
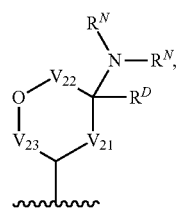 (q-11-V²⁴⁰)
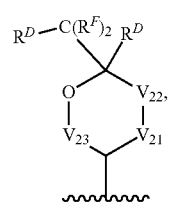 (2-12-V²⁴⁰)
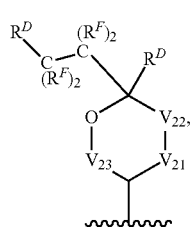 (q-13-V²⁴⁰)
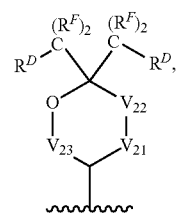 (q-14-V²⁴⁰)
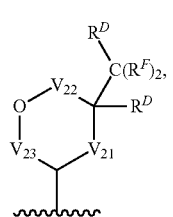 (q-15-V²⁴⁰)
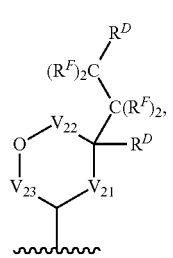 (q-16-V²⁴⁰)
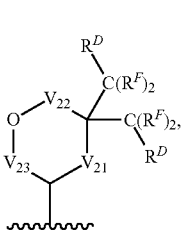 (q-17-V²⁴⁰)
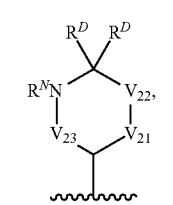 (q-7-V²⁴ᴺ)
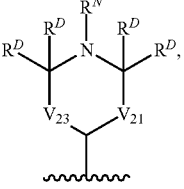 (q-8-V²⁴ᴺ)
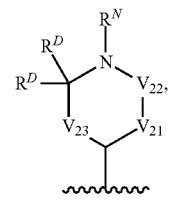 (q-9-V²⁴ᴺ)
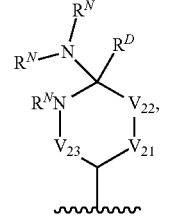 (q-10-V²⁴ᴺ)

(q-11-$V^{24N}$)
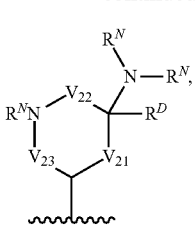

(q-12-$V^{24N}$)
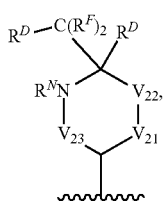

(q-13-$V^{24N}$)
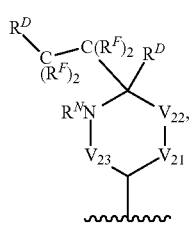

(q-14-$V^{24N}$)
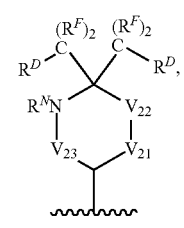

(q-15-$V^{24N}$)
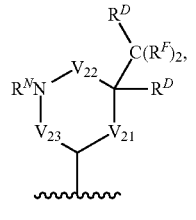

(q-16-$V^{24N}$)
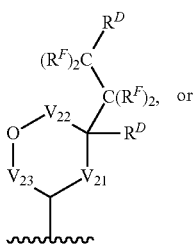

(q-17-$V^{24N}$)
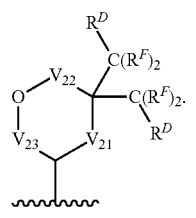

In certain embodiments, at least one instance of $R^D$ is hydrogen, e.g., each instance for (q-10); 1 or 2 instances for (q-7), (q-9), (q-12), (q-13), (q-14), (q-15), (q-16), and (q-17); and 1, 2, 3, or 4 instances for (q-8). However, in certain embodiments, at least one instance of $R^D$ is a non-hydrogen group, e.g., each instance for (q-10); 1 or 2 instances for (q-7), (q-9), (q-12), (q-13), (q-14), (q-15), (q-16), and (q-17); and 1, 2, 3, or 4 instances for (q-8). For example, in certain embodiments, each instance of $R^D$ is a non-hydrogen group.

In certain embodiments, two $R^D$ groups are joined to form an optionally substituted carbocyclic ring, e.g., an optionally substituted $C_{3-6}$ carbocyclic ring. In certain embodiments, two $R^D$ groups are joined to form an optionally substituted $C_3$ carbocyclic ring, optionally substituted $C_4$ carbocyclic ring, optionally substituted $C_5$ carbocyclic ring, or optionally substituted $C_6$ carbocyclic ring. In certain embodiments, the $R^D$ groups are joined to form an unsubstituted carbocyclic ring. However, in certain embodiments, the $R^D$ groups are joined to form a substituted carbocyclic ring, e.g., substituted with one or more alkyl groups.

In certain embodiments, two $R^D$ groups are joined to form an optionally substituted heterocyclic ring, e.g., an optionally substituted 3- to 6-membered heterocyclic ring comprising 1 or 2 heteroatoms selected from oxygen, nitrogen, or sulfur. In certain embodiments, two $R^D$ groups are joined to form an optionally substituted 3-membered heterocyclic ring, optionally substituted 4-membered heterocyclic ring, optionally substituted 5-membered heterocyclic ring, or optionally substituted 6-membered heterocyclic ring. In certain embodiments, the $R^D$ groups are joined to form an unsubstituted heterocyclic ring. However, in certain embodiments, the $R^D$ groups are joined to form a substituted heterocyclic ring, e.g., substituted with one or more alkyl groups.

In certain embodiments, two $R^N$ groups are joined to form an optionally substituted heterocyclic ring, e.g., an optionally substituted 3- to 6-membered heterocyclic ring. In certain embodiments, two $R^N$ groups are joined to form an optionally substituted 5-membered heterocyclic ring, or optionally substituted 6-membered heterocyclic ring. In certain embodiments, the $R^N$ groups are joined to form an unsubstituted heterocyclic ring. However, in certain embodiments, the $R^N$ groups are joined to form a substituted heterocyclic ring, e.g., substituted with one or more alkyl groups.

In certain embodiments, one $R^N$ group and one $R^D$ group (e.g., wherein the N atom to which the $R^N$ group is attached and the $R^D$ group are joined to the same carbon atom) are joined to form an optionally substituted heterocyclic ring, e.g., an optionally substituted 3- to 6-membered heterocyclic ring. In certain embodiments, one $R^N$ group and one $R^D$ group are joined to form an optionally substituted 5-membered heterocyclic ring, or optionally substituted 6-membered heterocyclic ring. In certain embodiments, one $R^N$ group and one $R^D$ group are joined to form an unsubstituted heterocyclic ring. However, in certain embodiments, one $R^N$ group and one $R^D$ group are joined to form a substituted heterocyclic ring, e.g., substituted with one or more alkyl groups.

In certain embodiments, Ring A ($R^W$ or $R^4$) is of Formula (q-18)-(q-31):

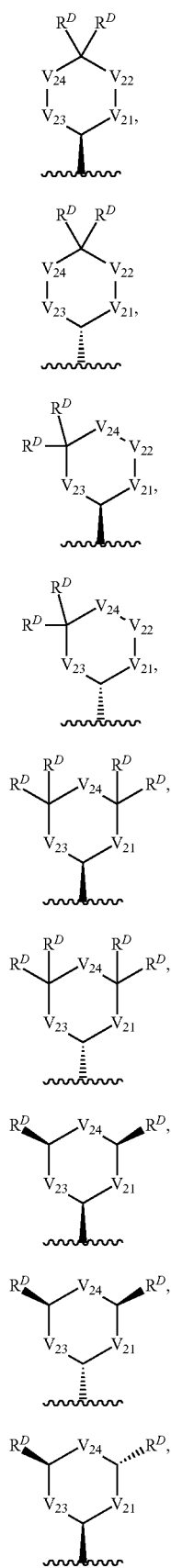
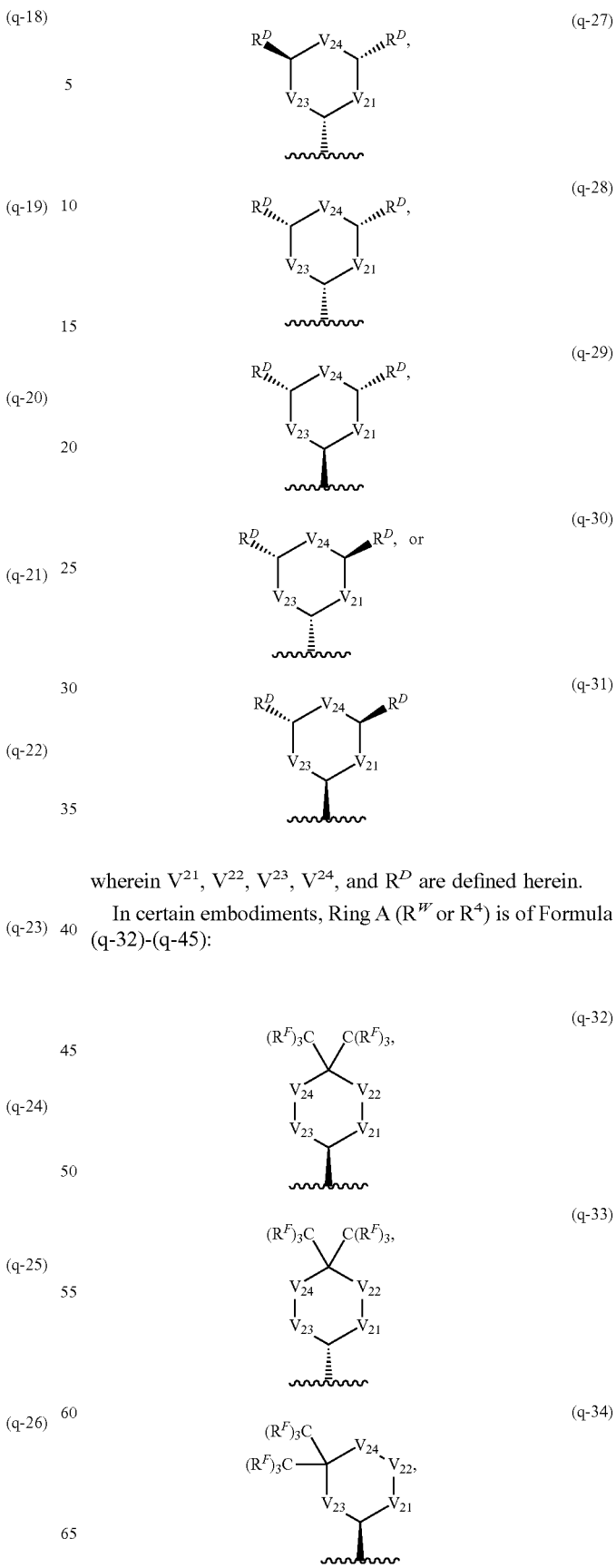
wherein $V^{21}$, $V^{22}$, $V^{23}$, $V^{24}$, and $R^D$ are defined herein.
In certain embodiments, Ring A ($R^W$ or $R^4$) is of Formula (q-32)-(q-45):

(q-35)
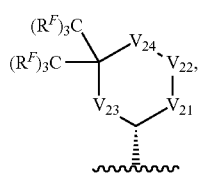
(q-36)
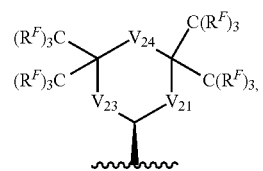
(q-37)
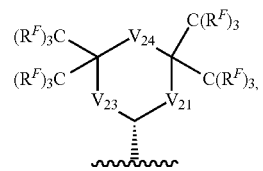
(q-38)
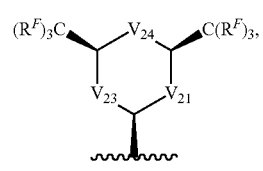
(q-39)
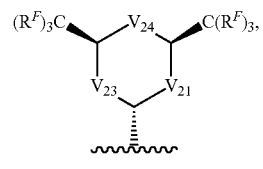
(q-40)
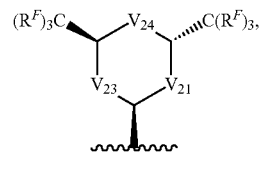
(q-41)
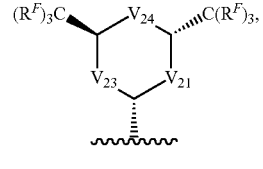
(q-42)
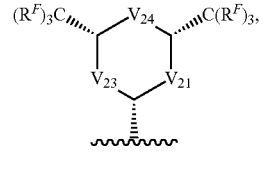
(q-43)
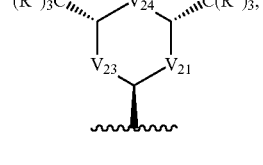
(q-44)
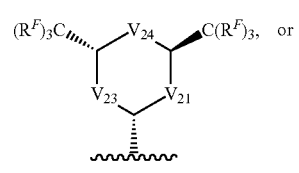
or
(q-45)
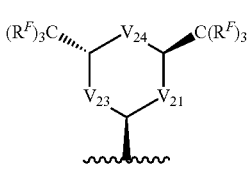
wherein $V^{21}$, $V^{22}$, $V^{23}$, $V^{24}$, and $R^F$ are defined herein.
In certain embodiments, Ring A ($R^W$ or $R^4$) is of Formula (q-46)-(q-49):
(q-46)
(q-47)
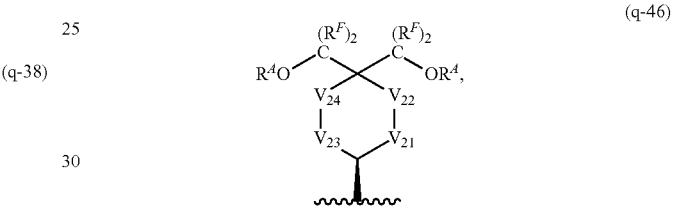
(q-48)
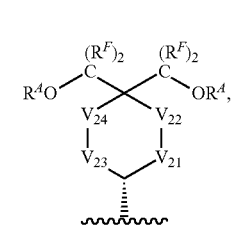
or
(q-49)
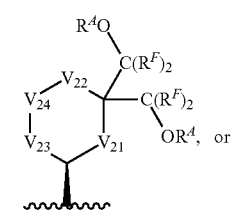
wherein $V^{21}$, $V^{22}$, $V^{23}$, $V^{24}$, $R^A$, and $R^F$ are defined herein.
In certain embodiments, Ring A ($R^W$ or $R^4$) is of Formula (q-50)-(q-57):

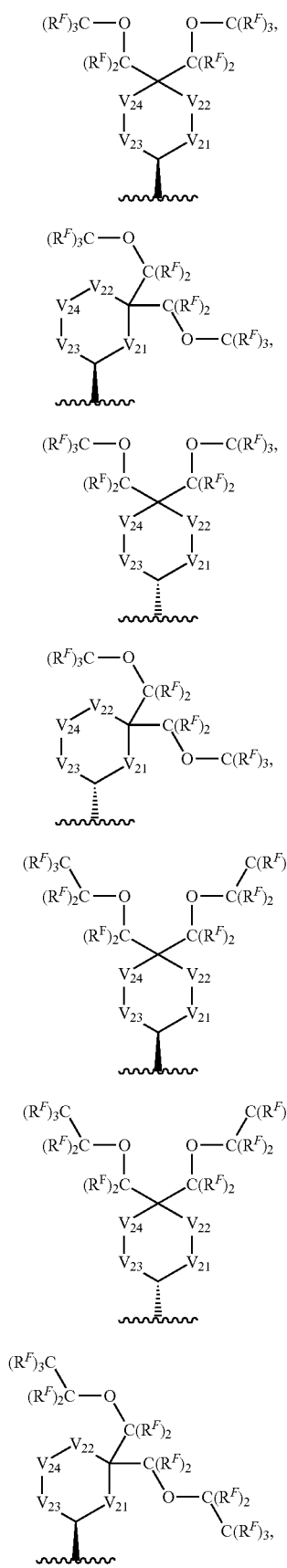
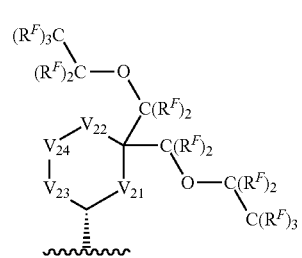
wherein $V^{21}$, $V^{22}$, $V^{23}$, $V^{24}$, and $R^F$ are defined herein.
In certain embodiments, Ring A ($R^W$ or $R^4$) is of Formula (q-58)-(q-72):
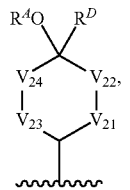

(q-64) 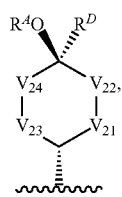
(q-65) 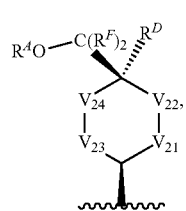
(q-66) 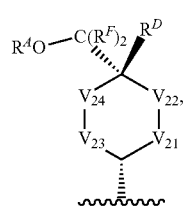
(q-67) 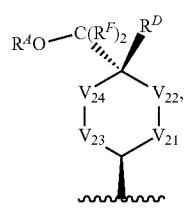
(q-68) 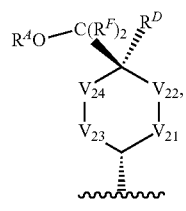
(q-69) 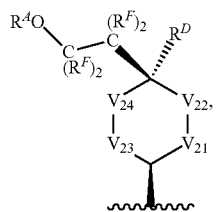
(q-70) 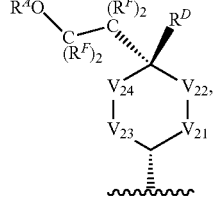
(q-71) 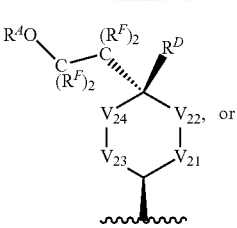 or
(q-72) 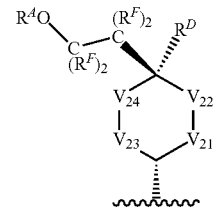
wherein $V^{21}$, $V^{22}$, $V^{23}$, $V^{24}$, $R^A$, $R^D$, and R are defined herein.
In certain embodiments, Ring A ($R^W$ or $R^4$) is of Formula (q-73) and (q-76)-(q-79):
(q-73) 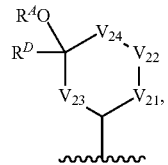
(q-76) 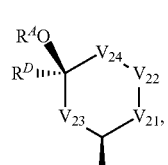
(q-77) 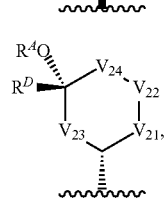
(q-78) 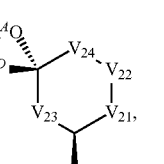 or
(q-79) 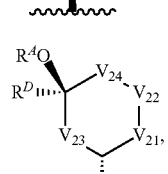
wherein $V^{21}$, $V^{22}$, $V^{23}$, $V^{24}$, $R^A$, $R^D$, and $R^F$ are defined herein.
In certain embodiments, Ring A ($R^W$ or $R^4$) is of Formula (q-74), (q-75) and (q-80)-(q-87):

(q-74)
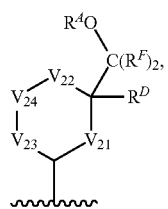
(q-75)
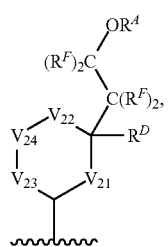
(q-80)
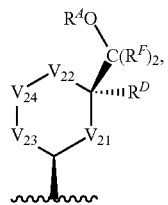
(q-81)
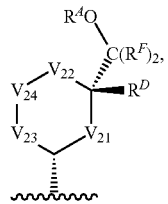
(q-82)
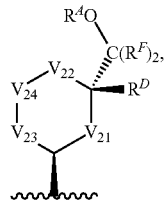
(q-83)
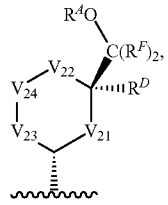
(q-84)
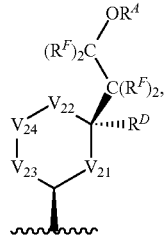
(q-85)
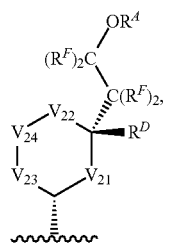
(q-86) or
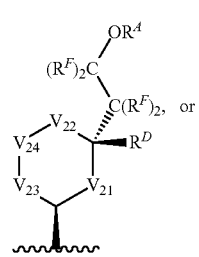
(q-87)
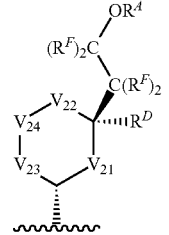
wherein $V^{21}$, $V^{22}$, $V^{23}$, $V^{24}$, $R^A$, $R^D$, and $R^F$ are defined herein.
In certain embodiments, Ring A ($R^W$ or $R^4$) is of Formula (q-88)-(q-102):
(q-88)
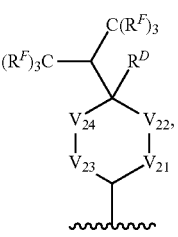
(q-89)
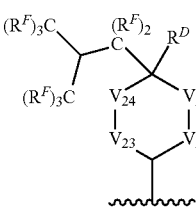
(q-90)
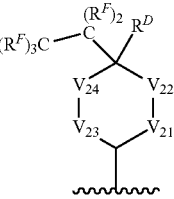

(q-91) 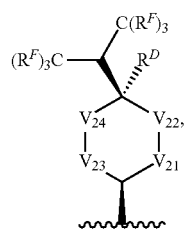
(q-92) 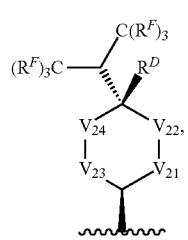
(q-93) 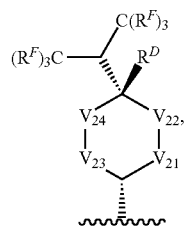
(q-94) 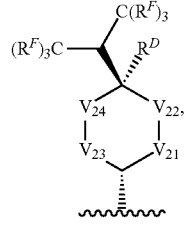
(q-95) 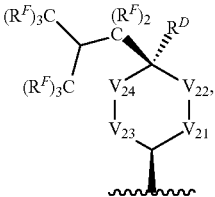
(q-96) 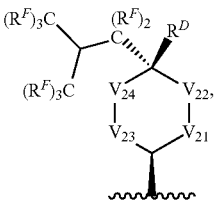
(q-97) 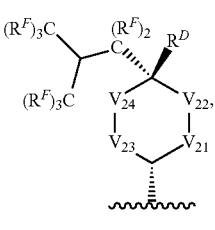
(q-98) 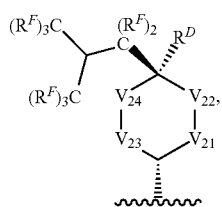
(q-99) 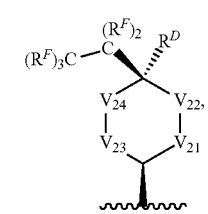
(q-100) 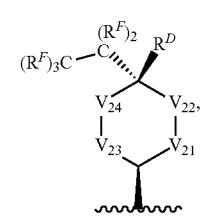
(q-101) 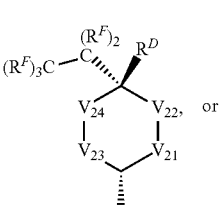
or
(q-102) 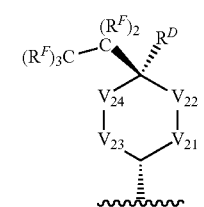
wherein $V^{21}$, $V^{22}$, $V^{23}$, $V^{24}$, $R^D$, and $R^F$ are defined herein.
In certain embodiments, Ring A ($R^W$ or $R^4$) is of Formula (q-103)-(q-117):
(q-103) 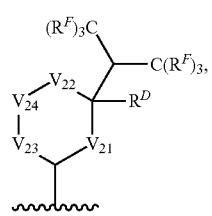

-continued
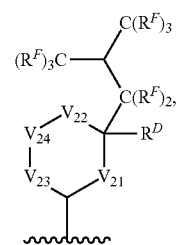
(q-104)
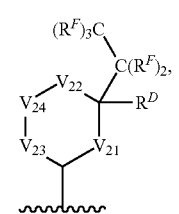
(q-105)
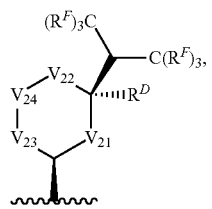
(q-106)
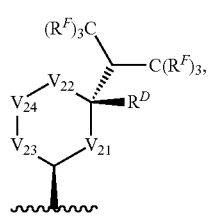
(q-107)
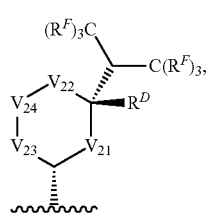
(q-108)
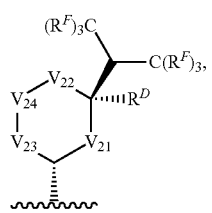
(q-109)
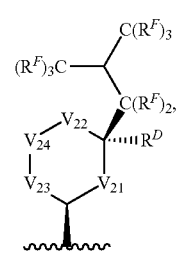
(q-110)
-continued
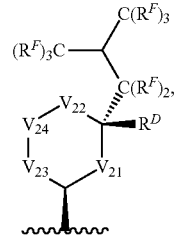
(q-111)
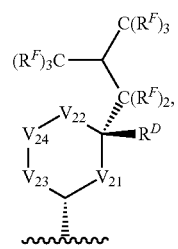
(q-112)
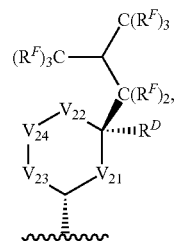
(q-113)
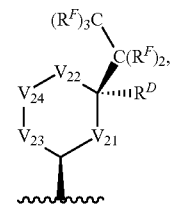
(q-114)
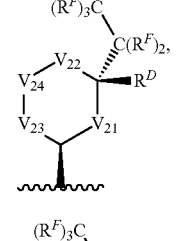
(q-115)
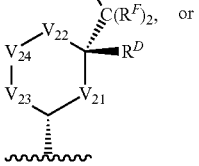
, or (q-116)
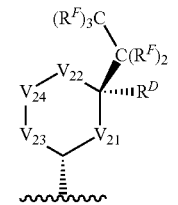
(q-117)
wherein $V^{21}$, $V^{22}$, $V^{23}$, $V^{24}$, $R^D$, and $R^F$ are defined herein.

In certain embodiments, Ring A ($R^W$ or $R^4$) is of Formula (q-7a)-(q-17a):
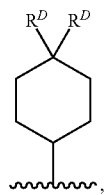 (q-7a)
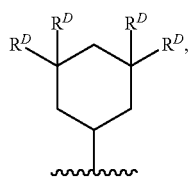 (q-8a)
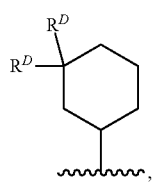 (q-9a)
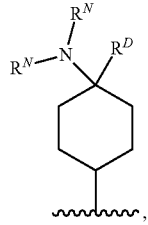 (q-10a)
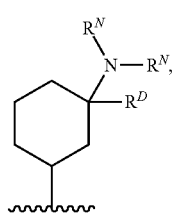 (q-11a)
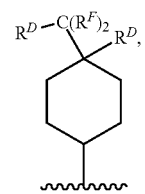 (q-12a)
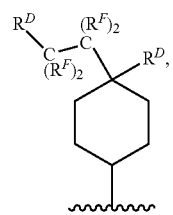 (q-13a)
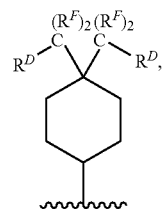 (q-14a)
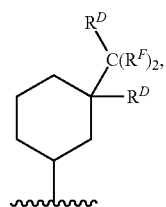 (q-15a)
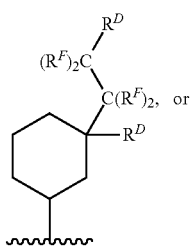 (q-16a)
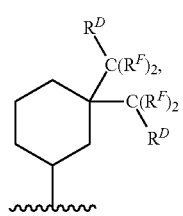 (q-17a)
wherein $R^D$, $R^N$, and $R^F$ are defined herein.
In certain embodiments, Ring A ($R^W$ or $R^4$) is of Formula (q-18a)-(q-31a):
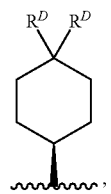 (q-18a)
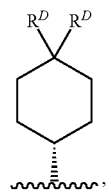 (q-19a)
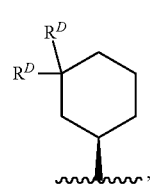 (q-20a)

(q-21a) 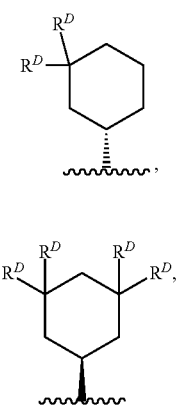
(q-22a)
(q-23a) 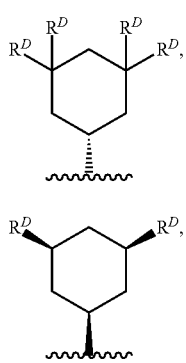
(q-24a)
(q-25a) 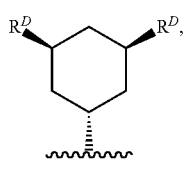
(q-26a) 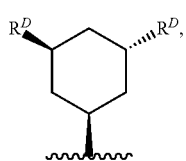
(q-27a) 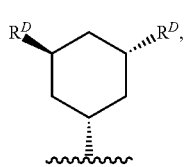
(q-28a) 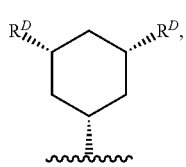
(q-29a) 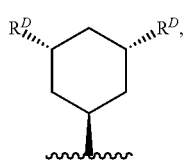
(q-30a) 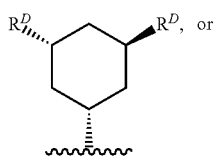 or
(q-31a) 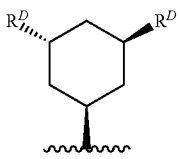
wherein $R^D$ is defined herein.
In certain embodiments, Ring A ($R^W$ or $R^4$) is of Formula (q-32a)-(q-45a):
(q-32a) 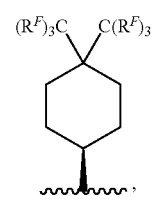
(q-33a)
(q-34a) 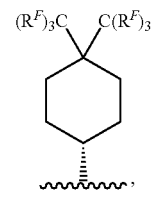
(q-35a) 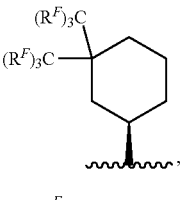
(q-36a) 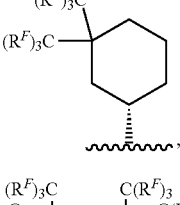
(q-37a) 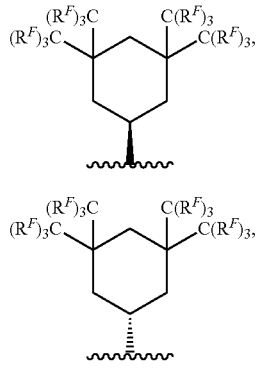

-continued
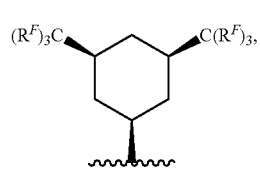
(q-38a)
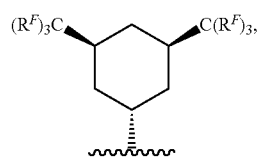
(q-39a)
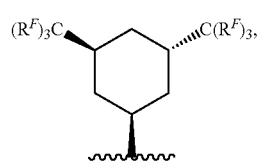
(q-40a)
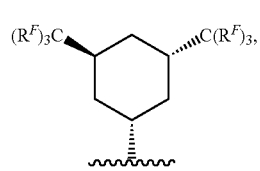
(q-41a)
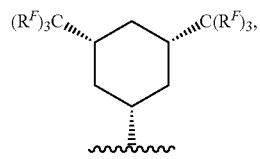
(q-42a)
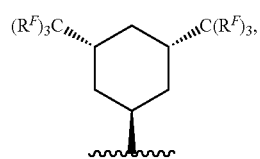
(q-43a)
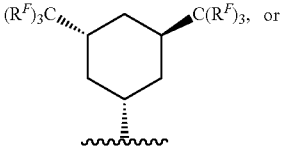
(q-44a), or
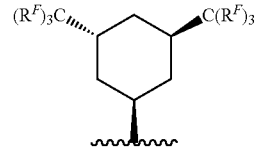
(q-45a)
wherein $R^F$ is defined herein.
In certain embodiments, Ring A $R^W$ or R) is of Formula (q-46a)-(q-49a):
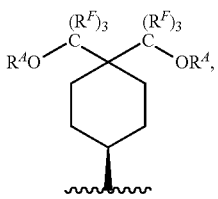
(q-46a)
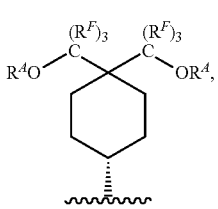
(q-47a)
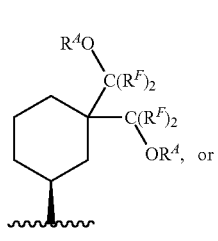
(q-48a)
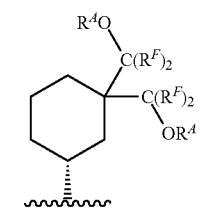
(q-49a)
wherein $R^A$ and $R^F$ are defined herein.
In certain embodiments, Ring A ($R^W$ or $R^4$) is of Formula (q-50a)-(q-57a):
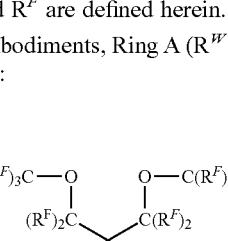
(q-50a)
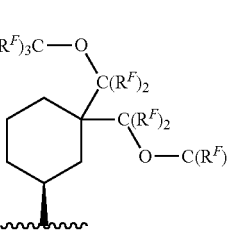
(q-51a)

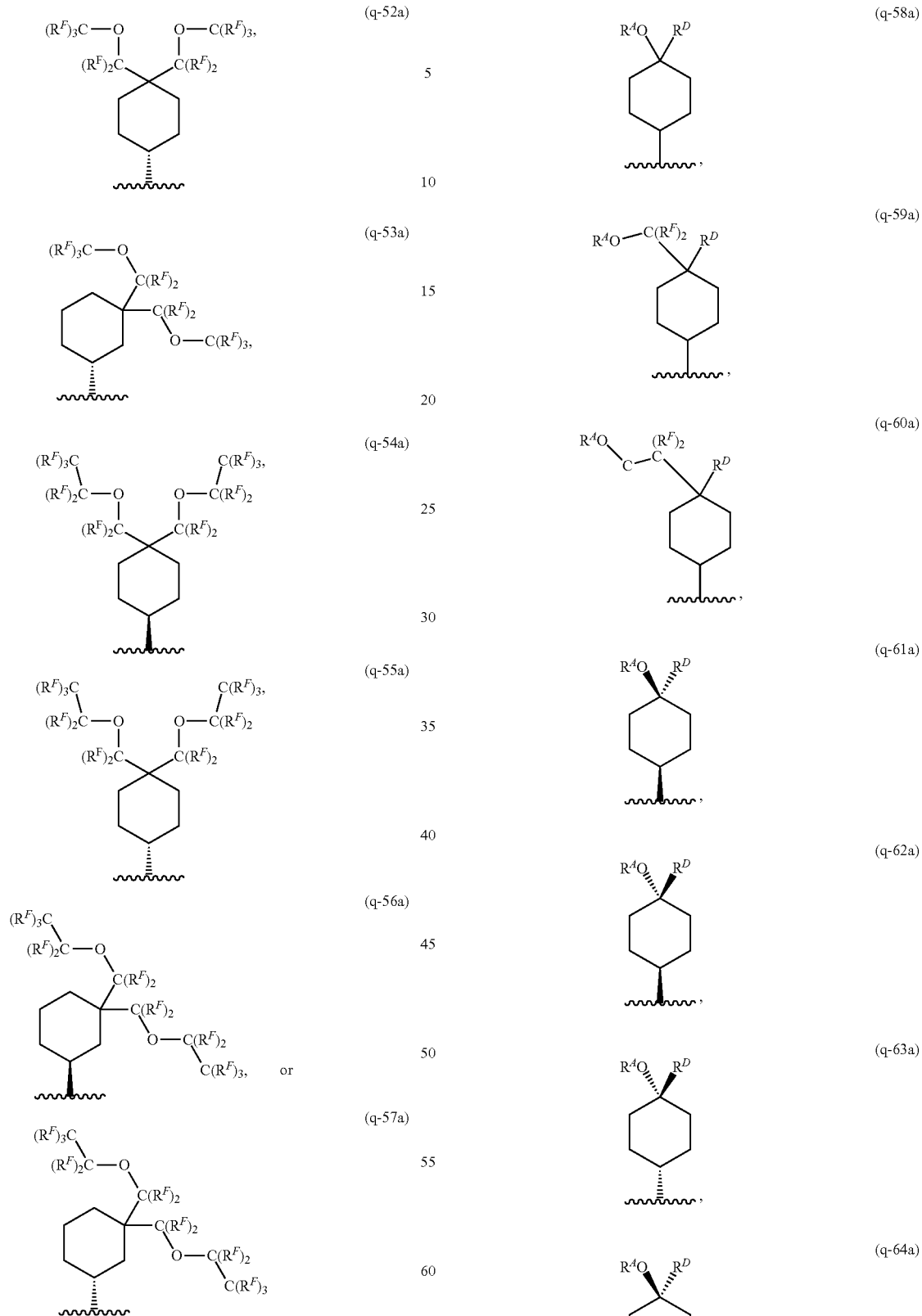
wherein $R^F$ is defined herein.
In certain embodiments, Ring A ($R^W$ or $R^4$) is of Formula (q-58a)-(q-72a):

(q-65a)
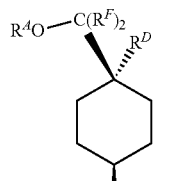
(q-66a)
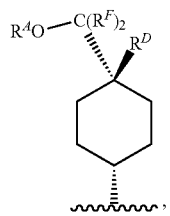
(q-67a)
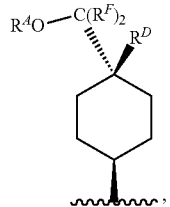
(q-68a)
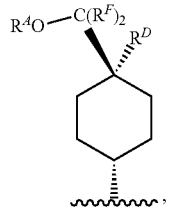
(q-69a)
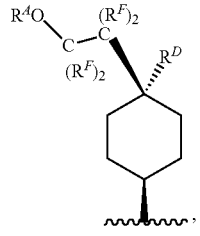
(q-70a)
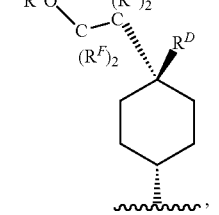
(q-71a)
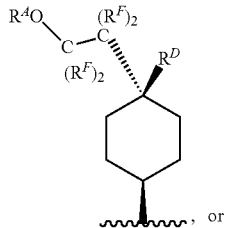, or
(q-72a)
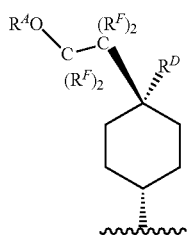
wherein $R^A$, $R^D$, and $R^F$ are defined herein.
In certain embodiments, $R^W$ (or Ring A) or $R^4$ (as provided in the above recited instance) is of Formula (q-73a), and (q-76a)-(q-79a):
(q-73a)
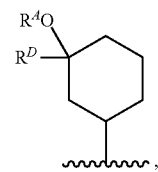
(q-76a)
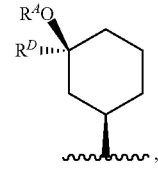
(q-77a)
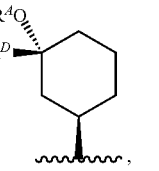
(q-78a)
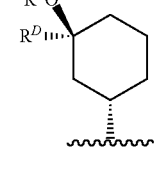, or
(q-79a)
wherein $R^A$, $R^D$, and $R^F$ are defined herein.
In certain embodiments, Ring A ($R^W$ or $R^4$) is of Formula (q-74a), (q-75a) and (q-80a)-(q-87a):

(q-74a) 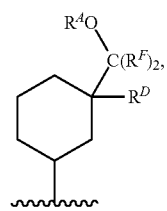
(q-75a) 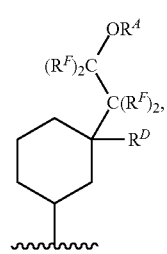
(q-80a) 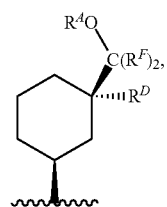
(q-81a) 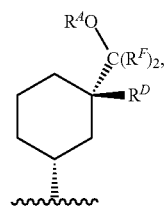
(q-82a) 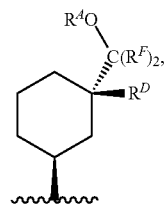
(q-83a) 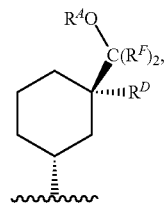
(q-84a) 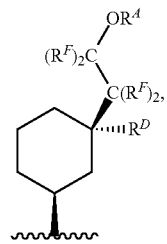
(q-85a) 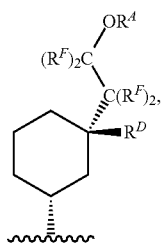
(q-86a) 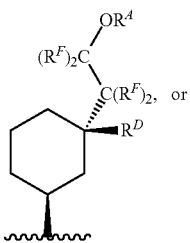, or
(q-87a) 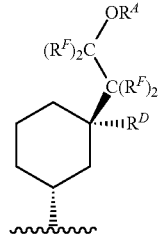
wherein $R^A$, $R^D$, and $R^F$ are defined herein.
In certain embodiments, Ring A ($R^W$ or $R^4$) is of Formula (q-88a)-(q-102a):
(q-88a) 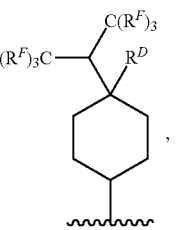
(q-89a) 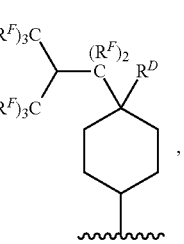
(q-90a) 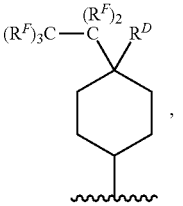

(q-91a) 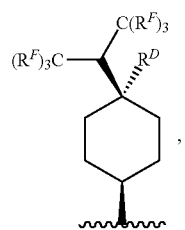
(q-92a) 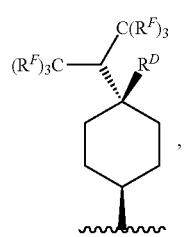
(q-93a) 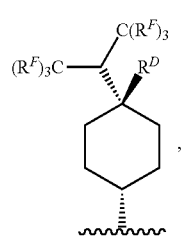
(q-94a) 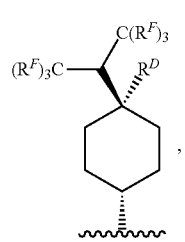
(q-95a) 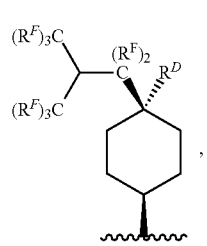
(q-96a) 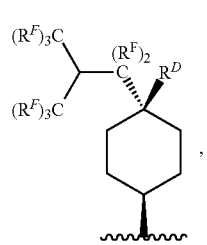
(q-97a) 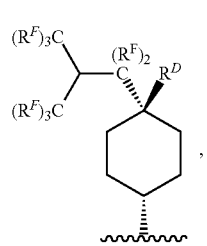
(q-98a) 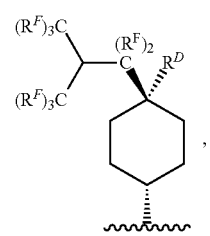
(q-99a) 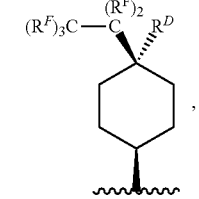
(q-100a) 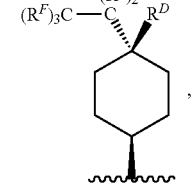
(q-101a) 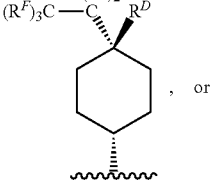
, or
(q-102a) 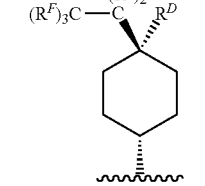
wherein $R^D$, and $R^F$ are defined herein.
In certain embodiments, Ring A ($R^W$ or $R^4$) is of Formula (q-103a)-(q-117a):
(q-103a) 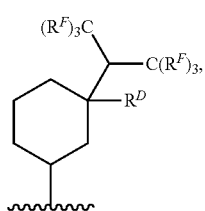

(q-104a)
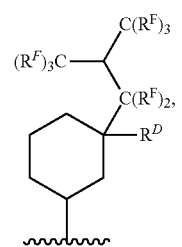
(q-105a)
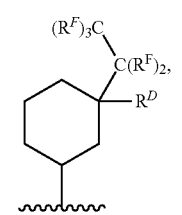
(q-106a)
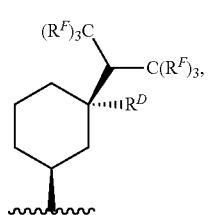
(q-107a)
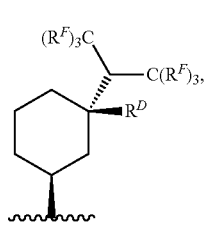
(q-108a)
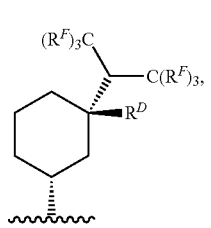
(q-109a)
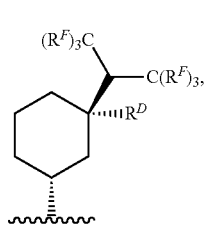
(q-110a)
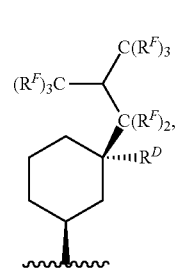
(q-111a)
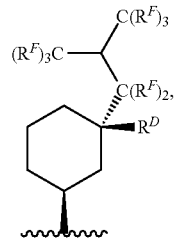
(q-112a)
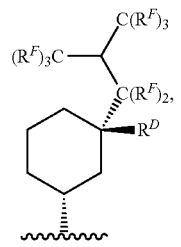
(q-113a)
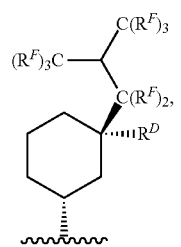
(q-114a)
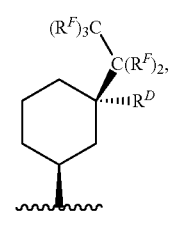
(q-115a)
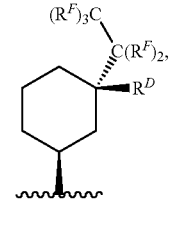
(q-116a) or
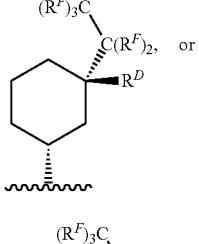
(q-117a)
wherein $V^{21}$, $V^{22}$, $V^{23}$, $V^{24}$, $R^D$, and $R^F$ are defined herein.

In certain embodiments, wherein, for example, 2 $R^D$ groups are joined to form a $C_{5-6}$ membered carbocyclic ring, or a 5-6-membered heterocyclic ring, Formula (q-7) is of Formula (r-1) and (r-2):

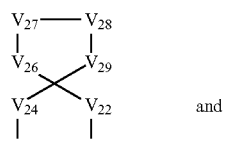
(r-1)

and

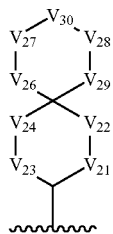
(r-2)

and Formula (q-9) is of Formula (r-3) and (r-4):

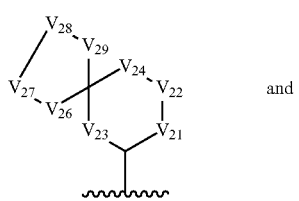
(r-3)

and

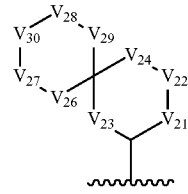
(r-4)

wherein:

$V^{21}$, $V^{22}$, $V^{23}$, and $V^{24}$ are as defined herein;

$V^{26}$, $V^{27}$, $V^{28}$, $V^{29}$, and $V^{30}$ are each independently O, S, $NR^{Na}$, C=O, or $C(R^E)_2$ as valency permits, provided no more than two of $V^{26}$, $V^{27}$, $V^{28}$, $V^{29}$, and $V^{30}$ is a heteroatom O, S, and $NR^{Na}$; alternatively wherein one of $V^{26}$, $V^{27}$, $V^{28}$, $V^{29}$, and $V^{30}$ and another of $V^{26}$, $V^{27}$, $V^{28}$, $V^{29}$, and $V^{30}$ adjacent to each other are joined to form an $N=C(R^E)$ or $C(R^E)=C(R^E)$ group;

each instance of $R^E$ is independently hydrogen, halo, —CN, —$NO_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, —$SR^A$, —C(=O)$R^A$, —C(O)$OR^A$, —C(O)$SR^A$, —C(O)N($R^B$)$_2$, —C(O)N($R^B$)N($R^B$)$_2$, —OC(O)$R^A$, —OC(O)N($R^B$)$_2$, —$NR^B$C(O)$R^A$, —$NR^B$C(O)N($R^B$)$_2$, —$NR^B$C(O)N($R^B$)N($R^B$)$_2$, —$NR^B$C(O)$OR^A$, —SC(O)$R^A$, —C(=$NR^B$)$R^A$, —C(=$NNR^B$)$R^A$, —C(=$NOR^A$)$R^A$, —C(=$NR^B$)N($R^B$)$_2$, —$NR^B$C(=$NR^B$)$R^B$, —C(=S)$R^A$, —C(=S)N($R^B$)$_2$, —$NR^B$C(=S)$R^A$, —S(O)$R^A$, —OS(O)$_2R^A$, —$SO_2R^A$, —$NR^B SO_2R^A$, or —$SO_2N(R^B)_2$; or two $R^E$ groups are joined to form an optionally substituted carbocyclic or optionally substituted heterocyclic ring; and each instance of $R^{Na}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)$R^A$, —C(=O)$OR^A$, —C(=O)$SR^A$, —C(=O)N($R^B$)$_2$, —C(=$NR^B$)$R^A$, —C(=$NNR^B$)$R^A$, —C(=$NOR^A$)$R^A$, —C(=$NR^B$)N($R^B$)$_2$, —C(=S)$R^A$, —C(=S)N($R^B$)$_2$, —S(=O)$R^A$, —$SO_2R^A$, —$SO_2N(R^B)_2$, or a nitrogen protecting group.

In certain embodiments, Formula (q-7) or (q-9) is of Formula (r-5) to (r-24):

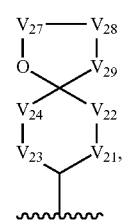
(r-5)

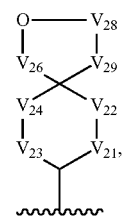
(r-6)

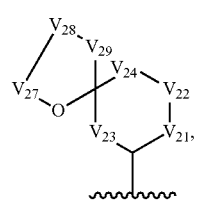
(r-7)

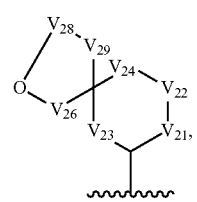
(r-8)

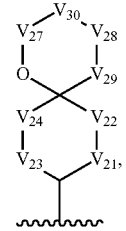
(r-9)

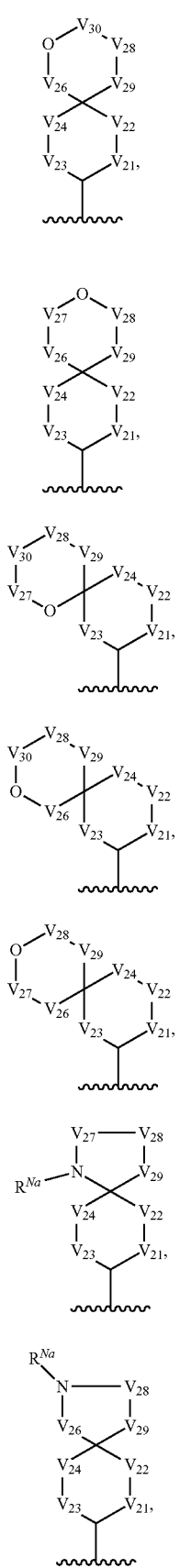
(r-10)
(r-11)
(r-12)
(r-13)
(r-14)
(r-15)
(r-16)
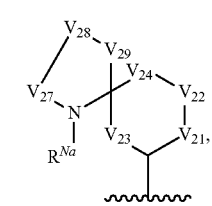
(r-17)
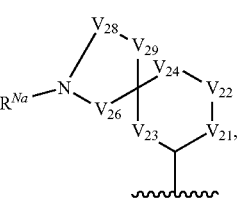
(r-18)
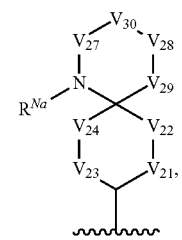
(r-19)
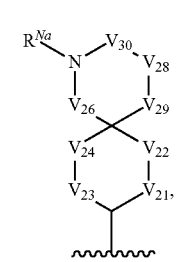
(r-20)
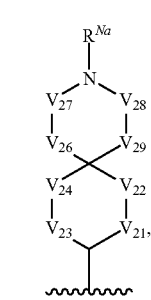
(r-21)
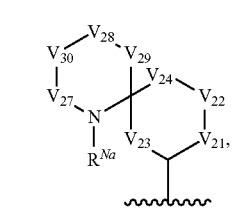
(r-22)
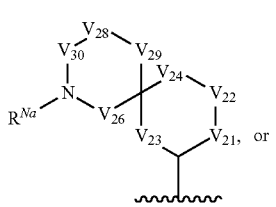
(r-23)

-continued
(r-24)
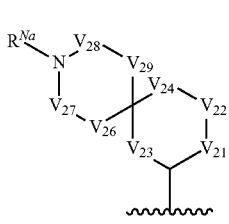
wherein $V^{21}$, $V^{22}$, $V^{23}$, $V^{24}$, $V^{26}$, $V^{27}$, $V^{28}$, $V^{29}$, $V^{30}$, and $R^{Na}$ are defined herein.
In certain embodiments, Formula (q-7) or (q-9) is of Formula (r-25) to (r-44):
(r-25)
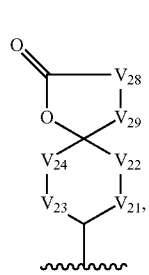
(r-26)
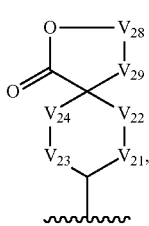
(r-27)
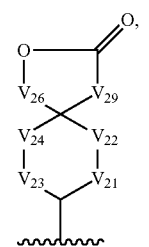
(r-28)
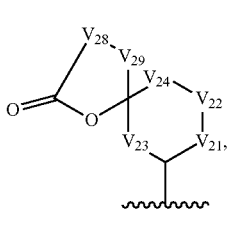
(r-29)
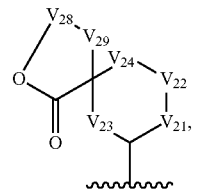
-continued
(r-30)
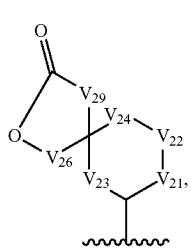
(r-31)
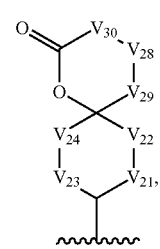
(r-32)
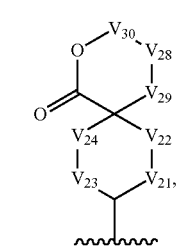
(r-33)
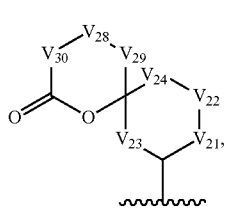
(r-34)
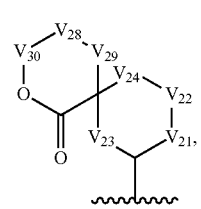
(r-35)
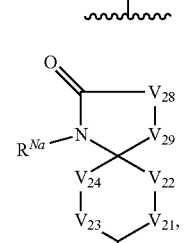
(r-36)
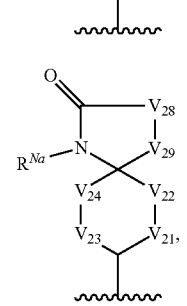

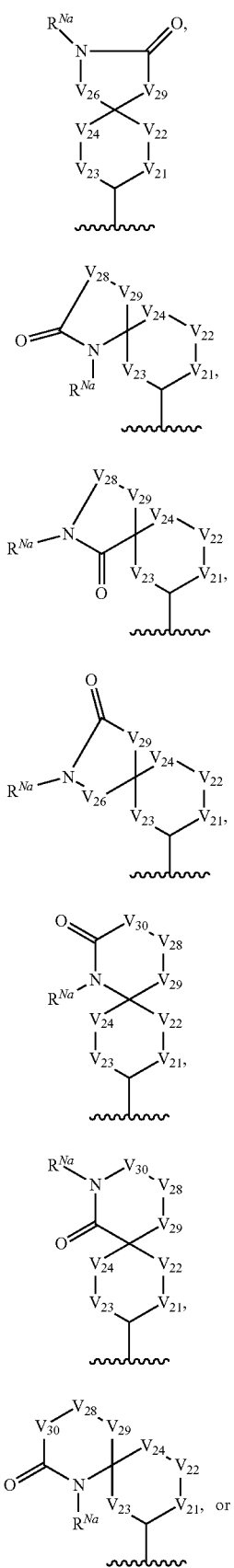
(r-37)
(r-38)
(r-39)
(r-40)
(r-41)
(r-42)
(r-43) or
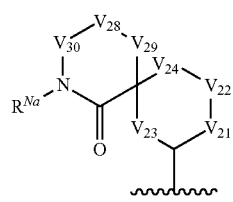
(r-44)
wherein $V^{21}$, $V^{22}$, $V^{23}$, $V^{24}$, $V^{26}$, $V^{27}$, $V^{28}$, $V^{29}$, $V^{30}$, and $R^{Na}$ are defined herein.
In certain embodiments, Formula (q-7) or (q-9) is of Formula (r-45) to (r-68):
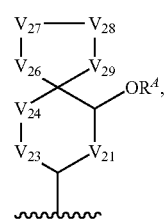
(r-45)
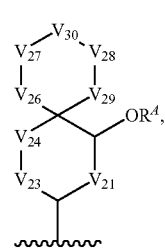
(r-46)
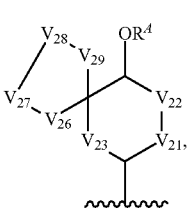
(r-47)
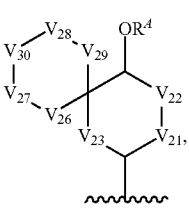
(r-48)
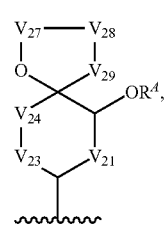
(r-49)

-continued
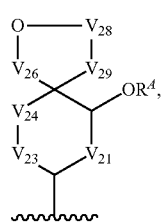
(r-50)
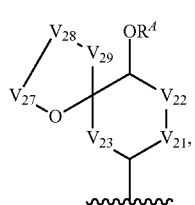
(r-51)
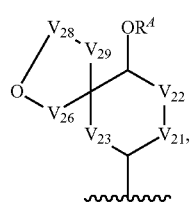
(r-52)
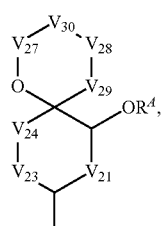
(r-53)
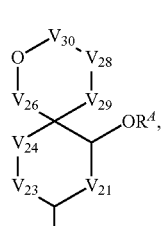
(r-54)
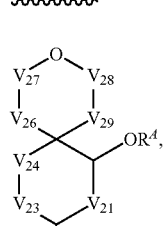
(r-55)
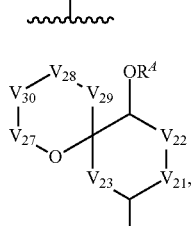
(r-56)
-continued
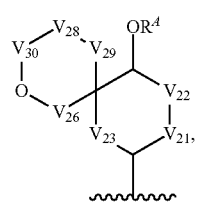
(r-57)
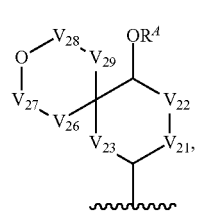
(r-58)
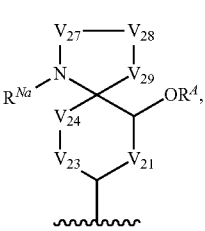
(r-59)
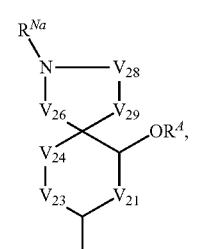
(r-60)
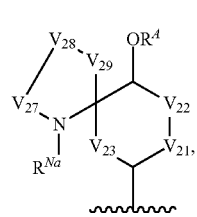
(r-61)
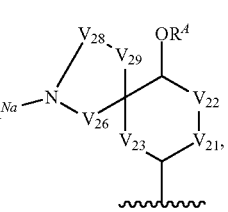
(r-62)
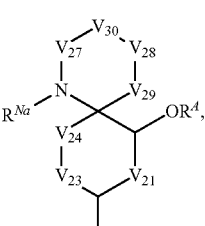
(r-63)

(r-64)
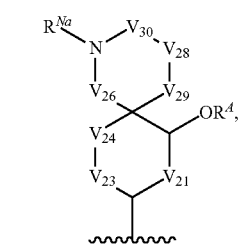
(r-65)
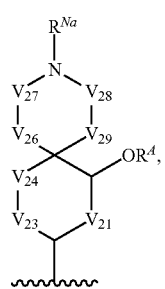
(r-66)
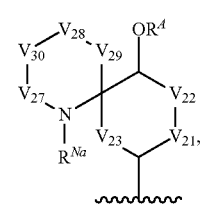
(r-67)
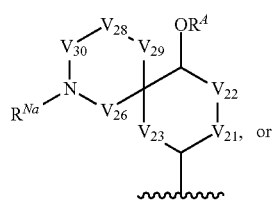
(r-68)
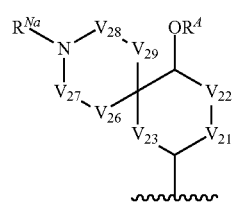
wherein $V^{21}$, $V^{22}$, $V^{23}$, $V^{24}$, $V^{26}$, $V^{27}$, $V^{28}$, $V^{29}$, $V^{30}$, $R^{Na}$, and $R^A$ are defined herein.
In certain embodiments, Formula (q-7) or (q-9) is of Formula (r-69) to (r-76):
(r-69)
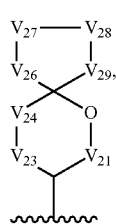
(r-70)
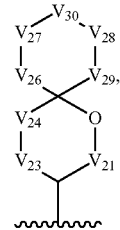
(r-71)
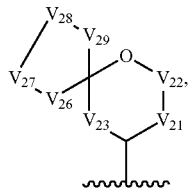
(r-72)
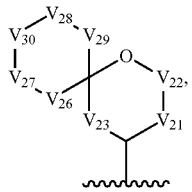
(r-73)
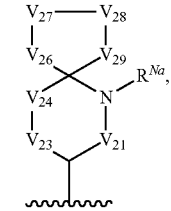
(r-74)
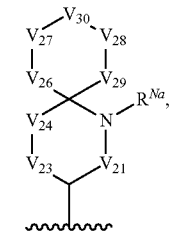
(r-75)
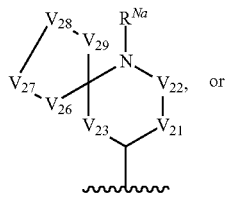
(r-76)
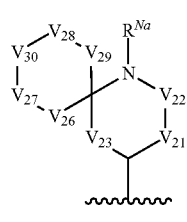
wherein $V^{21}$, $V^{22}$, $V^{23}$, $V^{24}$, $V^{26}$, $V^{27}$, $V^{28}$, $V^{29}$, $V^{30}$, and $R^{Na}$ are defined herein.
In certain embodiments, Formula (q-7) or (q-9) is of Formula (r-77) to (r-99):

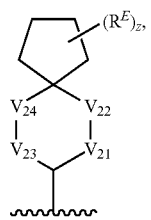 (r-77)
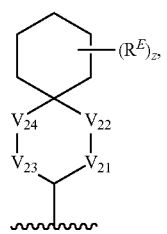 (r-78)
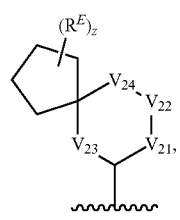 (r-79)
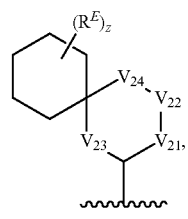 (r-80)
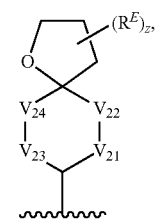 (r-81)
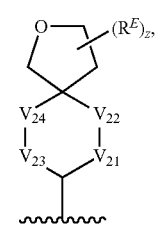 (r-82)
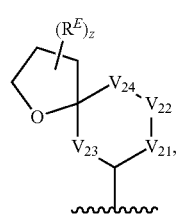 (r-83)
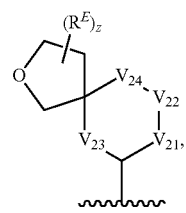 (r-84)
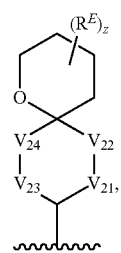 (r-85)
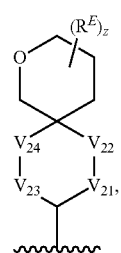 (r-86)
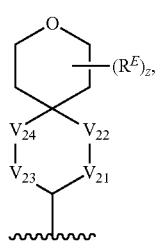 (r-87)
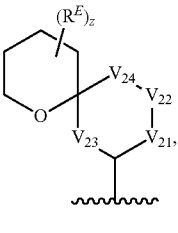 (r-88)
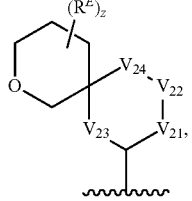 (r-89)
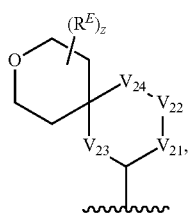 (r-90)

(r-91) 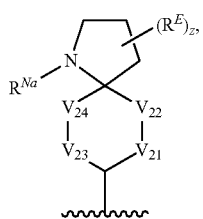
(r-91) 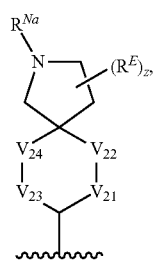
(r-92) 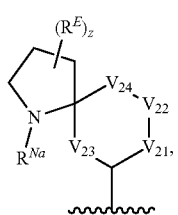
(r-93) 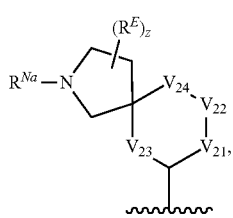
(r-94) 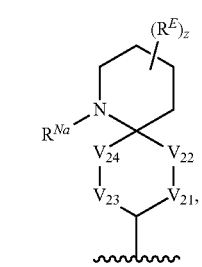
(r-95) 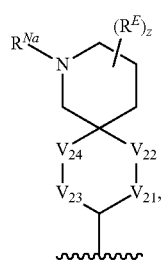
(r-96) 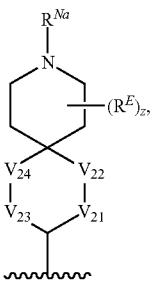
(r-97) 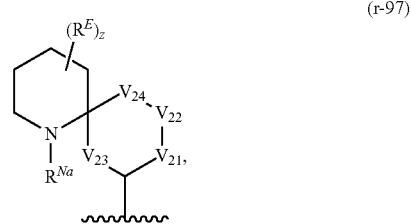
(r-98) 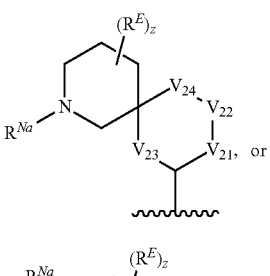, or
(r-99) 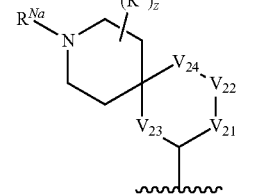
wherein $V^{21}$, $V^{22}$, $V^{23}$, $V^{24}$, $R^E$, and $R^{Na}$ are defined herein, and z is 0, 1, 2, 3, or 4.
In certain embodiments, Formula (q-7) or (q-9) is of Formula (r-100) to (r-119):
(r-100) 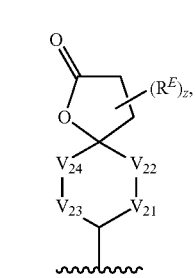
(r-101) 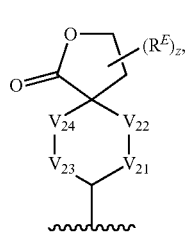

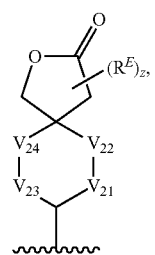
(r-102)
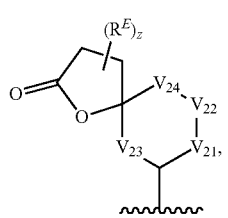
(r-103)
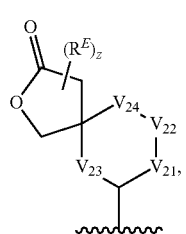
(r-104)
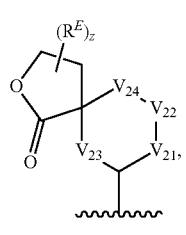
(r-105)
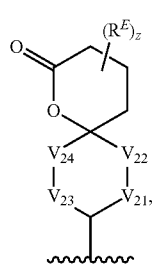
(r-106)
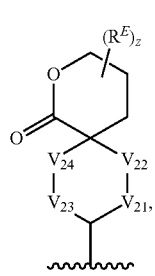
(r-107)
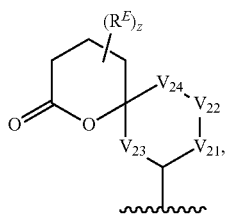
(r-108)
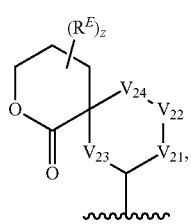
(r-109)
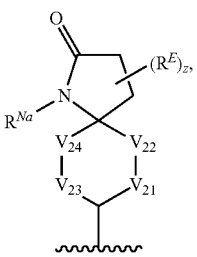
(r-110)
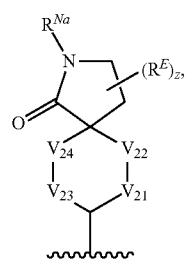
(r-111)
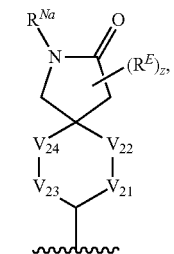
(r-112)
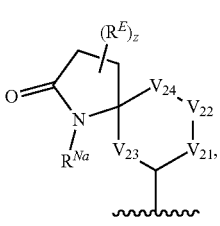
(r-113)

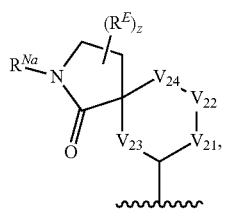 (r-114)
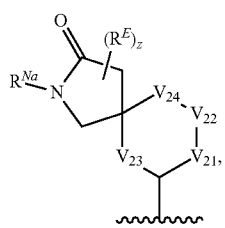 (r-115)
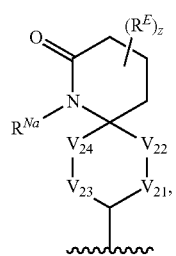 (r-116)
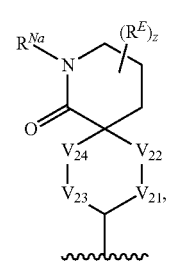 (r-117)
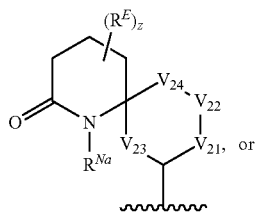 (r-118), or
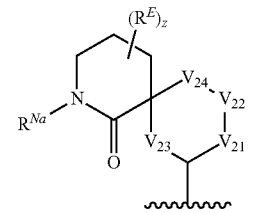 (r-119)
wherein $V^{21}$, $V^{22}$, $V^{23}$, $V^{24}$, $R^E$, and $R^{Na}$ are defined herein, and z is 0, 1, 2, 3, or 4.
In certain embodiments, Formula (q-7) is of Formula (r-120) to (r-143):
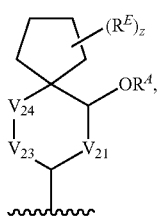 (r-120)
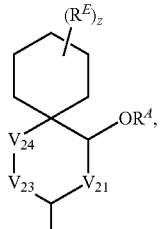 (r-121)
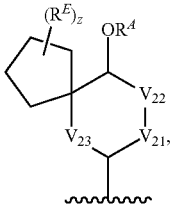 (r-122)
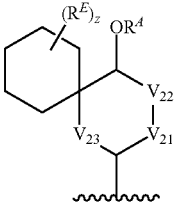 (r-123)
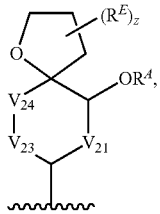 (r-124)
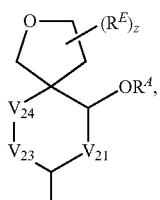 (r-125)
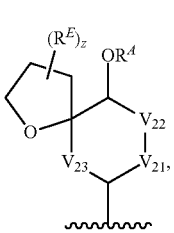 (r-126)

-continued
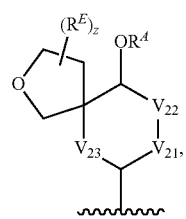 (r-127)
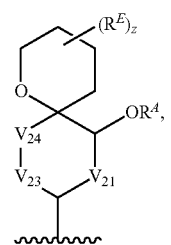 (r-128)
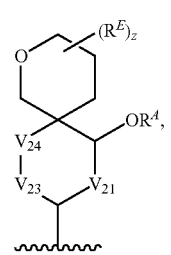 (r-129)
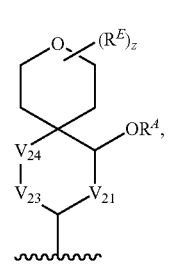 (r-130)
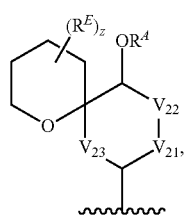 (r-131)
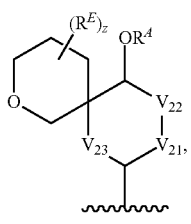 (r-132)
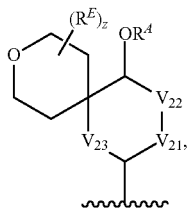 (r-133)
-continued
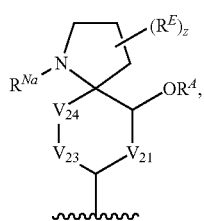 (r-134)
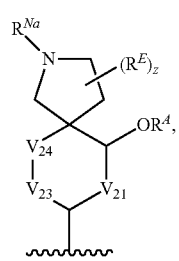 (r-135)
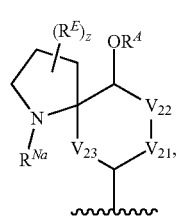 (r-136)
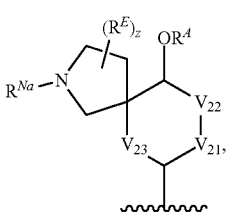 (r-137)
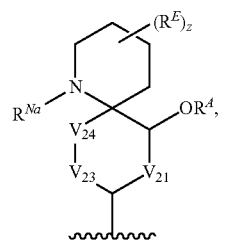 (r-138)
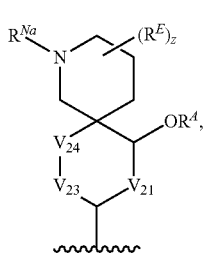 (r-139)

-continued
(r-140)
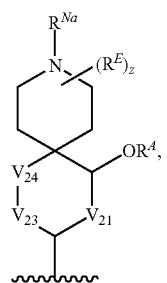
(r-141)
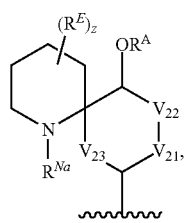
(r-142)
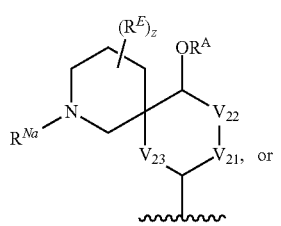
(r-143)
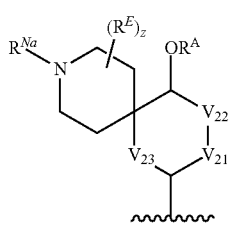
wherein $V^{21}$, $V^{22}$, $V^{23}$, $V^{24}$, $R^A$, $R^E$, and $R^{Na}$ are defined herein, and z is 0, 1, 2, 3, or 4.
In certain embodiments, Formula (q-7) is of Formula (r-144) to (r-147):
(r-144)
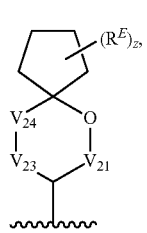
(r-145)
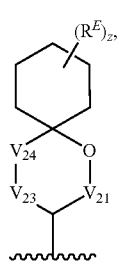
-continued
(r-146)
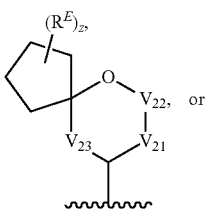
(r-147)
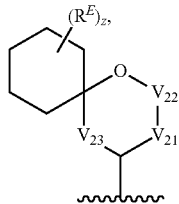
wherein $V^{21}$, $V^{22}$, $V^{23}$, $V^{24}$, and $R^E$ are defined herein, and z is 0, 1, 2, 3, or 4.
In certain embodiments, Formula (q-7) is of Formula (r-148) to (r-161):
(r-148)
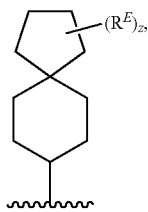
(r-149)
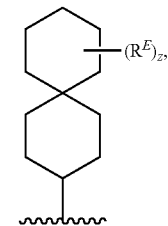
(r-150)
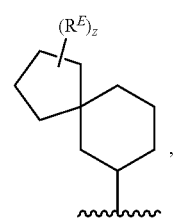
(r-151)
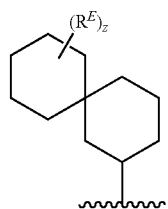

-continued
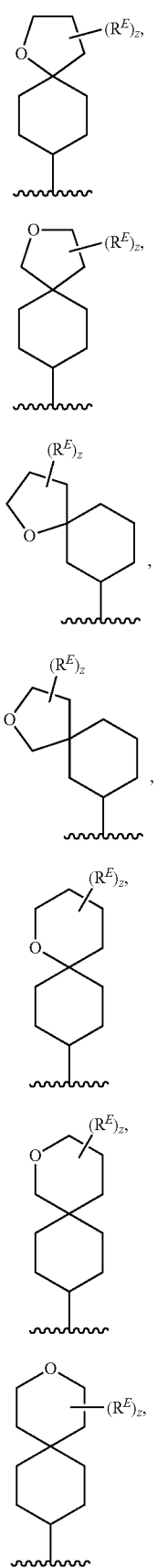
(r-152)
(r-153)
(r-154)
(r-155)
(r-156)
(r-157)
(r-158)
-continued
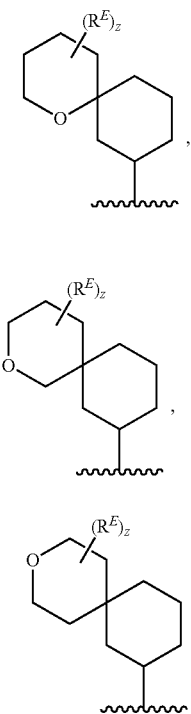
(r-159)
(r-160)
(r-161)
wherein $R^E$ is as defined herein, and z is 0, 1, 2, 3, or 4.
In certain embodiments, Formula (q-7) is of Formula (r-162) to (r-173):
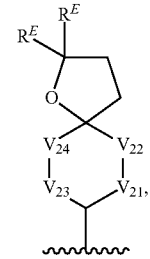
(r-162)
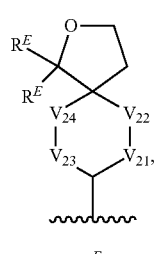
(r-163)
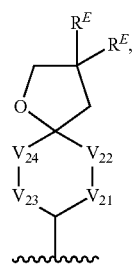
(r-164)

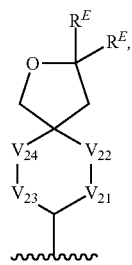 (r-165)
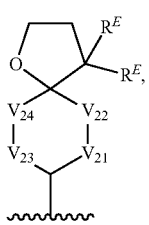 (r-166)
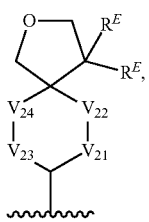 (r-167)
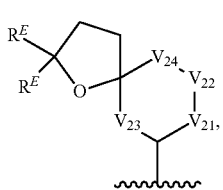 (r-168)
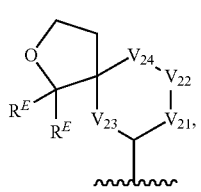 (r-169)
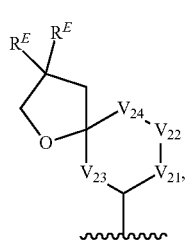 (r-170)
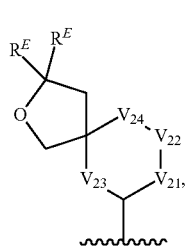 (r-171)
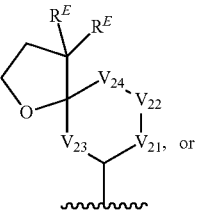 (r-172), or
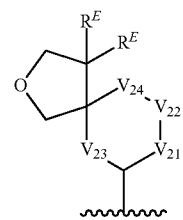 (r-173)
wherein $V^{21}$, $V^{22}$, $V^{23}$, $V^{24}$, and $R^E$ are defined herein.
In certain embodiments, Formula (q-7) is of Formula (r-174) to (r-185):
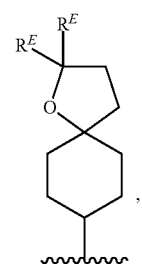 (r-174)
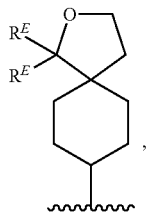 (r-175)
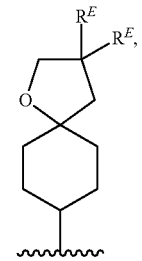 (r-176)
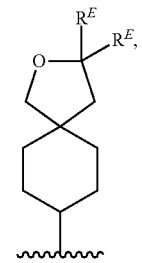 (r-177)

(r-178) 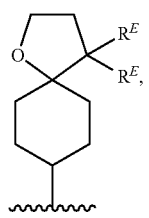
(r-179) 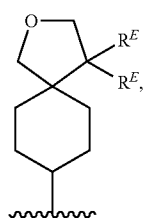
(r-180) 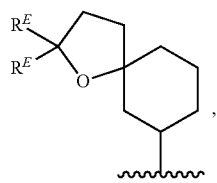
(r-181) 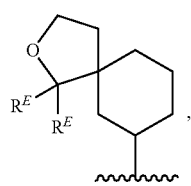
(r-182) 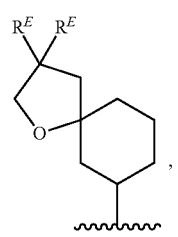
(r-183) 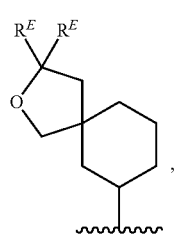
(r-184) 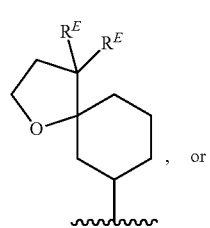, or
(r-185) 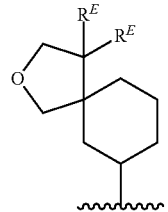
wherein $R^E$ is defined herein.
In certain embodiments, Formula (q-7) is of Formula (r-186) to (r-193):
(r-186) 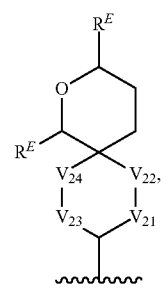
(r-187) 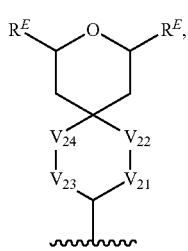
(r-188) 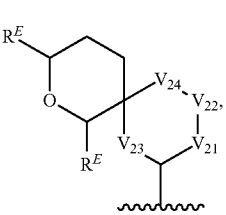
(r-189) 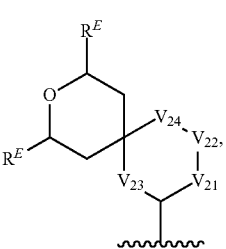

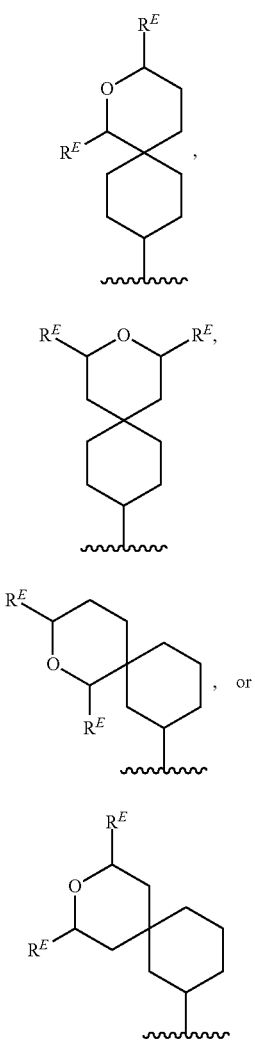
(r-190)
(r-191)
(r-192), or
(r-193)
wherein $V^{21}$, $V^{22}$, $V^{23}$, $V^{24}$, and $R^E$ are defined herein.
In certain embodiments, Formula (q-7) is of Formula (r-194) to (r-213):
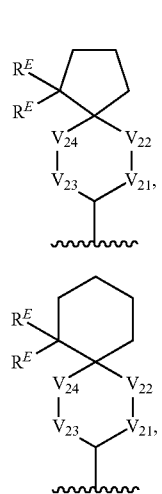
(r-194)
(r-195)
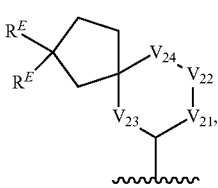
(r-196)
(r-197)
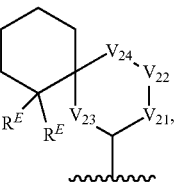
(r-198)
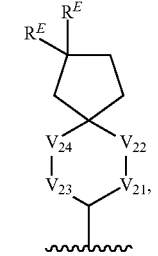
(r-199)
(r-200)
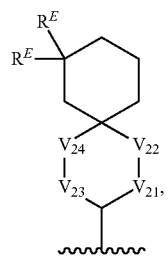
(r-201)
(r-202)
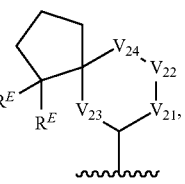

-continued
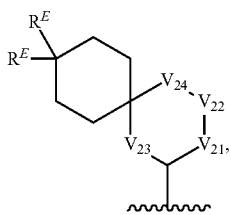
(r-203)
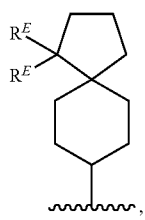
(r-204)
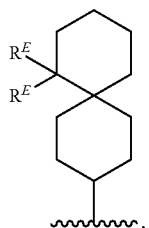
(r-205)
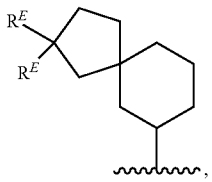
(r-206)
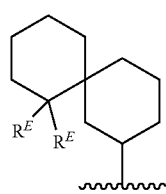
(r-207)
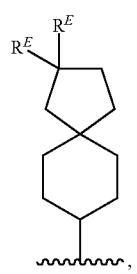
(r-208)
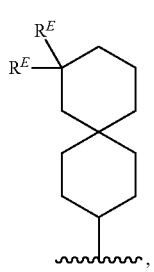
(r-209)
-continued
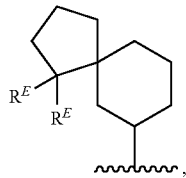
(r-210)
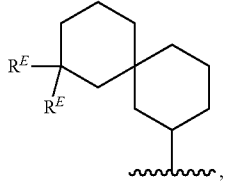
(r-211)
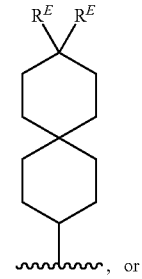
(r-212)
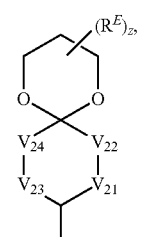
(r-213)
wherein $V^{21}$, $V^{22}$, $V^{23}$, $V^{24}$, and $R^E$ are defined herein.
In certain embodiments, Formula (q-7) is of Formula (r-214) to (r-217):
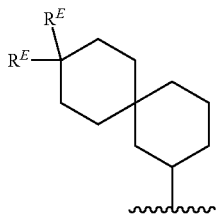
(r-214)
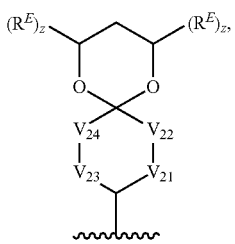
(r-215)

-continued

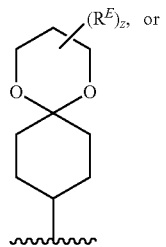
(r-216)

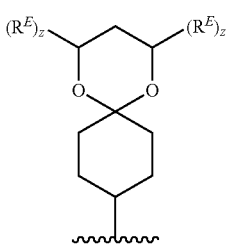
(r-217)

wherein $V^{21}$, $V^{22}$, $V^{23}$, $V^{24}$, z, and $R^E$ are defined herein.

In certain embodiments, Formula (q-7) is of Formula (r-218)-(r-227):

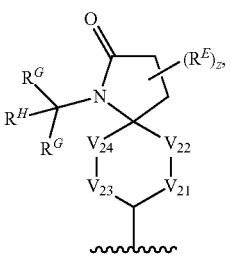
(r-218)

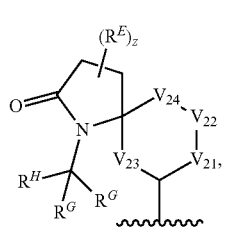
(r-219)

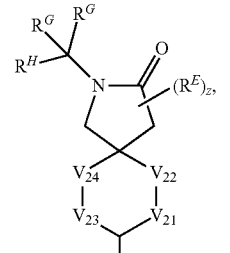
(r-220)

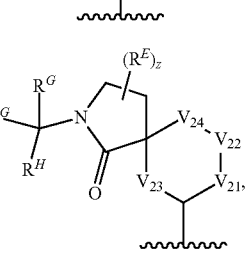
(r-221)

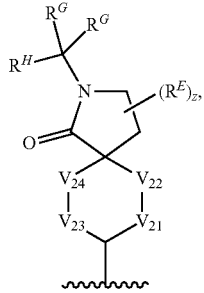
(r-222)

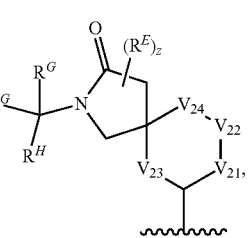
(r-223)

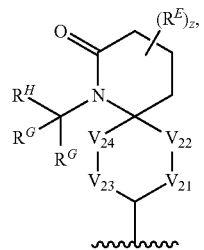
(r-224)

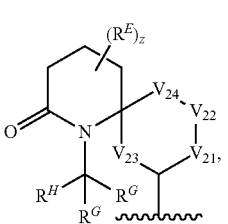
(r-225)

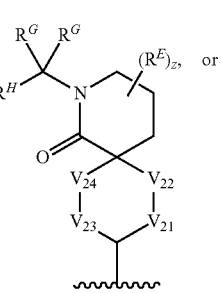
(r-226)

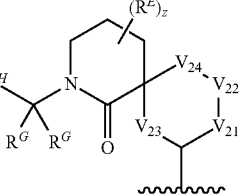
(r-227)

wherein $V^{21}$, $V^{22}$, $V^{23}$, $V^{24}$, z, and $R^E$ are defined herein;

each instance of $R^G$ is independently hydrogen, halo, optionally substituted alkyl, optionally substituted alkenyl, optionally substituted alkynyl, or optionally substituted carbocyclyl; or two R$^G$ groups can be taken together to form an optionally substituted carbocyclic ring; and R$^H$ is hydrogen, halo, optionally substituted alkyl, optionally substituted alkenyl, optionally substituted alkynyl, optionally substituted carbocyclyl, optionally substituted aryl, optionally substituted heterocyclyl, or optionally substituted heteroaryl.

In certain embodiments, Formula (q-7) is of Formula (r-228) to (r-230):

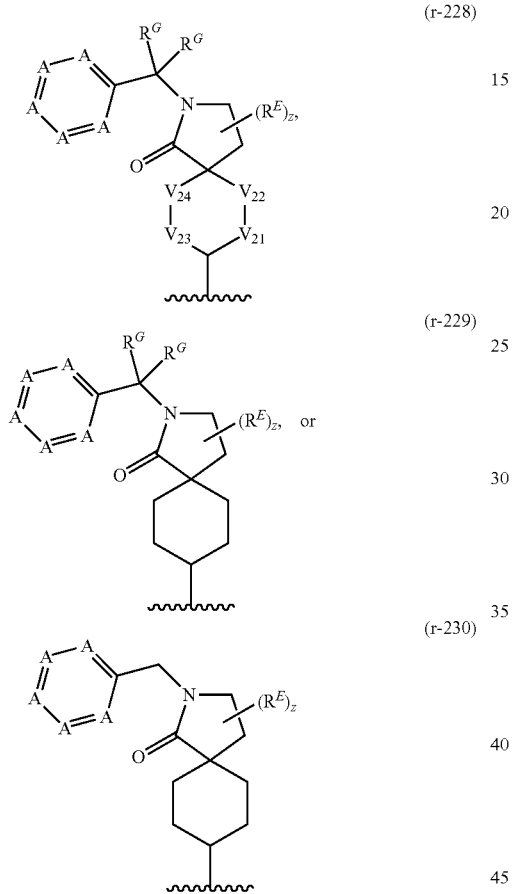

wherein V$^{21}$, V$^{22}$, V$^{23}$, V$^{24}$, R$^E$, and R$^G$ are defined herein;

z is 0, 1, 2, 3, or 4;

each instance of A is independently N or CR$^{Ha}$ provided that no more than 2 instances of A can be N; and each instance of R$^{Ha}$ is independently hydrogen, halo, —CN, —NO$_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —OR$^A$, —N(R$^B$)$_2$, —SR$^A$, —C(=O)R$^A$, —C(O)OR$^A$, —C(O)SR$^A$, —C(O)N(R$^B$)$_2$, —C(O)N(R$^B$)N(R$^B$)$_2$, —OC(O)R$^A$, —OC(O)N(R$^B$)$_2$, —NR$^B$C(O)R$^A$, —NR$^B$C(O)N(R$^B$)$_2$, —NR$^B$C(O)N(R$^B$)N(R$^B$)$_2$, —NR$^B$C(O)OR$^A$, —SC(O)R$^A$, —C(=NR$^B$)R$^A$, —C(=NNR$^B$)R$^A$, —C(=NOR$^A$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(O)R$^A$, —OS(O)$_2$R$^A$, —SO$_2$R$^A$, —NR$^B$SO$_2$R$^A$, or —SO$_2$N(R$^B$)$_2$.

In certain embodiments, Formula (q-7) is of Formula (r-231) to (r-233):

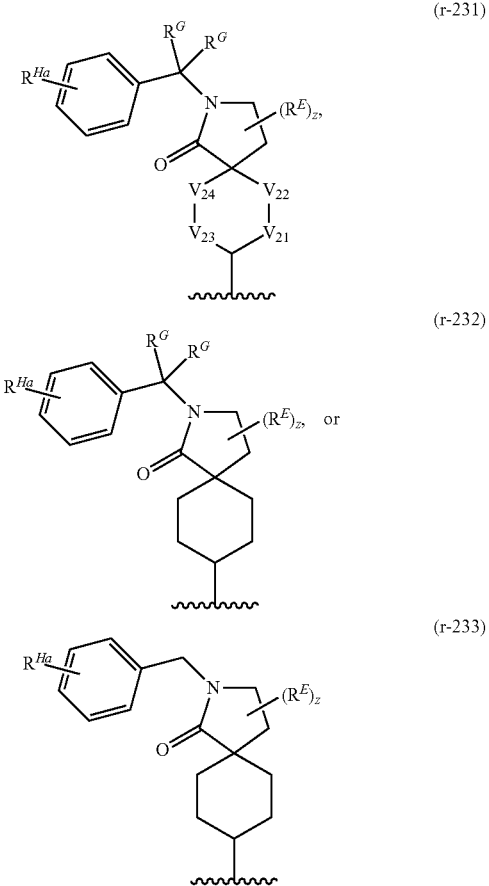

wherein V$^{21}$, V 22, V$^{23}$, V$^{24}$, z, R$^E$, R$^G$, and R$^{Ha}$ are defined herein.

In certain embodiments, Formula (q-7) is of Formula (r-234) to (r-236):

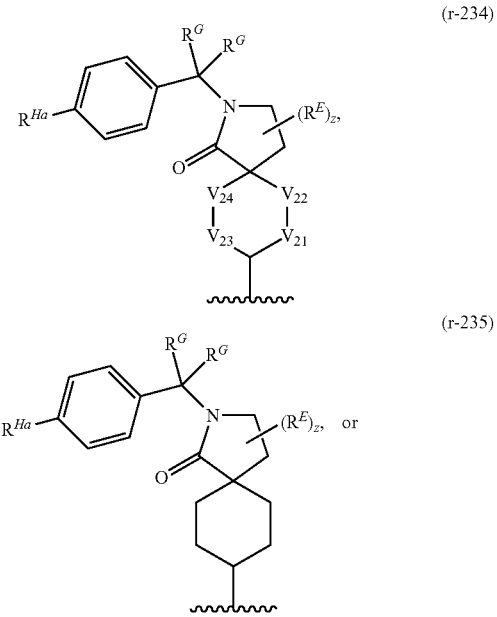

(r-236)

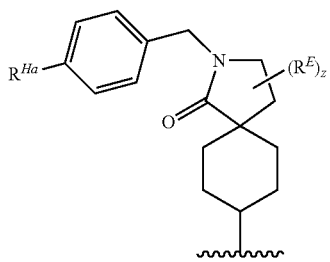

wherein $V^{21}$, $V\,22$, $V^{23}$, $V^{24}$, z, $R^E$, $R^G$, and $R^{Ha}$ are defined herein.

In some embodiments, $-L_1-R^W$ is optionally substituted carbocyclyl. In some embodiments, $-L_1-R^W$ is optionally substituted $C_{3-6}$ carbocyclyl. In some embodiments, $-L_1-R^W$ is unsubstituted cyclopropyl. In some embodiments, $-L_1-R^W$ is substituted cyclopropyl. In some embodiments, $-L_1-R^W$ is unsubstituted cyclobutyl. In some embodiments, $-L_1-R^W$ is substituted cyclobutyl. In some embodiments, $-L_1-R^W$ is unsubstituted cyclopentyl. In some embodiments, $-L_1-R^W$ is substituted cyclopentyl. In some embodiments, $-L_1-R^W$ is unsubstituted cyclohexyl. In some embodiments, $-L_1-R^W$ is substituted cyclohexyl. In some embodiments, $-L_1-R^W$ is optionally substituted cyclopentenyl or optionally substituted cyclohexenyl.

In some embodiments, $-L_1-R^W$ is optionally substituted heterocyclyl. In some embodiments, $-L_1-R^W$ is an optionally substituted 4- to 7-membered heterocyclyl ring having 1-2 heteroatoms independently selected from nitrogen, oxygen, and sulfur. In some embodiments, $-L_1-R^W$ is azetidinyl or oxetanyl. In some embodiments, $-L_1-R^W$ is optionally substituted tetrahydrofuranyl, optionally substituted pyrrolidinyl, optionally substituted dihydropyrrolyl, or optionally substituted pyrrolyl-2,5-dione. In some embodiments, $-L_1-R^W$ is optionally substituted piperidinyl, optionally substituted tetrahydropyranyl, optionally substituted dihydropyranyl, optionally substituted dihydropyridinyl, and optionally substituted thianyl. In certain embodiments, $-L_1-R^W$ is optionally substituted piperidinyl. In some embodiments, $-L_1-R^W$ is optionally substituted piperazinyl, optionally substituted morpholinyl, optionally substituted dithianyl, and optionally substituted dioxanyl. In some embodiments, $-L_1-R^W$ is a 5- or 6-membered heterocyclyl group fused to a $C_6$ aryl ring. In some embodiments, $-L_1-R^W$ is optionally substituted indolinyl, optionally substituted isoindolinyl, optionally substituted dihydrobenzofuranyl, optionally substituted dihydrobenzothienyl, or optionally substituted benzoxazolinonyl. In some embodiments, $-L_1-R^W$ is optionally substituted tetrahydroquinolinyl or optionally substituted tetrahydroisoquinolinyl.

In some embodiments, $-L_1-R^W$ is optionally substituted alkyl. In some embodiments, $-L_1-R^W$ is optionally substituted alkenyl. In some embodiments, $-L_1-R^W$ is optionally substituted alkynyl. In some embodiments, $-L_1-R^W$ is optionally substituted $C_{1-6}$ alkyl. In some embodiments, $-L_1-R^W$ is unsubstituted $C_{1-6}$ alkyl. In some embodiments, $-L_1-R^W$ is methyl, ethyl, propyl, or butyl. In some embodiments, $-L_1-R^W$ is isopropyl, isobutyl, or isoamyl. In some embodiments, $-L_1-R^W$ is optionally substituted $C_{2-6}$ alkenyl. In some embodiments, $-L_1-R^W$ is $C_{2-6}$ alkynyl.

As defined generally above, $R^3$ is hydrogen, $C_{1-4}$ alkyl, or $C_{3-4}$ cycloalkyl. In certain embodiments, $R^3$ is hydrogen. In certain embodiments, $R^3$ is $C_{1-4}$ alkyl. In certain embodiments, $R^3$ is methyl. In certain embodiments, $R^3$ is ethyl. In certain embodiments, $R^3$ is propyl or butyl. In certain embodiments, $R^3$ is cyclopropyl. In certain embodiment, $R^3$ is cyclobutyl.

As defined generally above, $R^4$ is hydrogen, optionally substituted $C_{1-6}$ alkyl, optionally substituted $C_{2-6}$ alkenyl, optionally substituted $C_{2-6}$ alkynyl, optionally substituted $C_{3-7}$ cycloalkyl, optionally substituted 4- to 7-membered heterocyclyl; or optionally substituted $C_{1-4}$ alkyl-Cy, wherein Cy is optionally substituted $C_{3-7}$ cycloalkyl, optionally substituted 4- to 7-membered heterocyclyl, optionally substituted aryl, or optionally substituted heteroaryl. Alternatively, when $L_1$ is a bond and $R^W$ is hydrogen, then X is $CR^5$, Z is N, and Y is $NR^4$, then $R^4$ is optionally substituted carbocyclyl or optionally substituted heterocyclyl as defined above and herein.

In certain embodiments, $R^4$ is hydrogen. In certain embodiments, $R^4$ is optionally substituted $C_{1-6}$ alkyl. In certain embodiments, $R^4$ is unsubstituted $C_{1-6}$ alkyl. In certain embodiments, $R^4$ is methyl, ethyl, or isopropyl. In certain embodiments, $R^4$ is substituted $C_{1-6}$ alkyl. In certain embodiments, $R^4$ is methoxyethyl. In certain embodiments, $R^4$ is hydroxyethyl or propane-1,2-diol. In certain embodiments, $R^4$ is optionally substituted $C_{3-7}$ cycloalkyl. In certain embodiments, $R^4$ is unsubstituted $C_{3-7}$ cycloalkyl. In certain embodiments, $R^4$ is cyclopropyl, cyclobutyl, cyclopentyl, or cyclohexyl. In certain embodiments, $R^4$ is optionally substituted 4- to 7-membered heterocyclyl. In certain embodiments, $R^4$ is optionally substituted 4- to 7-membered heterocyclyl having 1-2 heteroatoms independently selected from nitrogen, oxygen, and sulfur. In certain embodiments, $R^4$ is oxetane, tetrahydrofuran, or tetrahydropyran.

In certain embodiments, $R^4$ is optionally substituted $C_{1-4}$ alkyl-Cy, wherein Cy is optionally substituted $C_{3-7}$ cycloalkyl, optionally substituted 4- to 7-membered heterocyclyl, optionally substituted aryl, or optionally substituted heteroaryl. In some embodiments, Cy is optionally substituted $C_{3-7}$ cycloalkyl. In some embodiments, Cy is optionally substituted 4- to 7-membered heterocyclyl having 1-2 heteroatoms independently selected from nitrogen, oxygen, and sulfur. In some embodiments, Cy is oxetane, tetrahydrofuran, or tetrahydropyran. In some embodiments, Cy is optionally substituted aryl. In some embodiments, Cy is optionally substituted phenyl. In some embodiments, Cy is unsubstituted phenyl. In some embodiments, Cy is optionally substituted heteroaryl having 1-3 heteroatoms independently selected from nitrogen, oxygen, and sulfur. In some embodiments, Cy is optionally substituted 5- to 6-membered heteroaryl having 1-3 heteroatoms independently selected from nitrogen, oxygen, and sulfur. In some embodiments, Cy is pyridyl. In some embodiments, $R^4$ is

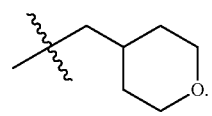 [SMILES: *CC1CCOCC1]

In some embodiments, $R^4$ is

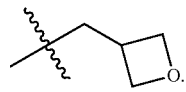

In some embodiments, $R^4$ is

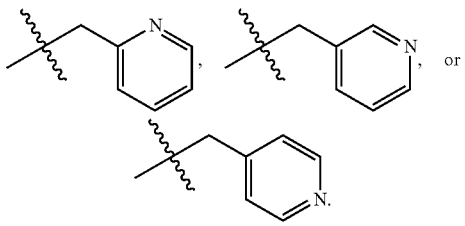

As defined generally above, $R^5$ is hydrogen, halo, —CN, optionally substituted $C_{1-4}$ alkyl, or optionally substituted $C_{3-4}$ cycloalkyl. In certain embodiments, $R^5$ is hydrogen. In certain embodiments, $R^5$ is halo. In certain embodiments, $R^5$ is chloro. In certain embodiments, $R^5$ is fluoro. In certain embodiments, $R^5$ is —CN. In certain embodiments, $R^5$ is optionally substituted $C_{1-4}$ alkyl. In certain embodiments, $R^5$ is unsubstituted $C_{1-4}$ alkyl. In certain embodiments, $R^5$ is methyl. In certain embodiments, $R^5$ is ethyl. In certain embodiments, $R^5$ is propyl or butyl. In certain embodiments, $R^5$ is $C_{1-4}$ alkyl substituted with one or more fluoro groups. In certain embodiments, $R^5$ is —$CF_3$. In certain embodiments, $R^5$ is —$CHF_2$. In certain embodiments, $R^5$ is optionally substituted $C_{3-4}$ cycloalkyl. In certain embodiments, $R^5$ is cyclopropyl or cyclobutyl.

As defined generally above, $R^x$ is optionally substituted $C_{1-4}$ alkyl or optionally substituted $C_{3-4}$ cycloalkyl. In certain embodiments, $R^x$ is optionally substituted $C_{1-4}$ alkyl. In certain embodiments, $R^x$ is unsubstituted $C_{1-4}$ alkyl. In certain embodiments, $R^x$ is methyl. In certain embodiments, $R^x$ is ethyl. In certain embodiments, $R^x$ is isopropyl. In certain embodiments, $R^x$ is propyl or butyl. In certain embodiments, $R^x$ is substituted $C_{1-4}$ alkyl. In certain embodiments, $R^x$ is $C_{1-4}$ alkyl substituted with hydroxyl or alkoxy. In certain embodiments, $R^x$ is hydroxyethyl or methoxyethyl. In certain embodiments, $R^x$ is optionally substituted $C_{3-4}$ cycloalkyl. In certain embodiments, $R^x$ is unsubstituted $C_{3-4}$ cycloalkyl. In certain embodiments, $R^x$ is cyclopropyl. In certain embodiments, $R^x$ is cyclobutyl.

As defined generally above, each $R^A$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom. In some embodiments, $R^A$ is hydrogen. In some embodiments, $R^A$ is optionally substituted alkyl. In some embodiments, $R^A$ is optionally substituted alkyl substituted with a Cy group to form optionally substituted alkyl-Cy, wherein Cy is described herein. In some embodiments, $R^A$ is optionally substituted alkenyl or optionally substituted alkynyl. In some embodiments, $R^A$ is optionally substituted carbocyclyl, optionally substituted heterocyclyl, optionally substituted aryl, or optionally substituted heteroaryl. In some embodiments, $R^A$ is an oxygen protecting group when attached to an oxygen atom. In some embodiments, $R^A$ is not an oxygen protecting group. In some embodiments, $R^A$ is sulfur protecting group when attached to a sulfur atom. In some embodiments, $R^A$ is not a sulfur protecting group.

As defined generally above, each $R^B$ is independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, and a nitrogen protecting group, or two $R^B$ groups or an $R^B$ group and an $R^W$ group on the same nitrogen are taken together with their intervening atoms to form an optionally substituted heterocyclic ring. In some embodiments, $R^B$ is hydrogen. In some embodiments, $R^B$ is optionally substituted alkyl. In some embodiments, $R^B$ is optionally alkyl substituted with a Cy group to form optionally substituted alkyl-Cy, wherein Cy is described herein. In some embodiments, $R^B$ is optionally substituted alkenyl or optionally substituted alkynyl. In some embodiments, $R^B$ is optionally substituted carbocyclyl, optionally substituted heterocyclyl, optionally substituted aryl, or optionally substituted heteroaryl. In some embodiments, $R^B$ is a nitrogen protecting group. In some embodiments, $R^B$ is not a nitrogen protecting group. In some embodiments, two $R^B$ groups are taken together with their intervening atoms to form an optionally substituted heterocyclic ring. In some embodiments, an $R^B$ group and an $R^W$ group on the same nitrogen are taken together with their intervening atoms to form an optionally substituted heterocyclic ring.

As defined generally above, each instance of $R^E$ is independently hydrogen, halo, —CN, —$NO_2$, optionally substituted alkyl, optionally substituted alkenyl, optionally substituted alkynyl, optionally substituted carbocyclyl, optionally substituted aryl, optionally substituted heterocyclyl, optionally substituted heteroaryl, —$OR^A$, —$N(R^B)_2$, —$SR^A$, —$C(=O)R^A$, —$C(O)OR^A$, —$C(O)SR^A$, —$C(O)N(R^B)_2$, —$C(O)N(R^B)N(R^B)_2$, —$OC(O)R^A$, —$OC(O)N(R^B)_2$, —$NR^BC(O)R^A$, —$NR^BC(O)N(R^B)_2$, —$NR^BC(O)N(R^B)N(R^B)_2$, —$NR^BC(O)OR^A$, —$SC(O)R^A$, —$C(=NR^B)R^A$, —$C(=NNR^B)R^A$, —$C(=NOR^A)R^A$, —$C(=NR^B)N(R^B)_2$, —$NR^BC(=NR^B)R^B$, —$C(=S)R^A$, —$C(=S)N(R^B)_2$, —$NR^BC(=S)R^A$, —$S(O)R^A$, —$OS(O)_2R^A$, —$SO_2R^A$, —$NR^BSO_2R^A$, or —$SO_2N(R^B)_2$; or two $R^E$ groups are joined to form an optionally substituted carbocyclic or optionally substituted heterocyclic ring. In certain embodiments, $R^E$ is hydrogen. In certain embodiments, $R^E$ is not hydrogen. In certain embodiments, $R^E$ is halo (e.g., fluoro, chloro, bromo, or iodo). In certain embodiments, $R^E$ is optionally substituted alkyl. In certain embodiments, $R^E$ is optionally substituted $C_{1-6}$ alkyl. In certain embodiments, $R^E$ is unsubstituted $C_{1-6}$ alkyl (e.g., methyl, ethyl, propyl, butyl, pentyl, or hexyl). In certain $R^E$ is unsubstituted branched $C_{3-6}$ alkyl (e.g., isopropyl, sec-butyl, tert-butyl, isopentyl, neopentyl, or 3-pentyl). In certain embodiments, $R^E$ is methyl. In certain embodiments, $R^E$ is $C_{1-6}$ haloalkyl (e.g., —$CF_3$, —$CF_2H$, or —$CF_2CH_3$). In certain embodiments, $R^E$ is —$CF_3$. In certain embodiments, $R^E$ is alkoxyalkyl (e.g. —$CH_2OR^A$ or —$CH_2CH_2OR^A$). In certain embodiments, $R^E$ is an optionally substituted carbocyclic ring (e.g., cyclopropyl, cyclobutyl, cyclopentyl, or cyclopropyl). In certain embodiments, $R^E$ is an unsubstituted carbocyclic ring (e.g., cyclopropyl, cyclobutyl, cyclopentyl, or cyclopropyl). In certain embodiments, $R^E$ is substituted phenyl. In certain embodiments, $R^E$ is unsubstituted phenyl. In certain embodiments, $R^E$ is an optionally substituted heterocyclic ring (e.g., azetidine, oxetane, furan, pyrrolidine, piperidine, piperazine, or morpholine). In certain embodiments, $R^E$ is an unsubstituted heterocyclic ring (e.g., azetidine, oxetane, furan, pyrrolidine, piperidine, piperazine, or morpholine). In certain embodiments, $R^E$ is an optionally substituted heteroaryl ring (e.g., pyrazole, imidazole, triazole, pyridine, pyrimidine, or pyridizine). In certain embodiments, $R^E$ is an unsubstituted heteroaryl ring (e.g., pyrazole, imidazole, triazole, pyridine, pyrimidine, or pyridizine). In certain embodiments, $R^E$ is alkoxy. In certain embodiments, $R^E$ is —$OR^A$; and $R^A$ is optionally substituted $C_{1-6}$ alkyl. In certain embodiments, $R^E$ is —$OR^A$; and $R^A$ is unsubstituted $C_{1-6}$ alkyl (e.g., methyl, ethyl, or propyl). In certain embodiments, two $R^E$ groups are joined to form an optionally substituted carbocyclic or optionally substituted heterocyclic ring. In certain embodiments, two $R^E$ groups are joined to form an optionally substituted carbocyclic ring (e.g., cyclopropyl, cyclobutyl, cyclopentyl, or cyclohexyl). In certain embodiments, two $R^E$ groups are joined to form an optionally substituted cyclopropyl ring. In certain embodiments, two $R^E$ groups are joined to form an unsubstituted carbocyclic ring (e.g., cyclopropyl, cyclobutyl, cyclopentyl, or cyclohexyl). In certain embodiments, two $R^E$ groups are joined to form an unsubstituted cyclopropyl ring.

Various combinations of certain above-described embodiments are further envisioned herein.

For example, in certain embodiments, provided are compounds of Formulae XII-a1 to XII-a5:

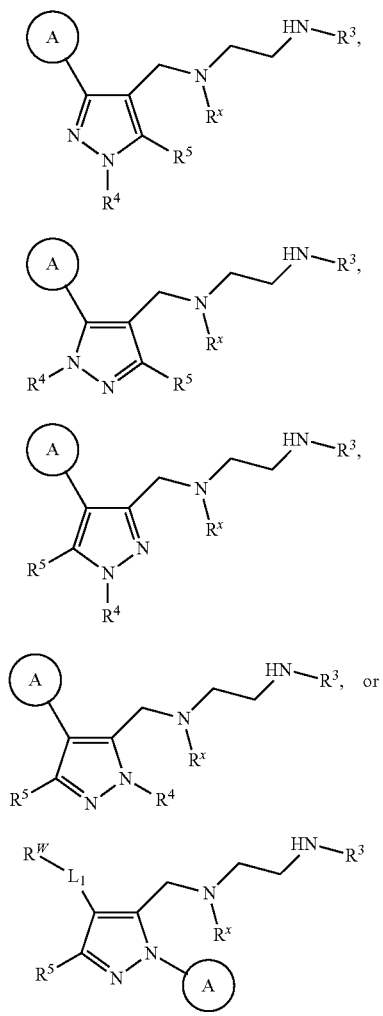

or pharmaceutically acceptable salt thereof; wherein $R^3$, $R^4$, $R^5$, and $R^x$ are defined herein; and Ring A is any of Formulae (q-7) to (q-117), (q-7a) to (q-117a), or (r-1) to (r-236). In certain embodiments, $R^3$ is hydrogen. In certain embodiments, $R^3$ is unsubstituted $C_{1-4}$ alkyl (e.g., methyl, ethyl, propyl, or butyl). In certain embodiments, $R^3$ is methyl. In certain embodiments, $R^4$ is hydrogen. In certain embodiments, $R^4$ is unsubstituted $C_{1-6}$ alkyl (e.g., methyl, ethyl, propyl, or butyl). In certain embodiments, $R^4$ is methyl. In certain embodiments, $R^x$ is unsubstituted $C_{1-4}$ alkyl (e.g., methyl, ethyl, propyl or butyl). In certain embodiments, $R^x$ is methyl. In certain embodiments, $R^5$ is hydrogen. In certain embodiments, $L_1$ is a bond and $R^W$ is hydrogen. In certain embodiments, $L_1$ is a bond, $R^W$ is hydrogen, and $R^5$ is hydrogen. In certain embodiments, $L_1$ is a bond and $R^W$ is halogen, e.g., fluoro, chloro, bromo, or iodo. In certain embodiments, $L_1$ is a bond and $R^W$ is optionally substituted $C_{1-6}$alkyl, e.g., unsubstituted $C_{1-4}$alkyl, e.g., methyl, ethyl, propyl, butyl, isopropyl, isobutyl, or isoamyl.

In certain embodiments, when Ring A is of Formula (q-7), provided are compounds of Formulae XII-b1 to XII-b5:

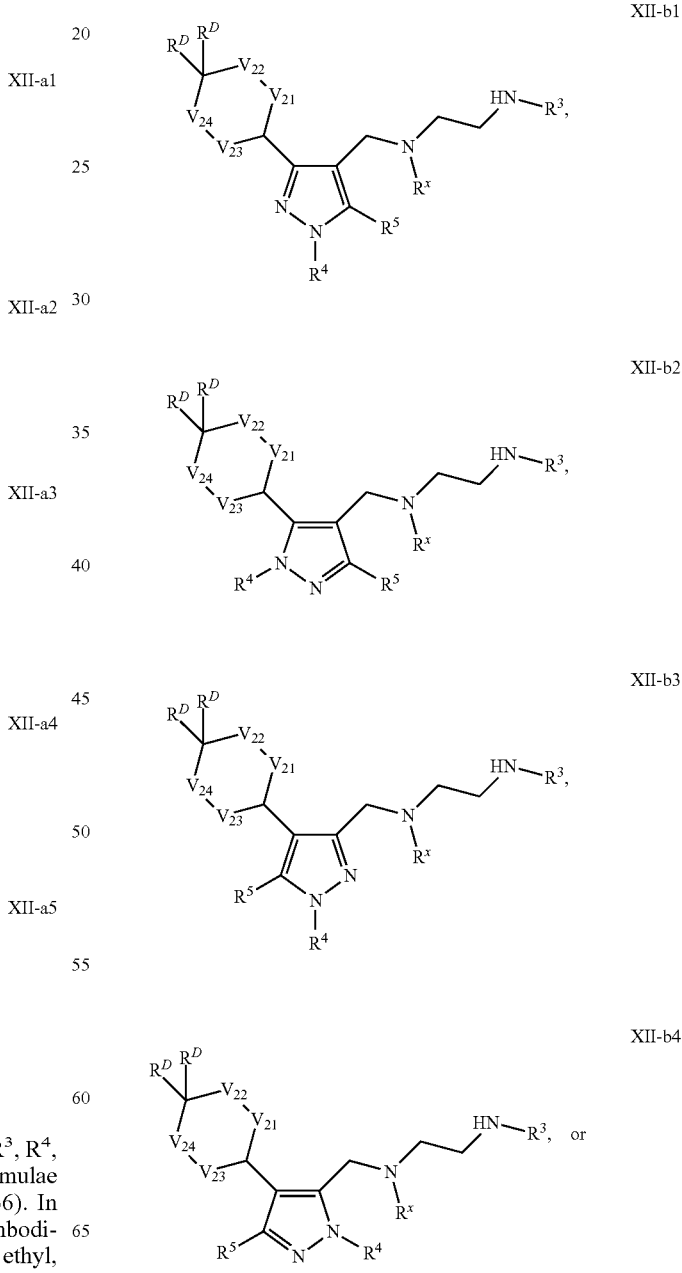

-continued

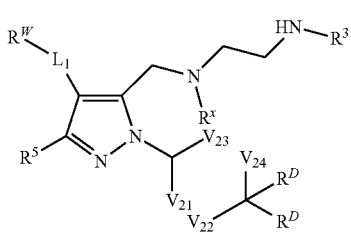

XII-b5 or pharmaceutically acceptable salt thereof; wherein $R^3$, $R^4$, $R^5$, $R^x$, $V_{21}$, $V_{22}$, $V_{23}$, $V_{24}$, and $R^D$ are defined herein. In certain embodiments, $R^3$ is hydrogen. In certain embodiments, $R^3$ is unsubstituted $C_{1-4}$ alkyl (e.g., methyl, ethyl, propyl, or butyl). In certain embodiments, $R^3$ is methyl. In certain embodiments, $R^4$ is hydrogen. In certain embodiments, $R^4$ is unsubstituted $C_{1-6}$ alkyl (e.g., methyl, ethyl, propyl, or butyl). In certain embodiments, $R^4$ is methyl. In certain embodiments, $R^x$ is unsubstituted $C_{1-4}$ alkyl (e.g., methyl, ethyl, propyl or butyl). In certain embodiments, $R^x$ is methyl. In certain embodiments, $R^5$ is hydrogen. In certain embodiments, at least one of $V_{21}$, $V_{22}$, $V_{23}$, and $V_{24}$ is —$CH_2$—. In certain embodiments, at least two of $V_{21}$, $V_{22}$, $V_{23}$, and $V_{24}$ are —$CH_2$—. In certain embodiments, at least three of $V_{21}$, $V_{22}$, $V_{23}$, and $V_{24}$ are —$CH_2$—. In certain embodiments, all four of $V_{21}$, $V_{22}$, $V_{23}$, and $V_{24}$ are —$CH_2$—. In certain embodiments, at least one of $V_{22}$ and $V_{24}$ is O or —$CH(OR^A)$—. In certain embodiments, $V_{22}$ is O. In certain embodiments, $V_{22}$ is —$CH(OR^A)$—. In certain embodiments, $V_{24}$ is O. In certain embodiments, $V_{24}$ is —$CH(OR^A)$—. In certain embodiments, at least one instance of $R^D$ is hydrogen. In certain embodiments, at least one instance of $R^D$ is halo (e.g., fluoro, chloro, or bromo). In certain embodiments, at least one instance of $R^D$ is optionally substituted alkyl. In certain embodiments, at least one instance of $R^D$ is optionally substituted $C_{1-4}$ alkyl. In certain embodiments, at least one instance of $R^D$ is unsubstituted $C_{1-4}$ alkyl (e.g., methyl, ethyl, propyl, or butyl). In certain embodiments, at least one instance of $R^D$ is unsubstituted branched $C_{3-4}$ alkyl (e.g., isopropyl, isobutyl, sec-butyl, or tert-butyl). In certain embodiments, one instance of $R^D$ is hydrogen; and the second instance of $R^D$ is optionally substituted alkyl. In certain embodiments, one instance of $R^D$ is hydrogen; and the second instance of $R^D$ is optionally substituted $C_{1-4}$ alkyl. In certain embodiments, one instance of $R^D$ is hydrogen; and the second instance of $R^D$ is unsubstituted $C_{1-4}$ alkyl (e.g., methyl, ethyl, propyl, or butyl). In certain embodiments, one instance of $R^D$ is hydrogen; and the second instance of $R^D$ is branched $C_{3-4}$ alkyl (e.g., isopropyl, isobutyl, sec-butyl, or tert-butyl). In certain embodiments, one instance of $R^D$ is hydrogen; and the second instance of $R^D$ is methyl. In certain embodiments, one instance of $R^D$ is hydrogen; and the second instance of $R^D$ is ethyl. In certain embodiments, one instance of $R^D$ is hydrogen; and the second instance of $R^D$ is isopropyl. In certain embodiments, one instance of $R^D$ is hydrogen; and the second instance of $R^D$ is isobutyl. In certain embodiments, both instances of $R^D$ are optionally substituted $C_{1-4}$ alkyl. In certain embodiments, both instances of $R^D$ are methyl. In certain embodiments, one instance of $R^D$ is hydrogen; and one instance of $R^D$ is —$OR^A$. In certain embodiments, at least one instance of $R^D$ is optionally substituted alkoxyalkyl (e.g., —$CH_2OR^A$, —$CH_2CH_2OR^A$, or —$CH_2CH_2CH_2OR^A$). In certain embodiments, both instances of $R^D$ is optionally substituted alkoxyalkyl (e.g., —$CH_2OR^A$, —$CH_2CH_2OR^A$, or —$CH_2CH_2CH_2OR^A$). In certain embodiments, two $R^D$ groups are joined to form an optionally substituted carbocyclic or optionally substituted heterocyclic ring. In certain embodiments, two $R^D$ groups are joined to form an optionally substituted cyclopentane. In certain embodiments, two $R^D$ groups are joined to form an optionally substituted cyclohexane. In certain embodiments, two $R^D$ groups are joined to form an optionally substituted furan. In certain embodiments, two $R^D$ groups are joined to form an optionally substituted pyran. In certain embodiments, two $R^D$ groups are joined to form an optionally substituted pyrrolidinone. In certain embodiments, two $R^E$ groups are joined to form an optionally substituted carbocyclic ring (e.g., cyclopropyl, cyclobutyl, cyclopentyl, or cyclohexyl). In certain embodiments, two $R^E$ groups are joined to form an optionally substituted cyclopropyl ring. In certain embodiments, two $R^E$ groups are joined to form an unsubstituted carbocyclic ring (e.g., cyclopropyl, cyclobutyl, cyclopentyl, or cyclohexyl). In certain embodiments, two $R^E$ groups are joined to form an unsubstituted cyclopropyl ring. In certain embodiments, $L_1$ is a bond and $R^W$ is hydrogen. In certain embodiments, $L_1$ is a bond, $R^W$ is hydrogen, and $R^5$ is hydrogen. In certain embodiments, $L_1$ is a bond and $R^W$ is halogen, e.g., fluoro, chloro, bromo, or iodo. In certain embodiments, $L_1$ is a bond and $R^W$ is optionally substituted $C_{1-6}$alkyl, e.g., unsubstituted $C_{1-4}$alkyl, e.g., methyl, ethyl, propyl, butyl, isopropyl, isobutyl, or isoamyl.

In certain embodiments, when Ring A is of Formula (q-9), provided are compounds of Formulae XII-c1 to XII-c5:

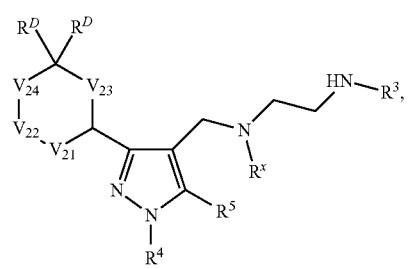

XII-c1

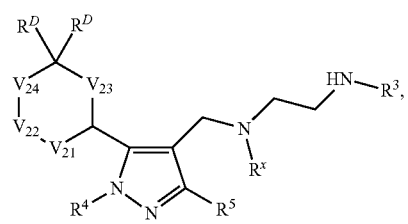

XII-c2

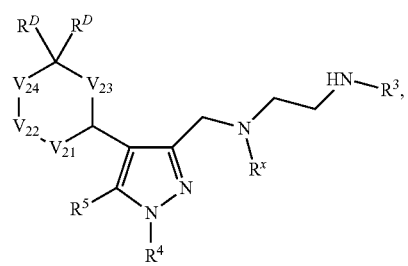

XII-c3

-continued

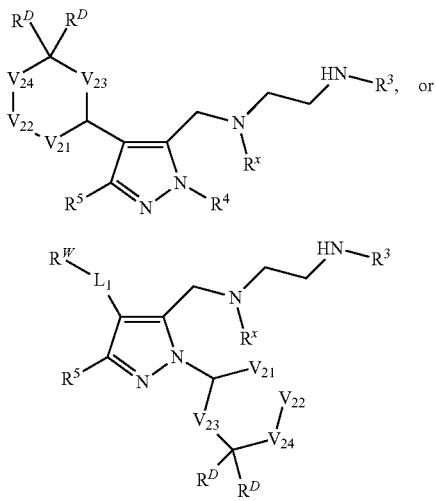

XII-c4

XII-c4 or pharmaceutically acceptable salt thereof; wherein $R^3$, $R^4$, $R^5$, $R^x$, $V_{21}$, $V_{22}$, $V_{23}$, $V_{24}$, and $R^D$ are defined herein. In certain embodiments, $R^3$ is hydrogen. In certain embodiments, $R^3$ is unsubstituted $C_{1-4}$ alkyl (e.g., methyl, ethyl, propyl, or butyl). In certain embodiments, $R^3$ is methyl. In certain embodiments, $R^4$ is hydrogen. In certain embodiments, $R^4$ is unsubstituted $C_{1-6}$ alkyl (e.g., methyl, ethyl, propyl, or butyl). In certain embodiments, $R^4$ is methyl. In certain embodiments, $R^x$ is unsubstituted $C_{1-4}$ alkyl (e.g., methyl, ethyl, propyl or butyl). In certain embodiments, $R^x$ is methyl. In certain embodiments, $R^5$ is hydrogen. In certain embodiments, at least one of $V_{21}$, $V_{22}$, $V_{23}$, and $V_{24}$ is —$CH_2$—. In certain embodiments, at least two of $V_{21}$, $V_{22}$, $V_{23}$, and $V_{24}$ are —$CH_2$—. In certain embodiments, at least three of $V_{21}$, $V_{22}$, $V_{23}$, and $V_{24}$ are —$CH_2$—. In certain embodiments, all four of $V_{21}$, $V_{22}$, $V_{23}$, and $V_{24}$ are —$CH_2$—. In certain embodiments, at least one of $V_{21}$ and $V_{22}$ is O or —$CH(OR^A)$—. In certain embodiments, $V_{22}$ is O. In certain embodiments, $V_{22}$ is —$CH(OR^A)$—. In certain embodiments, $V_{21}$ is O. In certain embodiments, $V_{21}$ is —$CH(OR^A)$—. In certain embodiments, at least one instance of $R^D$ is hydrogen. In certain embodiments, at least one instance of $R^D$ is halo (e.g., fluoro, chloro, or bromo). In certain embodiments, at least one instance of $R^D$ is optionally substituted alkyl. In certain embodiments, at least one instance of $R^D$ is optionally substituted $C_{1-4}$ alkyl. In certain embodiments, at least one instance of $R^D$ is unsubstituted $C_{1-4}$ alkyl (e.g., methyl, ethyl, propyl, or butyl). In certain embodiments, at least one instance of $R^D$ is unsubstituted branched $C_{3-4}$ alkyl (e.g., isopropyl, isobutyl, sec-butyl, or tert-butyl). In certain embodiments, one instance of $R^D$ is hydrogen; and the second instance of $R^D$ is optionally substituted alkyl. In certain embodiments, one instance of $R^D$ is hydrogen; and the second instance of $R^D$ is optionally substituted $C_{1-4}$ alkyl. In certain embodiments, one instance of $R^D$ is hydrogen; and the second instance of $R^D$ is unsubstituted $C_{1-4}$ alkyl (e.g., methyl, ethyl, propyl, or butyl). In certain embodiments, one instance of $R^D$ is hydrogen; and the second instance of $R^D$ is branched $C_{3-4}$ alkyl (e.g., isopropyl, isobutyl, sec-butyl, or tert-butyl). In certain embodiments, one instance of $R^D$ is hydrogen; and the second instance of $R^D$ is methyl. In certain embodiments, one instance of $R^D$ is hydrogen; and the second instance of $R^D$ is ethyl. In certain embodiments, one instance of $R^D$ is hydrogen; and the second instance of $R^D$ is isethylopropy. In certain embodiments, one instance of $R^D$ is hydrogen; and the second instance of $R^D$ is isobutyl. In certain embodiments, both instances of $R^D$ are optionally substituted $C_{1-4}$ alkyl. In certain embodiments, both instances of $R^D$ are methyl. In certain embodiments, one instance of $R^D$ is hydrogen; and one instance of $R^D$ is —$OR^A$. In certain embodiments, at least one instance of $R^D$ is optionally substituted alkoxyalkyl (e.g., —$CH_2OR^A$, —$CH_2CH_2OR^A$, or —$CH_2CH_2CH_2OR^A$). In certain embodiments, both instances of $R^D$ is optionally substituted alkoxyalkyl (e.g., —$CH_2OR^A$, —$CH_2CH_2OR^A$, or —$CH_2CH_2CH_2OR^A$). In certain embodiments, two $R^D$ groups are joined to form an optionally substituted carbocyclic or optionally substituted heterocyclic ring. In certain embodiments, two $R^D$ groups are joined to form an optionally substituted cyclopentane. In certain embodiments, two $R^D$ groups are joined to form an optionally substituted cyclohexane. In certain embodiments, two $R^D$ groups are joined to form an optionally substituted furan. In certain embodiments, two $R^D$ groups are joined to form an optionally substituted pyran. In certain embodiments, two $R^D$ groups are joined to form an optionally substituted pyrrolidinone. In certain embodiments, two $R^E$ groups are joined to form an optionally substituted carbocyclic ring (e.g., cyclopropyl, cyclobutyl, cyclopentyl, or cyclohexyl). In certain embodiments, two $R^E$ groups are joined to form an optionally substituted cyclopropyl ring. In certain embodiments, two $R^E$ groups are joined to form an unsubstituted carbocyclic ring (e.g., cyclopropyl, cyclobutyl, cyclopentyl, or cyclohexyl). In certain embodiments, two $R^E$ groups are joined to form an unsubstituted cyclopropyl ring. In certain embodiments, $L_1$ is a bond and $R^W$ is hydrogen. In certain embodiments, $L_1$ is a bond, $R^W$ is hydrogen, and $R^5$ is hydrogen. In certain embodiments, $L_1$ is a bond and $R^W$ is halogen, e.g., fluoro, chloro, bromo, or iodo. In certain embodiments, $L_1$ is a bond and $R^W$ is optionally substituted $C_{1-6}$alkyl, e.g., unsubstituted $C_{1-4}$alkyl, e.g., methyl, ethyl, propyl, butyl, isopropyl, isobutyl, or isoamyl.

In certain embodiments, when Ring A is of Formula (q-46) or (q-47), provided are compounds of Formulae XII-d1 to XII-d5:

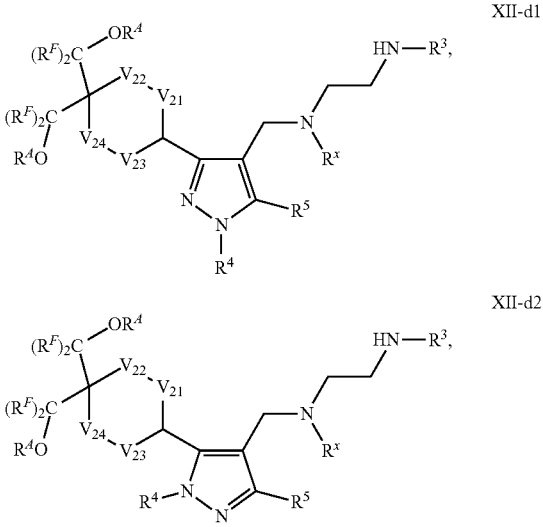

XII-d1

XII-d2

-continued

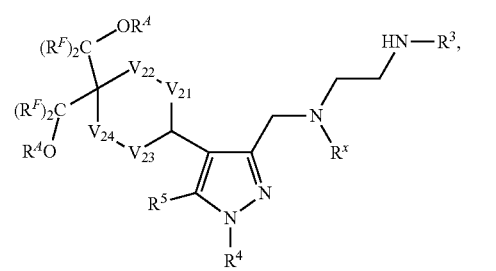

XII-d3

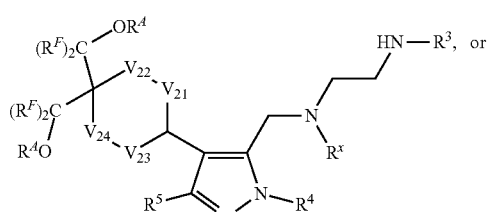

XII-d4

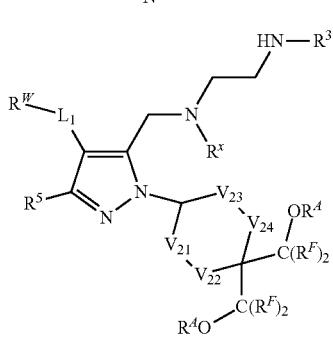

XII-d5 or pharmaceutically acceptable salt thereof; wherein $R^3$, $R^4$, $R^5$, $R^x$, $V_{21}$, $V_{22}$, $V_{23}$, $V_{24}$, $R^A$, and $R^F$ are defined herein. In certain embodiments, $R^3$ is hydrogen. In certain embodiments, $R^3$ is unsubstituted $C_{1-4}$ alkyl (e.g., methyl, ethyl, propyl, or butyl). In certain embodiments, $R^3$ is methyl. In certain embodiments, $R^4$ is hydrogen. In certain embodiments, $R^4$ is unsubstituted $C_{1-6}$ alkyl (e.g., methyl, ethyl, propyl, or butyl). In certain embodiments, $R^4$ is methyl. In certain embodiments, $R^x$ is unsubstituted $C_{1-4}$ alkyl (e.g., methyl, ethyl, propyl or butyl). In certain embodiments, $R^x$ is methyl. In certain embodiments, $R^5$ is hydrogen. In certain embodiments, at least one of $V_{21}$, $V_{22}$, $V_{23}$, and $V_{24}$ is —$CH_2$—. In certain embodiments, at least two of $V_{21}$, $V_{22}$, $V_{23}$, and $V_{24}$ are —$CH_2$—. In certain embodiments, at least three of $V_{21}$, $V_{22}$, $V_{23}$, and $V_{24}$ are —$CH_2$—. In certain embodiments, all four of $V_{21}$, $V_{22}$, $V_{23}$, and $V_{24}$ are —$CH_2$—. In certain embodiments, at least one of $V_{22}$ and $V_{24}$ is O or —CH($OR^A$)—. In certain embodiments, $V_{22}$ is O. In certain embodiments, $V_{22}$ is —CH($OR^A$)—. In certain embodiments, $V_{24}$ is O. In certain embodiments, $V_{24}$ is —CH($OR^A$)—. In certain embodiments, at least two instances of $R^F$ are hydrogen. In certain embodiments, all four instances of $R^F$ are hydrogen. In certain embodiments, each instance of $R^A$ is independently hydrogen. In certain embodiments, both instances of $R^A$ are hydrogen. In certain embodiments, neither instance of $R^A$ is hydrogen. In certain embodiments, at least one instance of $R^A$ is optionally substituted alkyl. In certain embodiments, both instances of $R^A$ are independently optionally substituted alkyl. In certain embodiments, at least one instance of $R^A$ is optionally substituted $C_{1-4}$ alkyl. In certain embodiments, both instances of $R^A$ are independently optionally substituted $C_{1-4}$ alkyl. In certain embodiments, at least one instance of $R^A$ is unsubstituted $C_{1-4}$ alkyl (e.g., methyl, ethyl, propyl, or butyl). In certain embodiments, both instances of $R^A$ are independently unsubstituted alkyl (e.g., methyl, ethyl, propyl, or butyl). In certain embodiments, at least one instance of $R^A$ is methyl. In certain embodiments, both instances of $R^A$ are methyl. In certain embodiments, at least one instance of $R^A$ is ethyl. In certain embodiments, both instances of $R^A$ are ethyl. In certain embodiments, two $R^E$ groups are joined to form an optionally substituted carbocyclic ring (e.g., cyclopropyl, cyclobutyl, cyclopentyl, or cyclohexyl). In certain embodiments, two $R^E$ groups are joined to form an optionally substituted cyclopropyl ring. In certain embodiments, two $R^E$ groups are joined to form an unsubstituted carbocyclic ring (e.g., cyclopropyl, cyclobutyl, cyclopentyl, or cyclohexyl). In certain embodiments, two $R^E$ groups are joined to form an unsubstituted cyclopropyl ring. In certain embodiments, $L_1$ is a bond and $R^W$ is hydrogen. In certain embodiments, $L_1$ is a bond, $R^W$ is hydrogen, and $R^5$ is hydrogen. In certain embodiments, $L_1$ is a bond and $R^W$ is halogen, e.g., fluoro, chloro, bromo, or iodo. In certain embodiments, $L_1$ is a bond and $R^W$ is optionally substituted $C_{1-6}$alkyl, e.g., unsubstituted $C_{1-4}$alkyl, e.g., methyl, ethyl, propyl, butyl, isopropyl, isobutyl, or isoamyl.

In certain embodiments, when Ring A is of Formula (q-58), provided are compounds of Formulae XII-e1 to XII-e5:

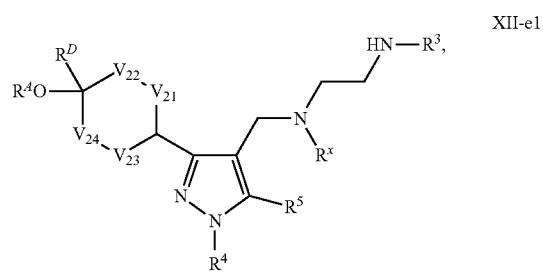

XII-e1

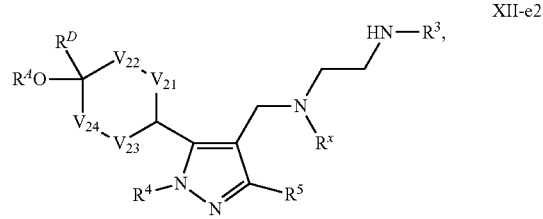

XII-e2

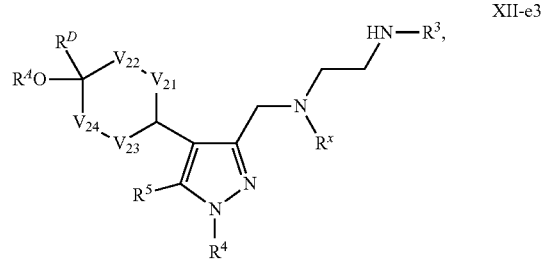

XII-e3

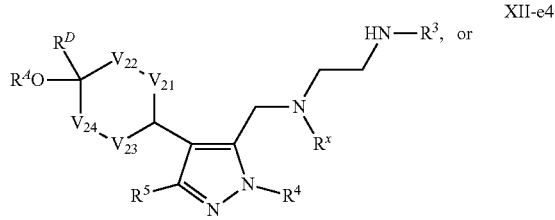

XII-e4

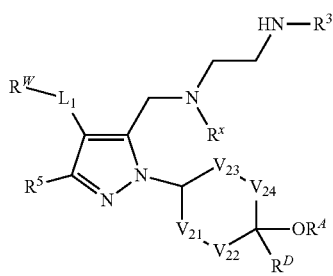

XII-e5

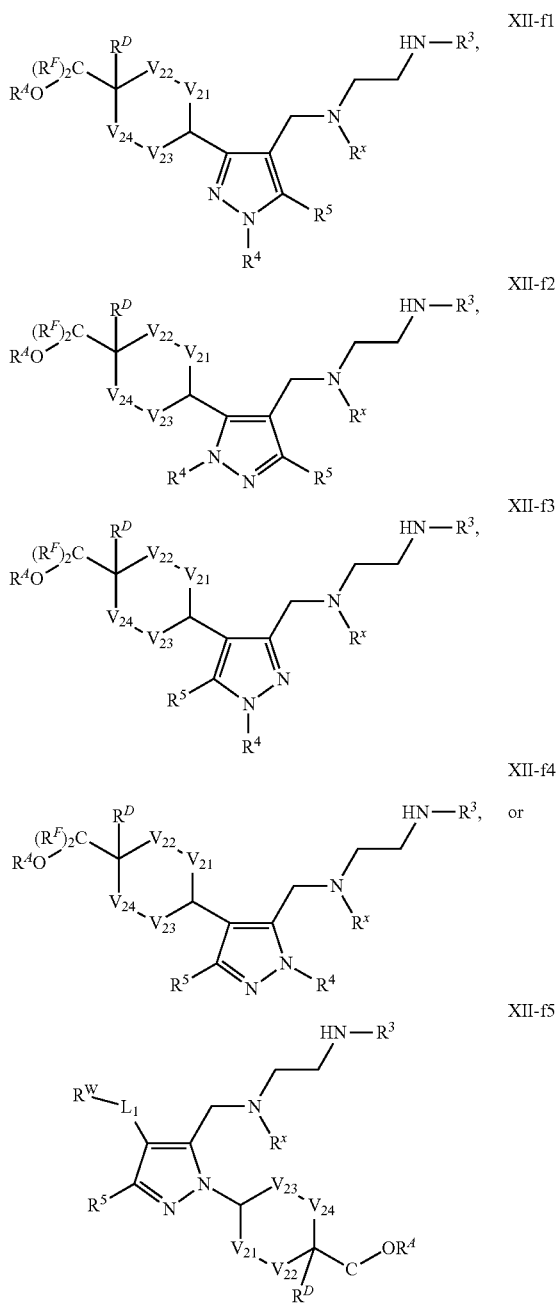

or pharmaceutically acceptable salt thereof; wherein $R^3$, $R^4$, $R^5$, $R^x$, $V_{21}$, $V_{22}$, $V_{23}$, $V_{24}$, $R^A$, and $R^D$ are defined herein. In certain embodiments, $R^3$ is hydrogen. In certain embodiments, $R^3$ is unsubstituted $C_{1-4}$ alkyl (e.g., methyl, ethyl, propyl, or butyl). In certain embodiments, $R^3$ is methyl. In certain embodiments, $R^4$ is hydrogen. In certain embodiments, $R^4$ is unsubstituted $C_{1-6}$ alkyl (e.g., methyl, ethyl, propyl, or butyl). In certain embodiments, $R^4$ is methyl. In certain embodiments, $R^x$ is unsubstituted $C_{1-4}$ alkyl (e.g., methyl, ethyl, propyl or butyl). In certain embodiments, $R^x$ is methyl. In certain embodiments, $R^5$ is hydrogen. In certain embodiments, at least one of $V_{21}$, $V_{22}$, $V_{23}$, and $V_{24}$ is —$CH_2$—. In certain embodiments, at least two of $V_{21}$, $V_{22}$, $V_{23}$, and $V_{24}$ are —$CH_2$—. In certain embodiments, at least three of $V_{21}$, $V_{22}$, $V_{23}$, and $V_{24}$ are —$CH_2$—. In certain embodiments, all four of $V_{21}$, $V_{22}$, $V_{23}$, and $V_{24}$ are —$CH_2$—. In certain embodiments, at least one of $V_{22}$ and $V_{24}$ is O or —CH($OR^A$)—. In certain embodiments, $V_{22}$ is O. In certain embodiments, $V_{22}$ is —CH($OR^A$)—. In certain embodiments, $V_{24}$ is O. In certain embodiments, $V_{24}$ is —CH($OR^A$)—. In certain embodiments, $R^D$ is hydrogen. In certain embodiments, $R^A$ is hydrogen. In certain embodiments, $R^A$ is not hydrogen. In certain embodiments, $R^A$ is optionally substituted alkyl. In certain embodiments, $R^A$ is optionally substituted $C_{1-6}$ alkyl. In certain embodiments, $R^A$ is unsubstituted $C_{1-6}$ alkyl (e.g., methyl, ethyl, propyl, butyl, pentyl, or hexyl). In certain embodiments, $R^A$ is unsubstituted branched $C_{3-6}$ alkyl (e.g., isopropyl, sec-butyl, tert-butyl, isopentyl, neopentyl, or 3-pentyl). In certain embodiments, $R^A$ is methyl. In certain embodiments, $R^A$ is ethyl. In certain embodiments, $R^A$ is 3-pentyl. In certain embodiments, $R^D$ is hydrogen; and $R^A$ is methyl. In certain embodiments, $R^D$ is hydrogen; and $R^A$ is ethyl. In certain embodiments, $R^D$ is hydrogen; and $R^A$ is 3-pentyl. In certain embodiments, two $R^E$ groups are joined to form an optionally substituted carbocyclic ring (e.g., cyclopropyl, cyclobutyl, cyclopentyl, or cyclohexyl). In certain embodiments, two $R^E$ groups are joined to form an optionally substituted cyclopropyl ring. In certain embodiments, two $R^E$ groups are joined to form an unsubstituted carbocyclic ring (e.g., cyclopropyl, cyclobutyl, cyclopentyl, or cyclohexyl). In certain embodiments, two $R^E$ groups are joined to form an unsubstituted cyclopropyl ring. In certain embodiments, $L_1$ is a bond and $R^W$ is hydrogen. In certain embodiments, $L_1$ is a bond, $R^W$ is hydrogen, and $R^5$ is hydrogen. In certain embodiments, $L_1$ is a bond and $R^W$ is halogen, e.g., fluoro, chloro, bromo, or iodo. In certain embodiments, $L_1$ is a bond and $R^W$ is optionally substituted $C_{1-6}$alkyl, e.g., unsubstituted $C_{1-4}$alkyl, e.g., methyl, ethyl, propyl, butyl, isopropyl, isobutyl, or isoamyl.

In certain embodiments, when Ring A is of Formula (q-59), provided are compounds of Formulae XII-f1 to XII-f5:

or pharmaceutically acceptable salt thereof; wherein $R^3$, $R^4$, $R^5$, $R^x$, $V_{21}$, $V_{22}$, $V_{23}$, $V_{24}$, $R^A$, $R^D$, and $R^F$ are defined herein. In certain embodiments, $R^3$ is hydrogen. In certain embodiments, $R^3$ is unsubstituted $C_{1-4}$ alkyl (e.g., methyl, ethyl, propyl, or butyl). In certain embodiments, $R^3$ is methyl. In certain embodiments, $R^4$ is hydrogen. In certain embodiments, $R^4$ is unsubstituted $C_{1-6}$ alkyl (e.g., methyl, ethyl, propyl, or butyl). In certain embodiments, $R^4$ is methyl. In certain embodiments, $R^x$ is unsubstituted $C_{1-4}$ alkyl (e.g., methyl, ethyl, propyl or butyl). In certain embodiments, $R^x$ is methyl. In certain embodiments, $R^5$ is hydrogen. In certain embodiments, at least one of $V_{21}$, $V_{22}$, $V_{23}$, and $V_{24}$ is —$CH_2$—. In certain embodiments, at least two of $V_{21}$, $V_{22}$, $V_{23}$, and $V_{24}$ are —$CH_2$—. In certain embodiments, at least three of $V_{21}$, $V_{22}$, $V_{23}$, and $V_{24}$ are —CH$_2$—. In certain embodiments, all four of V$_{21}$, V$_{22}$, V$_{23}$, and V$_{24}$ are —CH$_2$—. In certain embodiments, at least one of V$_{22}$ and V$_{24}$ is O or —CH(OR$^A$)—. In certain embodiments, V$_{22}$ is O. In certain embodiments, V$_{22}$ is —CH(OR$^A$)—. In certain embodiments, V$_{24}$ is O. In certain embodiments, V$_{24}$ is —CH(OR$^A$)—. In certain embodiments, both instances of R$^F$ are hydrogen. In certain embodiments, R$^D$ is hydrogen. In certain embodiments, R$^A$ is hydrogen. In certain embodiments, R$^A$ is not hydrogen. In certain embodiments, R$^A$ is optionally substituted alkyl. In certain embodiments, R$^A$ is optionally substituted C$_{1-6}$ alkyl. In certain embodiments, R$^A$ is unsubstituted C$_{1-6}$ alkyl (e.g., methyl, ethyl, propyl, butyl, pentyl, or hexyl). In certain embodiments, R$^A$ is unsubstituted branched C$_{3-6}$ alkyl (e.g., isopropyl, sec-butyl, tert-butyl, isopentyl, neopentyl, or 3-pentyl). In certain embodiments, R$^A$ is methyl. In certain embodiments, R$^A$ is ethyl. In certain embodiments, R$^A$ is 3-pentyl. In certain embodiments, R$^D$ is hydrogen; and R$^A$ is methyl. In certain embodiments, R$^D$ is hydrogen; and R$^A$ is ethyl. In certain embodiments, R$^D$ is hydrogen; and R$^A$ is 3-pentyl. In certain embodiments, two R$^E$ groups are joined to form an optionally substituted carbocyclic ring (e.g., cyclopropyl, cyclobutyl, cyclopentyl, or cyclohexyl). In certain embodiments, two R$^E$ groups are joined to form an optionally substituted cyclopropyl ring. In certain embodiments, two R$^E$ groups are joined to form an unsubstituted carbocyclic ring (e.g., cyclopropyl, cyclobutyl, cyclopentyl, or cyclohexyl). In certain embodiments, two R$^E$ groups are joined to form an unsubstituted cyclopropyl ring. In certain embodiments, L$_1$ is a bond and R$^W$ is hydrogen. In certain embodiments, L$_1$ is a bond, R$^W$ is hydrogen, and R$^5$ is hydrogen. In certain embodiments, L$_1$ is a bond and R$^W$ is halogen, e.g., fluoro, chloro, bromo, or iodo. In certain embodiments, L$_1$ is a bond and R$^W$ is optionally substituted C$_{1-6}$alkyl, e.g., unsubstituted C$_{1-4}$alkyl, e.g., methyl, ethyl, propyl, butyl, isopropyl, isobutyl, or isoamyl.

In certain embodiments, when Ring A is of Formula (q-60), provided are compounds of Formulae XII-g1 to XII-g5:

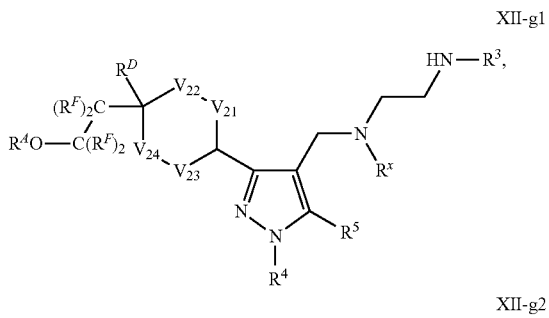

XII-g1

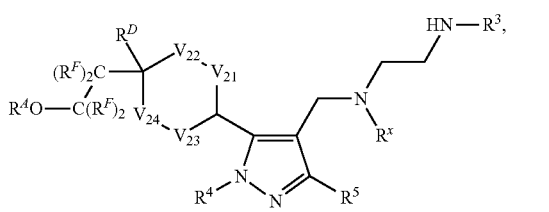

XII-g2

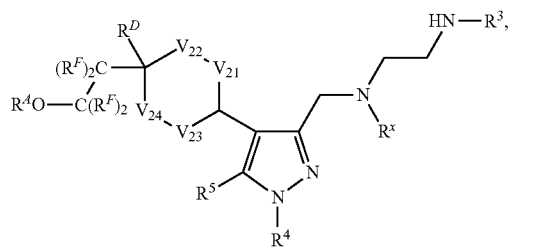

XII-g3

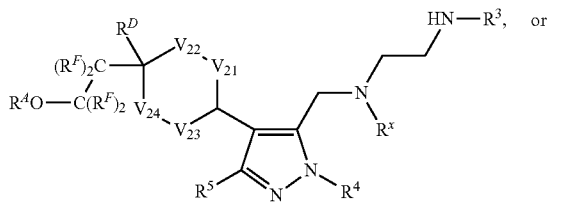

XII-g4, or

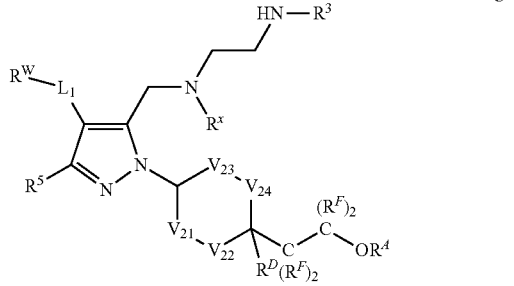

XII-g5 or pharmaceutically acceptable salt thereof; wherein R$^3$, R$^4$, R$^5$, R$^x$, V$_{21}$, V$_{22}$, V$_{23}$, V$_{24}$, R$^A$, R$^D$, and R$^F$ are defined herein. In certain embodiments, R$^3$ is hydrogen. In certain embodiments, R$^3$ is unsubstituted C$_{1-4}$ alkyl (e.g., methyl, ethyl, propyl, or butyl). In certain embodiments, R$^3$ is methyl. In certain embodiments, R$^4$ is hydrogen. In certain embodiments, R$^4$ is unsubstituted C$_{1-6}$ alkyl (e.g., methyl, ethyl, propyl, or butyl). In certain embodiments, R$^4$ is methyl. In certain embodiments, R$^x$ is unsubstituted C$_{1-4}$ alkyl (e.g., methyl, ethyl, propyl or butyl). In certain embodiments, R$^x$ is methyl. In certain embodiments, R$^5$ is hydrogen. In certain embodiments, at least one of V$_{21}$, V$_{22}$, V$_{23}$, and V$_{24}$ is —CH$_2$—. In certain embodiments, at least two of V$_{21}$, V$_{22}$, V$_{23}$, and V$_{24}$ are —CH$_2$—. In certain embodiments, at least three of V$_{21}$, V$_{22}$, V$_{23}$, and V$_{24}$ are —CH$_2$—. In certain embodiments, all four of V$_{21}$, V$_{22}$, V$_{23}$, and V$_{24}$ are —CH$_2$—. In certain embodiments, at least one of V$_{22}$ and V$_{24}$ is O or —CH(OR$^A$)—. In certain embodiments, V$_{22}$ is O. In certain embodiments, V$_{22}$ is —CH(OR$^A$)—. In certain embodiments, V$_{24}$ is O. In certain embodiments, V$_{24}$ is —CH(OR$^A$)—. In certain embodiments, at least two instances of R$^F$ are hydrogen. In certain embodiments, all four instances of R$^F$ are hydrogen. In certain embodiments, R$^D$ is hydrogen. In certain embodiments, R$^A$ is hydrogen. In certain embodiments, R$^A$ is not hydrogen. In certain embodiments, R$^A$ is optionally substituted alkyl. In certain embodiments, R$^A$ is optionally substituted C$_{1-6}$ alkyl. In certain embodiments, R$^A$ is unsubstituted C$_{1-6}$ alkyl (e.g., methyl, ethyl, propyl, butyl, pentyl, or hexyl). In certain embodiments, R$^A$ is unsubstituted branched C$_{3-6}$ alkyl (e.g., isopropyl, sec-butyl, tert-butyl, isopentyl, neopentyl, or 3-pentyl). In certain embodiments, R$^A$ is methyl. In certain embodiments, R$^A$ is ethyl. In certain embodiments, $R^A$ is 3-pentyl. In certain embodiments, $R^D$ is hydrogen; and $R^A$ is methyl. In certain embodiments, $R^D$ is hydrogen; and $R^A$ is ethyl. In certain embodiments, $R^D$ is hydrogen; and $R^A$ is 3-pentyl. In certain embodiments, two $R^E$ groups are joined to form an optionally substituted carbocyclic ring (e.g., cyclopropyl, cyclobutyl, cyclopentyl, or cyclohexyl). In certain embodiments, two $R^E$ groups are joined to form an optionally substituted cyclopropyl ring. In certain embodiments, two $R^E$ groups are joined to form an unsubstituted carbocyclic ring (e.g., cyclopropyl, cyclobutyl, cyclopentyl, or cyclohexyl). In certain embodiments, two $R^E$ groups are joined to form an unsubstituted cyclopropyl ring. In certain embodiments, $L_1$ is a bond and $R^W$ is hydrogen. In certain embodiments, $L_1$ is a bond, $R^W$ is hydrogen, and $R^5$ is hydrogen. In certain embodiments, $L_1$ is a bond and $R^W$ is halogen, e.g., fluoro, chloro, bromo, or iodo. In certain embodiments, $L_1$ is a bond and $R^W$ is optionally substituted $C_{1-6}$alkyl, e.g., unsubstituted $C_{1-4}$alkyl, e.g., methyl, ethyl, propyl, butyl, isopropyl, isobutyl, or isoamyl.

In certain embodiments, when Ring A is of Formula (r-1), provided are compounds of Formulae XII-h1 to XII-h5:

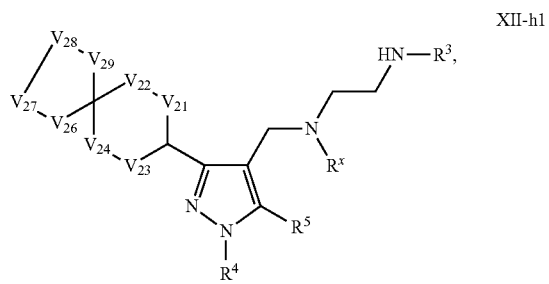

XII-h1

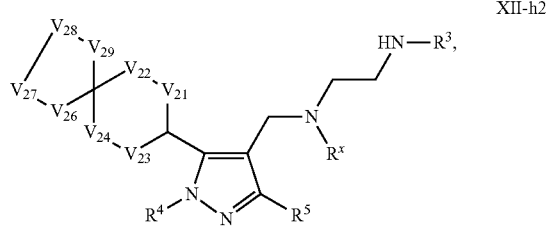

XII-h2

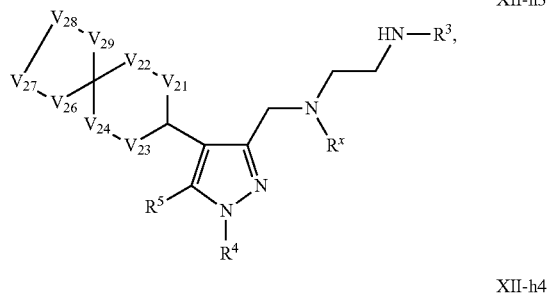

XII-h3

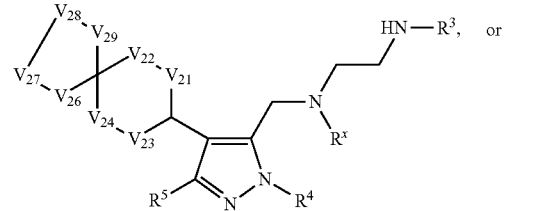

XII-h4

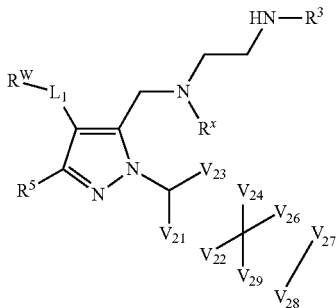

XII-h5 or pharmaceutically acceptable salt thereof; wherein $R^3$, $R^4$, $R^5$, $R^x$, $V_{21}$, $V_{22}$, $V_{23}$, $V_{24}$, $V_{26}$, $V_{27}$, $V_{28}$, and $V_{29}$ are defined herein. In certain embodiments, $R^3$ is hydrogen. In certain embodiments, $R^3$ is unsubstituted $C_{1-4}$ alkyl (e.g., methyl, ethyl, propyl, or butyl). In certain embodiments, $R^3$ is methyl. In certain embodiments, $R^4$ is hydrogen. In certain embodiments, $R^4$ is unsubstituted $C_{1-6}$ alkyl (e.g., methyl, ethyl, propyl, or butyl). In certain embodiments, $R^4$ is methyl. In certain embodiments, $R^x$ is unsubstituted $C_{1-4}$ alkyl (e.g., methyl, ethyl, propyl or butyl). In certain embodiments, $R^x$ is methyl. In certain embodiments, $R^5$ is hydrogen. In certain embodiments, at least one of $V_{21}$, $V_{22}$, $V_{23}$, and $V_{24}$ is —CH$_2$—. In certain embodiments, at least two of $V_{21}$, $V_{22}$, $V_{23}$, and $V_{24}$ are —CH$_2$—. In certain embodiments, at least three of $V_{21}$, $V_{22}$, $V_{23}$, and $V_{24}$ are —CH$_2$—. In certain embodiments, all four of $V_{21}$, $V_{22}$, $V_{23}$, and $V_{24}$ are —CH$_2$—. In certain embodiments, at least one of $V_{22}$ and $V_{24}$ is O or —CH(OR$^A$)—. In certain embodiments, $V_{22}$ is O. In certain embodiments, $V_{22}$ is —CH(OR$^A$)—. In certain embodiments, $V_{24}$ is O. In certain embodiments, $V_{24}$ is —CH(OR$^A$)—. In certain embodiments, exactly one instance of $V_{26}$, $V_{27}$, $V_{28}$, or $V_{29}$ is O. In certain embodiments, exactly two instances of $V_{26}$, $V_{27}$, $V_{28}$, or $V_{29}$ are O. In certain embodiments, exactly one instance of $V_{26}$, $V_{27}$, $V_{28}$, or $V_{29}$ is O; and all four of $V_{21}$, $V_{22}$, $V_{23}$, and $V_{24}$ are —CH$_2$—. In certain embodiments, exactly one instance of $V_{26}$, $V_{27}$, $V_{28}$, or $V_{29}$ is O; and a second instance of $V_{26}$, $V_{27}$, $V_{28}$, or $V_{29}$ is —C(R$^E$)$_2$—. In certain embodiments, exactly one instance of $V_{26}$, $V_{27}$, $V_{28}$, or $V_{29}$ is O; and a second instance of $V_{26}$, $V_{27}$, $V_{28}$, or $V_{29}$ is —C(Me)$_2$-. In certain embodiments, all four of $V_{26}$, $V_{27}$, $V_{28}$, and $V_{29}$ are —CH$_2$—. In certain embodiments, all eight of $V_{21}$, $V_{22}$, $V_{23}$, $V_{24}$, $V_{26}$, $V_{27}$, $V_{28}$, and $V_{29}$ are —CH$_2$—. In certain embodiments, exactly one instance of $V_{26}$, $V_{27}$, $V_{28}$, or $V_{29}$ is NR$^{Na}$; and a second instance of $V_{26}$, $V_{27}$, $V_{28}$, or $V_{29}$ is C=O. In certain embodiments, at least one instance of $V_{26}$, $V_{27}$, $V_{28}$, or $V_{29}$ is —C(R$^E$)$_2$—. In certain embodiments, exactly one instance of $V_{26}$, $V_{27}$, $V_{28}$, or $V_{29}$ is —C(R$^E$)$_2$—; and each instance of R$^E$ is independently halogen (e.g., fluoro, chloro, or bromo). In certain embodiments, two R$^E$ groups are joined to form an optionally substituted carbocyclic ring (e.g., cyclopropyl, cyclobutyl, cyclopentyl, or cyclohexyl). In certain embodiments, two R$^E$ groups are joined to form an optionally substituted cyclopropyl ring. In certain embodiments, two R$^E$ groups are joined to form an unsubstituted carbocyclic ring (e.g., cyclopropyl, cyclobutyl, cyclopentyl, or cyclohexyl). In certain embodiments, two R$^E$ groups are joined to form an unsubstituted cyclopropyl ring. In certain embodiments, $L_1$ is a bond and $R^W$ is hydrogen. In certain embodiments, $L_1$ is a bond, $R^W$ is hydrogen, and $R^5$ is hydrogen. In certain embodiments, $L_1$ is a bond and $R^W$ is halogen, e.g., fluoro, chloro, bromo, or iodo. In certain embodiments, $L_1$ is a bond and $R^W$ is optionally substituted $C_{1-6}$alkyl, e.g., unsubstituted $C_{1-4}$alkyl, e.g., methyl, ethyl, propyl, butyl, isopropyl, isobutyl, or isoamyl.

In certain embodiments, when Ring A is of Formula (r-3), provided are compounds of Formulae XII-i1 to XII-i5:

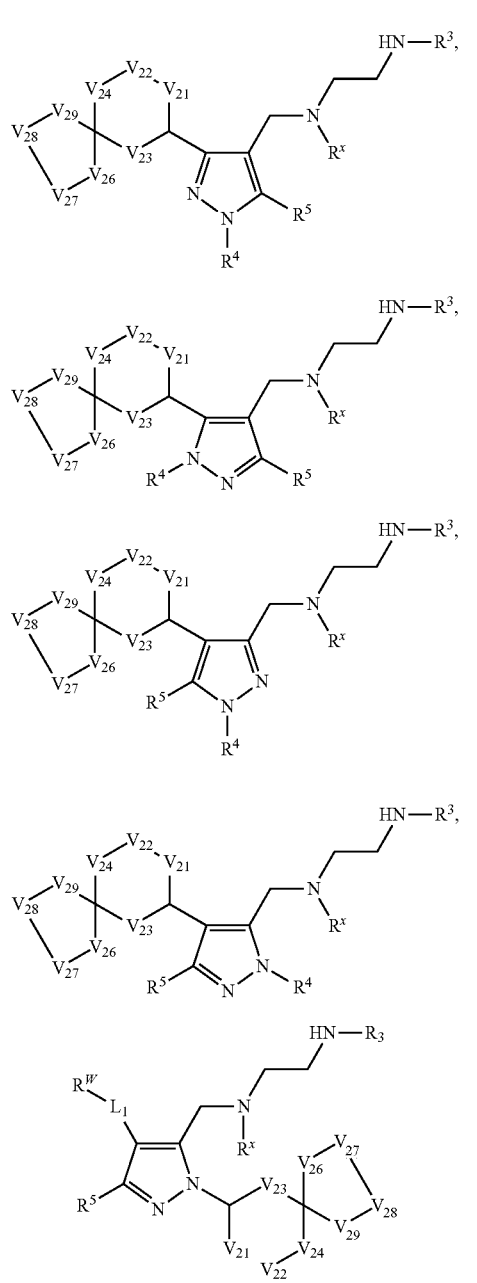

or pharmaceutically acceptable salt thereof; wherein $R^3$, $R^4$, $R^5$, $R^x$, $V_{21}$, $V_{22}$, $V_{23}$, $V_{24}$, $V_{26}$, $V_{27}$, $V_{28}$, and $V_{29}$ are defined herein. In certain embodiments, $R^3$ is hydrogen. In certain embodiments, $R^3$ is unsubstituted $C_{1-4}$ alkyl (e.g., methyl, ethyl, propyl, or butyl). In certain embodiments, $R^3$ is methyl. In certain embodiments, $R^4$ is hydrogen. In certain embodiments, $R^4$ is unsubstituted $C_{1-6}$ alkyl (e.g., methyl, ethyl, propyl, or butyl). In certain embodiments, $R^4$ is methyl. In certain embodiments, $R^x$ is unsubstituted $C_{1-4}$ alkyl (e.g., methyl, ethyl, propyl or butyl). In certain embodiments, $R^x$ is methyl. In certain embodiments, $R^5$ is hydrogen. In certain embodiments, at least one of $V_{21}$, $V_{22}$, $V_{23}$, and $V_{24}$ is —CH$_2$—. In certain embodiments, at least two of $V_{21}$, $V_{22}$, $V_{23}$, and $V_{24}$ are —CH$_2$—. In certain embodiments, at least three of $V_{21}$, $V_{22}$, $V_{23}$, and $V_{24}$ are —CH$_2$—. In certain embodiments, all four of $V_{21}$, $V_{22}$, $V_{23}$, and $V_{24}$ are —CH$_2$—. In certain embodiments, at least one of $V_{23}$ and $V_{24}$ is O or —CH(OR$^A$)—. In certain embodiments, $V_{23}$ is O. In certain embodiments, $V_{23}$ is —CH(OR$^A$)—. In certain embodiments, $V_{24}$ is O. In certain embodiments, $V_{24}$ is —CH(OR$^A$)—. In certain embodiments, exactly one instance of $V_{26}$, $V_{27}$, $V_{28}$, or $V_{29}$ is O. In certain embodiments, exactly two instances of $V_{26}$, $V_{27}$, $V_{28}$, or $V_{29}$ are O. In certain embodiments, exactly one instance of $V_{26}$, $V_{27}$, $V_{28}$, or $V_{29}$ is O; and all four of $V_{21}$, $V_{22}$, $V_{23}$, and $V_{24}$ are —CH$_2$—. In certain embodiments, exactly one instance of $V_{26}$, $V_{27}$, $V_{28}$, or $V_{29}$ is O; and a second instance of $V_{26}$, $V_{27}$, $V_{28}$, or $V_{29}$ is —C(R$^E$)$_2$—. In certain embodiments, exactly one instance of $V_{26}$, $V_{27}$, $V_{28}$, or $V_{29}$ is O; and a second instance of $V_{26}$, $V_{27}$, $V_{28}$, or $V_{29}$ is —C(Me)$_2$-. In certain embodiments, all four of $V_{26}$, $V_{27}$, $V_{28}$, and $V_{29}$ are —CH$_2$—. In certain embodiments, all eight of $V_{21}$, $V_{22}$, $V_{23}$, $V_{24}$, $V_{26}$, $V_{27}$, $V_{28}$, and $V_{29}$ are —CH$_2$—. In certain embodiments, exactly one instance of $V_{26}$, $V_{27}$, $V_{28}$, or $V_{29}$ is NR$^{Na}$; and a second instance of $V_{26}$, $V_{27}$, $V_{28}$, or $V_{29}$ is C=O. In certain embodiments, at least one instance of $V_{26}$, $V_{27}$, $V_{28}$, or $V_{29}$ is —C(R$^E$)$_2$—. In certain embodiments, exactly one instance of $V_{26}$, $V_{27}$, $V_{28}$, or $V_{29}$ is —C(R$^E$)$_2$—; and each instance of R$^E$ is independently halogen (e.g., fluoro, chloro, or bromo). In certain embodiments, two R$^E$ groups are joined to form an optionally substituted carbocyclic ring (e.g., cyclopropyl, cyclobutyl, cyclopentyl, or cyclohexyl). In certain embodiments, two R$^E$ groups are joined to form an optionally substituted cyclopropyl ring. In certain embodiments, two R$^E$ groups are joined to form an unsubstituted carbocyclic ring (e.g., cyclopropyl, cyclobutyl, cyclopentyl, or cyclohexyl). In certain embodiments, two R$^E$ groups are joined to form an unsubstituted cyclopropyl ring. In certain embodiments, $L_1$ is a bond and $R^W$ is hydrogen. In certain embodiments, $L_1$ is a bond, $R^W$ is hydrogen, and $R^5$ is hydrogen. In certain embodiments, $L_1$ is a bond and $R^W$ is halogen, e.g., fluoro, chloro, bromo, or iodo. In certain embodiments, $L_1$ is a bond and $R^W$ is optionally substituted $C_{1-6}$alkyl, e.g., unsubstituted $C_{1-4}$alkyl, e.g., methyl, ethyl, propyl, butyl, isopropyl, isobutyl, or isoamyl.

In certain embodiments, when Ring A is of Formula (r-2), provided are compounds of Formulae XII-j1 to XII-j5:

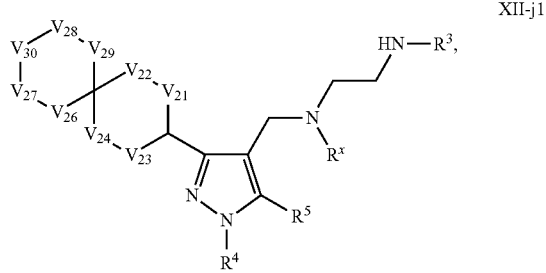

-continued

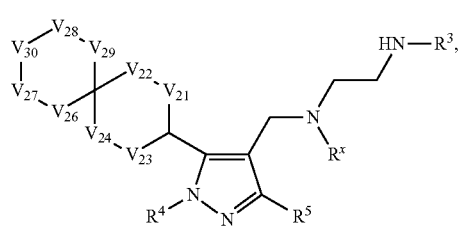

XII-j2

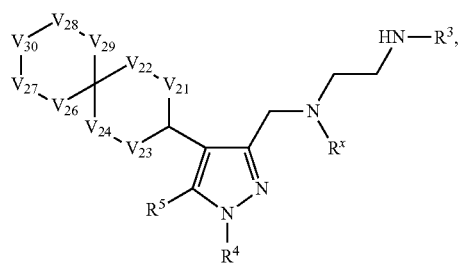

XII-j3

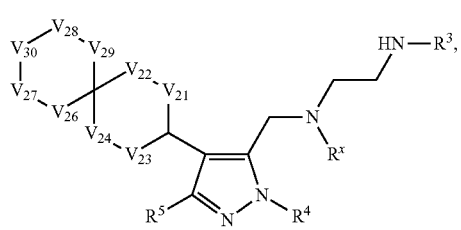

XII-j4 or

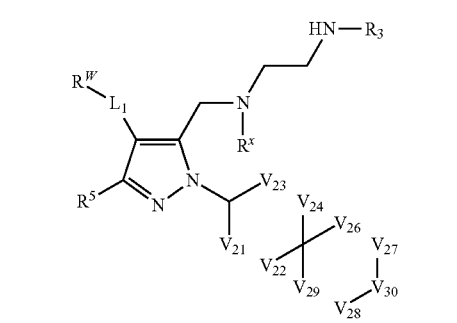

XII-j5 or pharmaceutically acceptable salt thereof; wherein $R^3$, $R^4$, $R^5$, $R^x$, $V_{21}$, $V_{22}$, $V_{23}$, $V_{24}$, $V_{26}$, $V_{27}$, $V_{28}$, $V_{29}$, and $V_{30}$ are defined herein. In certain embodiments, $R^3$ is hydrogen. In certain embodiments, $R^3$ is unsubstituted $C_{1-4}$ alkyl (e.g., methyl, ethyl, propyl, or butyl). In certain embodiments, $R^3$ is methyl. In certain embodiments, $R^4$ is hydrogen. In certain embodiments, $R^4$ is unsubstituted $C_{1-6}$ alkyl (e.g., methyl, ethyl, propyl, or butyl). In certain embodiments, $R^4$ is methyl. In certain embodiments, $R^x$ is unsubstituted $C_{1-4}$ alkyl (e.g., methyl, ethyl, propyl or butyl). In certain embodiments, $R^x$ is methyl. In certain embodiments, $R^5$ is hydrogen. In certain embodiments, at least one of $V_{21}$, $V_{22}$, $V_{23}$, and $V_{24}$ is —$CH_2$—. In certain embodiments, at least two of $V_{21}$, $V_{22}$, $V_{23}$, and $V_{24}$ are —$CH_2$—. In certain embodiments, at least three of $V_{21}$, $V_{22}$, $V_{23}$, and $V_{24}$ are —$CH_2$—. In certain embodiments, all four of $V_{21}$, $V_{22}$, $V_{23}$, and $V_{24}$ are —$CH_2$—. In certain embodiments, at least one of $V_{22}$ and $V_{24}$ is O or —$CH(OR^A)$—. In certain embodiments, $V_{22}$ is O. In certain embodiments, $V_{22}$ is —CH($OR^A$)—. In certain embodiments, $V_{24}$ is O. In certain embodiments, $V_{24}$ is —CH($OR^A$)—. In certain embodiments, exactly one instance of $V_{26}$, $V_{27}$, $V_{28}$, $V_{29}$, or $V_{30}$ is O. In certain embodiments, exactly two instances of $V_{26}$, $V_{27}$, $V_{28}$, $V_{29}$, or $V_{30}$ are O. In certain embodiments, exactly one instance of $V_{26}$, $V_{27}$, $V_{28}$, $V_{29}$, or $V_{30}$ is O; and all four of $V_{21}$, $V_{22}$, $V_{23}$, and $V_{24}$ are —$CH_2$—. In certain embodiments, exactly one instance of $V_{26}$, $V_{27}$, $V_{28}$, $V_{29}$, or $V_{30}$ is O; and a second instance of $V_{26}$, $V_{27}$, $V_{28}$, $V_{29}$, or $V_{30}$ is —$C(R^E)_2$—. In certain embodiments, exactly one instance of $V_{26}$, $V_{27}$, $V_{28}$, $V_{29}$, or $V_{30}$ is O; and a second instance of $V_{26}$, $V_{27}$, $V_{28}$, $V_{29}$, or $V_{30}$ is —$C(Me)_2$-. In certain embodiments, all five of $V_{26}$, $V_{27}$, $V_{28}$, $V_{29}$, and $V_{30}$ are —$CH_2$—. In certain embodiments, all nine of $V_{21}$, $V_{22}$, $V_{23}$, $V_{24}$, $V_{26}$, $V_{27}$, $V_{28}$, $V_{29}$, and $V_{30}$ are —$CH_2$—. In certain embodiments, exactly one instance of $V_{26}$, $V_{27}$, $V_{28}$, $V_{29}$, or $V_{30}$ is $NR^{Na}$; and a second instance of $V_{26}$, $V_{27}$, $V_{28}$, $V_{29}$, or $V_{30}$ is C=O. In certain embodiments, at least one instance of $V_{26}$, $V_{27}$, $V_{28}$, $V_{29}$, or $V_{30}$ is —$C(R^E)_2$—. In certain embodiments, exactly one instance of $V_{26}$, $V_{27}$, $V_{28}$, $V_{29}$, or $V_{30}$ is —$C(R^E)_2$—; and each instance of $R^E$ is independently halogen (e.g., fluoro, chloro, or bromo). In certain embodiments, $V_{30}$ is —$CF_2$—; and $V_{26}$, $V_{27}$, $V_{28}$, and $V_{29}$ are —$CH_2$—. In certain embodiments, $V_{30}$ is —$CF_2$—; and $V_{21}$, $V_{22}$, $V_{23}$, $V_{24}$, $V_{26}$, $V_{27}$, $V_{28}$, and $V_{29}$ are —$CH_2$—. In certain embodiments, two $R^E$ groups are joined to form an optionally substituted carbocyclic ring (e.g., cyclopropyl, cyclobutyl, cyclopentyl, or cyclohexyl). In certain embodiments, two $R^E$ groups are joined to form an optionally substituted cyclopropyl ring. In certain embodiments, two $R^E$ groups are joined to form an unsubstituted carbocyclic ring (e.g., cyclopropyl, cyclobutyl, cyclopentyl, or cyclohexyl). In certain embodiments, two $R^E$ groups are joined to form an unsubstituted cyclopropyl ring. In certain embodiments, $L_1$ is a bond and $R^W$ is hydrogen. In certain embodiments, $L_1$ is a bond, $R^W$ is hydrogen, and $R^5$ is hydrogen. In certain embodiments, $L_1$ is a bond and $R^W$ is halogen, e.g., fluoro, chloro, bromo, or iodo. In certain embodiments, $L_1$ is a bond and $R^W$ is optionally substituted $C_{1-6}$alkyl, e.g., unsubstituted $C_{1-4}$alkyl, e.g., methyl, ethyl, propyl, butyl, isopropyl, isobutyl, or isoamyl.

In certain embodiments, when Ring A is of Formula (r-4), provided are compounds of Formulae XII-k1 to XII-k5:

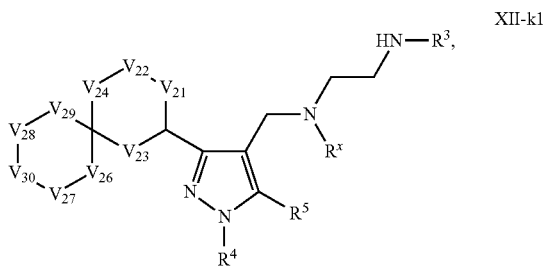

XII-k1

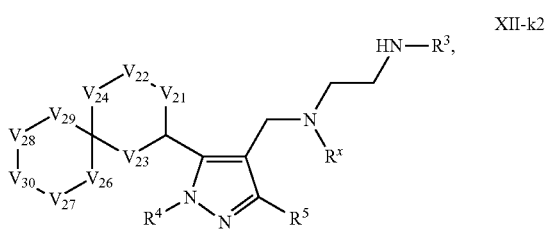

XII-k2

-continued

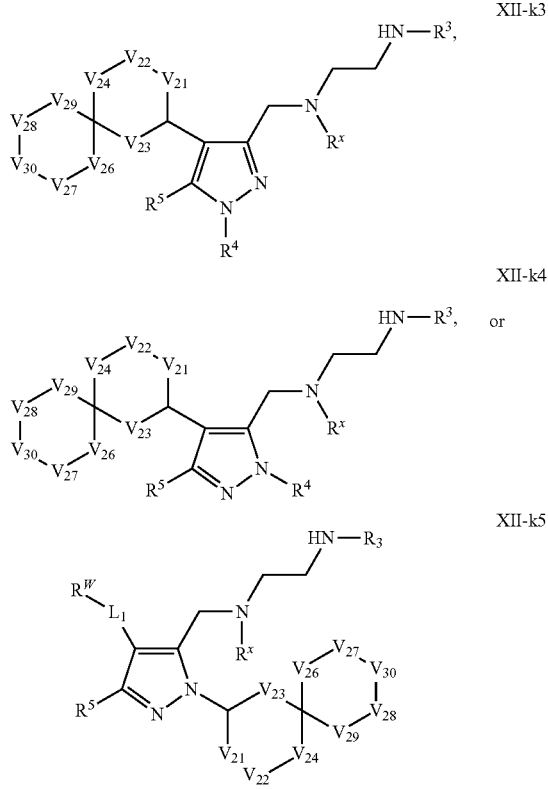

XII-k3

XII-k4

XII-k5 or pharmaceutically acceptable salt thereof; wherein $R^3$, $R^4$, $R^5$, $R^x$, $V_{21}$, $V_{22}$, $V_{23}$, $V_{24}$, $V_{26}$, $V_{27}$, $V_{28}$, $V_{29}$, and $V_{30}$ are defined herein. In certain embodiments, $R^3$ is hydrogen. In certain embodiments, $R^3$ is unsubstituted $C_{1-4}$ alkyl (e.g., methyl, ethyl, propyl, or butyl). In certain embodiments, $R^3$ is methyl. In certain embodiments, $R^4$ is hydrogen. In certain embodiments, $R^4$ is unsubstituted $C_{1-6}$ alkyl (e.g., methyl, ethyl, propyl, or butyl). In certain embodiments, $R^4$ is methyl. In certain embodiments, $R^x$ is unsubstituted $C_{1-4}$ alkyl (e.g., methyl, ethyl, propyl or butyl). In certain embodiments, $R^x$ is methyl. In certain embodiments, $R^5$ is hydrogen. In certain embodiments, at least one of $V_{21}$, $V_{22}$, $V_{23}$, and $V_{24}$ is —$CH_2$—. In certain embodiments, at least two of $V_{21}$, $V_{22}$, $V_{23}$, and $V_{24}$ are —$CH_2$—. In certain embodiments, at least three of $V_{21}$, $V_{22}$, $V_{23}$, and $V_{24}$ are —$CH_2$—. In certain embodiments, all four of $V_{21}$, $V_{22}$, $V_{23}$, and $V_{24}$ are —$CH_2$—. In certain embodiments, at least one of $V_{23}$ and $V_{24}$ is O or —$CH(OR^A)$—. In certain embodiments, $V_{23}$ is O. In certain embodiments, $V_{23}$ is —$CH(OR^A)$—. In certain embodiments, $V_{24}$ is O. In certain embodiments, $V_{24}$ is —$CH(OR^A)$—. In certain embodiments, exactly one instance of $V_{26}$, $V_{27}$, $V_{28}$, $V_{29}$, or $V_{30}$ is O. In certain embodiments, exactly two instances of $V_{26}$, $V_{27}$, $V_{28}$, $V_{29}$, or $V_{30}$ are O. In certain embodiments, exactly one instance of $V_{26}$, $V_{27}$, $V_{28}$, $V_{29}$, or $V_{30}$ is O; and all four of $V_{21}$, $V_{22}$, $V_{23}$, and $V_{24}$ are —$CH_2$—. In certain embodiments, exactly one instance of $V_{26}$, $V_{27}$, $V_{28}$, $V_{29}$, or $V_{30}$ is O; and a second instance of $V_{26}$, $V_{27}$, $V_{28}$, $V_{29}$, or $V_{30}$ is —$C(R^E)_2$—. In certain embodiments, exactly one instance of $V_{26}$, $V_{27}$, $V_{28}$, $V_{29}$, or $V_{30}$ is O; and a second instance of $V_{26}$, $V_{27}$, $V_{28}$, $V_{29}$, or $V_{30}$ is —$C(Me)_2$-. In certain embodiments, all five of $V_{26}$, $V_{27}$, $V_{28}$, $V_{29}$, and $V_{30}$ are —$CH_2$—. In certain embodiments, all nine of $V_{21}$, $V_{22}$, $V_{23}$, $V_{24}$, $V_{26}$, $V_{27}$, $V_{28}$, $V_{29}$, and $V_{30}$ are —$CH_2$—. In certain embodiments, exactly one instance of $V_{26}$, $V_{27}$, $V_{28}$, $V_{29}$, or $V_{30}$ is $NR^{Na}$; and a second instance of $V_{26}$, $V_{27}$, $V_{28}$, $V_{29}$, or $V_{30}$ is C=O. In certain embodiments, at least one instance of $V_{26}$, $V_{27}$, $V_{28}$, $V_{29}$, or $V_{30}$ is —$C(R^E)_2$—. In certain embodiments, exactly one instance of $V_{26}$, $V_{27}$, $V_{28}$, $V_{29}$, or $V_{30}$ is —$C(R^E)_2$—; and each instance of $R^E$ is independently halogen (e.g., fluoro, chloro, or bromo). In certain embodiments, $V_{30}$ is —$CF_2$—; and $V_{26}$, $V_{27}$, $V_{28}$, and $V_{29}$ are —$CH_2$—. In certain embodiments, $V_{30}$ is —$CF_2$—; and $V_{21}$, $V_{22}$, $V_{23}$, $V_{24}$, $V_{26}$, $V_{27}$, $V_{28}$, and $V_{29}$ are —$CH_2$—. In certain embodiments, two $R^E$ groups are joined to form an optionally substituted carbocyclic ring (e.g., cyclopropyl, cyclobutyl, cyclopentyl, or cyclohexyl). In certain embodiments, two $R^E$ groups are joined to form an optionally substituted cyclopropyl ring. In certain embodiments, two $R^E$ groups are joined to form an unsubstituted carbocyclic ring (e.g., cyclopropyl, cyclobutyl, cyclopentyl, or cyclohexyl). In certain embodiments, two $R^E$ groups are joined to form an unsubstituted cyclopropyl ring. In certain embodiments, $L_1$ is a bond and $R^W$ is hydrogen. In certain embodiments, $L_1$ is a bond, $R^W$ is hydrogen, and $R^5$ is hydrogen. In certain embodiments, $L_1$ is a bond and $R^W$ is halogen, e.g., fluoro, chloro, bromo, or iodo. In certain embodiments, $L_1$ is a bond and $R^W$ is optionally substituted $C_{1-6}$alkyl, e.g., unsubstituted $C_{1-4}$alkyl, e.g., methyl, ethyl, propyl, butyl, isopropyl, isobutyl, or isoamyl.

In certain embodiments, when Ring A is of Formula (r-81), provided are compounds of Formulae XII-11 to XII-15:

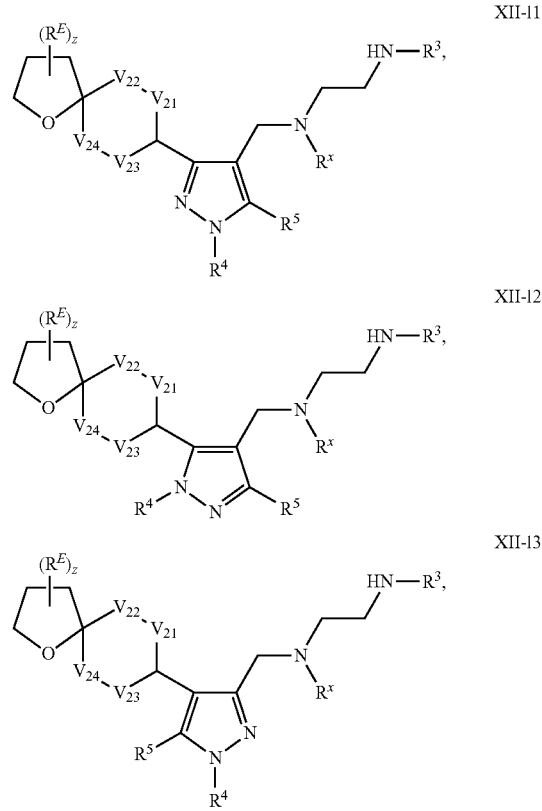

XII-11

XII-12

XII-13

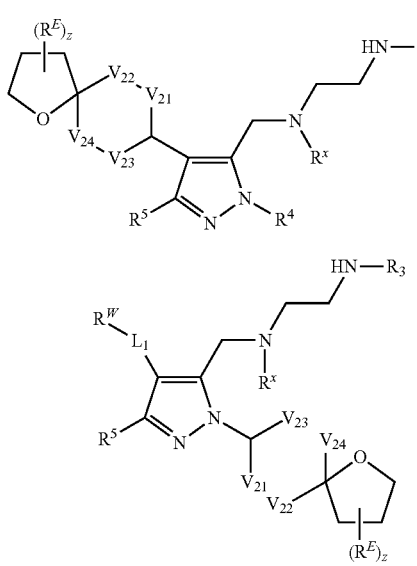

or pharmaceutically acceptable salt thereof; wherein $R^3$, $R^4$, $R^5$, $R^x$, $V_{21}$, $V_{22}$, $V_{23}$, $V_{24}$, z and $R^E$ are defined herein. In certain embodiments, $R^3$ is hydrogen. In certain embodiments, $R^3$ is unsubstituted $C_{1-4}$ alkyl (e.g., methyl, ethyl, propyl, or butyl). In certain embodiments, $R^3$ is methyl. In certain embodiments, $R^4$ is hydrogen. In certain embodiments, $R^4$ is unsubstituted $C_{1-6}$ alkyl (e.g., methyl, ethyl, propyl, or butyl). In certain embodiments, $R^4$ is methyl. In certain embodiments, $R^x$ is unsubstituted $C_{1-4}$ alkyl (e.g., methyl, ethyl, propyl or butyl). In certain embodiments, $R^x$ is methyl. In certain embodiments, $R^5$ is hydrogen. In certain embodiments, at least one of $V_{21}$, $V_{22}$, $V_{23}$, and $V_{24}$ is —CH$_2$—. In certain embodiments, at least two of $V_{21}$, $V_{22}$, $V_{23}$, and $V_{24}$ are —CH$_2$—. In certain embodiments, at least three of $V_{21}$, $V_{22}$, $V_{23}$, and $V_{24}$ are —CH$_2$—. In certain embodiments, all four of $V_{21}$, $V_{22}$, $V_{23}$, and $V_{24}$ are —CH$_2$—. In certain embodiments, at least one of $V_{23}$ and $V_{24}$ is O or —CH(OR$^4$)—. In certain embodiments, $V_{23}$ is O. In certain embodiments, $V_{23}$ is —CH(OR$^4$)—. In certain embodiments, $V_{24}$ is O. In certain embodiments, $V_{24}$ is —CH(OR$^4$)—. In certain embodiments, z is 2. In certain embodiments, at least one instance of $R^E$ is optionally substituted alkyl. In certain embodiments, at least one instance of $R^E$ is optionally substituted $C_{1-6}$ alkyl. In certain embodiments, at least one instance of $R^E$ is unsubstituted $C_{1-6}$ alkyl (e.g., methyl, ethyl, propyl, butyl, pentyl, or hexyl). In certain embodiments, at least one instance of $R^E$ is unsubstituted branched $C_{3-6}$ alkyl (e.g., isopropyl, sec-butyl, tert-butyl, isopentyl, neopentyl, or 3-pentyl). In certain embodiments, at least one instance of $R^E$ is methyl. In certain embodiments, at least two instances of $R^E$ are independently optionally substituted alkyl. In certain embodiments, at least two instances of $R^E$ are independently optionally substituted $C_{1-6}$ alkyl. In certain embodiments, at least two instances of $R^E$ are independently unsubstituted $C_{1-6}$ alkyl (e.g., methyl, ethyl, propyl, butyl, pentyl, or hexyl). In certain embodiments, at least two instances of $R^E$ are independently unsubstituted branched $C_{3-6}$ alkyl (e.g., isopropyl, sec-butyl, tert-butyl, isopentyl, neopentyl, or 3-pentyl). In certain embodiments, at least two instances of $R^E$ are methyl. In certain embodiments, z is 2; and each instance of $R^E$ is independently optionally substituted alkyl. In certain embodiments, z is 2; and each instance of $R^E$ is indepen-dently optionally substituted $C_{1-6}$ alkyl. In certain embodiments, z is 2; and each instance of $R^E$ is independently unsubstituted $C_{1-6}$ alkyl (e.g., methyl, ethyl, propyl, butyl, pentyl, or hexyl). In certain embodiments, z is 2; and each instance of $R^E$ is independently unsubstituted branched $C_{3-6}$ alkyl (e.g., isopropyl, sec-butyl, tert-butyl, isopentyl, neopentyl, or 3-pentyl). In certain embodiments, z is 2; and each instance of $R^E$ is methyl. In certain embodiments, z is 2; both instances of $R^E$ are attached to the same carbon; and each instance of $R^E$ is independently optionally substituted alkyl. In certain embodiments, z is 2; both instances of $R^E$ are attached to the same carbon; and each instance of $R^E$ is independently optionally substituted $C_{1-6}$ alkyl. In certain embodiments, z is 2; both instances of $R^E$ are attached to the same carbon; and each instance of $R^E$ is independently unsubstituted $C_{1-6}$ alkyl (e.g., methyl, ethyl, propyl, butyl, pentyl, or hexyl). In certain embodiments, z is 2; both instances of $R^E$ are attached to the same carbon; and each instance of $R^E$ is independently unsubstituted branched $C_{3-6}$ alkyl (e.g., isopropyl, sec-butyl, tert-butyl, isopentyl, neopentyl, or 3-pentyl). In certain embodiments, z is 2; both instances of $R^E$ are attached to the same carbon; and each instance of $R^E$ is methyl. In certain embodiments, two $R^E$ groups are joined to form an optionally substituted carbocyclic ring (e.g., cyclopropyl, cyclobutyl, cyclopentyl, or cyclohexyl). In certain embodiments, two $R^E$ groups are joined to form an optionally substituted cyclopropyl ring. In certain embodiments, two $R^E$ groups are joined to form an unsubstituted carbocyclic ring (e.g., cyclopropyl, cyclobutyl, cyclopentyl, or cyclohexyl). In certain embodiments, two $R^E$ groups are joined to form an unsubstituted cyclopropyl ring. In certain embodiments, $L_1$ is a bond and $R^W$ is hydrogen. In certain embodiments, $L_1$ is a bond, $R^W$ is hydrogen, and $R^5$ is hydrogen. In certain embodiments, $L_1$ is a bond and $R^W$ is halogen, e.g., fluoro, chloro, bromo, or iodo. In certain embodiments, $L_1$ is a bond and $R^W$ is optionally substituted $C_{1-6}$alkyl, e.g., unsubstituted $C_{1-4}$alkyl, e.g., methyl, ethyl, propyl, butyl, isopropyl, isobutyl, or isoamyl.

In certain embodiments, when Ring A is of Formula (r-82), provided are compounds of Formulae XII-m1 to XII-m5:

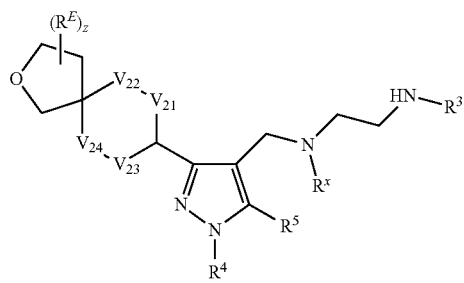

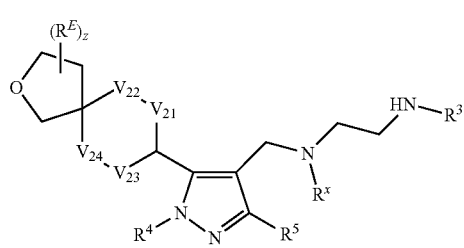

-continued

XII-m3

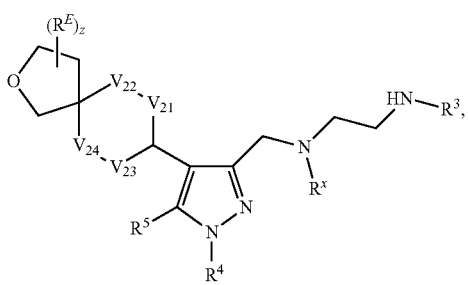

XII-m4

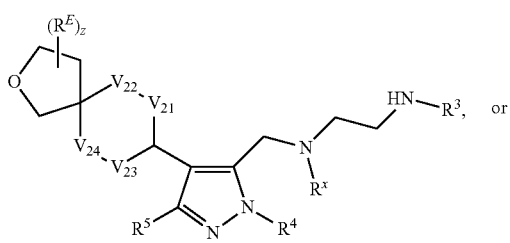

XII-m5

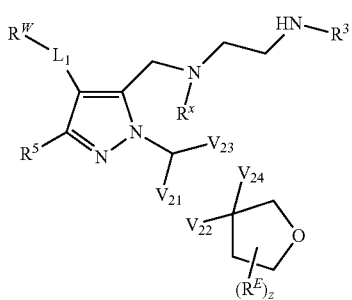

or pharmaceutically acceptable salt thereof; wherein $R^3$, $R^4$, $R^5$, $R^x$, $V_{21}$, $V_{22}$, $V_{23}$, $V_{24}$, z and $R^E$ are defined herein. In certain embodiments, $R^3$ is hydrogen. In certain embodiments, $R^3$ is unsubstituted $C_{1-4}$ alkyl (e.g., methyl, ethyl, propyl, or butyl). In certain embodiments, $R^3$ is methyl. In certain embodiments, $R^4$ is hydrogen. In certain embodiments, $R^4$ is unsubstituted $C_{1-6}$ alkyl (e.g., methyl, ethyl, propyl, or butyl). In certain embodiments, $R^4$ is methyl. In certain embodiments, $R^x$ is unsubstituted $C_{1-4}$ alkyl (e.g., methyl, ethyl, propyl or butyl). In certain embodiments, $R^x$ is methyl. In certain embodiments, $R^5$ is hydrogen. In certain embodiments, at least one of $V_{21}$, $V_{22}$, $V_{23}$, and $V_{24}$ is —CH$_2$—. In certain embodiments, at least two of $V_{21}$, $V_{22}$, $V_{23}$, and $V_{24}$ are —CH$_2$—. In certain embodiments, at least three of $V_{21}$, $V_{22}$, $V_{23}$, and $V_{24}$ are —CH$_2$—. In certain embodiments, all four of $V_{21}$, $V_{22}$, $V_{23}$, and $V_{24}$ are —CH$_2$—. In certain embodiments, at least one of $V_{23}$ and $V_{24}$ is O or —CH(OR$^A$)—. In certain embodiments, $V_{23}$ is O. In certain embodiments, $V_{23}$ is —CH(OR$^A$)—. In certain embodiments, $V_{24}$ is O. In certain embodiments, $V_{24}$ is —CH(OR$^A$)—. In certain embodiments, z is 2. In certain embodiments, at least one instance of $R^E$ is optionally substituted alkyl. In certain embodiments, at least one instance of $R^E$ is optionally substituted $C_{1-6}$ alkyl. In certain embodiments, at least one instance of $R^E$ is unsubstituted $C_{1-6}$ alkyl (e.g., methyl, ethyl, propyl, butyl, pentyl, or hexyl). In certain embodiments, at least one instance of $R^E$ is unsubstituted branched $C_{3-6}$ alkyl (e.g., isopropyl, sec-butyl, tert-butyl, isopentyl, neopentyl, or 3-pentyl). In certain embodiments, at least one instance of $R^E$ is methyl. In certain embodiments, at least two instances of $R^E$ are independently optionally substituted alkyl. In certain embodiments, at least two instances of $R^E$ are independently optionally substituted $C_{1-6}$ alkyl. In certain embodiments, at least two instances of $R^E$ are independently unsubstituted $C_{1-6}$ alkyl (e.g., methyl, ethyl, propyl, butyl, pentyl, or hexyl). In certain embodiments, at least two instances of $R^E$ are independently unsubstituted branched $C_{3-6}$ alkyl (e.g., isopropyl, sec-butyl, tert-butyl, isopentyl, neopentyl, or 3-pentyl). In certain embodiments, at least two instances of $R^E$ are methyl. In certain embodiments, z is 2; and each instance of $R^E$ is independently optionally substituted alkyl. In certain embodiments, z is 2; and each instance of $R^E$ is independently optionally substituted $C_{1-6}$ alkyl. In certain embodiments, z is 2; and each instance of $R^E$ is independently unsubstituted $C_{1-6}$ alkyl (e.g., methyl, ethyl, propyl, butyl, pentyl, or hexyl). In certain embodiments, z is 2; and each instance of $R^E$ is independently unsubstituted branched $C_{3-6}$ alkyl (e.g., isopropyl, sec-butyl, tert-butyl, isopentyl, neopentyl, or 3-pentyl). In certain embodiments, z is 2; and each instance of $R^E$ is methyl. In certain embodiments, z is 2; both instances of $R^E$ are attached to the same carbon; and each instance of $R^E$ is independently optionally substituted alkyl. In certain embodiments, z is 2; both instances of $R^E$ are attached to the same carbon; and each instance of $R^E$ is independently optionally substituted $C_{1-6}$ alkyl. In certain embodiments, z is 2; both instances of $R^E$ are attached to the same carbon; and each instance of $R^E$ is independently unsubstituted $C_{1-6}$ alkyl (e.g., methyl, ethyl, propyl, butyl, pentyl, or hexyl). In certain embodiments, z is 2; both instances of $R^E$ are attached to the same carbon; and each instance of $R^E$ is independently unsubstituted branched $C_{3-6}$ alkyl (e.g., isopropyl, sec-butyl, tert-butyl, isopentyl, neopentyl, or 3-pentyl). In certain embodiments, z is 2; both instances of $R^E$ are attached to the same carbon; and each instance of $R^E$ is methyl. In certain embodiments, two $R^E$ groups are joined to form an optionally substituted carbocyclic ring (e.g., cyclopropyl, cyclobutyl, cyclopentyl, or cyclohexyl). In certain embodiments, two $R^E$ groups are joined to form an optionally substituted cyclopropyl ring. In certain embodiments, two $R^E$ groups are joined to form an unsubstituted carbocyclic ring (e.g., cyclopropyl, cyclobutyl, cyclopentyl, or cyclohexyl). In certain embodiments, two $R^E$ groups are joined to form an unsubstituted cyclopropyl ring. In certain embodiments, $L_1$ is a bond and $R^W$ is hydrogen. In certain embodiments, $L_1$ is a bond, $R^W$ is hydrogen, and $R^5$ is hydrogen. In certain embodiments, $L_1$ is a bond and $R^W$ is halogen, e.g., fluoro, chloro, bromo, or iodo. In certain embodiments, $L_1$ is a bond and $R^W$ is optionally substituted $C_{1-6}$alkyl, e.g., unsubstituted $C_{1-4}$alkyl, e.g., methyl, ethyl, propyl, butyl, isopropyl, isobutyl, or isoamyl.

In certain embodiments, when Ring A is of Formula (r-85), provided are compounds of Formulae XII-n1 to XII-n5:

XII-n1

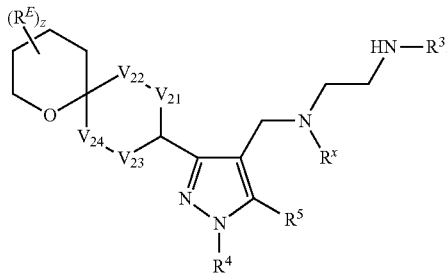

-continued

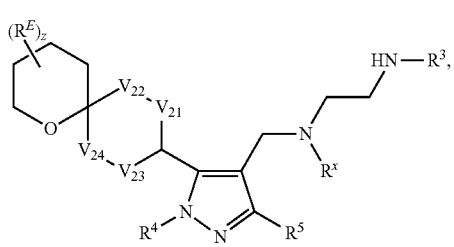

XII-n2

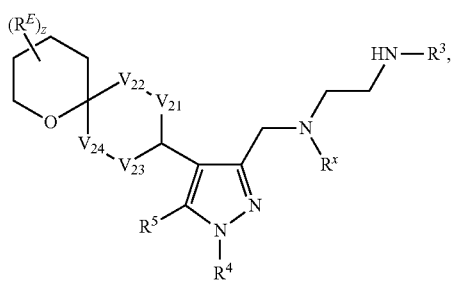

XII-n3

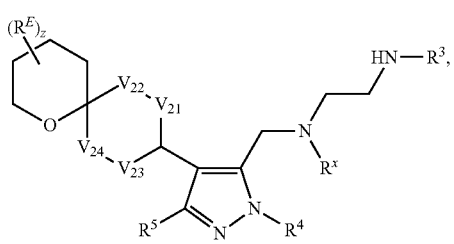

XII-n4 or

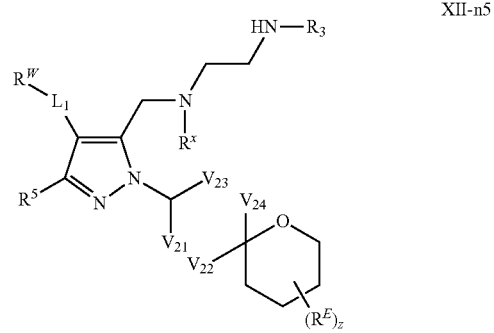

XII-n5 or pharmaceutically acceptable salt thereof; wherein $R^3$, $R^4$, $R^5$, $R^x$, $V_{21}$, $V_{22}$, $V_{23}$, $V_{24}$, z and $R^E$ are defined herein. In certain embodiments, $R^3$ is hydrogen. In certain embodiments, $R^3$ is unsubstituted $C_{1-4}$ alkyl (e.g., methyl, ethyl, propyl, or butyl). In certain embodiments, $R^3$ is methyl. In certain embodiments, $R^4$ is hydrogen. In certain embodiments, $R^4$ is unsubstituted $C_{1-6}$ alkyl (e.g., methyl, ethyl, propyl, or butyl). In certain embodiments, $R^4$ is methyl. In certain embodiments, $R^x$ is unsubstituted $C_{1-4}$ alkyl (e.g., methyl, ethyl, propyl or butyl). In certain embodiments, $R^x$ is methyl. In certain embodiments, $R^5$ is hydrogen. In certain embodiments, at least one of $V_{21}$, $V_{22}$, $V_{23}$, and $V_{24}$ is —$CH_2$—. In certain embodiments, at least two of $V_{21}$, $V_{22}$, $V_{23}$, and $V_{24}$ are —$CH_2$—. In certain embodiments, at least three of $V_{21}$, $V_{22}$, $V_{23}$, and $V_{24}$ are —$CH_2$—. In certain embodiments, all four of $V_{21}$, $V_{22}$, $V_{23}$, and $V_{24}$ are —$CH_2$—. In certain embodiments, at least one of $V_{23}$ and $V_{24}$ is O or —$CH(OR^4)$—. In certain embodiments, $V_{23}$ is O. In certain embodiments, $V_{23}$ is —$CH(OR^4)$—. In certain embodiments, $V_{24}$ is O. In certain embodiments, $V_{24}$ is —$CH(OR^4)$—. In certain embodiments, z is 2. In certain embodiments, at least one instance of $R^E$ is optionally substituted alkyl. In certain embodiments, at least one instance of $R^E$ is optionally substituted $C_{1-6}$ alkyl. In certain embodiments, at least one instance of $R^E$ is unsubstituted $C_{1-6}$ alkyl (e.g., methyl, ethyl, propyl, butyl, pentyl, or hexyl). In certain embodiments, at least one instance of $R^E$ is unsubstituted branched $C_{3-6}$ alkyl (e.g., isopropyl, sec-butyl, tert-butyl, isopentyl, neopentyl, or 3-pentyl). In certain embodiments, at least one instance of $R^E$ is methyl. In certain embodiments, at least two instances of $R^E$ are independently optionally substituted alkyl. In certain embodiments, at least two instances of $R^E$ are independently optionally substituted $C_{1-6}$ alkyl. In certain embodiments, at least two instances of $R^E$ are independently unsubstituted $C_{1-6}$ alkyl (e.g., methyl, ethyl, propyl, butyl, pentyl, or hexyl). In certain embodiments, at least two instances of $R^E$ are independently unsubstituted branched $C_{3-6}$ alkyl (e.g., isopropyl, sec-butyl, tert-butyl, isopentyl, neopentyl, or 3-pentyl). In certain embodiments, at least two instances of $R^E$ are methyl. In certain embodiments, z is 2; and each instance of $R^E$ is independently optionally substituted alkyl. In certain embodiments, z is 2; and each instance of $R^E$ is independently optionally substituted $C_{1-6}$ alkyl. In certain embodiments, z is 2; and each instance of $R^E$ is independently unsubstituted $C_{1-6}$ alkyl (e.g., methyl, ethyl, propyl, butyl, pentyl, or hexyl). In certain embodiments, z is 2; and each instance of $R^E$ is independently unsubstituted branched $C_{3-6}$ alkyl (e.g., isopropyl, sec-butyl, tert-butyl, isopentyl, neopentyl, or 3-pentyl). In certain embodiments, z is 2; and each instance of $R^E$ is methyl. In certain embodiments, z is 2; both instances of $R^E$ are attached to the same carbon; and each instance of $R^E$ is independently optionally substituted alkyl. In certain embodiments, z is 2; both instances of $R^E$ are attached to the same carbon; and each instance of $R^E$ is independently optionally substituted $C_{1-6}$ alkyl. In certain embodiments, z is 2; both instances of $R^E$ are attached to the same carbon; and each instance of $R^E$ is independently unsubstituted $C_{1-6}$ alkyl (e.g., methyl, ethyl, propyl, pentyl, or hexyl). In certain embodiments, z is 2; both instances of $R^E$ are attached to the same carbon; and each instance of $R^E$ is independently unsubstituted branched $C_{3-6}$ alkyl (e.g., isopropyl, sec-butyl, tert-butyl, isopentyl, neopentyl, or 3-pentyl). In certain embodiments, z is 2; both instances of $R^E$ are attached to the same carbon; and each instance of $R^E$ is methyl. In certain embodiments, z is 2; each instance of $R^E$ is attached to a different carbon; and each instance of $R^E$ is independently optionally substituted alkyl. In certain embodiments, z is 2; each instance of $R^E$ is attached to a different carbon; and each instance of $R^E$ is independently optionally substituted $C_{1-6}$ alkyl. In certain embodiments, z is 2; each instance of $R^E$ is attached to a different carbon; and each instance of $R^E$ is independently unsubstituted $C_{1-6}$ alkyl (e.g., methyl, ethyl, propyl, butyl, pentyl, or hexyl). In certain embodiments, z is 2; each instance of $R^E$ is attached to a different carbon; and each instance of $R^E$ is independently unsubstituted branched $C_{3-6}$ alkyl (e.g., isopropyl, sec-butyl, tert-butyl, isopentyl, neopentyl, or 3-pentyl). In certain embodiments, z is 2; each instance of $R^E$ is attached to a different carbon; and each instance of $R^E$ is methyl. In certain embodiments, two $R^E$ groups are joined to form an optionally substituted carbocyclic ring (e.g., cyclopropyl, cyclobutyl, cyclopentyl, or cyclohexyl). In certain embodiments, two $R^E$ groups are joined to form an optionally substituted cyclopropyl ring. In certain embodiments, two $R^E$ groups are joined to form an unsubstituted carbocyclic ring (e.g., cyclopropyl, cyclobutyl, cyclopentyl, or cyclohexyl). In certain embodiments, two $R^E$ groups are joined to form an unsubstituted cyclopropyl ring. In certain embodiments, $L_1$ is a bond and $R^W$ is hydrogen. In certain embodiments, $L_1$ is a bond, $R^W$ is hydrogen, and $R^5$ is hydrogen. In certain embodiments, $L_1$ is a bond and $R^W$ is halogen, e.g., fluoro, chloro, bromo, or iodo. In certain embodiments, $L_1$ is a bond and $R^W$ is optionally substituted $C_{1-6}$alkyl, e.g., unsubstituted $C_{1-4}$alkyl, e.g., methyl, ethyl, propyl, butyl, isopropyl, isobutyl, or isoamyl.

In certain embodiments, when Ring A is of Formula (r-86), provided are compounds of Formulae XII-o1 to XII-o5:

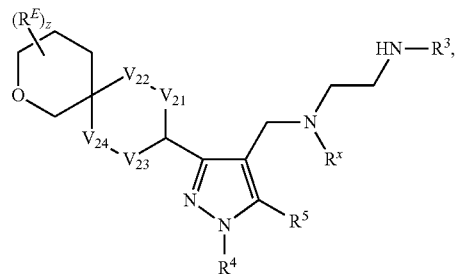

XII-o1

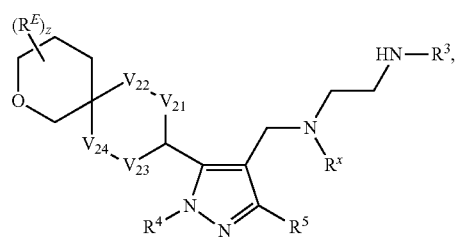

XII-o2

XII-o3

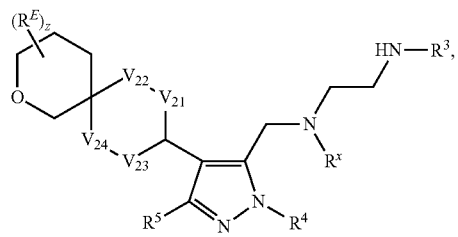

XII-o4 or

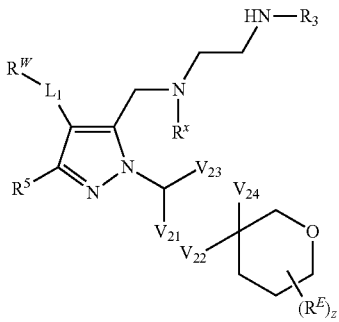

XII-o5 or pharmaceutically acceptable salt thereof; wherein $R^3$, $R^4$, $R^5$, $R^x$, $V_{21}$, $V_{22}$, $V_{23}$, $V_{24}$, z and $R^E$ are defined herein. In certain embodiments, $R^3$ is hydrogen. In certain embodiments, $R^3$ is unsubstituted $C_{1-4}$ alkyl (e.g., methyl, ethyl, propyl, or butyl). In certain embodiments, $R^3$ is methyl. In certain embodiments, $R^4$ is hydrogen. In certain embodiments, $R^4$ is unsubstituted $C_{1-6}$ alkyl (e.g., methyl, ethyl, propyl, or butyl). In certain embodiments, $R^4$ is methyl. In certain embodiments, $R^x$ is unsubstituted $C_{1-4}$ alkyl (e.g., methyl, ethyl, propyl or butyl). In certain embodiments, $R^x$ is methyl. In certain embodiments, $R^5$ is hydrogen. In certain embodiments, at least one of $V_{21}$, $V_{22}$, $V_{23}$, and $V_{24}$ is —$CH_2$—. In certain embodiments, at least two of $V_{21}$, $V_{22}$, $V_{23}$, and $V_{24}$ are —$CH_2$—. In certain embodiments, at least three of $V_{21}$, $V_{22}$, $V_{23}$, and $V_{24}$ are —$CH_2$—. In certain embodiments, all four of $V_{21}$, $V_{22}$, $V_{23}$, and $V_{24}$ are —$CH_2$—. In certain embodiments, at least one of $V_{23}$ and $V_{24}$ is O or —$CH(OR^A)$—. In certain embodiments, $V_{23}$ is O. In certain embodiments, $V_{23}$ is —$CH(OR^A)$—. In certain embodiments, $V_{24}$ is O. In certain embodiments, $V_{24}$ is —$CH(OR^A)$—. In certain embodiments, z is 2. In certain embodiments, at least one instance of $R^E$ is optionally substituted alkyl. In certain embodiments, at least one instance of $R^E$ is optionally substituted $C_{1-6}$ alkyl. In certain embodiments, at least one instance of $R^E$ is unsubstituted $C_{1-6}$ alkyl (e.g., methyl, ethyl, propyl, butyl, pentyl, or hexyl). In certain embodiments, at least one instance of $R^E$ is unsubstituted branched $C_{3-6}$ alkyl (e.g., isopropyl, sec-butyl, tert-butyl, isopentyl, neopentyl, or 3-pentyl). In certain embodiments, at least one instance of $R^E$ is methyl. In certain embodiments, at least two instances of $R^E$ are independently optionally substituted alkyl. In certain embodiments, at least two instances of $R^E$ are independently optionally substituted $C_{1-6}$ alkyl. In certain embodiments, at least two instances of $R^E$ are independently unsubstituted $C_{1-6}$ alkyl (e.g., methyl, ethyl, propyl, butyl, pentyl, or hexyl). In certain embodiments, at least two instances of $R^E$ are independently unsubstituted branched $C_{3-6}$ alkyl (e.g., isopropyl, sec-butyl, tert-butyl, isopentyl, neopentyl, or 3-pentyl). In certain embodiments, at least two instances of $R^E$ are methyl. In certain embodiments, z is 2; and each instance of $R^E$ is independently optionally substituted alkyl. In certain embodiments, z is 2; and each instance of $R^E$ is independently optionally substituted $C_{1-6}$ alkyl. In certain embodiments, z is 2; and each instance of $R^E$ is independently unsubstituted $C_{1-6}$ alkyl (e.g., methyl, ethyl, propyl, butyl, pentyl, or hexyl). In certain embodiments, z is 2; and each instance of $R^E$ is independently unsubstituted branched $C_{3-6}$ alkyl (e.g., isopropyl, sec-butyl, tert-butyl, neopentyl, or 3-pentyl). In certain embodiments, z is 2; and each instance of $R^E$ is methyl. In certain embodiments, z is 2; both instances of $R^E$ are attached to the same carbon; and each instance of $R^E$ is independently optionally substituted alkyl. In certain embodiments, z is 2; both instances of $R^E$ are attached to the same carbon; and each instance of $R^E$ is independently optionally substituted $C_{1-6}$ alkyl. In certain embodiments, z is 2; both instances of $R^E$ are attached to the same carbon; and each instance of $R^E$ is independently unsubstituted $C_{1-6}$ alkyl (e.g., methyl, ethyl, propyl, butyl, pentyl, or hexyl). In certain embodiments, z is 2; both instances of $R^E$ are attached to the same carbon; and each instance of $R^E$ is independently unsubstituted branched $C_{3-6}$ alkyl (e.g., isopropyl, sec-butyl, tert-butyl, isopentyl, neopentyl, or 3-pentyl). In certain embodiments, z is 2; both instances of $R^E$ are attached to the same carbon; and instance of $R^E$ is methyl. In certain embodiments, z is 2; each instance of $R^E$ is attached to a different carbon; and each instance of $R^E$ is independently optionally substituted alkyl. In certain embodiments, z is 2; each instance of $R^E$ is attached to a different carbon; and each instance of $R^E$ is independently optionally substituted $C_{1-6}$ alkyl. In certain embodiments, z is 2; each instance of $R^E$ is attached to a different carbon; and each instance of $R^E$ is independently unsubstituted $C_{1-6}$ alkyl (e.g., methyl, ethyl, propyl, butyl, pentyl, or hexyl). In certain embodiments, z is 2; each instance of $R^E$ is attached to a different carbon; and each instance of $R^E$ is independently unsubstituted branched $C_{3-6}$ alkyl (e.g., isopropyl, sec-butyl, tert-butyl, isopentyl, neopentyl, or 3-pentyl). In certain embodiments, z is 2; each instance of $R^E$ is attached to a different carbon; and each instance of $R^E$ is methyl. In certain embodiments, two $R^E$ groups are joined to form an optionally substituted carbocyclic ring (e.g., cyclopropyl, cyclobutyl, cyclopentyl, or cyclohexyl). In certain embodiments, two $R^E$ groups are joined to form an optionally substituted cyclopropyl ring. In certain embodiments, two $R^E$ groups are joined to form an unsubstituted carbocyclic ring (e.g., cyclopropyl, cyclobutyl, cyclopentyl, or cyclohexyl). In certain embodiments, two $R^E$ groups are joined to form an unsubstituted cyclopropyl ring. In certain embodiments, $L_1$ is a bond and $R^W$ is hydrogen. In certain embodiments, $L_1$ is a bond, $R^W$ is hydrogen, and $R^5$ is hydrogen. In certain embodiments, $L_1$ is a bond and $R^W$ is halogen, e.g., fluoro, chloro, bromo, or iodo. In certain embodiments, $L_1$ is a bond and $R^W$ is optionally substituted $C_{1-6}$alkyl, e.g., unsubstituted $C_{1-4}$alkyl, e.g., methyl, ethyl, propyl, butyl, isopropyl, isobutyl, or isoamyl.

In certain embodiments, when Ring A is of Formula (r-87), provided are compounds of Formulae XII-p1 to XII-p5:

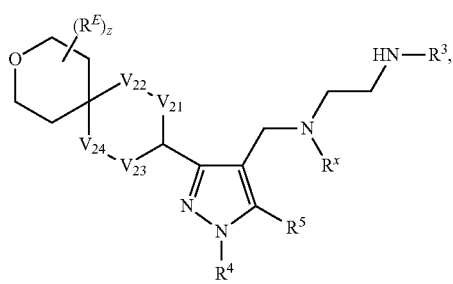

XII-p1

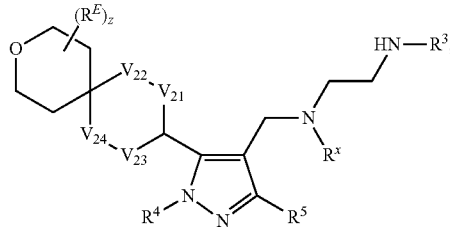

XII-p2

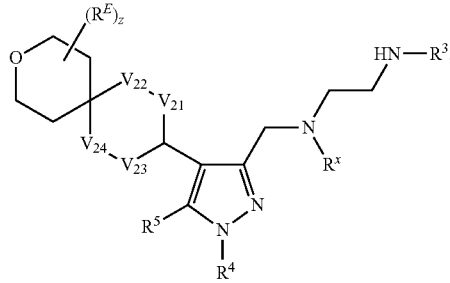

XII-p3

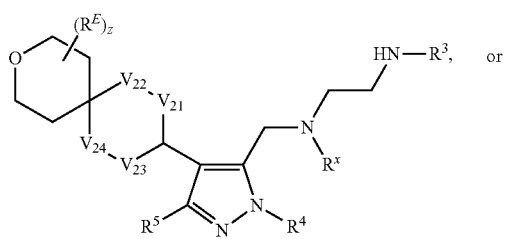

XII-p4

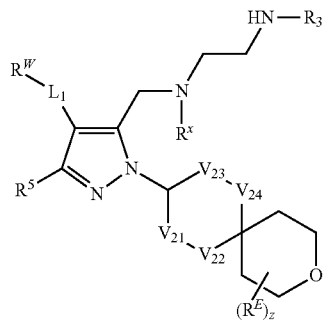

XII-p5 or pharmaceutically acceptable salt thereof; wherein $R^3$, $R^4$, $R^5$, $R^x$, $V_{21}$, $V_{22}$, $V_{23}$, $V_{24}$, z and $R^E$ are defined herein. In certain embodiments, $R^3$ is hydrogen. In certain embodiments, $R^3$ is unsubstituted $C_{1-4}$ alkyl (e.g., methyl, ethyl, propyl, or butyl). In certain embodiments, $R^3$ is methyl. In certain embodiments, $R^4$ is hydrogen. In certain embodiments, $R^4$ is unsubstituted $C_{1-6}$ alkyl (e.g., methyl, ethyl, propyl, or butyl). In certain embodiments, $R^4$ is methyl. In certain embodiments, $R^x$ is unsubstituted $C_{1-4}$ alkyl (e.g., methyl, ethyl, propyl or butyl). In certain embodiments, $R^x$ is methyl. In certain embodiments, $R^5$ is hydrogen. In certain embodiments, at least one of $V_{21}$, $V_{22}$, $V_{23}$, and $V_{24}$ is —$CH_2$—. In certain embodiments, at least two of $V_{21}$, $V_{22}$, $V_{23}$, and $V_{24}$ are —$CH_2$—. In certain embodiments, at least three of $V_{21}$, $V_{22}$, $V_{23}$, and $V_{24}$ are —$CH_2$—. In certain embodiments, all four of $V_{21}$, $V_{22}$, $V_{23}$, and $V_{24}$ are —$CH_2$—. In certain embodiments, at least one of $V_{23}$ and $V_{24}$ is O or —$CH(OR^A)$—. In certain embodiments, $V_{23}$ is O. In certain embodiments, $V_{23}$ is —$CH(OR^A)$—. In certain embodiments, $V_{24}$ is O. In certain embodiments, $V_{24}$ is —CH(OR$^A$)—. In certain embodiments, z is 2. In certain embodiments, at least one instance of R$^E$ is optionally substituted alkyl. In certain embodiments, at least one instance of R$^E$ is optionally substituted C$_{1-6}$ alkyl. In certain embodiments, at least one instance of R$^E$ is unsubstituted C$_{1-6}$ alkyl (e.g., methyl, ethyl, propyl, butyl, pentyl, or hexyl). In certain embodiments, at least one instance of R$^E$ is unsubstituted branched C$_{3-6}$ alkyl (e.g., isopropyl, sec-butyl, tert-butyl, isopentyl, neopentyl, or 3-pentyl). In certain embodiments, at least one instance of R$^E$ is methyl. In certain embodiments, at least two instances of R$^E$ are independently optionally substituted alkyl. In certain embodiments, at least two instances of R$^E$ are independently optionally substituted C$_{1-6}$ alkyl. In certain embodiments, at least two instances of R$^E$ are independently unsubstituted C$_{1-6}$ alkyl (e.g., methyl, ethyl, propyl, butyl, pentyl, or hexyl). In certain embodiments, at least two instances of R$^E$ are independently unsubstituted branched C$_{3-6}$ alkyl (e.g., isopropyl, sec-butyl, tert-butyl, isopentyl, neopentyl, or 3-pentyl). In certain embodiments, at least two instances of R$^E$ are methyl. In certain embodiments, z is 2; and each instance of R$^E$ is independently optionally substituted alkyl. In certain embodiments, z is 2; and each instance of R$^E$ is independently optionally substituted C$_{1-6}$ alkyl. In certain embodiments, z is 2; and each instance of R$^E$ is independently unsubstituted C$_{1-6}$ alkyl (e.g., methyl, ethyl, propyl, butyl, pentyl, or hexyl). In certain embodiments, z is 2; and each instance of R$^E$ is independently unsubstituted branched C$_{3-6}$ alkyl (e.g., isopropyl, sec-butyl, tert-butyl, isopentyl, neopentyl, or 3-pentyl). In certain embodiments, z is 2; and each instance of R$^E$ is methyl. In certain embodiments, z is 2; both instances of R$^E$ are attached to the same carbon; and each instance of R$^E$ is independently optionally substituted alkyl. In certain embodiments, z is 2; both instances of R$^E$ are attached to the same carbon; and each instance of R$^E$ is independently optionally substituted C$_{1-6}$ alkyl. In certain embodiments, z is 2; both instances of R$^E$ are attached to the same carbon; and each instance of R$^E$ is independently unsubstituted C$_{1-6}$ alkyl (e.g., methyl, ethyl, propyl, butyl, pentyl, or hexyl). In certain embodiments, z is 2; both instances of R$^E$ are attached to the same carbon; and each instance of R$^E$ is independently unsubstituted branched C$_{3-6}$ alkyl (e.g., isopropyl, sec-butyl, tert-butyl, isopentyl, neopentyl, or 3-pentyl). In certain embodiments, z is 2; both instances of R$^E$ are attached to the same carbon; and each instance of R$^E$ is methyl. In certain embodiments, z is 2; each instance of R$^E$ is attached to a different carbon; and each instance of R$^E$ is independently optionally substituted alkyl. In certain embodiments, z is 2; each instance of R$^E$ is attached to a different carbon; and each instance of R$^E$ is independently optionally substituted C$_{1-6}$ alkyl. In certain embodiments, z is 2; each instance of R$^E$ is attached to a different carbon; and each instance of R$^E$ is independently unsubstituted C$_{1-6}$ alkyl (e.g., methyl, ethyl, propyl, butyl, pentyl, or hexyl). In certain embodiments, z is 2; each instance of R$^E$ is attached to a different carbon; and each instance of R$^E$ is independently unsubstituted branched C$_{3-6}$ alkyl (e.g., isopropyl, sec-butyl, tert-butyl, isopentyl, neopentyl, or 3-pentyl). In certain embodiments, z is 2; each instance of R$^E$ is attached to a different carbon; and each instance of R$^E$ is methyl. In certain embodiments, two R$^E$ groups are joined to form an optionally substituted carbocyclic ring (e.g., cyclopropyl, cyclobutyl, cyclopentyl, or cyclohexyl). In certain embodiments, two R$^E$ groups are joined to form an optionally substituted cyclopropyl ring. In certain embodiments, two R$^E$ groups are joined to form an unsubstituted carbocyclic ring (e.g., cyclopropyl, cyclobutyl, cyclopentyl, or cyclohexyl). In certain embodiments, two R$^E$ groups are joined to form an unsubstituted cyclopropyl ring. In certain embodiments, L$_1$ is a bond and R$^W$ is hydrogen. In certain embodiments, L$_1$ is a bond, R$^W$ is hydrogen, and R$^5$ is hydrogen. In certain embodiments, L$_1$ is a bond and R$^W$ is halogen, e.g., fluoro, chloro, bromo, or iodo. In certain embodiments, L$_1$ is a bond and R$^W$ is optionally substituted C$_{1-6}$alkyl, e.g., unsubstituted C$_{1-4}$alkyl, e.g., methyl, ethyl, propyl, butyl, isopropyl, isobutyl, or isoamyl.

In certain embodiments, when Ring A is of Formula (r-214), provided are compounds of Formulae XII-q1 to XII-q5:

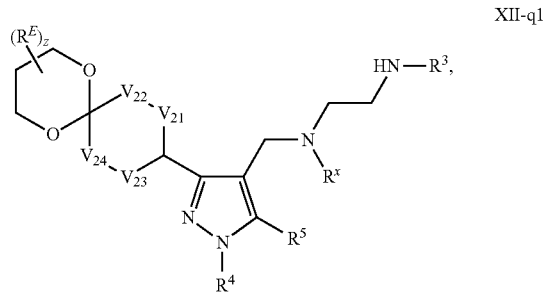

XII-q1

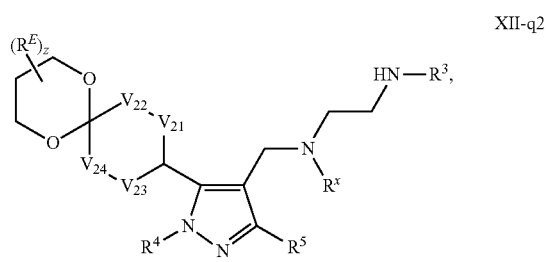

XII-q2

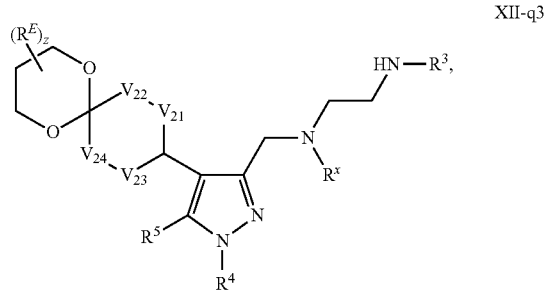

XII-q3

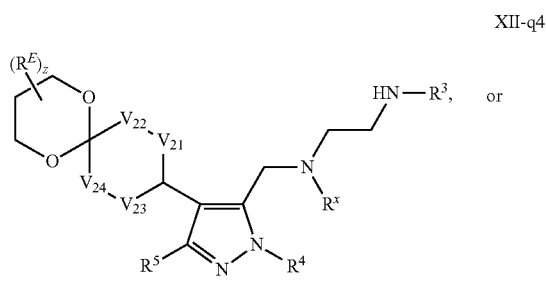

XII-q4 or

-continued

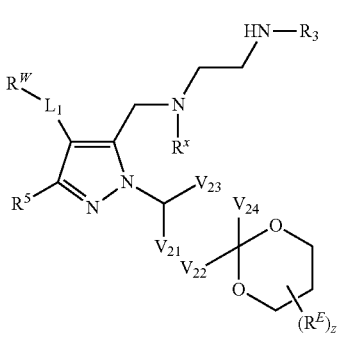

XII-q5 or pharmaceutically acceptable salt thereof; wherein $R^3$, $R^4$, $R^5$, $R^x$, $V_{21}$, $V_{22}$, $V_{23}$, $V_{24}$, z and $R^E$ are defined herein. In certain embodiments, $R^3$ is hydrogen. In certain embodiments, $R^3$ is unsubstituted $C_{1-4}$ alkyl (e.g., methyl, ethyl, propyl, or butyl). In certain embodiments, $R^3$ is methyl. In certain embodiments, $R^4$ is hydrogen. In certain embodiments, $R^4$ is unsubstituted $C_{1-6}$ alkyl (e.g., methyl, ethyl, propyl, or butyl). In certain embodiments, $R^4$ is methyl. In certain embodiments, $R^x$ is unsubstituted $C_{1-4}$ alkyl (e.g., methyl, ethyl, propyl or butyl). In certain embodiments, $R^x$ is methyl. In certain embodiments, $R^5$ is hydrogen. In certain embodiments, at least one of $V_{21}$, $V_{22}$, $V_{23}$, and $V_{24}$ is —CH$_2$—. In certain embodiments, at least two of $V_{21}$, $V_{22}$, $V_{23}$, and $V_{24}$ are —CH$_2$—. In certain embodiments, at least three of $V_{21}$, $V_{22}$, $V_{23}$, and $V_{24}$ are —CH$_2$—. In certain embodiments, all four of $V_{21}$, $V_{22}$, $V_{23}$, and $V_{24}$ are —CH$_2$—. In certain embodiments, at least one of $V_{23}$ and $V_{24}$ is O or —CH(OR$^4$)—. In certain embodiments, $V_{23}$ is O. In certain embodiments, $V_{23}$ is —CH(OR$^4$)—. In certain embodiments, $V_{24}$ is O. In certain embodiments, $V_{24}$ is —CH(OR$^4$)—. In certain embodiments, z is 2. In certain embodiments, at least one instance of $R^E$ is optionally substituted alkyl. In certain embodiments, at least one instance of $R^E$ is optionally substituted $C_{1-6}$ alkyl. In certain embodiments, at least one instance of $R^E$ is unsubstituted $C_{1-6}$ alkyl (e.g., methyl, ethyl, propyl, butyl, pentyl, or hexyl). In certain embodiments, at least one instance of $R^E$ is unsubstituted branched $C_{3-6}$ alkyl (e.g., isopropyl, sec-butyl, tert-butyl, isopentyl, neopentyl, or 3-pentyl). In certain embodiments, at least one instance of $R^E$ is methyl. In certain embodiments, at least two instances of $R^E$ are independently optionally substituted alkyl. In certain embodiments, at least two instances of $R^E$ are independently optionally substituted $C_{1-6}$ alkyl. In certain embodiments, at least two instances of $R^E$ are independently unsubstituted $C_{1-6}$ alkyl (e.g., methyl, ethyl, propyl, butyl, pentyl, or hexyl). In certain embodiments, at least two instances of $R^E$ are independently unsubstituted branched $C_{3-6}$ alkyl (e.g., isopropyl, sec-butyl, tert-butyl, isopentyl, neopentyl, or 3-pentyl). In certain embodiments, at least two instances of $R^E$ are methyl. In certain embodiments, z is 2; and each instance of $R^E$ is independently optionally substituted alkyl. In certain embodiments, z is 2; and each instance of $R^E$ is independently optionally substituted $C_{1-6}$ alkyl. In certain embodiments, z is 2; and each instance of $R^E$ is independently unsubstituted $C_{1-6}$ alkyl (e.g., methyl, ethyl, propyl, butyl, pentyl, or hexyl). In certain embodiments, z is 2; and each instance of $R^E$ is independently unsubstituted branched $C_{3-6}$ alkyl (e.g., isopropyl, sec-butyl, tert-butyl, isopentyl, neopentyl, or 3-pentyl). In certain embodiments, z is 2; and each instance of $R^E$ is methyl. In certain embodiments, z is 2; both instances of $R^E$ are attached to the same carbon; and each instance of $R^E$ is independently optionally substituted alkyl. In certain embodiments, z is 2; both instances of $R^E$ are attached to the same carbon; and each instance of $R^E$ is independently optionally substituted $C_{1-6}$ alkyl. In certain embodiments, z is 2; both instances of $R^E$ are attached to the same carbon; and each instance of $R^E$ is independently unsubstituted $C_{1-6}$ alkyl (e.g., methyl, ethyl, propyl, butyl, pentyl, or hexyl). In certain embodiments, z is 2; both instances of $R^E$ are attached to the same carbon; and each instance of $R^E$ is independently unsubstituted branched $C_{3-6}$ alkyl (e.g., isopropyl, sec-butyl, tert-butyl, isopentyl, neopentyl, or 3-pentyl). In certain embodiments, z is 2; both instances of $R^E$ are attached to the same carbon; and each instance of $R^E$ is methyl. In certain embodiments, z is 2; each instance of $R^E$ is attached to a different carbon; and each instance of $R^E$ is independently optionally substituted alkyl. In certain embodiments, z is 2; each instance of $R^E$ is attached to a different carbon; and each instance of $R^E$ is independently optionally substituted $C_{1-6}$ alkyl. In certain embodiments, z is 2; each instance of $R^E$ is attached to a different carbon; and each instance of $R^E$ is independently unsubstituted $C_{1-6}$ alkyl (e.g., methyl, ethyl, propyl, butyl, pentyl, or hexyl). In certain embodiments, z is 2; each instance of $R^E$ is attached to a different carbon; and each instance of $R^E$ is independently unsubstituted branched $C_{3-6}$ alkyl (e.g., isopropyl, sec-butyl, tert-butyl, isopentyl, neopentyl, or 3-pentyl). In certain embodiments, z is 2; each instance of $R^E$ is attached to a different carbon; and each instance of $R^E$ is methyl. In certain embodiments, two $R^E$ groups are joined to form an optionally substituted carbocyclic ring (e.g., cyclopropyl, cyclobutyl, cyclopentyl, or cyclohexyl). In certain embodiments, two $R^E$ groups are joined to form an optionally substituted cyclopropyl ring. In certain embodiments, two $R^E$ groups are joined to form an unsubstituted carbocyclic ring (e.g., cyclopropyl, cyclobutyl, cyclopentyl, or cyclohexyl). In certain embodiments, two $R^E$ groups are joined to form an unsubstituted cyclopropyl ring. In certain embodiments, $L_1$ is a bond and $R^W$ is hydrogen. In certain embodiments, $L_1$ is a bond, $R^W$ is hydrogen, and $R^5$ is hydrogen. In certain embodiments, $L_1$ is a bond and $R^W$ is halogen, e.g., fluoro, chloro, bromo, or iodo. In certain embodiments, $L_1$ is a bond and $R^W$ is optionally substituted $C_{1-6}$alkyl, e.g., unsubstituted $C_{1-4}$alkyl, e.g., methyl, ethyl, propyl, butyl, isopropyl, isobutyl, or isoamyl.

In certain embodiments, when Ring A is of Formula (r-222), provided are compounds of Formulae XII-r1 to XII-r5:

XII-r1

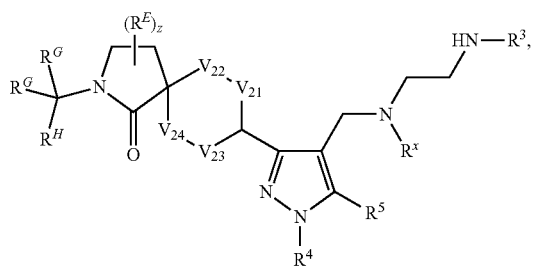

-continued

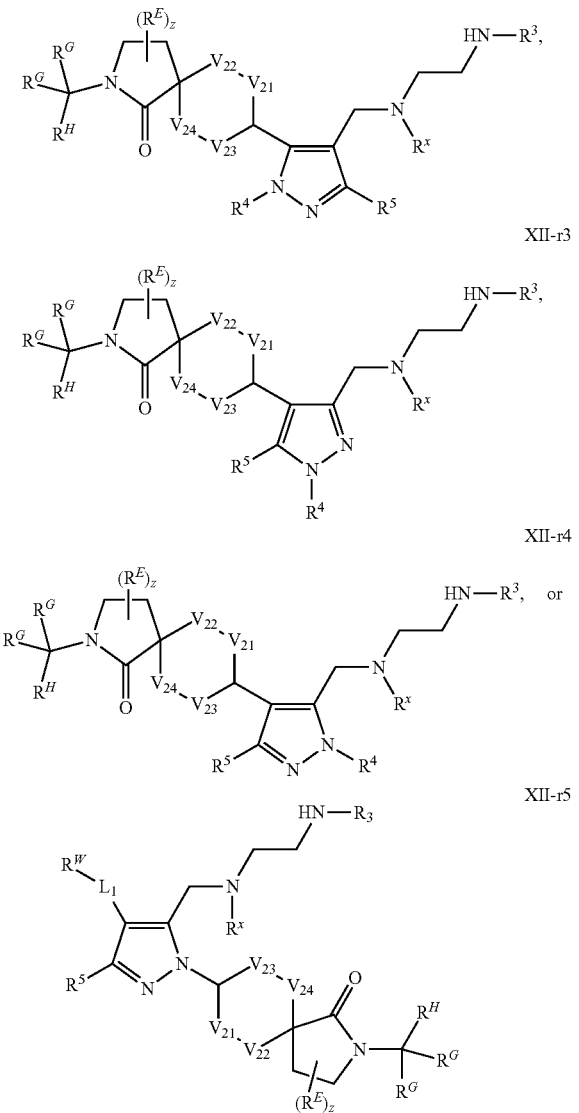

XII-r2

XII-r3

XII-r4

XII-r5 or pharmaceutically acceptable salt thereof; wherein $R^3$, $R^4$, $R^5$, $R^x$, $V_{21}$, $V_{22}$, $V_{23}$, $V_{24}$, z, $R^E$, $R^G$, and $R^H$ are defined herein. In certain embodiments, $R^3$ is hydrogen. In certain embodiments, $R^3$ is unsubstituted $C_{1-4}$ alkyl (e.g., methyl, ethyl, propyl, or butyl). In certain embodiments, $R^3$ is methyl. In certain embodiments, $R^4$ is hydrogen. In certain embodiments, $R^4$ is unsubstituted $C_{1-6}$ alkyl (e.g., methyl, ethyl, propyl, or butyl). In certain embodiments, $R^4$ is methyl. In certain embodiments, $R^x$ is unsubstituted $C_{1-4}$ alkyl (e.g., methyl, ethyl, propyl or butyl). In certain embodiments, $R^x$ is methyl. In certain embodiments, $R^5$ is hydrogen. In certain embodiments, at least one of $V_{21}$, $V_{22}$, $V_{23}$, and $V_{24}$ is —$CH_2$—. In certain embodiments, at least two of $V_{21}$, $V_{22}$, $V_{23}$, and $V_{24}$ are —$CH_2$—. In certain embodiments, at least three of $V_{21}$, $V_{22}$, $V_{23}$, and $V_{24}$ are —$CH_2$—. In certain embodiments, all four of $V_{21}$, $V_{22}$, $V_{23}$, and $V_{24}$ are —$CH_2$—. In certain embodiments, at least one of $V_{23}$ and $V_{24}$ is O or —CH($OR^A$)—. In certain embodiments, $V_{23}$ is O. In certain embodiments, $V_{23}$ is —CH($OR^A$)—. In certain embodiments, $V_{24}$ is O. In certain embodiments, $V_{24}$ is —CH($OR^A$)—. In certain embodiments, z is 0. In certain embodiments, at least one instance of $R^G$ is hydrogen. In certain embodiments, both instances of $R^G$ are hydrogen. In certain embodiments, $R^H$ is hydrogen. In certain embodiments, $R^H$ is optionally substituted alkyl. In certain embodiments, $R^H$ is optionally substituted $C_{1-6}$ alkyl. In certain embodiments, $R^H$ is unsubstituted $C_{1-6}$ alkyl (e.g., methyl, ethyl, propyl, butyl, pentyl, or hexyl). In certain embodiments, $R^H$ is unsubstituted branched $C_{3-6}$ alkyl (e.g., isopropyl, sec-butyl, tert-butyl, isopentyl, neopentyl, or 3-pentyl). In certain embodiments, $R^H$ is methyl. In certain embodiments, $R^H$ is ethyl. In certain embodiments, $R^H$ is isopropyl. In certain embodiments, $R^H$ is tert-butyl. In certain embodiments, $R^H$ is optionally substituted carbocyclyl (e.g., cyclopropyl, cyclobutyl, cyclopentyl, or cyclohexyl). In certain embodiments, $R^H$ is optionally substituted aryl. In certain embodiments, $R^H$ is optionally substituted heterocyclyl. In certain embodiments, $R^H$ is optionally substituted heteroaryl. In certain embodiments, two $R^E$ groups are joined to form an optionally substituted carbocyclic ring (e.g., cyclopropyl, cyclobutyl, cyclopentyl, or cyclohexyl). In certain embodiments, two $R^E$ groups are joined to form an optionally substituted cyclopropyl ring. In certain embodiments, two $R^E$ groups are joined to form an unsubstituted carbocyclic ring (e.g., cyclopropyl, cyclobutyl, cyclopentyl, or cyclohexyl). In certain embodiments, two $R^E$ groups are joined to form an unsubstituted cyclopropyl ring. In certain embodiments, $L_1$ is a bond and $R^W$ is hydrogen. In certain embodiments, $L_1$ is a bond, $R^W$ is hydrogen, and $R^5$ is hydrogen. In certain embodiments, $L_1$ is a bond and $R^W$ is halogen, e.g., fluoro, chloro, bromo, or iodo. In certain embodiments, $L_1$ is a bond and $R^W$ is optionally substituted $C_{1-6}$alkyl, e.g., unsubstituted $C_{1-4}$alkyl, e.g., methyl, ethyl, propyl, butyl, isopropyl, isobutyl, or isoamyl.

In certain embodiments, when Ring A is of Formula (r-231), provided are compounds of Formulae XII-s1 to XII-s5:

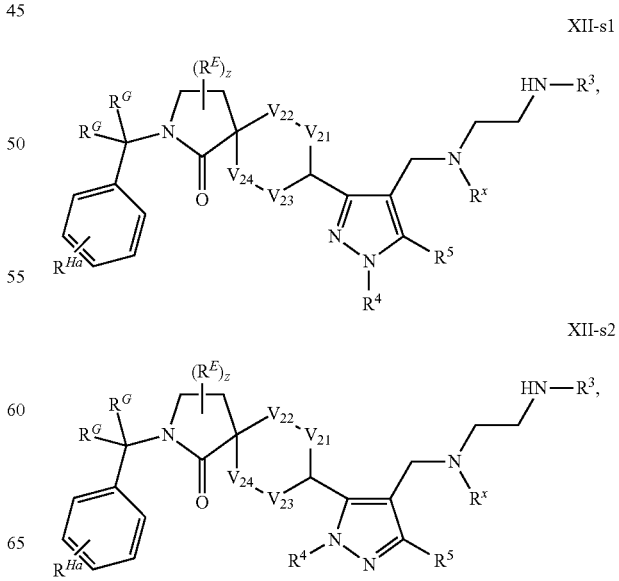

XII-s1

XII-s2

-continued

XII-s3

XII-s4

XII-s5 or pharmaceutically acceptable salt thereof; wherein $R^3$, $R^4$, $R^5$, $R^x$, $V_{21}$, $V_{22}$, $V_{23}$, $V_{24}$, z, $R^E$, $R^G$, and $R^{Ha}$ are defined herein. In certain embodiments, $R^3$ is hydrogen. In certain embodiments, $R^3$ is unsubstituted $C_{1-4}$ alkyl (e.g., methyl, ethyl, propyl, or butyl). In certain embodiments, $R^3$ is methyl. In certain embodiments, $R^4$ is hydrogen. In certain embodiments, $R^4$ is unsubstituted $C_{1-6}$ alkyl (e.g., methyl, ethyl, propyl, or butyl). In certain embodiments, $R^4$ is methyl. In certain embodiments, $R^x$ is unsubstituted $C_{1-4}$ alkyl (e.g., methyl, ethyl, propyl or butyl). In certain embodiments, $R^x$ is methyl. In certain embodiments, $R^5$ is hydrogen. In certain embodiments, at least one of $V_{21}$, $V_{22}$, $V_{23}$, and $V_{24}$ is —$CH_2$—. In certain embodiments, at least two of $V_{21}$, $V_{22}$, $V_{23}$, and $V_{24}$ are —$CH_2$—. In certain embodiments, at least three of $V_{21}$, $V_{22}$, $V_{23}$, and $V_{24}$ are —$CH_2$—. In certain embodiments, all four of $V_{21}$, $V_{22}$, $V_{23}$, and $V_{24}$ are —$CH_2$—. In certain embodiments, at least one of $V_{23}$ and $V_{24}$ is O or —$CH(OR^A)$—. In certain embodiments, $V_{23}$ is O. In certain embodiments, $V_{23}$ is —CH($OR^A$)—. In certain embodiments, $V_{24}$ is O. In certain embodiments, $V_{24}$ is —$CH(OR^A)$—. In certain embodiments, z is 0. In certain embodiments, at least one instance of $R^G$ is hydrogen. In certain embodiments, both instances of $R^G$ are hydrogen. In certain embodiments, $R^{Ha}$ is halogen (e.g., fluorine, chlorine, or bromine). In certain embodiments, $R^{Ha}$ is fluorine. In certain embodiments, two $R^E$ groups are joined to form an optionally substituted carbocyclic ring (e.g., cyclopropyl, cyclobutyl, cyclopentyl, or cyclohexyl). In certain embodiments, two $R^E$ groups are joined to form an optionally substituted cyclopropyl ring. In certain embodiments, two $R^E$ groups are joined to form an unsubstituted carbocyclic ring (e.g., cyclopropyl, cyclobutyl, cyclopentyl, or cyclohexyl). In certain embodiments, two $R^E$ groups are joined to form an unsubstituted cyclopropyl ring. In certain embodiments, $L_1$ is a bond and $R^W$ is hydrogen. In certain embodiments, $L_1$ is a bond, $R^W$ is hydrogen, and $R^5$ is hydrogen. In certain embodiments, $L_1$ is a bond and $R^W$ is halogen, e.g., fluoro, chloro, bromo, or iodo. In certain embodiments, $L_1$ is a bond and $R^W$ is optionally substituted $C_{1-6}$alkyl, e.g., unsubstituted $C_{1-4}$alkyl, e.g., methyl, ethyl, propyl, butyl, isopropyl, isobutyl, or isoamyl.

In certain embodiments, a provided compound is a compound listed in Table 1A, Table 1B, or a pharmaceutically acceptable salt thereof.

TABLE 1A

Exemplary Compounds

| Cmpd No | Structure | LC-MS m/z (M + H) |
|---|---|---|
| 1 | 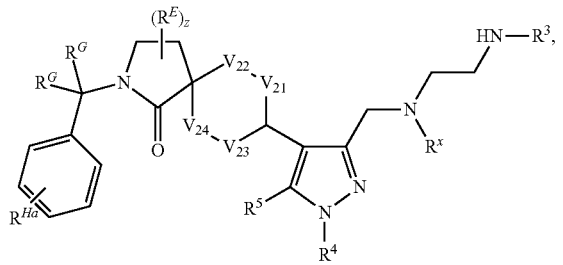 | 299.30 |
| 2 | 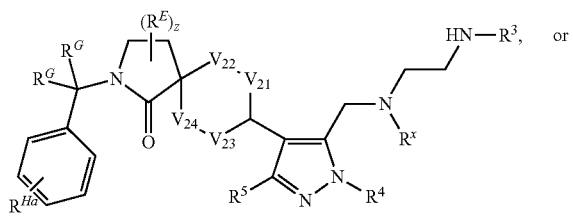 | 325.30 |
| 3 | 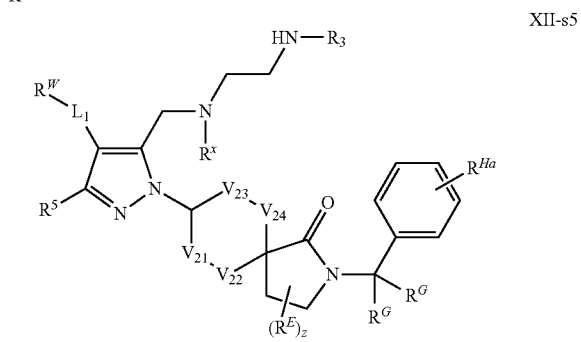 | 269.30 |

TABLE 1A-continued
Exemplary Compounds
| Cmpd No | Structure | LC-MS m/z (M + H) |
|---|---|---|
| 4 | 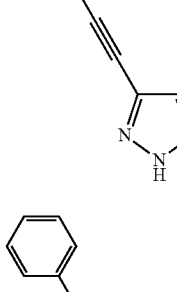 | 287.20 |
| 5 | 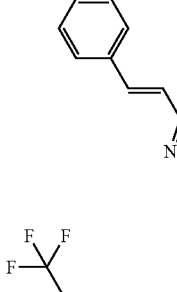 | 347.00 |
| 6 | 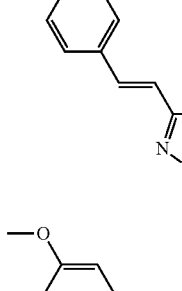 | 339.20 |
| 7 | 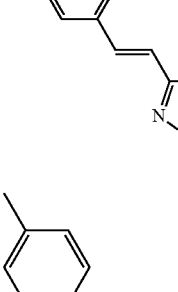 | 301.20 |
| 8 | 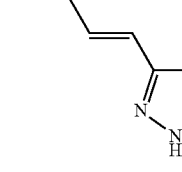 | 271.20 |
| 9 | 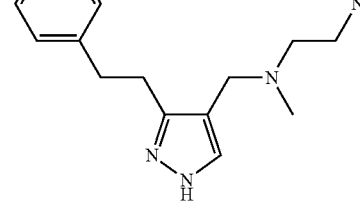 | 259.10 |
| 10 | 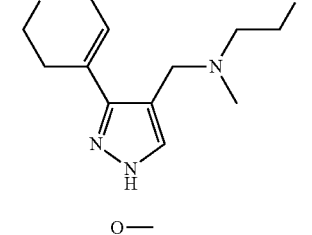 | 237.10 |
| 11 | 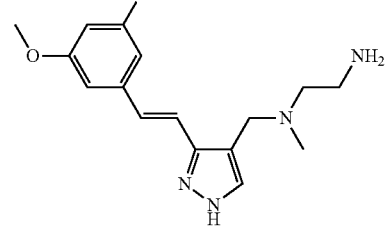 | 317.30 |
| 12 | 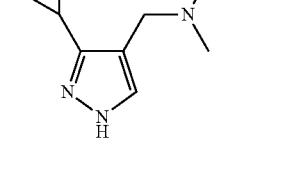 | 195.10 |
| 13 | 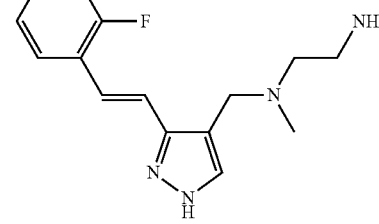 | 293.10 |
| 14 | 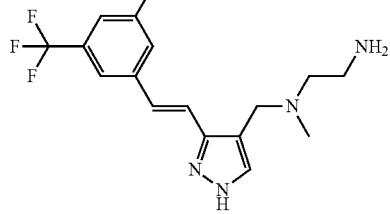 | 393.10 |

TABLE 1A-continued

Exemplary Compounds

| Cmpd No | Structure | LC-MS m/z (M + H) |
|---|---|---|
| 15 | 3,5-difluorostyryl-pyrazole-CH2-N(Me)-CH2CH2-NH2 | 293.10 |
| 16 | 3-(trifluoromethyl)styryl-pyrazole-CH2-N(Me)-CH2CH2-NH2 | 325.10 |
| 17 | 3-methoxystyryl-pyrazole-CH2-N(Me)-CH2CH2-NH2 | 287.30 |
| 18 | 4-(trifluoromethyl)styryl-pyrazole-CH2-N(Me)-CH2CH2-NH2 | 325.10 |
| 19 | methoxypropenyl-pyrazole-CH2-N(Me)-CH2CH2-NH2 | 225.20 |
| 20 | 3-fluorostyryl-pyrazole-CH2-N(Me)-CH2CH2-NH2 | — |
| 21 | isopropyl-pyrazole-CH2-N(Me)-CH2CH2-NH2 | 197.30 |
| 22 | cyclohexyl-pyrazole-CH2-N(Me)-CH2CH2-NH2 | 237.10 |
| 23 | 4-fluorophenethyl-pyrazole-CH2-N(Me)-CH2CH2-NH2 | 277.05 |
| 24 | cinnamyl-pyrazole-CH2-N(Me)-CH2CH2-NH2 | 271.40 |
| 25 | cyclopentenyl-pyrazole-CH2-N(Me)-CH2CH2-NH2 | 221.30 |
| 26 | cyclobutyl-pyrazole-CH2-N(Me)-CH2CH2-NH2 | 209.50 |

TABLE 1A-continued

Exemplary Compounds

| Cmpd No | Structure | LC-MS m/z (M + H) |
|---|---|---|
| 27 | 3-tert-butyl-pyrazol-4-yl-CH2-N(CH3)-CH2CH2-NH2 | 211.40 |
| 28 | 3-isobutyl-pyrazol-4-yl-CH2-N(CH3)-CH2CH2-NH2 | 211.70 |
| 29 | 3-propyl-pyrazol-4-yl-CH2-N(CH3)-CH2CH2-NH2 | 197.30 |
| 30 | 3-methyl-pyrazol-4-yl-CH2-N(CH3)-CH2CH2-NH2 | 169.80 |
| 31 | 3-cyclopentyl-pyrazol-4-yl-CH2-N(CH3)-CH2CH2-NH2 | 223.30 |
| 32 | 3-(1-phenylacetyl-piperidin-4-yl)-pyrazol-4-yl-CH2-N(CH3)-CH2CH2-NHCH3 | 370.00 |
| 33 | 3-cyclohexyl-pyrazol-4-yl-CH2-N(CH3)-CH2CH2-NH2 | 237.05 |
| 34 | 3-(1-isobutyryl-piperidin-4-yl)-pyrazol-4-yl-CH2-N(CH3)-CH2CH2-NHCH3 | 322.15 |
| 35 | 3-(4-methylcyclohexyl)-pyrazol-4-yl-CH2-N(CH3)-CH2CH2-NH2 | 251.00 |
| 36 | 3-(4,4-dimethylcyclohexyl)-pyrazol-4-yl-CH2-N(CH3)-CH2CH2-NH2 | 265.05 |
| 37 | 4-(4-methylcyclohexyl)-pyrazol-3-yl-CH2-N(CH3)-CH2CH2-NH2 | 251.10 |

TABLE 1A-continued

Exemplary Compounds

| Cmpd No | Structure | LC-MS m/z (M + H) |
|---|---|---|
| 38 | 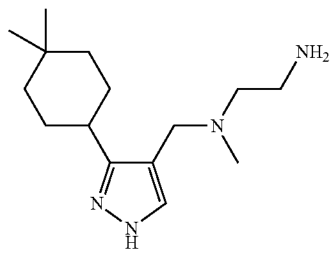 [SMILES: CN(CCN)Cc1c[nH]nc1C1CCC(C)(C)CC1] | 265.10 |
| 39 | 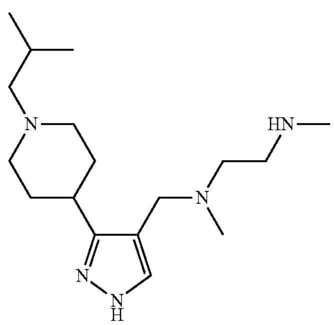 [SMILES: CNCCN(C)Cc1c[nH]nc1C1CCN(CC(C)C)CC1] | 308.20 |
| 40 | 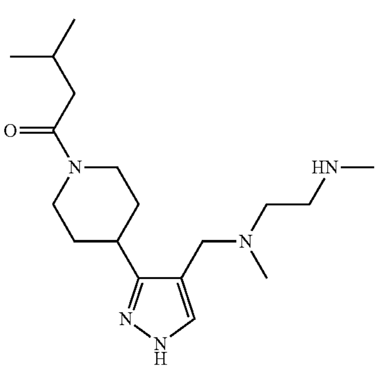 [SMILES: CNCCN(C)Cc1c[nH]nc1C1CCN(C(=O)CC(C)C)CC1] | 336.15 |
| 41 | 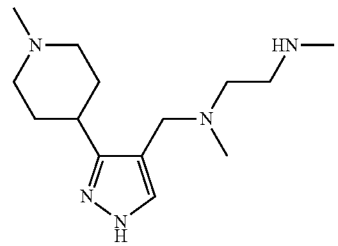 [SMILES: CNCCN(C)Cc1c[nH]nc1C1CCN(C)CC1] | 266.15 |
| 42 | 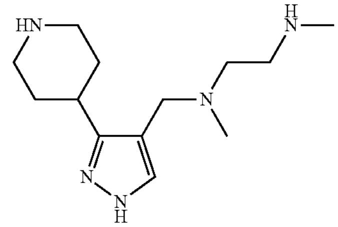 [SMILES: CNCCN(C)Cc1c[nH]nc1C1CCNCC1] | 252.10 |
| 43 | 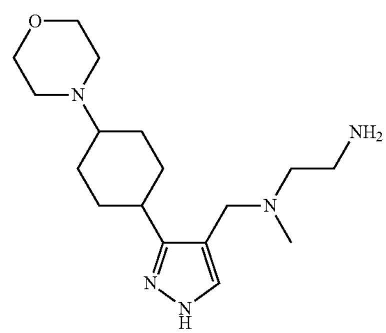 [SMILES: CN(CCN)Cc1c[nH]nc1C1CCC(N2CCOCC2)CC1] | 322.15 |
| 44 | 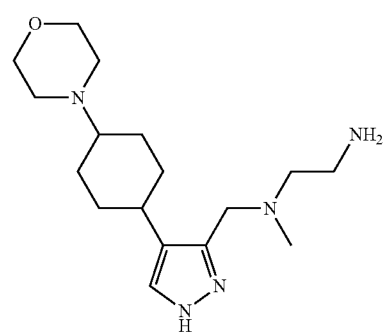 [SMILES: CN(CCN)Cc1n[nH]cc1C1CCC(N2CCOCC2)CC1] | 322.15 |

TABLE 1B

Exemplary Compounds

| Cmpd No | Structure | LC-MS m/z (M + H) |
|---|---|---|
| 45 | 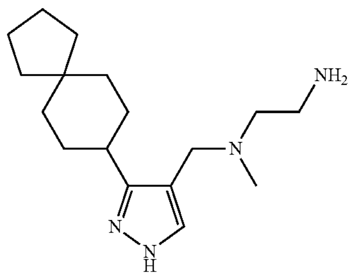 [SMILES: CN(CCN)Cc1c[nH]nc1C1CCC2(CCCC2)CC1] | 291.15 |
| 46 | 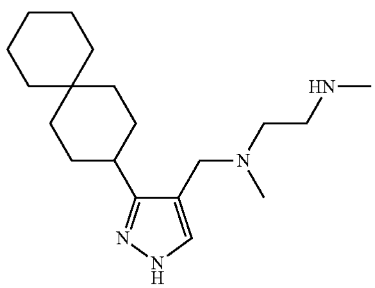 [SMILES: CNCCN(C)Cc1c[nH]nc1C1CCC2(CCCCC2)CC1] | 319.15 |
| 47 | 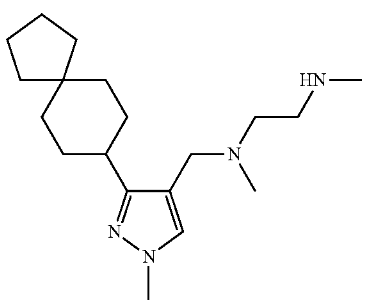 [SMILES: CNCCN(C)Cc1cn(C)nc1C1CCC2(CCCC2)CC1] | 319.15 |
| 48 | 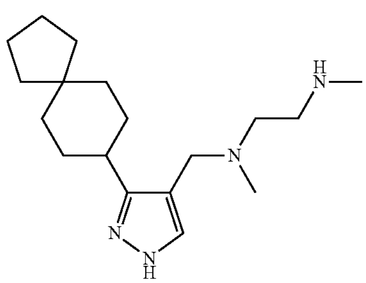 [SMILES: CNCCN(C)Cc1c[nH]nc1C1CCC2(CCCC2)CC1] | 305.15 |
| 49 | 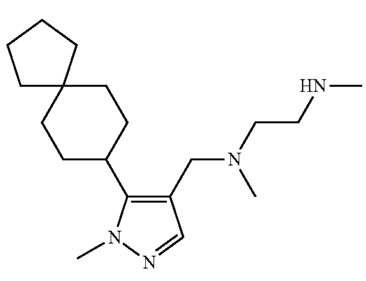 [SMILES: CNCCN(C)Cc1cnn(C)c1C1CCC2(CCCC2)CC1] | 319.15 |

TABLE 1B-continued
Exemplary Compounds
| Cmpd No | Structure | LC-MS m/z (M + H) |
|---|---|---|
| 50 | 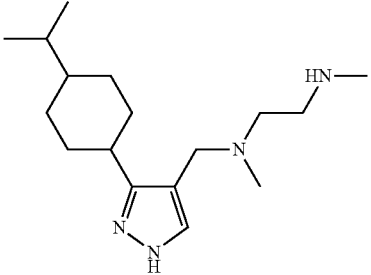 [SMILES: CNCCN(C)Cc1c[nH]nc1C1CCC(C(C)C)CC1] | 293.1 |
| 51 | 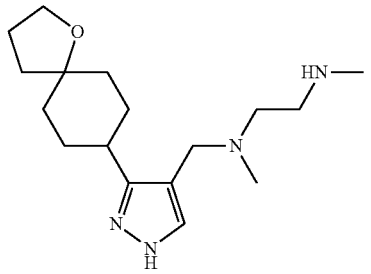 [SMILES: CNCCN(C)Cc1c[nH]nc1C1CCC2(CCCO2)CC1] | 307.10 |
| 52 | 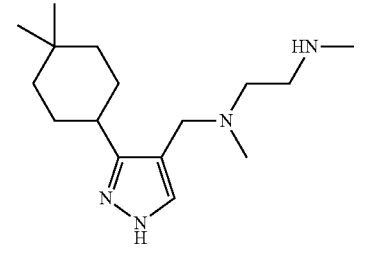 | 279.10 |
| 53 | 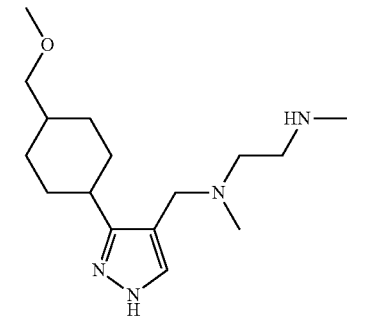 [SMILES: CNCCN(C)Cc1c[nH]nc1C1CCC(COC)CC1] | 295.1 |
| 54 | 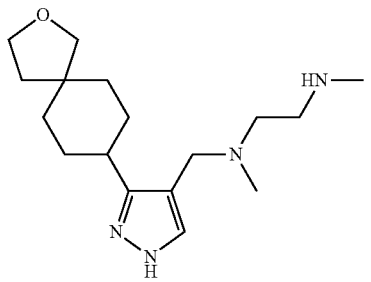 [SMILES: CNCCN(C)Cc1c[nH]nc1C1CCC2(CCOC2)CC1] | 307.1 |

TABLE 1B-continued
Exemplary Compounds
| Cmpd No | Structure | LC-MS m/z (M + H) |
|---|---|---|
| 55 | 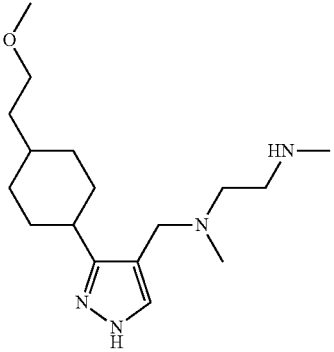 [SMILES: CNCCN(C)Cc1c[nH]nc1C1CCC(CCOC)CC1] | 309.1 |
| 56 | 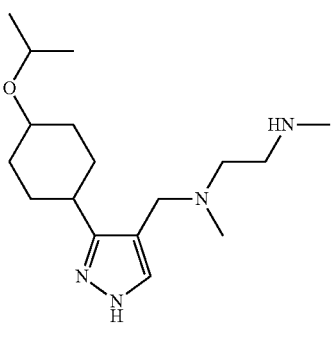 [SMILES: CNCCN(C)Cc1c[nH]nc1C1CCC(OC(C)C)CC1] | 309.15 |
| 57 | 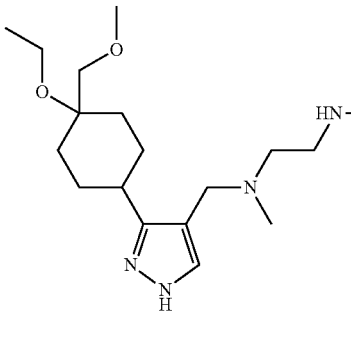 | 339.10 |
| 58 | 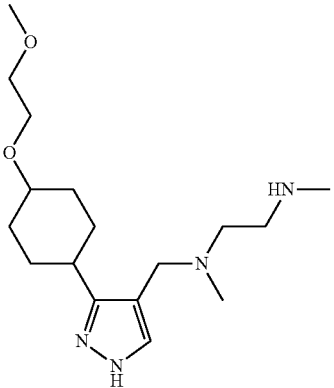 [SMILES: CNCCN(C)Cc1c[nH]nc1C1CCC(OCCOC)CC1] | 325.15 |

TABLE 1B-continued
Exemplary Compounds
| Cmpd No | Structure | LC-MS m/z (M + H) |
|---|---|---|
| 59 | 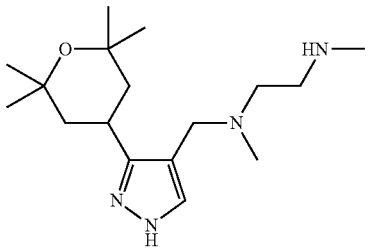 | 309.25 |
| 60 | 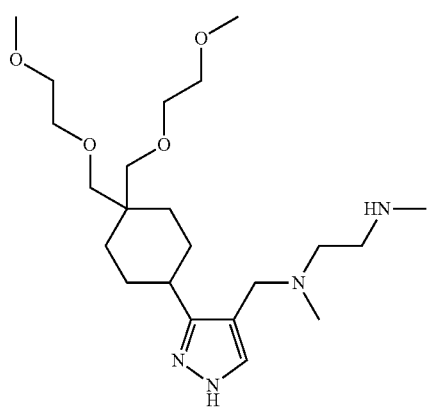 [SMILES: CNCCN(C)Cc1c[nH]nc1C1CCC(COCCOC)(COCCOC)CC1] | 427.25 |
| 61 | 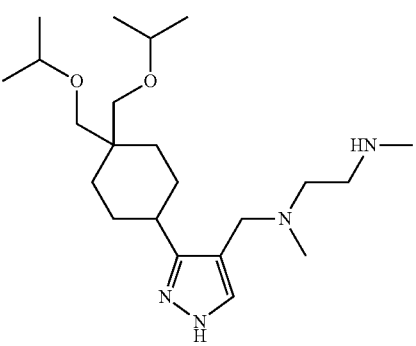 [SMILES: CNCCN(C)Cc1c[nH]nc1C1CCC(COC(C)C)(COC(C)C)CC1] | 395.3 |
| 62 | 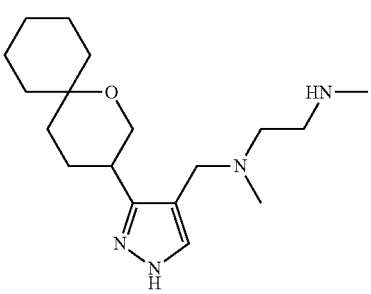 [SMILES: CNCCN(C)Cc1c[nH]nc1C1CCC2(CCCCC2)OC1] | — |

TABLE 1B-continued

Exemplary Compounds

| Cmpd No | Structure | LC-MS m/z (M + H) |
|---|---|---|
| 63 | 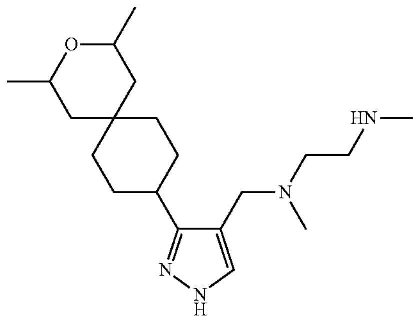 | 349.25 |
| 64 | 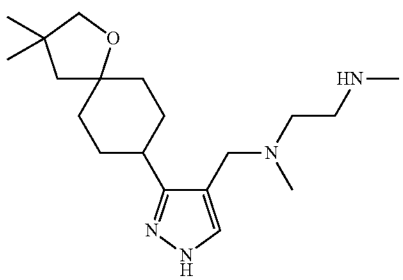 | — |
| 65 | 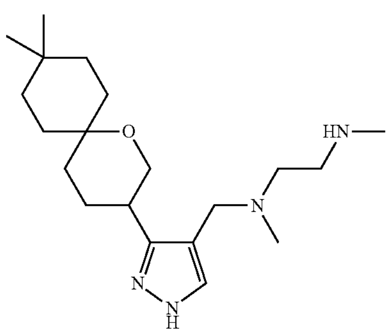 | — |
| 66 | 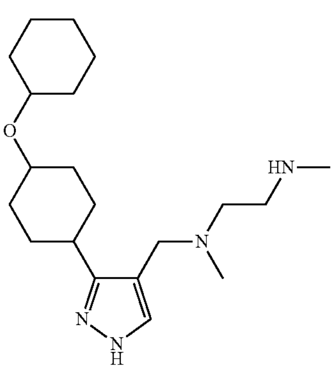 [SMILES: CNCCN(C)Cc1c[nH]nc1C1CCC(OC2CCCCC2)CC1] | — |

TABLE 1B-continued

Exemplary Compounds

| Cmpd No | Structure | LC-MS m/z (M + H) |
|---|---|---|
| 67 | 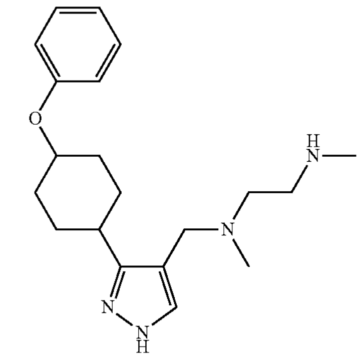 [SMILES: CNCCN(C)Cc1c[nH]nc1C1CCC(Oc2ccccc2)CC1] | 343.15 |
| 68 | 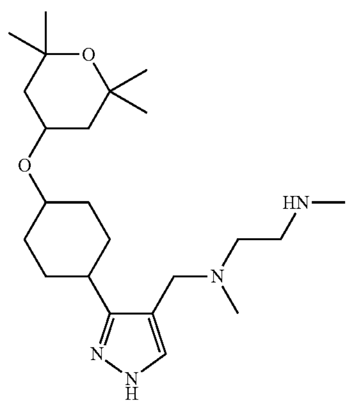 | — |
| 69 | 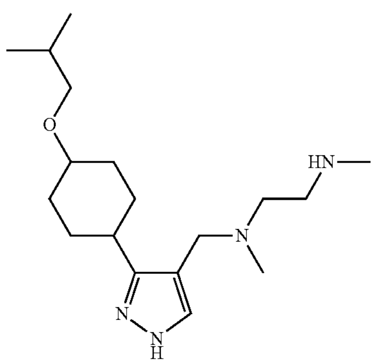 [SMILES: CNCCN(C)Cc1c[nH]nc1C1CCC(OCC(C)C)CC1] | — |
| 70 | 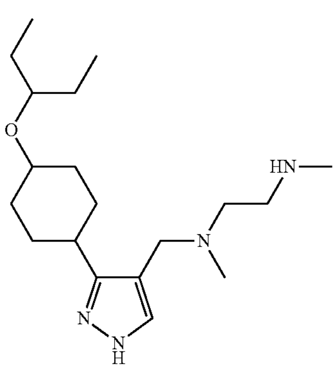 [SMILES: CCC(CC)OC1CCC(c2n[nH]cc2CN(C)CCNC)CC1] | 337.2 |

TABLE 1B-continued

Exemplary Compounds

| Cmpd No | Structure | LC-MS m/z (M + H) |
|---|---|---|
| 71 | 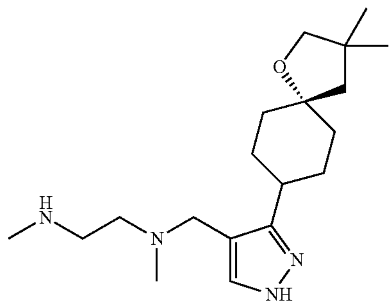 | — |
| 72 | 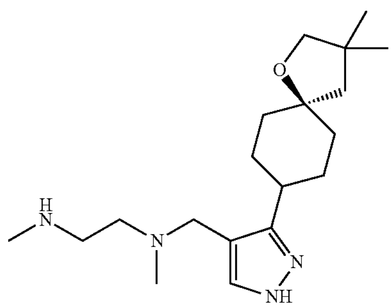 | — |
| 73 | 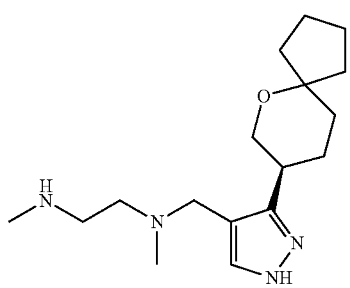 [SMILES: CNCCN(C)Cc1c[nH]nc1[C@@H]1CCC2(CCCC2)OC1] | — |
| 74 | 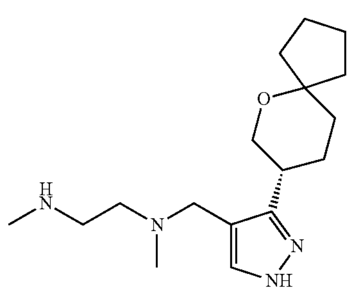 [SMILES: CNCCN(C)Cc1c[nH]nc1[C@H]1CCC2(CCCC2)OC1] | — |
| 75 | 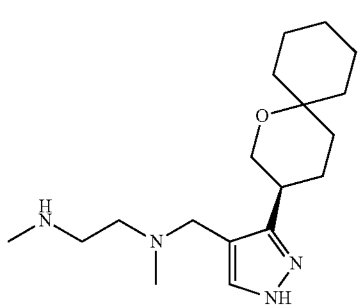 [SMILES: CNCCN(C)Cc1c[nH]nc1[C@@H]1CCC2(CCCCC2)OC1] | — |

TABLE 1B-continued

| Cmpd No | Structure | LC-MS m/z (M + H) |
|---|---|---|
| 76 | 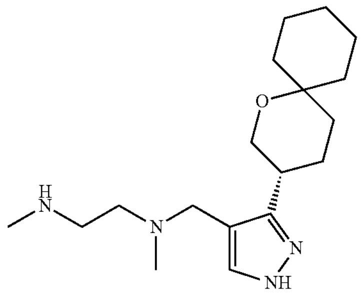 [SMILES: CNCCN(C)Cc1c[nH]nc1[C@H]1CCC2(CCCCC2)OC1] | — |
| 77 | 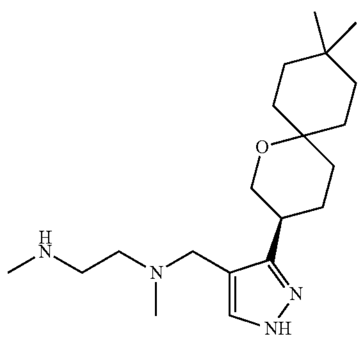 | — |
| 78 | 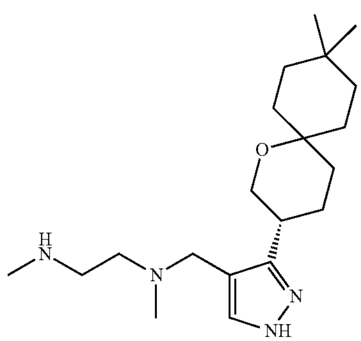 | — |
| 79 | 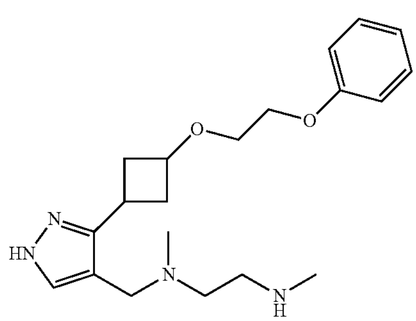 [SMILES: CNCCN(C)Cc1c[nH]nc1C1CC(OCCOc2ccccc2)C1] | — |

TABLE 1B-continued

Exemplary Compounds

| Cmpd No | Structure | LC-MS m/z (M + H) |
|---|---|---|
| 80 | 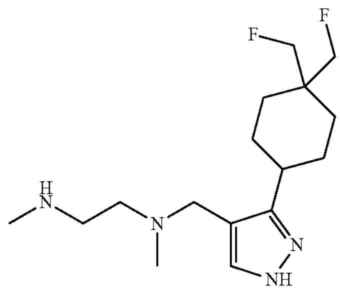 [SMILES: CNCCN(C)Cc1c[nH]nc1C1CCC(CF)(CF)CC1] | — |
| 81 | 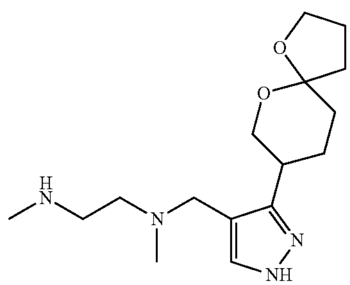 [SMILES: CNCCN(C)Cc1c[nH]nc1C1CCC2(CCCO2)OC1] | — |
| 82 | 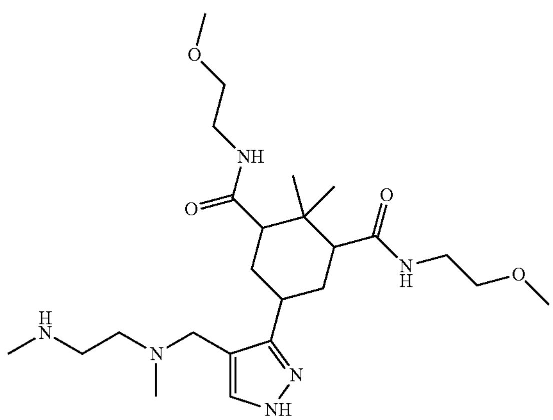 | — |
| 83 | 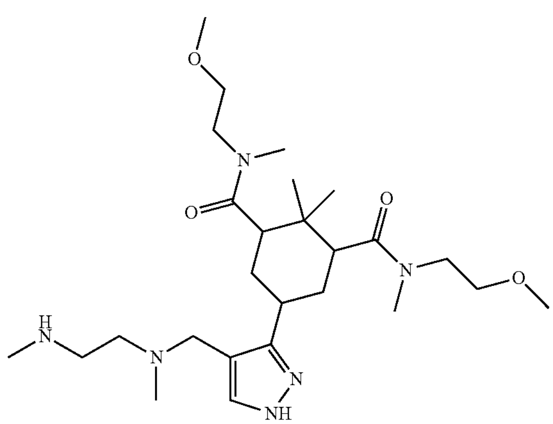 | — |

TABLE 1B-continued

Exemplary Compounds

| Cmpd No | Structure | LC-MS m/z (M + H) |
|---|---|---|
| 84 | 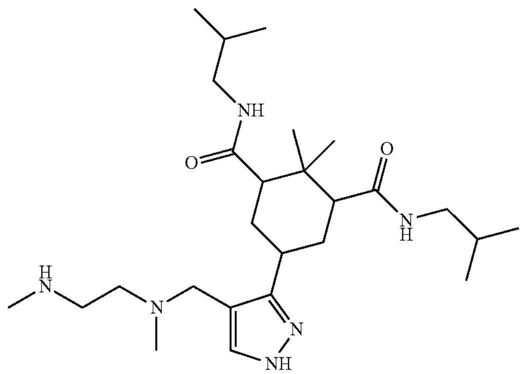 [SMILES: CNCCN(C)Cc1c[nH]nc1C1CC(C(=O)NCC(C)C)C(C)(C)C(C(=O)NCC(C)C)C1] | — |
| 85 | 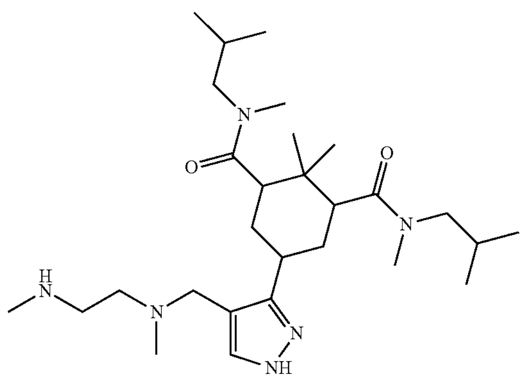 [SMILES: CNCCN(C)Cc1c[nH]nc1C1CC(C(=O)N(C)CC(C)C)C(C)(C)C(C(=O)N(C)CC(C)C)C1] | — |
| 86 | 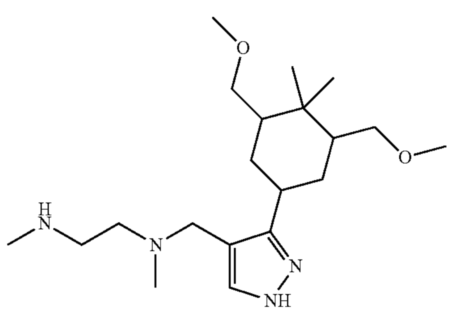 | — |
| 87 | 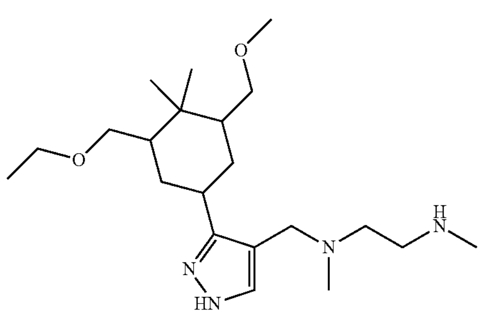 [SMILES: CCOCC1CC(c2n[nH]cc2CN(C)CCNC)CC(COC)C1(C)C] | — |

TABLE 1B-continued

Exemplary Compounds

| Cmpd No | Structure | LC-MS m/z (M + H) |
|---|---|---|
| 88 | 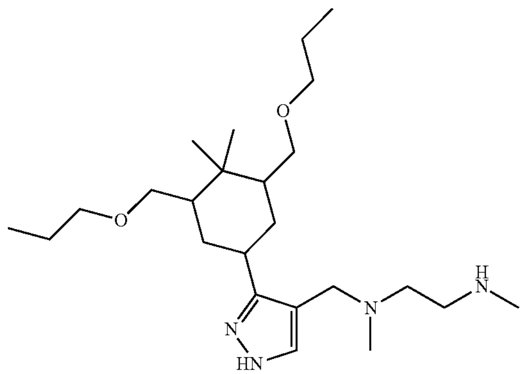 [SMILES: CCCOCC1CC(c2n[nH]cc2CN(C)CCNC)CC(COCCC)C1(C)C] | — |
| 89 | 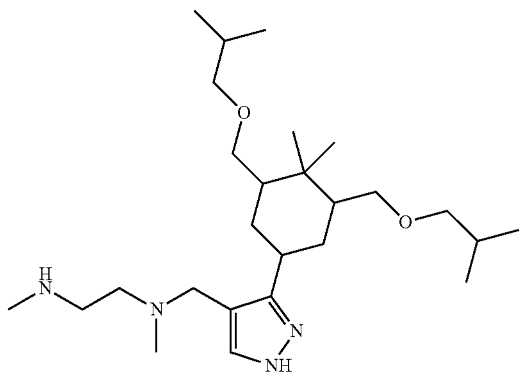 [SMILES: CNCCN(C)Cc1c[nH]nc1C1CC(COCC(C)C)C(C)(C)C(COCC(C)C)C1] | — |
| 90 | 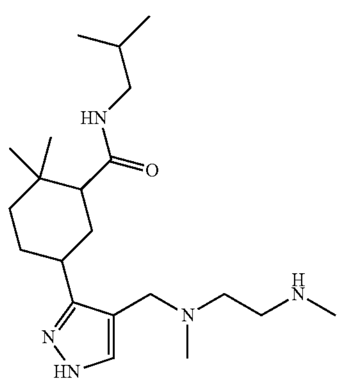 [SMILES: CNCCN(C)Cc1c[nH]nc1C1CCC(C)(C)C(C(=O)NCC(C)C)C1] | — |
| 91 | 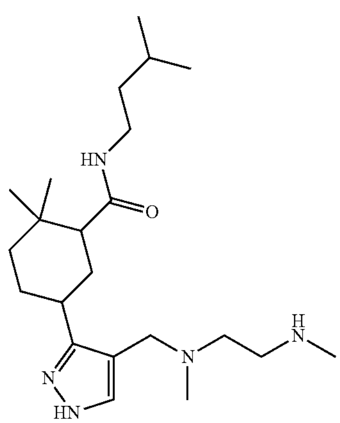 [SMILES: CNCCN(C)Cc1c[nH]nc1C1CCC(C)(C)C(C(=O)NCCC(C)C)C1] | — |

TABLE 1B-continued
Exemplary Compounds
| Cmpd No | Structure | LC-MS m/z (M + H) |
|---|---|---|
| 92 | 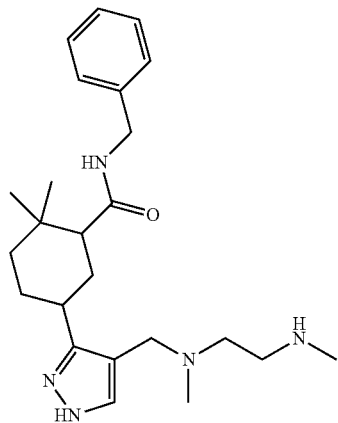 [SMILES: CNCCN(C)Cc1c[nH]nc1C1CCC(C)(C)C(C(=O)NCc2ccccc2)C1] | — |
| 93 | 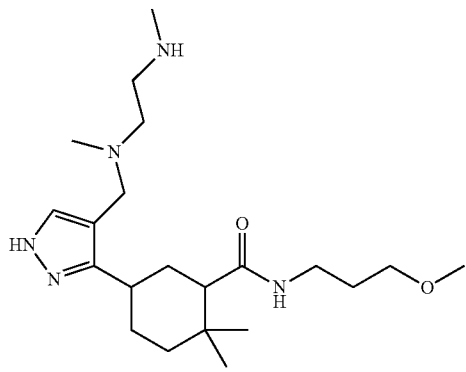 | — |
| 94 | 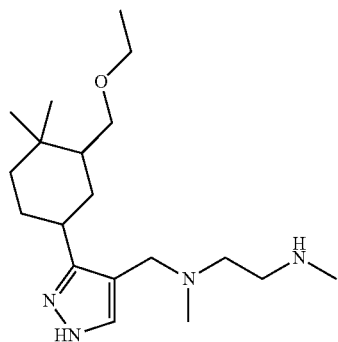 [SMILES: CCOCC1CC(c2n[nH]cc2CN(C)CCNC)CCC1(C)C] | — |

TABLE 1B-continued
Exemplary Compounds
| Cmpd No | Structure | LC-MS m/z (M + H) |
|---|---|---|
| 95 | 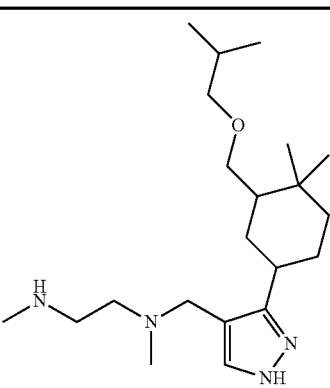 | — |
| 96 | 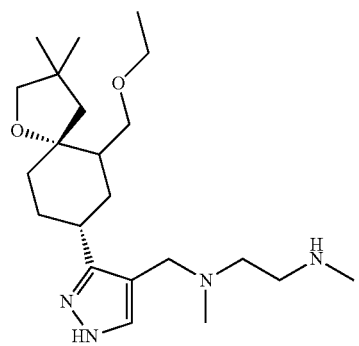 [SMILES: CCOCC1C[C@H](c2n[nH]cc2CN(C)CCNC)CC[C@@]12CC(C)(C)CO2] | — |
| 97 | 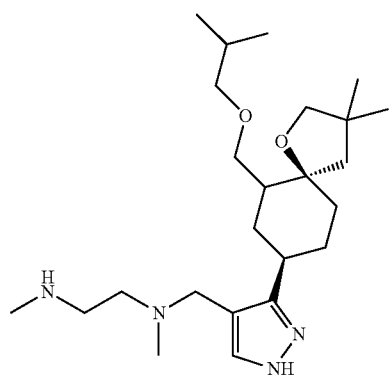 | — |
| 98 | 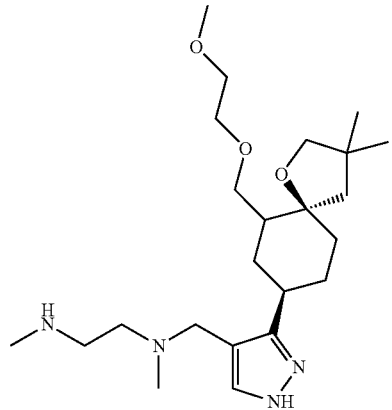 | — |

TABLE 1B-continued

Exemplary Compounds

| Cmpd No | Structure | LC-MS m/z (M + H) |
|---|---|---|
| 99 | 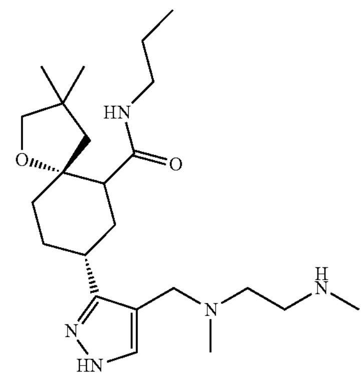 [SMILES: CCCNC(=O)C1C[C@H](c2n[nH]cc2CN(C)CCNC)CC[C@@]12CC(C)(C)CO2] | — |
| 100 | 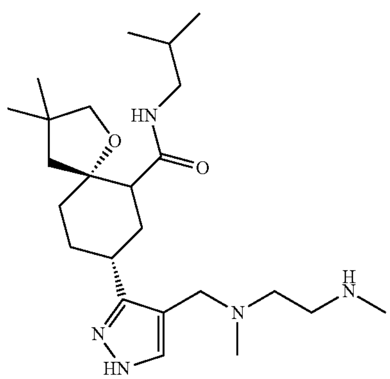 | — |
| 101 | 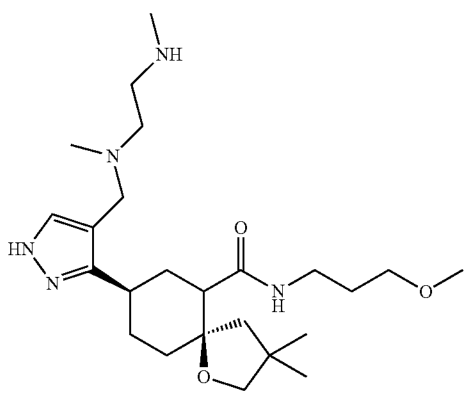 [SMILES: CNCCN(C)Cc1c[nH]nc1[C@@H]1CC[C@@]2(CC(C)(C)CO2)C(C(=O)NCCCOC)C1] | — |
| 102 | 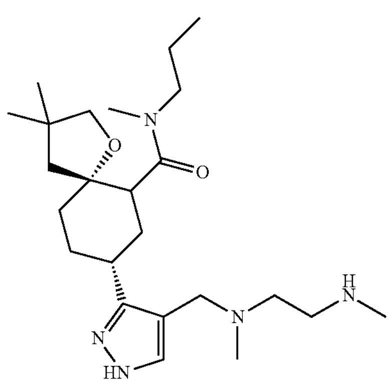 | — |

TABLE 1B-continued

Exemplary Compounds

| Cmpd No | Structure | LC-MS m/z (M + H) |
|---|---|---|
| 103 | 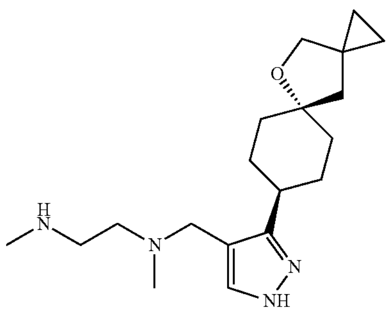 [SMILES: CNCCN(C)Cc1c[nH]nc1[C@H]1CC[C@]2(CC1)CC1(CC1)CO2] | — |
| 104 | 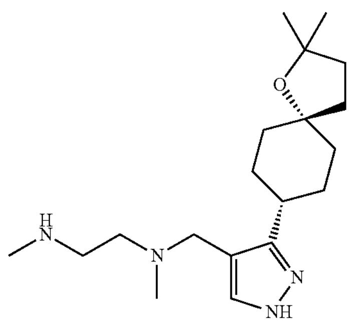 [SMILES: CNCCN(C)Cc1c[nH]nc1[C@H]1CC[C@]2(CCC(C)(C)O2)CC1] | — |
| 105 | 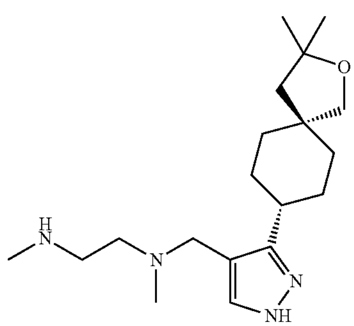 [SMILES: CNCCN(C)Cc1c[nH]nc1[C@H]1CC[C@]2(CC1)COC(C)(C)C2] | — |
| 106 | 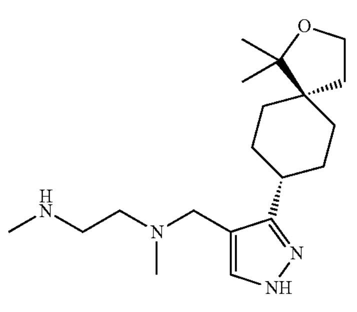 [SMILES: CNCCN(C)Cc1c[nH]nc1[C@H]1CC[C@@]2(CCOC2(C)C)CC1] | — |

TABLE 1B-continued

Exemplary Compounds

| Cmpd No | Structure | LC-MS m/z (M + H) |
|---|---|---|
| 107 | 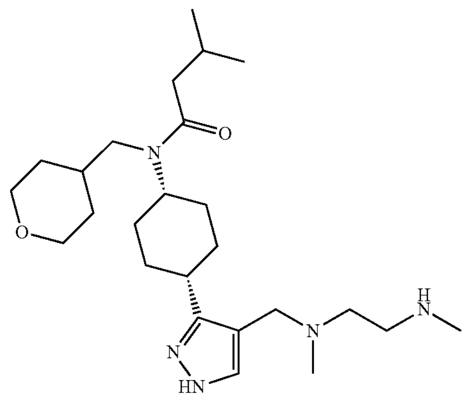 [SMILES: CNCCN(C)Cc1c[nH]nc1[C@H]1CC[C@@H](N(CC2CCOCC2)C(=O)CC(C)C)CC1] | 448.4 |
| 108 | 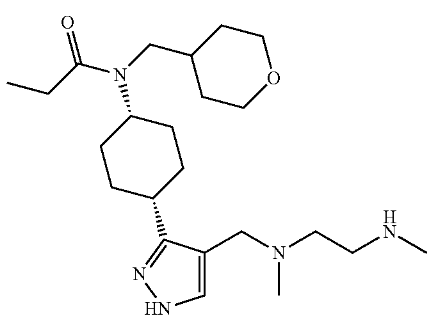 [SMILES: CCC(=O)N(CC1CCOCC1)[C@H]1CC[C@@H](c2n[nH]cc2CN(C)CCNC)CC1] | 420.2 |
| 109 | 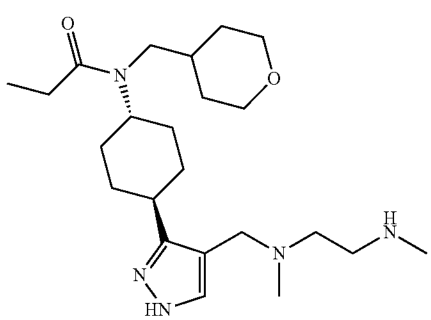 [SMILES: CCC(=O)N(CC1CCOCC1)[C@H]1CC[C@H](c2n[nH]cc2CN(C)CCNC)CC1] | 420.2 |
| 110 | 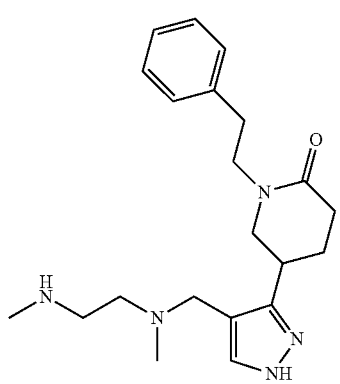 [SMILES: CNCCN(C)Cc1c[nH]nc1C1CCC(=O)N(CCc2ccccc2)C1] | 370.1 |

TABLE 1B-continued

Exemplary Compounds

| Cmpd No | Structure | LC-MS m/z (M + H) |
|---|---|---|
| 111 | 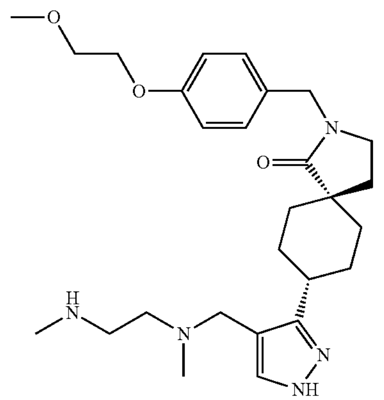 [SMILES: CNCCN(C)Cc1c[nH]nc1[C@H]1CC[C@]2(CCN(Cc3ccc(OCCOC)cc3)C2=O)CC1] | 484.2 |
| 112 | 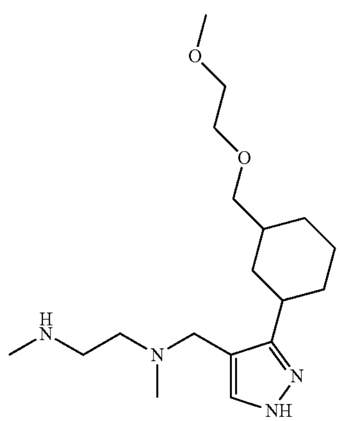 [SMILES: CNCCN(C)Cc1c[nH]nc1C1CCCC(COCCOC)C1] | 339.15 |
| 113 | 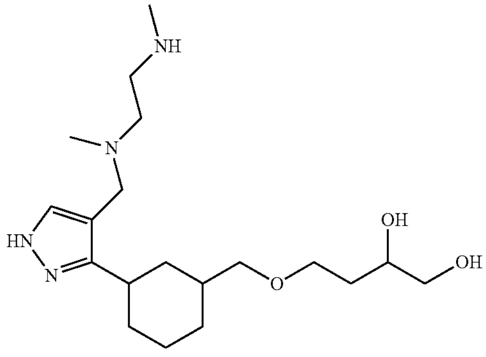 [SMILES: CNCCN(C)Cc1c[nH]nc1C1CCCC(COCCC(O)CO)C1] | 369.25 |

TABLE 1B-continued

Exemplary Compounds

| Cmpd No | Structure | LC-MS m/z (M + H) |
|---|---|---|
| 114 | 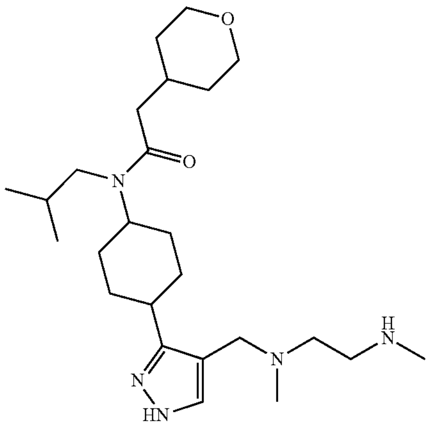 [SMILES: CNCCN(C)Cc1c[nH]nc1C1CCC(N(CC(C)C)C(=O)CC2CCOCC2)CC1] | 448.3 |
| 115 | 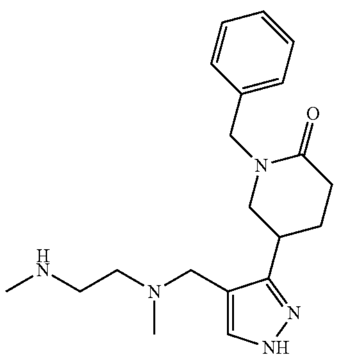 [SMILES: CNCCN(C)Cc1c[nH]nc1C1CCC(=O)N(Cc2ccccc2)C1] | 356.15 |
| 116 | 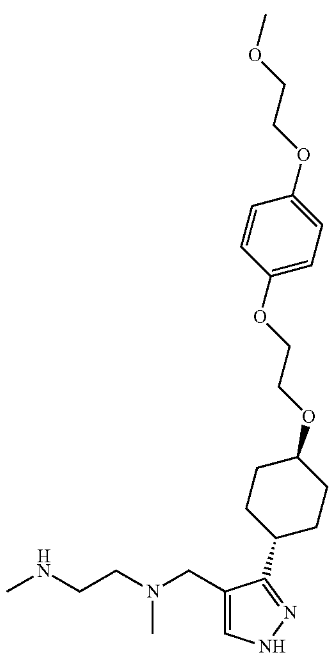 [SMILES: CNCCN(C)Cc1c[nH]nc1[C@H]1CC[C@H](OCCOc2ccc(OCCOC)cc2)CC1] | 461.4 |

TABLE 1B-continued

Exemplary Compounds

| Cmpd No | Structure | LC-MS m/z (M + H) |
|---|---|---|
| 117 | 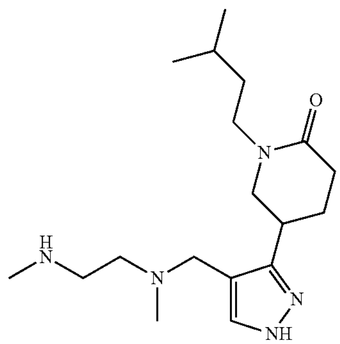 [SMILES: CNCCN(C)Cc1c[nH]nc1C1CCC(=O)N(CCC(C)C)C1] | 336.2 |
| 118 | 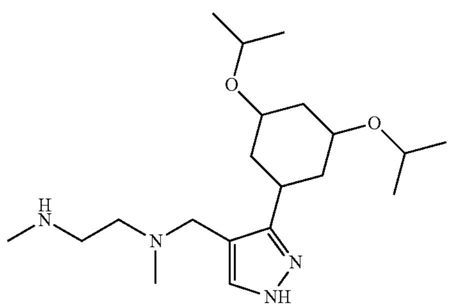 [SMILES: CNCCN(C)Cc1c[nH]nc1C1CC(OC(C)C)CC(OC(C)C)C1] | 367.3 |
| 119 | 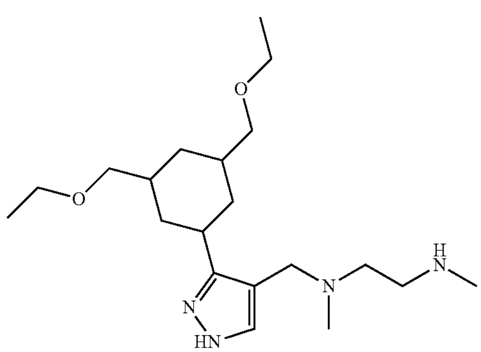 [SMILES: CCOCC1CC(COCC)CC(c2n[nH]cc2CN(C)CCNC)C1] | 367.3 |
| 120 | 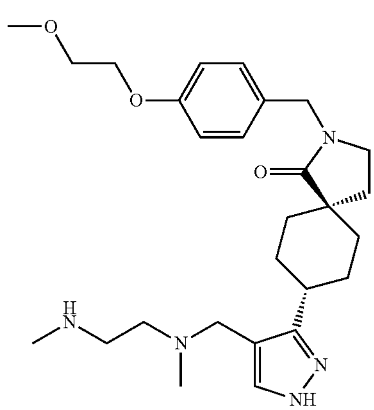 [SMILES: CNCCN(C)Cc1c[nH]nc1[C@H]1CC[C@@]2(CCN(Cc3ccc(OCCOC)cc3)C2=O)CC1] | 484.35 |

TABLE 1B-continued

Exemplary Compounds

| Cmpd No | Structure | LC-MS m/z (M + H) |
|---|---|---|
| 121 | 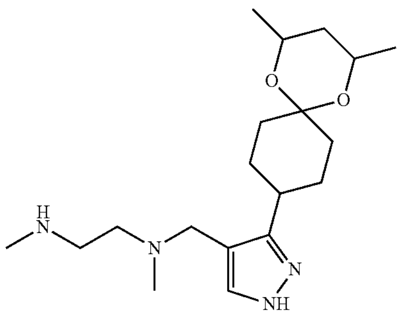 | 351.25 |
| 122 | 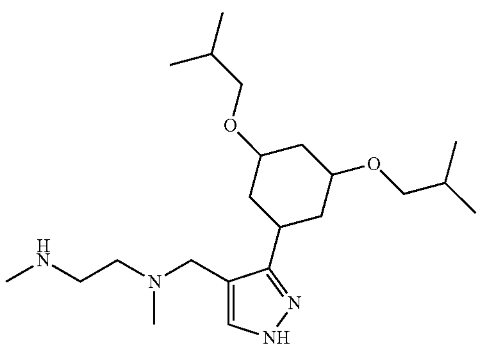 [SMILES: CNCCN(C)Cc1c[nH]nc1C1CC(OCC(C)C)CC(OCC(C)C)C1] | 395.25 |
| 123 | 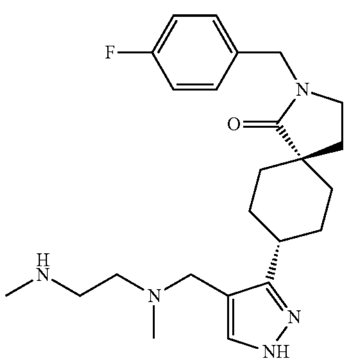 [SMILES: CNCCN(C)Cc1c[nH]nc1[C@H]1CC[C@]2(CCN(Cc3ccc(F)cc3)C2=O)CC1] | 428.3 |
| 124 | 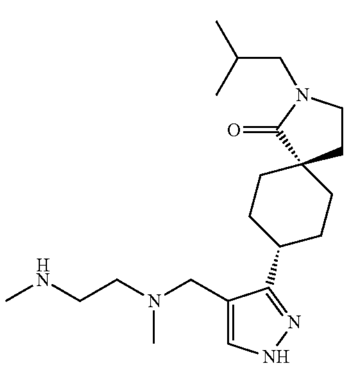 [SMILES: CNCCN(C)Cc1c[nH]nc1[C@H]1CC[C@]2(CCN(CC(C)C)C2=O)CC1] | 376.3 |

TABLE 1B-continued

Exemplary Compounds

| Cmpd No | Structure | LC-MS m/z (M + H) |
|---|---|---|
| 125 | 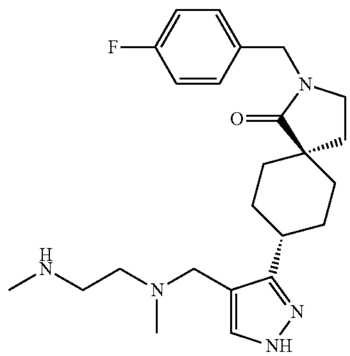 [SMILES: CNCCN(C)Cc1c[nH]nc1[C@H]1CC[C@@]2(CCN(Cc3ccc(F)cc3)C2=O)CC1] | 428.3 |
| 126 | 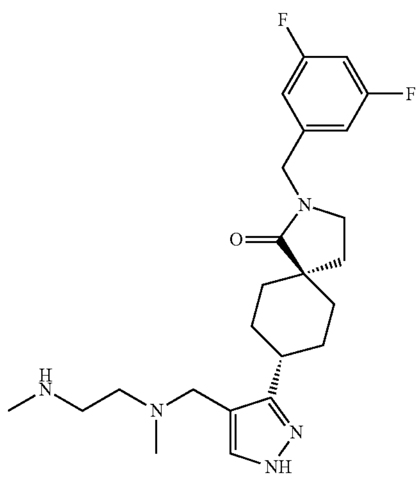 [SMILES: CNCCN(C)Cc1c[nH]nc1[C@H]1CC[C@@]2(CCN(Cc3cc(F)cc(F)c3)C2=O)CC1] | 446.3 |
| 127 | 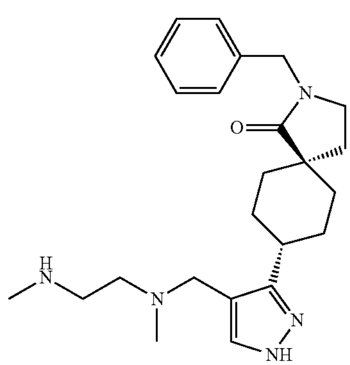 [SMILES: CNCCN(C)Cc1c[nH]nc1[C@H]1CC[C@@]2(CCN(Cc3ccccc3)C2=O)CC1] | 410.25 |

TABLE 1B-continued
Exemplary Compounds
| Cmpd No | Structure | LC-MS m/z (M + H) |
|---|---|---|
| 128 | 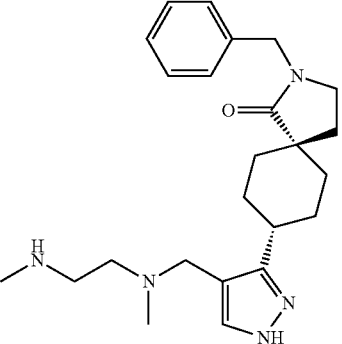 [SMILES: CNCCN(C)Cc1c[nH]nc1[C@H]1CC[C@]2(CCN(Cc3ccccc3)C2=O)CC1] | 410.3 |
| 129 | 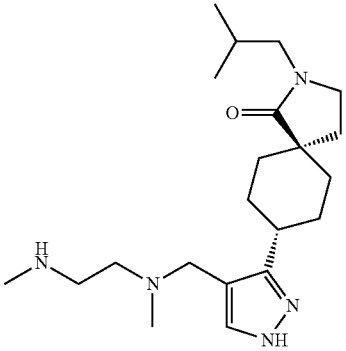 [SMILES: CNCCN(C)Cc1c[nH]nc1[C@H]1CC[C@@]2(CCN(CC(C)C)C2=O)CC1] | 376.3 |
| 130 | 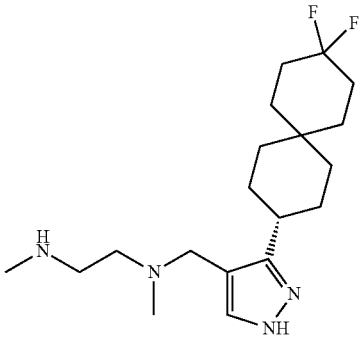 | 355.25 |
| 131 | 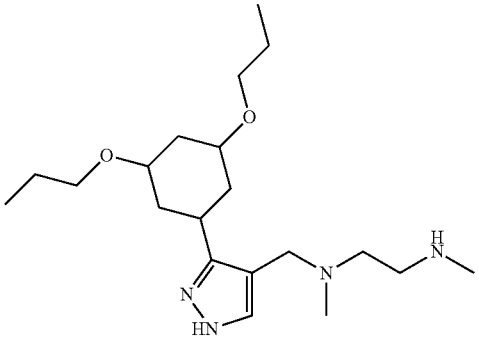 [SMILES: CCCOC1CC(OCCC)CC(c2n[nH]cc2CN(C)CCNC)C1] | 367.3 |

TABLE 1B-continued

Exemplary Compounds

| Cmpd No | Structure | LC-MS m/z (M + H) |
|---|---|---|
| 132 | 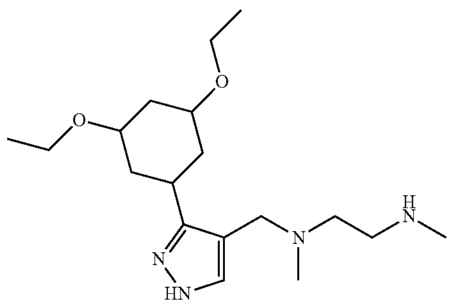 [SMILES: CCOC1CC(OCC)CC(c2n[nH]cc2CN(C)CCNC)C1] | 339.2 |
| 133 | 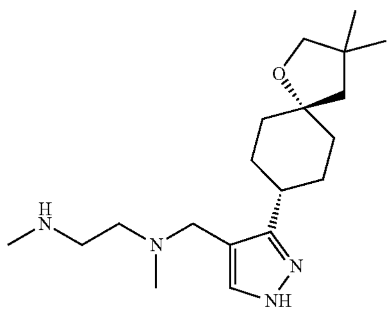 | 335.2 |
| 134 | 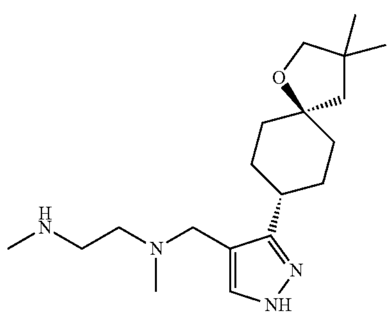 | 335.2 |
| 135 | 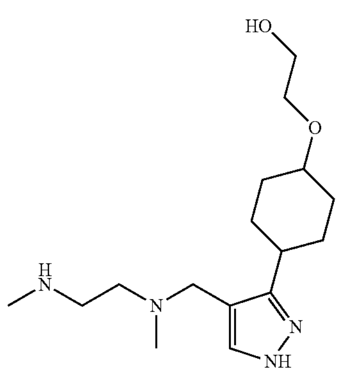 [SMILES: CNCCN(C)Cc1c[nH]nc1C1CCC(OCCO)CC1] | 311.25 |

TABLE 1B-continued
Exemplary Compounds
| Cmpd No | Structure | LC-MS m/z (M + H) |
|---|---|---|
| 136 | 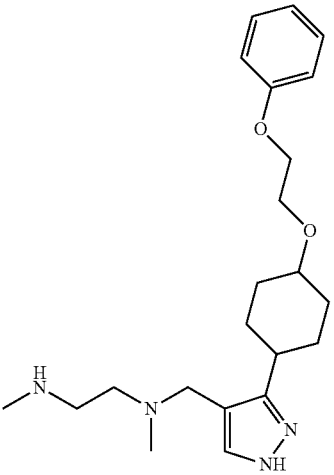 [SMILES: CNCCN(C)Cc1c[nH]nc1C1CCC(OCCOc2ccccc2)CC1] | 387.3 |
| 137 | 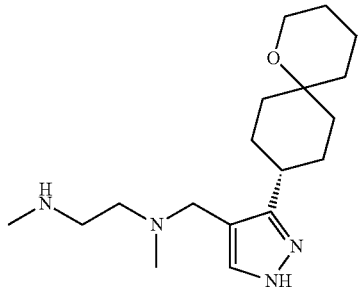 | 321.1 |
| 138 | 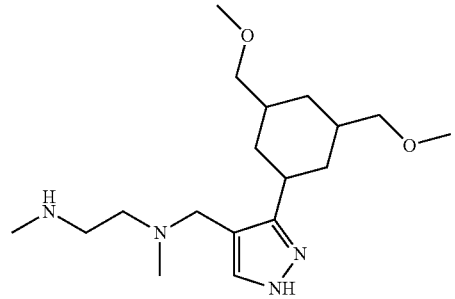 | 339.1 |
| 139 | 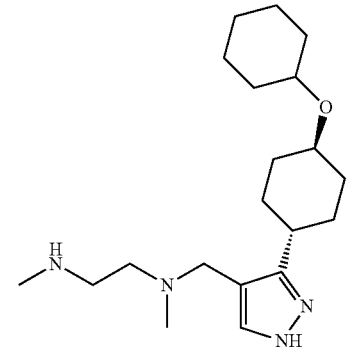 [SMILES: CNCCN(C)Cc1c[nH]nc1[C@H]1CC[C@H](OC2CCCCC2)CC1] | 349.25 |

TABLE 1B-continued

Exemplary Compounds

| Cmpd No | Structure | LC-MS m/z (M + H) |
|---|---|---|
| 140 | 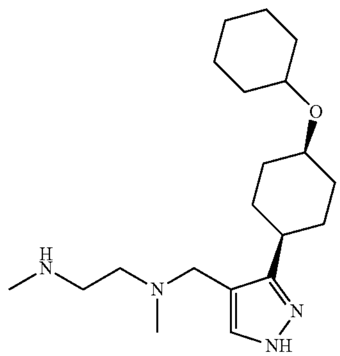 [SMILES: CNCCN(C)Cc1c[nH]nc1[C@H]1CC[C@@H](OC2CCCCC2)CC1] | 349.25 |
| 141 | 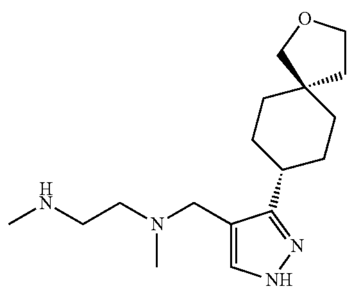 [SMILES: CNCCN(C)Cc1c[nH]nc1[C@H]1CC[C@@]2(CCOC2)CC1] | 307.15 |
| 142 | 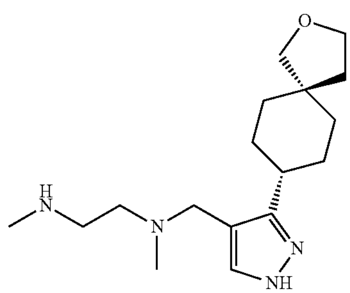 [SMILES: CNCCN(C)Cc1c[nH]nc1[C@H]1CC[C@]2(CCOC2)CC1] | 307.15 |
| 143 | 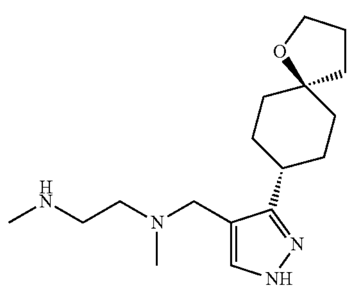 [SMILES: CNCCN(C)Cc1c[nH]nc1[C@H]1CC[C@@]2(CCCO2)CC1] | 307.25 |
| 144 | 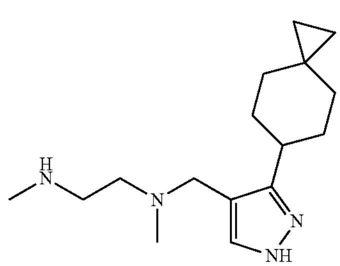 [SMILES: CNCCN(C)Cc1c[nH]nc1C1CCC2(CC1)CC2] | 277.15 |

TABLE 1B-continued
Exemplary Compounds
| Cmpd No | Structure | LC-MS m/z (M + H) |
|---|---|---|
| 145 | 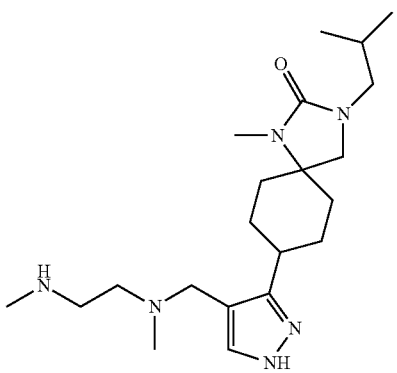 [SMILES: CNCCN(C)Cc1c[nH]nc1C1CCC2(CC1)CN(CC(C)C)C(=O)N2C] | 391.15 |
| 146 | 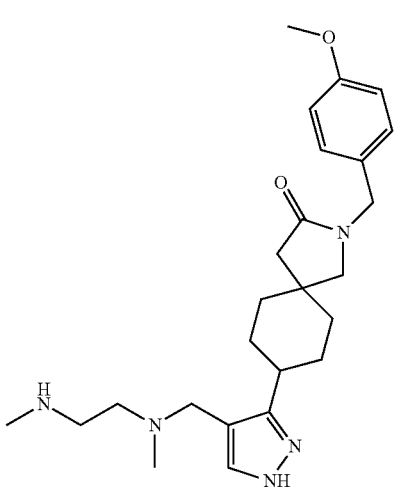 [SMILES: CNCCN(C)Cc1c[nH]nc1C1CCC2(CC1)CC(=O)N(Cc1ccc(OC)cc1)C2] | 440.15 |
| 147 | 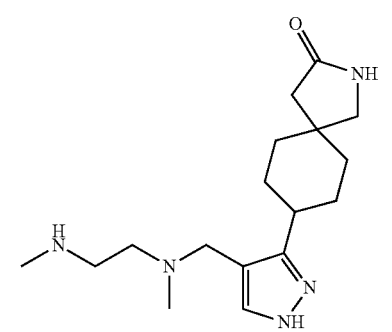 [SMILES: CNCCN(C)Cc1c[nH]nc1C1CCC2(CC1)CNC(=O)C2] | 320.1 |
| 148 | 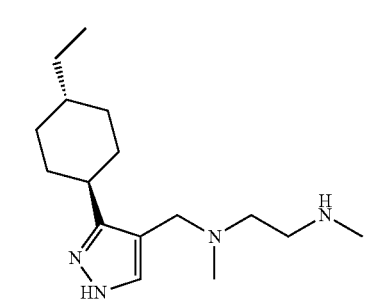 [SMILES: CC[C@H]1CC[C@H](c2n[nH]cc2CN(C)CCNC)CC1] | 279.25 |

TABLE 1B-continued

Exemplary Compounds

| Cmpd No | Structure | LC-MS m/z (M + H) |
|---|---|---|
| 149 | 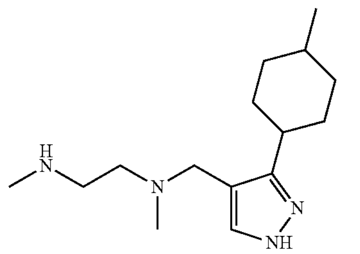 [SMILES: CNCCN(C)Cc1c[nH]nc1C1CCC(C)CC1] | 265.1 |
| 150 | 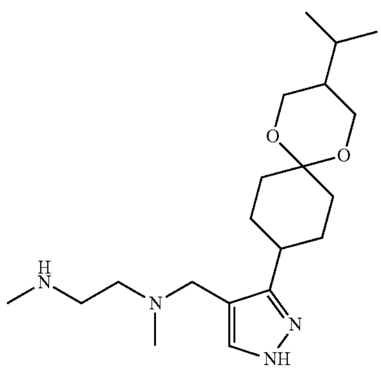 [SMILES: CNCCN(C)Cc1c[nH]nc1C1CCC2(CC1)OCC(C(C)C)CO2] | 365.25 |
| 151 | 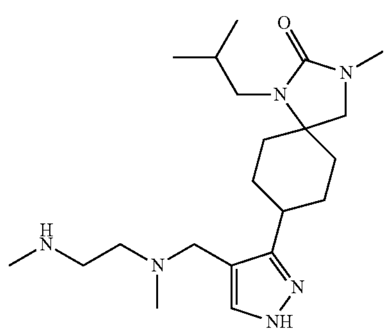 | 391.3 |
| 152 | 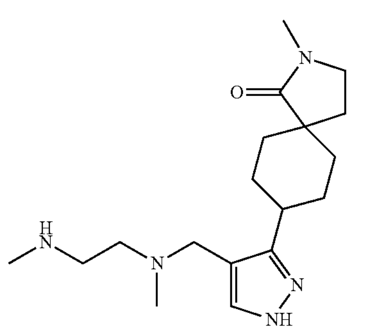 [SMILES: CNCCN(C)Cc1c[nH]nc1C1CCC2(CC1)CCN(C)C2=O] | 334.15 |

TABLE 1B-continued

Exemplary Compounds

| Cmpd No | Structure | LC-MS m/z (M + H) |
|---|---|---|
| 153 | 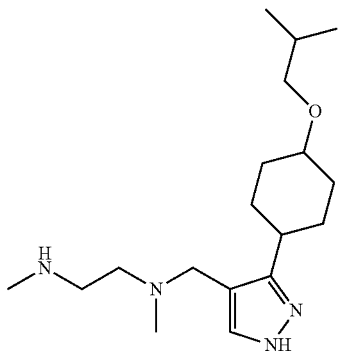 [SMILES: CNCCN(C)Cc1c[nH]nc1C1CCC(OCC(C)C)CC1] | 323.15 |
| 154 | 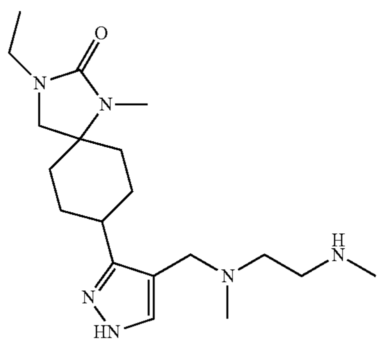 [SMILES: CCN1CC2(CCC(c3n[nH]cc3CN(C)CCNC)CC2)N(C)C1=O] | 363.15 |
| 155 | 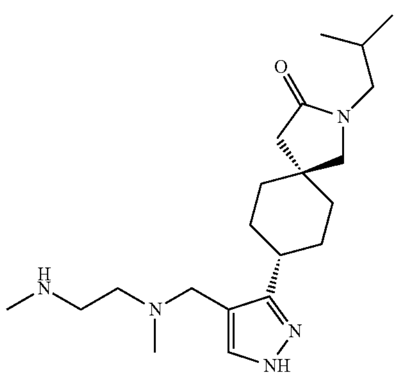 [SMILES: CNCCN(C)Cc1c[nH]nc1[C@H]1CC[C@]2(CC1)CC(=O)N(CC(C)C)C2] | 376.25 |
| 156 | 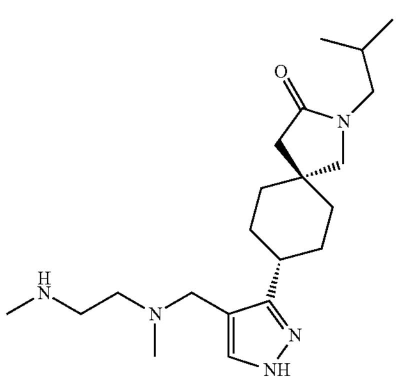 [SMILES: CNCCN(C)Cc1c[nH]nc1[C@H]1CC[C@@]2(CC1)CC(=O)N(CC(C)C)C2] | 376.25 |

TABLE 1B-continued
Exemplary Compounds
| Cmpd No | Structure | LC-MS m/z (M + H) |
|---|---|---|
| 157 | 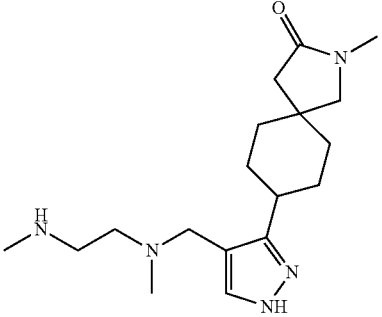 | 334.15 |
| 158 | 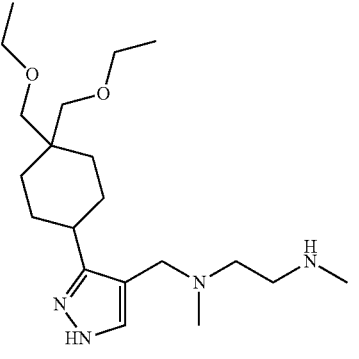 [SMILES: CCOCC1(COCC)CCC(c2n[nH]cc2CN(C)CCNC)CC1] | 367.2 |
| 159 | 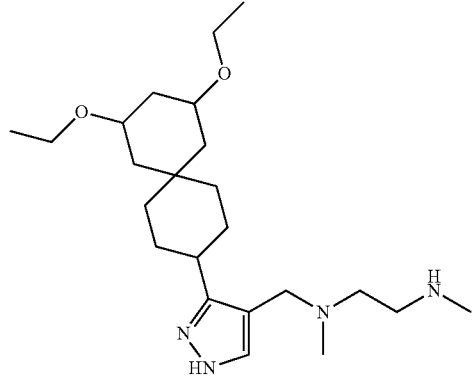 [SMILES: CCOC1CC(OCC)CC2(CCC(c3n[nH]cc3CN(C)CCNC)CC2)C1] | 407.35 |
| 160 | 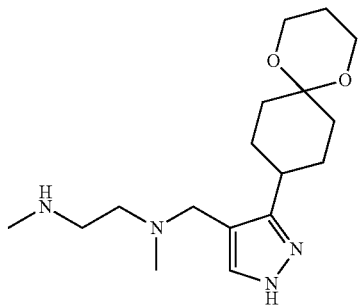 [SMILES: CNCCN(C)Cc1c[nH]nc1C1CCC2(CC1)OCCCO2] | 323.2 |

TABLE 1B-continued
Exemplary Compounds
| Cmpd No | Structure | LC-MS m/z (M + H) |
|---|---|---|
| 161 | 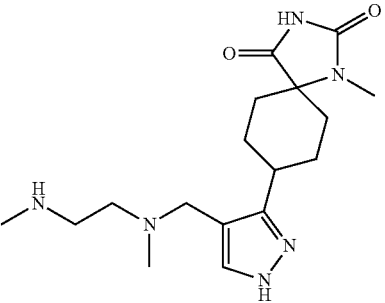 | 349 |
| 162 | 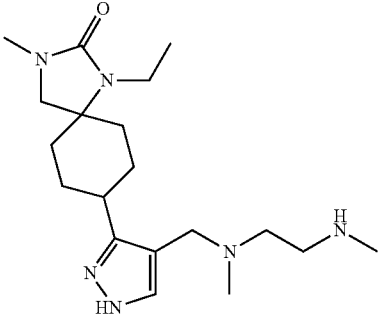 | 363.05 |
| 163 | 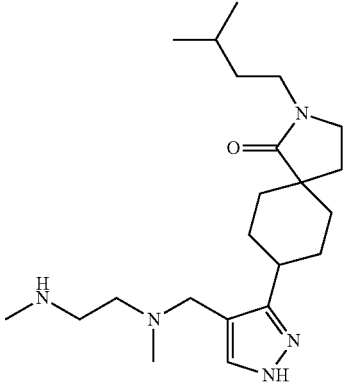 [SMILES: CNCCN(C)Cc1c[nH]nc1C1CCC2(CC1)CCN(CCC(C)C)C2=O] | 390.3 |
| 164 | 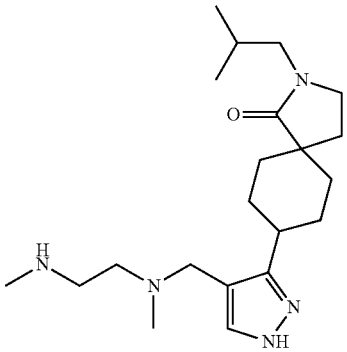 [SMILES: CNCCN(C)Cc1c[nH]nc1C1CCC2(CC1)CCN(CC(C)C)C2=O] | 376.25 |

TABLE 1B-continued
Exemplary Compounds
| Cmpd No | Structure | LC-MS m/z (M + H) |
|---|---|---|
| 165 | 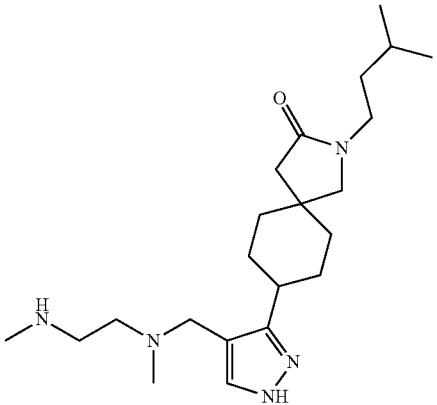 [SMILES: CNCCN(C)Cc1c[nH]nc1C1CCC2(CC1)CC(=O)N(CCC(C)C)C2] | 390.3 |
| 166 | 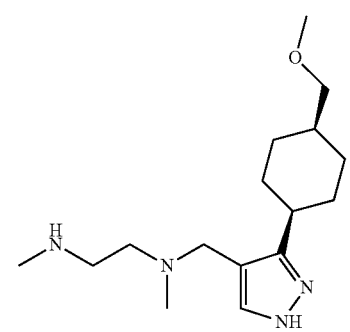 [SMILES: CNCCN(C)Cc1c[nH]nc1[C@H]1CC[C@@H](COC)CC1] | 295.1 |
| 167 | 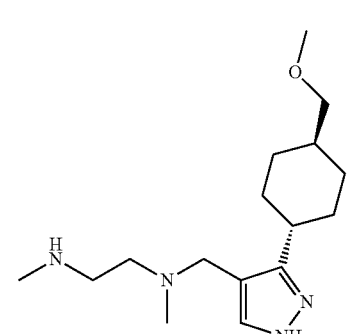 | 295.1 |
| 168 | 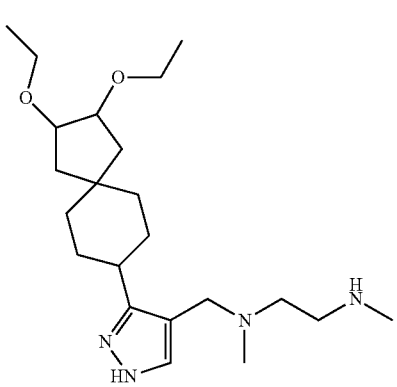 [SMILES: CCOC1CC2(CCC(c3n[nH]cc3CN(C)CCNC)CC2)CC1OCC] | 393.3 |

TABLE 1B-continued
Exemplary Compounds
| Cmpd No | Structure | LC-MS m/z (M + H) |
|---|---|---|
| 169 | 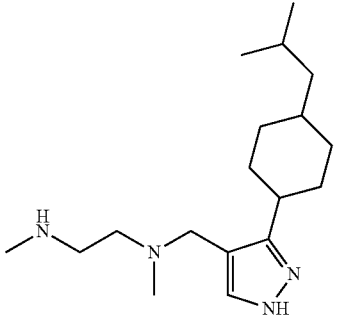 [SMILES: CNCCN(C)Cc1c[nH]nc1C1CCC(CC(C)C)CC1] | 307.15 |
| 170 | 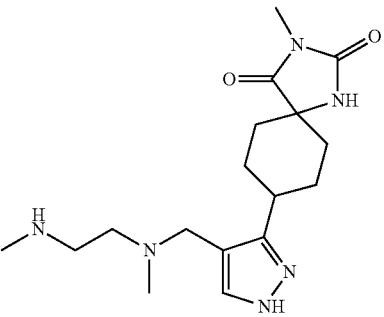 [SMILES: CNCCN(C)Cc1c[nH]nc1C1CCC2(CC1)NC(=O)N(C)C2=O] | 349.15 |
| 171 | 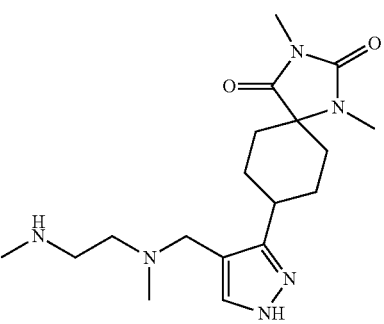 | 363.2 |
| 172 | 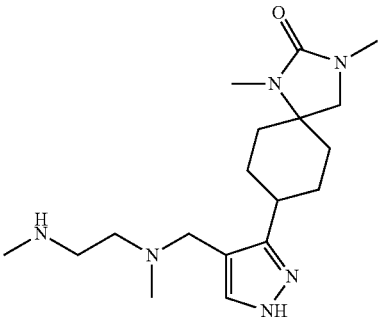 | 349.2 |

TABLE 1B-continued

Exemplary Compounds

| Cmpd No | Structure | LC-MS m/z (M + H) |
|---|---|---|
| 173 | 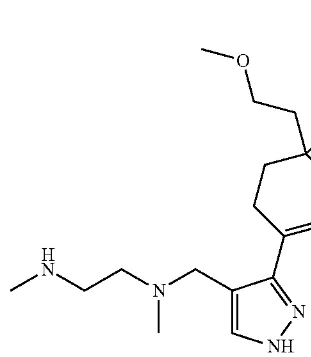 | 365.2 |
| 174 | 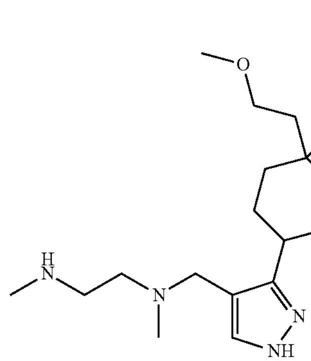 | 367.35 |
| 175 | 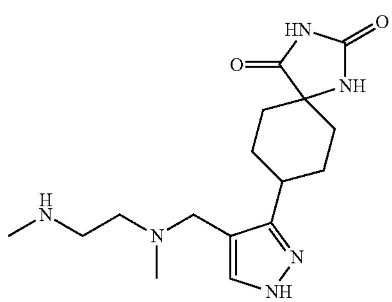 [SMILES: CNCCN(C)Cc1c[nH]nc1C1CCC2(CC1)NC(=O)NC2=O] | 335.1 |
| 176 | 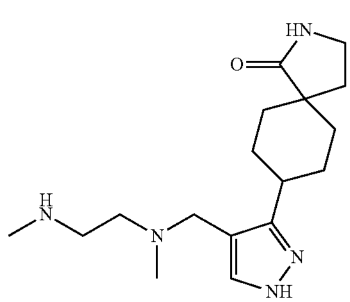 [SMILES: CNCCN(C)Cc1c[nH]nc1C1CCC2(CCNC2=O)CC1] | 320.1 |

TABLE 1B-continued

Exemplary Compounds

| Cmpd No | Structure | LC-MS m/z (M + H) |
|---|---|---|
| 177 | 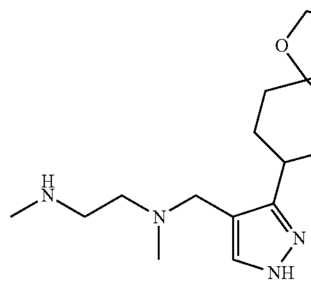 | 309.1 |
| 178 | 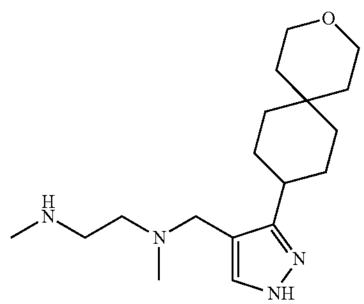 [SMILES: CNCCN(C)Cc1c[nH]nc1C1CCC2(CCOCC2)CC1] | 321.05 |
| 179 | 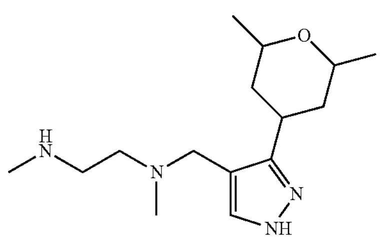 | 281.1 |
| 180 | 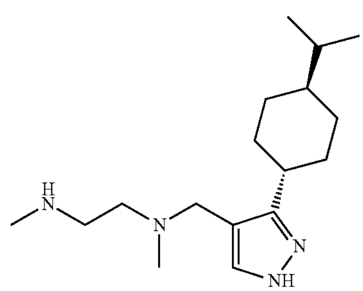 [SMILES: CNCCN(C)Cc1c[nH]nc1[C@H]1CC[C@H](C(C)C)CC1] | 293.15 |
| 181 | 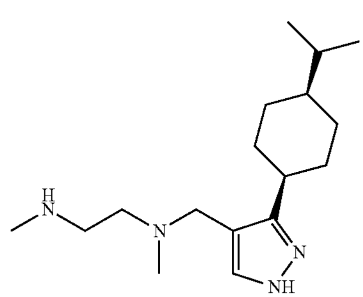 [SMILES: CNCCN(C)Cc1c[nH]nc1[C@H]1CC[C@@H](C(C)C)CC1] | 293.15 |

TABLE 1B-continued

Exemplary Compounds

| Cmpd No | Structure | LC-MS m/z (M + H) |
|---|---|---|
| 182 | 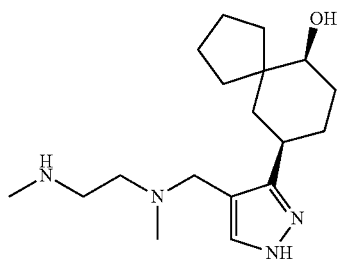 [SMILES: CNCCN(C)Cc1c[nH]nc1[C@@H]1CC[C@H](O)C2(CCCC2)C1] | 321.3 |
| 183 | 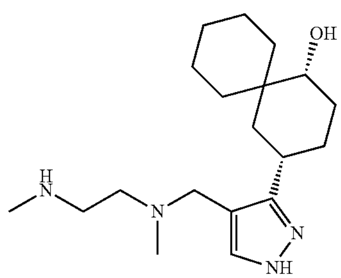 [SMILES: CNCCN(C)Cc1c[nH]nc1[C@H]1CC[C@@H](O)C2(CCCCC2)C1] | — |
| 184 | 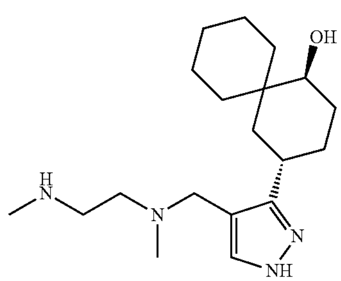 [SMILES: CNCCN(C)Cc1c[nH]nc1[C@H]1CC[C@H](O)C2(CCCCC2)C1] | — |
| 185 | 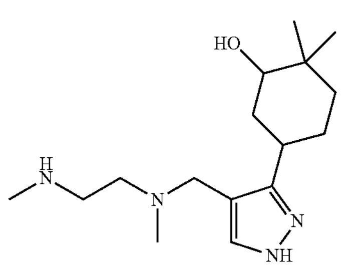 | 295.05 |

TABLE 1B-continued

Exemplary Compounds

| Cmpd No | Structure | LC-MS m/z (M + H) |
|---|---|---|
| 186 | 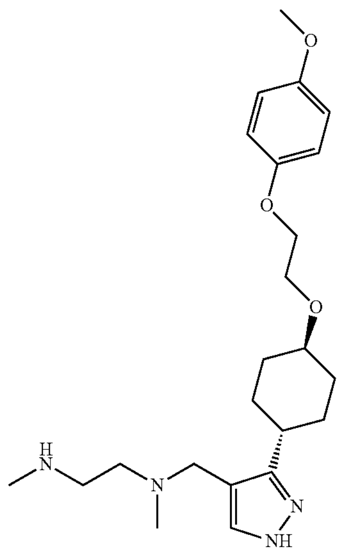 [SMILES: CNCCN(C)Cc1c[nH]nc1[C@H]1CC[C@H](OCCOc2ccc(OC)cc2)CC1] | 417.10 |
| 187 | 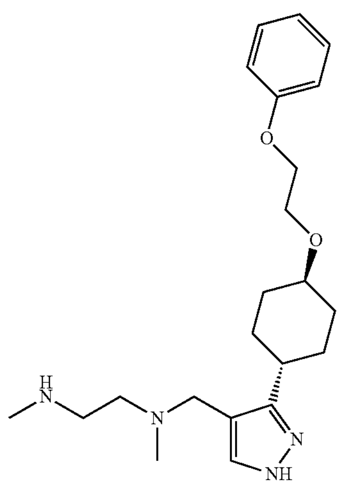 [SMILES: CNCCN(C)Cc1c[nH]nc1[C@H]1CC[C@H](OCCOc2ccccc2)CC1] | 387.10 |
| 188 | 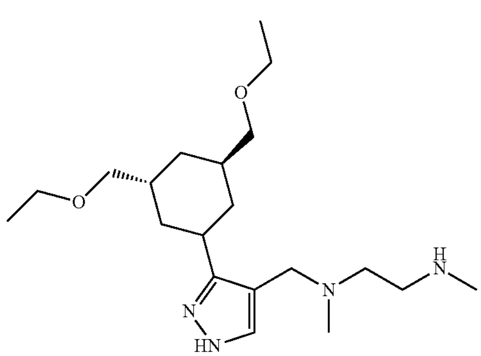 [SMILES: CCOC[C@H]1CC(c2n[nH]cc2CN(C)CCNC)C[C@H](COCC)C1] | 367.2 |

TABLE 1B-continued
Exemplary Compounds
| Cmpd No | Structure | LC-MS m/z (M + H) |
|---|---|---|
| 189 | 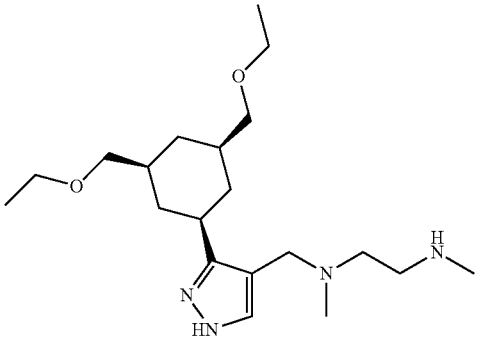 [SMILES: CCOC[C@@H]1C[C@H](COCC)C[C@H](c2n[nH]cc2CN(C)CCNC)C1] | 367.2 |
| 190 | 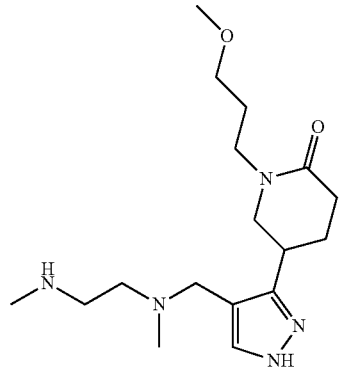 [SMILES: CNCCN(C)Cc1c[nH]nc1C1CCC(=O)N(CCCOC)C1] | 338.1 |
| 191 | 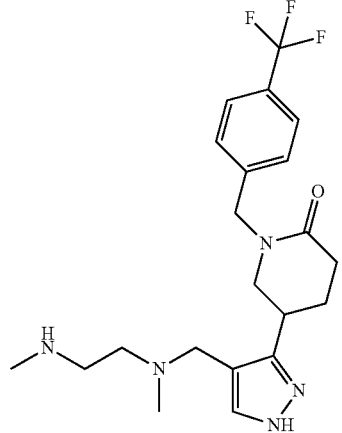 [SMILES: CNCCN(C)Cc1c[nH]nc1C1CCC(=O)N(Cc2ccc(C(F)(F)F)cc2)C1] | 424.2 |

TABLE 1B-continued

Exemplary Compounds

| Cmpd No | Structure | LC-MS m/z (M + H) |
|---|---|---|
| 192 | 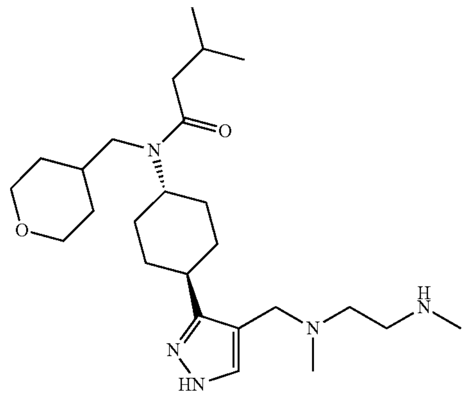 [SMILES: CNCCN(C)Cc1c[nH]nc1[C@H]1CC[C@H](N(CC2CCOCC2)C(=O)CC(C)C)CC1] | 448.2 |
| 193 | 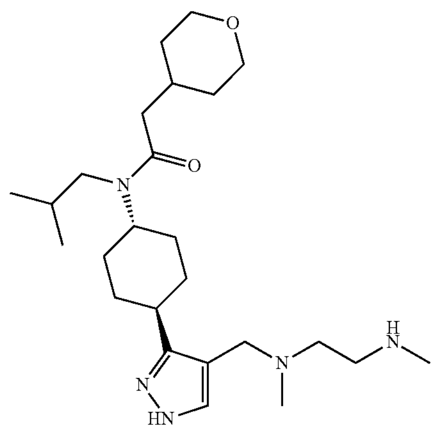 [SMILES: CNCCN(C)Cc1c[nH]nc1[C@H]1CC[C@H](N(CC(C)C)C(=O)CC2CCOCC2)CC1] | 448.4 |
| 194 | 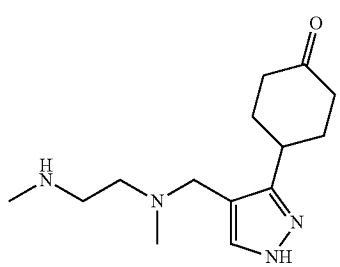 [SMILES: CNCCN(C)Cc1c[nH]nc1C1CCC(=O)CC1] | 265.1 |
| 195 | 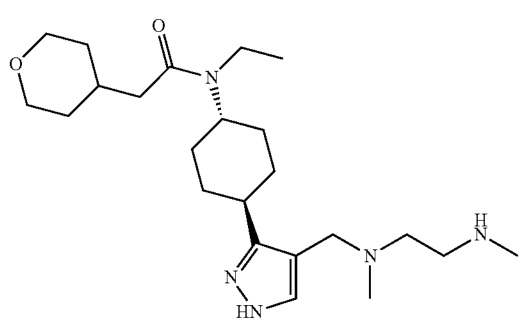 [SMILES: CCN(C(=O)CC1CCOCC1)[C@H]1CC[C@H](c2n[nH]cc2CN(C)CCNC)CC1] | 420.4 |

TABLE 1B-continued

Exemplary Compounds

| Cmpd No | Structure | LC-MS m/z (M + H) |
|---|---|---|
| 196 | | 420.5 |
| 197 | | 446.2 |
| 198 | | 309.2 |
| 199 | | 307.15 |

TABLE 1B-continued

Exemplary Compounds

| Cmpd No | Structure | LC-MS m/z (M + H) |
|---|---|---|
| 200 | 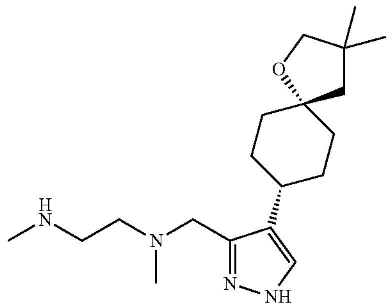 | 335.1 |
| 201 | 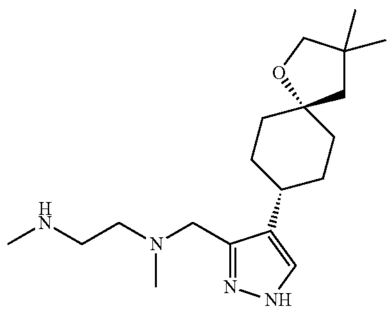 | 335.2 |
| 202 | 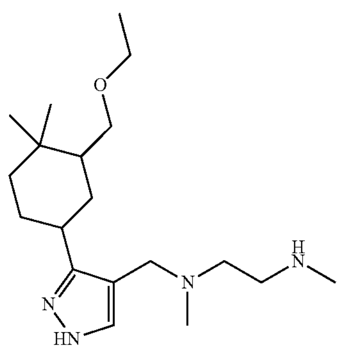 [SMILES: CCOCC1CC(c2n[nH]cc2CN(C)CCNC)CCC1(C)C] | 337.1 |
| 203 | 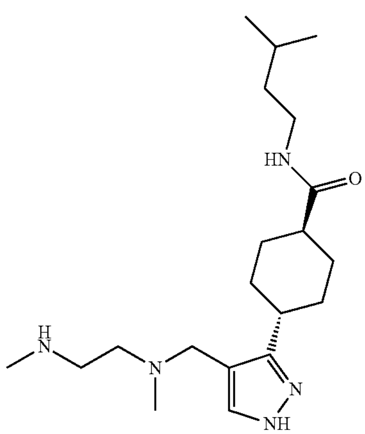 [SMILES: CNCCN(C)Cc1c[nH]nc1[C@H]1CC[C@H](C(=O)NCCC(C)C)CC1] | 364.2 |

TABLE 1B-continued

Exemplary Compounds

| Cmpd No | Structure | LC-MS m/z (M + H) |
|---|---|---|
| 204 | 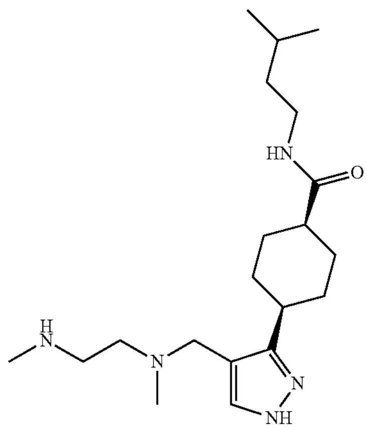 [SMILES: CNCCN(C)Cc1c[nH]nc1[C@H]1CC[C@@H](C(=O)NCCC(C)C)CC1] | 364.2 |
| 205 | 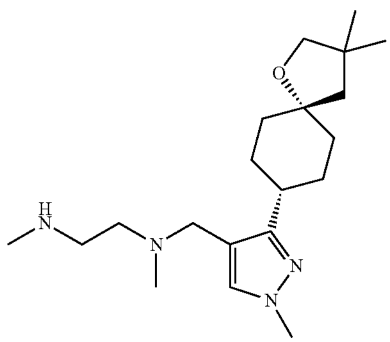 | 349.2 |
| 206 | 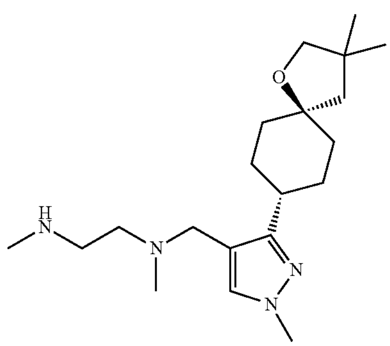 | 349.15 |
| 207 | 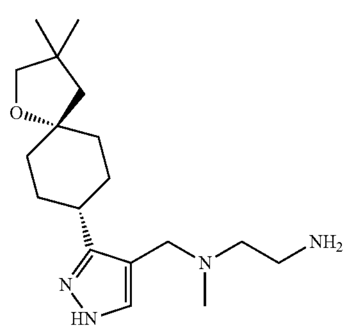 [SMILES: CN(CCN)Cc1c[nH]nc1[C@H]1CC[C@@]2(CC1)CC(C)(C)CO2] | 321.15 |

TABLE 1B-continued

Exemplary Compounds

| Cmpd No | Structure | LC-MS m/z (M + H) |
|---|---|---|
| 208 | 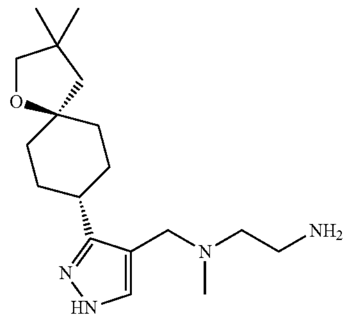 [SMILES: CN(CCN)Cc1c[nH]nc1[C@H]1CC[C@]2(CC1)CC(C)(C)CO2] | 321.1 |
| 209 | 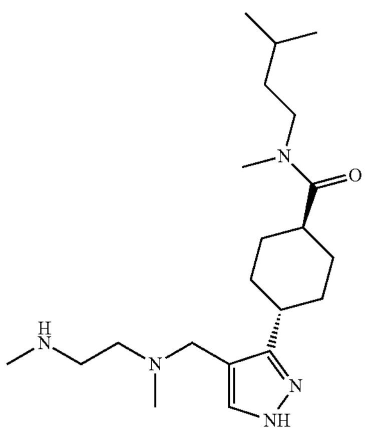 [SMILES: CNCCN(C)Cc1c[nH]nc1[C@H]1CC[C@H](C(=O)N(C)CCC(C)C)CC1] | 378.2 |
| 210 | 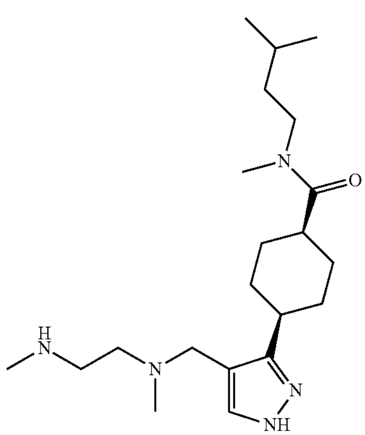 [SMILES: CNCCN(C)Cc1c[nH]nc1[C@H]1CC[C@@H](C(=O)N(C)CCC(C)C)CC1] | 378.2 |

TABLE 1B-continued

Exemplary Compounds

| Cmpd No | Structure | LC-MS m/z (M + H) |
|---|---|---|
| 211 | 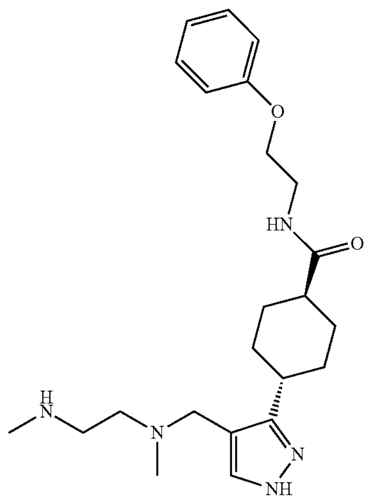 [SMILES: CNCCN(C)Cc1c[nH]nc1[C@H]1CC[C@H](C(=O)NCCOc2ccccc2)CC1] | 414.1 |
| 212 | 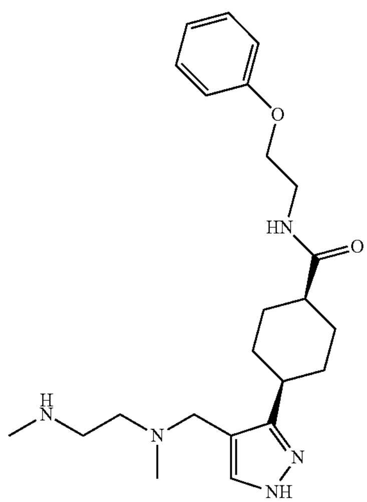 [SMILES: CNCCN(C)Cc1c[nH]nc1[C@H]1CC[C@@H](C(=O)NCCOc2ccccc2)CC1] | 414.1 |
| 213 | 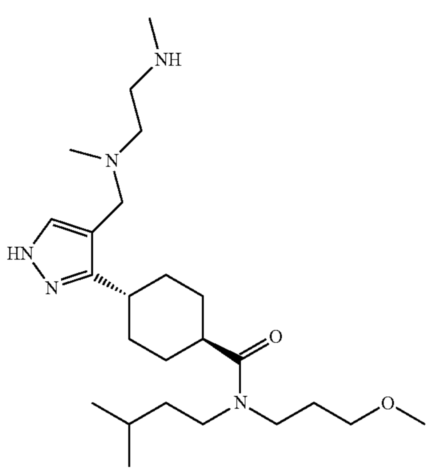 [SMILES: CNCCN(C)Cc1c[nH]nc1[C@H]1CC[C@H](C(=O)N(CCCOC)CCC(C)C)CC1] | 436.2 |

TABLE 1B-continued

| Cmpd No | Structure | LC-MS m/z (M + H) |
|---|---|---|
| 214 | 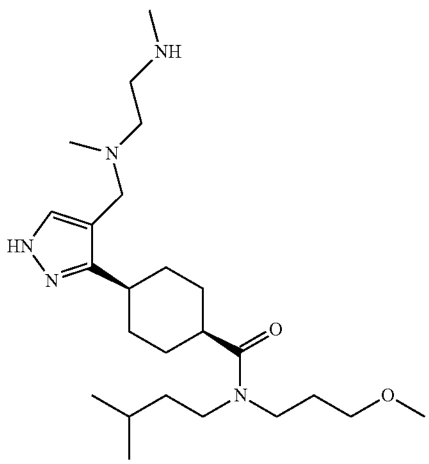 [SMILES: CNCCN(C)Cc1c[nH]nc1[C@H]1CC[C@@H](C(=O)N(CCCOC)CCC(C)C)CC1] | 436.2 |
| 215 | 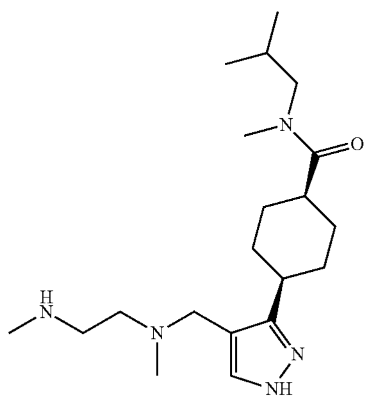 [SMILES: CNCCN(C)Cc1c[nH]nc1[C@H]1CC[C@@H](C(=O)N(C)CC(C)C)CC1] | 364.2 |
| 216 | 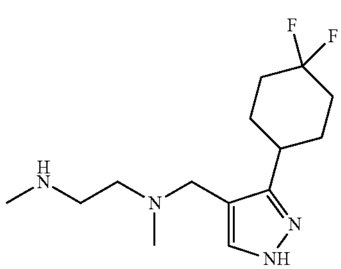 [SMILES: CNCCN(C)Cc1c[nH]nc1C1CCC(F)(F)CC1] | 287.05 |
| 217 | 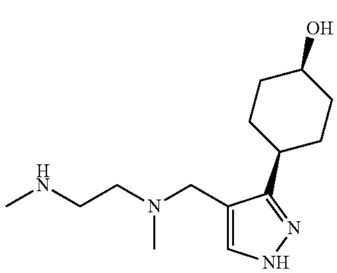 [SMILES: CNCCN(C)Cc1c[nH]nc1[C@H]1CC[C@@H](O)CC1] | 267.05 |

TABLE 1B-continued

Exemplary Compounds

| Cmpd No | Structure | LC-MS m/z (M + H) |
|---|---|---|
| 218 | 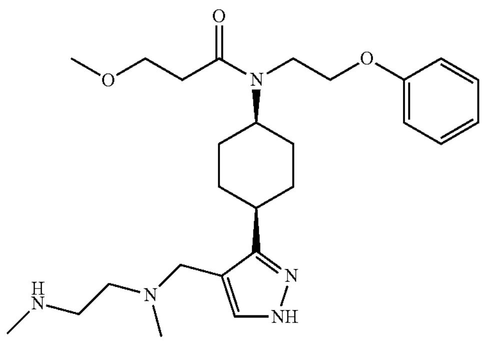 [SMILES: CNCCN(C)Cc1c[nH]nc1[C@H]1CC[C@@H](N(CCOc2ccccc2)C(=O)CCOC)CC1] | 472.4 |
| 219 | 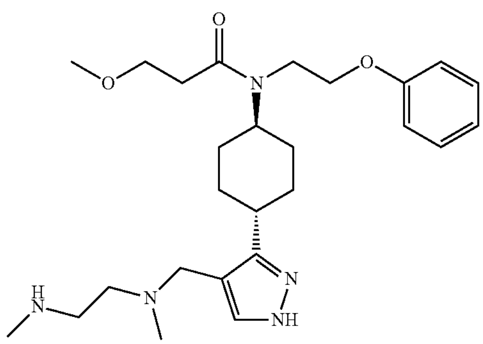 [SMILES: CNCCN(C)Cc1c[nH]nc1[C@H]1CC[C@H](N(CCOc2ccccc2)C(=O)CCOC)CC1] | 472.4 |
| 220 | 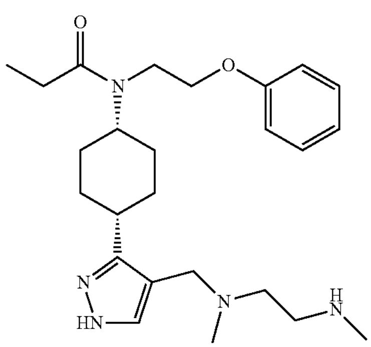 [SMILES: CCC(=O)N(CCOc1ccccc1)[C@H]1CC[C@@H](c2n[nH]cc2CN(C)CCNC)CC1] | 442.2 |
| 221 | 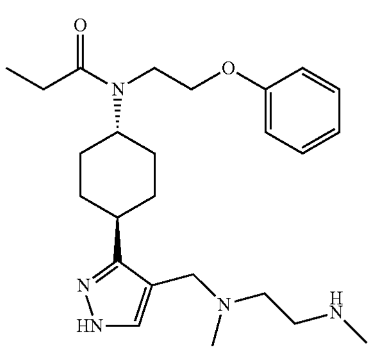 [SMILES: CCC(=O)N(CCOc1ccccc1)[C@H]1CC[C@H](c2n[nH]cc2CN(C)CCNC)CC1] | 442.2 |

TABLE 1B-continued

Exemplary Compounds

| Cmpd No | Structure | LC-MS m/z (M + H) |
|---|---|---|
| 222 | 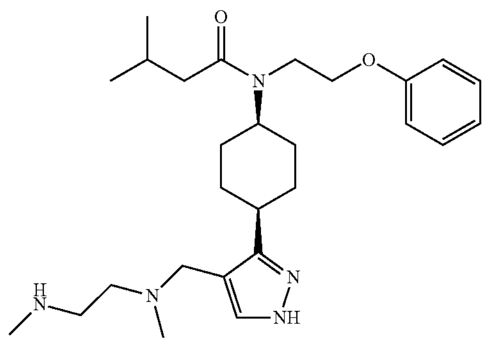 [SMILES: CNCCN(C)Cc1c[nH]nc1[C@H]1CC[C@@H](N(CCOc2ccccc2)C(=O)CC(C)C)CC1] | 470.2 |
| 223 | 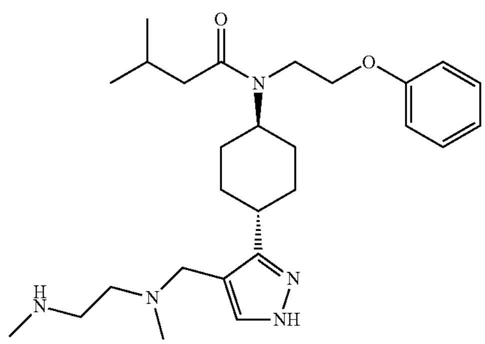 [SMILES: CNCCN(C)Cc1c[nH]nc1[C@H]1CC[C@H](N(CCOc2ccccc2)C(=O)CC(C)C)CC1] | 470.4 |
| 224 | 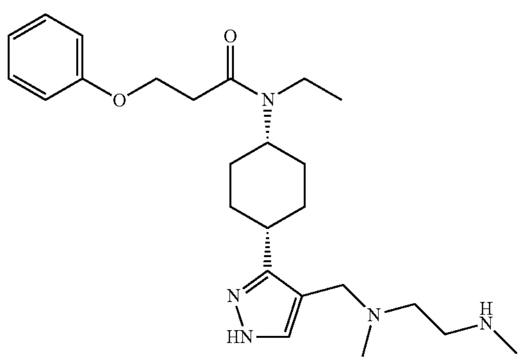 [SMILES: CCN(C(=O)CCOc1ccccc1)[C@H]1CC[C@@H](c2n[nH]cc2CN(C)CCNC)CC1] | 442.3 |
| 225 | 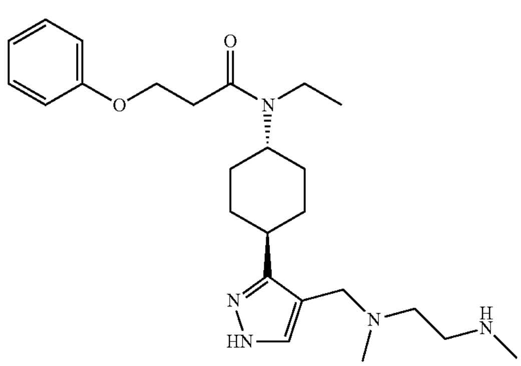 [SMILES: CCN(C(=O)CCOc1ccccc1)[C@H]1CC[C@H](c2n[nH]cc2CN(C)CCNC)CC1] | 442.3 |

TABLE 1B-continued

Exemplary Compounds

| Cmpd No | Structure | LC-MS m/z (M + H) |
|---|---|---|
| 226 | 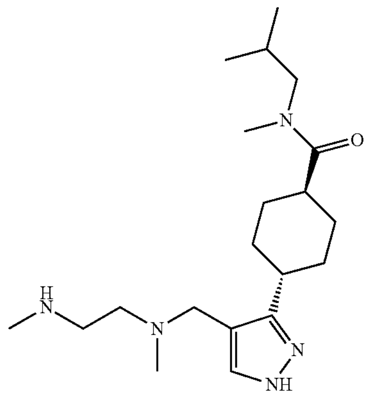 [SMILES: CNCCN(C)Cc1c[nH]nc1[C@H]1CC[C@H](C(=O)N(C)CC(C)C)CC1] | 364.2 |
| 227 | 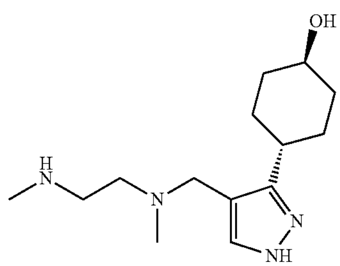 [SMILES: CNCCN(C)Cc1c[nH]nc1[C@H]1CC[C@H](O)CC1] | 267.05 |
| 228 | 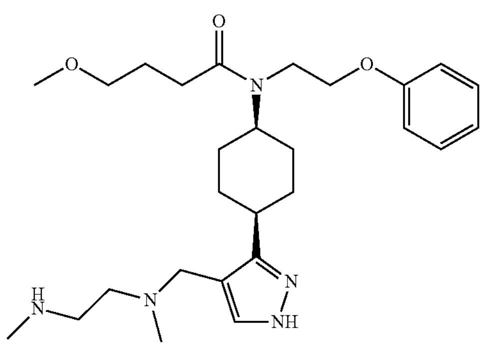 [SMILES: CNCCN(C)Cc1c[nH]nc1[C@H]1CC[C@@H](N(CCOc2ccccc2)C(=O)CCCOC)CC1] | 486.4 |
| 229 | 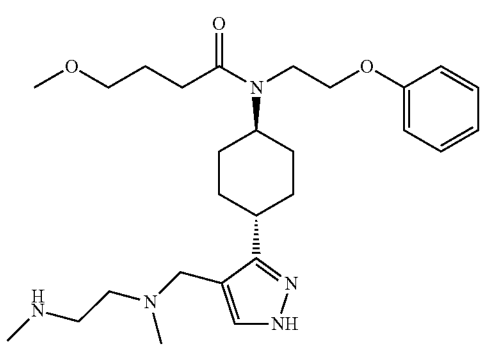 [SMILES: CNCCN(C)Cc1c[nH]nc1[C@H]1CC[C@H](N(CCOc2ccccc2)C(=O)CCCOC)CC1] | 486.4 |

TABLE 1B-continued

Exemplary Compounds

| Cmpd No | Structure | LC-MS m/z (M + H) |
|---|---|---|
| 230 | 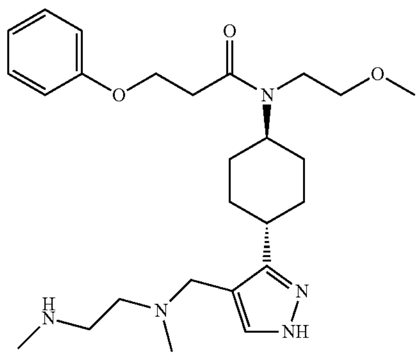 [SMILES: CNCCN(C)Cc1c[nH]nc1[C@H]1CC[C@H](N(CCOC)C(=O)CCOc2ccccc2)CC1] | 472.4 |
| 231 | 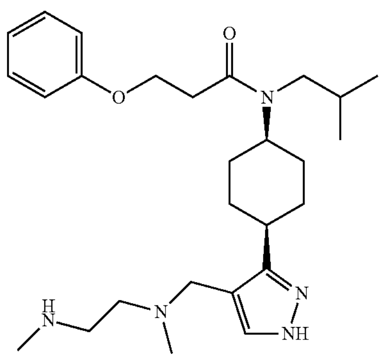 [SMILES: CNCCN(C)Cc1c[nH]nc1[C@H]1CC[C@@H](N(CC(C)C)C(=O)CCOc2ccccc2)CC1] | 470.2 |
| 232 | 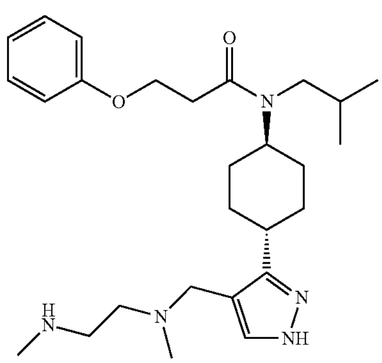 [SMILES: CNCCN(C)Cc1c[nH]nc1[C@H]1CC[C@H](N(CC(C)C)C(=O)CCOc2ccccc2)CC1] | 470.2 |
| 233 | 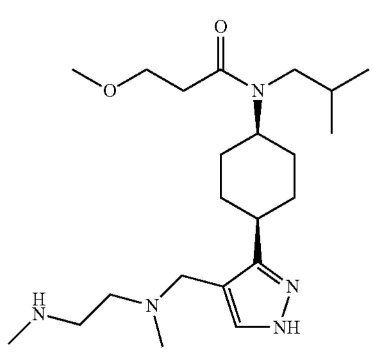 [SMILES: CNCCN(C)Cc1c[nH]nc1[C@H]1CC[C@@H](N(CC(C)C)C(=O)CCOC)CC1] | 408.2 |

TABLE 1B-continued

Exemplary Compounds

| Cmpd No | Structure | LC-MS m/z (M + H) |
|---|---|---|
| 234 | 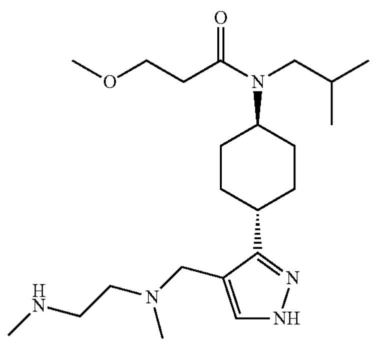 [SMILES: CNCCN(C)Cc1c[nH]nc1[C@H]1CC[C@H](N(CC(C)C)C(=O)CCOC)CC1] | 408.2 |
| 235 | 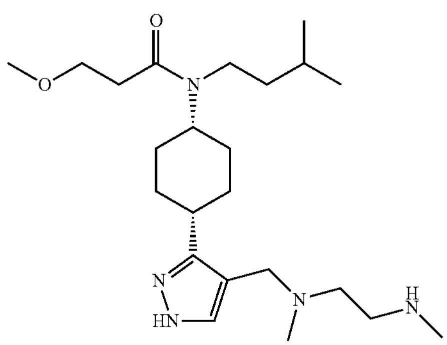 | 422.4 |
| 236 | 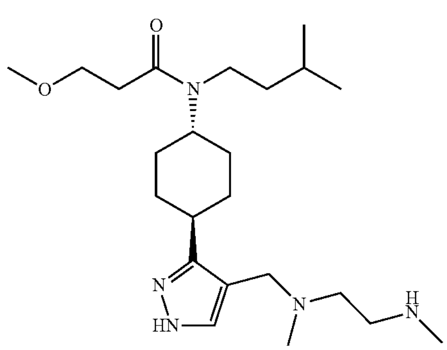 | 422.4 |
| 237 | 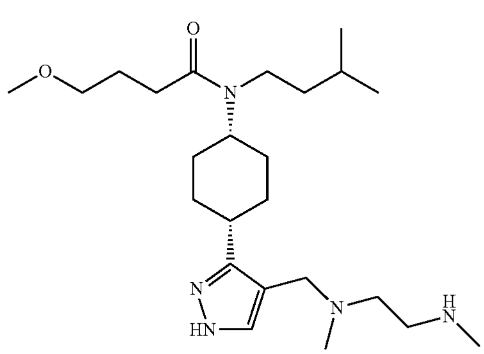 | 436.4 |

TABLE 1B-continued

Exemplary Compounds

| Cmpd No | Structure | LC-MS m/z (M + H) |
|---|---|---|
| 238 | 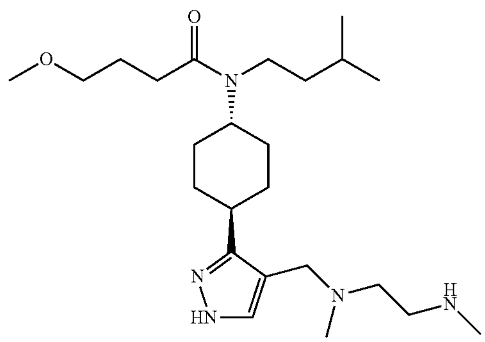 | 436.4 |
| 239 | 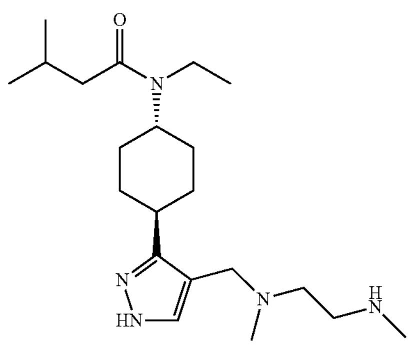 [SMILES: CCN(C(=O)CC(C)C)[C@H]1CC[C@H](c2n[nH]cc2CN(C)CCNC)CC1] | 378.3 |
| 240 | 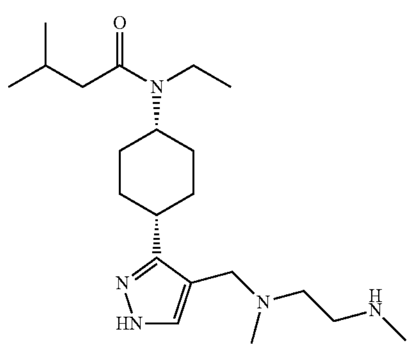 [SMILES: CCN(C(=O)CC(C)C)[C@H]1CC[C@@H](c2n[nH]cc2CN(C)CCNC)CC1] | 378.3 |
| 241 | 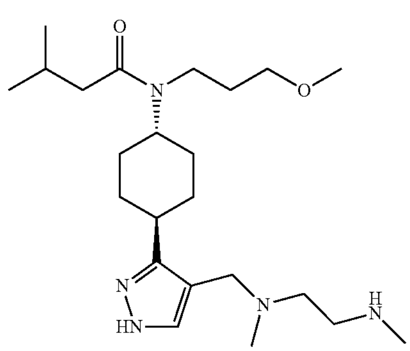 [SMILES: CNCCN(C)Cc1c[nH]nc1[C@H]1CC[C@H](N(CCCOC)C(=O)CC(C)C)CC1] | 422.2 |

TABLE 1B-continued
Exemplary Compounds
| Cmpd No | Structure | LC-MS m/z (M + H) |
|---|---|---|
| 242 | 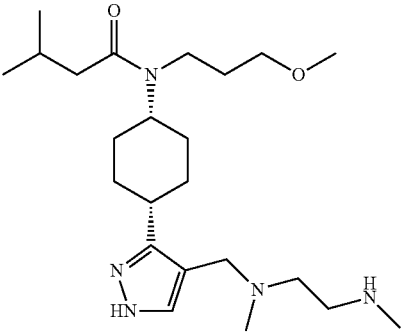 [SMILES: CNCCN(C)Cc1c[nH]nc1[C@H]1CC[C@@H](N(CCCOC)C(=O)CC(C)C)CC1] | 422.2 |
| 243 | 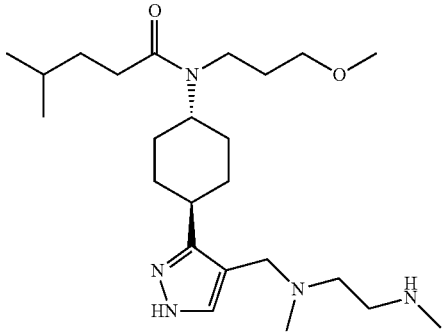 [SMILES: CNCCN(C)Cc1c[nH]nc1[C@H]1CC[C@H](N(CCCOC)C(=O)CCC(C)C)CC1] | 436.2 |
| 244 | 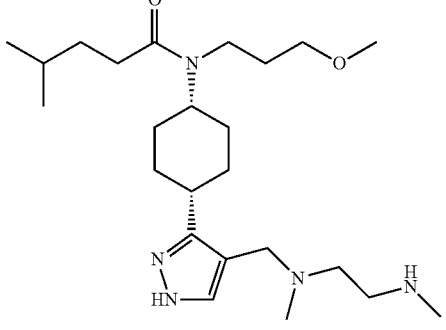 | 436.2 |
| 245 | 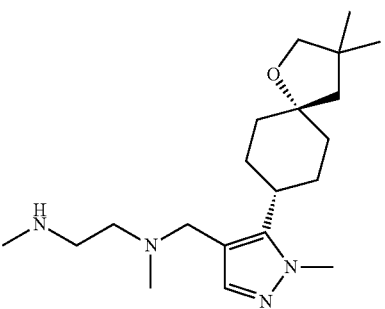 | 349.1 |

TABLE 1B-continued
Exemplary Compounds
| Cmpd No | Structure | LC-MS m/z (M + H) |
|---|---|---|
| 246 | 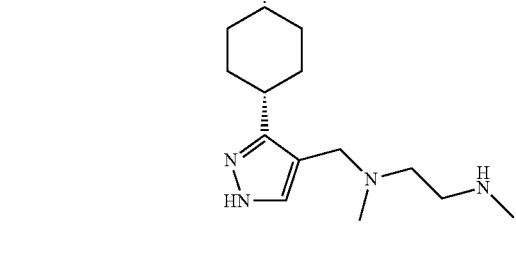 | 486.3 |
| 247 | 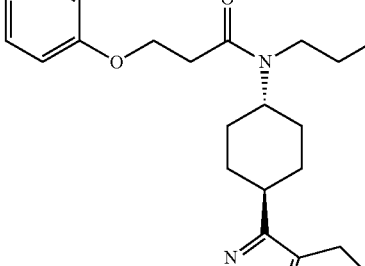 | 486.3 |
| 248 | 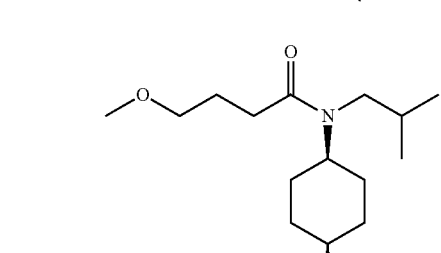 | 422.3 |
| 249 | 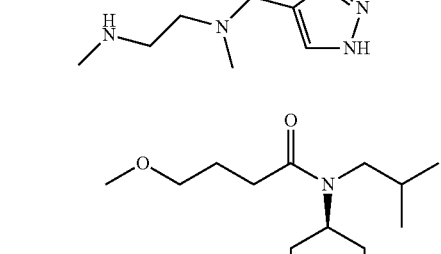 | 422.3 |

TABLE 1B-continued
Exemplary Compounds
| Cmpd No | Structure | LC-MS m/z (M + H) |
|---|---|---|
| 250 | 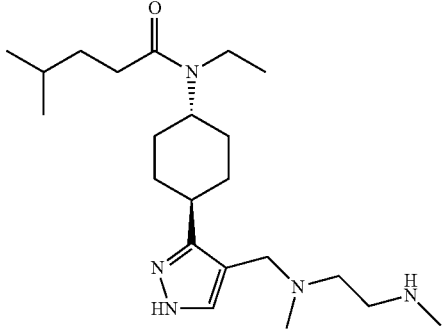 [SMILES: CCN(C(=O)CCC(C)C)[C@H]1CC[C@H](c2n[nH]cc2CN(C)CCNC)CC1] | 392.2 |
| 251 | 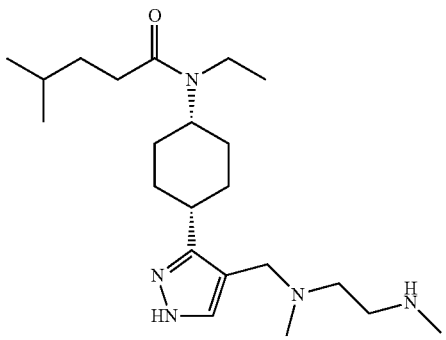 [SMILES: CCN(C(=O)CCC(C)C)[C@H]1CC[C@@H](c2n[nH]cc2CN(C)CCNC)CC1] | 392.3 |
| 252 | 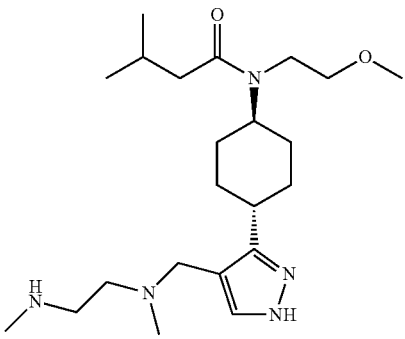 | 408.2 |
| 253 | 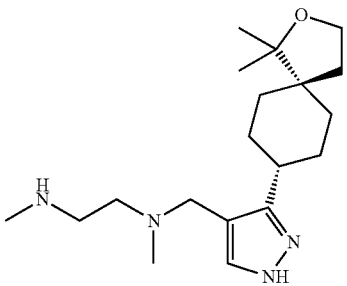 [SMILES: CNCCN(C)Cc1c[nH]nc1[C@H]1CC[C@]2(CCOC2(C)C)CC1] | 335.2 |

TABLE 1B-continued

Exemplary Compounds

| Cmpd No | Structure | LC-MS m/z (M + H) |
|---|---|---|
| 254 | 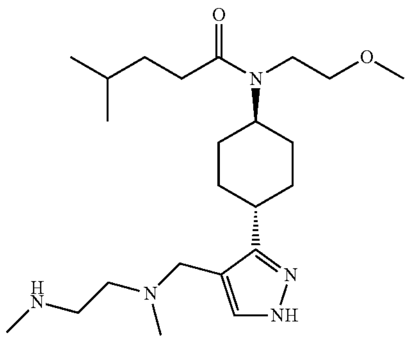 | 422.3 |
| 255 | 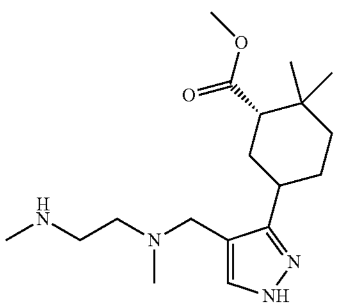 | — |
| 256 | 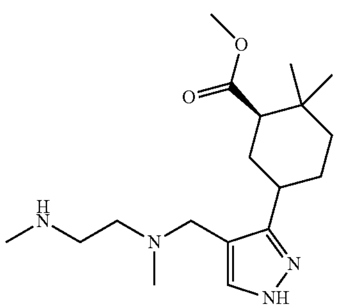 | 337.5 |
| 257 | 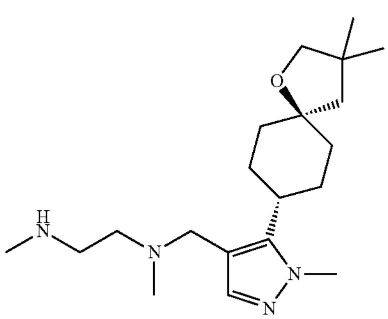 | 349.2 |

TABLE 1B-continued

Exemplary Compounds

| Cmpd No | Structure | LC-MS m/z (M + H) |
|---|---|---|
| 258 | 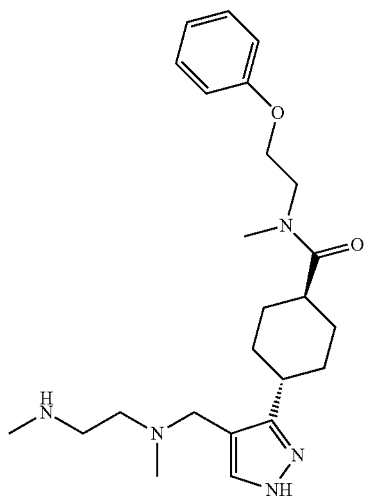 [SMILES: CNCCN(C)Cc1c[nH]nc1[C@H]1CC[C@H](C(=O)N(C)CCOc2ccccc2)CC1] | 428.1 |
| 259 | 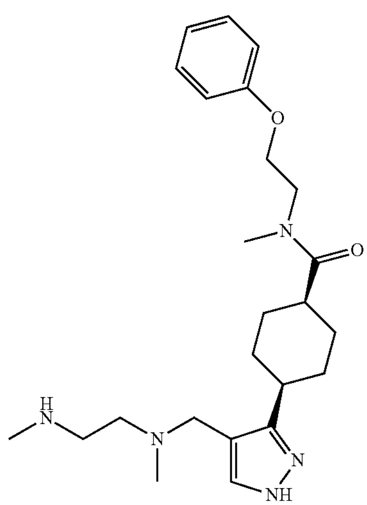 [SMILES: CNCCN(C)Cc1c[nH]nc1[C@H]1CC[C@@H](C(=O)N(C)CCOc2ccccc2)CC1] | 428.1 |
| 260 | 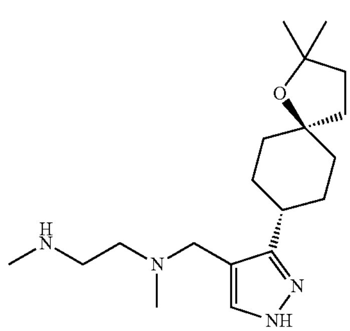 [SMILES: CNCCN(C)Cc1c[nH]nc1[C@H]1CC[C@@]2(CCC(C)(C)O2)CC1] | 335.1 |

TABLE 1B-continued

Exemplary Compounds

| Cmpd No | Structure | LC-MS m/z (M + H) |
|---|---|---|
| 261 | 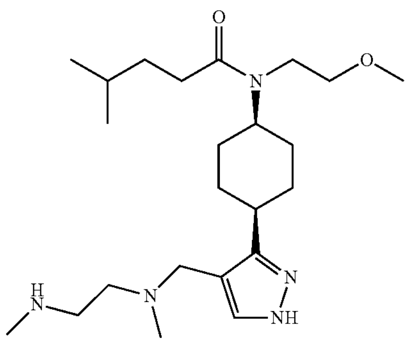 | 422.3 |
| 262 | 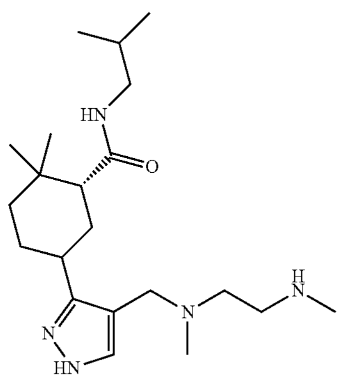 [SMILES: CNCCN(C)Cc1c[nH]nc1C1CCC(C)(C)[C@H](C(=O)NCC(C)C)C1] | 378.2 |
| 263 | 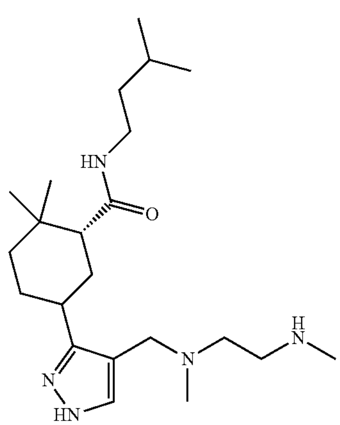 [SMILES: CNCCN(C)Cc1c[nH]nc1C1CCC(C)(C)[C@H](C(=O)NCCC(C)C)C1] | 392.2 |

TABLE 1B-continued
Exemplary Compounds
| Cmpd No | Structure | LC-MS m/z (M + H) |
|---|---|---|
| 264 | 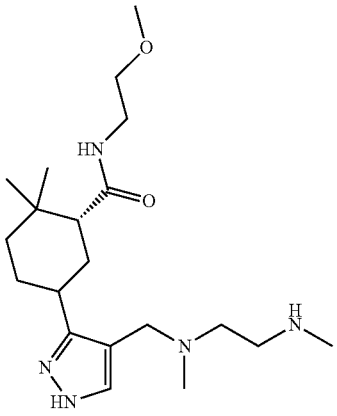 [SMILES: CNCCN(C)Cc1c[nH]nc1C1CCC(C)(C)[C@H](C(=O)NCCOC)C1] | 380.2 |
| 265 | 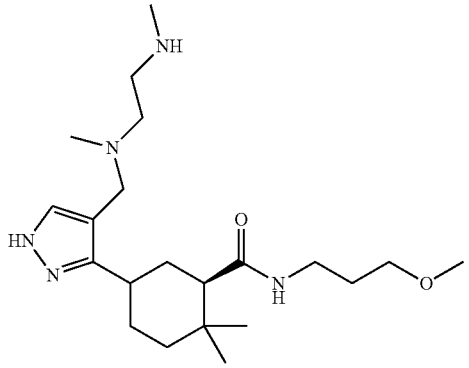 [SMILES: CNCCN(C)Cc1c[nH]nc1C1CCC(C)(C)[C@H](C(=O)NCCCOC)C1] | 394.2 |
| 266 | 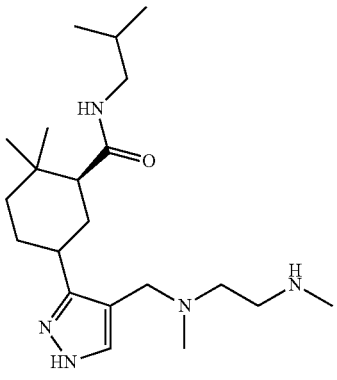 [SMILES: CNCCN(C)Cc1c[nH]nc1C1CCC(C)(C)[C@@H](C(=O)NCC(C)C)C1] | 378.15 |
| 267 | 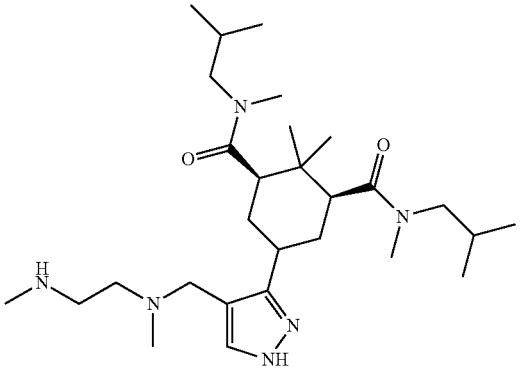 [SMILES: CNCCN(C)Cc1c[nH]nc1C1C[C@H](C(=O)N(C)CC(C)C)C(C)(C)[C@H](C(=O)N(C)CC(C)C)C1] | 505.2 |

TABLE 1B-continued

Exemplary Compounds

| Cmpd No | Structure | LC-MS m/z (M + H) |
|---|---|---|
| 268 | 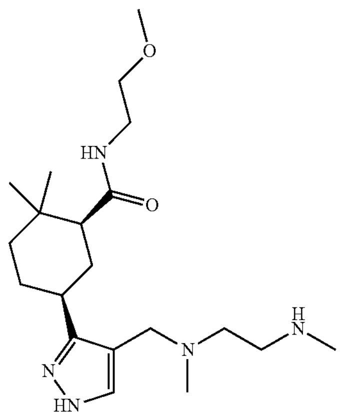 [SMILES: CNCCN(C)Cc1c[nH]nc1[C@H]1CCC(C)(C)[C@@H](C(=O)NCCOC)C1] | 380.3 |
| 269 | 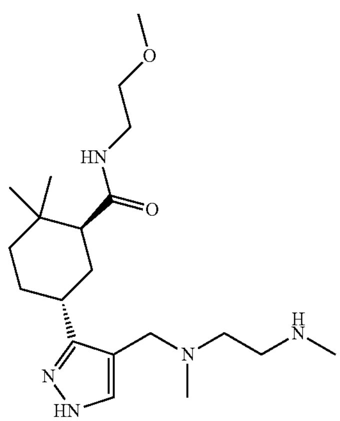 [SMILES: CNCCN(C)Cc1c[nH]nc1[C@@H]1CCC(C)(C)[C@@H](C(=O)NCCOC)C1] | 380.3 |
| 270 | 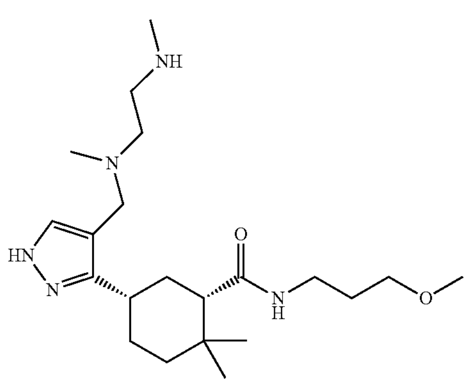 [SMILES: CNCCN(C)Cc1c[nH]nc1[C@H]1CCC(C)(C)[C@@H](C(=O)NCCCOC)C1] | 394.3 |

TABLE 1B-continued

Exemplary Compounds

| Cmpd No | Structure | LC-MS m/z (M + H) |
|---|---|---|
| 271 | 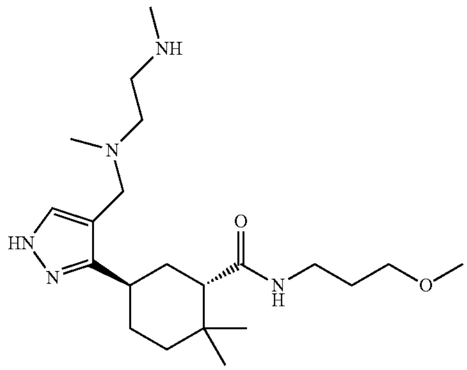 [SMILES: CNCCN(C)Cc1c[nH]nc1[C@@H]1CCC(C)(C)[C@@H](C(=O)NCCCOC)C1] | 394.5 |
| 272 | 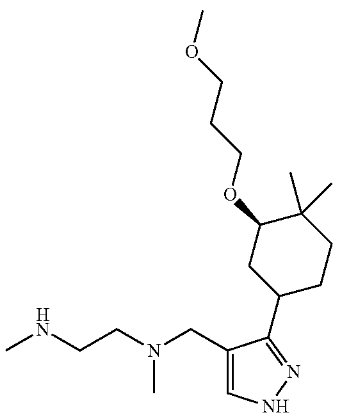 | 367.15 |
| 273 | 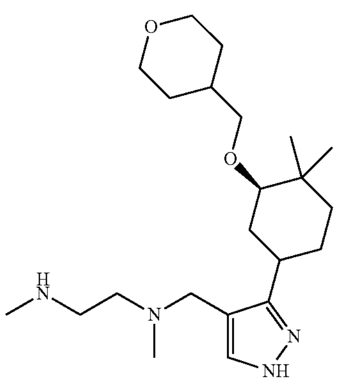 | 393.21 |
| 274 | 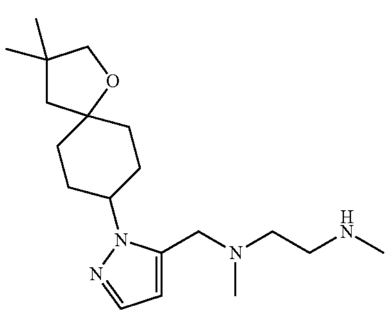 | 335.1 |

TABLE 1B-continued

Exemplary Compounds

| Cmpd No | Structure | LC-MS m/z (M + H) |
|---|---|---|
| 275 | 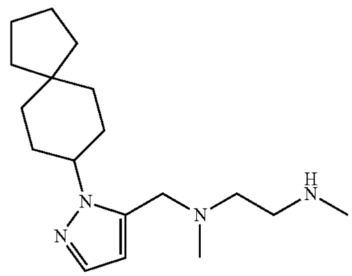 [SMILES: CNCCN(C)Cc1ccnn1C1CCC2(CCCC2)CC1] | 305.4 |

In certain embodiments, a provided compound inhibits an RMT (e.g., PRMT1, PRMT3, CARM1, PRMT6, and/or PRMT8). In certain embodiments, a provided compound inhibits wild-type PRMT1, PRMT3, CARM1, PRMT6, and/or PRMT8. In certain embodiments, a provided compound inhibits a mutant RMT. In certain embodiments, a provided compound inhibits PRMT1, PRMT3, CARM1, PRMT6, and/or PRMT8, e.g., as measured in an assay described herein. In certain embodiments, the RMT is from a human. In certain embodiments, a provided compound inhibits an RMT (e.g., PRMT1, PRMT3, CARM1, PRMT6, and/or PRMT8) at an $IC_{50}$ less than or equal to 10 μM. In certain embodiments, a provided compound inhibits an RMT (e.g., PRMT1, PRMT3, CARM1, PRMT6, and/or PRMT8) at an $IC_{50}$ less than or equal to 1 μM. In certain embodiments, a provided compound inhibits an RMT (e.g., PRMT1, PRMT3, CARM1, PRMT6, and/or PRMT8) at an $IC_{50}$ less than or equal to 0.1 μM. In certain embodiments, a provided compound inhibits an RMT (e.g., PRMT1, PRMT3, CARM1, PRMT6, and/or PRMT8) at an IC50 less than or equal to 0.01 μM. In certain embodiments, a provided compound inhibits an RMT (e.g., PRMT1, PRMT3, CARM1, PRMT6, and/or PRMT8) in a cell at an $EC_{30}$ less than or equal to 10 μM. In certain embodiments, a provided compound inhibits an RMT (e.g., PRMT1, PRMT3, CARM1, PRMT6, and/or PRMT8) in a cell at an $EC_{30}$ less than or equal to 12 μM. In certain embodiments, a provided compound inhibits an RMT (e.g., PRMT1, PRMT3, CARM1, PRMT6, and/or PRMT8) in a cell at an $EC_{30}$ less than or equal to 3 μM. In certain embodiments, a provided compound inhibits PRMT1 in a cell at an $EC_{30}$ less than or equal to 12 μM. In certain embodiments, a provided compound inhibits PRMT1 in a cell at an $EC_{30}$ less than or equal to 3 μM. In certain embodiments, a provided compound inhibits an RMT (e.g., PRMT1, PRMT3, CARM1, PRMT6, and/or PRMT8) in a cell at an $EC_{30}$ less than or equal to 1 μM. In certain embodiments, a provided compound inhibits an RMT (e.g., PRMT1, PRMT3, CARM1, PRMT6, and/or PRMT8) in a cell at an $EC_{30}$ less than or equal to 0.1 μM. In certain embodiments, a provided compound inhibits cell proliferation at an $EC_{50}$ less than or equal to 10 μM. In certain embodiments, a provided compound inhibits cell proliferation at an $EC_{50}$ less than or equal to 1 μM. In certain embodiments, a provided compound inhibits cell proliferation at an $EC_{50}$ less than or equal to 0.1 μM.

It will be understood by one of ordinary skill in the art that the RMT can be wild-type, or any mutant or variant.

The present disclosure provides pharmaceutical compositions comprising a compound described herein, e.g., a compound of Formula (I), or a pharmaceutically acceptable salt thereof, as described herein, and optionally a pharmaceutically acceptable excipient. It will be understood by one of ordinary skill in the art that the compounds described herein, or salts thereof, may be present in various forms, such as amorphous, hydrates, solvates, or polymorphs. In certain embodiments, a provided composition comprises two or more compounds described herein. In certain embodiments, a compound described herein, or a pharmaceutically acceptable salt thereof, is provided in an effective amount in the pharmaceutical composition. In certain embodiments, the effective amount is a therapeutically effective amount. In certain embodiments, the effective amount is an amount effective for inhibiting an RMT (e.g., PRMT1, PRMT3, CARM1, PRMT6, and/or PRMT8). In certain embodiments, the effective amount is an amount effective for treating an RMT-mediated disorder (e.g., a PRMT1-, PRMT3-, CARM1-, PRMT6-, and/or PRMT8-mediated disorder). In certain embodiments, the effective amount is a prophylactically effective amount. In certain embodiments, the effective amount is an amount effective to prevent an RMT-mediated disorder.

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing a compound described herein (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the present disclosure will vary, depending upon the identity, size, and/or condition of the subject treated and further depending upon the route by which the composition is to be administered. By way of example, the composition may comprise between 0.1% and 100% (w/w) active ingredient.

In some embodiments, a pharmaceutical composition described herein is sterilized.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60], sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol. Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the compounds described herein are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a provided compound may include ointments, pastes, creams, lotions, gels, powders, solutions, sprays, inhalants and/or patches. Generally, the active ingredient is admixed under sterile conditions with a pharmaceutically acceptable carrier and/or any desired preservatives and/or buffers as can be required. Additionally, the present disclosure encompasses the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically—administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A provided pharmaceutical composition can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A provided pharmaceutical composition can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A provided pharmaceutical composition can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of provided compositions will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, a compound described herein may be administered at dosage levels sufficient to deliver from about 0.001 mg/kg to about 1000 mg/kg, from about 0.01 mg/kg to about mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect.

In some embodiments, a compound described herein is administered one or more times per day, for multiple days. In some embodiments, the dosing regimen is continued for days, weeks, months, or years.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. In certain embodiments, a compound or composition provided herein is administered in combination with one or more additional therapeutically active agents that improve its bioavailability, reduce and/or modify its metabolism, inhibit its excretion, and/or modify its distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In certain embodiments, the additional therapeutically active agent is a compound of Formula (I). In certain embodiments, the additional therapeutically active agent is not a compound of Formula (I). In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of a provided compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, an additional therapeutically active agent is prednisolone, dexamethasone, doxorubicin, vincristine, mafosfamide, cisplatin, carboplatin, Ara-C, rituximab, azacitadine, panobinostat, vorinostat, everolimus, rapamycin, ATRA (all-trans retinoic acid), daunorubicin, decitabine, Vidaza, mitoxantrone, or IBET-151.

Also encompassed by the present disclosure are kits (e.g., pharmaceutical packs). The kits provided may comprise a provided pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of a provided pharmaceutical composition or compound. In some embodiments, a provided pharmaceutical composition or compound provided in the container and the second container are combined to form one unit dosage form. In some embodiments, a provided kits further includes instructions for use.

Compounds and compositions described herein are generally useful for the inhibition of RMT (e.g., PRMT1, PRMT3, CARM1, PRMT6, and/or PRMT8). In some embodiments, methods of treating an RMT-mediated disorder in a subject are provided which comprise administering an effective amount of a compound described herein (e.g., a compound of Formula (I)), or a pharmaceutically acceptable salt thereof), to a subject in need of treatment. In certain embodiments, the effective amount is a therapeutically effective amount. In certain embodiments, the effective amount is a prophylactically effective amount. In certain embodiments, the subject is suffering from a RMT-mediated disorder. In certain embodiments, the subject is susceptible to a RMT-mediated disorder.

As used herein, the term "RMT-mediated disorder" means any disease, disorder, or other pathological condition in which an RMT (e.g., PRMT1, PRMT3, CARM1, PRMT6, and/or PRMT8) is known to play a role. Accordingly, in some embodiments, the present disclosure relates to treating or lessening the severity of one or more diseases in which an RMT is known to play a role.

In some embodiments, the present disclosure provides a method of inhibiting an RMT comprising contacting the RMT with an effective amount of a compound described herein (e.g., a compound of Formula (I)), or a pharmaceutically acceptable salt thereof. The RMT may be purified or crude, and may be present in a cell, tissue, or subject. Thus, such methods encompass both inhibition of in vitro and in vivo RMT activity. In certain embodiments, the method is an in vitro method, e.g., such as an assay method. It will be understood by one of ordinary skill in the art that inhibition of an RMT does not necessarily require that all of the RMT be occupied by an inhibitor at once. Exemplary levels of inhibition of an RMT (e.g., PRMT1, PRMT3, CARM1, PRMT6, and/or PRMT8) include at least 10% inhibition, about 10% to about 25% inhibition, about 25% to about 50% inhibition, about 50% to about 75% inhibition, at least 50% inhibition, at least 75% inhibition, about 80% inhibition, about 90% inhibition, and greater than 90% inhibition.

In some embodiments, provided is a method of inhibiting RMT activity in a subject in need thereof (e.g., a subject diagnosed as having an RMT-mediated disorder) comprising administering to the subject an effective amount of a compound described herein (e.g., a compound of Formula (I)), or a pharmaceutically acceptable salt thereof, or a pharmaceutical composition thereof.

In certain embodiments, provided is a method of modulating gene expression in a cell which comprises contacting a cell with an effective amount of a compound of Formula (I), or a pharmaceutically acceptable salt thereof. In certain embodiments, the cell is in culture in vitro. In certain embodiments, the cell is in an animal, e.g., a human. In certain embodiments, the cell is in a subject in need of treatment.

In certain embodiments, provided is a method of modulating transcription in a cell which comprises contacting a cell with an effective amount of a compound of Formula (I), or a pharmaceutically acceptable salt thereof. In certain embodiments, the cell is in culture in vitro. In certain embodiments, the cell is in an animal, e.g., a human. In certain embodiments, the cell is in a subject in need of treatment.

In certain embodiments, a method is provided of selecting a therapy for a subject having a disease associated with an RMT-mediated disorder or mutation comprising the steps of determining the presence of an RMT-mediated disorder or gene mutation in an RMT gene (e.g., a PRMT1, PRMT3, CARM1, PRMT6, and/or PRMT8 gene) or and selecting, based on the presence of an RMT-mediated disorder a gene mutation in the RMT gene a therapy that includes the administration of a provided compound. In certain embodiments, the disease is cancer.

In certain embodiments, a method of treatment is provided for a subject in need thereof comprising the steps of determining the presence of an RMT-mediated disorder or a gene mutation in the RMT gene and treating the subject in need thereof, based on the presence of a RMT-mediated disorder or gene mutation in the RMT gene with a therapy that includes the administration of a provided compound. In certain embodiments, the subject is a cancer patient.

In some embodiments, a compound provided herein is useful in treating a proliferative disorder, such as cancer. For example, while not being bound to any particular mechanism, protein arginine methylation by PRMTs is a modification that has been implicated in signal transduction, gene transcription, DNA repair and mRNA splicing, among others; and overexpression of PRMTs within these pathways is often associated with various cancers. Thus, compounds which inhibit the action of PRMTs, as provided herein, are effective in the treatment of cancer.

In some embodiments, compounds provided herein are effective in treating cancer through the inhibition of PRMT1. For example, PRMT1 overexpression has been observed in various human cancers, including, but not limited to, breast cancer, prostate cancer, lung cancer, colon cancer, bladder cancer, and leukemia. In one example, PRMT1 specifically deposits an asymmetric dimethylarginine (aDMA) mark on histone H4 at arginine 3 (H4R3me2a), and this mark is associated with transcription activation. In prostate cancer, the methylation status of H4R3 positively correlates with increasing tumor grade and can be used to predict the risk of prostate cancer recurrence (Seligson et al., *Nature* 2005 435, 1262-1266). Thus, in some embodiments, inhibitors of PRMT1, as described herein, are useful in treating cancers associated with the methylation status of H4R3, e.g., prostate cancer. Additionally, the methylarginine effector molecule TDRD3 interacts with the H4R3me2a mark, and overexpression of TDRD3 is linked to poor prognosis for the survival of patients with breast cancer (Nagahata et al., *Cancer Sci.* 2004 95, 218-225). Thus, in some embodiments, inhibitors of PRMT1, as described herein, are useful in treating cancers associated with overexpression of TDRD3, e.g., breast cancer, as inhibition of PRMT1 leads to a decrease in methylation of H4R3, thereby preventing the association of overexpressed TDRD3 with H4R3me2a. In other examples, PRMT1 is known to have non-histone substrates. For example, PRMT1, when localized to the cytoplasm, methylates proteins that are involved in signal transduction pathways, e.g., the estrogen receptor (ER). The expression status of ER in breast cancer is critical for prognosis of the disease, and both genomic and non-genomic ER pathways have been implicated in the pathogenesis of breast cancer. For example, it has been shown that PRMT1 methylates ER, and that ERα methylation is required for the assembly of ERα with SRC (a proto-oncogene tyrosine-protein kinase) and focal adhesion kinase (FAK). Further, the silencing of endogenous PRMT1 resulted in the inability of estrogen to activate AKT. These results suggested that PRMT1-mediated ERα methylation is required for the activation of the SRC-PI3K-FAK cascade and AKT, coordinating cell proliferation and survival. Thus, hypermethylation of ERα in breast cancer is thought to cause hyperactivation of this signaling pathway, providing a selective survival advantage to tumor cells (Le Romancer et al., *Mol. Cell* 2008 31, 212-221; Le Romancer et al., Steroids 2010 75, 560-564). Accordingly, in some embodiments, inhibitors of PRMT1, as described herein, are useful in treating cancers associated with ERα methylation, e.g., breast cancer. In yet another example, PRMT1 has been shown to be involved in the regulation of leukemia development. For example, SRC-associated in mitosis 68 kDa protein (SAM68; also known as KHDRBS1) is a well-characterized PRMT1 substrate, and when either SAM68 or PRMT1 is fused directly to the myeloid/lymphoid leukemia (MLL) gene, these fusion proteins can activate MLL oncogenic properties, implying that the methylation of SAM68 by PRMT1 is a critical signal for the development of leukemia (Cheung et al., *Nature Cell Biol.* 2007 9, 1208-1215). Accordingly, in some embodiments, inhibitors of PRMT1, as described herein, are useful in treating cancers associated with SAM68 methylation, e.g., leukemia. In still another example, PRMT1 is implicated in leukemia development through its interaction with AE9a, a splice isoform of AML1-ETO (Shia et al., *Blood* 2012 119:4953-62). Knockdown of PRMT1 affects expression of certain AE9a-activated genes and suppresses AE9a's self-renewal capability. It has also been shown that AE9a recruits PRMT1 to AE9a activated gene promoters, which leads to increased H4 Arg3 methylation, H3 Lys9/14 acetylation, and transcription activated. Accordingly, in some embodiments, inhibitors of PRMT1, as described herein, are useful in treating cancers associated with AML1-ETO, e.g., leukemia. Thus, without being bound by any particular mechanism, the inhibition of PRMT1, e.g., by compounds described herein, is beneficial in the treatment of cancer.

In some embodiments, compounds provided herein are effective in treating cancer through the inhibition of PRMT3. In one example, the DAL1 tumor suppressor protein has been shown to interact with PRMT3 and inhibits its methyltransferase activity (Singh et al., *Oncogene* 2004 23, 7761-7771). Epigenetic downregulation of DAL1 has been reported in several cancers (e.g., meningiomas and breast cancer), thus PRMT3 is expected to display increased activity, and cancers that display DAL1 silencing may, in some aspects, be good targets for PRMT3 inhibitors, e.g., those described herein. Thus, without being bound by any particular mechanism, the inhibition of PRMT3, e.g., by compounds described herein, is beneficial in the treatment of cancer.

In some embodiments, compounds provided herein are effective in treating cancer through the inhibition of PRMT4, also known as CARM1. For example, PRMT4 levels have been shown to be elevated in castration-resistant prostate cancer (CRPC), as well as in aggressive breast tumors (Hong et al., *Cancer* 2004 101, 83-89; Majumder et al., *Prostate* 2006 66, 1292-1301). Thus, in some embodiments, inhibitors of PRMT4, as described herein, are useful in treating cancers associated with PRMT4 overexpression. PRMT4 has also been shown to affect ERα-dependent breast cancer cell differentiation and proliferation (Al-Dhaheri et al., *Cancer Res.* 2011 71, 2118-2128), thus in some aspects PRMT4 inhibitors, as described herein, are useful in treating ERα-dependent breast cancer by inhibiting cell differentiation and proliferation. In another example, PRMT4 has been shown to be recruited to the promoter of E2F1 (which encodes a cell cycle regulator) as a transcriptional co-activator (Frietze et al., *Cancer Res.* 2008 68, 301-306). Thus, PRMT4-mediated upregulation of E2F1 expression may contribute to cancer progression and chemoresistance as increased abundance of E2F1 triggers invasion and metastasis by activating growth receptor signaling pathways, which in turn promote an antiapoptotic tumor environment (Engelmann and Pützer, *Cancer Res* 2012 72; 571). Accordingly, in some embodiments, the inhibition of PRMT4, e.g., by compounds provided herein, is useful in treating cancers associated with E2F1 upregulation. Thus, without being bound by any particular mechanism, the inhibition of PRMT4, e.g., by compounds described herein, is beneficial in the treatment of cancer.

In some embodiments, compounds provided herein are effective in treating cancer through the inhibition of PRMT6. For example, PRMT6 has been reported to be overexpressed in a number of cancers, e.g., bladder and lung cancer (Yoshimatsu et al., *Int. J. Cancer* 2011 128, 562-573). Thus, in some embodiments, the inhibition of PRMT6, by compounds provided herein, is useful in treating cancers associated with PRMT6 overexpression. In some aspects, PRMT6 is primarily thought to function as a transcriptional repressor, although it has also been reported that PRMT6 functions as a co-activator of nuclear receptors. For example, as a transcriptional repressor, PRMT6 suppresses the expression of thrombospondin 1 (TSP1; also known as THBS1; a potent natural inhibitor of angiogenesis and endothelial cell migration) and p21 (a natural inhibitor of cyclin dependent kinase), thereby contributing to cancer development and progression (Michaud-Levesque and Richard, *J. Biol. Chem.* 2009 284, 21338-21346; Kleinschmidt et al., *PLoS ONE* 2012 7, e41446). Accordingly, in some embodiments, the inhibition of PRMT6, by compounds provided herein, is useful in treating cancer by preventing the repression of THBs1 and/or p21. Thus, without being bound by any particular mechanism, the inhibition of PRMT6, e.g., by compounds described herein, is beneficial in the treatment of cancer.

In some embodiments, compounds provided herein are effective in treating cancer through the inhibition of PRMT8. For example, deep-sequencing efforts of cancer genomes (e.g., COSMIC) have revealed that of all the PRMTs, PRMT8 is reported to be the most mutated. Of 106 sequenced genomes, 15 carry mutations in the PRMT8 coding region, and nine of these result in an amino acid change (Forbes et al., *Nucleic Acids Res.* 2011 39, D945-D950). Because of its high rate of mutation in cancer, PRMT8 is thought to contribute to the initiation or progression of cancer. Thus, without being bound by any particular mechanism, the inhibition of PRMT8, e.g., by compounds described herein, is beneficial in the treatment of cancer.

In some embodiments, compounds described herein are useful for treating a cancer including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (e.g., "Waldenstrim's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In some embodiments, a compound provided herein is useful in treating diseases associated with increased levels of circulating asymmetric dimethylarginine (aDMA), e.g., cardiovascular disease, diabetes, kidney failure, renal disease, pulmonary disease, etc. Circulating aDMA is produced by the proteolysis of asymmetrically dimethylated proteins. PRMTs which mediate aDMA methylation include, e.g., PRMT1, PRMT3, PRMT4, PRMT6, and PRMT8. aDMA levels are directly involved in various diseases as aDMA is an endogenous competitive inhibitor of nitric oxide synthase (NOS), thereby reducing the production of nitric oxide (NO) (Vallance et al., *J. Cardiovasc. Pharmacol.* 1992 20(Suppl. 12):S60-2). NO functions as a potent vasodilator in endothelial vessels, and as such inhibiting its production has major consequences on the cardiovascular system. For example, since PRMT1 is a major enzyme that generates aDMA, the dysregulation of its activity is likely to regulate cardiovascular diseases (Boger et al., *Ann. Med.* 2006 38:126-36), and other pathophysiological conditions such as diabetes mellitus (Sydow et al., *Vasc. Med.* 2005 10(Suppl. 1):S35-43), kidney failure (Vallance et al., *Lancet* 1992 339:572-5), and chronic pulmonary diseases (Zakrzewicz et al., *BMC Pulm. Med.* 2009 9:5). Additionally, it has been demonstrated that the expression of PRMT1 and PRMT3 are increased in coronary heart disease (Chen et al., *Basic Res. Cardiol.* 2006 101:346-53). In another example, aDMA elevation is seen in patients with renal failure, due to impaired clearance of this metabolite from the circulation (Jacobi et al., *Am. J. Nephrol.* 2008 28:224-37). Thus, circulating aDMA levels is observed in many pathophysiological situations. Accordingly, without being bound by any particular mechanism, the inhibition of PRMTs, e.g., by compounds described herein, results in the decrease of circulating aDMA, which is beneficial in the treatment of diseases associated with increased levels of circulating aDMA, e.g., cardiovascular disease, diabetes, kidney failure, renal disease, pulmonary disease, etc. In certain embodiments, a compound described herein is useful for treating or preventing vascular diseases.

In some embodiments, a compound provided herein is useful in treating metabolic disorders. For example, PRMT1 has been shown to enhance mRNA levels of FoxO1 target genes in gluconeogenesis, which results in increased hepatic glucose production, and knockdown of PRMT promotes inhibition of FoxO1 activity and thus inhibition of hepatic gluconeogenesis (Choi et al., *Hepatology* 2012 56:1546-56). Additionally, genetic haploinsufficiency of Prmt1 has been shown to reduce blood glucose levels in mouse models. Thus, without being bound by any particular mechanism, the inhibition of PRMT1, e.g., by compounds described herein, is beneficial in the treating of metabolic disorders, such as diabetes. In some embodiments, a provided compound is useful in treating type I diabetes. In some embodiments, a provided compound is useful in treating type II diabetes.

In some embodiments, a compound provided herein is useful in treating muscular dystrophies. For example, PRMT1, as well as PRMT3 and PRMT6, methylate the nuclear poly(A)-binding protein (PABPN1) in a region located near its C-terminus (Perreault et al., *J. Biol. Chem.* 2007 282:7552-62). This domain is involved in the aggregation of the PABPN1 protein, and abnormal aggregation of this protein is involved in the disease oculopharyngeal muscular dystrophy (Davies et al., *Int. J. Biochem. Cell. Biol.* 2006 38:1457-62). Thus, without being bound by any particular mechanism, the inhibition of PRMTs, e.g., by compounds described herein, is beneficial in the treatment of muscular dystrophies, e.g., oculopharyngeal muscular dystrophy, by decreasing the amount of methylation of PABPN1, thereby decreasing the amount of PABPN1 aggregation.

CARM1 is also the most abundant PRMT expressed in skeletal muscle cells, and has been found to selectively control the pathways modulating glycogen metabolism, and associated AMPK (AMP-activated protein kinase) and p38 MAPK (mitogen-activated protein kinase) expression. See, e.g., Wang et al., Biochem (2012) 444:323-331. Thus, in some embodiments, inhibitors of CARM1, as described herein, are useful in treating metabolic disorders, e.g., for example skeletal muscle metabolic disorders, e.g., glycogen and glucose metabolic disorders. Exemplary skeletal muscle metabolic disorders include, but are not limited to, Acid Maltase Deficiency (Glycogenosis type 2; Pompe disease), Debrancher deficiency (Glycogenosis type 3), Phosphorylase deficiency (McArdle's; GSD 5), X-linked syndrome (GSD9D), Autosomal recessive syndrome (GSD9B), Tarui's disease (Glycogen storage disease VII; GSD 7), Phosphoglycerate Mutase deficiency (Glycogen storage disease X; GSDX; GSD 10), Lactate dehydrogenase A deficiency (GSD 11), Branching enzyme deficiency (GSD 4), Aldolase A (muscle) deficiency, β-Enolase deficiency, Triosephosphate isomerase (TIM) deficiency, Lafora's disease (Progressive myoclonic epilepsy 2), Glycogen storage disease (Muscle, Type 0, Phosphoglucomutase 1 Deficiency (GSD 14)), and Glycogenin Deficiency (GSD 15).

In some embodiments, a compound provided herein is useful in treating autoimmune disease. For example, several lines of evidence strongly suggest that PRMT inhibitors may be valuable for the treatment of autoimmune diseases, e.g., rheumatoid arthritis. PRMTs are known to modify and regulate several critical immunomodulatory proteins. For example, post-translational modifications (e.g., arginine methylation), within T cell receptor signaling cascades allow T lymphocytes to initiate a rapid and appropriate immune response to pathogens. Co-engagement of the CD28 costimulatory receptor with the T cell receptor elevates PRMT activity and cellular protein arginine methylation, including methylation of the guanine nucleotide exchange factor Vav1 (Blanchet et al., *J. Exp. Med.* 2005 202:371-377). PRMT inhibitors are thus expected to diminish methylation of the guanine exchange factor Vav1, resulting in diminished IL-2 production. In agreement, siRNA directed against PRMT5 was shown to both inhibit NFAT-driven promoter activity and IL-2 secretion (Richard et al., *Biochem J.* 2005 388:379-386). In another example, PRMT1 is known to cooperate with PRMT4 to enhance NFkB p65-driven transcription and facilitate the transcription of p65 target genes like TNFα (Covic et al., *Embo. J.* 2005 24:85-96). Thus, in some embodiments, PRMT1 and/or PRMT4 inhibitors, e.g., those described herein, are useful in treating autoimmune disease by decreasing the transcription of p65 target genes like TNFα. These examples demonstrate an important role for arginine methylation in inflammation. Thus, without being bound by any particular mechanism, the inhibition of PRMTs, e.g., by compounds described herein, is beneficial in the treatment of autoimmune diseases.

In some embodiments, a compound provided herein is useful in treating neurological disorders, such as amyotrophic lateral sclerosis (ALS). For example, a gene involved in ALS, TLS/FUS, often contains mutated arginines in certain familial forms of this disease (Kwiatkowski et al., *Science* 2009 323:1205-8). These mutants are retained in the cytoplasm, which is similar to reports documenting the role arginine methylation plays in nuclear-cytoplasmic shuffling (Shen et al., *Genes Dev.* 1998 12:679-91). This implicates PRMT, e.g., PRMT1, function in this disease, as it was demonstrated that TLS/FUS is methylated on at least 20 arginine residues (Rappsilber et al., *Anal. Chem.* 2003 75:3107-14). Thus, in some embodiments, the inhibition of PRMTs, e.g., by compounds provided herein, are useful in treating ALS by decreasing the amount of TLS/FUS arginine methylation.

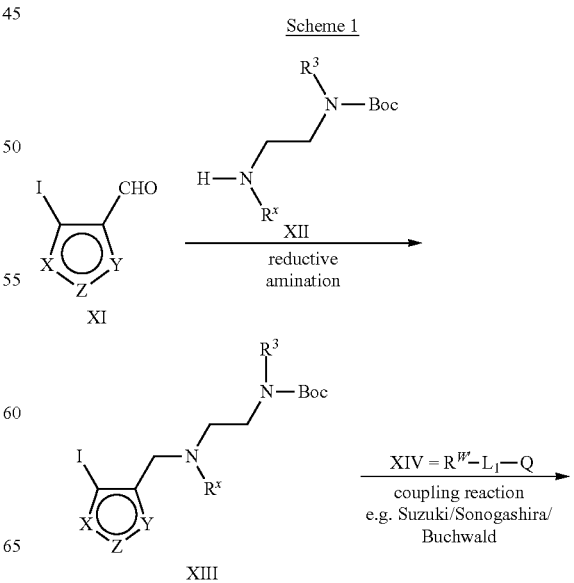

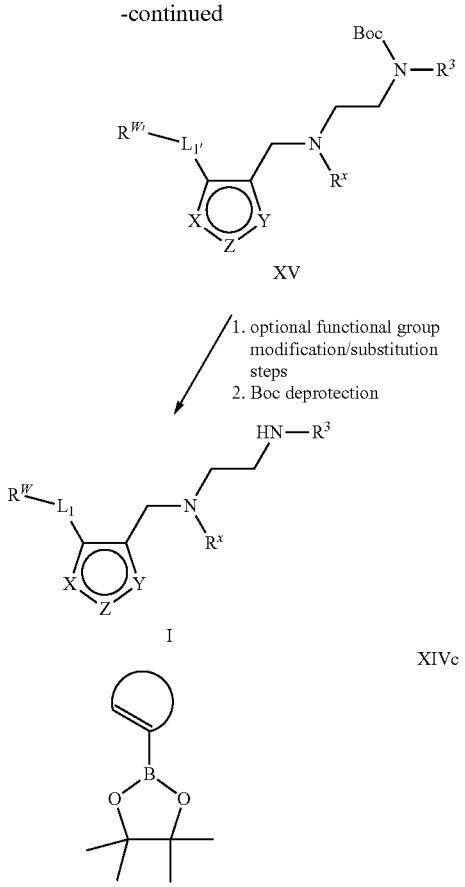

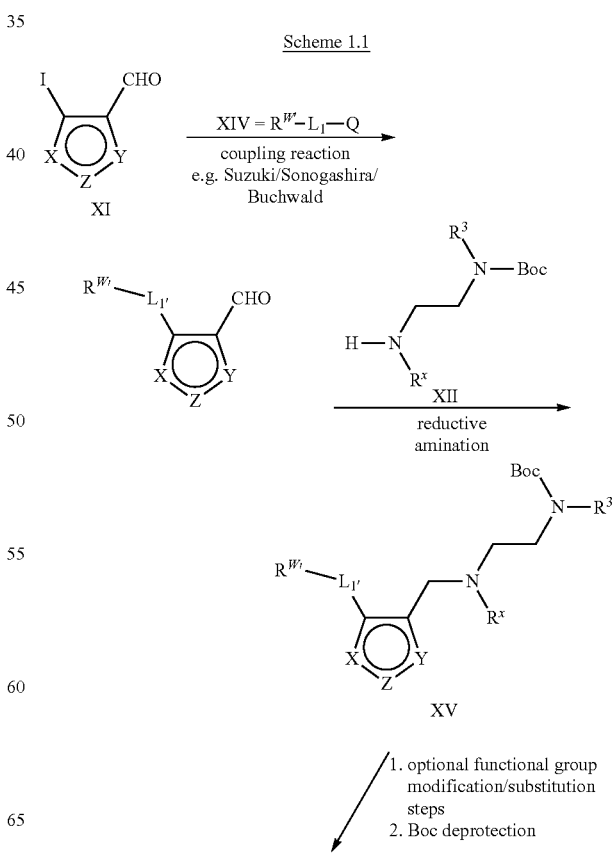

bond, $R^{W'}$ is a heterocycloalkenyl or cycloalkenyl group and Q is a pinacol borane group yields intermediates of general formula XV-c in which $L_{1'}$ is bond and $R^{W'}$ is a heterocycloalkenyl or cycloalkenyl group. In certain embodiments, compounds of formula I wherein $L_{1'}$ is bond and $R^W$ is a heterocyclyl or carbocyclyl group can be prepared by hydrogenation of intermediates of formula XV-c followed by Boc deprotection. In certain embodiments, compounds of formula I where $L_1$ is —O— can be synthesized from intermediates of general formula XIII by Goldberg reaction with alcohols of formula $R^W$OH followed by Boc deprotection. In certain embodiments, compounds of formula I where $L_1$ is —N($R^B$)— can be synthesized from intermediates of general formula XIII by palladium catalyzed Buchwald coupling reaction conditions with amines of formula $R^W$N($R^B$)H followed by Boc deprotection. In certain embodiments, compounds of formula I where $L_1$ is —C(=O)N$R^B$— can be synthesized from intermediates of general formula XIII under known copper catalyzed coupling reaction conditions of amides with aryliodides using copper iodide an amine ligand and a base with amides of formula $R^W$C(=O)NH$R^B$ followed by Boc deprotection.

Scheme 1.1 shows an alternative general synthesis route to pyrazole compounds of Formula (I), that involves reversal in the order of the first two steps of the reaction sequence detailed for Scheme 1.0. Thus, in the first step iodopyrazole carboxaldehydes of general formula XI are coupled with compounds or reagents of general formula XIV (e.g. via Suzuki reaction with pinacol boranes of general formula XIVc in which $L_{1'}$ is bond, $R^{W'}$ is a heterocycloalkenyl or cycloalkenyl group and Q is a pinacol borane group) and in a second step the corresponding reductive amination reaction to yield common intermediates of general formula XV is a carried out.

Scheme 1 shows an exemplary general synthesis route to pyrazole compounds of formula I, wherein $R^{W'}$ is either the same as $R^W$ or is precursor of $R^W$ and $L_{1'}$ is either the same as $L_1$ or is a precursor of $L_1$ and $R^W$, $L_1$, $R^x$, $R^3$, X, Y and Z are as defined above. In the first step iodopyrazole carboxaldehydes of general formula XI are allowed to react with mono-Boc protected ethylenediamines XII under reductive amination conditions (e.g. sodium cyanoborohydride and catalytic acid such as acetic acid) in an appropriate solvent such as methanol to give intermediates of general formula XIII. In certain embodiments, Sonagashira reaction of intermediates of general formula XIII with boronic acids or boronic esters of general formula XIV in which $L_{1'}$ is an acetylene linker and Q is a boronic acid or boronic ester group in the presence of a palladium catalyst (e.g. PdCl$_2$(dppf)) and a base (e.g. potassium carbonate) in an organic solvent (e.g. toluene) at elevated temperature yields intermediates of general formula XV-a in which $L_{1'}$ is an acetylene linker. Boc deprotection of intermediates of general formula XV-a gives acetylene compounds of formula VI-a. In certain embodiments, Suzuki reaction of intermediates of general formula XIII with boronic acids or boronic esters of general formula XIV in which $L_{1'}$ is a trans-olefin linker and Q is a boronic acid or boronic ester group in the presence of a palladium catalyst (e.g. PdCl$_2$(dppf)) and a base (e.g. potassium carbonate) in an organic solvent (e.g. toluene) at elevated temperature yields intermediates of general formula XV-b in which $L_{1'}$ is an olefin linker. Boc deprotection of intermediates of general formula XV-b gives olefin compounds of formula VI-b. In certain embodiments, Suzuki reaction of intermediates of general formula XIII with pinacol boranes of general formula XIVc in which $L_{1'}$ is -continued

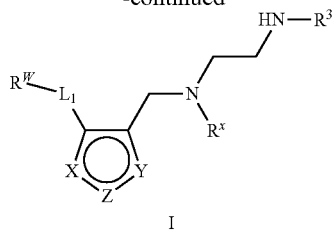

XIVc

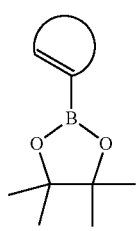

In certain embodiments, iodopyrazole carboxaldehydes of general formula XI may be prepared from suitable known pyrazole compound intermediates by established synthetic chemistry methods. Standard methods include direct iodination of a pyrazole 3-carboxylate and Sandmeyer reaction of a 3-amino pyrazole 4-carboxylate. In certain embodiments, iodopyrazole carboxaldehydes can be derived from iodopyrazole carboxylates by reduction to a hydroxymethyl group followed by oxidation to carboxaldehyde. In certain embodiments, mono-Boc protected ethylenediamines XII can be synthesized by standard methods known in the literature for derivatizing or preparing ethylenediamines. For example intermediates of formula XII may be prepared by treatment of the corresponding unprotected diamine precursors with $Boc_2O$ and purifying the mixture of mono and dibocylated products. In certain embodiments, pyrazole compounds of general formula II can be prepared from iodopyrazole carboxaldehydes of general formula XXI as depicted in Scheme 2. In certain embodiments where $R^4$ is hydrogen compounds of general formula II are equivalent to compounds of general formula III which are tautomers. In certain embodiments, $R^{4'}$ is a protecting group such as tetrahydropyranyl (THP) which maybe cleaved to hydrogen under acidic conditions in the final Boc-deprotection step. In certain embodiments, iodopyrazole carboxaldehydes of general formula XXI can be prepared as depicted in Scheme 3.

Scheme 2

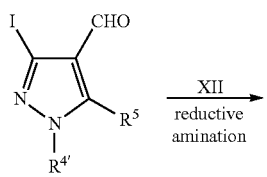

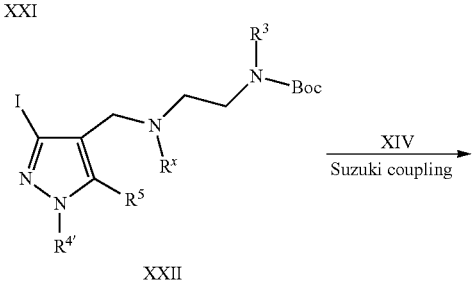

-continued

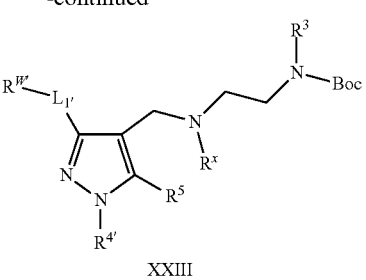

XXIII 1. optional functional group modification/substitution steps
2. Boc deprotection

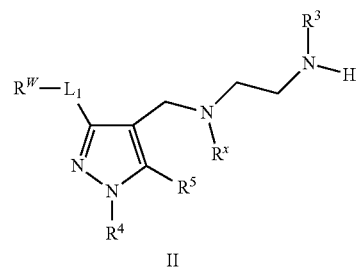

II

Scheme 3

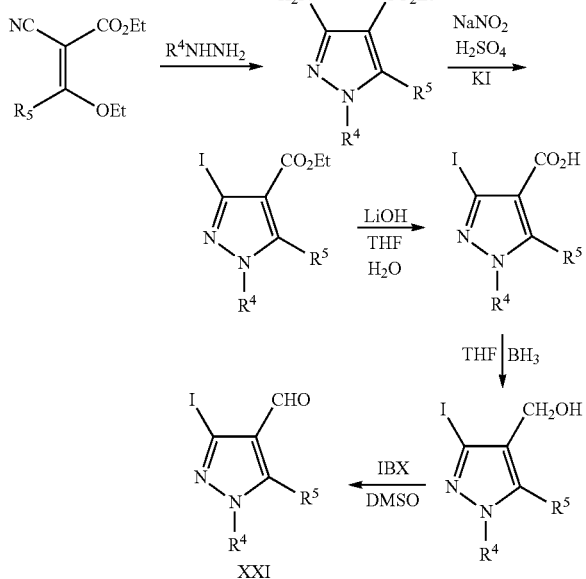

In certain embodiments, iodopyrazole carboxaldehydes of general formula XXI can be prepared as depicted in Scheme 4 which also provides iodopyrazole carboxyaldehydes of general formula XXXI. In certain embodiments, alkylation of intermediates of general formula XXX gives a mixture of pyrazole nitrogen alkylated isomers which are separated by chromatography to give pure isomers XXI and XXXI. In certain embodiments, pyrazole compounds of general formula III can be prepared from iodopyrazole carboxaldehydes of general formula XXXI as depicted in Scheme 5.

Scheme 4

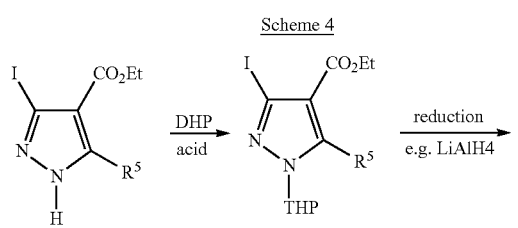

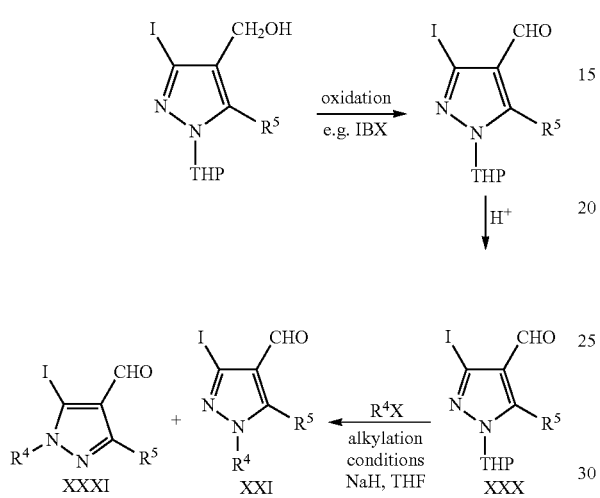

Scheme 5

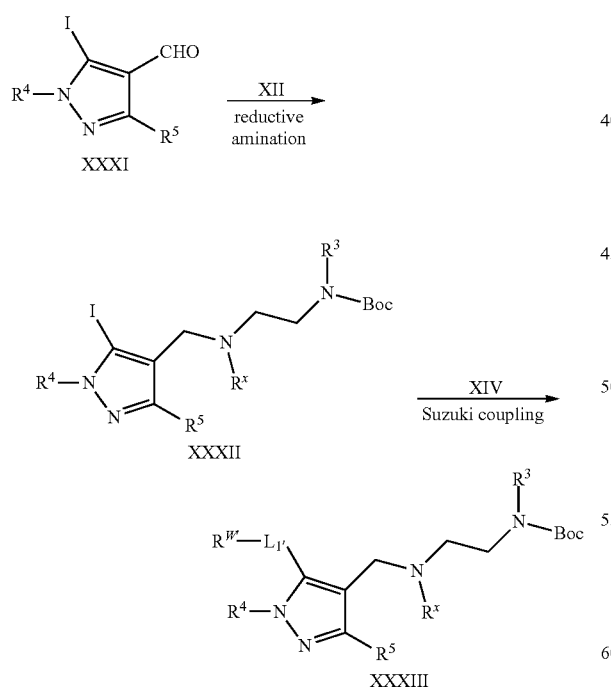

In certain embodiments, pyrazole compounds of general formula IV can be prepared from iodopyrazole carboxaldehydes of general formula XLI as depicted in Scheme 6. In certain embodiments where $R^4$ is hydrogen compounds of general formula IV are equivalent to compounds of general formula V which are tautomers. In certain embodiments where $R^4$ in compounds of formula IV is hydrogen, $R^{4'}$ in intermediate XLI may be a selected protecting group such as tetrahydropyranyl (THP) which can be cleaved to hydrogen under acidic conditions in the final Boc-deprotection step.

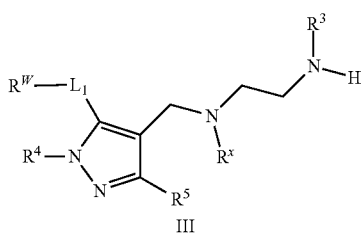

Scheme 6

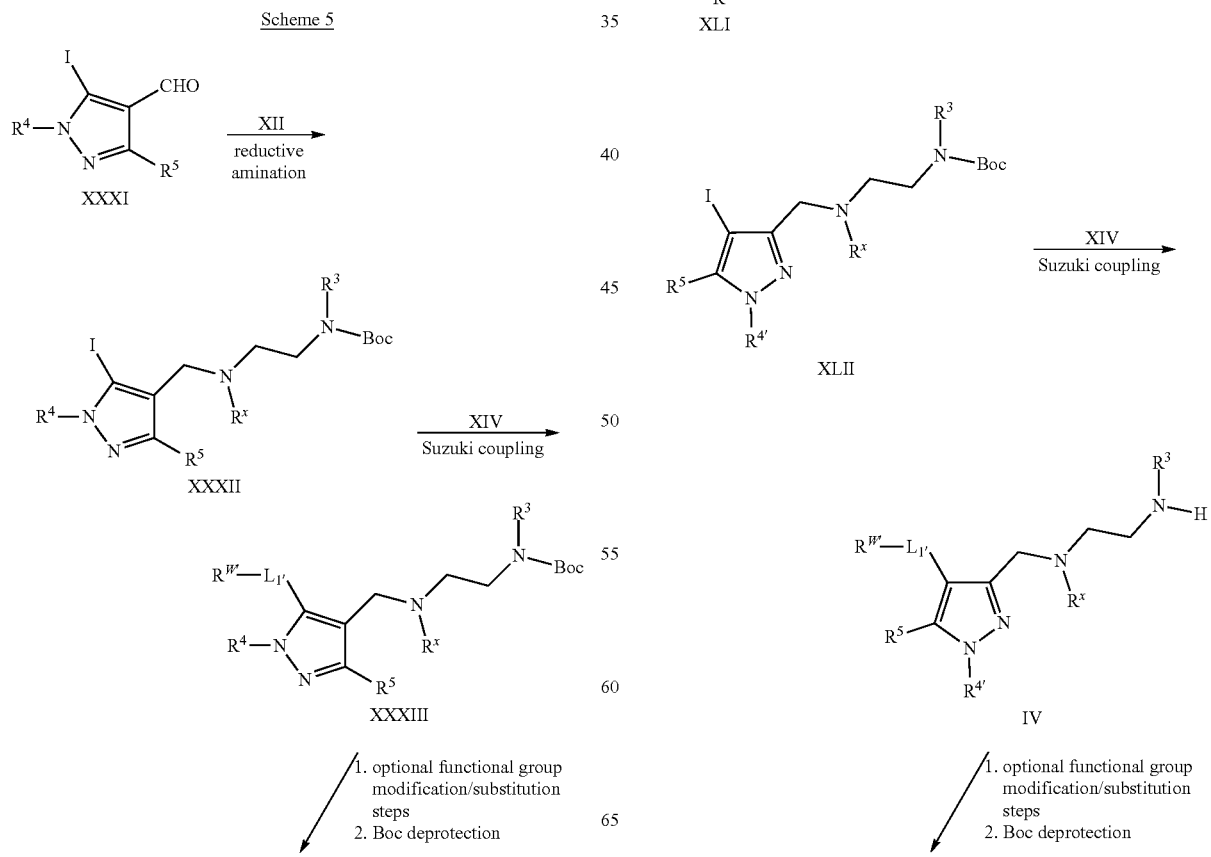

-continued

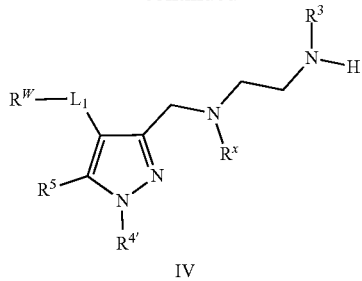

IV

In certain embodiments, iodopyrazole carboxaldehydes of general formula XLI and LI can be prepared as depicted in Scheme 7. In certain embodiments, an $R^4$ group of iodopyrazole carboxaldehydes may be introduced by alkylation of intermediates of formula XLVII. This reaction can give a mixture of intermediate compounds of formulas XLI and LI which may be separated by chromatography. In certain embodiments, THP protected intermediates of formula XLVI can be used to prepare compounds of formula IV where $R^4$=H as also depicted in Scheme 7.

In certain embodiments, pyrazole compounds of general formula V can be prepared from iodopyrazole carboxaldehydes of general formula LI as depicted in Scheme 8.

Scheme 8

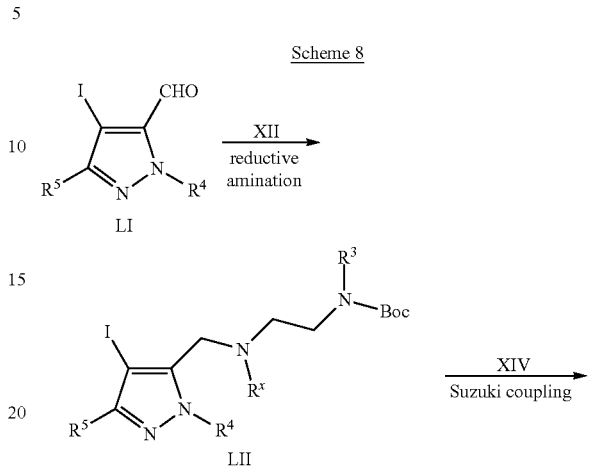

Scheme 7

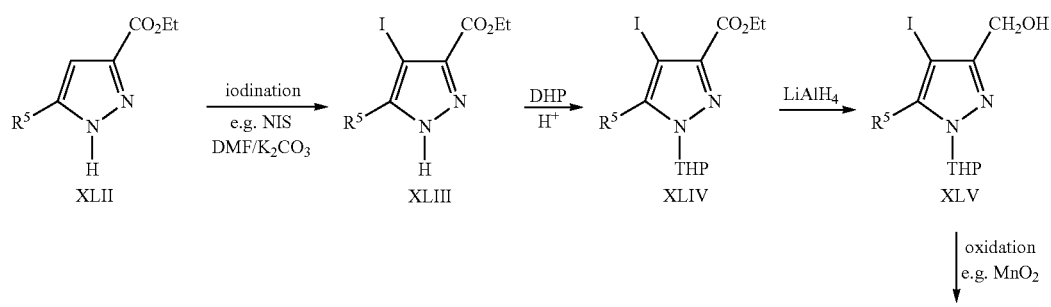

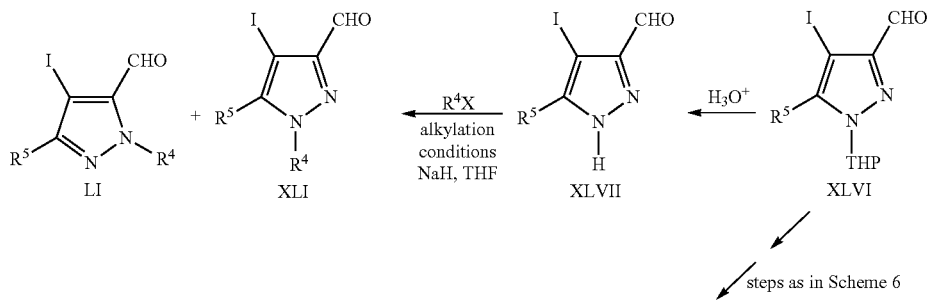

steps as in Scheme 6

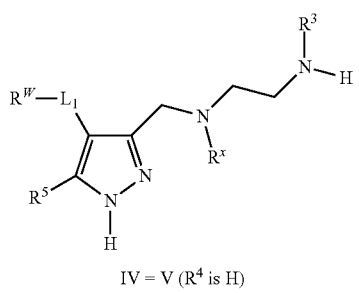

IV = V ($R^4$ is H)

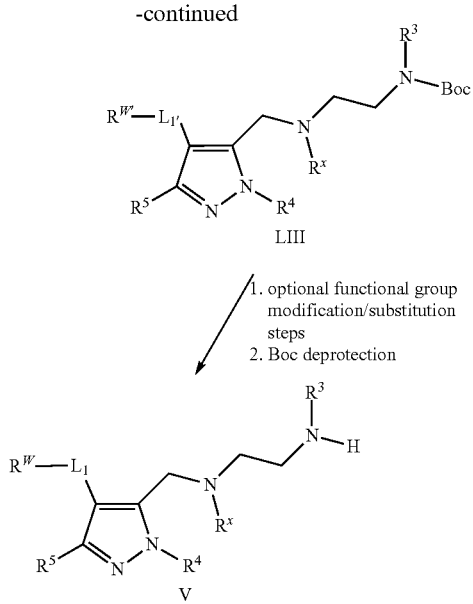

In certain embodiments, boronic acids or esters of general formula XIVa, XIVb and XIVc are commercially available. In certain embodiments, compounds of general formula XIVa, and XIVb can also be prepared from alkenyl bromides and terminal alkynes using standard methods such as treatment with n-BuLi followed by trapping the intermediate lithium species with trimethylborate. In certain embodiments, compounds of general formula XIVc can be prepared from the corresponding cyclic ketones LX via intermediate enol triflates as depicted in Scheme 9.

Scheme 9

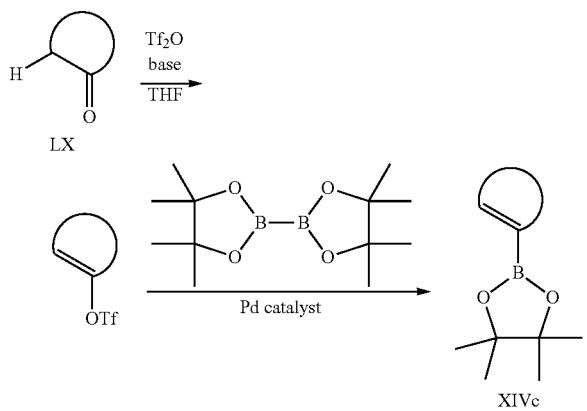

EXAMPLES

In order that the invention described herein may be more fully understood, the following examples are set forth. It should be understood that these examples are for illustrative purposes only and are not to be construed as limiting this invention in any manner.

Synthetic Methods

General methods and experimental procedures for preparing and characterizing compounds of the present invention are set forth below. Wherever needed, reactions were heated using conventional hotplate apparatus or heating mantle or microwave irradiation equipment. Reactions were conducted with or without stirring, under atmospheric or elevated pressure in either open or closed vessels. Reaction progress was monitored using conventional techniques such as TLC, HPLC, UPLC, or LCMS using instrumentation and methods described below. Reactions were quenched and crude compounds isolated using conventional methods as described in the specific examples provided. Solvent removal was carried out with or without heating, under atmospheric or reduced pressure, using either a rotary or centrifugal evaporator.

Compound purification was carried out as needed using a variety of traditional methods including, but not limited to, preparative chromatography under acidic, neutral, or basic conditions using either normal phase or reverse phase HPLC or flash columns or Prep-TLC plates. Compound purity and mass confirmations were conducted using standard HPLC and/or UPLC and/or MS spectrometers and/or LCMS and/or GC equipment (e.g., including, but not limited to the following instrumentation: Waters Alliance 2695 with 2996 PDA detector connected with ZQ detector and ESI source; Shimadzu LDMS-2020; Waters Acquity H Class with PDA detector connected with SQ detector and ESI source; Agilent 1100 Series with PDA detector; Waters Alliance 2695 with 2998 PDA detector; AB SCIEX API 2000 with ESI source; Agilent 7890 GC). Exemplified compounds were dissolved in either MeOH or MeCN to a concentration of approximately 1 mg/mL and analyzed by injection of 0.5-10 μL into an appropriate LCMS system using the methods provided in the following table:

| Method | Column | Mobile Phase A | Mobile Phase B | Flow Rate (mL/min) | Gradient Profile | MS Heat Block Temp (° C.) | MS Detector Voltage (kV) |
|---|---|---|---|---|---|---|---|
| A | Shim-pack XR-ODS 2.2 μm 3.0x50 mm | Water/0.05% TFA | ACN/0.05% TFA | 1 | 5% to 100% B in 2.0 minutes, 100% B for 1.1 minutes, 100% to 5% B in 0.2 minutes, then stop | 250 | 1.5 |

| Method | Column | Mobile Phase A | Mobile Phase B | Flow Rate (mL/min) | Gradient Profile | MS Heat Block Temp (° C.) | MS Detector Voltage (kV) |
|---|---|---|---|---|---|---|---|
| B | Gemini-NX 3 μm C18 110A | Water/0.04% Ammonia | ACN | 1 | 5% to 100% B in 2.0 minutes, 100% B for 1.1 minutes, 100% to 5% B in 0.1 minutes, then stop | 200 | 0.75 |
| C | Shim-pack XR-ODS 1.6 μm 2.0x50 mm | Water/0.05% FA | ACN/0.05% FA | 1 | 5% to 100% B in 2.0 minutes, 100% B for 1.1 minutes, 100% to 5% B in 0.1 minutes, then stop | 250 | 0.85 |
| D | Shim-pack XR-ODS 2.2 μm 3.0x50 mm | Water/0.05% TFA | ACN/0.05% TFA | 1 | 5% to 100% B in 2.0 minutes, 100% B for 1.1 minutes, 100% to 5% B in 0.1 minutes, then stop | 250 | 0.95 |
| E | Waters Xselect C18 3.5 μm 3.0x50 mm | Water/0.05% FA | ACN/0.05% FA | 0.9 | 5% to 100% B in 2.0 minutes, 100% B for 1.2 minutes, 100% to 5% B in 0.1 minutes, then stop | 250 | 1.5 |
| F | Shim-pack XR-ODS 2.2 μm 3.0x50 mm | Water/0.05% TFA | ACN/0.05% TFA | 1 | 5% to 80% B in 3.25 minutes, 80% B for 1.35 minutes, 80% to 5% B in 0.3 minutes, then stop | 200 | 0.95 |
| G | Shim-pack XR-ODS 2.2 μm 3.0x50 mm | Water/0.05% TFA | ACN/0.05% TFA | 1 | 5% to 70% B in 2.50 minutes, 70% B for 0.70 minutes, 70% to 5% B in 0.1 minutes, then stop | 200 | 0.95 |
| H | Shim-pack XR-ODS 2.2 μm 3.0x50 mm | Water/0.05% TFA | ACN/0.05% TFA | 1 | 5% to 100% B in 2.20 minutes, 100% B for 1.00 minutes, 100% to 5% B in 0.1 minutes, then stop | 250 | 0.95 |
| I | Shim-pack XR-ODS 2.2 μm 3.0x50 mm | Water/0.05% TFA | ACN/0.05% TFA | 1 | 5% to 100% B in 1.20 minutes, 100% B for 1.00 minutes, 100% to 5% B in 0.1 minutes, then stop | 250 | 0.95 |
| J | Shim-pack XR-ODS 2.2 μm 3.0x50 mm | Water/0.05% TFA | ACN/0.05% TFA | 1 | 5% to 70% B in 3.20 minutes, 70% B for 0.75 minutes, 70% to 5% B in 0.35 minutes, then stop | 250 | 0.95 |
| K | Shim-pack XR-ODS 2.2 μm 3.0x50 mm | Water/0.05% TFA | ACN/0.05% TFA | 1 | 5% to 80% B in 3.00 minutes, 80% B for 0.8 minutes, 80% to 5% B in 0.1 minutes, then stop | 250 | 1.5 |
| L | Shim-pack XR-ODS 2.2 μm 3.0x50 mm | Water/0.05% TFA | ACN/0.05% TFA | 1 | 5% to 100% B in 3.00 minutes, 100% B for 0.8 minutes, 100% to 5% B in 0.1 minutes, then stop | 250 | 1.5 |
| M | Shim-pack XR-ODS 2.2 μm 3.0x50 mm | Water/0.05% TFA | ACN/0.05% TFA | 1 | 5% to 100% B in 2.20 minutes, 100% B for 1.00 minutes, 100% to 5% B in 0.1 minutes, then stop | 250 | 1.5 |
| N | Shim-pack XR-ODS 2.2 μm 3.0x50 mm | Water/0.05% TFA | ACN/0.05% TFA | 1 | 5% to 80% B in 2.20 minutes, 80% B for 1.0 minutes, 80% to 5% B in 0.1 minutes, then stop | 250 | 1.5 |
| O | Zorbax Eclipse Plus C18 4.6x100 mm | Water/0.05% TFA | ACN/0.05% TFA | 1 | 5% to 70% B in 8.00 minutes, 70% B for 2.0 minutes, then stop | 250 | 1.5 |

-continued

| Method | Column | Mobile Phase A | Mobile Phase B | Flow Rate (mL/min) | Gradient Profile | MS Heat Block Temp (° C.) | MS Detector Voltage (kV) |
|---|---|---|---|---|---|---|---|
| P | Shim pack XR-ODS 2.2 μm 3.0x50 mm | Water/0.05% TFA | ACN/0.05% TFA | 1 | 5% to 65% B in 3.00 minutes, 65% B for 0.80 minutes, 100% to 5% B in 0.1 minutes, then stop | 250 | 1.5 |
| Q | Shim-pack XR-ODS 2.2 μm 3.0x50 mm | Water/0.05% TFA | ACN/0.05% TFA | 1 | 5% to 60% B in 2.50 minutes, 60% B for 0.7 minutes, 60% to 5% B in 0.1 minutes, then stop | 250 | 0.95 |
| R | Shim-pack XR-ODS 2.2 μm 3.0x50 mm | Water/0.05% TFA | ACN/0.05% TFA | 1 | 5% to 50% B in 2.50 minutes, 50% B for 0.7 minutes, 50% to 5% B in 0.1 minutes, then stop | 250 | 0.95 |
| S | XBridge C18 3.5 μm 3.0x50 mm | Water/0.05% TFA | ACN/0.05% TFA | 1 | 5% to 95% B in 2.20 minutes, 95% B for 1.00 minutes, 95% to 5% B in 0.1 minutes, then stop | 250 | 0.9 |
| T | Shim-pack XR-ODS 1.6 μm 2.0x50 mm | Water/0.05% FA | ACN/0.05% FA | 0.7 | 5% to 100% B in 2.0 minutes, 100% B for 1.1 minutes, 100% to 5% B in 0.1 minutes, then stop | 250 | 0.85 |
| U | Shim-pack XR-ODS 2.2 μm 3.0x50 mm | Water/0.05% TFA | ACN/0.05% TFA | 1 | 5% to 40% B in 2.50 minutes, 40% B for 0.7 minutes, 40% to 5% B in 0.1 minutes, then stop | 250 | 0.95 |
| V | Shim-pack XR-ODS 2.2 μm 3.0x50 mm | Water/0.05% TFA | ACN/0.05% TFA | 1 | 5% to 60% B in 4.20 minutes, 60% B for 1.0 minutes, 60% to 5% B in 0.1 minutes, then stop | 200 | 1.05 |
| W | Shim-pack XR-ODS 2.2 μm 3.0x50 mm | Water/0.05% TFA | ACN/0.05% TFA | 1 | 5% to 100% B in 2.20 minutes, 100% B for 1.00 minutes, 100% to 5% B in 0.1 minutes, then stop | 200 | 0.95 |
| X | Shim-pack XR-ODS 1.6 μm 2.0x50 mm | Water/0.05% FA | ACN/0.05% FA | 0.7 | 5% to 100% B in 2.0 minutes, 100% B for 1.1 minutes, 100% to 5% B in 0.1 minutes, then stop | 200 | 0.85 |
| Y | Ecliplis Plus C18 3.5 μm 4.6x50 mm | Water/0.05% TFA | ACN | 1 | 5% to 100% B in 2.0 minutes, 100% B for 1.0 minutes, 100% to 5% B in 0.1 minutes, then stop | 250 | 1 |
| Z | Ecliplis Plus C18 3.5 μm 4.6x50 mm | Water/ 10 mM ammonium carbonate | ACN/5% water | 1 | 5% to 100% B in 2.0 minutes, 100% B for 1.0 minutes, 100% to 5% B in 0.1 minutes, then stop | 250 | 1.1 |
| A1 | Shim-pack XR-ODS 2.2 μm 3.0x50 mm | Water/0.05% TFA | ACN | 1 | 5% to 100% B in 2.0 minutes, 100% B for 1.0 minutes, 100% to 5% B in 0.1 minutes, then stop | 250 | 1 |
| A2 | Ecliplis Plus C18 3.5 μm 4.6x50 mm | Water/ 10 mM ammonium acetate | ACN | 1 | 5% to 100% B in 2.0 minutes, 100% B for 1.4 minutes, 100% to 5% B in 0.1 minutes, then stop | 250 | 0.95 |
| A3 | Acquity BEH C18 1.7 μm 2.1X50 mm | Water/ 5 mM ammonium acetate/ 0.1% FA | ACN/0.1% FA | 0.55 | 5% B at 0.01 min up to 0.4 min, 35% B at 0.8 min, 55% B at 1.2 min, 100% B in 1.3 minutes, at 2.5 min up to 3.30 min, 5% B at 3.31 min up to 4.0 min, then stop | | |

| Method | Column | Mobile Phase A | Mobile Phase B | Flow Rate (mL/min) | Gradient Profile | MS Heat Block Temp (° C.) | MS Detector Voltage (kV) |
|---|---|---|---|---|---|---|---|
| A4 | Shim-pack XR-ODS 3.0x50 mm | Water/0.05% TFA | ACN/0.05% TFA | 1 | 5% to 30% B in 8.0 minutes, 30% B for 2.0 minutes, then stop | 250 | 1.5 |
| A5 | Shim-pack XR-ODS 3.0x50 mm | Water/0.05% TFA | ACN/0.05% TFA | 1 | 5% to 100% B in 2.2 minutes, 100% B for 1.0 minutes, 100% to 5% B in 0.1 minutes, then stop | 250 | 1.5 |
| A6 | Atlantis HILIC 3.0x100 mm | Water/0.05% TFA | ACN/0.05% TFA | 0.8 | 95% to 60% B in 4.0 minutes, 60% B for 4.0 minutes, then stop | 250 | 1.5 |
| A7 | Shim-pack XR-ODS 3.0x50 mm | Water/0.05% TFA | ACN/0.05% TFA | 1 | 5% B for 0.5 minutes, 5% to 75% B at 2.2 minutes, 100% B for 1.0 minutes, 100% to 5% B in 0.1 minutes, then stop | 250 | 1.5 |
| A8 | Zorbax SB-C18 5 μm 4.6x150 mm | Water/0.05% TFA | ACN/0.05% TFA | 1.2 | 5% to 70% B in 10.0 minutes, 70% B for 5.0 minutes, then stop | 250 | 1.05 |
| A9 | Shim-pack XR-ODS 3.0x50 mm | Water/0.05% TFA | ACN/0.05% TFA | 1 | 5% to 40% B in 4.4 minutes, 40% B for 0.9 minutes, then stop | 250 | 0.95 |
| A10 | Atlantis T3 3 μm 4.6x100 mm | Water/0.05% TFA | ACN/0.05% TFA | 1 | 5% to 50% B in 8.0 minutes, 50% B for 2.0 minutes, then stop | 200 | 1.05 |
| A11 | Shim-pack XR-ODS 3.0x50 mm | Water/0.05% TFA | ACN/0.05% TFA | 1 | 5% B for 0.5 minutes, 5% to 100% B in 1.7 minutes, 100% B for 1.0 minute, 100% to 5% B in 0.1 minute, then stop | 250 | 1.50 |

Compound structure confirmations were carried out using standard 300 or 400 MHz NMR spectrometers with NOe's conducted whenever necessary.

The following abbreviations are used herein:

| Abbreviation | Meaning |
|---|---|
| ACN | acetonitrile |
| atm. | atmosphere |
| DCM | dichloromethane |
| DHP | dihydropyran |
| DIBAL | diisobutyl aluminum hydride |
| DIEA | diisopropyl ethylamine |
| DMF | dimethyl formamide |
| DMF-DMA | dimethyl formamide dimethyl acetal |
| DMSO | dimethyl sulfoxide |
| dppf | 1,1'-bis(diphenylphosphino)ferrocene |
| EA | ethyl acetate |
| ESI | electrospray ionization |
| EtOH | ethanol |
| FA | formic acid |
| GC | gas chromatography |
| h | hour |
| Hex | hexanes |
| HMDS | hexamethyl disilazide |
| HPLC | high performance liquid chromatography |
| IPA | isopropanol |
| LCMS | liquid chromatography/mass spectrometry |
| MeOH | methanol |
| min | minutes |
| NBS | N-bromo succinimide |
| NCS | N-chloro succinimide |
| NIS | N-iodo succinimide |
| NMR | nuclear magnetic resonance |
| NOe | nuclear Overhauser effect |
| Prep. | preparative |
| PTSA | para-toluene sulfonic acid |
| Rf | retardation factor |
| rt | room temperature |
| RT | retention time |
| sat. | saturated |
| SGC | silica gel chromatography |
| TBAF | tetrabutyl ammonium fluoride |
| TEA | triethylamine |
| TFA | trifluoroacetic acid |
| THF | tetrahydrofuran |
| TLC | thin layer chromatography |
| UPLC | ultra performance liquid chromatography |
| LiHMDS | lithium hexamethyldisilazide |
| TMAD | tetramethyl azocarboxamide |

INTERMEDIATE SYNTHESIS

Synthesis of intermediate tert-butyl (2-(((3-iodo-1-(tetrahydro-2H-pyran-2-yl)-1H-pyrazol-4-yl)methyl)(methyl)amino)ethyl)carbamate

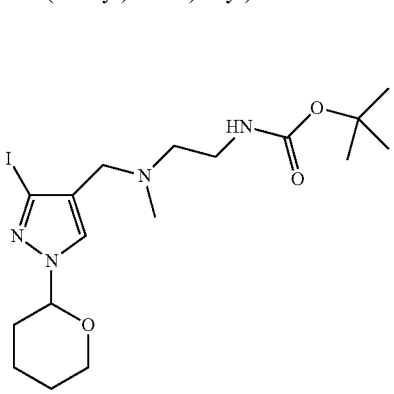

Step 1: tert-butyl (2-(((3-iodo-1-(tetrahydro-2H-pyran-2-yl)-1H-pyrazol-4-yl)methyl)(methyl)amino)ethyl)carbamate

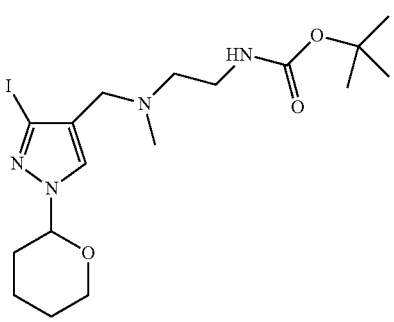 [SMILES: CN(CCNC(=O)OC(C)(C)C)Cc1cn(C2CCCCO2)nc1I]

A mixture of 3-iodo-1-(oxan-2-yl)-1H-pyrazole-4-carbaldehyde (3.2 g, 10.45 mmol, 1.00 equiv), tert-butyl N-[2-(methylamino)ethyl]carbamate (2.2 g, 12.63 mmol, 1.21 equiv) and NaBH(OAc)$_3$ (6.65 g, 31.38 mmol, 3.00 equiv) in dichloroethane (30 mL) was stirred for 2 h at room temperature. The reaction was quenched with 50 mL of saturated aqueous sodium bicarbonate solution. The resulting mixture was extracted with 3×200 mL of dichloromethane. The combined organic layers was dried over anhydrous sodium sulfate and concentrated under vacuum. The residue was purified on a silica gel column eluted with 30-100% ethyl acetate in petroleum ether to give 4.05 g (83%) of tert-butyl (2-(((3-iodo-1-(tetrahydro-2H-pyran-2-yl)-1H-pyrazol-4-yl)methyl)(methyl)amino)ethyl)carbamate as a light yellow oil. $^1$H-NMR (300 MHz, CDCl$_3$): δ 7.48 (s, 1H), 5.35-5.30 (m, 1H), 4.13-4.03 (m, 1H), 3.71-3.63 (m, 1H), 3.36 (s, 2H), 3.26-3.25 (m, 2H), 2.52-2.49 (m, 2H), 2.21 (s, 3H), 2.09-2.01 (m, 3H), 1.68-1.58 (m, 3H), 1.44 (s, 9H) ppm. LCMS (method C, ESI): RT=0.58 min, m/z=465.0 [M+H]$^+$.

Synthesis of intermediate tert-butyl (2-(((3-iodo-1-(tetrahydro-2H-pyran-2-yl)-1H-pyrazol-4-yl)methyl)(methyl)amino)ethyl)(methyl)carbamate

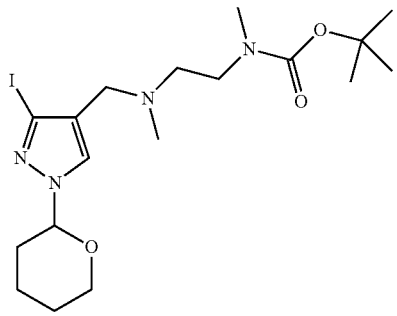 [SMILES: CN(CCN(C)C(=O)OC(C)(C)C)Cc1cn(C2CCCCO2)nc1I]

Step 1: Ethyl 3-iodo-1H-pyrazole-4-carboxylate

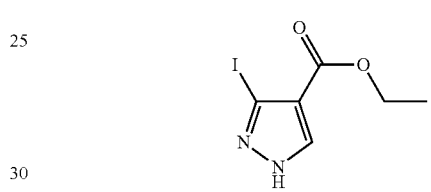

To a stirred solution of ethyl 3-amino-1H-pyrazole-4-carboxylate (10 g, 64.45 mmol, 1.00 equiv) in 50% sulfuric acid (90 mL) at 5° C. was added dropwise a solution of NaNO$_2$ (7.4 g, 107.25 mmol, 1.66 equiv) in water (15 mL). The reaction was stirred at 5° C. for another 30 min. A solution of KI (32.1 g, 193.37 mmol, 3.00 equiv) in water (15 mL) was added dropwise at 5° C. The reaction was allowed to stir at 5° C. for 1 h and then quenched by the addition of 50 mL of water. The precipitate was collected by filtration and then dissolved in 150 mL of ethyl acetate. The resulting solution was washed sequentially with 1×100 mL of saturated Na$_2$SO$_3$ solution, 1×100 mL of saturated sodium bicarbonate solution and 1×100 mL of brine. The organic layer was dried over anhydrous sodium sulfate and concentrated under vacuum to give 10.8 g (63%) of ethyl 3-iodo-1H-pyrazole-4-carboxylate as a yellow solid. $^1$H-NMR (300 MHz, CDCl$_3$): δ 8.18 (s, 1H), 4.38-4.29 (m, 2H), 1.41-1.33 (m, 3H) ppm. LCMS (method B, ESI): RT=1.36 min, m/z=267.0 [M+H]$^+$.

Step 2: Ethyl 3-iodo-1-(tetrahydro-2H-pyran-2-yl)-1H-pyrazole-4-carboxylate

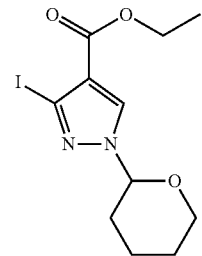 [SMILES: CCOC(=O)c1cn(C2CCCCO2)nc1I]

A solution of ethyl 3-iodo-1H-pyrazole-4-carboxylate (10.8 g, 40.60 mmol, 1.00 equiv), 3,4-dihydro-2H-pyran (10 g, 118.88 mmol, 2.93 equiv) and TsOH (780 mg, 4.53 mmol, 0.11 equiv) in THF (100 mL) was stirred for 2 h at 60° C. The reaction mixture was cooled to room temperature and quenched by the addition of 100 mL of saturated sodium bicarbonate solution. The resulting solution was extracted with 2×80 mL of dichloromethane. The combined organic layers was dried over anhydrous sodium sulfate and concentrated under vacuum. The residue was purified on a silica gel column eluted with ethyl acetate/petroleum ether (1:20) to give 13 g (91%) of ethyl 3-iodo-1-(oxan-2-yl)-1H-pyrazole-4-carboxylate as a yellow oil. $^1$H-NMR (400 MHz, CDCl$_3$): δ 8.04 (s, 1H), 5.40-5.38 (m, 1H), 4.34-4.29 (m, 2H), 4.08-4.05 (m, 1H), 3.73-3.70 (m, 1H), 2.07-1.98 (m, 3H), 1.69-1.62 (m, 3H), 1.39-1.32 (m, 3H) ppm. LCMS (method C, ESI): RT=1.53 min, m/z=351.0 [M+H]$^+$.

Step 3: 3-Iodo-1-(tetrahydro-2H-pyran-2-yl)-1H-pyrazole-4-carboxylic acid

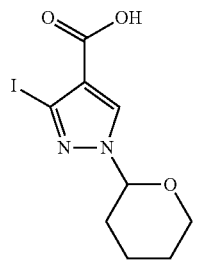 [SMILES: O=C(O)c1cn(C2CCCCO2)nc1I]

To a solution of ethyl 3-iodo-1-(oxan-2-yl)-1H-pyrazole-4-carboxylate (85 g, 242.75 mmol, 1.00 equiv) in THF (300 mL) and methanol (300 mL) was added a solution of LiOH (17.5 g, 730.69 mmol, 3.01 equiv) in water (400 mL). The resulting solution was stirred at room temperature overnight and then concentrated under vacuum to remove the organic solvent. The resulting solution was diluted with 400 mL of H$_2$O and then acidified to pH 6.0 with 1M hydrochloric acid. The mixture was extracted with 3×800 mL of dichloromethane. The combined organic layers was washed with 3×1000 mL of brine, dried over anhydrous sodium sulfate and concentrated under vacuum to give 75 g (96%) of 3-iodo-1-(oxan-2-yl)-1H-pyrazole-4-carboxylic acid as an off-white solid. LCMS (method D, ESI): RT=1.23 min, m/z=323.0 [M+H]$^+$.

Step 4: (3-iodo-1-(tetrahydro-2H-pyran-2-yl)-1H-pyrazol-4-yl)methanol

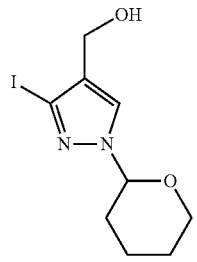 [SMILES: OCc1cn(C2CCCCO2)nc1I]

To a solution of 3-iodo-1-(oxan-2-yl)-1H-pyrazole-4-carboxylic acid (28 g, 86.93 mmol, 1.00 equiv) in anhydrous THF (300 mL) maintained under nitrogen at 5° C. was added a 1M solution of BH$_3$ in THF (300 mL) dropwise with stirring. The reaction was stirred overnight at room temperature and then quenched by the addition of 300 mL of saturated NH$_4$Cl solution. The resulting mixture was extracted with 3×1000 mL of dichloromethane. The combined organic layers was dried over anhydrous sodium sulfate and concentrated under vacuum. The residue was purified on a silica gel column eluted with ethyl acetate/petroleum ether (1:1) to give 12.67 g (47%) of (3-iodo-1-(oxan-2-yl)-1H-pyrazol-4-yl)methanol as a white solid. $^1$H-NMR (400 MHz, DMSO-d6): δ 7.73 (s, 1H), 5.37-5.34 (m, 1H), 4.92 (s, 1H), 4.20 (d, J=3.6 Hz, 2H), 3.89-3.88 (m, 1H), 3.65-3.57 (m, 1H), 2.09-2.00 (m, 1H), 1.99-1.90 (m, 2H), 1.69-1.61 (m, 1H), 1.49-1.46 (m, 2H) ppm. LCMS (method A, ESI): RT=1.16 min, m/z=309.0 [M+H].

Step 5: 3-Iodo-1-(tetrahydro-2H-pyran-2-yl)-1H-pyrazole-4-carbaldehyde

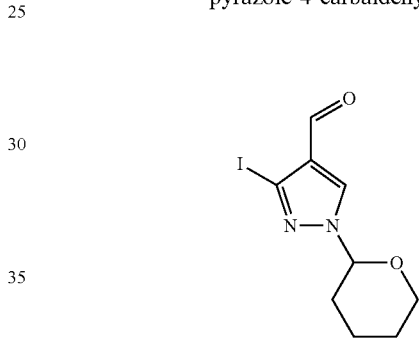

Into a 250-mL 3-necked round-bottom flask purged and. To a stirred solution of oxalyl chloride (18.576 g, 146.35 mmol, 3.01 equiv) in anhydrous dichloromethane (300 mL) maintained under nitrogen at −78° C. was added DMSO (15.138 g, 193.75 mmol, 3.98 equiv) dropwise. The reaction mixture was stirred at −65° C. for 30 min. A solution of (3-iodo-1-(oxan-2-yl)-1H-pyrazol-4-yl)methanol (15.0 g, 48.68 mmol, 1.00 equiv) in dichloromethane (100 mL) was then added dropwise at −65° C. and the reaction was stirred for another 60 min at −65° C. Triethylamine (40.6 mL) was added dropwise at −65° C. and the reaction was stirred for 30 min at −65° C. The reaction was warmed to 0° C. then quenched by the addition of 100 mL of saturated NH$_4$Cl solution. The resulting mixture was extracted with 3×400 mL of dichloromethane. The combined organic layers was dried over anhydrous sodium sulfate and concentrated under vacuum. The residue was purified on a silica gel column eluted with ethyl acetate/petroleum ether (1:20) to give 13.48 g (90%) of 3-iodo-1-(oxan-2-yl)-1H-pyrazole-4-carbaldehyde as a golden oil. $^1$H-NMR (300 MHz, DMSO-d6): δ 9.69 (s, 1H), 8.57 (s, 1H), 5.49 (dd, J=2.7 Hz, 9.9 Hz, 1H), 3.95-3.91 (m, 1H), 3.68-3.62 (m, 1H), 2.11-2.01 (m, 3H), 1.69-1.62 (m, 3H) ppm. LCMS (method A, ESI): RT=1.35 min, m/z=307.0 [M+H]+.

333

Step 6: tert-Butyl (2-(((3-iodo-1-(tetrahydro-2H-pyran-2-yl)-1H-pyrazol-4-yl)methyl)(methyl)amino)ethyl)(methyl)carbamate

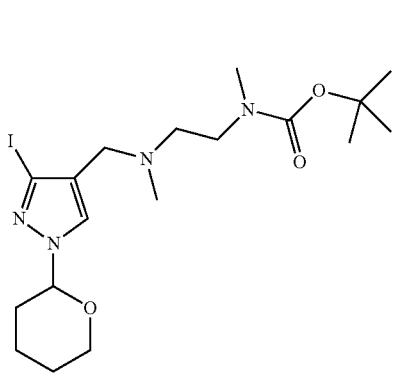 [SMILES: CN(CCN(C)C(=O)OC(C)(C)C)Cc1cn(C2CCCCO2)nc1I]

A mixture of 3-iodo-1-(oxan-2-yl)-1H-pyrazole-4-carbaldehyde (21.5 g, 70.24 mmol, 1.00 equiv), tert-butyl N-methyl-N-(2-(methylamino)ethyl)carbamate (20 g, 106.23 mmol, 1.51 equiv) and NaBH(OAc)$_3$ (29.8 g, 137.98 mmol, 1.96 equiv) in dichloroethane (300 mL) was stirred for 1 h at room temperature. The reaction was diluted with 300 mL of dichloromethane and then washed with 3×300 mL of brine. The organic layer was dried over anhydrous sodium sulfate and concentrated under vacuum. The residue was purified on a silica gel column eluted with 0-7% methanol in dichloromethane to give 31 g (92%) of tert-butyl (2-(((3-iodo-1-(tetrahydro-2H-pyran-2-yl)-1H-pyrazol-4-yl)methyl)(methyl)amino)ethyl)(methyl)carbamate as a yellow oil. $^1$H-NMR (300 MHz, CDCl$_3$): δ 7.62 (s, 1H), 5.34-5.30 (m, 1H), 4.06-4.02 (m, 1H), 3.68-3.62 (m, 1H), 3.42-3.38 (m, 4H), 2.85 (s, 4H), 2.62-2.53 (m, 2H), 2.47-2.46 (m, 2H), 2.13-1.97 (m, 3H), 1.74-1.69 (m, 3H), 1.46 (s, 9H) ppm. LCMS (method A, ESI): RT=1.17 min, m/z=479.0 [M+H]$^+$.

Compound 23

N$^1$-((3-(4-fluorophenethyl)-1H-pyrazol-4-yl)methyl)-N$^1$-methylethane-1,2-diamine

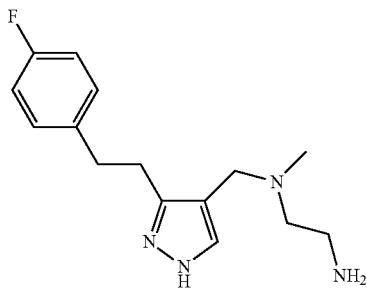 [SMILES: CN(CCN)Cc1c[nH]nc1CCc1ccc(F)cc1]

334

Step 1: (R/S) (E)-3-(4-fluorostyryl)-1-(tetrahydro-2H-pyran-2-yl)-1H-pyrazole-4-carbaldehyde

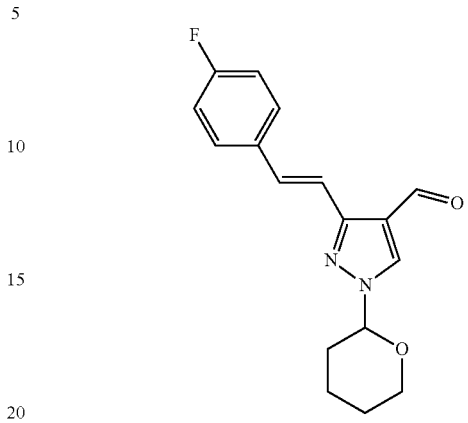

A mixture of (R/S) 3-iodo-1-(oxan-2-yl)-1H-pyrazole-4-carbaldehyde (800 mg, 2.61 mmol, 1.00 equiv), 1-ethenyl-4-fluorobenzene (957 mg, 7.84 mmol, 3.00 equiv), Pd(PPh$_3$)$_4$ (302 mg, 0.26 mmol, 0.10 equiv) and potassium carbonate (1082 mg, 7.83 mmol, 3.00 equiv) in N,N-dimethylformamide (10 mL) was stirred under nitrogen at 100° C. overnight. The reaction was cooled to room temperature then quenched by the addition of 100 mL of water. The resulting mixture was extracted with 3×100 mL of ethyl acetate. The combined organic layers was washed with 3×100 mL of brine, dried over anhydrous sodium sulfate and concentrated under vacuum. The residue was purified on a silica gel column eluted with 1-15% ethyl acetate in petroleum ether to give 220 mg (28%) of (E)-3-(4-fluorostyryl)-1-(tetrahydro-2H-pyran-2-yl)-1H-pyrazole-4-carbaldehyde as a yellow oil. LCMS (method D, ESI): RT=1.49 min, m/z=301.0 [M+H]$^+$.

Step 2: (R/S) (E)-tert-butyl 2-(((3-(4-fluorostyryl)-1-(tetrahydro-2H-pyran-2-yl)-1H-pyrazol-4-yl)methyl)(methyl)amino)ethyl)carbamate

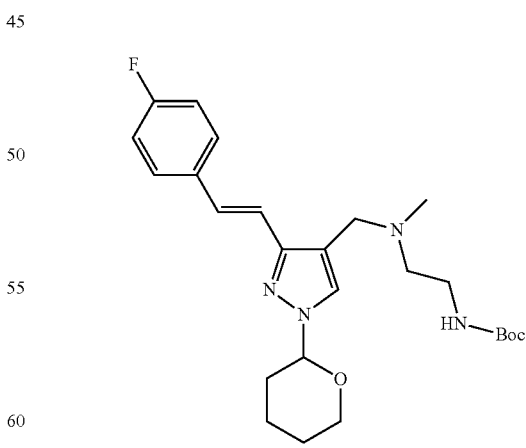

To a solution of (R/S) (E)-3-(4-fluorostyryl)-1-(tetrahydro-2H-pyran-2-yl)-1H-pyrazole-4-carbaldehyde (220 mg, 0.73 mmol, 1.00 equiv) and tert-butyl N-[2-(methylamino)ethyl]carbamate (153 mg, 0.88 mmol, 1.20 equiv) in 1,2-dichloroethane (10 mL) was added NaBH(OAc)$_3$ (311 mg, 1.44 mmol, 1.97 equiv). The reaction was stirred at room temperature for 2 h and then diluted with 100 mL of ethyl acetate. The resulting mixture was washed with 3×100 mL of brine, dried over anhydrous sodium sulfate and concentrated under vacuum. The residue was purified on a silica gel column eluted with 20-60% ethyl acetate in petroleum ether to give 220 mg (65%) of (R/S) (E)-tert-butyl 2-(((3-(4-fluorostyryl)-1-(tetrahydro-2H-pyran-2-yl)-1H-pyrazol-4-yl)methyl)(methyl)amino)ethyl)carbamate as a yellow oil. $^1$H-NMR (300 MHz, CDCl$_3$): δ 8.20 (br s, 1H), 7.51-7.36 (m, 3H), 7.05 (t, J=8.7 Hz, 2H), 6.90 (d, J=15.9 Hz, 1H), 5.38 (t, J=2.7 Hz, 1H), 4.12 (s, 2H), 3.75-3.68 (m, 1H), 3.51 (br s, 2H), 2.98 (br s, 1H), 2.60 (br s, 2H), 2.19-2.08 (m, 6H), 1.72-1.62 (m, 3H) ppm. LCMS (method D, ESI): RT=1.31 min, m/z=459.2 [M+H]+.

Step 3: (R/S) tert-butyl 2-(((3-(4-fluorophenethyl)-1-(tetrahydro-2H-pyran-2-yl)-1H-pyrazol-4-yl)methyl)(methyl)amino)ethyl)carbamate

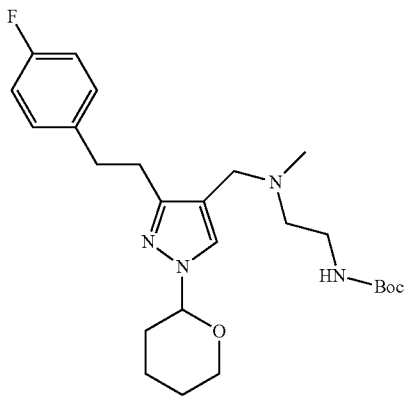 [SMILES: CN(CCNC(=O)OC(C)(C)C)Cc1cn(C2CCCCO2)nc1CCc1ccc(F)cc1]

A mixture of (R/S) (E)-tert-butyl 2-(((3-(4-fluorostyryl)-1-(tetrahydro-2H-pyran-2-yl)-1H-pyrazol-4-yl)methyl)(methyl)amino)ethyl)carbamate (220 mg, 0.48 mmol, 1.00 equiv) and Raney Ni (20 mg) in methanol (50 mL) was stirred under hydrogen at room temperature for 4 h. The catalyst was removed by filtration and the filtrate was concentrated under vacuum. The residue was purified on a silica gel column eluted with 1-7% of ethyl acetate in petroleum ether to yield 150 mg (68%) of (R/S) tert-butyl 2-(((3-(4-fluorophenethyl)-1-(tetrahydro-2H-pyran-2-yl)-1H-pyrazol-4-yl)methyl)(methyl)amino)ethyl)carbamate as a colorless oil. $^1$H-NMR (300 MHz, CDCl$_3$): δ 7.11 (t, J=7.8 Hz, 2H), 6.94 (t, J=8.7 Hz, 2H), 5.31 (d, J=6.6 Hz, 1H), 4.08 (d, J=11.4 Hz, 1H), 3.69 (t, J=11.4 Hz, 1H), 3.44 (br s, 4H), 3.00-2.85 (m, 4H), 2.12-2.09 (m, 3H), 1.76-1.52 (m, 6H), 1.45 (s, 9H) ppm. LCMS (method D, ESI): RT=1.29 min, m/z=461.2 [M+H]+.

Step 4: N$^1$-((3-(4-fluorophenethyl)-1H-pyrazol-4-yl)methyl)-N$^1$-methylethane-1,2-diamine (Compound 23)

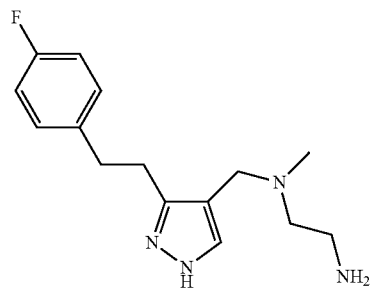 [SMILES: CN(CCN)Cc1c[nH]nc1CCc1ccc(F)cc1]

A solution of (R/S) tert-butyl 2-(((3-(4-fluorophenethyl)-1-(tetrahydro-2H-pyran-2-yl)-1H-pyrazol-4-yl)methyl)(methyl)amino)ethyl)carbamate (150 mg, 0.33 mmol, 1.00 equiv) in 3N hydrochloric acid (20 mL) was stirred overnight at 60° C. The resulting mixture was cooled to room temperature and washed with 3×20 mL of dichloromethane. The aqueous layer was concentrated under vacuum and the crude product was purified by Prep-HPLC with the following conditions (Prep-HPLC-025): Column, XBridge Prep Phenyl OBD Column, 5 μm, 19×150 mm; mobile phase, water with 10 mmol NH$_4$HCO$_3$ and MeCN (20.0% MeCN up to 30.0% in 10 min, up to 95.0% in 1 min, hold 95.0% in 1 min, down to 20.0% in 2 min); Detector, UV 254/220 nm to give 42.9 mg (26%) of N$^1$-((3-(4-fluorophenethyl)-1H-pyrazol-4-yl)methyl)-N$^1$-methylethane-1,2-diamine trifluoroacetate as a yellow oil. $^1$H-NMR (300 MHz, D$_2$O) δ: 7.70 (s, 1H), 6.98-6.86 (m, 4H), 3.86 (s, 2H), 3.30 (s, 4H), 2.97-2.80 (m, 4H), 2.58 (s, 3H) ppm. LCMS (method G, ESI): RT=1.22 min, m/z=277.1 [M+H]$^+$.

Compound 28

N$^1$-((3-iso-butyl-1H-pyrazol-4-yl)methyl)-N$^1$-methylethane-1,2-diamine

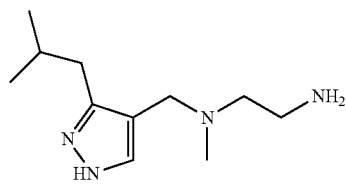

Step 1: tert-butyl 2-(((3-iso-butyl-1-(tetrahydro-2H-pyran-2-yl)-1H-pyrazol-4-yl)methyl)(methyl)amino)ethyl)carbamate

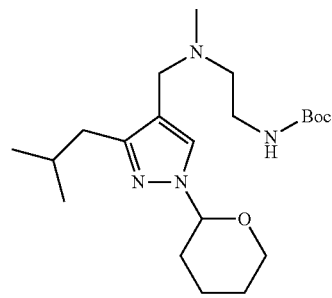 [SMILES: CC(C)Cc1nn(C2CCCCO2)cc1CN(C)CCNC(=O)OC(C)(C)C]

A mixture of (R/S) tert-butyl N-[2-([[3-iodo-1-(oxan-2-yl)-1H-pyrazol-4-yl]methyl](methyl)amino)ethyl]carbamate (400 mg, 0.86 mmol, 1.00 equiv), (2-methylpropyl)boronic acid (168 mg, 1.65 mmol, 1.50 equiv), $K_3PO_4 \cdot 3H_2O$ (877 mg, 3.00 equiv) and A-Phos-PdCl$_2$ (77.8 mg, 0.10 equiv) in ethylene glycol dimethyl ether (20 mL) and H$_2$O (2 mL) was stirred under nitrogen at 100° C. overnight. The resulting mixture was cooled to room temperature and concentrated under vacuum. The residue was purified by Prep-HPLC with the following conditions (1#-Pre-HPLC-005 (Waters)): Column, XBridge Shield RP18 OBD Column, 5 m, 19×150 mm; mobile phase, water with 10 mmol NH$_4$HCO$_3$ and CH$_3$CN (18% CH$_3$CN up to 58% in 10 min, up to 95% in 1 min, down to 18% in 2 min); Detector, UV 254/220 nm to give 50 mg (15%) of tert-butyl 2-(((3-iso-butyl-1-(tetrahydro-2H-pyran-2-yl)-1H-pyrazol-4-yl)methyl)(methyl)amino)ethyl)carbamate as a colorless oil. LCMS (method A, ESI): RT=1.27 min, m/z=395.0 [M+H]$^+$.

Step 2: $N^1$-((3-iso-butyl-1H-pyrazol-4-yl)methyl)-$N^1$-methylethane-1,2-diamine Compound 28

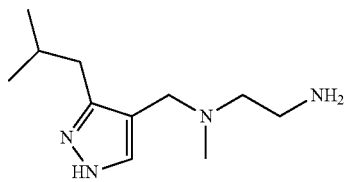

A solution of tert-butyl 2-(((3-iso-butyl-1-(tetrahydro-2H-pyran-2-yl)-1H-pyrazol-4-yl)methyl)(methyl)amino)ethyl)carbamate (50 mg, 0.13 mmol, 1.00 equiv) in THF (10 mL) and 12N hydrochloric acid (2 mL) was stirred overnight at 25° C. The resulting mixture was concentrated under vacuum. The residue was diluted with 5 mL of tetrahydrofuran and the pH value of the solution was adjusted to 9 with 10% sodium carbonate solution. The resulting mixture was concentrated under vacuum and the residue was dissolved in 5 mL of methanol then purified by Prep-HPLC with the following conditions (1#-Pre-HPLC-005 (Waters)): Column, XBridge Shield RP18 OBD Column, 5 μm, 19×150 mm; mobile phase, water with 10 mmol NH$_4$HCO$_3$ and CH$_3$CN (18% CH$_3$CN up to 58% in 10 min, up to 95% in 1 min, down to 18% in 2 min); Detector, UV 254/220 nm to yield 6 mg (23%) of $N^1$-((3-iso-butyl-1H-pyrazol-4-yl)methyl)-$N^1$-methylethane-1,2-diamine as a light yellow oil. $^1$H-NMR (300 MHz, CD$_3$OD) 7.49 (s, 1H), 3.44 (s, 2H), 2.84-2.80 (m, 2H), 2.56-2.50 (m, 4H), 2.21 (s, 3H), 2.03-1.93 (m, 1H), 0.95-0.92 (m, 6H) ppm. LCMS (method AA1 ESI): RT=1.02 min, m/z=211.0 [M+H]$^+$.

Compound 37

$N^1$-methyl-$N^1$-((3-(4-methylcyclohexyl)-1H-pyrazol-4-yl)methyl)ethane-1,2-diamine

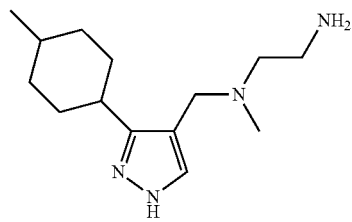 [SMILES: CC1CCC(c2n[nH]cc2CN(C)CCN)CC1]

Step 1: (R/S) tert-butyl 2-(methyl((3-(4-methylcyclohex-1-enyl)-1-(tetrahydro-2H-pyran-2-yl)-1H-pyrazol-4-yl)methyl)amino)ethyl)carbamate

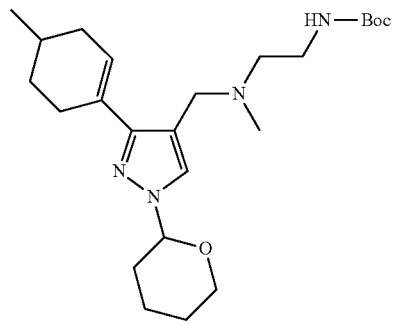 [SMILES: CC1CC=C(c2nn(C3CCCCO3)cc2CN(C)CCNC(=O)OC(C)(C)C)CC1]

A mixture of (R/S) tert-butyl N-[2-([[3-iodo-1-(oxan-2-yl)-1H-pyrazol-4-yl]methyl](methyl)amino)ethyl]carbamate (50 mg, 0.11 mmol, 1.00 equiv), potassium carbonate (45 mg, 0.33 mmol, 3.02 equiv), 4,4,5,5-tetramethyl-2-(4-methylcyclohex-1-en-1-yl)-1,3,2-dioxaborolane (36 mg, 0.16 mmol, 1.51 equiv), Pd(dppf)Cl$_2$ (8 mg, 0.01 mmol, 0.10 equiv) in water (1 mL) and 1,4-dioxane (10 mL) was stirred under nitrogen at 100° C. overnight. The reaction mixture was cooled to room temperature and concentrated under vacuum. The residue was purified on a silica gel column eluted with 0-50% of ethyl acetate in petroleum ether to give 30 mg (64%) of (R/S) tert-butyl 2-(methyl((3-(4-methylcyclohex-1-enyl)-1-(tetrahydro-2H-pyran-2-yl)-1H-pyrazol-4-yl)methyl)amino)ethyl)carbamate as a brown oil. $^1$H-NMR (300 MHz, CDCl$_3$): δ 7.29 (s, 1H), 6.14-6.13 (m, 1H), 5.36-5.32 (m, 1H), 4.16-4.07 (m, 2H), 3.70-3.27 (m, 2H), 2.54-2.29 (m, 6H), 2.54-2.29 (m, 4H), 2.22 (s, 3H), 2.13-2.07 (m, 3H), 1.86-1.56 (m, 4H), 1.47 (s, 9H), 1.46-1.38 (m, 3H) ppm. LCMS (method A, ESI): RT=1.31 min, m/z=433.0 [M+H]$^+$.

Step 2: (R/S) tert-butyl 2-(methyl((3-(4-methylcyclohexyl)-1-(tetrahydro-2H-pyran-2-yl)-1H-pyrazol-4-yl)methyl)amino)ethyl)carbamate

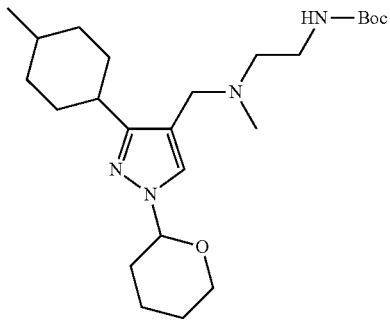 [SMILES: CC1CCC(c2nn(C3CCCCO3)cc2CN(C)CCNC(=O)OC(C)(C)C)CC1]

A mixture of (R/S) tert-butyl 2-(methyl((3-(4-methylcyclohex-1-enyl)-1-(tetrahydro-2H-pyran-2-yl)-1H-pyrazol-4-yl)methyl)amino)ethyl)carbamate (200 mg, 0.46 mmol, 1.00 equiv) and 10% palladium on carbon (30 mg) catalyst in methanol (20 mL) was stirred under 20 atm of hydrogen in a 50-mL high pressure reactor at 25° C. for 2 days. The catalyst was removed by filtration and the filtrate was concentrated under vacuum to give 200 mg of crude (R/S) tert-butyl 2-(methyl((3-(4-methylcyclohexyl)-1-(tetrahydro-2H-pyran-2-yl)-1H-pyrazol-4-yl)methyl)amino)ethyl)carbamate as a yellow oil. The crude product was used in the next step without further purification. LCMS (method C, ESI): RT=0.77 min, m/z=435.0 [M+H]$^+$.

Step 3: N$^1$-methyl-N$^1$-((3-(4-methylcyclohexyl)-1H-pyrazol-4-yl)methyl)ethane-1,2-diamine (Compound 37)

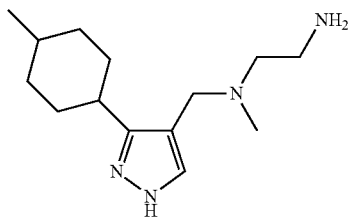 [SMILES: CC1CCC(c2n[nH]cc2CN(C)CCN)CC1]

A solution of (R/S) tert-butyl 2-(methyl((3-(4-methylcyclohexyl)-1-(tetrahydro-2H-pyran-2-yl)-1H-pyrazol-4-yl)methyl)amino)ethyl)carbamate (200 mg, 0.46 mmol, 1.00 equiv) in 4N hydrochloric acid (10 mL) was stirred at 60° C. for 2 h. The resulting mixture was cooled to room temperature and concentrated under vacuum. The crude product was purified by Prep-HPLC with the following conditions (2#-Waters 2767-2(HPLC-08)): Column, XBridge Shield RP 18, 5 μm, 19×150 mm; mobile phase, water with 50 mmol CF$_3$COOH and CH$_3$CN (10.0% CH$_3$CN up to 28.0% in 2 min, up to 46.0% in 10 min, up to 100.0% in 1 min, down to 10.0% in 1 min); Detector, UV 254 nm to yield 62.3 mg (28%) of N$^1$-methyl-N$^1$-((3-(4-methylcyclohexyl)-1H-pyrazol-4-yl)methyl)ethane-1,2-diamine trifluoroacetate as a colorless semi-solid. $^1$H-NMR (300 MHz, D$_2$O): δ 7.78 (s, 1H), 4.28 (s, 2H), 3.47-3.31 (m, 4H), 2.79-2.60 (s, 4H), 2.74-2.70 (m, 1H), 1.90-1.25 (m, 8H), 0.89 (d, J=7.2 Hz, 3H) ppm. LCMS (method V, ESI): RT=1.51 min, 9.12 min, m/z=251.1 [M+H]$^+$.

Compound 38

N$^1$-((3-(4,4-dimethylcyclohexyl)-1H-pyrazol-4-yl)methyl)-N$^1$-methylethane-1,2-diamine

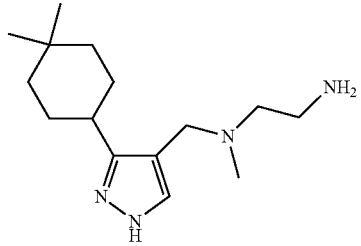 [SMILES: CN(CCN)Cc1c[nH]nc1C1CCC(C)(C)CC1]

Step 1: (R/S) tert-butyl 2-(((3-(4,4-dimethylcyclohex-1-enyl)-1-(tetrahydro-2H-pyran-2-yl)-1H-pyrazol-4-yl)methyl)(methyl)amino)ethyl)carbamate

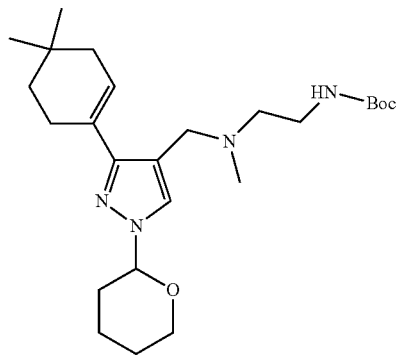 [SMILES: CN(CCNC(=O)OC(C)(C)C)Cc1cn(C2CCCCO2)nc1C1=CCC(C)(C)CC1]

A mixture of (R/S) tert-butyl N-[2-([[3-iodo-1-(oxan-2-yl)-1H-pyrazol-4-yl]methyl](methyl)amino)ethyl]carbamate (300 mg, 0.65 mmol, 1.00 equiv), Pd(dppf)Cl$_2$ (52 mg, 0.07 mmol, 0.11 equiv), 2-(4,4-dimethylcyclohex-1-enyl)-4,4,5,5-tetramethyl-1,3,2-dioxaborolane (229 mg, 0.97 mmol, 1.50 equiv) and potassium carbonate (268 mg, 1.94 mmol, 3.00 equiv) in 1,4-dioxane (20 mL) and water (4 mL) was stirred under nitrogen at 100° C. overnight. The resulting mixture was cooled to room temperature and concentrated under vacuum. The residue was purified on a silica gel column eluted with 1-41% of ethyl acetate in petroleum ether to give 250 mg (87%) of (R/S) tert-butyl 2-(((3-(4,4-dimethylcyclohex-1-enyl)-1-(tetrahydro-2H-pyran-2-yl)-1H-pyrazol-4-yl)methyl)(methyl)amino)ethyl)carbamate as a yellow oil. $^1$H-NMR (300 MHz, CDCl$_3$): δ 7.50 (s, 1H), 6.14-6.13 (m, 1H), 5.36-5.32 (m, 1H), 4.18-4.07 (m, 2H), 3.74-3.67 (m, 1H), 3.41-3.25 (m, 4H), 2.51-2.50 (m, 3H), 2.20-2.02 (m, 6H), 1.73-1.71 (m, 3H), 1.70-1.66 (m, 6H), 1.47 (s, 9H), 1.28-1.26 (m, 4H) ppm. LCMS (method D, ESI): RT=1.33 min, m/z=447.0 [M+H]$^+$.

Step 2: (R/S) tert-butyl 2-(((3-(4,4-dimethylcyclohexyl)-1-(tetrahydro-2H-pyran-2-yl)-1H-pyrazol-4-yl)methyl)(methyl)amino)ethyl)carbamate

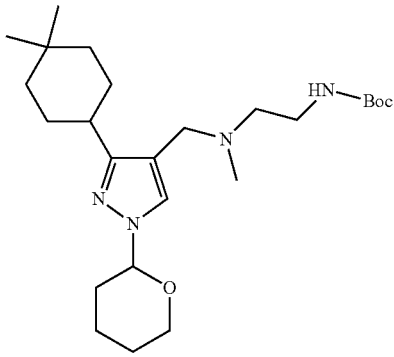 [SMILES: CN(CCNC(=O)OC(C)(C)C)Cc1cn(C2CCCCO2)nc1C1CCC(C)(C)CC1]

A mixture of (R/S) tert-butyl 2-(((3-(4,4-dimethylcyclohex-1-enyl)-1-(tetrahydro-2H-pyran-2-yl)-1H-pyrazol-4-yl)methyl)(methyl)amino)ethylcarbamate (250 mg, 0.56 mmol, 1.00 equiv) and 10% palladium on carbon (30 mg) catalyst in methanol (20 mL) was stirred under 20 atm. of hydrogen in a 50-mL high pressure reactor at 25° C. for 2 days. The catalyst was removed by filtration. The filtrate was concentrated under vacuum to give 250 mg of crude (R/S) tert-butyl 2-(((3-(4,4-dimethylcyclohexyl)-1-(tetrahydro-2H-pyran-2-yl)-1H-pyrazol-4-yl)methyl)(methyl)amino)ethyl)carbamate as a yellow oil. The crude product was used in the next step without further purification. LCMS (method C, ESI): RT=0.80 min, m/z=449.0 [M+H]$^+$.

Step 3: $N^1$-((3-(4,4-dimethylcyclohexyl)-1H-pyrazol-4-yl)methyl)-$N^1$-methylethane-1,2-diamine (Compound 38)

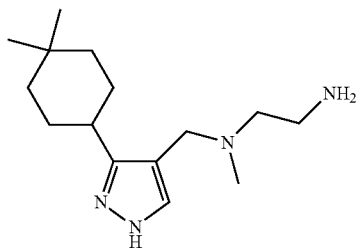 [SMILES: CN(CCN)Cc1c[nH]nc1C1CCC(C)(C)CC1]

A solution of (R/S) tert-butyl 2-(((3-(4,4-dimethylcyclohexyl)-1-(tetrahydro-2H-pyran-2-yl)-1H-pyrazol-4-yl)methyl)(methyl)amino)ethylcarbamate (250 mg, 0.56 mmol, 1.00 equiv) in 4N hydrochloric acid (10 mL) was stirred at 60° C. for 2 h. The reaction mixture was cooled to room temperature and concentrated under vacuum. The crude product was purified by Prep-HPLC with the following conditions (2#-Waters 2767-2 (HPLC-08)): Column, XBridge Shield RP 18, 5 μm, 19×150 mm; mobile phase, water with 50 mmol CF$_3$COOH and CH$_3$CN (10.0% CH$_3$CN up to 28.0% in 2 min, up to 46.0% in 10 min, up to 100.0% in 1 min, down to 10.0% in 1 min); Detector, UV 254 nm to yield 171.2 mg (62%) of $N^1$-((3-(4,4-dimethylcyclohexyl)-1H-pyrazol-4-yl)methyl)-$N^1$-methylethane-1,2-diamine trifluoroacetate as a light yellow oil. $^1$H-NMR (300 MHz, D$_2$O): δ 7.75 (s, 1H), 4.30 (s, 2H), 3.47-3.35 (m, 4H), 2.77 (s, 3H), 2.68-2.58 (m, 1H), 1.71-1.53 (m, 4H), 1.49-1.37 (m, 2H), 1.31-1.17 (m, 2H), 1.89 (s, 3H), 1.87 (s, 3H) ppm. LCMS (method M, ESI): RT=1.15, m/z=265.1 [M+H]$^+$.

Compound 39

$N^1$-((3-(1-isobutylpiperidin-4-yl)-1H-pyrazol-4-yl)methyl)-$N^1$,$N^2$-dimethylethane-1,2-diamine

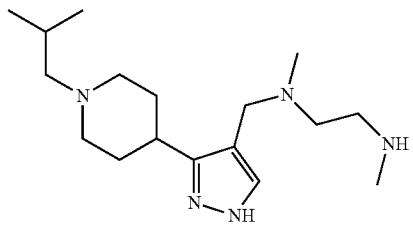 [SMILES: CNCCN(C)Cc1c[nH]nc1C1CCN(CC(C)C)CC1]

Step 1: (R/S) tert-butyl 2-(((3-(1-isobutylpiperidin-4-yl)-1-(tetrahydro-2H-pyran-2-yl)-1H-pyrazol-4-yl)methyl)(methyl)amino)ethyl)(methyl)carbamate

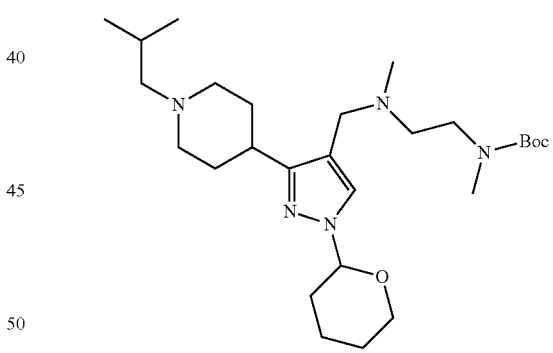

To a solution of (R/S) tert-butyl N-methyl-N-[2-[methyl([[1-(oxan-2-yl)-3-(piperidin-4-yl)-1H-pyrazol-4-yl]methyl])amino]ethyl]carbamate (250 mg, 0.57 mmol, 1.00 equiv) and 2-methylpropanal (62 mg, 0.86 mmol, 1.50 equiv) in 1,2-dichloroethane (15 mL) was added NaBH(OAc)$_3$ (364 mg, 3.00 equiv). The resulting solution was stirred at room temperature overnight and then concentrated under vacuum to give 160 mg of crude (R/S) tert-butyl 2-(((3-(1-isobutylpiperidin-4-yl)-1-(tetrahydro-2H-pyran-2-yl)-1H-pyrazol-4-yl)methyl)(methyl)amino)ethyl(methyl)carbamate as a light yellow oil. LCMS (method A, ESI): RT=1.52 min, m/z=492.2 [M+H]+.

Step 2: $N^1$-((3-(1-isobutylpiperidin-4-yl)-1H-pyrazol-4-yl)methyl)-$N^1$,$N^2$-dimethylethane-1,2-diamine (Compound 39)

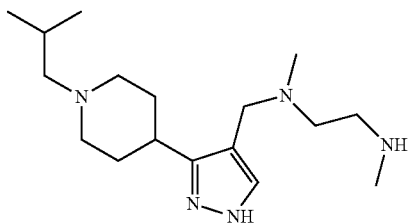 [SMILES: CNCCN(C)Cc1c[nH]nc1C1CCN(CC(C)C)CC1]

A solution of tert-butyl 2-(((3-(1-isobutylpiperidin-4-yl)-1-(tetrahydro-2H-pyran-2-yl)-1H-pyrazol-4-yl)methyl)(methyl)amino)ethyl)(methyl)carbamate (130 mg, 0.26 mmol, 1.00 equiv) in ethanol (2 mL), 1,4-dioxane (4 mL) and 3N hydrochloric acid (2 mL) was stirred at room temperature overnight. The reaction mixture was concentrated under vacuum and the residue was purified by Pre-HPLC with the following conditions (1#-Pre-HPLC-005 (Waters)): Column, SunFire Prep C18 OBD Column, 5 μm, 19×150 mm; mobile phase, phase A: water with 0.05% TFA; phase B: MeCN (5% $CH_3CN$ up to 17% in 10 min, down to 0% in 0 min); Detector, UV 254/220 nm to give 39.5 mg (28%) of $N^1$-((3-(1-isobutylpiperidin-4-yl)-1H-pyrazol-4-yl)methyl)-$N^1$,$N^2$-dimethylethane-1,2-diamine trifluoroacetate as a colorless solid. $^1$H-NMR (300 MHz, $D_2O$): δ 7.81 (s, 1H), 4.32 (s, 2H), 3.71-3.35 (m, 7H), 3.15-2.89 (m, 4H), 2.82-2.68 (m, 6H), 2.22-1.92 (m, 5H), 0.93 (d, J=6.8 Hz, 6H) ppm. LCMS (method U, ESI): m/z=308.2 $[M+H]^+$.

Compound 40

3-methyl-1-(4-(4-((methyl(2-(methylamino)ethyl)amino)methyl)-1H-pyrazol-3-yl)piperidin-1-yl)butan-1-one

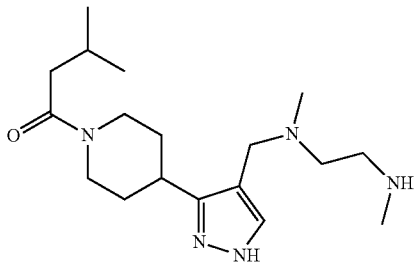 [SMILES: CNCCN(C)Cc1c[nH]nc1C1CCN(C(=O)CC(C)C)CC1]

Step 1: (R/S)benzyl 4-(4-(((2-(tert-butoxycarbonyl(methyl)amino)ethyl)(methyl)amino)methyl)-1-(tetrahydro-2H-pyran-2-yl)-1H-pyrazol-3-yl)-5,6-dihydropyridine-1(2H)-carboxylate

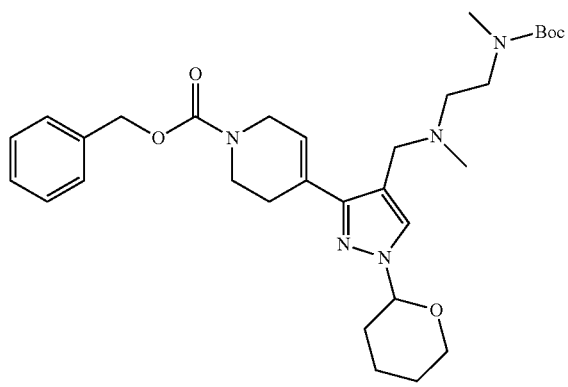 [SMILES: CN(CCN(C)C(=O)OC(C)(C)C)Cc1cn(C2CCCCO2)nc1C1=CCN(C(=O)OCc2ccccc2)CC1]

A mixture of (R/S) tert-butyl N-[2-([[4-iodo-1-(oxan-2-yl)-1H-pyrrol-3-yl]methyl](methyl)amino)ethyl]-N-methylcarbamate (3.15 g, 6.60 mmol, 1.00 equiv), benzyl 4-(tetramethyl-1,3,2-dioxaborolan-2-yl)-1,2,3,6-tetrahydropyridine-1-carboxylate (2.5 g, 7.28 mmol, 1.10 equiv), Pd(dppf)Cl$_2$ (1.39 g, 1.90 mmol, 0.29 equiv) and potassium carbonate (2.72 g, 19.68 mmol, 2.98 equiv) in 1,4-dioxane (30 mL) and water (3 mL) was stirred under nitrogen at 100° C. overnight. The reaction was cooled to room temperature and then quenched by the addition of 30 mL of water. The resulting mixture was extracted with 3×250 mL of ethyl acetate. The combined organic layers was dried over anhydrous sodium sulfate and concentrated under vacuum. The residue was purified on a silica gel column eluted with 0-15% of ethyl acetate in petroleum ether to give 2.1 g (56%) of (R/S)benzyl 4-(4-(((2-(tert-butoxycarbonyl(methyl)amino)ethyl)(methyl)amino)methyl)-1-(tetrahydro-2H-pyran-2-yl)-1H-pyrazol-3-yl)-5,6-dihydropyridine-1(2H)-carboxylate as a yellow oil. $^1$H-NMR (300 MHz, CDCl$_3$): δ 7.58-7.49 (m, 1H), 7.49-7.35 (m, 4H), 7.35-7.30 (m, 1H), 5.33-5.30 (m, 1H), 5.20 (s, 2H), 4.25-4.00 (m, 3H), 3.70-3.69 (m, 3H), 3.39-3.31 (m, 3H), 2.84 (m, 3H), 2.66 (m, 2H), 2.50 (m, 2H), 2.25 (m, 2H), 2.08-2.07 (m, 3H), 1.73-1.62 (m, 4H), 1.46 (s, 9H), 1.31-1.27 (m, 1H) ppm. LCMS (method A, ESI): RT=0.74 min, m/z=568.0 $[M+H]^+$.

Step 2: (R/S) tert-butyl methyl(2-(methyl((3-(piperidin-4-yl)-1-(tetrahydro-2H-pyran-2-yl)-1H-pyrazol-4-yl)methyl)amino)ethyl)carbamate

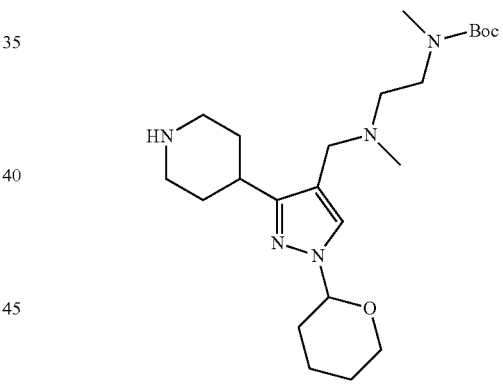

A mixture of benzyl 4-(4-(((2-(tert-butoxycarbonyl(methyl)amino)ethyl)(methyl)amino)methyl)-1-(tetrahydro-2H-pyran-2-yl)-1H-pyrazol-3-yl)-5,6-dihydropyridine-1(2H)-carboxylate (2 g, 3.52 mmol, 1.00 equiv) and 10% palladium on carbon (2 g) catalyst in methanol (100 mL) was stirred under 1 atmosphere of hydrogen at room temperature for 6 h. The catalyst was removed by filtration and the filtrate was concentrated under vacuum to yield 1.1 g (72%) of (R/S) tert-butyl methyl(2-(methyl((3-(piperidin-4-yl)-1-(tetrahydro-2H-pyran-2-yl)-1H-pyrazol-4-yl)methyl)amino)ethyl)carbamate as a brown oil. $^1$H-NMR (300 MHz, CDCl$_3$): δ 7.46 (s, 1H), 5.33-5.32 (m, 1H), 4.24-4.06 (m, 1H), 3.75-3.66 (m, 1H), 3.51 (s, 1H), 3.41-3.15 (m, 6H), 2.95-2.70 (m, 6H), 2.62-2.40 (m, 2H), 2.22 (s, 3H), 1.55-1.41 (m, 10H), 1.35-1.21 (m, 1H) ppm. LCMS (method A, ESI): RT=1.49 min, m/z=436.2 $[M+H]^+$.

Step 3: (R/S) tert-butyl methyl(2-(methyl((3-(1-(3-methylbutanoyl)piperidin-4-yl)-1-(tetrahydro-2H-pyran-2-yl)-1H-pyrazol-4-yl)methyl)amino)ethyl)carbamate

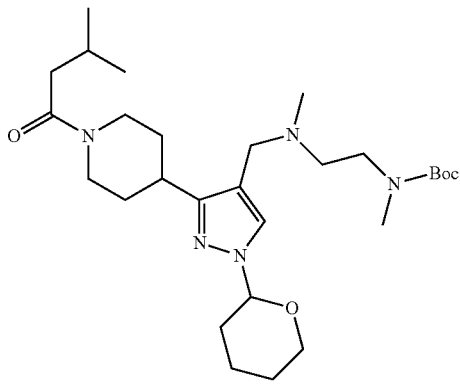 [SMILES: CC(C)CC(=O)N1CCC(c2nn(C3CCCCO3)cc2CN(C)CCN(C)C(=O)OC(C)(C)C)CC1]

To a solution of (R/S) tert-butyl methyl(2-(methyl((3-(piperidin-4-yl)-1-(tetrahydro-2H-pyran-2-yl)-1H-pyrazol-4-yl)methyl)amino)ethyl)carbamate (200 mg, 0.46 mmol, 1.00 equiv) and triethylamine (1.14 g, 11.26 mmol, 24.52 equiv) in dichloromethane (15 mL) was added 3-methylbutanoyl chloride (67 mg, 0.56 mmol, 1.21 equiv). The resulting solution was stirred at room temperature for 2 h. The reaction was then quenched by the addition of 2 mL of water. The organic layer was dried over anhydrous sodium sulfate and concentrated under vacuum to give 250 mg of crude (R/S) tert-butyl methyl(2-(methyl((3-(1-(3-methylbutanoyl)piperidin-4-yl)-1-(tetrahydro-2H-pyran-2-yl)-1H-pyrazol-4-yl)methyl)amino)ethyl)carbamate as a yellow solid. LCMS (method D, ESI): RT=1.22 min, m/z=520.0 [M+H]$^+$.

Step 4: 3-methyl-1-(4-(4-((methyl(2-(methylamino)ethyl)amino)methyl)-1H-pyrazol-3-yl)piperidin-1-yl)butan-1-one (Compound 40)

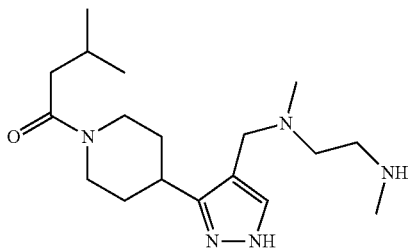 [SMILES: CNCCN(C)Cc1c[nH]nc1C1CCN(C(=O)CC(C)C)CC1]

A solution of tert-butyl methyl(2-(methyl((3-(1-(3-methylbutanoyl)piperidin-4-yl)-1-(tetrahydro-2H-pyran-2-yl)-1H-pyrazol-4-yl)methyl)amino)ethyl)carbamate (110 mg, 0.21 mmol, 1.00 equiv) in ethanol (2 mL), 1,4-dioxane (4 mL) and 12N hydrochloric acid (2 mL) was stirred at room temperature overnight. The resulting mixture was concentrated under vacuum and the residue was purified by Pre-HPLC with the following conditions (1#-Pre-HPLC-005 (Waters)): Column, XBridge Shield RP18 OBD Column, 5 μm, 19×150 mm; mobile phase, water with 10 mmol NH$_4$HCO$_3$ and CH$_3$CN (18% CH$_3$CN up to 58% in 10 min, up to 95% in 1 min, down to 18% in 2 min); Detector, UV 254/220 nm to give 17.7 mg (25%) of 3-methyl-1-(4-(4-((methyl(2-(methylamino)ethyl)amino)methyl)-1H-pyrazol-3-yl)piperidin-1-yl)butan-1-one as a colorless solid. $^1$H-NMR (300 MHz, D$_2$O): δ 7.53 (s, 1H), 4.50-4.40 (m, 1H), 4.10-4.00 (m, 1H), 3.44 (s, 2H), 3.25-3.10 (m, 1H), 3.09-2.95 (m, 1H), 2.80-2.65 (m, 3H), 2.53-2.43 (m, 2H), 2.40-2.20 (m, 5H), 2.13 (s, 3H), 2.00-1.75 (m, 3H), 1.72-1.43 (m, 2H), 0.88 (d, J=6.8 Hz, 6H) ppm. LCMS (method R, ESI): RT=1.26 min, m/z=336.2 [M+H]+.

Compound 43

N$^1$-methyl-N$^1$-((3-(4-morpholinocyclohexyl)-1H-pyrazol-4-yl)methyl)ethane-1,2-diamine

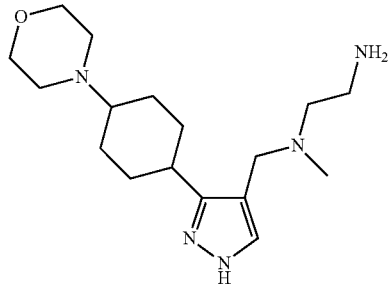 [SMILES: CN(CCN)Cc1c[nH]nc1C1CCC(N2CCOCC2)CC1]

Step 1: (R/S) tert-butyl 2-(methyl((3-(4-morpholinocyclohex-1-enyl)-1-(tetrahydro-2H-pyran-2-yl)-1H-pyrazol-4-yl)methyl)amino)ethyl)carbamate

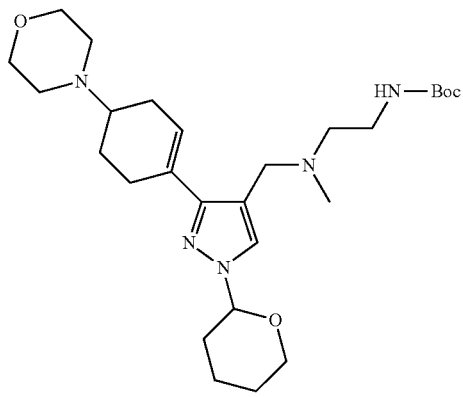 [SMILES: CN(CCNC(=O)OC(C)(C)C)Cc1cn(C2CCCCO2)nc1C1=CCC(N2CCOCC2)CC1]

A mixture of (R/S) tert-butyl N-[2-([[3-iodo-1-(oxan-2-yl)-1H-pyrazol-4-yl]methyl](methyl)amino)ethyl]carbamate (400 mg, 0.86 mmol, 1.00 equiv), Pd(dppf)Cl$_2$ (66 mg, 0.09 mmol, 0.10 equiv), potassium carbonate (356 mg, 2.58 mmol, 2.99 equiv) and 4-[4-(tetramethyl-1,3,2-dioxaborolan-2-yl)cyclohex-3-en-1-yl]morpholine (379 mg, 1.29 mmol, 1.50 equiv) in 1,4-dioxane (20 mL) and water (2 mL) was stirred under nitrogen at 100° C. overnight. The resulting mixture was cooled to room temperature then concentrated under vacuum. The residue was purified on a silica gel column eluted with 0-3% of methanol in dichloromethane to give 320 mg (74%) of (R/S) tert-butyl 2-(methyl((3-(4-morpholinocyclohex-1-enyl)-1-(tetrahydro-2H-pyran-2-yl)-1H-pyrazol-4-yl)methyl)amino)ethyl)carbamate as a brown oil. $^1$H-NMR (300 MHz, CDCl$_3$): δ 7.52 (s, 1H), 6.13-6.12

(m, 1H), 5.35-5.31 (m, 1H), 4.18-4.11 (m, 2H), 3.80-3.78 (m, 5H), 3.45-3.43 (m, 2H), 3.26-3.25 (m, 2H), 2.69-2.63 (m, 5H), 2.54-2.48 (m, 4H), 2.25-2.20 (m, 4H), 2.13-2.02 (m, 4H), 1.67-1.61 (m, 4H), 1.47 (s, 9H) ppm. LCMS (method A, ESI): RT=1.00 min, m/z=504.0 [M+H]+.

Step 2: (R/S) tert-butyl 2-(methyl((3-(4-morpholinocyclohexyl)-1-(tetrahydro-2H-pyran-2-yl)-1H-pyrazol-4-yl)methyl)amino)ethyl)carbamate

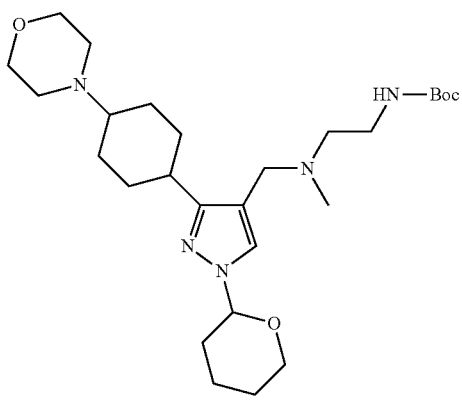 [SMILES: CN(CCNC(=O)OC(C)(C)C)Cc1cn(C2CCCCO2)nc1C1CCC(N2CCOCC2)CC1]

A mixture of (R/S) tert-butyl 2-(methyl((3-(4-morpholinocyclohex-1-enyl)-1-(tetrahydro-2H-pyran-2-yl)-1H-pyrazol-4-yl)methyl)amino)ethyl)carbamate (300 mg, 0.60 mmol, 1.00 equiv) and 10% palladium on carbon (20 mg) catalyst in acetic acid (15 mL) was stirred under 20 atm of hydrogen in a 50-mL high pressure reactor at 25° C. for 3 days. The catalyst was removed by filtration and the filtrate was concentrated under vacuum to give 300 mg of crude (R/S) tert-butyl 2-(methyl((3-(4-morpholinocyclohexyl)-1-(tetrahydro-2H-pyran-2-yl)-1H-pyrazol-4-yl)methyl)amino)ethyl)carbamate as a yellow oil. The crude product was used in the next step without further purification. LCMS (method A, ESI): RT=1.01 min, m/z=506.0 [M+H]+.

Step 3: $N^1$-methyl-$N^1$-((3-(4-morpholinocyclohexyl)-1H-pyrazol-4-yl)methyl)ethane-1,2-diamine (Compound 43)

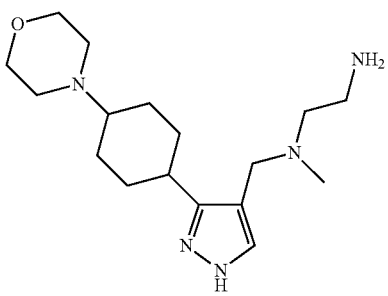 [SMILES: CN(CCN)Cc1c[nH]nc1C1CCC(N2CCOCC2)CC1]

A solution of (R/S) tert-butyl 2-(methyl((3-(4-morpholinocyclohexyl)-1-(tetrahydro-2H-pyran-2-yl)-1H-pyrazol-4-yl)methyl)amino)ethyl)carbamate (300 mg, 0.59 mmol, 1.00 equiv) in 4N hydrochloric acid (15 mL) was stirred at 60° C. for 2 h. The resulting mixture was cooled to room temperature then concentrated under vacuum. The crude product was purified by Prep-HPLC with the following conditions (Waters 2767-2(HPLC-08)): Column, XBridge Shield RP 18, 5 μm, 19×150 mm; mobile phase, water with 50 mmol $CF_3COOH$ and $CH_3CN$ (10.0% $CH_3CN$ up to 28.0% in 2 min, up to 46.0% in 10 min, up to 100.0% in 1 min, down to 10.0% in 1 min); Detector, UV 254 nm to afford 36.5 mg (11%) of $N^1$-methyl-$N^1$-((3-(4-morpholinocyclohexyl)-1H-pyrazol-4-yl)methyl)ethane-1,2-diamine trifluoroacetate as a white solid. $^1$H-NMR (300 MHz, $CD_3OD$): δ 7.47 (s, 1H), 3.78-3.71 (m, 4H), 3.47 (s, 2H), 2.88-2.80 (m, 2H), 2.80-2.70 (m, 1H), 2.70-2.62 (m, 4H), 2.57-2.50 (m, 2H), 2.45-2.27 (m, 1H), 2.23 (s, 3H), 2.16-1.93 (m, 4H), 1.75-1.57 (m, 2H), 1.50-1.34 (m, 2H) ppm. LCMS (method M, ESI): m/z=322.2 [M+H]+.

Compound 44

$N^1$-methyl-$N^1$-((4-((4-morpholinocyclohexyl)-1H-pyrazol-3-yl)ethyl)ethane-1,2-diamine

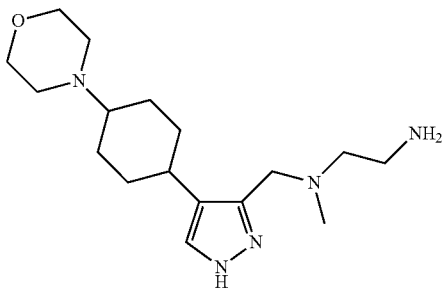 [SMILES: CN(CCN)Cc1n[nH]cc1C1CCC(N2CCOCC2)CC1]

Step 1: 4-morpholinocyclohex-1-enyl trifluoromethanesulfonate

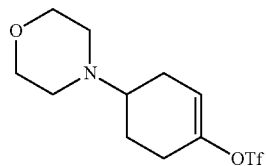 [SMILES: O=S(=O)(OC1=CCC(N2CCOCC2)CC1)C(F)(F)F]

To a stirred solution of 4-(morpholin-4-yl)cyclohexan-1-one (920 mg, 5.02 mmol, 1.00 equiv) in anhydrous tetrahydrofuran (20 mL) maintained under nitrogen at −78° C. was added dropwise a 1M solution of LiHMDS (6 mL) in tetrahydrofuran. After stirring for 1 h at −78° C., a solution of 1,1,1-trifluoro-N-phenyl-N-(trifluoromethane)-sulfonylmethanesulfonamide (1.97 g, 5.51 mmol, 1.10 equiv) in tetrahydrofuran (6 mL) was added. The reaction was warmed to room temperature and stirred for 12 h. The resulting solution was concentrated under vacuum and the residue was purified on a silica gel column eluted with 50-100% of ethyl acetate in petroleum ether to give 420 mg (27%) of 4-morpholinocyclohex-1-enyl trifluoromethanesulfonate as a yellow oil. $^1$H-NMR (300 MHz, $CDCl_3$): δ 5.80-5.70 (m, 1H), 3.90-3.75 (m, 4H), 2.75-2.00 (m, 10H), 1.70-1.50 (m, 1H) ppm.

Step 2: 4-(4-(4,4,5,5-tetramethyl-1,3,2-dioxaborolan-2-yl)cyclohex-3-enyl)morpholine

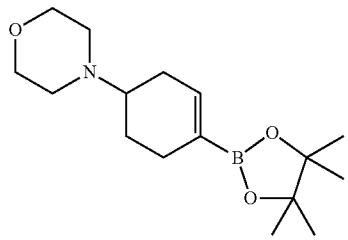 [SMILES: CC1(C)OB(C2=CCC(N3CCOCC3)CC2)OC1(C)C]

A mixture of 4-morpholinocyclohex-1-enyl trifluoromethanesulfonate (4 g, 12.69 mmol, 1.00 equiv), 4,4,5,5-tetramethyl-2-(tetramethyl-1,3,2-dioxaborolan-2-yl)-1,3,2-dioxaborolane (3.87 g, 15.24 mmol, 1.20 equiv), potassium acetate (3.73 g, 38.01 mmol, 3.00 equiv) and Pd(dppf)Cl$_2$ (930 mg, 1.27 mmol, 0.10 equiv) in 1,4-dioxane (100 mL) was refluxed under nitrogen for 12 h. The reaction mixture was cooled to room temperature, filtered and then concentrated under vacuum. The residue was purified on a silica gel column eluted with 50-100% of ethyl acetate in petroleum ether to give 3.2 g (86%) of 4-(4-(4,4,5,5-tetramethyl-1,3,2-dioxaborolan-2-yl)cyclohex-3-enyl)morpholine as a yellow oil. $^1$H-NMR (300 MHz, CDCl$_3$): δ 6.60-6.55 (m, 1H), 3.80-3.66 (m, 4H), 2.70-2.25 (m, 8H), 2.20-1.90 (m, 4H), 1.25 (s, 12H) ppm.

Step 3: (R/S) 4-(4-morpholinocyclohex-1-enyl)-1-(tetrahydro-2H-pyran-2-yl)-1H-pyrazole-3-carbaldehyde

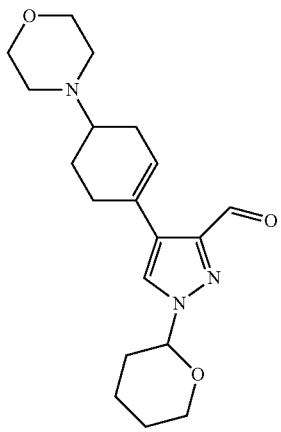 [SMILES: O=Cc1nn(C2CCCCO2)cc1C1=CCC(N2CCOCC2)CC1]

A mixture of 4-(4-(4,4,5,5-tetramethyl-1,3,2-dioxaborolan-2-yl)cyclohex-3-enyl)morpholine (293 mg, 1.00 mmol, 1.00 equiv), (R/S) 4-iodo-1-(oxan-2-yl)-1H-pyrazole-3-carbaldehyde (306 mg, 1.00 mmol, 1.00 equiv), K$_3$PO$_4$ (640 mg, 3.02 mmol, 3.02 equiv) and Pd(dppf)Cl$_2$ (65.1 mg, 0.10 mmol, 0.10 equiv) in ethylene glycol dimethyl ether (5 mL) was stirred under nitrogen at 85° C. for 12 h. The reaction was cooled to room temperature and concentrated under vacuum. The residue was purified on a silica gel column eluted with 50-100% of ethyl acetate in petroleum ether to give 280 mg (81%) of (R/S) 4-(4-morpholinocyclohex-1-enyl)-1-(tetrahydro-2H-pyran-2-yl)-1H-pyrazole-3-carbaldehyde as a brown oil. LCMS (method C, ESI): RT=0.70 min, m/z=346.2 [M+H]$^+$.

Step 4: (R/S) tert-butyl 2-(methyl((4-(4-morpholinocyclohex-1-enyl)-1-(tetrahydro-2H-pyran-2-yl)-1H-pyrazol-3-yl)methyl)amino)ethyl)carbamate

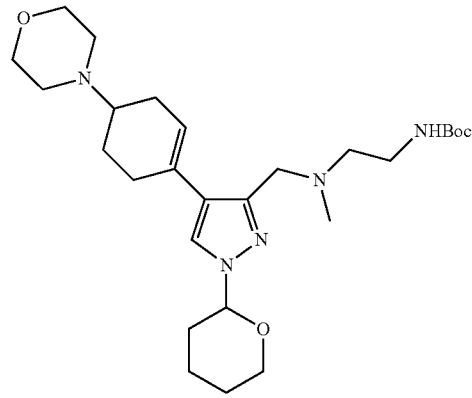 [SMILES: CN(CCNC(=O)OC(C)(C)C)Cc1nn(C2CCCCO2)cc1C1=CCC(N2CCOCC2)CC1]

To a solution of (R/S) 4-(4-morpholinocyclohex-1-enyl)-1-(tetrahydro-2H-pyran-2-yl)-1H-pyrazole-3-carbaldehyde (500 mg, 1.45 mmol, 1.00 equiv) and tert-butyl N-[2-(methylamino)ethyl]carbamate (378 mg, 2.17 mmol, 1.50 equiv) in 1,2-dichloroethane (20 mL) was added NaBH(OAc)$_3$ (612 mg, 2.89 mmol, 1.99 equiv). The reaction mixture was stirred at room temperature for 12 h and then quenched with saturated NaHCO$_3$ solution (10 mL). The organic layer was dried over anhydrous sodium sulfate and concentrated under vacuum. The residue was purified on a silica gel column eluted with 20-100% of ethyl acetate in petroleum ether to give 300 mg (41%) of (R/S) tert-butyl 2-(methyl((4-(4-morpholinocyclohex-1-enyl)-1-(tetrahydro-2H-pyran-2-yl)-1H-pyrazol-3-yl)methyl)amino)ethyl)carbamate as a brown oil. LCMS (method A, ESI): RT=0.66 min, m/z=504.4 [M+H]$^+$.

Step 5: (R/S) tert-butyl 2-(methyl((4-(4-morpholinocyclohexyl)-1-(tetrahydro-2H-pyran-2-yl)-1H-pyrazol-3-yl)methyl)amino)ethyl)carbamate

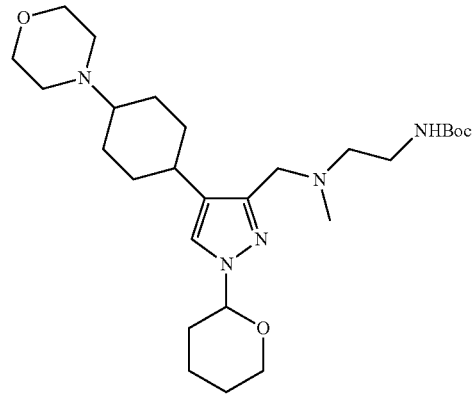 [SMILES: CN(CCNC(=O)OC(C)(C)C)Cc1nn(C2CCCCO2)cc1C1CCC(N2CCOCC2)CC1]

A mixture of (R/S) tert-butyl 2-(methyl((4-(4-morpholinocyclohex-1-enyl)-1-(tetrahydro-2H-pyran-2-yl)-1H- pyrazol-3-yl)methyl)amino)ethyl)carbamate (252 mg, 0.50 mmol, 1.00 equiv) and 10% palladium on carbon catalyst (25 mg) in acetic acid (10 mL) was stirred in a 30-mL pressure reactor under 20 atm. of hydrogen at 25° C. for 12 h. The catalyst was removed by filtration and the filtrate was concentrated to give 250 mg (99%) of (R/S) tert-butyl 2-(methyl((4-(4-morpholinocyclohexyl)-1-(tetrahydro-2H-pyran-2-yl)-1H-pyrazol-3-yl)methyl)amino)ethyl)carbamate as a yellow oil. LCMS (method C, ESI): RT=0.66 min, m/z=506.4 [M+H]$^+$.

Step 6: N$^1$-methyl-N$^1$-((4-(4-morpholinocyclohexyl)-1H-pyrazol-3-yl)methyl)ethane-1,2-diamine (Compound 44)

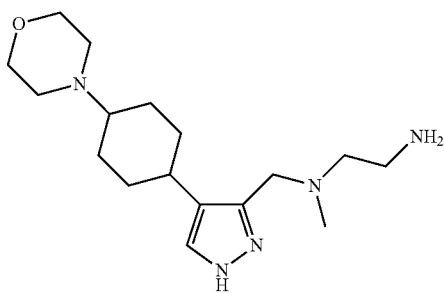 [SMILES: CN(CCN)Cc1n[nH]cc1C1CCC(N2CCOCC2)CC1]

A mixture of (R/S) tert-butyl 2-(methyl((4-(4-morpholinocyclohexyl)-1-(tetrahydro-2H-pyran-2-yl)-1H-pyrazol-3-yl)methyl)amino)ethyl)carbamate (253 mg, 0.50 mmol, 1.00 equiv) in a saturated solution of hydrogen chloride in 1,4-dioxane (20 mL) was stirred at 25° C. for 24 h. The resulting mixture was concentrated under vacuum and the crude product (150 mg) was purified by Prep-HPLC with the following conditions (Prep-HPLC-005): Column, XBridge Prep C18 OBD Column, 5 μm, 19×150 mm; mobile phase, water with 10 mmol NH$_4$HCO$_3$ and MeCN (hold 4% MeCN in 5 min, up to 5% in 10 min); Detector, UV 254/220 nm to give 30 mg (19%) of N$^1$-methyl-N$^1$-((4-(4-morpholinocyclohexyl)-1H-pyrazol-3-yl)methyl)ethane-1,2-diamine as a colorless oil. $^1$H-NMR (300 MHz, CD$_3$OD): δ 7.40 (s, 1H), 3.75-3.65 (m, 4H), 3.58 (s, 2H), 2.80-2.72 (m, 2H), 2.69-2.27 (m, 8H), 2.19 (s, 3H), 2.12-1.93 (m, 4H), 1.55-1.28 (m, 4H) ppm. LCMS (method W): m/z=322.2 [M+H]$^+$.

Compound 106

Methyl [2-(methylamino)ethyl]([3-[(5R,8R)-1,1-dimethyl-2-oxaspiro[4.5]decan-8-yl]-1H-pyrazol-4-yl]methyl)amine

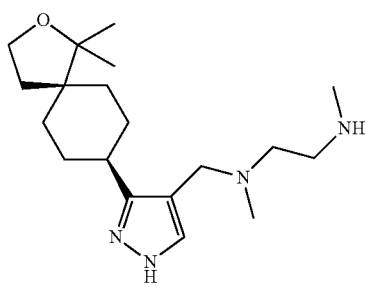 [SMILES: CNCCN(C)Cc1c[nH]nc1[C@H]1CC[C@@]2(CCOC2(C)C)CC1]

Step 1: 1,4,10-trioxadispiro[4.2.48.25]tetradecan-9-one

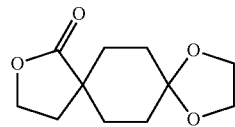 [SMILES: O=C1OCCC12CCC1(CC2)OCCO1]

Into a 500-mL 3-necked round-bottom flask was placed THF (150 mL), LDA (1.3 equiv, prepared from 36 mL of n-BuLi (2.5 M in hexane) reacted with 13.8 mL of diisopropylamine for 30 min at −50° C.). Then ethyl 1,4-dioxaspiro[4.5]decane-8-carboxylate (15 g, 70.01 mmol, 1.0 equiv) was added and stirred for 30 min at −70° C., followed by oxirane (0.22 g/mL in THF, 28 mL) at −78° C. The resulting solution was stirred for 2 h at −70° C. The reaction was quenched by 100 mL of NH$_4$Cl (sat. aq.), then treated with 100 mL of EtOAc. The organic phase was separated and then washed with 150 mL of brine. The organic phase was dried and concentrated under vacuum. The residue was purified by flash chromatography on silica gel using ethyl acetate/petroleum ether (1:2) as eluent to give 4.5 g (30%) of 1,4,10-trioxadispiro[4.2.4.2]tetradecan-9-one as a yellow solid. $^1$H-NMR (300 MHz, CDCl$_3$): δ 4.28 (t, J=6.6 Hz, 2H), 4.10-3.85 (m, 4H), 2.17 (t, J=6.6 Hz, 2H), 2.15-1.85 (m, 4H), 1.80-1.50 (m, 4H).

Step 2: 2-[8-(2-hydroxyethyl)-1,4-dioxaspiro[4.5]decan-8-yl]propan-2-ol

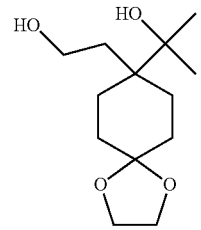 [SMILES: CC(C)(O)C1(CCO)CCC2(CC1)OCCO2]

To a stirred solution of 1,4,10-trioxadispiro[4.2.4.2]tetradecan-9-one (3.18 g, 14.98 mmol, 1.0 equiv) in THF (100 mL) at 0° C. was added dropwise a solution of MeMgBr (1M in ether, 75 mL, 5.0 equiv). The resulting solution was allowed to warm to room temperature and stirred for 12 h at room temperature. The reaction was quenched with 40 mL of NH$_4$Cl (sat. aq.), then treated with 300 mL of EtOAc. The organic phase was separated and then washed with 100 mL brine then dried with anhydrous Na$_2$SO$_4$. Concentration under reduced pressure afforded 4.9 g (crude) of 2-[8-(2-hydroxyethyl)-1,4-dioxaspiro[4.5]decan-8-yl]propan-2-ol as yellow oil. $^1$H-NMR (300 MHz, CDCl$_3$): δ 4.00-3.90 (m, 4H), 3.80-3.40 (m, 4H), 1.95-1.50 (m, 10H), 1.40-1.10 (m, 6H).

Step 3: 9,9-dimethyl-1,4,10-trioxadispiro[4.2.4⁸.2⁵] tetradecane

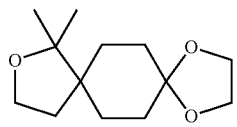 [SMILES: CC1(C)OCCC12CCC1(CC2)OCCO1]

Into a 250-mL round-bottom flask was placed 2-[8-(2-hydroxyethyl)-1,4-dioxaspiro[4.5]decan-8-yl]propan-2-ol (4.91 g, 20.10 mmol, 1.00 equiv), dichloromethane (60 mL), 4-dimethylaminopyridine (300 mg, 2.46 mmol, 0.12 equiv) and triethylamine (20 mL). Tosylchloride (5.34 g, 28.01 mmol, 1.39 equiv) was added and the resulting solution was stirred for 12 h at room temperature then concentrated to dryness under reduced pressure. The residue was purified by flash chromatography on silica gel using ethyl acetate/petroleum ether (1:2) as eluent to give 3.5 g (77%) of 9,9-dimethyl-1,4,10-trioxadispiro[4.2.4⁸.2⁵]tetradecane as a yellow oil. $^1$H-NMR (300 MHz, CDCl$_3$): δ 3.84 (s, 4H), 3.66 (t, J=7.5 Hz, 2H), 2.51 (t, J=7.5 Hz, 2H), 1.70-1.25 (m, 8H), 0.99 (s, 6H).

Step 4: 1,1-dimethyl-2-oxaspiro[4.5]decan-8-one

Into a 100-mL round-bottom flask purged and maintained with an atmosphere of nitrogen was placed 9,9-dimethyl-1,4,10-trioxadispiro[4.2.4.2]tetradecane (1.765 g, 7.80 mmol, 1.00 equiv), tetrahydrofuran (16 mL) and hydrochloric acid (12N, 16 mL). The resulting solution was stirred for 6 h at room temperature then extracted with 3×50 mL of ethyl acetate. The combined organic layers were dried over anhydrous sodium sulfate and concentrated under vacuum to afford 1.259 g (89%) of 1,1-dimethyl-2-oxaspiro[4.5]decan-8-one as a light yellow solid.

Step 5: 1,1-dimethyl-2-oxaspiro[4.5]dec-7-en-8-yl trifluoromethanesulfonate

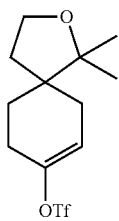 [SMILES: CC1(C)OCCC12CC=C(OS(=O)(=O)C(F)(F)F)CC2]

To a solution of 1,1-dimethyl-2-oxaspiro[4.5]decan-8-one (1.695 g, 9.30 mmol, 1.00 equiv) in THF (50 mL) at −70° C. under dry nitrogen was added dropwise a solution of LiHMDS (1M in THF, 14 mL). The reaction mixture was stirred for 1 h at −70° C. then treated with 1,1,1-trifluoro-N-phenyl-N-(trifluoromethane) sulfonylmethanesulfona- mide (3.490 g, 9.77 mmol, 1.05 equiv) and stirred at −70° C. for another 0.5 h. The resulting solution was allowed to warm to room temperature and stirred for another 12 hours then concentrated under vacuum. The residue was purified by flash chromatography on silica using ethyl acetate/petroleum ether (2:1) as eluent to afford 2.458 g (84%) of 1,1-dimethyl-2-oxaspiro[4.5]dec-7-en-8-yl trifluoromethanesulfonate as a colorless oil. $^1$H-NMR (300 MHz, CDCl$_3$): δ 5.80-5.70 (m, 1H), 3.95-3.80 (m, 2H), 2.50-2.35 (m, 2H), 2.30-2.15 (m, 1H), 2.10-1.50 (m, 5H).

Step 6: 2-[1,1-dimethyl-2-oxaspiro[4.5]dec-7-en-8-yl]-4,4,5,5-tetramethyl-1,3,2-dioxaborolane

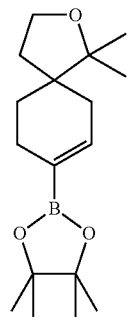

Into a 50-mL round-bottom flask purged and maintained with an inert atmosphere of nitrogen was placed 1,1-dimethyl-2-oxaspiro[4.5]dec-7-en-8-yl trifluoromethanesulfonate (1.472 g, 4.68 mmol, 1.00 equiv), 4,4,4',4',5,5,5',5'-octamethyl-2,2'-bi(1,3,2-dioxaborolane) (1.786 g), 1,4-dioxane (20 mL), potassium acetate (1.378 g, 14.04 mmol, 3.00 equiv) and PdCl$_2$(dppf) (343 mg). The resulting solution was stirred for 12 h at 100° C. then quenched by the addition of 10 mL of water/ice. The resulting solution was extracted with 200 mL of ethyl acetate and the combined organic layers washed with 50 mL of brine, dried over anhydrous sodium sulfate and concentrated under vacuum. The residue was purified by flash chromatography on silica gel using ethyl acetate/petroleum ether (2:1) as eluent to afford 715 mg (52%) of 2-[1,1-dimethyl-2-oxaspiro[4.5]dec-7-en-8-yl]-4,4,5,5-tetramethyl-1,3,2-dioxaborolane as a white solid.

Step 7: (R/S) tert-butyl N-(2-[[(3-[1,1-dimethyl-2-oxaspiro[4.5]dec-7-en-8-yl]-1-(oxan-2-yl)-1H-pyrazol-4-yl)methyl](methyl)amino]ethyl)-N-methylcarbamate

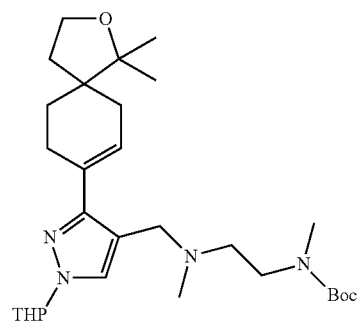

Into a 50-mL round-bottom flask purged and maintained with an inert atmosphere of nitrogen was placed 2-[1,1-dimethyl-2-oxaspiro[4.5]dec-7-en-8-yl]-4,4,5,5-tetramethyl-1,3,2-dioxaborolane (1.164 g, 3.98 mmol, 1.00 equiv), tert-butyl N-[2-([[3-iodo-1-(oxan-2-yl)-1H-pyrazol-4-yl]methyl](methyl)amino)ethyl]-N-methylcarbamate (2.096 g, 4.38 mmol, 1.10 equiv), potassium carbonate (1.650 g, 11.94 mmol, 3.00 equiv), 1,4-dioxane (20 mL), water (2 mL) and PdCl$_2$(dppf) (292 mg). The resulting solution was stirred for 16 h at 100° C. then quenched by the addition of 10 mL of water/ice. The resulting solution was extracted with 100 mL of ethyl acetate and the organic layer separated and washed with 50 mL of brine, dried over anhydrous sodium sulfate and then concentrated under vacuum. The residue was purified by flash chromatography on silica gel column using ethyl acetate/petroleum ether (1:1) as eluent to afford 1.081 g (53%) of (R/S) tert-butyl N-(2-[[(3-[1,1-dimethyl-2-oxaspiro[4.5]dec-7-en-8-yl]-1-(oxan-2-yl)-1H-pyrazol-4yl)methyl](methyl)amino]ethyl)-N-methylcarbamate as a yellow oil.

Step 8 (R/S) tert-butyl N-(2-[[(3-[1,1-dimethyl-2-oxaspiro[4.5]decan-8-yl]-1-(oxan-2-yl)-1H-pyrazol-4-yl)methyl](methyl)amino]ethyl)-N-methylcarbamate

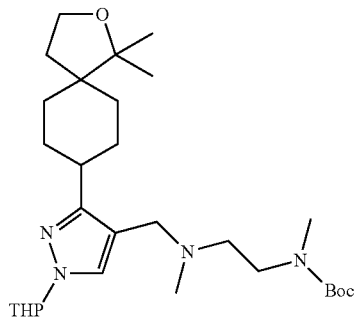

Into a 100-mL round-bottom flask purged and maintained with an inert atmosphere of nitrogen was placed (R/S) tert-butyl N-(2-[[(3-[1,1-dimethyl-2-oxaspiro[4.5]dec-7-en-8-yl]-1-(oxan-2-yl)-1H-pyrazol-4yl)methyl](methyl)amino]ethyl)-N-methylcarbamate (1.081 g, 2.09 mmol, 1.00 equiv), tetrahydrofuran (25 mL), and 10% Pd(OH)$_2$/C (400 mg, 2.85 mmol, 1.36 equiv). The resulting solution was stirred for 5 h at room temperature under 3 atmospheres of hydrogen. The resulting mixture was filtered and the filtrate concentrated under vacuum to afford 860 mg (79%) of (R/S) tert-butyl N-(2-[[(3-[1,1-dimethyl-2-oxaspiro[4.5]decan-8-yl]-1-(oxan-2-yl)-1H-pyrazol-4-yl)methyl](methyl)amino]ethyl)-N-methylcarbamate as a light yellow oil.

Step 9: Methyl[2-(methylamino)ethyl]([3-[(5R,8S)-1,1-dimethyl-2-oxaspiro[4.5]decan-8-yl]-1H-pyrazol-4-yl]methyl)amine (Compound 106)

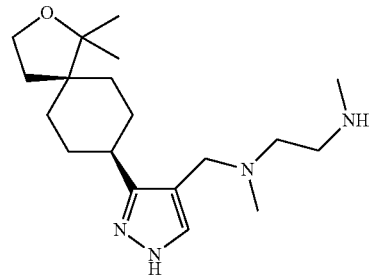 [SMILES: CNCCN(C)Cc1c[nH]nc1[C@H]1CC[C@@]2(CCOC2(C)C)CC1]

A solution of (R/S) tert-butyl N-(2-[[(3-[1,1-dimethyl-2-oxaspiro[4.5]decan-8-yl]-1-(oxan-2-yl)-1H-pyrazol-4-yl)methyl](methyl)amino]ethyl)-N-methylcarbamate (400 mg, 1.20 mmol, 1.00 equiv) in methanol (6 mL) was treated with hydrochloric acid (12N, 2 mL) and stirred for 1 h at room temperature then for an additional 2 h at 50° C. The reaction was then quenched by the addition of 20 mL of sodium bicarbonate (sat. aq.) and the resulting mixture concentrated under vacuum to remove the majority of the methanol. The resulting solution was extracted with 2×30 mL of dichloromethane and the organic layers combined and dried over anhydrous sodium sulfate and concentrated under vacuum. The crude product (200 mg) was purified by Chiral prep-HPLC. Column: IC4.6×100 nm, Size: 0.46×10 cm, 5 μm; Mobile phase: Hex (0.2% IPA): IPA=85:15; Flow: 1.0 ml/min; Detector: UV-220 nm; Instrument: LC-05; Temperature: 25° C. This resulted in 32.6 mg of methyl[2-(methylamino)ethyl]([3-[(5R,8R)-1,1-dimethyl-2-oxaspiro[4.5]decan-8-yl]-1H-pyrazol-4-yl]methyl)amine as a colorless solid. $^1$H-NMR (300 MHz, D$_2$O): δ 7.50 (s, 1H), 3.76 (t, J=7.5 Hz, 2H), 3.42 (s, 2H), 2.80-2.45 (m, 5H), 2.31 (s, 3H), 2.12 (s, 3H), 2.01 (t, J=7.5 Hz, 2H), 1.80-1.25 (m, 8H), 1.05 (s, 6H) ppm. LCMS (method A11, ESI): RT=1.44 min, m/z=335.0 [M+H]$^+$.

Compound 133 & 134

Methyl[2-(methylamino)ethyl]([3-[(5s,8s)-3,3-dimethyl-1-oxaspiro[4.5]decan-8-yl]-1H-pyrazol-4-yl]methyl)amine and methyl[2-(methylamino)ethyl]([3-[(5r,8r)-3,3-dimethyl-1-oxaspiro[4.5]decan-8-yl]-1H-pyrazol-4-yl]methyl)amine

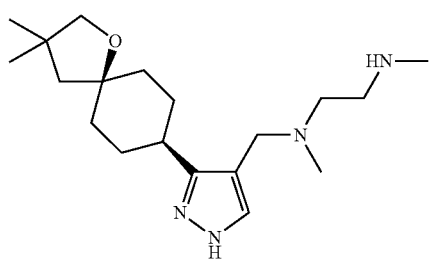

357
-continued

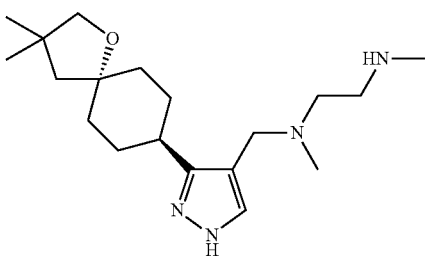

Step 1: 3-(benzyloxy)-2,2-dimethylpropan-1-ol

Into a 250-mL round-bottom flask, was placed 2,2-dimethylpropane-1,3-diol (10.4 g, 99.86 mmol) and N,N-dimethylformamide (100 mL). This was followed by the addition of 60% sodium hydride (4 g, 100.00 mmol), in portions at 0° C. To this was added (bromomethyl)benzene (13.68 g, 79.98 mmol) at 0° C. The resulting solution was stirred for 12 h at room temperature and then diluted with 200 mL of NH$_4$Cl (sat. aq). The resulting solution was extracted with 2×200 mL of ethyl acetate and the organic layers were combined and dried over anhydrous sodium sulfate and concentrated under vacuum. The residue was purified by silica gel column with ethyl acetate/petroleum ether (1:10) to obtain 12 g (62%) of 3-(benzyloxy)-2,2-dimethylpropan-1-ol as light yellow oil. 1H NMR (300 MHz, DMSO-d$_6$): δ7.43-7.24 (m, 5H), 4.51-4.41 (m, 3H), 3.25-3.15 (m, 4H), 0.84 (s, 6H) ppm.

Step 2: [(3-iodo-2,2-dimethylpropoxy)methyl]benzene

Into a 250-mL round-bottom flask, was placed 3-(benzyloxy)-2,2-dimethylpropan-1-ol (4 g, 20.59 mmol), imidazole (2.80 g, 41.18 mmol), triphenylphosphine (8.1 g, 30.88 mmol), and tetrahydrofuran (100 mL). This was followed by the addition of iodine (7.85 g, 30.93 mmol) in portions at 0° C. The resulting solution was stirred for 12 h at room temperature and then for an additional 4 hours at 80° C. and then concentrated under vacuum. The residue was purified by silica gel column with petroleum ether to obtain 6 g (96%) of [(3-iodo-2,2-dimethylpropoxy)methyl]benzene as colorless oil. 1H NMR (300 MHz, DMSO-d$_6$): δ7.42-7.20 (m, 5H), 4.49 (s, 2H), 3.30 (s, 2H), 3.24 (s, 2H), 1.00 (s, 6H) ppm.

358
Step 3: 8-[3-(benzyloxy)-2,2-dimethylpropyl]-1,4-dioxaspiro[4.5]decan-8-ol

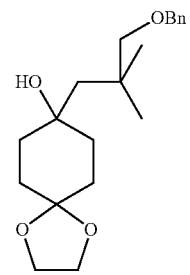 [SMILES: CC(C)(COCc1ccccc1)CC1(O)CCC2(CC1)OCCO2]

Into a 250-mL 3-necked round-bottom flask that was maintained with an atmosphere of nitrogen, was placed tetrahydrofuran (30 mL). This was followed by the addition of t-BuLi (1.3M in pentane, 40 mL) dropwise with stirring at −78° C. To this was added a solution of [(3-iodo-2,2-dimethylpropoxy)methyl]benzene (6.08 g, 20.00 mmol) in tetrahydrofuran (30 mL) dropwise with stirring at −78° C. and the resulting mixture was stirred at −78° C. for 1 h. To the mixture was added a solution of 1,4-dioxaspiro[4.5]decan-8-one (4.69 g, 30.00 mmol, 1.50 equiv) in tetrahydrofuran (30 mL) dropwise with stirring at −78° C. The resulting solution was stirred for 1 h at −78° C., and then was warmed to room temperature slowly. The reaction mixture was diluted with 120 mL of NH$_4$Cl (sat. aq). The organic layer was collected and the aqueous layer was extracted with 2×100 mL of ethyl acetate and the organic layers were combined and dried over anhydrous sodium sulfate and concentrated under vacuum. The residue was applied onto a C18 gel column with H$_2$O/CH$_3$CN (3:7) to obtain 3.5 g (52%) of 8-[3-(benzyloxy)-2,2-dimethylpropyl]-1,4-dioxaspiro[4.5]decan-8-ol as light yellow oil. $^1$H NMR (400 MHz, DMSO-d$_6$): δ 7.42-7.20 (m, 5H), 4.46 (s, 2H), 3.92 (s, 1H), 3.82 (s, 4H), 3.21 (s, 2H), 1.80-1.67 (m, 2H), 1.66-1.55 (m, 2H), 1.55-1.45 (m, 2H), 1.5-1.35 (m, 4H), 1.00 (s, 6H) ppm.

Step 4: 8-(3-hydroxy-2,2-dimethylpropyl)-1,4-dioxaspiro[4.5]decan-8-ol

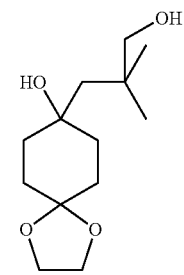

Into a 100-mL round-bottom flask, was placed 8-[3-(benzyloxy)-2,2-dimethylpropyl]-1,4-dioxaspiro[4.5]decan-8-ol (3.35 g, 10.02 mmol), tetrahydrofuran (40 mL), and 10% palladium/carbon (0.34 g). This was followed by the addition of formic acid (3.5 mL) dropwise with stirring. Hydrogen (3 atm) was then applied to the reaction mixture and the resulting solution stirred for 4 h at room temperature. The solids were removed by filtration and the solution was concentrated under vacuum. The residue was purified by silica gel column with ethyl acetate/petroleum ether (1:1) to obtain 1.5 g (61%) of 8-(3-hydroxy-2,2-dimethylpropyl)-1,4-dioxaspiro[4.5]decan-8-ol as a white solid. $^1$H NMR (300 MHz, DMSO-d$_6$): δ 4.85 (t, J=5.4 Hz, 1H), 4.48 (s, 1H), 3.82 (s, 4H), 3.17 (d, J=5.4 Hz, 2H), 1.83-1.58 (m, 4H), 1.58-1.35 (m, 6H), 0.90 (s, 6H) ppm.

Step 5: 11,11-dimethyl-1,4,9-trioxadispiro[4.2.4ˆ[8].2ˆ[5]]tetradecane

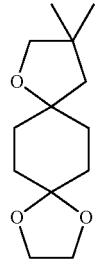

Into a 250-mL round-bottom flask purged and maintained with an inert atmosphere of nitrogen, was placed 8-(3-hydroxy-2,2-dimethylpropyl)-1,4-dioxaspiro[4.5]decan-8-ol (4 g, 16.37 mmol), tributylphosphane (6.62 g, 32.72 mmol), and tetrahydrofuran (60 mL). A solution of TMAD (5.64 g, 32.75 mmol) in tetrahydrofuran (80 mL) was added dropwise with stirring at −40° C. The reaction mixture was stirred for 1 h at −40° C. and then an additional 12 h at room temperature. The resulting mixture was concentrated under vacuum. The residue was purified by silica gel column with ethyl acetate/petroleum ether (1:4) to obtain 3.2 g (86%) of 11,11-dimethyl-1,4,9-trioxadispiro[4.2.4ˆ[8].2ˆ[5]]tetradecane as colorless oil. $^1$H NMR (400 MHz, DMSO-d$_6$): δ3.83 (s, 4H), 3.38 (s, 2H), 1.78-1.63 (m, 4H), 1.63-1.42 (m, 6H), 1.03 (s, 6H) ppm.

Step 6: 3,3-dimethyl-1-oxaspiro[4.5]decan-8-one

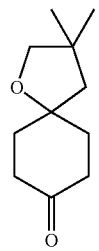

Into a 100-mL round-bottom flask, was placed 11,11-dimethyl-1,4,9-trioxadispiro[4.2.4ˆ[8].2ˆ[5]]tetradecane (2.0 g, 8.84 mmol, 1.00 equiv), tetrahydrofuran (45 mL), and hydrochloric solution (15 mL of a 3M solution in tetrahydrofuran). The resulting solution was stirred for 24 h at room temperature and then the tetrahydrofuran was removed under vacuum. The resulting solution was extracted with 3×50 mL of ethyl acetate and the combined organic layers was washed with 1×25 mL of Na$_2$CO$_3$ (sat. aq.), dried over anhydrous sodium sulfate and concentrated under vacuum to obtain 1.4 g (87%) of 3,3-dimethyl-1-oxaspiro[4.5]decan-8-one as light yellow oil. $^1$H NMR (300 MHz, CDCl$_3$): δ3.58 (s, 2H), 2.78-2.60 (m, 2H), 2.32-2.17 (m, 2H), 2.17-2.05 (m, 2H), 1.92-1.75 (m, 2H), 1.88 (s, 2H) 1.15 (s, 6H) ppm.

Step 7: 3,3-dimethyl-1-oxaspiro[4.5]dec-7-en-8-yl trifluoromethanesulfonate

Into a 250-mL round-bottom flask purged and maintained with an inert atmosphere of nitrogen, was placed LiHMDS (12 mL of a 1 M solution in tetrahydrofuran). A solution of 3,3-dimethyl-1-oxaspiro[4.5]decan-8-one (1.46 g, 8.01 mmol) in tetrahydrofuran (10 mL) was added at −50° C. and the reaction mixture stirred at −50° C. for 15 min. To this was added a solution of 1,1,1-trifluoro-N-phenyl-N-(trifluoromethane)sulfonylmethanesulfonamide (2.86 g, 8.01 mmol) in tetrahydrofuran (30 mL) at −50° C. The resulting solution was stirred for 1 h at −50° C. and then for an additional 1 h at room temperature. The resulting mixture was concentrated under vacuum. The residue was purified by silica gel column with ethyl acetate/petroleum ether (1:9) to obtain 1.23 g (49%) of 3,3-dimethyl-1-oxaspiro[4.5]dec-7-en-8-yl trifluoromethanesulfonate as light yellow oil. $^1$H NMR (300 MHz, CDCl$_3$): δ5.64 (d, J=2.7 Hz, 1H), 3.57-3.50 (m, 2H), 2.69-2.50 (m, 1H), 2.50-2.22 (m, 3H), 2.01-1.87 (m, 1H), 1.85-1.72 (m, 1H), 1.72-1.51 (m, 2H), 1.12 (s, 6H) ppm.

Step 8: 2-[3,3-dimethyl-1-oxaspiro[4.5]dec-7-en-8-yl]-4,4,5,5-tetramethyl-1,3,2-dioxaborolane

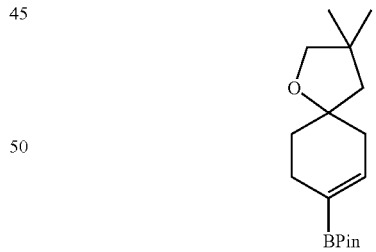

Into a 50-mL round-bottom flask purged and maintained with an inert atmosphere of nitrogen, was placed 3,3-dimethyl-1-oxaspiro[4.5]dec-7-en-8-yl trifluoromethanesulfonate (1.26 g, 4.01 mmol), 4,4,5,5-tetramethyl-2-(tetramethyl-1,3,2-dioxaborolan-2-yl)-1,3,2-dioxaborolane (1.22 g, 4.80 mmol), 1,4-dioxane (15 mL), potassium acetate (1.18 g, 12.02 mmol), and PdCl$_2$(dppf)CH$_2$Cl$_2$ (327 mg, 0.40 mmol). The resulting solution was stirred for 15 h at 100° C. and then concentrated under vacuum. The residue was purified by silica gel column with ethyl acetate/petroleum ether (10:1) to obtain 0.97 g (83%) of 2-[3,3-dimethyl-1-oxaspiro[4.5]dec-7-en-8-yl]-4,4,5,5-tetramethyl-1,3,2-dioxaborolane as yellow oil. $^1$H NMR (400 MHz, CDCl$_3$): δ6.46 (d, J=1.6 Hz, 1H), 3.52 (s, 2H), 2.50-2.07 (m, 4H), 1.80-1.54 (m, 4H), 1.26 (s, 12H), 1.11 (s, 6H) ppm.

Step 9: 3-[3,3-dimethyl-1-oxaspiro[4.5]dec-7-en-8-yl]-1-(oxan-2-yl)-1H-pyrazole-4-carbaldehyde

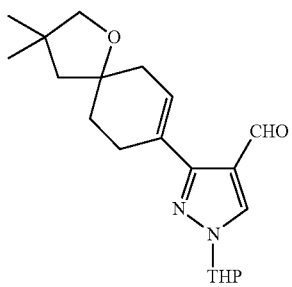

Into a 20-mL sealed tube purged and maintained with an inert atmosphere of nitrogen, was placed 3-iodo-1-(oxan-2-yl)-1H-pyrazole-4-carbaldehyde (964 mg, 3.15 mmol), 2-[3,3-dimethyl-1-oxaspiro[4.5]dec-7-en-8-yl]-4,4,5,5-tetramethyl-1,3,2-dioxaborolane (920 mg, 3.15 mmol), Cs$_2$CO$_3$ (3080 mg, 9.45 mmol), 1,4-dioxane/H$_2$O (v/v=10:1) (10 mL), and PdCl$_2$(dppf)CH$_2$Cl$_2$ (257 mg, 0.31 mmol). The resulting solution was stirred for 15 h at 100° C. and then concentrated under vacuum. The resulting residue was diluted with 50 mL of H$_2$O and then the mixture was extracted with 2×30 mL of ethyl acetate and the organic layers were combined and dried over anhydrous sodium sulfate and concentrated under vacuum. The residue was purified by silica gel column with ethyl acetate/petroleum ether (1:2) to obtain 630 mg (58%) of 3-[3,3-dimethyl-1-oxaspiro[4.5]dec-7-en-8-yl]-1-(oxan-2-yl)-1H-pyrazole-4-carbaldehyde as yellow oil. LCMS: m/z=345.2[M+1]; $^1$H NMR (400 MHz, CDCl$_3$): δ9.90 (s, 1H), 8.13 (s, 1H), 6.30-6.20 (m, 1H), 5.40-5.30 (m, 1H), 4.15-4.00 (m, 1H), 3.78-3.64 (m, 1H), 3.57 (s, 2H), 2.86-2.30 (m, 4H), 2.20-1.86 (m, 4H), 1.86-1.60 (m, 6H), 1.13 (s, 6H) ppm.

Step 10: tert-butyl N-(2-[[(3-[3,3-dimethyl-1-oxaspiro[4.5]dec-7-en-8-yl]-1-(oxan-2-yl)-1H-pyrazol-4-yl)methyl](methyl)amino]ethyl)-N-methylcarbamate

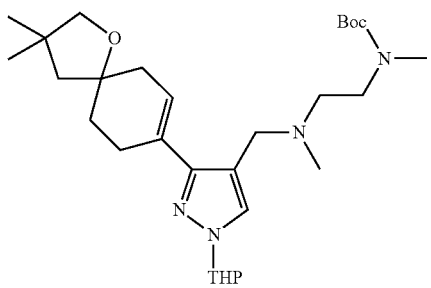

Into a 100-mL round-bottom flask, was placed 3-[3,3-dimethyl-1-oxaspiro[4.5]dec-7-en-8-yl]-1-(oxan-2-yl)-1H-pyrazole-4-carbaldehyde (630 mg, 1.83 mmol), tert-butyl N-methyl-N-[2-(methylamino)ethyl]carbamate (516 mg, 2.74 mmol), ClCH$_2$CH$_2$Cl (20 mL), and NaBH(AcO)$_3$ (3.1 g, 14.62 mmol). The resulting solution was stirred for 5 h at 0° C. and then quenched by the addition of 30 mL of Na$_2$CO$_3$ (sat. aq.). The resulting solution was extracted with 3×50 mL of ethyl acetate and the organic layers combined and dried over anhydrous sodium sulfate and concentrated under vacuum. The residue was purified by silica gel column with ethyl acetate/petroleum ether (3:2) to obtain 720 mg (76%) of tert-butyl N-(2-[[(3-[3,3-dimethyl-1-oxaspiro[4.5]dec-7-en-8-yl]-1-(oxan-2-yl)-1H-pyrazol-4-yl)methyl](methyl)amino]ethyl)-N-methylcarbamate as light yellow oil. LCMS: m/z=517.5 [M+1]; $^1$H NMR (400 MHz, CDCl$_3$): δ7.46 (s, 1H), 6.07 (s, 1H), 5.45-5.35 (m, 1H), 4.10-4.00 (m, 1H), 3.72-3.62 (m, 1H), 3.60-3.50 (m, 2H), 3.45-3.20 (m, 4H), 2.83 (s, 3H), 2.77-2.64 (m, 1H), 2.64-2.28 (m, 5H), 2.22 (s, 3H), 2.13-1.96 (m, 3H), 1.90-1.52 (m, 7H), 1.32 (s, 9H), 1.13 (s, 3H), 1.11 (s, 3H) ppm.

Step 11: tert-butyl N-(2-[[(3-[3,3-dimethyl-2-oxaspiro[4.5]decan-8-yl]-1-(oxan-2-yl)-1H-pyrazol-4-yl)methyl](methyl)amino]-ethyl)-N-methylcarbamate

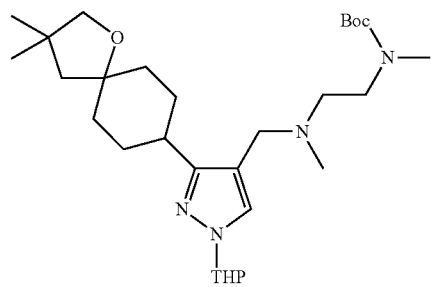

Into a 30-mL pressure tank reactor, was placed tert-butyl N-(2-[[(3-[3,3-dimethyl-2-oxaspiro[4.5]dec-7-en-8-yl]-1-(oxan-2-yl)-1H-pyrazol-4-yl)methyl](methyl)amino]ethyl)-N-methylcarbamate (720 mg, 1.39 mmol), acetic acid (10 mL), and 10% palladium/carbon (100 mg). The reaction mixture was then subjected to hydrogen gas (pressure 10 atm) and stirred for 6 h at 50° C. The solids were removed by filtration and the solution was concentrated under vacuum to obtain 1 g (97%) of tert-butyl N-(2-[[(3-[3,3-dimethyl-2-oxaspiro[4.5]decan-8-yl]-1-(oxan-2-yl)-1H-pyrazol-4-yl)methyl](methyl)amino]-ethyl)-N-methylcarbamate as light yellow oil.

Step 12: Methyl[2-(methylamino)ethyl]([3-[(5s,8s)-3,3-dimethyl-1-oxaspiro[4.5]decan-8-yl]-1H-pyrazol-4-yl]methyl)amine and methyl[2-(methylamino)ethyl]([3-[(5r,8r)-3,3-dimethyl-1-oxaspiro[4.5]decan-8-yl]-1H-pyrazol-4-yl]methyl)amine (Compound 134 & Compound 135)

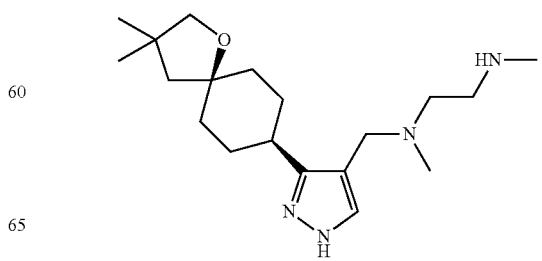

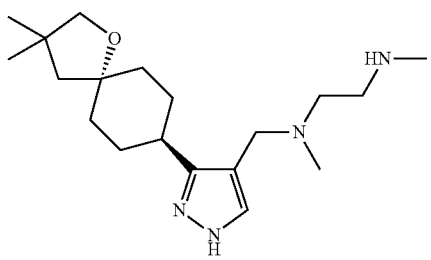

Into a 50-mL round-bottom flask, was placed tert-butyl N-(2-[[(3-[3,3-dimethyl-1-oxaspiro[4.5]decan-8-yl]-1-(oxan-2-yl)-1H-pyrazol-4-yl)methyl](methyl)amino]ethyl)-N-methylcarbamate (1 g, 1.93 mmol), and hydrogen chloride/methanol (saturated, 10 mL). The resulting solution was stirred for 5 h at room temperature and then concentrated under vacuum. The residue was purified by Prep-HPLC with the following conditions (Prep-HPLC-045): Column, Jupiter 4u Proteo 90A, AXIA Packed, 21.2×250 mm 4 um 9 nm; mobile phase, water with 0.05% TFA and ACN (5.0% ACN up to 30.0% in 8 min, hold 30.0% in 2 min); Detector, UV 220 nm. This resulted in 480.8 mg (44%) of methyl[2-(methylamino)ethyl]([3-[(5 s,8 s)-3,3-dimethyl-1-oxaspiro[4.5]decan-8-yl]-1H-pyrazol-4-yl]methyl)amine trifluoroacetate salt as a white semi-solid; LCMS: m/z=335.2 [M+1]; $^1$H NMR (300 MHz, D$_2$O): δ7.73 (s, 1H), 4.28 (s, 2H), 3.50-3.40 (m, 6H), 2.74-2.68 (m, 7H), 1.90-1.86 (m, 2H), 1.68-1.42 (m, 8H) 1.00 (s, 6H) ppm. And 152.6 mg (14%) of methyl[2-(methylamino)ethyl]([3-[(5r,8r)-3,3-dimethyl-1-oxaspiro[4.5]decan-8-yl]-1H-pyrazol-4-yl]methyl)amine trifluoroacetate salt as a white semi-solid; LCMS: m/z=335.2 [M+1];]; $^1$H NMR (300 MHz, D$_2$O): δ7.73 (s, 1H), 4.28 (s, 2H), 3.46-3.34 (m, 6H), 2.74-2.69 (m, 7H), 1.83-1.75 (m, 4H), 1.70 (m, 2H), 1.57-1.46 (m, 4H), 1.00 (s, 6H) ppm.

Compound 158

([3-[4,4-bis(ethoxymethyl)cyclohexyl]-1H-pyrazol-4-yl]methyl)(methyl) [2-(methylamino)ethyl]amine hydrochloride salt

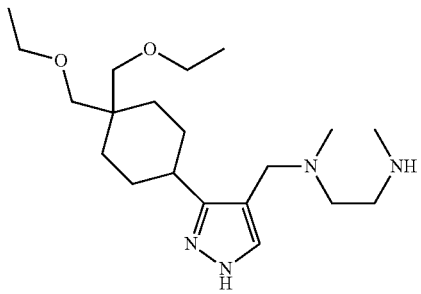 [SMILES: CCOCC1(COCC)CCC(c2n[nH]cc2CN(C)CCNC)CC1]

Step 1: ethyl 1,4-dioxaspiro[4.5]decane-8-carboxylate

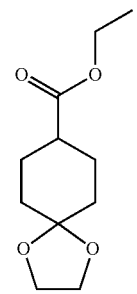

Into a 500-mL round-bottom flask was placed ethyl 4-oxocyclohexane-1-carboxylate (150 g, 881.29 mmol, 1.00 equiv), cyclohexane (300 mL), H$_2$NSO$_3$H (3 g) and ethane-1,2-diol (65.7 g, 1.06 mol, 1.20 equiv). The resulting solution was stirred overnight at 100° C. and then diluted with 300 mL of ethyl acetate. The resulting mixture was washed with 2×200 mL of brine and then concentrated under vacuum. This resulted in 152 g (80%) of ethyl 1,4-dioxaspiro[4.5]decane-8-carboxylate as yellow oil. $^1$H-NMR (300 MHz, CDCl$_3$): δ 4.05 (q, J=7.1 Hz, 2H), 3.95 (s, 4H), 2.44-2.23 (m, 1H), 2.00-1.70 (m, 6H), 1.65-1.47 (m, 2H), 1.25 (t, J=7.1 Hz, 3H) ppm.

Step 2: 8,8-diethyl 1,4-dioxaspiro[4.5]decane-8,8-dicarboxylate

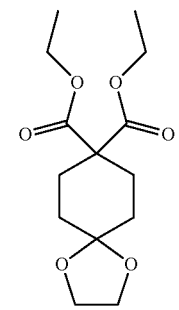 [SMILES: CCOC(=O)C1(C(=O)OCC)CCC2(CC1)OCCO2]

Into a 2-L 3-necked round-bottom flask purged and maintained with an inert atmosphere of nitrogen was placed (i-Pr)$_2$NH (45.2 g) and tetrahydrofuran (1500 mL). Then n-BuLi (2.5M in hexane, 179.8 mL) was added dropwise at −50° C. The resulting mixture was reacted for 30 min at −50° C. Then ethyl 1,4-dioxaspiro[4.5]decane-8-carboxylate (80 g, 373.38 mmol, 1.00 equiv) was added into mixture at −78° C. After 1 hour, chloro(ethoxy)methanone (60 g, 552.87 mmol, 1.48 equiv) was added dropwise at −78° C. The resulting solution was stirred for another 30 min at −78° C. The reaction was then quenched by the addition of 500 mL of water. The resulting solution was extracted with 3×800 mL of ethyl acetate and the organic layers combined and concentrated under vacuum. This resulted in 82 g (77%) of 8,8-diethyl 1,4-dioxaspiro[4.5]decane-8,8-dicarboxylate as light yellow oil. $^1$H-NMR (400 MHz, CDCl$_3$): δ 4.18 (q, J=7.1 Hz, 4H), 3.94 (s, 4H), 2.18 (t, J=6.2 Hz, 4H), 1.69 (t, J=6.2 Hz, 4H), 1.25 (t, J=7.1 Hz, 6H) ppm.

Step 3: [8-(hydroxymethyl)-1,4-dioxaspiro[4.5]decan-8-yl]methanol

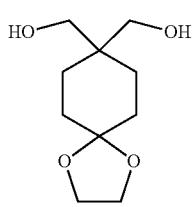

Into a 2500-mL 3-necked round-bottom flask purged and maintained with an inert atmosphere of nitrogen was placed LiAlH$_4$ (47.9 g, 1.26 mol, 4.02 equiv) and tetrahydrofuran (1 L). This was followed by the addition of 8,8-diethyl 1,4-dioxaspiro[4.5]decane-8,8-dicarboxylate (90 g, 314.33 mmol, 1.00 equiv) in tetrahydrofuran (200 mL) dropwise with stirring at −20° C. The resulting solution was stirred overnight at room temperature. The reaction was then quenched by the addition of 500 g of Na$_2$SO$_4$.10H$_2$O. The solids were filtered out. The resulting mixture was concentrated under vacuum to give 35 g (55%) of [8-(hydroxymethyl)-1,4-dioxaspiro[4.5]decan-8-yl]methanol as a white solid. $^1$H-NMR (300 MHz, MeOD): δ 3.94 (s, 4H), 3.49 (s, 4H), 1.69-1.59 (m, 4H), 1.59-1.44 (m, 4H) ppm.

Step 4: 8,8-bis(ethoxymethyl)-1,4-dioxaspiro[4.5]decane

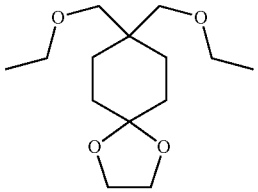 [SMILES: CCOCC1(COCC)CCC2(CC1)OCCO2]

Into a 1000-mL 3-necked round-bottom flask purged and maintained with an inert atmosphere of nitrogen was placed [8-(hydroxymethyl)-1,4-dioxaspiro[4.5]decan-8-yl]methanol (35 g, 173.06 mmol, 1.00 equiv) and N,N-dimethylformamide (400 mL). This was followed by the addition of sodium hydride (21 g, 525.00 mmol, 3.03 equiv, 60%), in portions at 0° C. The mixture was stirred for 30 min at room temperature. To this was added iodoethane (108 g, 692.46 mmol, 4.00 equiv) dropwise with stirring. The resulting solution was stirred overnight at room temperature. The reaction was then quenched by the addition of 300 mL of water. The resulting solution was extracted with 3×200 mL of ethyl acetate and the organic layers combined. The resulting mixture was washed with 300 mL of brine. The mixture was dried over anhydrous sodium sulfate and concentrated under vacuum. The residue was purified by silica gel column with ethyl acetate/petroleum ether (1:20). This resulted in 30 g (67%) of 8,8-bis(ethoxymethyl)-1,4-dioxaspiro[4.5]decane as yellow oil. $^1$H-NMR (300 MHz, CDCl$_3$) δ: 3.93 (s, 4H), 3.46 (q, J=7.0 Hz, 4H), 3.29 (s, 4H), 1.65-1.50 (m, 8H), 1.16 (t, J=7.0 Hz, 6H) ppm.

Step 5: 4,4-bis(ethoxymethyl)cyclohexan-1-one

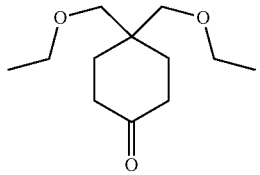

Into a 1000-mL round-bottom flask, was placed 8,8-bis(ethoxymethyl)-1,4-dioxaspiro[4.5]decane (30 g, 116.12 mmol, 1.00 equiv), FeCl$_3$-6H$_2$O (62 g, 230.48 mmol, 1.98 equiv) and dichloromethane (300 mL). The resulting solution was stirred overnight at room temperature. The resulting mixture was washed with 3×150 mL of water and 150 mL of Na$_2$CO$_3$ (sat. aq.). The resulting mixture was washed with 150 mL of brine. The mixture was dried over anhydrous sodium sulfate and concentrated under vacuum to give 22.8 g (92%) of 4,4-bis(ethoxymethyl)cyclohexan-1-one as yellow oil. $^1$H-NMR (300 MHz, CDCl$_3$) δ: 3.46 (q, J=7.0 Hz, 4H), 3.37 (s, 4H), 2.36 (t, J=14.1 Hz, 4H), 1.77 (t, J=14.1 Hz, 4H), 1.18 (t, J=7.0 Hz, 6H) ppm.

Step 6: 4,4-bis(ethoxymethyl)cyclohex-1-en-1-yl trifluoromethanesulfonate

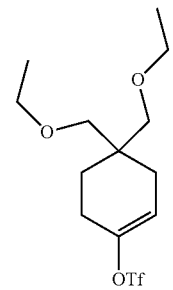 [SMILES: CCOCC1(COCC)CC=C(OS(=O)(=O)C(F)(F)F)CC1]

Into a 1-L 3-necked round-bottom flask purged and maintained with an inert atmosphere of nitrogen was placed 4,4-bis(ethoxymethyl)cyclohexan-1-one (22.8 g, 106.39 mmol, 1.00 equiv) and THF (400 mL). This was followed by the addition of LiHMDS (1M in THF, 117.2 mL) dropwise with stirring at −50° C. The resulting solution was stirred for 1 hr. at −30° C. To this was added a solution of 1,1,1-trifluoro-N-phenyl-N-(trifluoromethane) sulfonylmethanesulfonamide (41.8 g, 117.00 mmol, 1.10 equiv) in tetrahydrofuran (40 mL) dropwise with stirring at −30° C. The resulting solution was allowed to react, with stirring, for an additional 4 hrs. at room temperature. The reaction was then quenched by the addition of 100 mL of NH$_4$Cl (sat. aq.). The resulting solution was extracted with 2×100 mL of ethyl acetate and the organic layers combined. The resulting mixture was concentrated under vacuum. The residue was purified by silica gel column with petroleum ether (100%) to give 29 g (79%) of 4,4-bis(ethoxymethyl)cyclohex-1-en-1-yl trifluoromethanesulfonate as brown oil. $^1$H-NMR (300 MHz, CDCl$_3$) δ: 5.78-5.61 (m, 1H), 3.44 (q, J=7.0 Hz, 4H), 3.27 (q, J=7.0 Hz, 4H), 2.49-2.21 (m, 2H), 2.20-2.00 (m, 2H), 1.74 (t, J=6.5 Hz, 2H), 1.18 (t, J=7.0 Hz, 6H) ppm.

Step 7: 2-[4,4-bis(ethoxymethyl)cyclohex-1-en-1-yl]-4,4,5,5-tetramethyl-1,3,2-dioxaborolane

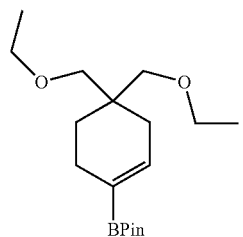

Into a 100-mL round-bottom flask purged and maintained with an inert atmosphere of nitrogen, was placed 4,4-bis(ethoxymethyl)cyclohex-1-en-1-yl trifluoromethanesulfonate (29 g, 83.8 mmol, 1.00 equiv), KOAc (32.4 g, 331 mmol, 3.95 equiv), Pd(dppf)Cl₂ (6.13 g, 8.38 mmol, 0.10 equiv), 4,4,5,5-tetramethyl-2-(tetramethyl-1,3,2-dioxaborolan-2-yl)-1,3,2-dioxaborolane (25.5 g, 100.6 mmol, 1.19 equiv) and 1,4-dioxane (300 mL). The resulting solution was stirred overnight at 100° C. in an oil bath. The reaction was then quenched by the addition of 200 mL of water. The resulting solution was extracted with 3×100 mL of ethyl acetate and the organic layers combined and dried over anhydrous sodium sulfate. The solids were filtered out and the solution concentrated under vacuum. The residue was purified by silica gel column with ethyl acetate/petroleum ether (1:20). This resulted in 22 g (81%) of 2-[4,4-bis(ethoxymethyl)cyclohex-1-en-1-yl]-4,4,5,5-tetramethyl-1,3,2-dioxaborolane as colorless oil. ¹H-NMR (300 MHz, CDCl₃) δ: 6.67-6.35 (m, 1H), 3.44 (q, J=7.0 Hz, 4H), 3.24 (q, J=7.0 Hz, 4H), 2.18-2.05 (m, 2H), 2.03-1.84 (m, 2H), 1.50 (t, J=6.3 Hz, 2H), 1.15 (t, J=7.0 Hz, 6H) ppm.

Step 8: tert-butyl N-[2-[([3-[4,4-bis(ethoxymethyl)cyclohex-1-en-1-yl]-1-(oxan-2-yl)-1H-pyrazol-4-yl]methyl)(methyl)amino]ethyl]-N-methylcarbamate

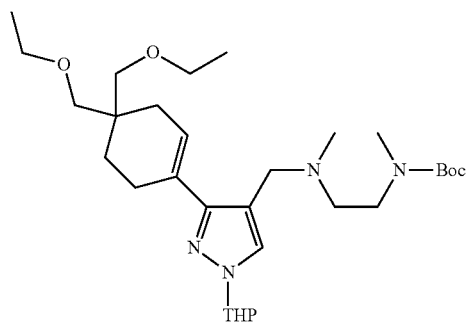

Into a 1-L round-bottom flask purged and maintained with an inert atmosphere of nitrogen was placed 2-[4,4-bis(ethoxymethyl)cyclohex-1-en-1-yl]-4,4,5,5-tetramethyl-1,3,2-dioxaborolane (22 g, 67.85 mmol, 1.00 equiv), Pd(dppf)Cl₂ (3.38 g, 4.62 mmol, 0.07 equiv), potassium carbonate (19.2 g, 138.92 mmol, 2.05 equiv), water (50 mL), tert-butyl N-[2-([3-iodo-1-(oxan-2-yl)-1H-pyrazol-4-yl]methyl(methyl)amino)ethyl]-N-methylcarbamate (18 g, 37.63 mmol, 0.55 equiv) and 1,4-dioxane (500 mL). The resulting solution was stirred overnight at 100° C. in an oil bath. The solids were filtered out. The resulting mixture was concentrated under vacuum. The residue was purified by silica gel column with ethyl acetate/petroleum ether (50%). This resulted in 18 g (48%) of tert-butyl N-[2-[([3-[4,4-bis(ethoxymethyl)cyclohex-1-en-1-yl]-1-(oxan-2-yl)-1H-pyrazol-4-yl]methyl)(methyl)amino]ethyl]-N-methylcarbamate as brown oil. ¹H-NMR (300 MHz, CDCl₃) δ: 7.46 (s, 1H), 6.08 (s, 1H), 5.40-5.22 (m, 1H), 4.12-4.00 (m, 1H), 3.76-3.60 (m, 1H), 3.58-3.20 (m, 8H), 2.83 (s, 3H), 2.57 (s, 3H), 2.45 (s, 2H), 2.15-1.95 (m, 4H), 1.82-1.52 (m, 6H), 1.44 (s, 6H), 1.35 (s, 9H), 1.15 (t, J=7.0 Hz, 6H) ppm.

Step 9: tert-butyl N-[2-[([3-[4,4-bis(ethoxymethyl)cyclohexyl]-1-(oxan-2-yl)-1H-pyrazol-4-yl]methyl)(methyl)amino]ethyl]-N-methylcarbamate

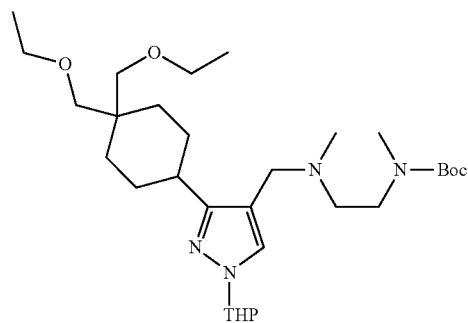

Into a 1-L round-bottom flask, was placed tert-butyl N-[2-[([3-[4,4-bis(ethoxymethyl)cyclohex-1-en-1-yl]-1-(oxan-2-yl)-1H-pyrazol-4-yl]methyl)(methyl)amino]ethyl]-N-methylcarbamate (18.0 g, 32.85 mmol, 1.00 equiv), 10% Pd(OH)₂/C (20 g) and tetrahydrofuran (400 mL). Hydrogen (3 atm) was then applied to the reaction mixture. The resulting solution was stirred for 7 h at room temperature. The solids were filtered out and the solution concentrated under vacuum. The residue was purified by silica gel column with dichloromethane/methanol (3.5%). This resulted in 8.8 g (49%) of tert-butyl N-[2-[([3-[4,4-bis(ethoxymethyl)cyclohexyl]-1-(oxan-2-yl)-1H-pyrazol-4-yl]methyl)(methyl)amino]ethyl]-N-methylcarbamate as yellow oil. ¹H-NMR (400 MHz, CDCl₃) δ: 7.36 (s, 1H), 5.30-5.10 (m, 1H), 4.00-3.85 (m, 1H), 3.68-3.50 (m, 2H), 3.56-3.46 (m, 6H), 3.35-3.27 (m, 4H), 3.14 (s, 2H), 2.77 (s, 3H), 2.69-2.37 (m, 3H), 1.94 (s, 3H), 1.80-1.46 (m, 9H), 1.37 (s, 9H), 1.30-1.15 (m, 4H), 1.10 (t, J=7.0 Hz, 6H) ppm.

Step 10: ([3-[4,4-bis(ethoxymethyl)cyclohexyl]-1H-pyrazol-4-yl]methyl)(methyl)[2-(methylamino)ethyl]amine hydrochloride salt (Compound 158)

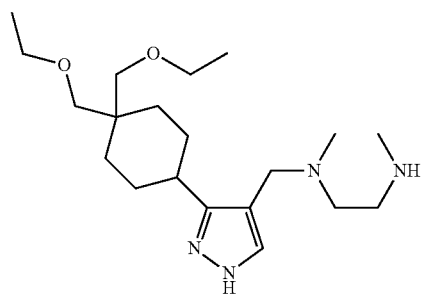 [SMILES: CCOCC1(COCC)CCC(c2n[nH]cc2CN(C)CCNC)CC1]

Into a 500-mL round-bottom flask was placed tert-butyl N-[2-[([3-[4,4-bis(ethoxymethyl)cyclohexyl]-1-(oxan-2-yl)-1H-pyrazol-4-yl]methyl)(methyl)amino]ethyl]-N-methylcarbamate (8.8 g, 15.98 mmol, 1.00 equiv) and dichloromethane (300 mL). Hydrogen chloride gas was bubbled into the reaction mixture. The resulting solution was stirred for 4 h at room temperature and then concentrated under vacuum. The resulting residue was washed with 1 L of hexane. The solids were collected by filtration. This resulted in 5.90 g (84%) of ([3-[4,4-bis(ethoxymethyl)cyclohexyl]-1H-pyrazol-4-yl]methyl)(methyl)[2-(methylamino)ethyl] amine hydrochloride salt as an off-white solid. $^1$H-NMR (300 MHz, D$_2$O) δ: 7.75 (s, 1H), 4.30 (s, 2H), 3.57-3.43 (m, 10H), 3.23 (s, 2H), 2.80-2.67 (m, 7H), 1.64-1.54 (m, 6H), 1.35-1.20 (m, 2H), 1.15-1.05 (m, 6H) ppm. LCMS (method M, ESI), RT=1.25 min, m/z=367.3 [M−2HCl+H]$^+$.

Compound 182

9-[4-({methyl[2-(methylamino)ethyl]amino}methyl)-1H-pyrazol-3-yl]spiro[4.5]decan-6-ol

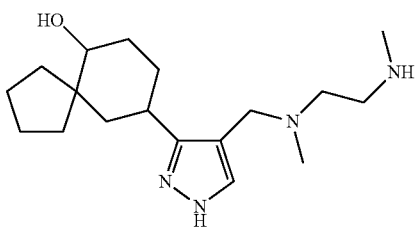 [SMILES: CNCCN(C)Cc1c[nH]nc1C1CCC(O)C2(CCCC2)C1]

Step 1: 1,4-dioxadispiro[4.1.4$^7$.3$^5$]tetradecan-12-one

To a solution of 1,4-dioxaspiro[4.5]decan-8-one (5 g, 32.01 mmol) in toluene (90 ml) was added $^t$BuOK (632.26 mg, 5.63 mmol) and the reaction mixture stirred at room temperature for 5 mins. 1,4-Dibromobutane (4 ml, 33.62 mmol) was added and the reaction was heated at reflux for 20 hours. The reaction was monitored by TLC (heptane:EtOAc 80/20, PMA). The reaction was cooled at room temperature, quenched with an aqueous saturated NH$_4$Cl solution and then diluted with EtOAc. The two layers were separated and the aqueous layer was further extracted with EtOAc (1×). The combined organic layers were washed with water (1×) and brine (1×), dried (MgSO$_4$) and concentrated to give a crude oil. This product was dissolved in a minimum amount of DCM and loaded on a 340 g SNAP KP column and eluted with heptane:EtOAc 6% to 40% on Biotage to give: 3.9 g (58%) of 1,4-dioxadispiro[4.1.4$^7$.3$^5$]tetradecan-12-one. $^1$H-NMR (500 MHz, Chloroform-d) δ 4.02-3.88 (m, 4H), 2.59-2.50 (m, 2H), 2.05 (dd, J=7.9, 4.7 Hz, 2H), 1.99-1.95 (m, 2H), 1.93 (s, 2H), 1.60-1.46 (m, 6H).

Step 2: 1,4-dioxadispiro[4.1.4$^7$.3$^5$]tetradecan-12-ol

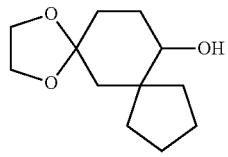 [SMILES: OC1CCC2(CC13CCCC3)OCCO2]

A solution of 1,4-dioxadispiro[4.1.4$^7$.3$^5$]tetradecan-12-one (3.9 g, 18.55 mmol) in MeOH (100 ml) was cooled to 0° C. NaBH$_4$ (1.75 g, 46.37 mmol) was added in small portions. The reaction was left to stir at 0° C. for 1 hour and then quenched with water. The resulting mixture was stirred for 10 mins at room temperature and then diluted with water and EtOAc. The aqueous layer was back extracted with EtOAc and the combined organic layers were washed with water (1×) and brine (2×), dried (MgSO$_4$) filtered and the filtrate was concentrated in vacuo to give an oil, 2.96 g (75%) of 1,4-dioxadispiro[4.1.4$^7$.3$^5$]tetradecan-12-ol. This material was used in the next step without further purification. $^1$H-NMR (500 MHz, Chloroform-d) δ 3.93 (s, 4H), 3.52 (dd, J=6.7, 2.4 Hz, 1H), 1.90-1.76 (m, 3H), 1.77-1.42 (m, 12H).

Step 3: tert-butyl({1,4-dioxadispiro[4.1.4$^7$.3$^5$]tetradecan-12-yloxy})dimethylsilane

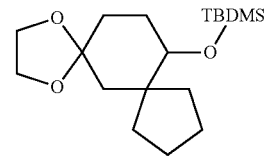

To a solution of 1,4-dioxadispiro[4.1.4$^7$.3$^5$]tetradecan-12-ol (2.96 g, 13.94 mmol) in DMF (40 ml) was added tert-butyl(chloro)dimethylsilane (2.31 g, 15.34 mmol) and 1H-imidazole (1.9 g, 27.89 mmol). The reaction was stirred at room temperature overnight. The reaction mixture was diluted with water and extracted with ether (3×). The combined organic layers were washed with water (2×) and brine (2×), dried (MgSO$_4$), filtered and concentrated to give an oil. This was purified by dissolving in a minimum amount of DCM, loading on a 25 g KP SNAP column, eluting with 5%-35% of EtOAc in heptane to give 3.73 g (82%) of tert-butyl({1,4-dioxadispiro[4.1.4$^7$.3$^5$]tetradecan-12-yloxy})dimethylsilane. $^1$H-NMR (500 MHz, Chloroform-d) δ 3.97-3.83 (m, 4H), 3.44 (dd, J=5.5, 2.2 Hz, 1H), 1.89 (td, J=12.1, 4.0 Hz, 1H), 1.83 (d, J=13.5 Hz, 1H), 1.79-1.46 (m, 9H), 1.43-1.30 (m, 3H), 0.89 (s, 9H), 0.04 (s, 6H).

Step 4: 10-[(tert-butyldimethylsilyl)oxy]spiro[4.5]decan-7-one

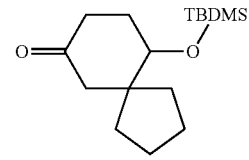

To a solution of tert-butyl({1,4-dioxadispiro[4.1.4$^7$.3$^5$] tetradecan-12-yloxy})dimethylsilane (3.7 g, 11.33 mmol) in DCM (120 ml) was added trichloroiron hexahydrate (15.31 g, 56.65 mmol) and the resulting suspension was stirred at room temperature for 2 hours. The reaction was monitored by TLC (9:1 heptane/EtOAc, DNP stain). The reaction mixture was diluted with DCM, decanted to remove most of the solid inorganics and washed with aqueous saturated NaHCO$_3$ (1×), water (1×), brine (1×), dried over MgSO$_4$, Step 5: 10-[(tert-butyldimethylsilyl)oxy]spiro[4.5]
dec-6-en-7-yl trifluoromethane sulfonate and 10-
[(tert-butyldimethylsilyl)oxy]spiro[4.5]dec-7-en-7-yl
trifluoromethane sulfonate

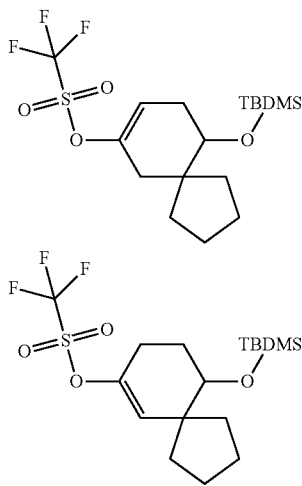

A solution of 10-[(tert-butyldimethylsilyl)oxy]spiro[4.5]decan-7-one (3.2 g, 11.33 mmol) in THF (45 ml) was cooled to −78° C. under nitrogen. A 2M solution of LDA in heptanes-THF (7.9 ml) was added and the resulting solution was stirred at −78° C. for 1 hour. 1,1,1-Trifluoro-N-phenyl-N-[(trifluoromethyl)sulfonyl]methanesulfonamide (4.45 g, 12.46 mmol) was added at −78° C. to the reaction as a solution in THF (15 ml) and the reaction was stirred at −78° C. for 1 hour and then left to warm to room temperature and stir overnight. The reaction was quenched by addition of water and diluted with EtOAc. The combined organic layers were washed with water (1×) and brine (2×), dried (MgSO$_4$), filtered and the filtrate was concentrated in vacuo to give an oil. This material was dissolved in a minimum amount of DCM and was loaded on a 100 g KP SNAP column and eluted with heptane-EtOAc 0% to 25%, to give 2.81 g (60%) of a mixture of 10-[(tert-butyldimethylsilyl)oxy]spiro[4.5]dec-6-en-7-yl trifluoromethanesulfonate and 10-[(tert-butyldimethylsilyl)oxy]spiro[4.5]dec-7-en-7-yl trifluoromethanesulfonate as a clear oil. NMR showed a ratio of 9:1 for the two isomers. $^1$H-NMR (500 MHz, Chloroform-d) δ 5.59 (t, J=3.8 Hz, 0.9H), 5.53 (s, 0.1H), 3.60 (dd, J=6.2, 3.3 Hz, 0.1H), 3.56 (t, J=4.2 Hz, 0.9H), 2.46-2.40 (m, 1H), 2.40-2.32 (m, 1H), 2.13 (ddq, J=17.9, 4.2, 2.2 Hz, 1H), 2.07 (d, J=16.6 Hz, 1H), 1.70-1.57 (m, 5H), 1.46-1.32 (m, 3H), 0.87 (s, 9H), 0.06 (d, J=4.3 Hz, 6H).

Step 6: tert-butyldimethyl{[9-(tetramethyl-1,3,2-dioxaborolan-2-yl)spiro[4.5]dec-8-en-6-yl]oxy}silane and tert-butyldimethyl{[9-(tetramethyl-1,3,2-dioxaborolan-2-yl)spiro[4.5]dec-9-en-6-yl]oxy}silane

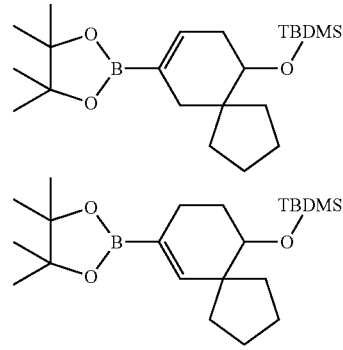

A suspension of 10-[(tert-butyldimethylsilyl)oxy]spiro[4.5]dec-6-en-7-yl trifluoromethanesulfonate and 10-[(tert-butyldimethylsilyl)oxy]spiro[4.5]dec-7-en-7-yl trifluoromethanesulfonate (0.74 g, 2.89 mmol), potassium acetate (1.78 g, 18.09 mmol), bis[3-(diphenylphosphanyl)cyclopenta-2,4-dien-1-yl]iron; dichloromethane, dichloropalladium (99 mg, 0.12 mmol) in 1,4-dioxane (10 ml) was purged with nitrogen for 5 minutes and then heated at 80° C. in a pressure tube overnight. The mixture was allowed to cool at room temperature and diluted with EtOAc and filtered through Celite®. The filtrate was washed with water (1×), brine (1×) and dried over MgSO$_4$. The solvent was evaporated and the residue purified on a 50 g KP SNAP column on Biotage eluting with a gradient of heptane:EtOAc (0% to 20%) to give 0.41 g (43%) of a mixture of tert-butyldimethyl{[9-(tetramethyl-1,3,2-dioxaborolan-2-yl)spiro[4.5]dec-8-en-6-yl]oxy}silane and tert-butyldimethyl {[9-(tetramethyl-1,3,2-dioxaborolan-2-yl)spiro[4.5]dec-9-en-6-yl]oxy}silane, 409 mg (43%) in a 9:1 ratio as shown by NMR. $^1$H-NMR (500 MHz, Chloroform-d) δ 6.45-6.38 (m, 0.9H), 6.28 (t, J=1.8 Hz, 0.1H), 3.67-3.57 (m, 1H), 2.29 (dtt, J=18.7, 4.2, 2.0 Hz, 1H), 2.20 (dd, J=17.4, 1.7 Hz, 1H), 2.12-2.01 (m, 1H), 1.94 (dt, J=17.5, 2.5 Hz, 1H), 1.71-1.45 (m, 8H), 1.26 (s, 12H), 0.87 (s, 9H), 0.02 (d, J=3.7 Hz, 6H).

Step 7A: tert-butyl N-[2-({[3-iodo-1-(oxan-2-yl)-1H-pyrazol-4-yl]methyl}(methyl)amino)ethyl]-N-methylcarbamate

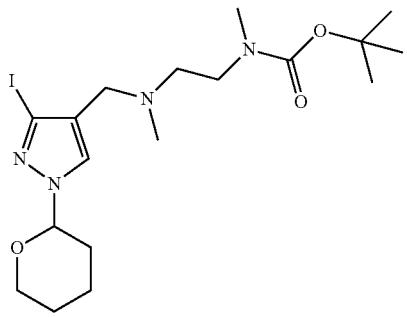 [SMILES: CN(CCN(C)C(=O)OC(C)(C)C)Cc1cn(C2CCCCO2)nc1I]

filtered and the filtrate was concentrated in vacuo to give a clear oil: 3.22 g (99%) of 10-[(tert-butyldimethylsilyl)oxy]spiro[4.5]decan-7-one. This material was used in the next step. $^1$H-NMR (500 MHz, Chloroform-d) δ 3.62 (t, J=3.3 Hz, 1H), 2.67-2.54 (m, 2H), 2.16 (dtd, J=14.2, 4.6, 2.1 Hz, 1H), 2.06 (d, J=13.4 Hz, 1H), 1.90 (dt, J=8.1, 4.2 Hz, 2H), 1.76-1.48 (m, 5H), 1.38 (ddd, J=12.1, 6.7, 5.2 Hz, 1H), 1.28 (ddd, J=19.8, 7.7, 4.8 Hz, 2H), 0.92 (s, 9H), 0.10 (d, J=2.9 Hz, 6H).

To a solution of 3-iodo-1-(oxan-2-yl)-1H-pyrazole-4-carbaldehyde (7.42 g, 24.25 mmol) in 1,2-dichloroethane (160 ml) was added tert-butyl N-methyl-N-[2-(methylamino)ethyl]carbamate (90%, 6.14 g, 29.34 mmol) followed by the addition of NaBH(OAc)₃ (10.28 g, 48.49 mmol). The resulting mixture was stirred at room temperature. The reaction mixture was diluted with DCM, washed with brine (2×), dried over MgSO₄, and dried in vacuo. Purification by flash chromatography using a Biotage Isolera system with a 100 g KP SNAP cartridge, eluting with a gradient of MeOH in DCM (0 to 10%) afforded tert-butyl N-[2-({[3-iodo-1-(oxan-2-yl)-1H-pyrazol-4-yl]methyl}(methyl)amino)ethyl]-N-methyl carbamate as a white solid after crystallization from heptane-ether 8.4 g (72%). ¹H NMR (500 MHz, Chloroform-d) δ 7.88-7.35 (m, 1H), 5.32 (dd, J=9.5, 2.6 Hz, 1H), 4.09-3.99 (m, 1H), 3.72-3.58 (m, 1H), 3.55-3.23 (m, 4H), 2.85 (s, 3H), 2.69-2.43 (m, 2H), 2.39-2.16 (m, 3H), 2.14-1.92 (m, 3H), 1.73-1.49 (m, 3H), 1.44 (s, 9H).

Step 7B: tert-butyl N-(2-{[(3-{10-[(tert-butyldimethylsilyl)oxy]spiro[4.5]dec-7-en-7-yl}-1-(oxan-2-yl) pyrazol-4-yl)methyl](methyl)amino}ethyl)-N-methylcarbamate TBDMS

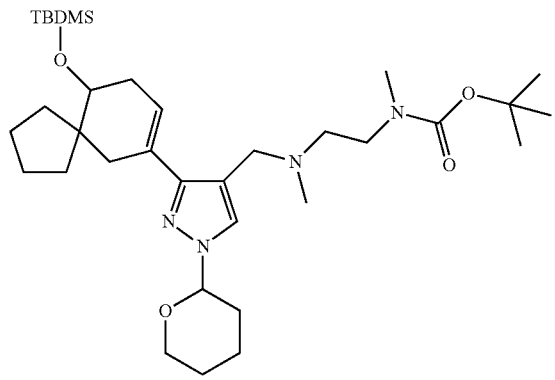

A suspension of tert-butyl N-[2-({[3-iodo-1-(oxan-2-yl)-1H-pyrazol-4-yl]methyl}(methyl)amino)ethyl]-N-methylcarbamate (488 mg, 1.02 mmol), tert-butyldimethyl {[9-(tetramethyl-1,3,2-dioxaborolan-2-yl)spiro[4.5]dec-8-en-6-yl]oxy}silane and tert-butyldimethyl{[9-(tetramethyl-1,3,2-dioxaborolan-2-yl)spiro[4.5]dec-9-en-6-yl]oxy}silane (400 mg, 1.02 mmol) in 1,4-dioxane (2 ml) and aqueous 2M sodium carbonate (1.53 ml) was degassed by bubbling nitrogen for 5 mins. Bis[3-(diphenylphosphanyl)cyclopenta-2,4-dien-1-yl]iron, dichloromethane, and dichloropalladium (42 mg, 0.05 mmol) was added and the reaction was heated at 80° C. overnight. The reaction mixture was left to cool to room temperature and then diluted with EtOAc, filtered through Celite® and the solids were washed with EtOAc. The combined filtrates were washed with water (1×) and brine (2×), dried (MgSO₄), filtered and concentrated to give an orange oil. This material was purified by loading as a solution in DCM on a 25 g SNAP column on Biotage and elution with a gradient of heptane-EtOAc 35% to 100% to give tert-butyl N-(2-{[(3-{10-[(tert-butyldimethylsilyl)oxy]spiro[4.5]dec-7-en-7-yl}-1-(oxan-2-yl)pyrazol-4-yl)methyl](methyl)amino}ethyl)-N-methylcarbamate, 0.45 g (72%). LC-MS: 2.42 min (3 min method), m/z=617.35. ¹H-NMR (500 MHz, Chloroform-d) δ 7.41 (d, J=3.9 Hz, 1H), 5.91 (d, J=21.6 Hz, 1H), 5.26 (dd, J=8.9, 2.8 Hz, 1H), 4.04-3.97 (m, 1H), 3.69-3.56 (m, 2H), 3.27 (d, J=49.4 Hz, 4H), 2.77 (s, 3H), 2.53-2.37 (m, 3H), 2.33 (d, J=18.3 Hz, 1H), 2.25 (d, J=16.6 Hz, 1H), 2.17 (s, 3H), 2.14-2.05 (m, 1H), 1.98 (dd, J=10.2, 2.9 Hz, 3H), 1.67-1.46 (m, 11H), 1.38 (s, 9H), 0.84-0.80 (m, 9H), 0.00 (s, 6H).

Step 8: tert-butyl N-(2-{[(3-{10-[(tert-butyldimethylsilyl)oxy]spiro[4.5]decan-7-yl}-1-(oxan-2-yl)-1H-pyrazol-4-yl)methyl](methyl)amino}ethyl)-N-methylcarbamate

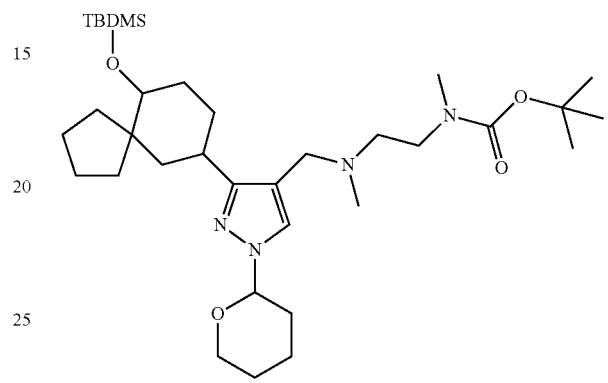

A suspension of tert-butyl N-(2-{[(3-{10-[(tert-butyldimethylsilyl)oxy]spiro[4.5]dec-7-en-7-yl}-1-(oxan-2-yl)-1H-pyrazol-4-yl)methyl](methyl)amino}ethyl)-N-methylcarbamate (453 mg, 0.73 mmol) and Pd/C (10%, 156 mg, 0.147 mmol) in EtOH (10 ml) was stirred at room temperature under an atmosphere of hydrogen for 2 days. The reaction mixture was filtered through Celite® and the filtrate concentrated to give an oil that was purified on Biotage using a SNAP KP 25 g column, eluting with a gradient of heptane-EtOAc 25% to 100% to give tert-butyl N-(2-{[(3-{10-[(tert-butyldimethylsilyl)oxy]spiro[4.5]decan-7-yl}-1-(oxan-2-yl)-1H-pyrazol-4-yl)methyl](methyl)amino}ethyl)-N-methylcarbamate, 120 mg (26%). LC-MS: 2.16 min (3 min method), m/z=619.35. ¹H-NMR (500 MHz, Chloroform-d) δ 7.46 (d, J=10.4 Hz, 1H), 5.31-5.24 (m, 1H), 4.05 (d, J=11.5 Hz, 1H), 3.67 (td, J=11.2, 2.2 Hz, 1H), 3.48-3.21 (m, 5H), 2.88-2.73 (m, 4H), 2.55-2.38 (m, 2H), 2.22 (s, 3H), 2.07-1.88 (m, 6H), 1.70-1.48 (m, 12H), 1.43 (d, J=10.5 Hz, 11H), 0.92 (s, 9H), 0.05 (s, 6H).

Step 9: 9-[4-({methyl[2-(methylamino)ethyl]amino}methyl)-1H-pyrazol-3-yl]spiro[4.5]decan-6-ol (Compound 182)

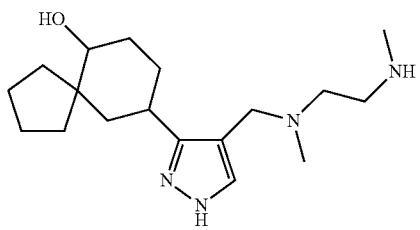 [SMILES: CNCCN(C)Cc1c[nH]nc1C1CCC(O)C2(CCCC2)C1]

A suspension of tert-butyl N-(2-{[(3-{10-[(tert-butyldimethylsilyl)oxy]spiro[4.5]decan-7-yl}-1-(oxan-2-yl)-1H-pyrazol-4-yl)methyl](methyl)amino}ethyl)-N-methylcarbamate (77 mg, 0.12 mmol) in aqueous 6M HCl (0.56 ml) was stirred at room temperature overnight. It was diluted with water and extracted with DCM (2×). The combined organic layers were concentrated to give an oily residue that was dissolved in 1 ml DMSO-CH$_3$CN (1:1) and purified on the Gilson3 using a high pH prep-HPLC method to give 9-[4-({methyl[2-(methylamino)ethyl]amino}methyl)-1H-pyrazol-3-yl]spiro[4.5]decan-6-ol, 13 mg (33%) as a white solid. LC-MS: 4.3 min (7 min, high pH), m/z=321.3. $^1$H-NMR (500 MHz, Methanol-d4) δ 7.47 (s, 0.1H), 7.42 (s, 0.9H), 3.49 (s, 1H), 3.42 (s, 2H), 2.93 (tt, J=12.7, 3.4 Hz, 1H), 2.71 (t, J=6.5 Hz, 2H), 2.52 (t, J=6.5 Hz, 2H), 2.37 (s, 3H), 2.20 (s, 3H), 1.99-1.85 (m, 2H), 1.86-1.72 (m, 3H), 1.72-1.50 (m, 6H), 1.47-1.30 (m, 3H).

Compounds 183 & 184

Racemic Mixture of (1R,4S)-4-[4-({methyl[2-(methylamino)ethyl]amino}methyl)-1H-pyrazol-3-yl]spiro[5.5]undecan-1-ol (Compound 183)

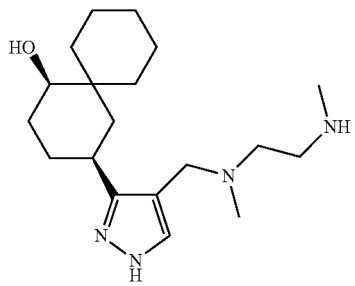 [SMILES: CNCCN(C)Cc1c[nH]nc1[C@H]1CC[C@@H](O)C2(CCCCC2)C1]

Racemic Mixture of (1S,4S)-4-[4-({methyl[2-(methylamino)ethyl]amino}methyl)-1H-pyrazol-3-yl]spiro[5.5]undecan-1-ol (Compound 184)

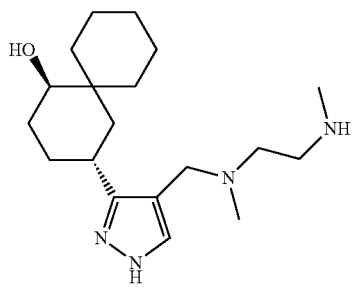 [SMILES: CNCCN(C)Cc1c[nH]nc1[C@@H]1CC[C@@H](O)C2(CCCCC2)C1]

Step 1: 1,4-dioxadispiro[4.1.5$^7$.3$^5$]pentadecan-13-one

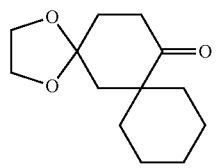 [SMILES: O=C1CCC2(CC13CCCCC3)OCCO2]

To a solution of 1,4-dioxaspiro[4.5]decan-8-one (5 g, 32.01 mmol) and 1,5-dibromopentane (7.36 g, 32 mmol) in toluene (120 ml) was added $^t$BuOK (3.59 g, 32 mmol) at RT. The solution was refluxed overnight. The reaction was cooled to RT and quenched with HCl (0.5N, 10 ml). The phases were separated and the aqueous was extracted with DCM (3×30 ml). The organic extracts were combined and dried over Na$_2$SO$_4$ and evaporated to dryness. The residue was purified by Biotage (SNAP 340 g, eluent heptane/EtOAc 95/5 to 60/40) to afford 2.35 g of the title compound (33%) as a light colourless oil. $^1$H-NMR (500 MHz, Chloroform-d) δ 4.08-3.91 (m, 4H), 2.61-2.42 (m, 2H), 2.01-1.95 (m, 2H), 1.93 (s, 2H), 1.83-1.72 (m, 2H), 1.58-1.38 (m, 7H), 1.38-1.28 (m, 1H). Rf=0.47 (heptane/EtOAc 7/3).

Step 2: 1,4-dioxadispiro[4.1.5$^7$.3$^5$]pentadecan-13-ol

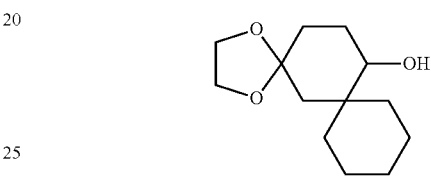

Sodium borohydride (0.99 g, 26.19 mmol) was added at 0° C. and under nitrogen to 1,4-dioxadispiro[4.1.5$^7$.3$^5$]pentadecan-13-one (2.35 g, 10.48 mmol) in MeOH (120 ml). The reaction was stirred at 0° C. until completion (6 h). The reaction was quenched slowly with water (100 mL). DCM (50 mL) was added and the layers separated. The aqueous layer was extracted with DCM (2×50 mL). The organic layers were combined, dried over Na$_2$SO$_4$, filtered and concentrated in vacuo to afford 2.18 g of desired 1,4-dioxadispiro[4.1.57.35]pentadecan-13-ol (92%). $^1$H-NMR (500 MHz, Chloroform-d) δ 3.97-3.86 (m, 4H), 3.52-3.44 (m, 1H), 1.90-1.79 (m, 3H), 1.77-1.62 (m, 2H), 1.61-1.34 (m, 10H), 1.35-1.18 (m, 2H). Rf=0.35 (heptane/EtOAc 7/3).

Step 3: tert-butyl({1,4-dioxadispiro[4.1.5$^7$.3$^5$]pentadecan-13-yloxy})dimethylsilane

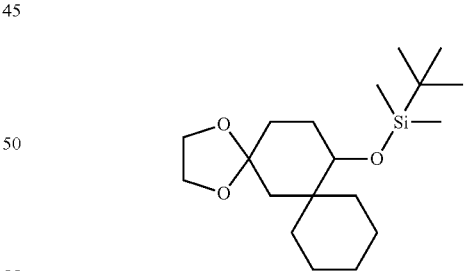

To a solution of 1,4-dioxadispiro[4.1.5$^7$.3$^5$]pentadecan-13-ol (2.18 g, 9.63 mmol) in DMF (20 ml) was added tert-butyl(chloro)dimethylsilane (2.18 g, 14.45 mmol) and 1H-imidazole (1.32 g, 19.27 mmol). The reaction was stirred at RT overnight. The reaction mixture was diluted with water and extracted with EtOAc (3×50 ml). The combined organic layers were dried (Na$_2$SO$_4$) and concentrated. The residue was purified by Biotage (SNAP 100 g, eluent heptane/EtOAc 95/5 to 80/20) to afford 2.45 g of desired material (75%). $^1$H-NMR (500 MHz, Chloroform-d) δ 4.02-3.80 (m, 4H), 3.49-3.38 (m, 1H), 1.89 (td, J=12.2, 4.2 Hz, 1H), 1.84-1.71 (m, 2H), 1.64-1.15 (m, 13H), 0.89 (s, 9H), 0.04 (d, J=2.2 Hz, 6H). Rf=0.60 (EtOAc/heptane 10/90).

Step 4: 5-[(tert-butyldimethylsilyl)oxy]spiro[5.5]undecan-2-one

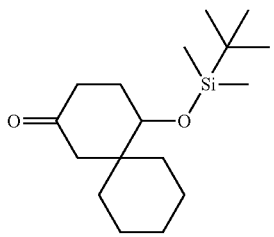 [SMILES: CC(C)(C)[Si](C)(C)OC1CCC(=O)CC12CCCCC2]

To a solution of tert-butyl({1,4-dioxadispiro[4.1.5⁷.3⁵]pentadecan-13-yloxy})dimethylsilane (2.45 g, 7.19 mmol) in DCM (100 ml) was added iron trichloride hexahydrate (1.94 g, 7.19 mmol). After 2 h, no more starting material was detected by TLC. The reaction mixture was washed with water (50 ml), aq sat NaHCO$_3$ (50 ml), brine (50 ml), the organic layer was dried over Na$_2$SO$_4$ and evaporated to dryness to afford 2.08 g of ketone as a clear oil (97%). $^1$H-NMR (500 MHz, Chloroform-d) δ 3.67 (s, 1H), 2.67-2.48 (m, 2H), 2.26-2.11 (m, 2H), 2.00 (dddd, J=14.5, 12.2, 5.4, 2.5 Hz, 1H), 1.87 (ddt, J=14.2, 7.1, 3.7 Hz, 1H), 1.64-1.17 (m, 10H), 0.92 (s, 9H), 0.10 (t, J=2.9 Hz, 6H). Rf=0.40 (EtOAc/heptane 10/90).

Step 5: 5-[(tert-butyldimethylsilyl)oxy]spiro[5.5]undec-2-en-2-yl trifluoromethanesulfonate

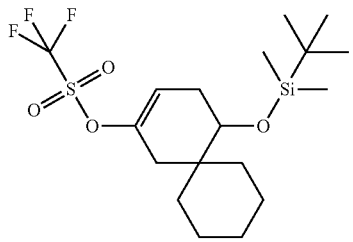 [SMILES: CC(C)(C)[Si](C)(C)OC1CC=C(OS(=O)(=O)C(F)(F)F)CC12CCCCC2]

A stirred solution of 5-[(tert-butyldimethylsilyl)oxy]spiro[5.5]undecan-2-one (2 g, 6.8 mmol) was dissolved in dry THF (160 mL) and cooled to −78° C. To this 0.18M LHMDS in THF (73.5 mL) was added dropwise. The reaction was stirred for 45 min and a solution of N-(5-chloropyridin-2-yl)-1,1,1-trifluoro-N-[(trifluoromethyl)sulfonyl]methanesulfonamide (5 g, 12.75 mmol) in THF (60 mL) was added dropwise over 10 minutes, the reaction was stirred at −78° C. for 1 hr, then allowed to warm to RT over 3 hr. The reaction was quenched by addition of sat. NH$_4$Cl (100 mL). EtOAc (100 mL) was added and the organic layer separated. The aqueous layer was washed (2×100 mL EtOAc), and the organics combined, dried (Na$_2$SO$_4$), filtered, and solvent removed under reduced pressure to leave 8.4 g yellow crude material. The crude product was purified using silica gel column chromatography (Biotage SNAP-HP 100 g cartridge, dry loaded, eluent heptane:EtOAc 99:1 to 9:1) to afford 2.16 g of the target material as a colourless free flowing oil (71%, 95% purity). $^1$H-NMR (500 MHz, Chloroform-d) δ 5.54 (d, J=4.1 Hz, 1H), 3.51 (t, J=3.9 Hz, 1H), 2.48-2.30 (m, 2H), 2.16-2.06 (m, 2H), 1.64-1.17 (m, 10H), 0.88 (s, 9H), 0.05 (s, 6H). Rf=0.61 (EtOAc/heptane 5/95). LC-MS: 2.72 min (hydrophobic LC-MS method), no ionisation.

Step 6: tert-butyldimethyl{[4-(tetramethyl-1,3,2-dioxaborolan-2-yl)spiro[5.5]undec-3-en-1-yl]oxy}silane

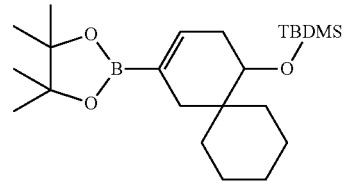

5-[(tert-butyldimethylsilyl)oxy]spiro[5.5]undec-2-en-2-yl trifluoromethanesulfonate (90%, 500 mg, 1.05 mmol), 4,4,4',4',5,5,5',5'-octamethyl-2,2'-bi-1,3,2-dioxaborolane (320 mg, 1.26 mmol), Pd(dppf)Cl$_2$ (43 mg, 0.05 mmol) and potassium acetate (770 mg, 7.87 mmol) were suspended in dioxane (5 ml). The solution was degassed with nitrogen for 10 min and then heated to 80° C. After 2 h, no SM was visible by LCMS but still a trace by TLC. The reaction was allowed to cool to RT and stirred O/N. Water (10 ml) was added and the reaction was extracted with EtOAc (2×20 ml). The combined organic layers were washed with water (10 ml) and was dried over Na$_2$SO$_4$ and evaporated to dryness. The residue was purified by Biotage (SNAP 50 g, eluent heptane/EtOAc 100/0 to 90/10) to afford 310 mg of desired boronic ester (65%) as a colourless oil. $^1$H-NMR (500 MHz, Chloroform-d) δ 6.57 (s, OH), 6.45-6.32 (m, 1H), 3.58-3.40 (m, 1H), 2.36 (dd, J=17.6, 1.9 Hz, 1H), 2.30-2.20 (m, 1H), 2.05 (ddd, J=18.8, 5.9, 3.1 Hz, 1H), 1.79 (dd, J=17.6, 2.2 Hz, 1H), 1.60-1.06 (m, 22H), 0.91-0.83 (m, 9H), 0.01 (d, J=1.4 Hz, 6H). Rf=0.47 (EtOAc/heptane 5/95). LC-MS: 2.85 min (hydrophobic LC-MS method), no ionisation.

Step 7: tert-butyl N-(2-{[(3-{5-[(tert-butyldimethylsilyl)oxy]spiro[5.5]undec-2-en-2-yl}-1-(oxan-2-yl)-1H-pyrazol-4-yl)methyl](methyl)amino}ethyl)-N-methylcarbamate

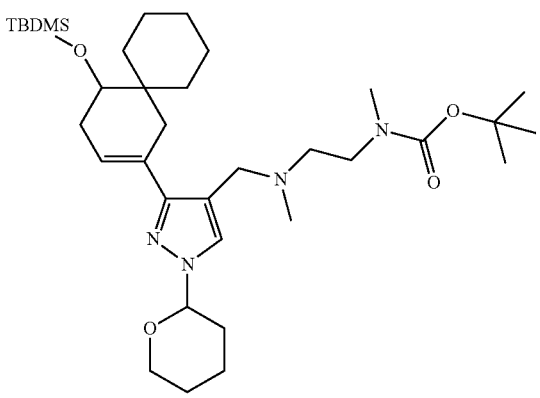

tert-Butyldimethyl {[4-(tetramethyl-1,3,2-dioxaborolan-2-yl)spiro[5.5]undec-3-en-1-yl]oxy}silane (90%, 200 mg, 0.44 mmol), tert-butyl-N-(2-{[(3-iodo-1H-pyrazol-4-yl)methyl](methyl)amino}ethyl)-N-methylcarbamate (140 mg, 0.29 mmol), Pd(dppf)Cl$_2$ (24 mg, 29 μmol) and dipotassium carbonate (122 mg, 0.88 mmol) were suspended in a mixture of dioxane (14 ml) and water (1 ml). The reaction was degassed with nitrogen for 10 min and then heated to 100° C. under nitrogen. After overnight, TLC and LCMS showed the presence of desired material. The solvent was removed under reduced pressure and the residue was purified by Biotage (SNAP 50 g, eluent heptane/EtOAc 83/17 to 0/100) to afford 140 mg of desired alkene (87%) as a yellow oil. $^1$H-NMR (500 MHz, Chloroform-d) δ 7.56-7.40 (m, 1H), 6.00-5.85 (m, 1H), 5.32 (dd, J=9.2, 2.9 Hz, 1H), 4.06 (d, J=9.9 Hz, 1H), 3.72-3.64 (m, 1H), 3.60 (t, J=5.4 Hz, 1H), 3.43-3.21 (m, 3H), 2.82 (s, 2H), 2.62 (d, J=14.6 Hz, 1H), 2.46 (s, 2H), 2.34 (d, J=17.8 Hz, 1H), 2.19 (d, J=19.2 Hz, 4H), 1.93 (d, J=15.1 Hz, 1H), 1.76-1.34 (m, 18H), 1.24 (s, 9H), 0.88 (s, 9H), 0.04 (d, J=2.3 Hz, 6H). LCMS: 1.59 min (2 min method), m/z=631.25. Rf=0.30 (heptane/EtOAc, 3/7, UV and PMA).

Step 8: Racemic tert-butyl N-{2-[({3-[(2S,5S)-5-[(tert-butyldimethylsilyl)oxy]spiro[5.5]undecan-2-yl]-1-(oxan-2-yl)-1H-pyrazol-4-yl}methyl)(methyl)amino]ethyl}-N-methylcarbamate and racemic tert-butyl N-{2-[({3-[(2S,5R)-5-[(tert-butyldimethylsilyl)oxy]spiro[5.5]undecan-2-yl]-1-(oxan-2-yl)-1H-pyrazol-4-yl}methyl)(methyl)amino]ethyl}-N-methylcarbamate Isomer 1

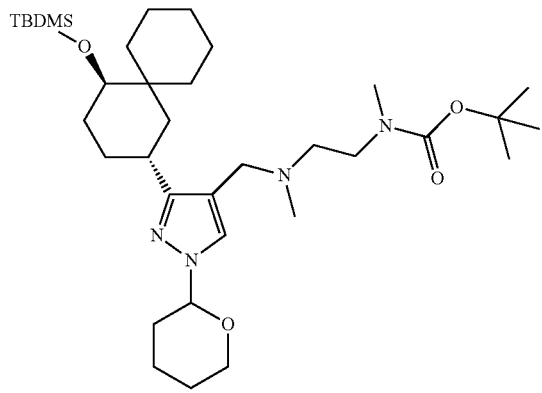

Isomer 2

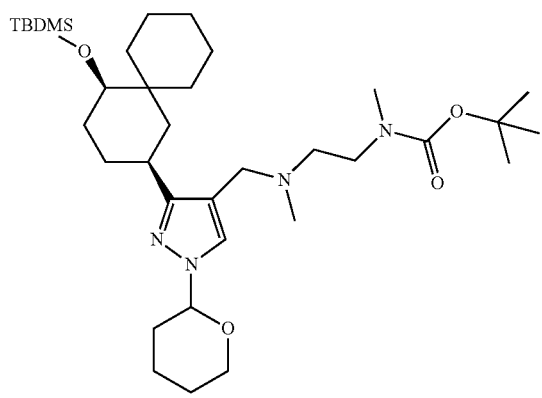

tert-Butyl N-(2-{[(3-{5-[(tert-butyldimethylsilyl)oxy]spiro[5.5]undec-2-en-2-yl}-1H-pyrazol-4-yl)methyl](methyl)amino}ethyl)-N-methylcarbamate (140 mg, 0.26 mmol) and palladium on carbon (10%) (27 mg, 0.26 mmol) were suspended in EtOH (5 ml). The reaction was stirred at RT under hydrogen atmosphere. LCMS after overnight shows only starting material. The solution was filtered on Celite and washed with MeOH (2×10 ml). The filtrate was evaporated and the residue was dissolved in EtOH (5 ml) and palladium on carbon (10%) (27 mg, 0.26 mmol) added. The reaction was stirred at RT under hydrogen atmosphere for 36 h. The solution was filtered on Celite and washed with MeOH (2×10 ml). The filtrate was evaporated and the residue was purified by Biotage (SNAP HP 10 g, eluent heptane/EtOAc 95/5 to 0/100) to afford 40 mg of deaminated side product (43%) as a yellow oil, 10 mg of isomer 1 (7%) as a yellow oil and 40 mg of isomer 2 (28%) as a yellow oil. Deaminated side product: $^1$H-NMR (500 MHz, Chloroform-d) δ 7.30-7.27 (m, 1H), 5.31-5.23 (m, 1H), 4.10-4.00 (m, 1H), 3.73-3.62 (m, 1H), 3.56-3.50 (m, 1H), 2.97-2.85 (m, 1H), 2.08 (s, 3H), 2.06-1.96 (m, 4H), 1.85-1.72 (m, 2H), 1.72-1.62 (m, 4H), 1.62-1.51 (m, 4H), 1.43 (dd, J=10.3, 5.5 Hz, 4H), 1.40-1.19 (m, 4H), 0.91 (d, J=3.3 Hz, 9H), 0.05 (d, J=3.9 Hz, 6H). Rf=0.80 (heptane/EtOAc 3/7). LC-MS: 2.73 min (hydrophobic LC-MS method), m/z=447.2. Isomer 1: $^1$H-NMR (500 MHz, Chloroform-d) δ 7.53-7.39 (m, 1H), 5.35-5.22 (m, 1H), 4.04 (d, J=9.9 Hz, 1H), 3.75-3.61 (m, 1H), 3.56-3.21 (m, 5H), 2.96-2.78 (m, 4H), 2.61-2.38 (m, 2H), 2.30-2.15 (m, 3H), 2.11-1.88 (m, 5H), 1.84-1.50 (m, 12H), 1.50-1.39 (m, 14H), 1.30-1.16 (m, 13H), 0.92 (s, 9H), 0.09--0.00 (m, 6H). Rf=0.44 (heptane/EtOAc 3/7). LC-MS: 1.72 min (2.5 minute LC-MS method), m/z=633.25. Isomer 2: $^1$H-NMR (500 MHz, Chloroform-d) δ 7.56-7.37 (m, 1H), 5.32-5.24 (m, 1H), 4.04 (d, J=9.9 Hz, 1H), 3.67 (td, J=10.1, 8.9, 4.3 Hz, 1H), 3.55-3.18 (m, 5H), 2.90 (t, J=12.9 Hz, 1H), 2.82 (s, 3H), 2.58-2.39 (m, 2H), 2.29-2.18 (m, 3H), 2.05-1.91 (m, 4H), 1.83-1.50 (m, 9H), 1.50-1.39 (m, 13H), 1.36-1.20 (m, 5H), 0.92 (s, 9H), 0.05 (d, J=4.9 Hz, 6H). Rf=0.35 (heptane/EtOAc 3/7). LC-MS: 1.66 min (2.5 minute LC-MS method), m/z=633.25.

Step 9 (Isomer 2): Racemic Mixture of (1R,4S)-4-[4-({Methyl[2-(methylamino)ethyl]amino}methyl)-1H-pyrazol-3-yl]spiro[5.5]undecan-1-ol (Compound 183)

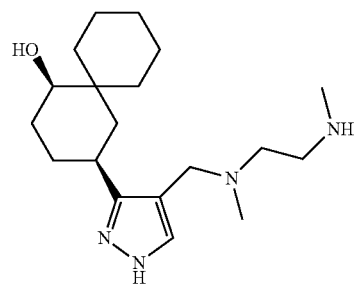

tert-Butyl N-(2-{[(3-{5-[(tert-butyldimethylsilyl)oxy]spiro[5.5]undecan-2-yl}-1-(oxan-2-yl)-1H-pyrazol-4-yl)methyl](methyl)amino}ethyl)-N-methylcarbamate (40 mg, 0.06 mmol) was dissolved in dioxane (1 ml) and HCl (6M, 1 ml) was added. The reaction was monitored by LCMS. After 2 h, no more starting material was left and full conversion to the desired mass detected (mass trace only).

The solvent was removed under reduced pressure and the residue was purified by SCX (2 g) column eluting with MeOH (10 ml) then MeOH/NH₃ (10 ml) to afford 20 mg (85%) of the desired material at 90% purity (assessed by ¹H-NMR). ¹H-NMR (500 MHz, Chloroform-d) δ 7.40 (s, 1H), 3.67 (s, 1H), 3.36 (s, 2H), 2.99 (tt, J=13.0, 3.7 Hz, 1H), 2.68 (t, J=6.0 Hz, 2H), 2.50 (t, J=5.9 Hz, 2H), 2.41 (s, 3H), 2.18-2.15 (m, 1H), 2.14 (s, 3H), 2.09-1.97 (m, 1H), 1.95-1.84 (m, 1H), 1.83-1.69 (m, 3H), 1.62 (d, J=10.2 Hz, 4H), 1.54-1.26 (m, 9H).

Step 9 (isomer 1): Racemic mixture of (1S,4S)-4-[4-({methyl[2-(methylamino)ethyl]amino}methyl)-1H-pyrazol-3-yl]spiro[5.5]undecan-1-ol (Compound 184)

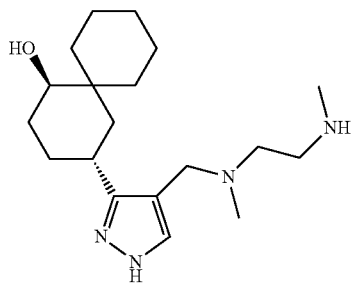 [SMILES: CNCCN(C)Cc1c[nH]nc1[C@@H]1CC[C@@H](O)C2(CCCCC2)C1]

Similarly, 5 mg of title compound were isolated from 10 mg reaction (85% yield, 80% purity). ¹H-NMR (500 MHz, Chloroform-d) δ 7.47-7.32 (m, 1H), 3.68 (s, 1H), 3.41-3.34 (m, 2H), 3.05-2.91 (m, 1H), 2.89-2.75 (m, 3H), 2.64-2.55 (m, 2H), 2.53-2.44 (m, 3H), 2.31-2.20 (m, 1H), 2.19-2.14 (m, 2H), 2.08-1.96 (m, 1H), 1.94-1.83 (m, 1H), 1.81-1.70 (m, 2H), 1.70-1.55 (m, 4H), 1.55-1.19 (m, 10H).

Compound 185

2,2-dimethyl-5-[4-({methyl[2-(methylamino)ethyl]amino}methyl)-1H-pyrazol-3-yl]cyclohexan-1-ol

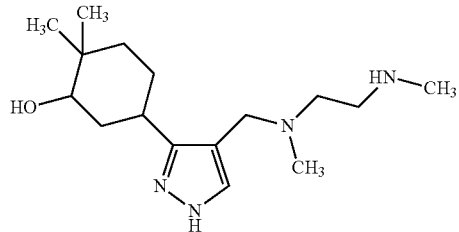 [SMILES: CNCCN(C)Cc1c[nH]nc1C1CCC(C)(C)C(O)C1]

Step 1:
5,5-dimethyl-7-oxabicyclo[4.1.0]heptan-2-one

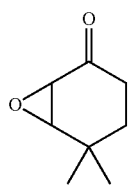

To an ice-cold solution of 4,4-dimethyl-cyclohex-2-enone (1.00 g, 8.05 mmol) in methanol (8 mL) was added 35% hydrogen peroxide (4.6 mL, 40.91 mmol) followed by 0.5 N NaOH (2.2 mL, 1.1 mmol). The mixture was stirred at 0° C. for 5 h, stored in a fridge (4° C.) overnight and then stirred at 0° C. for another 5 h. After this time the reaction mixture was concentrated in vacuo, then water (15 mL) was added, and the mixture extracted with dichloromethane (3×50 mL). The organic layers were combined, washed with 10% Na₂SO₃ (2×40 mL) and brine, dried over Na₂SO₄, filtered and concentrated at reduced pressure to afford 5,5-dimethyl-7-oxa-bicyclo[4.1.0]heptan-2-one as a colourless oil (1.18 g, quant): MS (ESI+) for C₈H₁₂O₂ m/z 141.0 (M+H)⁺; HPLC purity 88% (ret. time, 1.00 min); ¹H-NMR (500 MHz, Chloroform-d) δ 3.23 (d, J=4.0 Hz, 1H), 3.18 (dd, J=4.0, 1.1 Hz, 1H), 2.41 (ddd, J=18.9, 6.4, 3.0 Hz, 1H), 2.19 (ddd, J=18.9, 11.7, 7.0 Hz, 1H), 1.91 (ddd, J=13.5, 11.9, 6.4 Hz, 1H), 1.34 (dddd, J=13.6, 7.0, 3.0, 1.2 Hz, 1H), 1.22 (s, 3H), 1.07 (s, 3H).

Step 2: 3-hydroxy-4,4-dimethylcyclohexan-1-one

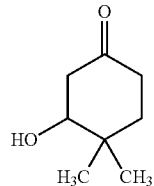

Lithium (sticks) metal (74.27 mg, 10.70 mmol) was added to a solution of naphthalene (1.83 g, 14.27 mmol) in dry THF (25 ml) at RT and stirred until the metal was dissolved (~3 h) before cooling to −78° C. A solution of 5,5-dimethyl-7-oxabicyclo[4.1.0]heptan-2-one (0.50 g, 3.57 mmol) in dry THF (10 ml) was then added and stirred for 20 min. Water (5 ml) was added and the reaction was allowed to warm to RT. Water (20 ml) was added to the reaction mixture and the product extracted with Et₂O (2×50 ml). This was dried over Na₂SO₄, filtered and evaporated in vacuo. Purification by silica gel column chromatography, on a Biotage Isolera system, using a 25 g KP-Sil SNAP cartridge, eluting with EtOAc:heptanes+1% TEA (1:9-9:1), gave the desired product as a colourless oil (210 mg, 41%): ¹H-NMR (500 MHz, Chloroform-d) δ 3.72 (dd, J=8.1, 4.3 Hz, 1H), 2.67 (ddd, J=14.9, 4.3, 1.0 Hz, 1H), 2.48-2.40 (m, 1H), 2.39-2.32 (m, 2H), 1.89 (dt, J=13.3, 6.6 Hz, 1H), 1.51 (ddd, J=14.3, 8.3, 6.4 Hz, 1H), 1.15 (s, 3H), 1.10 (s, 3H).

Step 3: 3-[(tert-butyldimethylsilyl)oxy]-4,4-dimethylcyclohexan-1-one

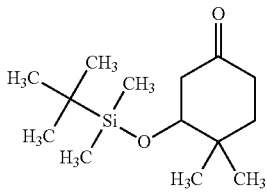

tert-Butyldimethylsilylchloride (0.43 g, 2.84 mmol) was added to a solution of 3-hydroxy-4,4-dimethylcyclohexan- 1-one (0.34 g, 2.37 mmol) and imidazole (0.39 g, 5.69 mmol) in DCM (10 ml) at RT and stirred over the weekend. The reaction mixture was diluted with DCM (50 ml) and washed with water (50 ml) and then brine (50 ml), dried over $Na_2SO_4$, filtered and evaporated in vacuo. Purification by silica gel column chromatography, on a Biotage Isolera system, using a 25 g KP-Sil SNAP cartridge, eluting with EtOAc:heptanes (1:9-2:8-1) gave the desired product as a colourless oil (193 mg, 31%): $^1$H-NMR (500 MHz, Chloroform-d) δ 3.64 (dd, J=7.4, 4.2 Hz, 1H), 2.59-2.52 (m, 1H), 2.39-2.25 (m, 3H), 1.90-1.81 (m, 1H), 1.47-1.40 (m, 1H), 1.07 (s, 3H), 1.01 (s, 3H), 0.88 (s, 9H), 0.05 (d, J=6.0 Hz, 6H).

Step 4: 5-[(tert-butyldimethylsilyl)oxy]-4,4-dimethylcyclohex-1-en-1-yl trifluoromethanesulfonate

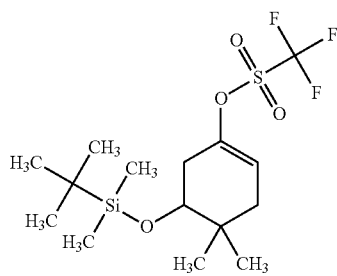 [SMILES: CC1(C)CC=C(OS(=O)(=O)C(F)(F)F)CC1O[Si](C)(C)C(C)(C)C]

2 M LDA in THF (0.96 ml, 1.92 mmol) was added to a solution of 3-[(tert-butyldimethylsilyl)oxy]-4,4-dimethylcyclohexan-1-one (0.35 g, 1.37 mmol) in dry THF (10 ml) at −78° C. and stirred for 1 hr under $N_2$. 1,1,1-trifluoro-N-phenyl-N-[(trifluoromethyl)sulfonyl]methanesulfonamide (0.59 g, 0.53 mmol) was added to the reaction as a solution in THF (1 ml) and the reaction was stirred at −78° C. for 1 hour and then left to warm to RT and stirred overnight. The reaction was quenched by the addition of water (1 ml) and diluted with ethyl acetate (30 ml). This was washed with water (30 ml) then brine (30 ml), dried over $Na_2SO_4$, filtered and evaporated in vacuo, to give an oil. This was dissolved in minimum amount of DCM and was loaded on a 25 g KP SNAP column and eluted with heptane-EtOAc 0% to 6% to give 335 mg (62%) of the desired product as a colourless oil: $^1$H-NMR (500 MHz, Chloroform-d) δ 5.62-5.48 (m, 1H), 3.54-3.44 (m, 1H), 2.50-2.42 (m, 1H), 2.24-2.15 (m, 1H), 2.11-2.03 (m, 1H), 1.85-1.77 (m, 1H), 0.85-0.81 (m, 15H), −0.01 (d, J=7.3 Hz, 6H).

Step 5: tert-butyl({[6,6-dimethyl-3-(tetramethyl-1,3,2-dioxaborolan-2-yl)cyclohex-3-en-1-yl]oxy})dimethylsilane

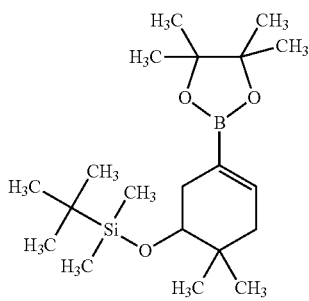 [SMILES: CC1(C)CC=C(B2OC(C)(C)C(C)(C)O2)CC1O[Si](C)(C)C(C)(C)C]

A suspension of 5-[(tert-butyldimethylsilyl)oxy]-4,4-dimethylcyclohex-1-en-1-yl trifluoromethanesulfonate (0.34 g, 0.86 mmol), 4,4,4',4',5,5,5',5'-octamethyl-2,2'-bi-1,3,2-dioxaborolane (0.33 g, 1.29 mmol) and KOAc (0.59 g, 6.04 mmol) in 1,4-dioxane (5 ml) was degassed with a nitrogen sparge for 10 min whilst stirring at RT. Bis[3-(diphenylphosphanyl)cyclopenta-2,4-dien-1-yl]iron, dichloromethane and dichloro palladium (0.07 g, 0.09 mmol) was added to this suspension and stirred at 90° C. for 3.5 h before allowing to cool to RT overnight. The reaction mixture was diluted with EtOAc (10 ml) and water (10 ml). The organic layer was separated and the aqueous was extracted with EtOAc (10 ml). The combined organic layers were dried over $Na_2SO_4$, filtered and evaporated in vacuo. Purification by silica gel column chromatography, on a Biotage Isolera system, using a 25 g KP-Sil SNAP cartridge, eluting with EtOAc:heptanes (0-1), gave the desired product as a colourless oil (250 mg, 79%): $^1$H-NMR (500 MHz, Chloroform-d) δ 6.49-6.15 (m, 1H), 3.52-3.42 (m, 1H), 2.32-2.21 (m, 1H), 2.12-1.98 (m, 2H), 1.93-1.83 (m, 1H), 1.25 (d, J=3.3 Hz, 12H), 0.91 (s, 3H), 0.87 (d, J=3.8 Hz, 9H), 0.82 (d, J=3.4 Hz, 3H), 0.07--0.02 (m, 6H).

Step 6: tert-butyl N-(2-{[(3-{5-[(tert-butyldimethylsilyl)oxy]-4,4-dimethylcyclohex-1-en-1-yl}-1-(oxan-2-yl)-1H-pyrazol-4-yl)methyl](methyl)amino}ethyl)-N-methylcarbamate

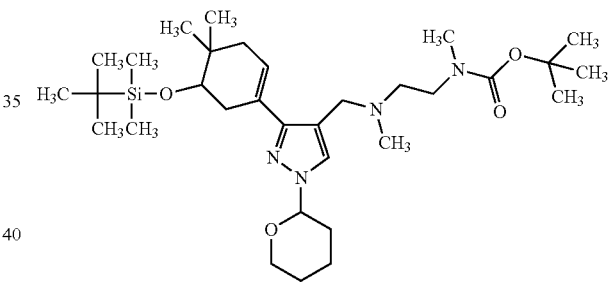

A suspension of tert-butyl({[6,6-dimethyl-3-(tetramethyl-1,3,2-dioxaborolan-2-yl)cyclohex-3-en-1-yl]oxy})dimethylsilane (0.15 g, 0.41 mmol), tert-butyl N-[2-({[3-iodo-1-(oxan-2-yl)-1H-pyrazol-4-yl]methyl}(methyl)amino)ethyl]-N-methylcarbamate (0.13 g, 0.27 mmol) and KOAc (0.11 g, 0.82 mmol) in 1,4-dioxane (10 ml) and water (1 ml) was degassed with a nitrogen sparge for 10 min whilst stirring. $Pd(dppf)Cl_2 \cdot DCM$ (0.02 g, 0.03 mmol) was added to the reaction mixture which was then stirred at 100° C. for 18 hr in a sealed tube. The reaction was then allowed to cool to RT and evaporated in vacuo. The residue was absorbed onto silica gel (~5 ml). Purification by silica gel column chromatography, on a Biotage Isolera system, using a 25 g KP-Sil SNAP cartridge, eluting with EtOAc:heptanes (+1% TEA, 1:9-1), gave the desired product as a yellow oil (120 mg, 75%): MS (ESI+) for $C_{32}H_{58}N_4O_4Si$ m/z 591.25 (M+H)$^+$; HPLC purity 100% (ret. time, 1.39 min); $^1$H-NMR (500 MHz, Chloroform-d) δ 7.68-7.40 (m, 1H), 6.06-5.73 (m, 1H), 5.37-5.27 (m, 1H), 4.09-4.02 (m, 1H), 3.72-3.64 (m, 1H), 3.61 (dd, J=8.0, 5.4 Hz, 1H), 3.48-3.31 (m, 2H), 3.27 (s, 1H), 3.18-3.05 (m, 1H), 2.94-2.75 (m, 3H), 2.71-2.61 (m, 1H), 2.54-2.40 (m, 2H), 2.40-2.30 (m, 1H), 2.27-2.16 (m, 2H), 2.13-1.95 (m, 5H), 1.66 (d, J=8.9 Hz, 2H), 1.49-1.39 (m, 9H), 0.96-0.79 (m, 15H), 0.13--0.01 (m, 6H).

Step 7: tert-butyl N-(2-{[(3-{3-[(tert-butyldimethyl-silyl)oxy]-4,4-dimethylcyclohexyl}-1-(oxan-2-yl)-1H-pyrazol-4-yl)methyl](methyl)amino}ethyl)-N-methylcarbamate

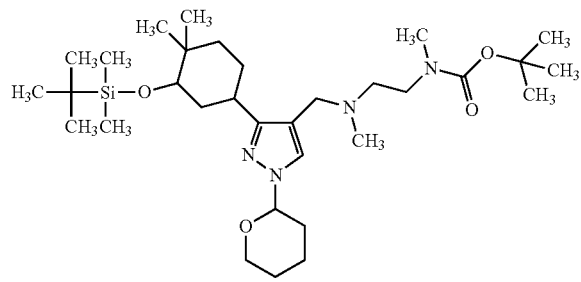 [SMILES: CN(CCN(C)C(=O)OC(C)(C)C)Cc1cn(C2CCCCO2)nc1C1CCC(C)(C)C(O[Si](C)(C)C(C)(C)C)C1]

A mixture of tert-butyl N-(2-{[(3-{3-[(tert-butyldimethylsilyl)oxy]-4,4-dimethylcyclohex-1-en-1-yl}-1-(oxan-2-yl)-1H-pyrazol-4-yl)methyl](methyl)amino}ethyl)-N-methylcarbamate (120 mg, 0.20 mmol) and 10% Pd—C (0.01 g) in EtOH (10 ml) was stirred under an atmosphere of hydrogen for 18 hrs. This was filtered and recharged with another portion of 10% Pd—C and hydrogen and stirred overnight. The reaction mixture was filtered and evaporated in vacuo. Purification by silica gel column chromatography, on a Biotage Isolera system, using a 10 g KP-Sil SNAP cartridge, eluting with EtOAc:heptanes (1:9-1), gave the desired product as a colourless glass (49 mg, 40%): MS (ESI+) for $C_{32}H_{60}N_4O_4Si$ m/z 593.25 (M+H)$^+$; HPLC purity 99% (ret. time, 1.41 min); $^1$H-NMR (500 MHz, Chloroform-d) δ 7.44 (d, J=25.2 Hz, 1H), 5.34-5.23 (m, 1H), 4.09-4.00 (m, 1H), 3.74-3.62 (m, 1H), 3.53-3.22 (m, 5H), 2.91-2.78 (m, 3H), 2.74-2.63 (m, 1H), 2.45 (s, 2H), 2.19 (d, J=19.7 Hz, 3H), 2.07-1.96 (m, 3H), 1.76 (tt, J=13.0, 7.9 Hz, 3H), 1.70-1.48 (m, 5H), 1.48-1.39 (m, 10H), 1.34-1.16 (m, 3H), 0.95-0.90 (m, 7H), 0.86 (s, 9H).

Step 8: 2,2-dimethyl-5-[4-({methyl[2-(methylamino)ethyl]amino}methyl)-1H-pyrazol-3-yl]cyclohexan-1-ol (Compound 185)

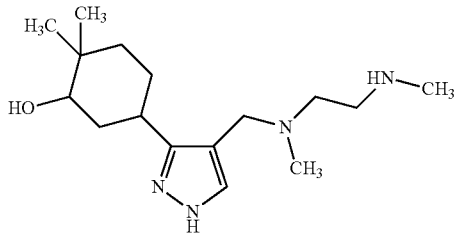 [SMILES: CNCCN(C)Cc1c[nH]nc1C1CCC(C)(C)C(O)C1]

6 N HCl (2 ml) was added to a solution of tert-butyl N-(2-{[(3-{3-[(tert-butyldimethylsilyl)oxy]-4,4-dimethylcyclohexyl}-1-(oxan-2-yl)-1H-pyrazol-4-yl)methyl](methyl)amino}ethyl)-N-methylcarbamate (49 mg, 0.08 mmol) in 1,4-dioxane (2 ml) at 0° C. and stirred whilst allowing to warm to RT. The reaction was stirred overnight then evaporated to dryness, then evaporated from MeOH (2×10 ml). The product was dissolved in MeOH (5 ml) and eluted onto a 2 g Isolute SCX-2 cartridge. MeOH (2×10 ml) was eluted then the product was released with 7 N NH$_3$ in MeOH (2×10 ml). This was evaporated to dryness to give ~20 mg of the product. Purification by silica gel column chromatography, on a Biotage Isolera system, using a 10 g KP-Sil SNAP cartridge, eluting with DCM:MeOH (1:9) and then 7 N NH$_3$ in MeOH:DCM (1:99-1:9) gave the desired product as a colourless glass (16 mg, 66%): $^1$H-NMR (500 MHz, Methanol-d4) δ 7.44 (s, 1H), 3.43 (d, J=8.9 Hz, 2H), 3.40-3.35 (m, 1H), 2.84 (ddt, J=12.5, 7.9, 4.0 Hz, 1H), 2.76-2.64 (m, 2H), 2.52 (td, J=6.5, 2.5 Hz, 2H), 2.38 (d, J=6.3 Hz, 3H), 2.20 (d, J=3.4 Hz, 3H), 1.76 (ddd, J=24.8, 12.4, 4.2 Hz, 3H), 1.63-1.50 (m, 2H), 1.41-1.26 (m, 2H), 1.04 (d, J=7.1 Hz, 3H), 0.98 (d, J=4.2 Hz, 3H); MS (ESI+) for $C_{16}H_{30}N_4O$ m/z 295.05 (M+H)$^+$.

Compound 200

Methyl[2-(methylamino)ethyl]([4-[(5S,8S)-3,3-dimethyl-1-oxaspiro[4.5]decan-8-yl]-1H-pyrazol-3-yl]methyl)amine trifluoroacetic acid salt

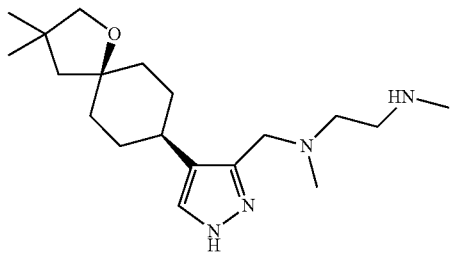

Step 1: (R/S)-4-[3,3-dimethyl-1-oxaspiro[4.5]dec-7-en-8-yl]-1-(oxan-2-yl)-1H-pyrazole-3-carbaldehyde

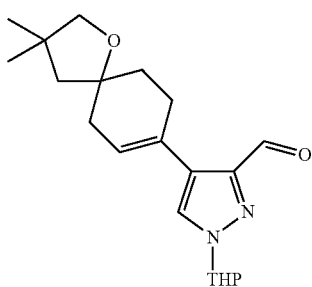

Into a 50-mL round-bottom flask purged and maintained with an atmosphere of nitrogen was added 2-[3,3-dimethyl-1-oxaspiro[4.5]dec-7-en-8-yl]-4,4,5,5-tetramethyl-1,3,2-dioxaborolane (500 mg, 1.71 mmol, 1.00 equiv), 4-iodo-1-(oxan-2-yl)-1H-pyrazole-3-carbaldehyde (523 mg, 1.71 mmol, 1.00 equiv), Pd(dppf)Cl$_2$ (124 mg, 0.17 mmol, 0.10 equiv), K$_3$PO$_4$ (1.087 g, 5.12 mmol, 2.99 equiv), ethylene glycol dimethyl ether (10 mL) and water (1 mL). The resulting solution was stirred overnight at 75° C. in an oil bath. The resulting mixture was concentrated under vacuum. The residue was purified by flash chromatography on silica gel using ethyl acetate/petroleum ether (1:4) as eluent to afford 270 mg (46%) of (R/S) 4-[3,3-dimethyl-1-oxaspiro[4.5]dec-7-en-8-yl]-1-(oxan-2-yl)-1H-pyrazole-3-carbaldehyde as a yellow oil.

Step 2: (R/S) tert-butyl N-(2-[[(4-[3,3-dimethyl-1-oxaspiro[4.5]dec-7-en-8-yl]-1-(oxan-2-yl)-1H-pyrazol-3-yl)methyl](methyl)amino]ethyl)-N-methylcarbamate

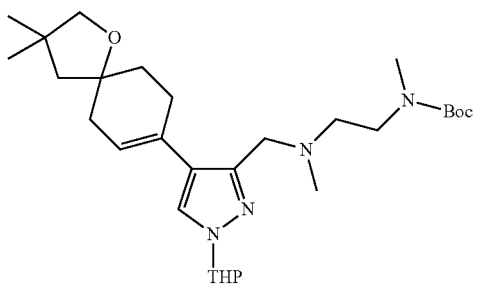

Into a 50-mL round-bottom flask was placed 4-[3,3-dimethyl-1-oxaspiro[4.5]dec-7-en-8-yl]-1-(oxan-2-yl)-1H-pyrazole-3-carbaldehyde (270 mg, 0.78 mmol, 1.00 equiv), tert-butyl N-methyl-N-[2-(methylamino)ethyl]carbamate (220 mg, 1.17 mmol, 1.49 equiv) and dichlorethane (10 mL). NaBH(OAc)$_3$ (496 mg, 2.34 mmol, 2.98 equiv) was added portionwise and the resultant mixture stirred overnight at room temperature. The reaction was quenched with 15 mL of water and extracted with 3×15 mL of dichloromethane. The combined organic layers were washed with 20 mL of brine and dried over anhydrous sodium sulfate and then concentrated under vacuum. The residue was purified by flash chromatography on silica gel using dichloromethane/methanol (20:1) to afford 300 mg (74%) of (R/S) tert-butyl N-(2-[[(4-[3,3-dimethyl-1-oxaspiro[4.5]dec-7-en-8-yl]-1-(oxan-2-yl)-1H-pyrazol-3-yl)methyl](methyl)amino]ethyl)-N-methylcarbamate as a colorless oil. $^1$H-NMR (300 MHz, CDCl$_3$): δ 7.43 (s, 1H), 5.78-5.50 (m, 1H), 4.79-4.58 (m, 1H), 4.15-3.77 (m, 2H), 3.77-3.40 (m, 4H), 3.40-3.05 (m, 2H), 3.00-2.68 (m, 4H), 2.68-1.99 (m, 10H), 1.99-1.82 (m, 2H), 1.82-1.50 (m, 6H), 1.44 (s, 9H), 1.13 (s, 6H) ppm.

Step 3: (R/S) tert-butyl N-(2-[[(4-[3,3-dimethyl-1-oxaspiro[4.5]decan-8-yl]-1-(oxan-2-yl)-1H-pyrazol-3-yl)methyl]amino]ethyl)-N-methylcarbamate

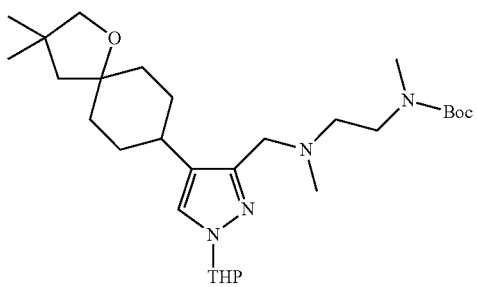

Into a 100-mL round-bottom flask was placed tert-butyl N-(2-[[(4-[3,3-dimethyl-1-oxaspiro[4.5]dec-7-en-8-yl]-1-(oxan-2-yl)-1H-pyrazol-3-yl)methyl](methyl)amino]ethyl)-N-methylcarbamate (300 mg, 0.58 mmol, 1.00 equiv), 10% Pd(OH)$_2$/C (300 mg) and tetrahydrofuran (30 mL). The resulting reaction mixture was stirred for 1 h at room temperature under 3 atmospheres of hydrogen. The reaction vessel was purged with an inert gas and the mixture filtered under a blanket of inert gas. The filtrate was concentrated under vacuum to provide 300 mg (100%) of (R/S) tert-butyl N-(2-[[(4-[3,3-dimethyl-1-oxaspiro[4.5]decan-8-yl]-1-(oxan-2-yl)-1H-pyrazol-3-yl)methyl](methyl)amino]ethyl)-N-methylcarbamate as a colorless oil. $^1$H-NMR (300 MHz, CDCl$_3$): δ 7.45 (s, 1H), 5.74-5.53 (m, 1H), 4.10-3.98 (m, 1H), 3.40-3.25 (m, 3H), 2.79 (s, 3H), 2.60-2.30 (m, 5H), 2.30-2.15 (m, 3H), 1.99-1.75 (m, 8H), 1.75-1.50 (m, 10H), 1.42 (s, 9H), 1.10 (s, 6H).

Step 4: Methyl[2-(methylamino)ethyl]([4-[(5S,8S)-3,3-dimethyl-1-oxaspiro[4.5]decan-8-yl]-1H-pyrazol-3-yl]methyl)amine trifluoroacetic acid salt (Compound 200)

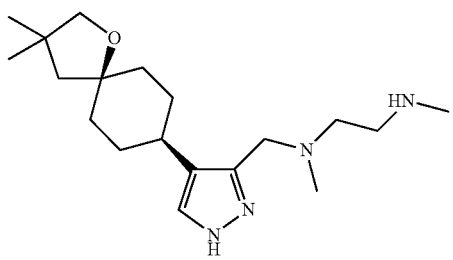

Into a 50-mL round-bottom flask was placed (R/S) tert-butyl N-(2-[[(4-[3,3-dimethyl-1-oxaspiro[4.5]decan-8-yl]-1-(oxan-2-yl)-1H-pyrazol-3-yl)methyl](methyl)amino]ethyl)-N-methylcarbamate (300 mg, 0.58 mmol, 1.00 equiv), trifluoroacetic acid (5 mL) and dichloromethane (5 mL). The resulting solution was stirred for 30 min at room temperature and then concentrated under vacuum. The crude product (307 mg) was purified by Prep-HPLC with the following conditions (Prep-HPLC-005(Waters): Column, Atlantis Prep OBD T3 Column, 19×150 mm, 5 μm; mobile phase, water with 0.05% trifluoroacetic acid and CH$_3$CN (up to 3.0% in 10 min, up to 100% in 1 min, hold at 100% for 1 min); Detector, UV 220 nm. This resulted in 154.5 mg (50%) of (R/S)methyl[2-(methylamino)ethyl]([4-[(5S,8S)-3,3-dimethyl-1-oxaspiro[4.5]decan-8-yl]-1H-pyrazol-3-yl]methyl)amine trifluoroacetic acid salt as a colorless solid. $^1$H-NMR (300 MHz, D$_2$O) δ: 7.71 (s, 1H), 4.49 (s, 2H), 3.70-3.50 (m, 6H), 2.94 (s, 3H), 2.80 (s, 3H), 2.62-2.49 (m, 1H), 2.05-1.87 (m, 2H), 1.79-1.52 (m, 8H), 1.10 (s, 6H) ppm.

Compound 205

Methyl([1-methyl-3-[(5S,8S)-3,3-dimethyl-1-oxaspiro[4.5]decan-8-yl]-1H-pyrazol-4-yl]methyl) [2-(methylamino)ethyl]amine hydrochloride

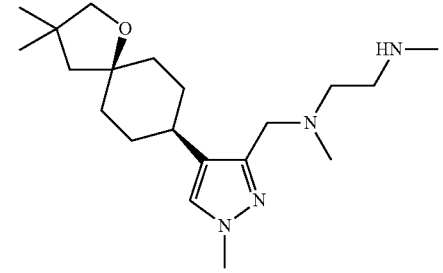

Step 1: 3-[3,3-dimethyl-1-oxaspiro[4.5]dec-7-en-8-yl]-1-methyl-1H-pyrazole-4-carbaldehyde

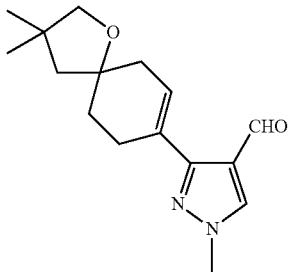 [SMILES: Cn1cc(C=O)c(C2=CCC3(CC2)CC(C)(C)CO3)n1]

To a stirred mixture of 3-[3,3-dimethyl-1-oxaspiro[4.5]dec-7-en-8-yl]-H-pyrazole-4-carbaldehyde (2 g, 7.68 mmol, 1.00 equiv) and potassium carbonate (3.18 g, 23.01 mmol, 2.99 equiv) in CH$_3$CN (40 mL) at 0° C. was added CH$_3$I (5.46 g, 38.47 mmol, 5.01 equiv) dropwise. The resulting mixture was stirred overnight at room temperature then filtered and concentrated under vacuum. The resultant residue was dissolved in H$_2$O (30 mL) and extracted with 3×20 mL of dichloromethane. The combined organic layers were washed with 3×20 mL of brine then dried over anhydrous sodium sulfate. The residue was partially purified by flash chromatography on silica gel column using ethyl acetate/petroleum ether (gradient: 1:9-1:2) as eluent. The resultant material was re-purified by Prep-HPLC with the following conditions: Column: XBridge C18, 19×150 mm, 5 m; Mobile Phase A: Water/0.05% NH$_4$HCO$_3$, Mobile Phase B: ACN; Flow rate: 30 mL/min; Gradient: 20% B to 85% B in 10 min; 254 nm. This resulted in 1.04 g (49%) of 3-[3,3-dimethyl-1-oxaspiro[4.5]dec-7-en-8-yl]-1-methyl-1H-pyrazole-4-carbaldehyde as a white solid. $^1$H-NMR (400 MHz, CDCl$_3$) δ: 9.88 (s, 1H), 7.86 (s, 1H), 6.18-6.16 (m, 1H), 3.90 (s, 3H), 3.59-3.54 (m, 3H), 2.78-2.70 (m, 1H), 2.59-2.35 (m, 3H), 2.63-2.56 (m, 1H), 1.96-1.90 (m, 1H), 1.75-1.61 (m, 2H), 1.13 (s, 6H) ppm. And another isomer, 0.45 g (21.2%) of 3-[3,3-dimethyl-1-oxaspiro[4.5]dec-7-en-8-yl]-2-methyl-pyrazole-4-carbaldehyde. $^1$H-NMR (400 MHz, CDCl$_3$) δ: 9.70 (s, 1H), 7.91 (s, 1H), 5.84-5.82 (m, 1H), 3.80 (s, 3H), 3.60-3.54 (m, 3H), 2.57-2.26 (m, 4H), 2.01-1.94 (m, 1H), 1.85-1.80 (m, 1H), 1.78-1.60 (m, 1H), 1.15 (s, 6H) ppm.

Step 2: tert-butyl N-(2-[[(3-[3,3-dimethyl-1-oxaspiro[4.5]dec-7-en-8-yl]-1-methyl-1H-pyrazol-4-yl)methyl](methyl)amino]ethyl)-N-methylcarbamate

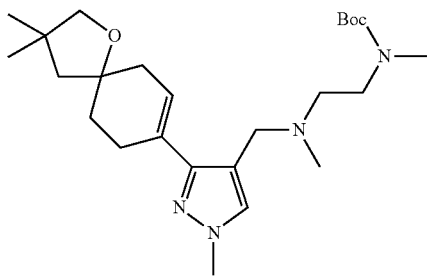

To a solution of 3-[3,3-dimethyl-1-oxaspiro[4.5]dec-7-en-8-yl]-1-methyl-1H-pyrazole-4-carbaldehyde (1.04 g, 3.79 mmol, 1.00 equiv) and tert-butyl N-methyl-N-[2-(methylamino)ethyl]carbamate (1.07 g, 5.68 mmol, 1.50 equiv) in dichloroethane (20 mL) was added NaBH(OAc)$_3$ (2.41 g) portionwise. The resulting mixture was stirred overnight at 50° C. in an oil bath then cooled to room temperature and quenched by the addition of 5 mL of NH$_4$Cl (sat. aq.). The resulting mixture was dissolved in dichloromethane (40 mL) and washed with 3×20 mL of brine then dried over anhydrous sodium sulfate. The residue was purified by flash chromatography on silica gel column using dichloromethane/methanol (20:1) as eluent to afford 1.50 g (89%) of tert-butyl N-(2-[[(3-[3,3-dimethyl-1-oxaspiro[4.5]dec-7-en-8-yl]-1-methyl-1H-pyrazol-4-yl)methyl](methyl)amino]ethyl)-N-methylcarbamate as a yellow oil. $^1$H-NMR (300 MHz, D$_2$O) δ: 8.12 (s, 1H), 5.72-5.70 (m, 1H), 4.25-3.94 (m, 4H), 3.75-3.34 (m, 5H), 3.16-2.88 (m, 4H), 2.51-2.04 (m, 7H), 1.93-1.62 (m, 5H), 1.45 (s, 9H), 1.13 (s, 6H).

Step 3: N-methyl-N-[2-[methyl([1-methyl-3-[(5s,8s)-3,3-dimethyl-1-oxaspiro[4.5]decan-8-yl]-1H-pyrazol-4-yl]methyl)amino]ethyl]carbamate

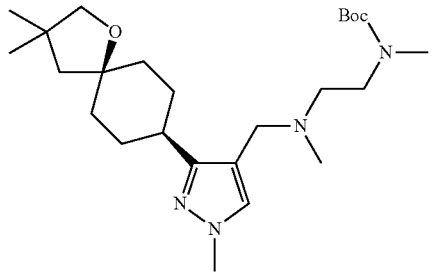

Into a 250-mL round-bottom flask was placed tert-butyl N-(2-[[(3-[3,3-dimethyl-1-oxaspiro[4.5]dec-7-en-8-yl]-1-methyl-1H-pyrazol-4-yl)methyl](methyl)amino]ethyl)-N-methylcarbamate (1.50 g, 3.36 mmol, 1.00 equiv), tetrahydrofuran (30 mL), and 10% Pd(OH)$_2$/C (1.50 g). The resulting mixture was stirred overnight at room temperature under 3 atmospheres of hydrogen. The resulting mixture was filtered then concentrated under vacuum. The residue was partially purified by flash chromatography on silica gel column using dichloromethane/methanol (20:1) as eluent. The partially purified material was then repurified under the following conditions: Column: XBridge C18, 19×150 mm, 5 μm; Mobile Phase A: Water/0.05% NH$_4$HCO$_3$, Mobile Phase B: ACN; Flow rate: 30 mL/min; Gradient: 20% B to 85% B in 10 min; 254 nm. This resulted in 1.0 g (66%) of tert-butyl N-methyl-N-[2-[methyl([1-methyl-3-[(5S,8S)-3,3-dimethyl-1-oxaspiro[4.5]decan-8-yl]-1H-pyrazol-4-yl]methyl)amino]ethyl]carbamate as a yellow oil. $^1$H-NMR (400 MHz, CD$_3$Cl) δ: 7.14 (s, 1H), 3.80-3.78 (m, 4H), 3.51 (s, 3H), 3.36-3.28 (m, 3H), 2.85 (s, 3H), 2.58-2.46 (m, 2H), 2.28-2.22 (m, 3H), 2.01-1.84 (m, 4H), 1.68-1.53 (m, 4H), 1.55 (s, 2H), 1.43 (s, 9H), 1.13 (s, 6H).

Step 4: Methyl([1-methyl-3-[(5S,8S)-3,3-dimethyl-1-oxaspiro[4.5]decan-8-yl]-1H-pyrazol-4-yl]methyl)[2-(methylamino)ethyl]amine hydrochloride (Compound 205)

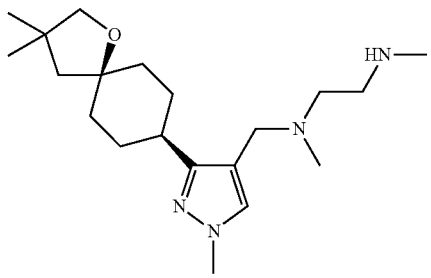

Into a 25-mL round-bottom flask was placed tert-butyl N-methyl-N-[2-[methyl([1-methyl-3-[(5S,8S)-3,3-dimethyl-1-oxaspiro[4.5]decan-8-yl]-1H-pyrazol-4-yl]methyl)amino]ethyl]carbamate (230 mg, 0.51 mmol, 1.00 equiv) and dichloromethane (10 mL). Hydrogen chloride gas was bubbled through the reaction mixture. The reaction mixture was then stirred for 0.5 h at room temperature then extracted with 3×10 mL of water and the aqueous layers combined and concentrated under vacuum. This resulted in 131 mg (61%) of methyl([1-methyl-3-[(5S,8S)-3,3-dimethyl-1-oxaspiro[4.5]decan-8-yl]-1H-pyrazol-4-yl]methyl)[2-(methylamino)ethyl]amine hydrochloride as a colorless solid. $^1$H-NMR (400 MHz, D$_2$O): 7.66 (s, 1H), 4.25 (s, 2H), 3.74 (s, 3H), 3.50-3.40 (m, 6H), 2.74 (s, 3H), 2.70 (s, 3H), 2.64-2.54 (m, 1H), 2.60 (s, 1H), 1.89 (d, 2H, J=16 Hz), 1.70-1.42 (m, 8H), 0.99 (s, 6H). LCMS (method A5, ESI): RT=1.33 min, m/z=349.2 [M+H]$^+$. Compound 206 Methyl([1-methyl-3-[(5R,8S)-3,3-dimethyl-1-oxaspiro[4.5]decan-8-yl]-1H-pyrazol-4-yl]methyl) [2-(methylamino)ethyl]amine hydrochloride

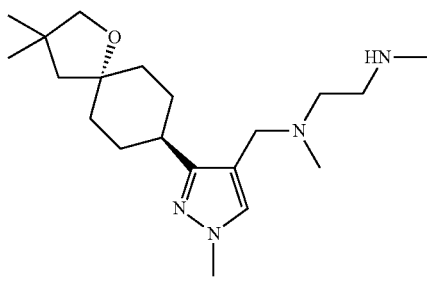

Step 1: Methyl([1-methyl-3-[(5R,8S)-3,3-dimethyl-1-oxaspiro[4.5]decan-8-yl]-1H-pyrazol-4-yl]methyl)[2-(methylamino)ethyl]amine hydrochloride (Compound 206)

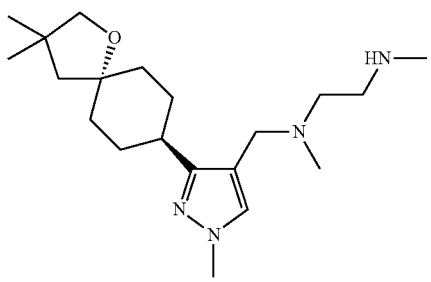

Into a 25-mL round-bottom flask was placed tert-butyl N-methyl-N-[2-[methyl([1-methyl-3-[(5R,8R)-3,3-dimethyl-1-oxaspiro[4.5]decan-8-yl]-1H-pyrazol-4-yl]methyl)amino]ethyl]carbamate (80 mg, 178.32 mmol, 1.00 equiv) and dichloromethane (10 mL). Hydrogen chloride (gas) was bubbled through the reaction mixture. The reaction mixture was then stirred overnight at room temperature and then extracted with 3×10 mL of water and the aqueous layers combined and concentrated under vacuum. This resulted in 23.1 mg of methyl([1-methyl-3-[(5R,8R)-3,3-dimethyl-1-oxaspiro[4.5]decan-8-yl]-1H-pyrazol-4-yl]methyl)[2-(methylamino)ethyl]amine hydrochloride as a colorless solid. $^1$H-NMR (400 MHz, D$_2$O) δ: 7.66 (s, 1H), 4.25 (s, 2H), 3.74 (s, 3H), 3.50-3.40 (m, 6H), 2.74 (s, 3H), 2.70 (s, 3H), 2.67-2.55 (m, 1H), 1.87-1.68 (m, 6H), 1.52-1.42 (m, 4H), 1.02 (s, 6H). LCMS (method A5, ESI): RT=1.32 min, m/z=349.15 [M+H]$^+$.

Compound 245

Methyl ([2-[methyl([1-methyl-5-[(5S,8S)-3,3-dimethyl-1-oxaspiro[4.5]decan-8-yl]-1H-pyrazol-4-yl]methyl)amino]ethyl])amine trifluoroacetic acid salt

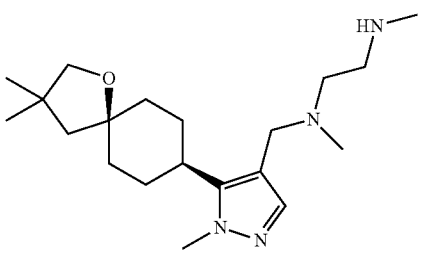

Step 1: 3-Iodo-1H-pyrazole-4-carbaldehyde

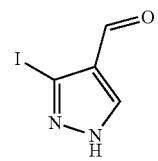

To stirred solution of 3-iodo-1-(oxan-2-yl)-1H-pyrazole-4-carbaldehyde (3 g, 9.80 mmol, 1.00 equiv) in dichloromethane (10 mL) was added trifluoroacetic acid (10 mL). The resulting solution was stirred for 3 h at room temperature then concentrated under vacuum and the resulting residue was treated with sufficient sodium carbonate (sat. aq.) solution to afford a mixture of pH 8. The resulting solution was extracted with 50 mL of dichloromethane and the organic layer washed with brine (3×50 mL) and dried over anhydrous sodium sulfate and concentrated under vacuum. The residue was purified by flash chromatography on silica gel using dichloromethane/petroleum ether (1:3) as eluent to afford 1.4 g (64%) of 3-iodo-1H-pyrazole-4-carbaldehyde as a white solid. $^1$H-NMR (300 MHz, CDCl$_3$): δ 9.89 (s, 1H), 8.04 (s, 1H) ppm.

Step 2: 5-iodo-1-methyl-1H-pyrazole-4-carbaldehyde

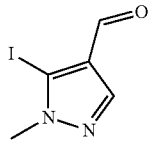

To a stirred solution of 3-iodo-1H-pyrazole-4-carbaldehyde (1.4 g, 6.31 mmol, 1.00 equiv) in CH$_3$CN (20 mL) at 0° C. was added potassium carbonate (2.5 g, 18.09 mmol, 2.87 equiv) followed by dropwise addition of CH$_3$I (980 mg, 6.90 mmol, 1.09 equiv). The resulting mixture was stirred for 3 h at room temperature, then filtered and concentrated under vacuum. The residue was purified by flash chromatography on silica gel using ethyl acetate/petroleum ether (1:10) as eluent to afford 400 mg (27%) of 5-iodo-1-methyl-1H-pyrazole-4-carbaldehyde as a white solid. $^1$H-NMR (300 MHz, CDCl$_3$): δ 9.61 (s, 1H), 8.02 (s, 1H), 3.92 (s, 3H) ppm.

Step 3: 5-[3,3-dimethyl-1-oxaspiro[4.5]dec-7-en-8-yl]-1-methyl-1H-pyrazole-4-carbaldehyde

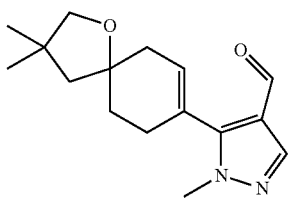 [SMILES: Cn1ncc(C=O)c1C1=CCC2(CC1)CC(C)(C)CO2]

Into a 50-mL 3-necked round-bottom flask purged and maintained with an inert atmosphere of nitrogen was placed 2-[3,3-dimethyl-1-oxaspiro[4.5]dec-7-en-8-yl]-4,4,5,5-tetramethyl-1,3,2-dioxaborolane (686 mg, 2.35 mmol, 1.00 equiv), 1,4-dioxane (20 mL), 5-iodo-1-methyl-1H-pyrazole-4-carbaldehyde (370 mg, 1.57 mmol, 0.67 equiv), Pd(dppf)Cl$_2$ (115 mg, 0.16 mmol, 0.07 equiv), water (2 mL) and potassium carbonate (650 mg, 4.70 mmol, 2.00 equiv). The resulting mixture was stirred overnight at 80° C. then concentrated under vacuum. The residue was purified by flash chromatography on silica gel column using ethyl acetate/petroleum ether (1:7) as eluent to afford 340 mg (53%) of 5-[3,3-dimethyl-1-oxaspiro[4.5]dec-7-en-8-yl]-1-methyl-1H-pyrazole-4-carbaldehyde as a light yellow oil. $^1$H-NMR (300 MHz, CDCl$_3$): δ 9.70 (s, 1H), 7.92 (s, 1H), 5.84-5.83 (m, 1H), 3.80 (s, 3H), 3.60 (s, 2H), 2.57-2.26 (m, 4H), 2.04-1.68 (m, 4H), 1.21-1.10 (m, 6H) ppm.

Step 4: (5-[3,3-dimethyl-1-oxaspiro[4.5]decan-8-yl]-1-methyl-1H-pyrazol-4-yl)methanol

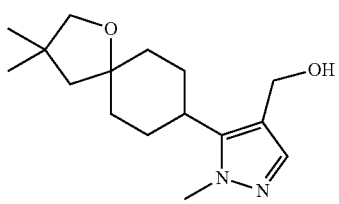 [SMILES: Cn1ncc(CO)c1C1CCC2(CC1)CC(C)(C)CO2]

Into a 50-mL round-bottom flask was placed 5-[3,3-dimethyl-1-oxaspiro[4.5]decan-8-yl]-1-methyl-1H-pyrazole-4-carbaldehyde (340 mg, 1.23 mmol, 1.00 equiv), tetrahydrofuran (20 mL) and 10% Pd(OH)$_2$/C (680 mg). The resulting mixture was stirred overnight at room temperature under 3 atmospheres of hydrogen then filtered and concentrated under vacuum to afford 340 mg of (5-[3,3-dimethyl-1-oxaspiro[4.5]decan-8-yl]-1-methyl-1H-pyrazol-4-yl)methanol as light yellow oil.

Step 5: tert-butyl N-(2-[[(5-[3,3-dimethyl-1-oxaspiro[4.5]decan-8-yl]-1-methyl-1H-pyrazol-4-yl)methyl](methyl)amino]ethyl)-N-methylcarbamate

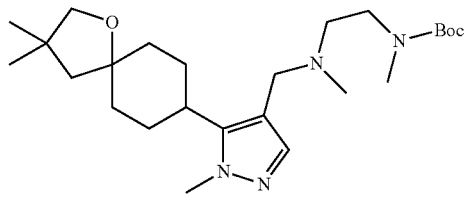 [SMILES: CN(CCN(C)C(=O)OC(C)(C)C)Cc1cnn(C)c1C1CCC2(CC1)CC(C)(C)CO2]

To a solution of (5-[3,3-dimethyl-1-oxaspiro[4.5]decan-8-yl]-1-methyl-1H-pyrazol-4-yl)methanol (340 mg, 1.22 mmol, 1.00 equiv) and triethylamine (371 mg, 3.67 mmol, 3.00 equiv) in dichloromethane (8 mL) at 0° C. was added methanesulfonyl chloride (167.3 mg) dropwise with stirring. The resulting solution was stirred for 30 min at room temperature then treated with tert-butyl N-methyl-N-[2-(methylamino)ethyl]carbamate (276 mg, 1.47 mmol, 1.20 equiv). The resulting solution was stirred for 2 h at room temperature then quenched by the addition of 20 mL of water. The resulting mixture was extracted with 3×50 mL of dichloromethane and the organic layers combined and dried over anhydrous sodium sulfate and concentrated under vacuum to afford 128 mg (23%) of tert-butyl N-(2-[[(5-[3,3-dimethyl-1-oxaspiro[4.5]decan-8-yl]-1-methyl-1H-pyrazol-4-yl)methyl](methyl)amino]ethyl)-N-methylcarbamate as a light yellow oil. $^1$H-NMR (300 MHz, CD$_3$OD): δ 7.30 (s, 1H), 3.83 (s, 3H), 3.53 (s, 2H), 3.43-3.31 (m, 4H), 2.91-2.83 (m, 4H), 2.53-2.50 (m, 2H), 2.25-2.07 (m, 5H), 1.97-1.93 (m, 2H), 1.63-1.49 (m, 15H), 1.18-1.10 (m, 6H) ppm.

Step 6: Methyl ([2-[methyl([1-methyl-5-[(5S,8S)-3,3-dimethyl-1-oxaspiro[4.5]decan-8-yl]-1H-pyrazol-4-yl]methyl)amino]ethyl])amine trifluoroacetic acid salt (Compound 245)

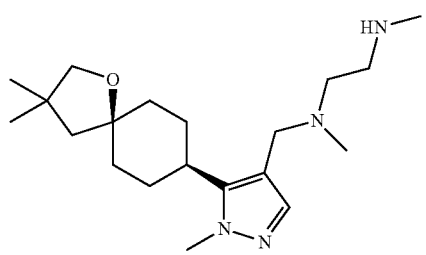

Into a 8-mL sealed tube was placed tert-butyl N-(2-[[(5-[3,3-dimethyl-1-oxaspiro[4.5]decan-8-yl]-1-methyl-1H-pyrazol-4-yl)methyl](methyl)amino]ethyl)-N-methylcarbamate (37 mg, 0.08 mmol, 1.00 equiv), dichloromethane (1 mL) and CF$_3$COOH (1 mL). The resulting solution was stirred for 30 min at room temperature then concentrated under vacuum. The resultant residue was purified by reverse phase HPLC using the following conditions: Column: Sunfire C18, 19×150 mm, 5 μm; Mobile Phase A: Water/0.05% TFA, Mobile Phase B: ACN; Flow rate: 30 mL/min; Gradient: 5% B to 55% B in 10 min; 254 nm. This resulted in 18.9 mg (40%) of methyl ([2-[methyl([1-methyl-5-[(5S,8S)-3,3-dimethyl-1-oxaspiro[4.5]decan-8-yl]-1H-pyrazol-4-yl]methyl)amino]ethyl])amine trifluoroacetic acid salt as a colorless oil. $^1$H-NMR (300 MHz, D$_2$O): δ 7.53 (s, 1H), 4.33 (s, 2H), 3.81 (s, 3H), 3.52-3.40 (m, 6H), 2.91-2.69 (m, 7H), 2.00-1.72 (m, 4H), 1.69-1.45 (m, 6H), 1.00 (s, 6H). LCMS (method W, ESI): RT=1.37 min, m/z=349.1 [M+H].

Compound 217

4-[4-([methyl[2-(methylamino)ethyl]amino]methyl)-1H-pyrazol-3-yl]cyclohexan-1-ol trifluoroacetate

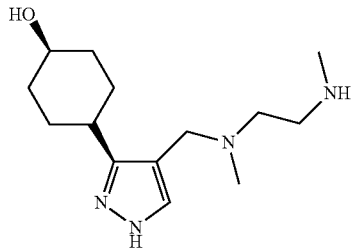

Step 1: 1,4-dioxaspiro[4.5]dec-7-en-8-yl trifluoromethanesulfonate

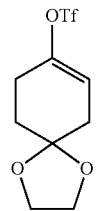

To a solution of 1,4-dioxaspiro[4.5]decan-8-one (80 g, 512.23 mmol, 1.00 equiv) in THF (500 mL) at −78° C. was added LiHMDS (615 mL of a 1 M solution in THF) dropwise over approximately 25 min then stirred for 2 h at −40° C. The reaction mixture was then cooled to −78° C. and treated with 1,1,1-trifluoro-N-phenyl-N-(trifluoromethane)sulfonylmethanesulfonamide (220 g, 615.82 mmol, 1.20 equiv) dropwise.

The resulting solution was allowed to warm to room temperature and stirred overnight then quenched by the addition of 100 mL of NH$_4$Cl (sat. aq.). The resulting mixture was extracted with 500 mL of ethyl acetate and the organic extract washed with 3×500 mL of brine and dried over anhydrous sodium sulfate. The crude product was purified by flash chromatography on silica gel column using ethyl acetate/petroleum ether (gradient: 1% to 3% EA) as eluent to afford 166 g of 1,4-dioxaspiro[4.5]dec-7-en-8-yl trifluoromethanesulfonate as a yellow oil. $^1$H-NMR (300 MHz, CDCl$_3$): 5.68-5.64 (m, 1H), 3.99 (s, 4H), 2.56-2.51 (m, 2H), 2.42-2.41 (m, 2H), 1.90 (t, J=6.6 Hz, 2H) ppm.

Step 2: 2-[1,4-dioxaspiro[4.5]dec-7-en-8-yl]-4,4,5,5-tetramethyl-1,3,2-dioxaborolane

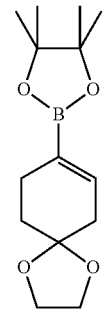

Into a 3-L 4-necked round-bottom flask was placed 1,4-dioxaspiro[4.5]dec-7-en-8-yl trifluoromethanesulfonate (80 g, 277.55 mmol, 1.00 equiv), B$_2$Pin$_2$ (85 g, 334.65 mmol, 1.21 equiv), Pd(dppf)Cl$_2$ (20 g, 27.33 mmol, 0.10 equiv), KOAc (82 g, 835.54 mmol, 3.01 equiv) and 1,4-dioxane (800 mL). The resulting solution was stirred overnight at 80° C. using an oil bath then cooled to room temperature and concentrated under vacuum. The residue was extracted with 1 L of ethyl acetate and the organic layer washed with 3×1 L of brine and dried over anhydrous sodium sulfate and concentrated under vacuum. The residue was purified by flash chromatography on silica gel column using ethyl acetate/petroleum ether (gradient: 5% to 10% ethyl acetate) to afford 36 g (49%) of 2-[1,4-dioxaspiro[4.5]dec-7-en-8-yl]-4,4,5,5-tetramethyl-1,3,2-dioxaborolane as a yellow solid. $^1$H-NMR (300 MHz, CDCl$_3$): 6.46-6.47 (m, 1H), 3.98 (s, 4H), 2.39-2.35 (m, 4H), 1.73 (t, J=4.8 Hz, 2H), 1.26 (s, 12H) ppm.

Step 3: 3-[1,4-dioxaspiro[4.5]dec-7-en-8-yl]-1-(oxan-2-yl)-1H-pyrazole-4-carbaldehyde

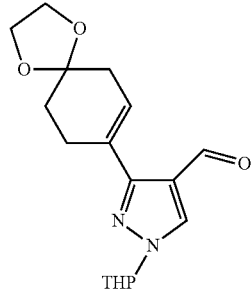

Into a 2-L 4-necked round-bottom flask was placed 2-[1,4-dioxaspiro[4.5]dec-7-en-8-yl]-4,4,5,5-tetramethyl-1,3,2-dioxaborolane (44 g, 165.33 mmol, 1.00 equiv) and 3-iodo-1-(oxan-2-yl)-1H-pyrazole-4-carbaldehyde (45.5 g, 148.64 mmol, 0.90 equiv). This was followed by the addition of Pd(dppf)Cl$_2$ (12 g, 16.40 mmol, 0.10 equiv). To this was added K$_3$PO$_4$ (105 g, 494.66 mmol, 2.99 equiv), ethylene glycol dimethyl ether (500 mL) and water (50 mL). The resulting mixture was stirred overnight at 75° C. in an oil bath then cooled to room temperature and concentrated under vacuum. The residue was extracted with 500 mL of ethyl acetate and the organic layer washed with 3×500 mL of brine and dried over anhydrous sodium sulfate and concentrated under vacuum. The residue was purified by flash chromatography on silica gel column using ethyl acetate/petroleum ether (gradient: 20% to 30% EA) as eluent to afford 35.5 g (67%) of (R/S) 3-[1,4-dioxaspiro[4.5]dec-7-en-8-yl]-1-(oxan-2-yl)-1H-pyrazole-4-carbaldehyde as a light yellow solid. $^1$H-NMR (300 MHz, CDCl$_3$): 9.91 (s, 1H), 8.26 (s, 1H), 6.29-6.26 (m, 1H), 5.38-5.34 (m, 1H), 4.09-4.01 (m, 5H), 3.74-3.63 (m, 1H), 2.79-2.74 (m, 2H), 2.50-2.49 (d, J=3.6 Hz, 2H), 2.12-1.89 (m, 5H), 1.72-1.60 (m, 3H) ppm.

Step 4: (R/S) tert-butyl N-(2-[[(3-[1,4-dioxaspiro [4.5]dec-7-en-8-yl]-1-(oxan-2-yl)-1H-pyrazol-4-yl) methyl](methyl)amino]ethyl)-N-methylcarbamate

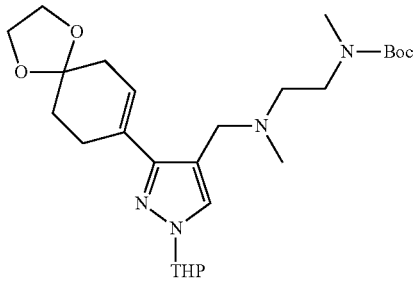

To a stirred solution of (R/S) 3-[1,4-dioxaspiro[4.5]dec-7-en-8-yl]-1-(oxan-2-yl)-1H-pyrazole-4-carbaldehyde (25 g, 78.53 mmol, 1.00 equiv) and tert-butyl N-methyl-N-[2-(methylamino)ethyl]carbamate (17.7 g, 94.02 mmol, 1.20 equiv) in dichloroethane (250 mL) at 0° C. was added NaBH(OAc)$_3$ (50 g, 235.91 mmol, 3.00 equiv) portionwise. The resulting mixture was allowed to warm to room temperature, stirred overnight and then quenched by the addition of 50 mL of NH$_4$Cl (sat. aq.). The resulting mixture was extracted with 500 mL of CH$_2$Cl$_2$ and the organic phase washed with 3×500 mL of brine and dried over anhydrous sodium sulfate and concentrated under vacuum. The residue was purified by flash chromatography on silica gel column using ethyl acetate/petroleum ether (1:2) as eluent to afford 30.3 g (79%) of (R/S) tert-butyl N-(2-[[(3-[1,4-dioxaspiro [4.5]dec-7-en-8-yl]-1-(oxan-2-yl)-1H-pyrazol-4-yl)methyl] (methyl)amino]ethyl)-N-methylcarbamate as a yellow oil. $^1$H-NMR (300 MHz, CDCl$_3$): 7.50 (s, 1H), 6.26 (br, 1H), 5.38-5.34 (m, 1H), 4.09-3.99 (m, 5H), 3.74-3.69 (m, 1H), 3.42 (br, 2H), 2.86 (s, 3H), 2.84-2.07 (m, 8H), 2.04 (s, 3H), 1.85 (t, J=6.6 Hz, 2H), 1.68-1.52 (m, 6H), 1.58 (s, 9H) ppm.

Step 5: (R/S) tert-butyl N-(2-[[(3-[1,4-dioxaspiro [4.5]decan-8-yl]-1-(oxan-2-yl)-1H-pyrazol-4-yl) methyl](methyl)amino]ethyl)-N-methylcarbamate

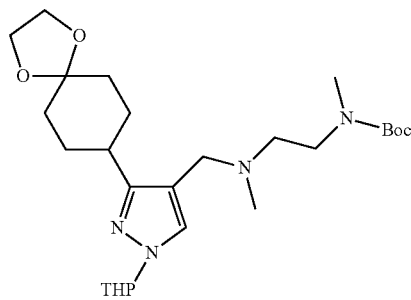

Into a 1-L round-bottom flask was placed (R/S) tert-butyl N-(2-[[(3-[1,4-dioxaspiro[4.5]dec-7-en-8-yl]-1-(oxan-2-yl)-1H-pyrazol-4-yl)methyl](methyl)amino]ethyl)-N-methyl-carbamate (15 g, 30.57 mmol, 1.00 equiv), THF (500 mL) and 10% Pd(OH)$_2$/C (9 g). The resulting mixture was stirred for 2 h at room temperature under 3 atmospheres of hydrogen. The resulting mixture was filtered and concentrated under vacuum to afford 11.5 g (76%) of (R/S) tert-butyl N-(2-[[(3-[1,4-dioxaspiro[4.5]decan-8-yl]-1-(oxan-2-yl)-1H-pyrazol-4-yl)methyl](methyl)amino]ethyl)-N-methyl-carbamate as yellow oil. $^1$H-NMR (300 MHz, CDCl$_3$): 7.41 (s, 1H), 5.30-5.25 (m, 1H), 4.11-3.95 (m, 5H), 3.70-3.62 (m, 1H), 3.36 (br, 4H), 2.83 (s, 3H), 2.74-2.66 (m, 1H), 2.47 (s, 3H), 2.04 (s, 3H), 2.04-1.82 (m, 10H), 1.68-1.52 (m, 6H), 1.48 (s, 9H) ppm.

Step 6: (R/S) tert-butyl N-methyl-N-[2-[methyl([[1-(oxan-2-yl)-3-(4-oxocyclohexyl)-1H-pyrazol-4-yl] methyl])amino]ethyl]carbamate

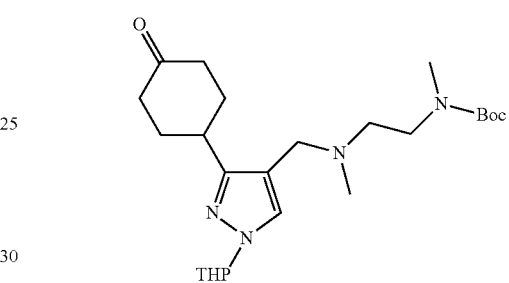

Into a 250-mL round-bottom flask was placed tert-butyl N-(2-[[(3-[1,4-dioxaspiro[4.5]decan-8-yl]-1-(oxan-2-yl)-1H-pyrazol-4-yl)methyl](methyl)amino]ethyl)-N-methyl-carbamate (13.5 g, 27.40 mmol, 1.00 equiv), dichloromethane (130 mL) and FeCl$_3$·6H$_2$O (26 g, 96.30 mmol, 3.51 equiv). The resulting solution was stirred for 2 h at room temperature then extracted with dichloromethane (200 mL). The organic phase was washed sequentially with 3×100 mL of brine, 3×100 mL sodium bicarbonate (sat. aq.) and then again with 3×100 mL of brine. The mixture was dried over anhydrous sodium sulfate and concentrated under vacuum. The residue was purified by flash chromatography on silica gel column using methanol/dichloromethane (gradient: 1% to 5% MeOH) to afford 7.5 g (61%) of tert-butyl N-methyl-N-[2-[methyl([[1-(oxan-2-yl)-3-(4-oxocyclohexyl)-1H-pyrazol-4-yl]methyl])amino]ethyl]carbamate as a yellow oil.

Step 7: (R/S)N-[2-([[3-(4-hydroxycyclohexyl)-1-(oxan-2-yl)-1H-pyrazol-4-yl]methyl](methyl)amino) ethyl]-N-methylcarbamate

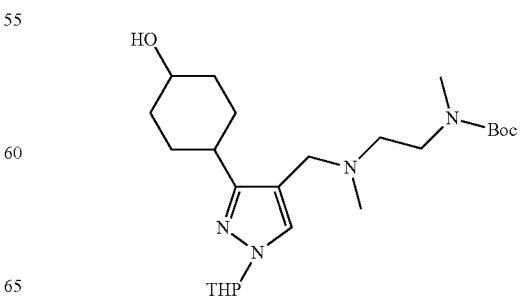

To a stirred solution of (R/S) tert-butyl N-methyl-N-[2-[methyl([[1-(oxan-2-yl)-3-(4-oxocyclohexyl)-1H-pyrazol-4-yl]methyl])amino]ethyl]carbamate (500 mg, 1.11 mmol) in methanol (5 mL) at 0° C. was added NaBH₄ (85 mg, 2.24 mmol) portionwise. The resulting mixture was stirred for 1 h at room temperature then quenched by the addition of 5 mL of NH₄Cl (sat. aq.). The resulting mixture was concentrated under vacuum to afford 380 mg (76%) of (R/S) tert-butyl N-[2-([[3-(4-hydroxycyclohexyl)-1-(oxan-2-yl)-1H-pyrazol-4-yl]methyl](methyl)amino)ethyl]-N-methyl-carbamate as a light yellow oil. ¹H-NMR (400 MHz, CDCl₃): δ 7.41 (s, 1H), 5.28 (t, J=6.0 Hz, 1H), 4.05 (d, J=8.0 Hz, 1H), 3.74-3.62 (m, 2H), 3.41-3.25 (m, 3H), 2.84 (s, 3H), 2.68-2.56 (m, 2H), 2.20 (s, 3H), 2.09-1.82 (m, 6H), 1.74-1.52 (m, 7H), 1.51-1.29 (m, 13H) ppm.

Step 8: tert-butyl 2-(((3-((1S,4S)-4-hydroxycyclo-hexyl)-1H-pyrazol-4-yl)methyl)(methyl)amino)ethyl (methyl)carbamate

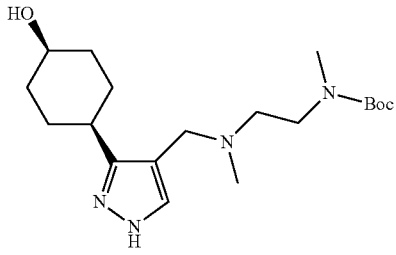 [SMILES: CN(CCN(C)C(=O)OC(C)(C)C)Cc1c[nH]nc1[C@H]1CC[C@@H](O)CC1]

A solution of (R/S) tert-butyl N-[2-([[3-(4-hydroxycyclohexyl)-1-(oxan-2-yl)-1H-pyrazol-4-yl]methyl](methyl) amino)ethyl]-N-methylcarbamate (380 mg, 0.84 mmol, 1.00 equiv) in methanol (30 mL) was treated with aqueous hydrochloric acid (12N, 0.06 mL) and stirred overnight at room temperature. The pH value of the solution was adjusted to 7-8 with ammonia and the mixture dried over anhydrous sodium sulfate and concentrated under vacuum. The residue was purified by reverse phase HPLC with the following conditions:

Column: Sunfire C18, 19×150 mm, 5 μm; Mobile Phase A: Water/0.05% ammonium hydroxide Mobile Phase B: ACN; Flow rate: 30 mL/min; Gradient: 5% B to 55% B in 10 min; Detector: 254 nm. This resulted in the cis-isomer 30 mg of tert-butyl 2-(((3-((1S,4S)-4-hydroxycyclohexyl)-1H-pyrazol-4-yl)methyl)(methyl)amino)ethyl(methyl)carbamate. LCMS (method D, ESI): RT=1.12 min, m/z=367.0 [M+H]. And the trans-isomer 130 mg of tert-butyl 2-(((3-((1R,4R)-4-hydroxycyclohexyl)-1H-pyrazol-4-yl)methyl) (methyl)amino)ethyl(methyl)carbamate as a light yellow oil.

Step 9: 4-[4-([methyl[2-(methylamino)ethyl]amino] methyl)-1H-pyrazol-3-yl]cyclohexan-1-ol trifluoro-acetate (Compound 217)

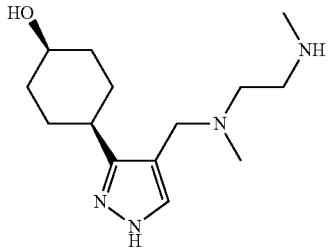 [SMILES: CNCCN(C)Cc1c[nH]nc1[C@H]1CC[C@@H](O)CC1]

A solution of tert-butyl 2-(((3-((1S,4S)-4-hydroxycyclo-hexyl)-1H-pyrazol-4-yl)methyl)(methyl)amino)ethyl (methyl)carbamate (30 mg, 0.08 mmol, 1.00 equiv) in dichloromethane (2 mL) was treated with trifluoroacetic acid (2 mL) and stirred for 5 min at room temperature. The resulting mixture was concentrated under vacuum to afford 28.6 mg (71%) of 4-[4-([methyl[2-(methylamino)ethyl] amino]methyl)-1H-pyrazol-3-yl]cyclohexan-1-ol trifluoro-acetate salts as a light yellow oil. ¹H-NMR (300 MHz, D₂O): δ 7.70 (s, 1H), 4.30 (s, 2H), 4.70-4.00 (m, 1H), 3.51-3.40 (m, 4H), 2.82-2.66 (m, 7H), 1.86-1.52 (m, 8H) ppm. LCMS (method A6, ESI): RT=2.78 min, m/z=267.05 [M+H]⁺.

Compound 227

4-[4-([methyl[2-(methylamino)ethyl]amino]methyl)-1H-pyrazol-3-yl]cyclohexan-1-ol trifluoroacetate

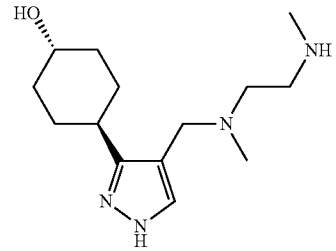 [SMILES: CNCCN(C)Cc1c[nH]nc1[C@H]1CC[C@H](O)CC1]

Step 1: 4-[4-([methyl[2-(methylamino)ethyl]amino] methyl)-1H-pyrazol-3-yl]cyclohexan-1-ol trifluoro-acetate (Compound 227)

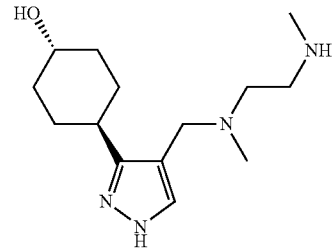 [SMILES: CNCCN(C)Cc1c[nH]nc1[C@H]1CC[C@H](O)CC1]

A solution of tert-butyl 2-(((3-((1R,4R)-4-hydroxycyclo-hexyl)-1H-pyrazol-4-yl)methyl)(methyl)amino)ethyl (methyl)carbamate (130 mg, 0.35 mmol, 1.00 equiv)) in dichloromethane (2 mL) was treated with trifluoroacetic acid (2 mL) and stirred for 5 min at room temperature. The resulting mixture was concentrated under vacuum to afford 120.9 mg (69%) of 4-[4-([methyl[2-(methylamino)ethyl] amino]methyl)-1H-pyrazol-3-yl]cyclohexan-1-ol trifluoro-acetate as a light yellow oil. ¹H-NMR (300 MHz, D₂O): δ 7.70 (s, 1H), 4.30 (s, 2H), 3.71-3.60 (m, 1H), 3.51-3.41 (m, 4H), 2.78-2.60 (m, 7H), 2.01-1.91 (m, 2H), 1.87-1.75 (m, 2H), 1.61-1.45 (m, 2H), 1.40-1.22 (m, 2H) ppm. LCMS (method A6, ESI): RT=2.83 min, m/z=267.1 [M+H]⁺.

Compound 263

(1S)-2,2-dimethyl-5-[4-({methyl[2-(methylamino)ethyl]amino}methyl)-1H-pyrazol-3-yl]-N-(3-methylbutyl)cyclohexane-1-carboxamide

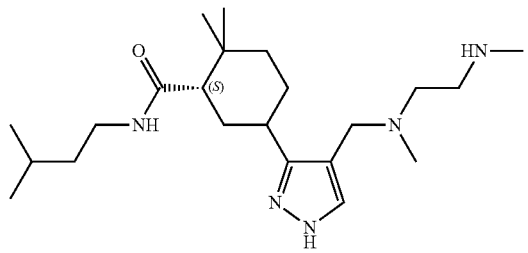

Step 1: (2S)-2-(methoxymethyl)-N-methylidenepyrrolidin-1-amine

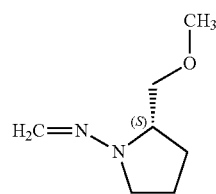

To an ice cold solution of (2S)-2-(methoxymethyl)pyrrolidin-1-amine (5.0 g, 38.41 mmol) in DCM (75 mL) was added paraformaldehyde (1.38 g, 46.09 mmol). The mixture was left to stir at RT over the weekend. Water (25 mL) was added, and the phases were separated. The aqueous phase was extracted with DCM (3×30 mL). The combined organics were washed with water (20 ml), brine (20 ml), dried over $Na_2SO_4$, filtered and evaporated to dryness. Purification by silica gel column chromatography, on a Biotage Isolera system, using a 100 g HP-Sil SNAP cartridge, eluting with EtOAc:heptane (1:99-4:6), gave the desired product as a colourless oil (4.19 g, 76%): MS (ESI) for $C_7H_{14}N_2O$ m/z 143.0 (M+H)$^+$; HPLC purity 100% (ret. time, 0.81 min); $^1$H-NMR (500 MHz, Chloroform-d) δ 6.13 (d, J=11.6 Hz, 1H), 6.02 (d, J=11.6 Hz, 1H), 3.62-3.51 (m, 2H), 3.49-3.42 (m, 1H), 3.38 (s, 3H), 3.33 (ddd, J=9.9, 7.3, 3.4 Hz, 1H), 2.83 (q, J=7.9 Hz, 1H), 2.04-1.87 (m, 3H), 1.86-1.75 (m, 1H).

Step 2: (3S)-3-[(E)-N-[(2S)-2-(methoxymethyl)pyrrolidin-1-yl]carboximidoyl]-4,4-dimethylcyclohexan-1-one

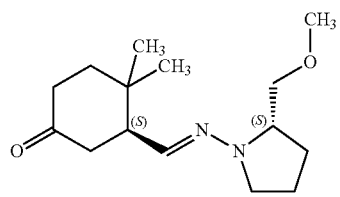

To a cooled (−78° C.) solution of 4,4-dimethylcyclohex-2-en-1-one (4.57 g, 36.83 mmol) in dry THF (100 mL) were sequentially added tert-butyl(dimethyl)silyl trifluoromethanesulfonate (7.45 ml, 32.41 mmol) and pre-cooled (−78° C.) (2S)-2-(methoxymethyl)-N-methylidenepyrrolidin-1-amine (4.19 g, 29.47 mmol) under a $N_2$ atmosphere. After 45 min 1M N,N,N-tributylbutan-1-aminium fluoride (44.20 ml, 44.20 mmol) was added and the mixture was allowed to warm to RT and stirred until LC/MS indicated total consumption of the silyl enol ether (overnight). The reaction mixture was diluted with t-butylmethylether (100 ml) and washed with water (2×100 ml). The aqueous was then extracted with t-butylmethylether (100 ml). The combined organic layers were washed with brine (100 ml), dried over $Na_2SO_4$, filtered and evaporated in vacuo to give a dark brown oil. Purification by silica gel column chromatography, on a Biotage Isolera system, using a 340 g KP-Sil SNAP cartridge, eluting with EtOAc:heptanes (1:9-6:4), gave the desired product as a yellow oil (4.6 g, 59%): MS (ESI) for $C_{15}H_{26}N_2O_2$ m/z 266.95 (M+H)$^+$; HPLC purity 100% (ret. time, 1.11 min); $^1$H-NMR (500 MHz, Chloroform-d) δ 6.60-6.51 (m, 1H), 3.56-3.49 (m, 1H), 3.47-3.41 (m, 1H), 3.40-3.28 (m, 5H), 2.73 (q, J=8.0 Hz, 1H), 2.56-2.25 (m, 5H), 2.01-1.84 (m, 3H), 1.83-1.70 (m, 2H), 1.67-1.60 (m, 1H), 1.07 (d, J=11.2 Hz, 6H).

Step 3: 3(1S)-2,2-dimethyl-5-oxocyclohexane-1-carbaldehyde

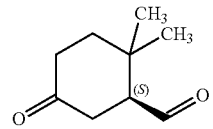

A solution of (3S)-3-[(E)-N-[(2S)-2-(methoxymethyl)pyrrolidin-1-yl]carboximidoyl]-4,4-dimethylcyclohexan-1-one (13.7 g, 51.43 mmol) in DCM (250 ml) was cooled to −78° C. and dry ozone was bubbled through until appearance of a permanent green/blue colour (~4 h) and then continued for a further 30 min. The reaction mixture was sparged with nitrogen for 20 min. Dimethylsulfide (3.9 ml, 62.13 mmol) was added and the reaction mixture stirred at RT for 30 min before evaporating in vacuo. Purification by silica gel column chromatography, on a Biotage Isolera system, using a 340 g KP-Sil SNAP cartridge, eluting with EtOAc:heptanes (1:9-7:3), gave the desired product as a yellow oil (4.02 g, 46%): $^1$H-NMR (500 MHz, Chloroform-d) δ 9.85 (d, J=1.5 Hz, 1H), 2.67-2.62 (m, 1H), 2.61-2.54 (m, 1H), 2.48-2.40 (m, 1H), 2.39-2.29 (m, 2H), 1.78-1.71 (m, 2H), 1.32 (s, 3H), 1.15 (s, 3H).

Step 4: (1S)-2,2-dimethyl-5-oxocyclohexane-1-carboxylic acid

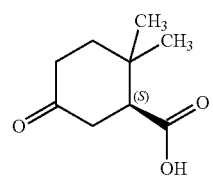

(1S)-2,2-Dimethyl-5-oxocyclohexane-1-carbaldehyde (4.02 g, 23.46 mmol) in ether (200 ml) was cooled to −30° C. and treated with 2M trioxochromium-sulfuric acid (1:1) (58.66 ml, 117.31 mmol Jones Reagent). After 30 min at −30° C. the mixture was stirred for a further 2 hr whilst allowing to warm to RT. The reaction mixture was cooled to 0° C. and basified with 1N NaOH (~650 ml) and washed with t-butylmethylether (~2×500 ml). The aqueous layer was acidified to acid pH with 2 N $H_2SO_4$ (~160 ml) and the product was extracted with EtOAc (3×800 ml). The combined organic layers were dried over $Na_2SO_4$, filtered, concentrated and co-evaporated with heptane (~50 ml). Purification by silica gel column chromatography, on a Biotage Isolera system, using a 100 g KP-Sil SNAP cartridge, eluting with MeOH:DCM (1:99-1:9), gave the desired product as an off-white solid (3.04 g, 76%): $^1$H-NMR (500 MHz, Chloroform-d) δ 2.73-2.57 (m, 2H), 2.51-2.40 (m, 2H), 2.38-2.31 (m, 1H), 1.95-1.86 (m, 1H), 1.72-1.63 (m, 1H), 1.22 (s, 3H), 1.17 (s, 3H).

Step 5: methyl (1S)-2,2-dimethyl-5-oxocyclohexane-1-carboxylate

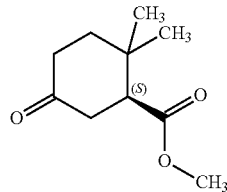

MeI (1.22 mL, 19.65 mmol) was added to a suspension of (1S)-2,2-dimethyl-5-oxocyclohexane-1-carboxylic acid (3.04 g, 17.86 mmol) and $K_2CO_3$ (2.72 g, 19.65 mmol) in acetone (45 mL) and heated to 60° C. for 18 h. This was then allowed to cool to RT, filtered using additional DCM 2×20 ml, and evaporated in vacuo. Purification by silica gel column chromatography, on a Biotage Isolera system, using a 100 g KP-Sil SNAP cartridge, eluting with EtOAc:heptanes (1:9-1), gave the desired product as a colourless oil (2.80 g, 85%): $^1$H-NMR (250 MHz, Chloroform-d) δ 3.69 (s, 3H), 2.73-2.54 (m, 2H), 2.53-2.24 (m, 3H), 1.95-1.80 (m, 1H), 1.74-1.59 (m, 1H), 1.16 (s, 3H), 1.11 (s, 3H).

Step 6: methyl (1S)-6,6-dimethyl-3-(trifluoromethanesulfonyloxy)cyclohex-3-ene-1-carboxylate

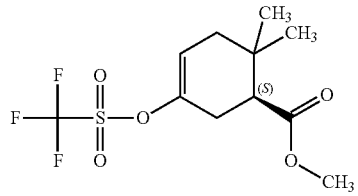

To a cold [0° C.] solution of methyl (1S)-2,2-dimethyl-5-oxocyclohexane-1-carboxylate (1.7 g, 9.27 mmol) in 1,2-dichloroethane (50 ml) was added 2,6-di-tert-butylpyridine (2.28 ml, 10.15 mmol) followed by slow addition of a solution of $Tf_2O$ (1.65 ml, 9.79 mmol). The reaction was allowed to warm to RT overnight. The solvent was evaporated and the residue was partitioned between water (50 ml) and t-butylmethylether-EtOAc (120 ml, ~10:1). The organic layer was separated, washed with water (25 ml), sat $NaHCO_3$ (25 ml), brine (25 ml), dried over $Na_2SO_4$, filtered and concentrated. The residue was absorbed onto silica gel, and purified by silica gel column chromatography, eluting with EtOAc:heptanes (0-1:4) to give the desired product as a yellow oil (2.1 g, 72%): $^1$H-NMR (500 MHz, Chloroform-d) δ 5.71 (t, J=3.9 Hz, 1H), 2.73-2.62 (m, 1H), 2.60-2.53 (m, 1H), 2.50-2.39 (m, 1H), 2.12-2.04 (m, 2H), 1.04 (s, 3H), 1.01 (s, 3H).

Step 7: methyl (1S)-6,6-dimethyl-3-(tetramethyl-1,3,2-dioxaborolan-2-yl)cyclohex-3-ene-1-carboxylate

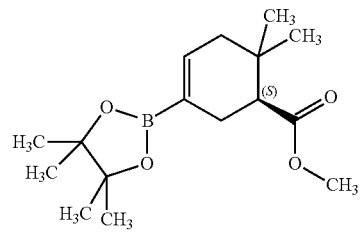

A suspension of methyl (1S)-6,6-dimethyl-3-(trifluoromethanesulfonyloxy)cyclohex-3-ene-1-carboxylate (2.10 g, 6.64 mmol), KOAc (4.89 g, 49.80 mmol) and 4,4,4',4',5,5,5',5'-octamethyl-2,2'-bi-1,3,2-dioxaborolane (2.02 g, 7.97 mmol) in 1,4-dioxane (120 ml) was degassed for 10 min under a nitrogen sparge at RT. Pd(dppf).$Cl_2$ (0.04 g, 0.05 mmol) was added to the reaction mixture and stirred at 90° C. for 3 h, then allowed to stir whilst cooling to RT. The reaction mixture was diluted with EtOAc (130 ml) and washed with water (130 ml). The aqueous layer was extracted with EtOAc (130 ml), the combined organics washed with brine (50 ml), dried over $Na_2SO_4$, filtered and evaporated in vacuo. Purification by silica gel column chromatography, on a Biotage Isolera system, using a 100 g KP-Sil SNAP cartridge, eluting with EtOAc:heptanes (1:99-3:7), gave the desired product as a white solid (1.62 g, 83%): $^1$H-NMR (250 MHz, Chloroform-d) δ 6.59-6.39 (m, 1H), 3.64 (s, 3H), 2.36 (s, 3H), 2.07-1.90 (m, 2H), 1.25 (s, 12H), 0.96 (d, J=4.2 Hz, 6H).

Step 8: methyl (1S)-3-(4-{[(2-{[(tert-butoxy)carbonyl](methyl)amino}ethyl)(methyl)amino]methyl}-1-(oxan-2-yl)-1H-pyrazol-3-yl)-6,6-dimethylcyclohex-3-ene-1-carboxylate

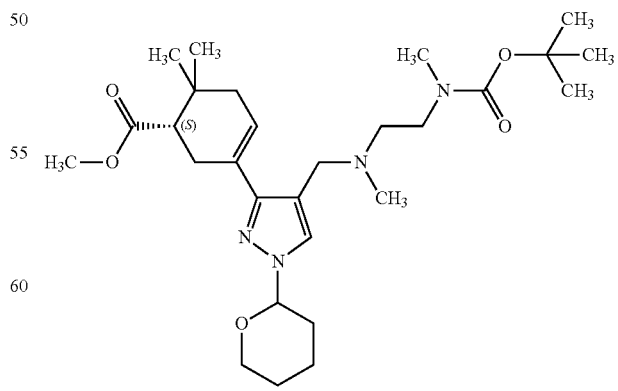

A suspension of methyl (1S)-6,6-dimethyl-3-(tetramethyl-1,3,2-dioxaborolan-2-yl)cyclohex-3-ene-1-carboxylate (1.62 g, 5.51 mmol), tert-butyl N-[2-({[3-iodo-1-(oxan-2-yl)-1H-pyrazol-4-yl]methyl}(methyl)amino)ethyl]-N-methylcarbamate (2.63 g, 5.51 mmol), $K_2CO_3$ (2.30 g, 16.63 mmol) and Pd(dppf)Cl$_2$.DCM (0.45 g, 0.55 mmol) in 1,4-dioxane (100 ml) and water (10 ml) was stirred under a $N_2$ sparge for 10 min at RT. This was then heated to 90° C. and stirred overnight under $N_2$. The reaction mixture was allowed to cool to RT before evaporating to dryness. MeOH (2×20 ml) was added to the residue and evaporated to dryness in vacuo. Purification by silica gel column chromatography, on a Biotage Isolera system, using a 100 g KP-Sil SNAP cartridge, eluting with THF:heptanes (1:99-12:88), gave the desired product as a tan oil (1.89 g, 57%): MS (ESI+) for $C_{28}H_{46}N_4O_5$ m/z 519.10 (M+H)$^+$; HPLC purity 86% (ret. time, 1.14 min); $^1$H-NMR (500 MHz, Chloroform-d) δ 7.56-7.38 (m, 1H), 6.12 (s, 1H), 5.34-5.23 (m, 1H), 4.05 (d, J=10.0 Hz, 1H), 3.73-3.59 (m, 4H), 3.45-3.22 (m, 4H), 2.82 (s, 3H), 2.77-2.63 (m, 2H), 2.57-2.39 (m, 3H), 2.21 (s, 3H), 2.16-1.95 (m, 5H), 1.73-1.56 (m, 3H), 1.44 (s, 9H), 1.03 (m, 6H).

Step 9: methyl (1S)-5-(4-{[(2-{[(tert-butoxy)carbonyl](methyl)amino}ethyl)(methyl)amino]methyl}-1-(oxan-2-yl)-1H-pyrazol-3-yl)-2,2-dimethylcyclohexane-1-carboxylate

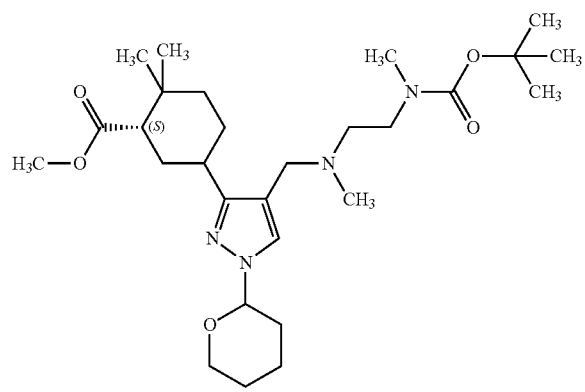

10% Pd—C (189 mg) was added to a solution of methyl (1S)-3-(4-{[(2-{[(tert-butoxy)carbonyl](methyl)amino}ethyl)(methyl)amino]methyl}-11-(oxan-2-yl)-1H-pyrazol-3-yl)-6,6-dimethylcyclohex-3-ene-1-carboxylate (1.89 mg, 3.13 mmol) in EtOH (30 ml) and stirred under an atmosphere of hydrogen for 3 h. An additional 189 mg of 10% Pd—C was added and the reaction continued overnight. After stirring overnight an additional 189 mg of 10% Pd—C was added and the reaction continued for 3 h. This was then filtered and re-treated with 10% Pd—C (190 mg) and hydrogen for 4 h. The reaction mixture was filtered and allowed to stand over the weekend. The reaction mixture was then treated with 10% Pd—C (0.5 g) and hydrogen for a further 48 hrs before filtering through Celite and evaporating to dryness. Purification by silica gel column chromatography, on a Biotage Isolera system, using a 100 g KP-Sil SNAP cartridge, eluting with THF:heptanes (1:9-1), gave the desired product as a colourless oil (1.11 g, 68%): MS (ESI+) for $C_{28}H_{48}N_4O_5$ m/z 521.30 (M+H)$^+$; HPLC purity 95% (ret. time, 1.07 min); $^1$H-NMR (500 MHz, Chloroform-d) δ 7.41 (m, 1H), 5.28 (dt, J=9.3, 4.2 Hz, 1H), 4.05 (d, J=10.1 Hz, 1H), 3.71-3.64 (m, 1H), 3.64 (s, 3H), 3.31 (d, J=31.3 Hz, 4H), 2.83 (s, 3H), 2.66 (ddt, J=12.5, 7.4, 3.7 Hz, 1H), 2.46 (s, 2H), 2.35-2.28 (m, 1H), 2.20 (s, 3H), 2.13-1.95 (m, 4H), 1.92-1.76 (m, 3H), 1.75-1.49 (m, 5H), 1.44 (s, 9H), 1.03 (d, J=7.0 Hz, 6H).

Step 10: tert-butyl N-{2-[({3-[(3S)-4,4-dimethyl-3-[(3-methylbutyl)carbamoyl]cyclohexyl]-1-(oxan-2-yl)-1H-pyrazol-4-yl}methyl)(methyl)amino]ethyl}-N-methylcarbamate

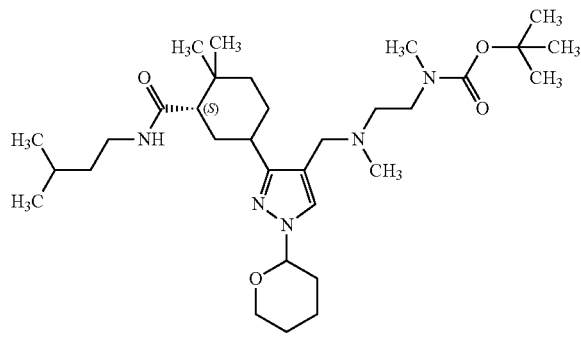

To a solution of 2 M Me$_3$Al in toluene (230 µl, 0.46 mmol) was added a solution of 3-methylbutan-1-amine (53.5 µl, 0.46 mmol) in toluene (1 ml) in a sealed tube. After 5 min, a solution of methyl (1S)-5-(4-{[(2-{[(tert-butoxy)carbonyl](methyl)amino}ethyl)(methyl)amino]methyl}-1-(oxan-2-yl)-1H-pyrazol-3-yl)-2,2-dimethylcyclohexane-1-carboxylate (200 mg, 0.0.38 mmol) in toluene (3 ml) was added. The reaction was sealed and heated to 110° C. for 18 h. The reaction was allowed to cool to RT and MeOH (25 ml) was added. The mixture was stirred at RT with Celite (~5 g) filtered and the pad washed with MeOH (10 ml). The filtrates were concentrated. The crude product was absorbed onto silica gel (2 ml). Purification by silica gel column chromatography, on a Biotage Isolera system, using a 10 g HP-Sil SNAP cartridge, eluting with THF:heptanes (1:9-1), gave the desired product as a colourless glass (160 mg, 72%): MS (ESI+) for $C_{32}H_{57}N_5O_4$ m/z 576.3 (M+H)$^+$; HPLC purity 100% (ret. time, 1.14 min); $^1$H-NMR (500 MHz, Chloroform-d) δ 7.57-7.34 (m, 1H), 5.84-5.39 (m, 1H), 5.28 (s, 1H), 4.05 (d, J=11.9 Hz, 1H), 3.72-3.62 (m, 1H), 3.41-3.14 (m, 4H), 2.82 (s, 2H), 2.77-2.36 (m, 2H), 2.18 (s, 2H), 2.03 (d, J=17.2 Hz, 5H), 1.92-1.73 (m, 2H), 1.66 (s, 3H), 1.55 (s, 9H), 1.52-1.42 (m, 9H), 1.41-1.30 (m, 3H), 1.13-1.06 (m, 2H), 1.03 (s, 3H), 0.93-0.86 (m, 6H).

Step 11: (1S)-2,2-dimethyl-5-[4-({methyl[2-(methylamino)ethyl]amino}methyl)-1H-pyrazol-3-yl]-N-(3-methylbutyl)cyclohexane-1-carboxamide (Compound 263)

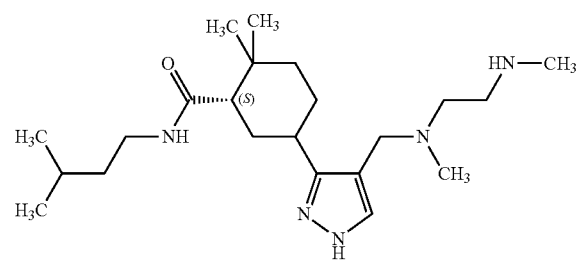

6 N HCl (2 ml) was added to a solution of tert-butyl N-{2-[({3-[(3R)-4,4-dimethyl-3-[(3-methylbutyl)carbamoyl]cyclohexyl]-1-(oxan-2-yl)-1H-pyrazol-4-yl}methyl)(methyl)amino]ethyl}-N-methylcarbamate (160 mg, 0.28 mmol) in 1,4-dioxane (1 ml) at 0° C. and stirred for 5 min. This was then allowed to continue at RT for 18 hr before evaporating in vacuo. MeOH (10 ml) was added to the residue and evaporated to dryness again. MeOH (5 ml) was added to the residue and this solution was passed through an Isolute SCX 2 cartridge (2 g) followed by MeOH (2×5 ml). The product was eluted with 7 N NH$_3$ in MeOH (15 ml). This was then evaporated to dryness to give 90 mg (83%, 8:1 cis:trans mixture) the desired product as a colourless glass: MS (ESI+) for C$_{22}$H$_{41}$N$_5$O m/z 392.2 (M+H)$^+$; HPLC purity 100% (ret. time, 2.47 min); $^1$H-NMR (500 MHz, Methanol-d$_4$) δ 7.43 (s, 1H), 3.42 (d, J=4.5 Hz, 2H), 3.27-3.18 (m, 1H), 3.18-3.08 (m, 1H), 2.85-2.75 (m, 1H), 2.71 (t, J=6.5 Hz, 2H), 2.52 (t, J=6.5 Hz, 2H), 2.44-2.35 (m, 3H), 2.24-2.13 (m, 4H), 2.07 (q, J=12.8 Hz, 1H), 1.90-1.78 (m, 1H), 1.75-1.58 (m, 3H), 1.58-1.51 (m, 1H), 1.49-1.31 (m, 3H), 1.11 (d, J=6.8 Hz, 3H), 1.00 (d, J=18.6 Hz, 3H), 0.93 (s, 3H), 0.92 (s, 3H).

Compound 271

(1S,5R)—N-(3-methoxypropyl)-2,2-dimethyl-5-[4-({methyl[2-(methylamino)ethyl]amino}methyl)-1H-pyrazol-3-yl]cyclohexane-1-carboxamide

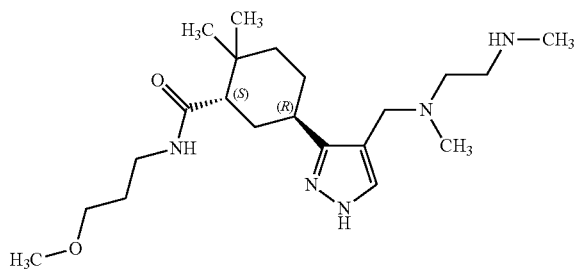

Step 1: tert-butyl N-{2-[({3-[(3S)-3-[(3-methoxypropyl)carbamoyl]-4,4-dimethylcyclohexyl]-1-(oxan-2-yl)-1H-pyrazol-4-yl}methyl)(methyl)amino]ethyl}-N-methylcarbamate

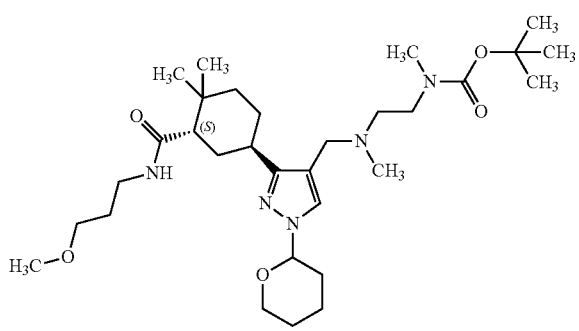

To a solution of 2 M Me$_3$Al in toluene (230 μl, 0.46 mmol) was added a solution of 3-methoxypropylamine (47.0 μl, 0.46 mmol) in toluene (1 ml) in a sealed tube. After 5 min, a solution of methyl (1S)-5-(4-{[(2-{[(tert-butoxy)carbonyl](methyl)amino}ethyl)(methyl)amino]methyl}-1-(oxan-2-yl)-1H-pyrazol-3-yl)-2,2-dimethylcyclohexane-1-carboxylate (200 mg, 0.38 mmol) in toluene (3 ml) was added. The reaction was sealed and heated to 110° C. for 18 h. The reaction was allowed to cool to RT and MeOH (25 ml) was added. The mixture was stirred at RT with Celite (~5 g) and filtered and the pad washed with MeOH (10 ml). The filtrates were concentrated. The crude product was absorbed onto silica gel (2 ml). Purification by silica gel column chromatography, on a Biotage Isolera system, using a 25 g KP-Sil SNAP cartridge, eluting with THF:heptanes (1:9-1), gave the desired product as a colourless glass (130 mg, 58%): MS (ESI+) for C$_{31}$H$_{55}$N$_5$O$_5$ m/z 578.35 (M+H)$^+$; HPLC purity 100% (ret. time, 1.11 min); $^1$H-NMR (500 MHz, Chloroform-d) δ 7.67-7.30 (m, 1H), 5.37-5.18 (m, 1H), 4.04 (d, J=11.0 Hz, 1H), 3.67 (t, J=11.4 Hz, 1H), 3.45 (t, J=5.5 Hz, 2H), 3.39-3.20 (m, 8H), 3.02-2.77 (m, 3H), 2.70 (s, 1H), 2.46 (s, 2H), 2.19 (s, 2H), 2.10-1.96 (m, 5H), 1.85 (s, 1H), 1.80-1.73 (m, 3H), 1.72-1.62 (m, 3H), 1.57 (s, 6H), 1.45 (s, 9H), 1.09 (s, 3H), 1.06-1.01 (m, 3H).

Step 2: (1S,5R)—N-(3-methoxypropyl)-2,2-dimethyl-5-[4-({methyl[2-(methylamino)ethyl]amino}methyl)-1H-pyrazol-3-yl]cyclohexane-1-carboxamide Compound 271

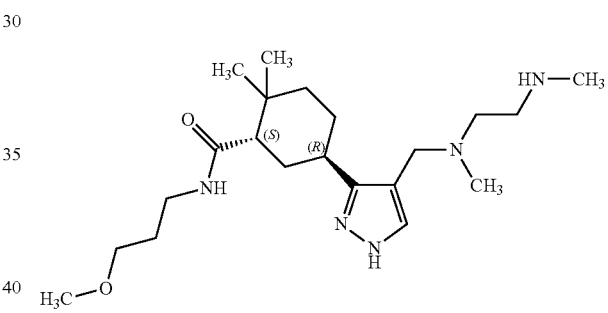

6 N HCl (2 ml) was added to a solution of tert-butyl N-{2-[({3-[(3S)-3-[(3-methoxypropyl)carbamoyl]-4,4-dimethylcyclohexyl]-1-(oxan-2-yl)-1H-pyrazol-4-yl}methyl)(methyl)amino]ethyl}-N-methylcarbamate (130 mg, 0.23 mmol) in 1,4-dioxane (1 ml) at 0° C. and stirred for 5 min. This was then allowed to continue at RT for 18 hr before evaporating in vacuo. MeOH (10 ml) was added to the residue and evaporated to dryness again. MeOH (5 ml) was added to the residue and this solution was passed through an Isolute SCX 2 cartridge (2 g) followed by MeOH (2×5 ml). The product was eluted with 7 N NH$_3$ in MeOH (15 ml). This was then evaporated to dryness to give 69 mg (78%) of the desired product as a colourless glass. The diastereoisomers were separated by prep HPLC under high pH conditions to give 3 mg of the desired product: MS (ESI+) for C$_{21}$H$_{39}$N$_5$O$_2$ m/z 394.5 (M+H)$^+$; HPLC purity 91% (ret. time, 1.00 min); $^1$H-NMR (500 MHz, Methanol-d4) δ 7.43 (s, 1H), 3.69 (s, 1H), 3.51-3.39 (m, 4H), 3.32 (d, J=1.0 Hz, 3H), 3.31-3.24 (m, 1H), 3.22-3.12 (m, 1H), 2.92 (t, J=5.8 Hz, 2H), 2.63-2.50 (m, 5H), 2.20 (d, J=10.8 Hz, 4H), 2.15-1.99 (m, 2H), 1.87-1.65 (m, 5H), 1.38-1.27 (m, 1H), 1.13 (s, 3H), 0.99 (s, 3H) (plus 51 mg of (1S,5S)—N-(3-methoxypropyl)-2,2-dimethyl-5-[4-({methyl[2-(methylamino)ethyl]amino}methyl)-1H-pyrazol-3-yl]cyclohexane-1-carboxamide).

Compound 273

({3-[(3R)-4,4-dimethyl-3-(oxan-4-ylmethoxy)cyclohexyl]-1H-pyrazol-4-yl}methyl)(methyl)[2-(methylamino)ethyl]amine

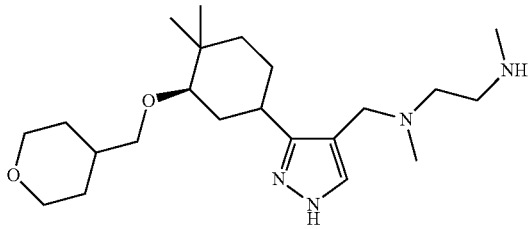 [SMILES: CNCCN(C)Cc1c[nH]nc1C1CCC(C)(C)[C@H](OCC2CCOCC2)C1]

Step 1: (1S,6S)-5,5-dimethyl-7-oxabicyclo[4.1.0]heptan-2-one

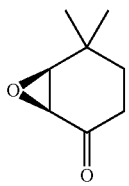

(1S,2S)-1,2-diphenylethane-1,2-diamine (3.42 g, 16.11 mmol) and trifluoroacetic acid (1.2 ml, 16.11 mmol) were dissolved in 1,4-dioxane (150 ml). The solution was stirred for 30 min before adding 4,4-dimethylcyclohex-2-en-1-one (10 g, 80.53 mmol) and hydrogen peroxide (10.58 ml, 120.79 mmol 35% in water). The reaction was stirred and heated to 50° C. for 72 h after which time the reaction was quenched with NH$_4$Cl (saturated, 100 ml). The solution was extracted with DCM (4×100 ml). The combined organic extracts were dried over Na$_2$SO$_4$ and evaporated to dryness to afford 12.5 g of desired material (containing ~10% 1,4-dioxane w/w). $^1$H-NMR (250 MHz, Chloroform-d) δ 3.23 (d, J=4.0 Hz, 1H), 3.17 (dd, J=4.0, 1.2 Hz, 1H), 2.41 (ddd, J=18.8, 6.5, 3.2 Hz, 1H), 2.19 (ddd, J=18.7, 11.5, 6.9 Hz, 1H), 1.90 (td, J=12.5, 11.5, 6.5 Hz, 1H), 1.35 (dtd, J=9.9, 3.1, 1.2 Hz, 1H), 1.22 (s, 3H), 1.06 (s, 3H). Rf=0.30 (3% 7 N NH$_3$ in MeOH in DCM).

Step 2: (3R)-3-hydroxy-4,4-dimethylcyclohexan-1-one

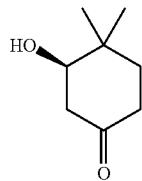

At RT under nitrogen, lithium (1.63 g, 235 mmol) was added to a solution of naphthalene (40 g, 314 mmol) in dry THF (600 ml). The solution quickly turned dark green and the reaction was stirred at RT until full dissolution of the lithium (~5 h). The solution was cooled to −78° C. and a solution of (1S,6S)-5,5-dimethyl-7-oxabicyclo[4.1.0]heptan-2-one (11 g, 78.47 mmol) in dry THF (300 ml) was added. The reaction was stirred for 1 h then quenched with water (30 ml) and allowed to warm to RT. A further 300 ml of water was added and the solution was extracted with Et$_2$O (2×500 ml). The combined organic extracts were dried over Na$_2$SO$_4$ and evaporated to dryness. The residue was purified by Biotage (SNAP 340 g, eluent heptane/EtOAc/NEt$_3$ 90/10/1 to 10/90/1) to afford 5.81 g of title compound (52%) as an orange oil. $^1$H-NMR (500 MHz, Chloroform-d) δ 3.77-3.62 (m, 1H), 2.64 (ddd, J=14.9, 4.3, 1.0 Hz, 1H), 2.46-2.36 (m, 1H), 2.36-2.25 (m, 2H), 1.94-1.82 (m, 1H), 1.83-1.76 (m, 1H), 1.54-1.44 (m, 1H), 1.13 (s, 3H), 1.07 (s, 3H). Rf=0.30 (EtOAc/heptane/NEt$_3$ (6/4/0.1).

Step 3: (3R)-3-[(tert-butyldimethylsilyl)oxy]-4,4-dimethylcyclohexan-1-one

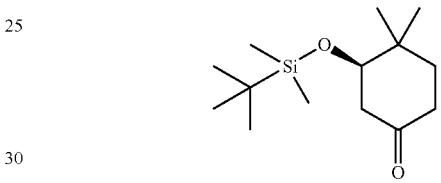

(3R)-3-hydroxy-4,4-dimethylcyclohexan-1-one (5.81 g, 40.86 mmol), tert-butyl(chloro)dimethylsilane (9.24 g, 61.29 mmol) and 1H-imidazole (6.95 g, 102.15 mmol) were dissolved in DMF (50 ml). The reaction was stirred at RT overnight; no starting material was detected by TLC. The reaction was quenched with saturated aqueous ammonium chloride solution (30 ml) and was extracted with EtOAc (3×30 ml); the combined organic layers were washed with water (30 ml) and dried over Na$_2$SO$_4$, evaporated and co-evaporated with toluene (4×50 ml) to dryness affording 8.4 g of the title compound isolated as a yellow oil (80%). $^1$H-NMR (500 MHz, Chloroform-d) δ 3.64 (dd, J=7.4, 4.1 Hz, 1H), 2.63-2.49 (m, 1H), 2.39-2.25 (m, 3H), 1.95-1.78 (m, 1H), 1.43 (dt, J=13.8, 7.1 Hz, 1H), 1.07 (s, 3H), 1.01 (s, 3H), 0.88 (s, 9H), 0.04 (d, J=6.0 Hz, 6H). Rf=0.53 (heptane/EtOAc 85/15).

Step 4: (3R)-3-[(tert-butyldimethylsilyl)oxy]-4,4-dimethylcyclohex-1-en-1-yl trifluoromethanesulfonate

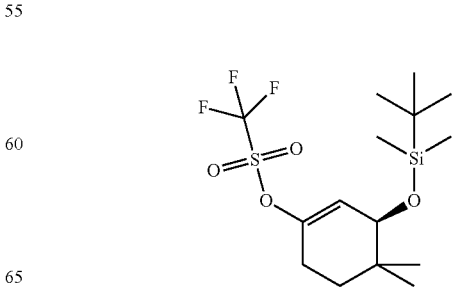

(3R)-3-[(tert-Butyldimethylsilyl)oxy]-4,4-dimethylcyclohexan-1-one (3 g, 11.7 mmol) was dissolved in dry THF (250 ml). The solution was cooled to −78° C. and 1 M lithium 1,1,1,3,3,3-hexamethyldisilazan-2-ide (23.4 ml) was slowly added. The reaction was stirred for 45 min and a solution of N-(5-chloropyridin-2-yl)-1,1,1-trifluoro-N-[(trifluoromethyl)sulfonyl]methanesulfonamide (8.59 g, 21.88 mmol) in dry THF (60 ml) was slowly added. The reaction was allowed to warm to RT and stirred for 3 h. The reaction was quenched with NH₄Cl (saturated, 100 ml) and extracted with EtOAc (3×100 ml). The combined organic extracts were dried over Na₂SO₄ and evaporated to dryness and the residue purified by Biotage (SNAP HP 100 g, eluent heptane/EtOAc 100/0 to 90/10) to afford 3.1 g of title compound as a 1:1 mix of isomers (61%). ¹H-NMR (500 MHz, Chloroform-d) δ 5.74-5.52 (m, 1H), 3.57 (t, J=5.3 Hz, 1H), 2.53 (dd, J=17.3, 2.2 Hz, 1H), 2.32-2.21 (m, 1H), 2.13 (ddt, J=17.6, 4.4, 2.5 Hz, 1H), 1.88 (ddt, J=17.5, 4.4, 2.4 Hz, 1H), 0.96-0.84 (m, 15H), 0.06 (d, J=7.4 Hz, 6H).

Step 5: tert-butyl({[(1R)-6,6-dimethyl-3-(tetramethyl-1,3,2-dioxaborolan-2-yl)cyclohex-2-en-1-yl]oxy})dimethylsilane

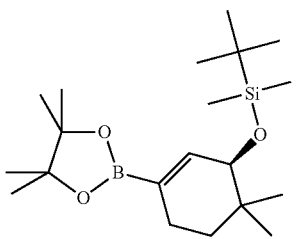

A suspension of (3R)-3-[(tert-butyldimethylsilyl)oxy]-4,4-dimethylcyclohex-1-en-1-yl trifluoromethanesulfonate (90%, 3.11 g, 7.2 mmol), 4,4,4',4',5,5,5',5'-octamethyl-2,2'-bi-1,3,2-dioxaborolane (2.74 g, 10.81 mmol) and potassium acetate (3.15 ml, 50.43 mmol) in 1,4-dioxane (100 ml) was degassed with a N₂ sparge for 10 min whilst stirring at RT. Bis[3-(diphenylphosphanyl)cyclopenta-2,4-dien-1-yl]iron; dichloromethane; dichloropalladium (0.59 g, 0.72 mmol) was added to this suspension and stirred at 90° C. for 3.5 h before allowing to cool to RT overnight. The reaction mixture was diluted with EtOAc (50 ml) and water (50 ml). The organic layer was separated and the aqueous was extracted with EtOAc (3×50 ml). The combined organic layers were dried over Na₂SO₄, filtered and evaporated in vacuo. Purification by silica gel column chromatography, on a Biotage Isolera system, using a 100 g HP-Sil SNAP cartridge, eluting with EtOAc:heptanes (0-5:95), gave the desired product as an orange oil (2.02 g, 76%). ¹H-NMR (500 MHz, Chloroform-d) δ 6.50-6.12 (m, 1H), 3.90-3.41 (m, 1H), 2.34-2.18 (m, 1H), 2.18-1.96 (m, 2H), 1.96-1.82 (m, 1H), 1.25 (d, J=3.2 Hz, 12H), 0.95-0.80 (m, 15H), 0.11--0.01 (m, 6H).

Step 6: tert-butyl N-{2-[({3-[(3R)-3-[(tert-butyldimethylsilyl)oxy]-4,4-dimethylcyclohex-1-en-1-yl]-1-(oxan-2-yl)-1H-pyrazol-4-yl}methyl)(methyl)amino]ethyl}-N-methylcarbamate

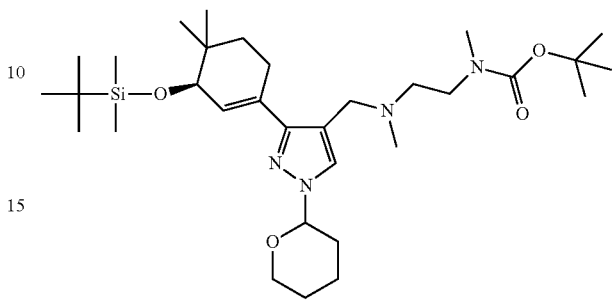

tert-Butyl({[(1R)-6,6-dimethyl-3-(tetramethyl-1,3,2-dioxaborolan-2-yl)cyclohex-2-en-1-yl]oxy})dimethylsilane (2 g, 5.46 mmol), tert-butyl N-[2-({[3-iodo-1-(oxan-2-yl)-1H-pyrazol-4-yl]methyl}(methyl)amino)ethyl]-N-methylcarbamate (2.61 g, 5.46 mmol) and potassium carbonate (2.26 g, 16.37 mmol) were suspended in 1,4-dioxane/water (240 ml, 7/1). The solution was degassed with nitrogen for 10 min and Pd(dppf)Cl₂ (0.45 g, 0.55 mmol) was added. The reaction was heated to 100° C. After overnight, the solvents were evaporated. The residue was purified by Biotage (SNAP HP 100 g, eluent heptane/EtOAc (+1% NEt₃) 95/5 to 60/40) to afford 2.5 g of the title compound as a yellow oil (62%; at 80% purity). ¹H-NMR (500 MHz, Chloroform-d) δ 7.61-7.36 (m, 1H), 6.14-5.72 (m, 1H), 5.43-5.23 (m, 1H), 4.08-3.92 (m, 1H), 3.76-3.57 (m, 1H), 3.51-3.19 (m, 5H), 2.99-2.62 (m, 6H), 2.60-2.30 (m, 3H), 2.28-2.14 (m, 3H), 2.13-1.94 (m, 4H), 1.76-1.51 (m, 6H), 1.51-1.37 (m, 9H), 1.00-0.79 (m, 18H), 0.13--0.03 (m, 6H). Rf=0.29 (EtOAc/heptane 7/3+1% NEt₃).

Step 7: tert-butyl N-{2-[({3-[(3R)-3-[(tert-butyldimethylsilyl)oxy]-4,4-dimethylcyclohexyl]-1-(oxan-2-yl)-1H-pyrazol-4-yl}methyl)(methyl)amino]ethyl}-N-methylcarbamate

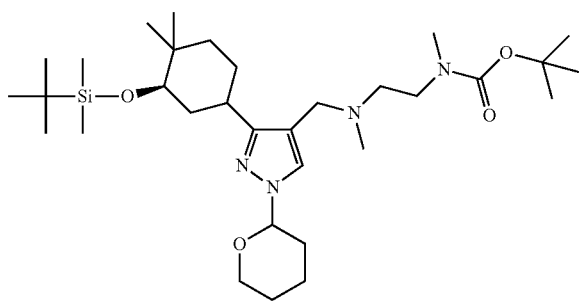 [SMILES: CN(CCN(C)C(=O)OC(C)(C)C)Cc1cn(C2CCCCO2)nc1C1CCC(C)(C)[C@H](O[Si](C)(C)C(C)(C)C)C1]

A solution of tert-butyl N-{2-[({3-[(3R)-3-[(tert-butyldimethylsilyl)oxy]-4,4-dimethylcyclohex-1-en-1-yl]-1-(oxan-2-yl)-1H-pyrazol-4-yl}methyl)(methyl)amino]ethyl}-N-methylcarbamate (80%, 1 g, 1.35 mmol) in EtOH (10 ml) was cautiously added onto a purged [nitrogen] suspension of Raney-Nickel catalyst (2.5 ml) in EtOH (20 ml). The resulting solution was purged with nitrogen (3×), hydrogen (2×) and left under an atmosphere of hydrogen at RT. After overnight, an aliquot was analysed showing only starting material. Additional 7.5 ml of catalyst was added and the reaction was left stirring under hydrogen atmosphere for 6 h, after which time LCMS showed complete conversion to the desired product. The solution was filtered through Celite and the pad was washed with EtOAc (150 ml). The filtrate was evaporated under reduced pressure and co-evaporated with toluene to afford 870 mg of the title compound as light yellow oil (92%). $^1$H-NMR (250 MHz, Chloroform-d) δ 7.45 (d, J=11.3 Hz, 1H), 5.41-5.17 (m, 1H), 4.06 (d, J=8.3 Hz, 1H), 3.67 (t, J=11.2 Hz, 1H), 3.34 (d, J=8.8 Hz, 6H), 2.85 (d, J=12.0 Hz, 5H), 2.68 (s, 1H), 2.47 (s, 2H), 2.20 (d, J=9.2 Hz, 3H), 2.02 (s, 3H), 1.93-1.36 (m, 13H), 1.25 (d, J=6.2 Hz, 2H), 1.06-0.79 (m, 15H), 0.02 (d, J=7.0 Hz, 6H).

Step 8: tert-butyl N-{2-[({3-[(3R)-3-hydroxy-4,4-dimethylcyclohexyl]-1-(oxan-2-yl)-1H-pyrazol-4-yl}methyl)(methyl)amino]ethyl}-N-methylcarbamate

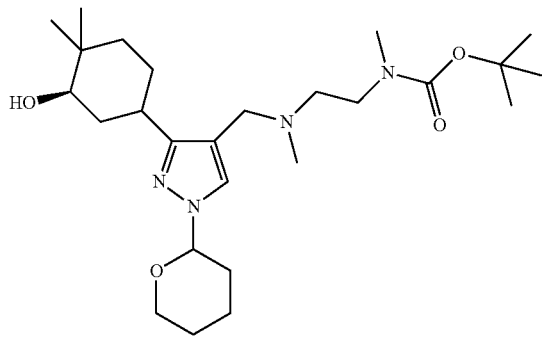 [SMILES: CN(CCN(C)C(=O)OC(C)(C)C)Cc1cn(C2CCCCO2)nc1C1CCC(C)(C)[C@H](O)C1]

tert-Butyl N-{2-[({3-[(3R)-3-[(tert-butyldimethylsilyl)oxy]-4,4-dimethylcyclohexyl]-1-(oxan-2-yl)-1H-pyrazol-4-yl}methyl)(methyl)amino]ethyl}-N-methylcarbamate (85%, 870 mg, 1.25 mmol) was dissolved in 1 M TBAF in THF (12 ml). The reaction was heated to 60° C. and stirred overnight. The reaction was quenched with water (10 ml) and was extracted with EtOAc (3×20 ml). The combined organic extracts were dried over Na$_2$SO$_4$ and evaporated and to dryness. The residue was purified by Biotage (SNAP 50 g, eluent DCM/MeOH 100/0 to 90/10) to afford 450 mg of title compound as a light yellow oil (60%). $^1$H-NMR (250 MHz, Chloroform-d) δ 7.53-7.31 (m, 1H), 5.30-5.13 (m, 1H), 3.98 (d, J=10.3 Hz, 1H), 3.60 (td, J=11.1, 2.8 Hz, 1H), 3.31 (dd, J=12.4, 6.8 Hz, 9H), 2.89 (dd, J=10.3, 6.5 Hz, 1H), 2.78 (d, J=13.1 Hz, 9H), 2.50-2.29 (m, 2H), 2.12 (s, 3H), 1.91 (d, J=20.2 Hz, 4H), 1.77-1.47 (m, 8H), 1.37 (d, J=7.5 Hz, 26H), 1.24-1.12 (m, 2H), 1.04-0.83 (m, 8H). Rf=0.14 (DCM/MeOH 95/5).

Step 9: tert-butyl N-{2-[({3-[(3R)-4,4-dimethyl-3-(oxan-4-ylmethoxy)cyclohexyl]-1-(oxan-2-yl)-1H-pyrazol-4-yl}methyl)(methyl)amino]ethyl}-N-methylcarbamate

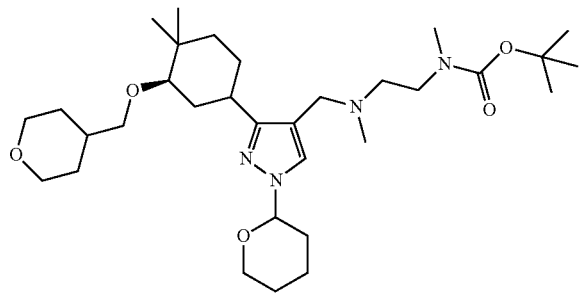 [SMILES: CN(CCN(C)C(=O)OC(C)(C)C)Cc1cn(C2CCCCO2)nc1C1CCC(C)(C)[C@H](OCC2CCOCC2)C1]

Potassium hexamethyldisilazide (3.44 ml, 0.91 M in THF) and 18-crown-6 (17 mg, 0.06 mmol) were added to a solution of tert-butyl N-{2-[({3-[(3R)-3-hydroxy-4,4-dimethylcyclohexyl]-1-(oxan-2-yl)-1H-pyrazol-4-yl}methyl)(methyl)amino]ethyl}-N-methylcarbamate (300 mg, 0.63 mmol) in dry toluene (10 ml). The reaction was stirred at RT for 1 h, then 4-(bromomethyl)tetrahydro-2H-pyran (250 μl, 1.88 mmol) was added and the solution was heated to 70° C. while monitoring by LCMS. Further aliquots of potassium hexamethyldisilazide (1.5 ml, 0.91 M in THF) and 4-(bromomethyl)tetrahydro-2H-pyran (100 μl, 0.75 mmol) were added after 16 h, 24 h, 48 h and 72 h. The reaction was stopped after 1 week. The solution was washed with water (25 ml) and extracted with EtOAc (3×30 ml). The combined organic extracts were dried over Na$_2$SO$_4$ and evaporated to dryness. The crude residue was purified by low pH prep HPLC in three injections; the product rich fractions were combined (co-evaporated with toluene) to afford 7 mg of desired alkylated (2%). 60 mg starting material were also recovered. $^1$H-NMR (500 MHz, Chloroform-d) δ 7.89-7.43 (m, 1H), 5.40-5.20 (m, 1H), 4.15-3.86 (m, 3H), 3.81-3.62 (m, 2H), 3.61-3.31 (m, 7H), 3.16-3.05 (m, 1H), 2.97-2.71 (m, 5H), 2.68-2.50 (m, 2H), 2.48-2.22 (m, 3H), 2.13-1.92 (m, 4H), 1.89-1.18 (m, 21H), 1.02 (s, 3H), 0.95 (s, 3H). LC-MS: 1.24 min (2.5 minute LC-MS method), m/z=577.35.

Step 10: ({3-[(3R)-4,4-dimethyl-3-(oxan-4-ylmethoxy)cyclohexyl]-1H-pyrazol-4-yl}methyl)(methyl)[2-(methylamino)ethyl]amine (Compound 273)

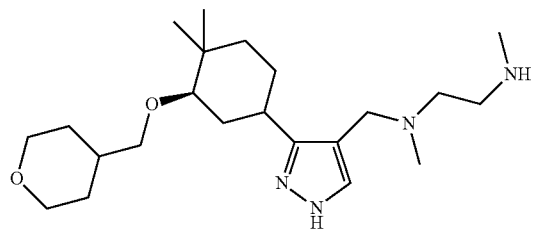 [SMILES: CNCCN(C)Cc1c[nH]nc1C1CCC(C)(C)[C@H](OCC2CCOCC2)C1]

tert-Butyl N-{2-[({3-[(3R)-4,4-dimethyl-3-(oxan-4-ylmethoxy)cyclohexyl]-1-(oxan-2-yl)-1H-pyrazol-4-yl}methyl)(methyl)amino]ethyl}-N-methylcarbamate (7 mg, 0.01 mmol) was dissolved in 1,4-dioxane (2 ml) and HCl (6 N, 1 ml) was added. After 2 h stirring at RT, the solvent was removed under reduced pressure to afford 4 mg the title compound (84%). $^1$H-NMR (500 MHz, Methanol-d4) δ 8.44 (s, 1H), 4.68-4.43 (m, 2H), 3.92 (d, J=11.5 Hz, 2H), 3.84-3.57 (m, 4H), 3.51 (dd, J=8.8, 6.2 Hz, 1H), 3.46-3.37 (m, 2H), 3.28-3.16 (m, 2H), 2.93 (d, J=4.3 Hz, 3H), 2.80 (s, 3H), 2.24-2.13 (m, 1H), 1.87-1.48 (m, 8H), 1.41-1.25 (m, 2H), 1.06 (d, J=2.6 Hz, 3H), 1.00 (s, 3H). LC-MS: 2.47 min (7 min method), m/z=393.2.

Compound 274

$N^1$-((4-(4-fluorophenyl)isoxazol-5-yl)methyl)-$N^1$-methylethane-1,2-diamine trifluoroacetate

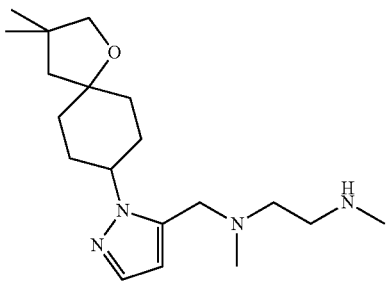

Step 1: 3,3-dimethyl-1-oxaspiro[4.5]decan-8-ylidene](tert-butoxy)carbohydrazide

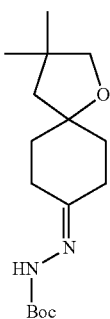 [SMILES: CC1(C)COC2(CCC(=NNC(=O)OC(C)(C)C)CC2)C1]

Into a 50-mL round-bottom flask, was placed hexane (10 mL), (tert-butoxy)carbohydrazide (2.64 g, 19.98 mmol, 1.00 equiv), and 3,3-dimethyl-1-oxaspiro[4.5]decan-8-one (3.65 g, 20.03 mmol, 1.00 equiv). The resulting solution was stirred for 15 h at 75° C. and then allowed to cool to room temperature. The solids were collected by filtration to give 4 g (67%) of 3,3-dimethyl-1-oxaspiro[4.5]decan-8-ylidene](tert-butoxy)carbohydrazide as a white solid. $^1$H-NMR (300 MHz, DMSO-d6): δ 9.52 (s, 1H), 3.43 (s, 2H), 2.48-2.09 (m, 4H), 1.86-1.46 (m, 6H), 1.42 (s, 9H), 1.06 (s, 6H) ppm.

Step 2: 3,3-dimethyl-1-oxaspiro[4.5]decan-8-yl] (tert-butoxy)carbohydrazide

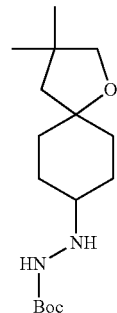

Into a 250-mL round-bottom flask, was placed 3,3-dimethyl-1-oxaspiro[4.5]decan-8-ylidene](tert-butoxy)carbohydrazide (3.5 g, 11.81 mmol, 1.00 equiv), ethanol (60 mL), and 10% palladium/carbon (0.35 g). Hydrogen (3 atm) was then applied to the reaction mixture. The reaction mixture was stirred for 48 h at room temperature. The solids were filtered and the solution was concentrated under vacuum. This resulted in 3.5 g (99%) of 3,3-dimethyl-1-oxaspiro[4.5] decan-8-yl](tert-butoxy)carbohydrazide as a white solid. $^1$H-NMR (300 MHz, DMSO-d6): δ 8.15 (s, 1H), 4.12 (s, 1H), 3.36 (s, 2H), 2.79-2.56 (m, 1H), 1.80-1.60 (m, 2H), 1.46-1.34 (m, 3H), 1.34-1.20 (m, 14H), 1.02 (s, 6H) ppm.

Step 3: [3,3-dimethyl-1-oxaspiro[4.5]decan-8-yl]hydrazine hydrochloride salts

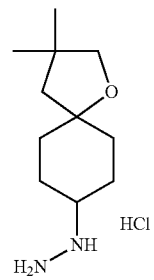

Into a 100-mL round-bottom flask, was placed 3,3-dimethyl-1-oxaspiro[4.5]decan-8-yl](tert-butoxy)carbohydrazide (3.5 g, 11.73 mmol, 1.00 equiv) and a solution of saturated hydrogen chloride gas in methanol (35 mL). The resulting solution was stirred for 15 h at room temperature and then concentrated under vacuum. This resulted in 2.7 g (98%) of [3,3-dimethyl-1-oxaspiro[4.5]decan-8-yl]hydrazine hydrochloride salts as a white solid. $^1$H-NMR (300 MHz, D$_2$O): δ 3.43 (s, 2H), 3.18-3.00 (m, 1H), 2.10-1.75 (m, 4H), 1.75-1.25 (m, 6H), 1.00 (s, 6H) ppm.

417

Step 4: 1-[3,3-dimethyl-1-oxaspiro[4.5]decan-8-yl]-1H-pyrazole-5-carbaldehyde

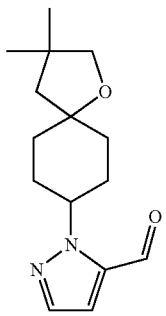 [SMILES: CC1(C)COC2(CCC(n3nccc3C=O)CC2)C1]

Into a 100-mL round-bottom flask, was placed [3,3-dimethyl-1-oxaspiro[4.5]decan-8-yl]hydrazine hydrochloride (1.0 g, 4.26 mmol, 1.00 equiv), [(1E)-4,4-dimethoxy-3-oxobut-1-en-1-yl]dimethylamine (740 mg, 4.27 mmol, 1.00 equiv), and methanol (25 mL). The resulting solution was stirred for 15 h at 70° C. and then concentrated under vacuum. The residue was diluted with THF (10 mL) and hydrochloric acid (1N, 15 mL) and then stirred at room temperature for 2 h. The THF was removed under vacuum and the residue was extracted with 3×30 mL of ethyl acetate and the organic layers combined and dried over anhydrous sodium sulfate and concentrated under vacuum. The residue was purified by silica gel column with ethyl acetate/petroleum ether (2:3). This resulted in 250 mg (22%) of 1-[3,3-dimethyl-1-oxaspiro[4.5]decan-8-yl]-1H-pyrazole-5-carbaldehyde as a white solid. $^1$H-NMR (300 MHz, CDCl$_3$): δ 9.85 (s, 1H), 7.54 (d, J=2.1 Hz, 1H), 6.87 (d, J=2.1 Hz, 1H), 5.05-4.90 (m, 1H), 3.51 (s, 2H), 2.45-2.25 (m, 2H), 2.05-1.90 (m, 2H), 1.90-1.75 (m, 2H), 1.65-1.50 (m, 4H), 1.10 (s, 6H) ppm.

Step 5: tert-butyl N-(2-[[(1-[3,3-dimethyl-1-oxaspiro[4.5]decan-8-yl]-1H-pyrazol-5-yl)methyl](methyl)amino]ethyl)-N-methylcarbamate

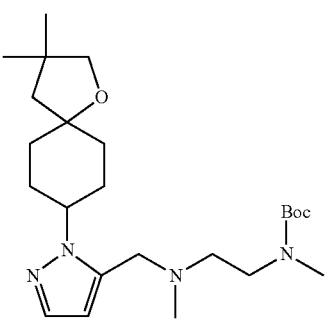

Into a 250-mL round-bottom flask, was placed 1-[3,3-dimethyl-1-oxaspiro[4.5]decan-8-yl]-1H-pyrazole-5-carbaldehyde (524 mg, 2.00 mmol, 1.00 equiv), tert-butyl N-methyl-N-[2-(methylamino)ethyl]carbamate (590 mg, 3.13 mmol, 1.57 equiv), ClCH$_2$CH$_2$Cl (50 mL). Then NaBH(OAc)$_3$ (3.39 g, 16.00 mmol, 8.01 equiv) was added by batchwise at 0° C. The resulting solution was stirred for 3 h at 0° C. The reaction was then quenched by the addition of 50 mL of Na$_2$CO$_3$ (sat. aq.). The resulting solution was extracted with 3×50 mL of ethyl acetate and the organic layers combined and dried over anhydrous sodium sulfate and concentrated under vacuum. The residue was applied onto a C18 gel column with CH$_3$CN/H$_2$O (4:1). This resulted in 650 mg (75%) of tert-butyl N-(2-[[(1-[3,3-dimethyl-1-oxaspiro[4.5]decan-8-yl]-1H-pyrazol-5-yl)methyl](methyl)amino]ethyl)-N-methylcarbamate as light yellow oil.

Step 6: N$^1$-((4-(4-fluorophenyl)isoxazol-5-yl)methyl)-N$^1$-methylethane-1,2-diamine trifluoroacetic acid (Compound 274)

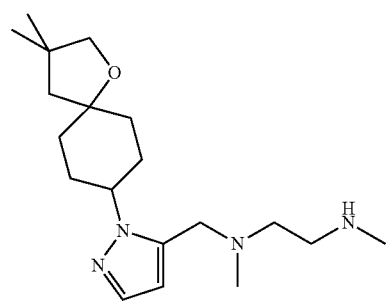

Into a 50-mL round-bottom flask, was placed tert-butyl N-(2-[[(1-[3,3-dimethyl-1-oxaspiro[4.5]decan-8-yl]-1H-pyrazol-5-yl)methyl](methyl)amino]ethyl)-N-methylcarbamate (600 mg, 1.38 mmol, 1.00 equiv) and ta solution of saturated hydrogen chloride gas in methanol (6 mL). The resulting solution was stirred for 3 h at room temperature and then concentrated under vacuum. The crude product was purified by Prep-HPLC with the following conditions (Prep-HPLC-025): Column, XBridge Shield RP18 OBD Column, 5 um, 19*150 mm; mobile phase, Water with 10 mmol TFA and MeCN (5.0% MeCN up to 21.0% in 6 min, 21.0% 7 min); Detector, UV 254/220 nm. This resulted in 550 mg (71%) of N$^1$-((4-(4-fluorophenyl)isoxazol-5-yl)methyl)-N$^1$-methylethane-1,2-diamine trifluoroacetic acid salt as a colorless oil. $^1$H-NMR (300 MHz, CDCl$_3$): δ7.60 (d, J=1.8 Hz, 1H), 6.53 (d, J=1.8 Hz, 1H), 4.57 (s, 2H), 4.32-4.15 (m, 1H), 3.61-3.41 (m, 2H), 2.81 (s, 3H), 2.70 (s, 3H), 2.15-1.85 (m, 4H), 1.77-1.45 (m, 6H), 0.98 (s, 6H) ppm. LCMS (method A, ESI): RT=4.73 min, m/z=335 [M+H]$^+$.

Compound 275

Methyl[2-(methylamino)ethyl][(1-[spiro[4.5]decan-8-yl]-1H-pyrazol-5-yl)methyl]amine trifluoroacetate

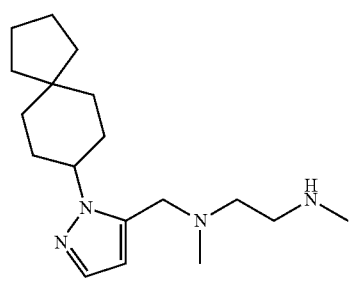 [SMILES: CNCCN(C)Cc1ccnn1C1CCC2(CCCC2)CC1]

Step 1: spiro[4.5]decan-8-ylidene (tert-butoxy)carbohydrazide

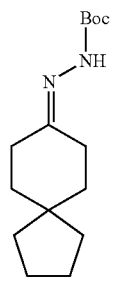

Into a 100-mL round-bottom flask, was placed spiro[4.5]decan-8-one (1.52 g, 9.98 mmol, 1.00 equiv), (tert-butoxy)carbohydrazide (1.32 g, 9.99 mmol, 1.00 equiv), hexane (20 mL). The resulting solution was stirred for 12 h at 75° C. then cooled to room temperature and concentrated under vacuum. The residue was triturated with 1×5 mL of hexane and the solids were collected by filtration to afford 2.13 g (80%) of spiro[4.5]decan-8-ylidene (tert-butoxy)carbohydrazide as a white solid. $^1$H-NMR (300 MHz, DMSO-d6): δ 9.49 (s, 1H), 2.29 (d, J=6.3 Hz, 2H), 2.18 (d, J=6.3 Hz, 2H), 1.67-1.32 (m, 21H) ppm.

Step 2: spiro[4.5]decan-8-ylhydrazine hydrochloride

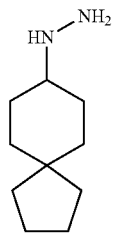

To a solution of spiro[4.5]decan-8-ylidene (tert-butoxy)carbohydrazide (2 g, 7.51 mmol, 1.00 equiv) in tetrahydrofuran (10 mL) at −40° C. under dry nitrogen was added a solution of borane (1 M in THF; 8.3 mL, 1.10 equiv) dropwise over approximately 20 min. The resulting solution was stirred for 1 h at room temperature then treated dropwise with hydrochloric acid (6 N, 5 mL) with stirring. The resulting solution was stirred for 12 h at room temperature and then concentrated under vacuum. The residue was triturated with 1×50 mL of ether and the solids were collected by filtration to afford 2.5 g (crude) of spiro[4.5]decan-8-ylhydrazine hydrochloride as a white solid. $^1$H-NMR (300 MHz, DMSO-d6): δ2.94-2.80 (m, 1H), 1.95-1.80 (m, 2H), 1.45-1.45 (m, 6H), 1.45-1.29 (m, 6H), 1.29-1.15 (m, 2H) ppm.

Step 3: 1-[spiro[4.5]decan-8-yl]-1H-pyrazole-5-carbaldehyde

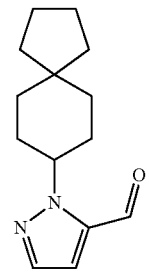 [SMILES: O=Cc1ccnn1C1CCC2(CCCC2)CC1]

Into a 100-mL round-bottom flask, was placed spiro[4.5]decan-8-ylhydrazine hydrochloride (1.64 g, 8.01 mmol, 1.00 equiv), [(1E)-4,4-dimethoxy-3-oxobut-1-en-1-yl]dimethylamine (2.08 g, 12.01 mmol, 1.50 equiv), methanol (40 mL). The resulting solution was stirred for 12 h at 75° C. then cooled to room temperature and concentrated under vacuum. The residue was diluted with 10 mL of hydrochloric acid (6 N) and 30 mL THF and the resulting solution stirred for 2 h at room temperature. The resulting mixture was extracted with 3×50 mL of ethyl acetate and the combined organic layers dried over anhydrous sodium sulfate and concentrated under vacuum. The residue was purified by flash chromatography on silica gel column using ethyl acetate/petroleum ether (1:10) as eluent to afford 160 mg (9%) of 1-[spiro[4.5]decan-8-yl]-1H-pyrazole-5-carbaldehyde as a light yellow oil. $^1$H-NMR (300 MHz, CDCl$_3$): δ 9.86 (s, 1H), 7.56 (d, J=1.8 Hz, 1H), 6.89 (d, J=1.8 Hz, 1H), 5.05-4.90 (m, 1H), 2.16-1.95 (m, 2H), 1.95-1.80 (m, 2H), 1.75-1.35 (m, 12H) ppm.

Step 4: tert-butyl N-methyl-N-(2-[methyl[(1-[spiro[4.5]decan-8-yl]-1H-pyrazol-5-yl)methyl]amino]ethyl)carbamate

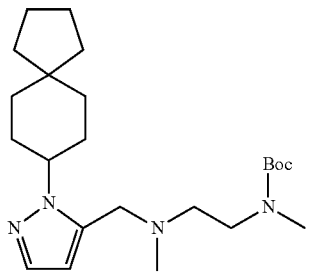 [SMILES: CN(CCN(C)C(=O)OC(C)(C)C)Cc1ccnn1C1CCC2(CCCC2)CC1]

To a solution of 1-[spiro[4.5]decan-8-yl]-1H-pyrazole-5-carbaldehyde (210 mg, 0.90 mmol, 1.00 equiv) and tert-butyl N-methyl-N-[2-(methylamino)ethyl]carbamate (340 mg, 1.81 mmol, 2.00 equiv) in DCE (20 mL) was added NaBH(OAc)$_3$ (1.54 g, 7.26 mmol, 8.04 equiv) portionwise. The resulting solution was stirred for 12 h at room temperature then quenched with 20 mL of sodium carbonate (sat. aq.). The organic layer was collected and the aqueous layer was extracted with 2×20 mL of ethyl acetate and the organic layers combined. The combined organics were dried over anhydrous sodium sulfate and concentrated under vacuum. The residue was purified by flash chromatography on silica gel column using ethyl acetate/petroleum ether (1:1) as eluent to afford 240 mg (66%) of tert-butyl N-methyl-N-(2-[methyl[(1-[spiro[4.5]decan-8-yl]-1H-pyrazol-5-yl)methyl]amino]ethyl)carbamate as a light yellow oil. $^1$H-NMR (300 MHz, CDCl$_3$): δ7.44 (s, 1H), 6.08 (s, 1H), 4.28-4.11 (m, 1H), 3.50 (s, 2H), 3.42-3.20 (m, 2H), 2.83 (s, 3H), 2.61-2.41 (m, 2H), 2.23 (s, 3H), 2.12-1.98 (m, 2H), 1.85-1.72 (m, 2H), 1.70-1.51 (m, 6H), 1.51-1.32 (m, 15H) ppm.

Step 5: methyl[2-(methylamino)ethyl][(1-[spiro[4.5]decan-8-yl]-1H-pyrazol-5-yl)methyl]amine trifluoroacetate (Compound 275)

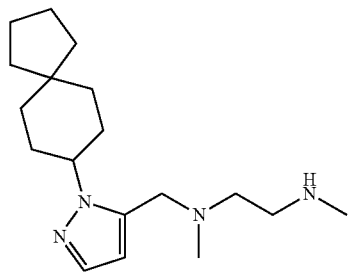 [SMILES: CNCCN(C)Cc1ccnn1C1CCC2(CCCC2)CC1]

Into a 50-mL round-bottom flask, was placed tert-butyl N-methyl-N-(2-[methyl[(1-[spiro[4.5]decan-8-yl]-1H-pyrazol-5-yl)methyl]amino]ethyl)carbamate (210 mg, 0.52 mmol, 1.00 equiv) which was then dissolved in a solution of saturated hydrogen chloride gas in 1,4-dioxane (10 mL). The reaction mixture was stirred for 12 h at room temperature and the resultant precipitate was collected by filtration. The crude product was purified by Prep-HPLC with the following conditions (Prep-HPLC-025): Column, XBridge Shield RP18 OBD Column, 5 μm, 19×150 mm; mobile phase, Water with 10 mmol TFA and MeCN (5.0% MeCN up to 36.0% in 10 min); Detector, UV 254/220 nm. This resulted in 200 mg (72%) of methyl[2-(methylamino)ethyl][(1-[spiro[4.5]decan-8-yl]-1H-pyrazol-5-yl)methyl]amine trifluoroacetate as a white semi-solid. $^1$H-NMR (300 MHz, D$_2$O): δ 7.58 (d, J=2.1 Hz, 1H), 6.50 (d, J=2.1 Hz, 1H), 4.54 (s, 2H), 4.22-4.16 (m, 1H), 3.61-3.36 (m, 8H), 2.88 (s, 3H), 2.67 (s, 3H), 1.98-1.75 (m, 2H), 1.74-1.57 (m, 2H), 1.57-1.20 (m, 12H). LCMS (method A, ESI): RT=1.09 min, m/z=305.4 [M+1]$^+$.

Biological Methods
PRMT1 Biochemical Assay
General Materials.

S-adenosylmethionine (SAM), S-adenosylhomocysteine (SAH), bicine, Tween20, dimethylsulfoxide (DMSO), bovine skin gelatin (BSG), and Tris(2-carboxyethyl)phosphine hydrochloride solution (TCEP) were purchased from Sigma-Aldrich at the highest level of purity possible. $^3$H-SAM was purchase from American Radiolabeled Chemicals with a specific activity of 80 Ci/mmol. 384-well streptavidin Flashplates were purchased from PerkinElmer.

Substrates.

Peptide representative of human histone H4 residues 36-50 was synthesized with an N-terminal linker-affinity tag motif and a C-terminal amide cap by 21$^{st}$ Century Biochemicals. The peptide was purified by high-performance liquid chromatography (HPLC) to greater than 95% purity and confirmed by liquid chromatography mass spectrometry (LC-MS). The sequence was Biot-Ahx-RLARRGGVKRIS-GLI-amide (SEQ ID NO.:1).

Molecular Biology:

Full-length human PRMT1 isoform 1 (NM_001536.5) transcript clone was amplified from an HEK 293 cDNA library, incorporating flanking 5' sequence encoding a FLAG tag (DYKDDDDK) (SEQ ID NO.:2) fused directly to Met 1 of PRMT1. The amplified gene was subcloned into pFast-BacI (Life Technologies) modified to encode an N-terminal GST tag and a TEV cleavage sequence (SEQ ID NO.: 3)
(MSPILGYWKIKGLVQPTRLLLEYLEEKYEEHLYERDEGDKWRNKKFELG

LEFPNLPYYIDGDVKLTQSMAIIRYIADKHNMLGGCPKERAEISMLEGAV

LDIRYGVSRIAYSKDFETLKVDFLSKLPEMLKMFEDRLCHKTYLNGDHVT

HPDFMLYDALDVVLYMDPMCLDAFPKLVCFKKRIEAIPQIDKYLKSSKYI

AWPLQGWQATFGGGDHPPKSDENLYFQGGNS) fused to Asp of the Flag tag of PRMT1.

Protein Expression.

Recombinant baculovirus were generated according to Bac-to-Bac kit instructions (Life Technologies). Protein over-expression was accomplished by infecting exponentially growing High Five insect cell culture at 1.5×10$^6$ cell/ml with 1:100 ratio of virus. Infections were carried out at 27° C. for 48 hours, harvested by centrifugation, and stored at −80° C. for purification.

Protein Purification.

Expressed full-length human GST-tagged PRMT1 protein was purified from cell paste by glutathione sepharose affinity chromatography after equilibration of the resin with 50 mM phosphate buffer, 200 mM NaCl, 5% glycerol, 5 mM β-mercaptoethanol, pH 7.8 (Buffer A). GST-tagged PRMT1 was eluted with 50 mM Tris, 2 mM glutathione, pH 7.8, dialysed in buffer A and concentrated to 1 mg/mL. The purity of recovered protein was 73%. Reference: Wasilko, D. J. and S. E. Lee: "TIPS: titerless infected-cells preservation and scale-up" Bioprocess J., 5 (2006), pp. 29-32.

Predicted Translations:

GST-tagged PRMT1
(SEQ ID NO.: 4)
MSPILGYWKIKGLVQPTRLLLEYLEEKYEEHLYERDEGDKWRNKKFELGL

EFPNLPYYIDGDVKLTQSMAIIRYIADKHNMLGGCPKERAEISMLEGAVL

DIRYGVSRIAYSKDFETLKVDFLSKLPEMLKMFEDRLCHKTYLNGDHVTH

PDFMLYDALDVVLYMDPMCLDAFPKLVCFKKRIEAIPQIDKYLKSSKYIA

WPLQGWQATFGGGDHPPKSDENLYFQGGNSDYKDDDDKMAAAEAANCIME

NFVATLANGMSLQPPLEEVSCGQAESSEKPNAEDMTSKDYYFDSYAHFGI

HEEMLKDEVRTLTYRNSMFHNRHLFKDKVVLDVGSGTGILCMFAAKAGAR

KVIGIECSSISDYAVKIVKANKLDHVVTIIKGKVEEVELPVEKVDIIISE

WMGYCLFYESMLNTVLYARDKWLAPDGLIFPDRATLYVTAIEDRQYKDYK

IHWWENVYGFDMSCIKDVAIKEPLVDVVDPKQLVTNACLIKEVDIYTVKV

EDLTFTSPFCLQVKRNDYVHALVAYFNIEFTRCHKRTGFSTSPESPYTHW

KQTVFYMEDYLTVKTGEEIFGTIGMRPNAKNNRDLDFTIDLDFKGQLCEL

SCSTDYRMR

General Procedure for PRMT1 Enzyme Assays on Peptide Substrates.

The assays were all performed in a buffer consisting of 20 mM Bicine (pH=7.6), 1 mM TCEP, 0.005% BSG, and 0.002% Tween 20, prepared on the day of use. Compounds in 100% DMSO (1 ul) were spotted into a polypropylene 384-well V-bottom plates (Greiner) using a Platemate Plus outfitted with a 384-channel head (Thermo Scientific). DMSO (1 ul) was added to Columns 11, 12, 23, 24, rows A-H for the maximum signal control and 1 ul of SAH, a known product and inhibitor of PRMT1, was added to columns 11, 12, 23, 24, rows I-P for the minimum signal control. A cocktail (40 ul) containing the PRMT1 enzyme was added by Multidrop Combi (Thermo-Fisher). The compounds were allowed to incubate with PRMT1 for 30 min at room temperature, then a cocktail (10 ul) containing SAM and peptide was added to initiate the reaction (final volume=51 ul). The final concentrations of the components were as follows: PRMT1 was 0.5 nM, $^3$H-SAM was 200 nM, non-radiolabeled SAM was 1.5 uM, peptide was 20 nM, SAH in the minimum signal control wells was 1 mM, and the DMSO concentration was 2%. The assays were stopped by the addition of non-radiolabeled SAM (10 ul) to a final concentration of 300 uM, which dilutes the $^3$H-SAM to a level where its incorporation into the peptide substrate is no longer detectable. 50 ul of the reaction in the 384-well polypropylene plate was then transferred to a 384-well Flashplate and the biotinylated peptides were allowed to bind to the streptavidin surface for at least 1 hour before being washed once with 0.1% Tween20 in a Biotek ELx405 µlate washer. The plates were then read in a PerkinElmer TopCount plate reader to measure the quantity of $^3$H-labeled peptide bound to the Flashplate surface, measured as disintegrations per minute (dpm) or alternatively, referred to as counts per minute (cpm).

% Inhibition Calculation $$\% \ inh = 100 - \left(\frac{dpm_{cmpd} - dpm_{min}}{dpm_{max} - dpm_{min}}\right) \times 100$$

Where dpm=disintegrations per minute, cmpd=signal in assay well, and min and max are the respective minimum and maximum signal controls.

Four-Parameter IC50 Fit $$Y = Bottom + \frac{(Top - Bottom)}{\left(1 + \left(\frac{X}{IC_{50}}\right)^{Hill\ Coefficient}\right)}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

PRMT6 Biochemical Assay

General Materials.

S-adenosylmethionine (SAM), S-adenosylhomocysteine (SAH), bicine, Tween20, dimethylsulfoxide (DMSO), bovine skin gelatin (BSG), sodium butyrate and Tris(2-carboxyethyl)phosphine hydrochloride solution (TCEP) were purchased from Sigma-Aldrich at the highest level of purity possible. $^3$H-SAM was purchase from American Radiolabeled Chemicals with a specific activity of 80 Ci/mmol. 384-well streptavidin Flashplates were purchased from PerkinElmer.

Substrates.

Peptide representative of human histone H4 residues 36-50 was synthesized with an N-terminal linker-affinity tag motif and a C-terminal amide cap by 21$^{st}$ Century Biochemicals. The peptide was purified by high-performance liquid chromatography (HPLC) to greater than 95% purity and confirmed by liquid chromatography mass spectrometry (LC-MS). The sequence was Biot-Ahx-RLARRGGVKRIS-GLI-amide and contained a monomethylated lysine at position 44 (SEQ ID NO.:5).

Molecular Biology:

Full-length human PRMT6 (NM_018137.2) transcript clone was amplified from an HEK 293 cDNA library, incorporating a flanking 5' sequence encoding a FLAG tag (MDYKDDDDK) (SEQ ID NO.:6) fused directly to Ser 2 of PRMT6 and a 3' sequence encoding a hexa His sequence (HHHHHH) (SEQ ID NO.: 17) fused directly to Asp 375. The amplified gene was subcloned into pFastBacMam (Viva Biotech).

Protein Expression.

Recombinant baculovirus were generated according to Bac-to-Bac kit instructions (Life Technologies). Protein over-expression was accomplished by infecting exponentially growing HEK 293F cell culture at 1.3×10$^6$ cell/ml with virus (MOI=10) in the presence of 8 mM sodium butyrate. Infections were carried out at 37° C. for 48 hours, harvested by centrifugation, and stored at −80° C. for purification.

Protein Purification.

Expressed full-length human Flag- and His-tagged PRMT6 protein was purified from cell paste by NiNTA agarose affinity chromatography after equilibration of the resin with buffer containing 50 mM Tris, 300 mM NaCl, 10% glycerol, pH 7.8 (Buffer Ni-A). Column was washed with 20 mM imidazole in the same buffer and Flag-PRMT6-His was eluted with 150 mM imidazole. Pooled fractions were dialysed against buffer Ni-A and further purified by anti-flag M2 affinity chromatography. Flag-PRMT6-His was eluted with 200 ug/ml FLAG peptide in the same buffer. Pooled fractions were dialysed in 20 mM Tris, 150 mM NaCl, 10% glycerol and 5 mM β-mercaptoethanol, pH 7.8. The purity of recovered protein was 95%.

Predicted Translations:

Flag-PRMT6-His (SEQ ID NO.: 7)

```
Flag-PRMT6-His
                                        (SEQ ID NO.: 7)
MDYKDDDDKSQPKKRKLESGGGGEGGEGTEEEDGAEREAALERPRRTKRE

RDQLYYECYSDVSVHEEMIADRVRTDAYRLGILRNWAALRGKTVLDVGAG

TGILSIFCAQAGARRVYAVEASAIWQQAREVVRFNGLEDRVHVLPGPVET

VELPEQVDAIVSEWMGYGLLHESMLSSVLHARTKWLKEGGLLLPASAELF

IAPISDQMLEWRLGFWSQVKQHYGVDMSCLEGFATRCLMGHSEIVVQGLS

GEDVLARPQRFAQLELSRAGLEQELEAGVGGRFRCSCYGSAPMHGFAIWF

QVTFPGGESEKPLVLSTSPFHPATHWKQALLYLNEPVQVEQDTDVSGEIT

LLPSRDNPRRLRVLLRYKVGDQEEKTKDFAMEDHHHHHH
```

General Procedure for PRMT6 Enzyme Assays on Peptide Substrates.

The assays were all performed in a buffer consisting of 20 mM Bicine (pH=7.6), 1 mM TCEP, 0.005% BSG, and 0.002% Tween 20, prepared on the day of use. Compounds in 100% DMSO (1 ul) were spotted into a polypropylene 384-well V-bottom plates (Greiner) using a Platemate Plus outfitted with a 384-channel head (Thermo Scientific).

DMSO (1 ul) was added to Columns 11, 12, 23, 24, rows A-H for the maximum signal control and 1 ul of SAH, a known product and inhibitor of PRMT6, was added to columns 11, 12, 23, 24, rows I-P for the minimum signal control. A cocktail (40 ul) containing the PRMT6 enzyme was added by Multidrop Combi (Thermo-Fisher). The compounds were allowed to incubate with PRMT6 for 30 min at room temperature, then a cocktail (10 ul) containing SAM and peptide was added to initiate the reaction (final volume=51 ul). The final concentrations of the components were as follows: PRMT6 was 1 nM, $^3$H-SAM was 200 nM, non-radiolabeled SAM was 250 nM, peptide was 75 nM, SAH in the minimum signal control wells was 1 mM, and the DMSO concentration was 2%. The assays were stopped by the addition of non-radiolabeled SAM (10 ul) to a final concentration of 400 uM, which dilutes the $^3$H-SAM to a level where its incorporation into the peptide substrate is no longer detectable. 50 ul of the reaction in the 384-well polypropylene plate was then transferred to a 384-well Flashplate and the biotinylated peptides were allowed to bind to the streptavidin surface for at least 1 hour before being washed once with 0.1% Tween20 in a Biotek ELx405 plate washer. The plates were then read in a PerkinElmer TopCount plate reader to measure the quantity of $^3$H-labeled peptide bound to the Flashplate surface, measured as disintegrations per minute (dpm) or alternatively, referred to as counts per minute (cpm).

% Inhibition Calculation $$\% \ inh = 100 - \left(\frac{dpm_{cmpd} - dpm_{min}}{dpm_{max} - dpm_{min}}\right) \times 100$$

Where dpm=disintegrations per minute, cmpd=signal in assay well, and min and max are the respective minimum and maximum signal controls.

Four-Parameter IC50 Fit $$Y = \text{Bottom} + \frac{(\text{Top} - \text{Bottom})}{\left(1 + \left(\frac{X}{IC_{50}}\right)^{Hill \ Coefficient}\right)}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

PRMT8 Biochemical Assay

General Materials.

S-adenosylmethionine (SAM), S-adenosylhomocysteine (SAH), bicine, Tween20, dimethylsulfoxide (DMSO), bovine skin gelatin (BSG), isopropyl-β-D-thiogalactopyranoside (IPTG), and Tris(2-carboxyethyl)phosphine hydrochloride solution (TCEP) were purchased from Sigma-Aldrich at the highest level of purity possible. $^3$H-SAM was purchase from American Radiolabeled Chemicals with a specific activity of 80 Ci/mmol. 384-well streptavidin Flashplates were purchased from PerkinElmer.

Substrates.

Peptide representative of human histone H4 residues 31-45 was synthesized with an N-terminal linker-affinity tag motif and a C-terminal amide cap by 21$^{st}$ Century Biochemicals. The peptide was purified by high-performance liquid chromatography (HPLC) to greater than 95% purity and confirmed by liquid chromatography mass spectrometry (LC-MS). The sequence was Biot-Ahx-KPAIRRLARRG-GVKR-amide (SEQ ID NO.:8).

Molecular Biology:

Full-length human PRMT8 (NM_019854.4) isoform 1 transcript clone was amplified from an HEK 293 cDNA library and subcloned into pGEX-4T-1 (GE Life Sciences). The resulting construct encodes an N-terminal GST tag and a thrombin cleavage sequence

```
                                        (SEQ ID NO.: 9)
(MSPILGYWKIKGLVQPTRLLLEYLEEKYEEHLYERDEGDKWRNKKFELG

LEFPNLPYYIDGDVKLTQSMAIIRYIADKHNMLGGCPKERAEISMLEGAV

LDIRYGVSRIAYSKDFETLKVDFLSKLPEMLKMFEDRLCHKTYLNGDHVT

HPDFMLYDALDVVLYMDPMCLDAFPKLVCFKKRIEAIPQIDKYLKSSKYI

AWPLQGWQATFGGGDHPPKSDLVPRGSPEF) fused directly to

Met 1 of PRMT8.
```

Protein Expression.

*E. coli* (BL21(DE3) Gold, Stratagene) made competent by the CaCl$_2$ method were transformed with the PRMT8 construct and ampicillin selection. Protein over-expression was accomplished by growing the PRMT8 expressing *E. coli* clone and inducing expression with 0.3 mM IPTG at 16° C. The culture was grown for 12 hours, harvested by centrifugation, and stored at −80° C. for purification.

Protein Purification.

Expressed full-length human GST-tagged PRMT8 protein was purified from cell paste by glutathione sepharose affinity chromatography after the resin was equilibrated with 50 mM phosphate buffer, 200 mM NaCl, 5% glycerol, 5 mM (3-mercaptoethanol, pH 7.8 (Buffer A). GST-tagged PRMT8 was eluted with 50 mM Tris, 2 mM glutathione, pH 7.8. Pooled fractions were cleaved by thrombin (10U) and dialysed in buffer A. GST was removed by reloading the cleaved protein sample onto glutathione sepharose column and PRMT8 was collected in the flow-through fractions. PRMT8 was purified further by ceramic hydroxyapatite chromatography. The column was washed with 50 mM phosphate buffer, 100 mM NaCl, 5% glycerol, 5 mM β-mercaptoethanol, pH 7.8 and PRMT8 was eluted by 100 mM phosphate in the same buffer. Protein was concentrated and buffer was exchanged to 50 mM Tris, 300 mM NaCl, 10% glycerol, 5 mM β-mercaptoethanol, pH 7.8 by ultrafiltration. The purity of recovered protein was 89%.

Predicted Translations:

```
GST-tagged PRMT8
                                        (SEQ ID NO.: 10)
MSPILGYWKIKGLVQPTRLLLEYLEEKYEEHLYERDEGDKWRNKKFELGL

EFPNLPYYIDGDVKLTQSMAIIRYIADKHNMLGGCPKERAEISMLEGAVL

DIRYGVSRIAYSKDFETLKVDFLSKLPEMLKMFEDRLCHKTYLNGDHVTH

PDFMLYDALDVVLYMDPMCLDAFPKLVCFKKRIEAIPQIDKYLKSSKYIA

WPLQGWQATFGGGDHPPKSDLVPRGSPEFMGMKHSSRCLLLRRKMAENAA

ESTEVNSPPSQPPQPVVPAKPVQCVHHVSTQPSCPGRGKMSKLLNPEEMT

SRDYYFDSYAHFGIHEEMLKDEVRTLTYRNSMYHNKHVFKDKVVLDVGSG

TGILSMFAAKAGAKKVFGIECSSISDYSEKIIKANHLDNIITIFKGKVEE
```

-continued

```
VELPVEKVDIIISEWMGYCLFYESMLNTVIFARDKWLKPGGLMFPDRAAL

YVVAIEDRQYKDFKIHWWENVYGFDMTCIRDVAMKEPLVDIVDPKQVVTN

ACLIKEVDIYTVKTEELSFTSAFCLQIQRNDYVHALVTYFNIEFTKCHKK

MGFSTAPDAPYTHWKQTVFYLEDYLTVRRGEEIYGTISMKPNAKNVRDLD

FTVDLDFKGQLCETSVSNDYKMR
```

General Procedure for PRMT8 Enzyme Assays on Peptide Substrates.

The assays were all performed in a buffer consisting of 20 mM Bicine (pH=7.6), 1 mM TCEP, 0.005% BSG, and 0.002% Tween 20, prepared on the day of use. Compounds in 100% DMSO (1 ul) were spotted into a polypropylene 384-well V-bottom plates (Greiner) using a Platemate Plus outfitted with a 384-channel head (Thermo Scientific). DMSO (1 ul) was added to Columns 11, 12, 23, 24, rows A-H for the maximum signal control and 1 ul of SAH, a known product and inhibitor of PRMT8, was added to columns 11, 12, 23, 24, rows I-P for the minimum signal control. A cocktail (40 ul) containing the PRMT8 enzyme was added by Multidrop Combi (Thermo-Fisher). The compounds were allowed to incubate with PRMT8 for 30 min at room temperature, then a cocktail (10 ul) containing $^3$H-SAM and peptide was added to initiate the reaction (final volume=51 ul). The final concentrations of the components were as follows: PRMT8 was 1.5 nM, $^3$H-SAM was 50 nM, non-radiolabeled SAM was 550 nM, peptide was 150 nM, SAH in the minimum signal control wells was 1 mM, and the DMSO concentration was 2%. The assays were stopped by the addition of non-radiolabeled SAM (10 ul) to a final concentration of 400 uM, which dilutes the $^3$H-SAM to a level where its incorporation into the peptide substrate is no longer detectable. 50 ul of the reaction in the 384-well polypropylene plate was then transferred to a 384-well Flashplate and the biotinylated peptides were allowed to bind to the streptavidin surface for at least 1 hour before being washed once with 0.1% Tween20 in a Biotek ELx405 µlate washer. The plates were then read in a PerkinElmer TopCount plate reader to measure the quantity of $^3$H-labeled peptide bound to the Flashplate surface, measured as disintegrations per minute (dpm) or alternatively, referred to as counts per minute (cpm).

% Inhibition Calculation $$\% \: inh = 100 - \left(\frac{dpm_{cmpd} - dpm_{min}}{dpm_{max} - dpm_{min}}\right) \times 100$$

Where dpm=disintegrations per minute, cmpd=signal in assay well, and min and max are the respective minimum and maximum signal controls.

Four-Parameter IC50 Fit $$Y = Bottom + \frac{(Top - Bottom)}{\left(1 + \left(\frac{X}{IC_{50}}\right)^{Hill \: Coefficient}\right)}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

PRMT3 Biochemical Assay

General Materials.

S-adenosylmethionine (SAM), S-adenosylhomocysteine (SAH), bicine, Tween20, dimethylsulfoxide (DMSO), bovine skin gelatin (BSG),), isopropyl-β-D-thiogalactopyranoside (IPTG), and Tris(2-carboxyethyl)phosphine hydrochloride solution (TCEP) were purchased from Sigma-Aldrich at the highest level of purity possible. $^3$H-SAM was purchase from American Radiolabeled Chemicals with a specific activity of 80 Ci/mmol. 384-well streptavidin Flashplates were purchased from PerkinElmer.

Substrates.

Peptide containing the classic RMT substrate motif was synthesized with an N-terminal linker-affinity tag motif and a C-terminal amide cap by 21$^{st}$ Century Biochemicals. The peptide was purified by high-performance liquid chromatography (HPLC) to greater than 95% purity and confirmed by liquid chromatography mass spectrometry (LC-MS). The sequence was Biot-Ahx-GGRGGFGGRGGFGGRGGFG-amide (SEQ ID NO.:11).

Molecular Biology

Full-length human PRMT3 (NM_005788.3) isoform 1 transcript clone was amplified from an HEK 293 cDNA library and subcloned into pGEX-KG (GE Life Sciences). The resulting construct encodes an N-terminal GST tag and a thrombin cleavage sequence

```
                                          (SEQ ID NO.: 12)
(MSPILGYWKIKGLVQPTRLLLEYLEEKYEEHLYERDEGDKWRNKKFELG

LEFPNLPYYIDGDVKLTQSMAIIRYIADKHNMLGGCPKERAEISMLEGAV

LDIRYGVSRIAYSKDFETLKVDFLSKLPEMLKMFEDRLCHKTYLNGDHVT

HPDFMLYDALDVVLYMDPMCLDAFPKLVCFKKRIEAIPQIDKYLKSSKYI

AWPLQGWQATFGGGDHPPKSDLVPRGS) fused directly to Cys 2 of PRMT3.
```

Protein Expression.

E. coli (BL21(DE3) Gold, Stratagene) made competent by the CaCl$_2$ method were transformed with the PRMT3 construct and ampicillin selection. Protein over-expression was accomplished by growing the PRMT3 expressing E. coli clone and inducing expression with 0.3 mM IPTG at 16° C. The culture was grown for 12 hours, harvested by centrifugation, and stored at −80° C. for purification.

Protein Purification.

Expressed full-length human GST-tagged PRMT3 protein was purified from cell paste by glutathione sepharose affinity chromatography after equilibration of the resin with 50 mM phosphate buffer, 200 mM NaCl, 5% glycerol, 1 mM EDTA, 5 mM β-mercaptoethanol, pH 6.5 (Buffer A). GST-tagged PRMT3 was eluted with 50 mM Tris, 2 mM glutathione, pH 7.1 and 50 mM Tris, 20 mM glutathione, pH 7.1. Pooled fractions were dialysed in 20 mM Tris, 50 mM NaCl, 5% glycerol, 1 mM EDTA, 1 mM DTT, pH 7.5 (Buffer B) and applied to a Q Sepharose Fast Flow column. GST-tagged PRMT3 was eluted by 500 mM NaCl in buffer B. Pooled fractions were dialyzed in 25 mM phosphate buffer, 100 mM NaCl, 5% glycerol, 2 mM DTT, pH 6.8 (Buffer C) and loaded on to a ceramic hydroxyapatite column. GST-tagged PRMT3 eluted with 25-400 mM phosphate in buffer C. Protein was concentrated and buffer was exchanged to 20 mM Tris, 150 mM NaCl, 5% glycerol, 5 mM β-mercaptoethanol, pH 7.8 by ultrafiltration. The purity of recovered protein was 70%.

Predicted Translations:

GST-tagged PRMT3
(SEQ ID NO.: 13)
MSPILGYWKIKGLVQPTRLLLEYLEEKYEEHLYERDEGDKWRNKKFELGL

EFPNLPYYIDGDVKLTQSMAIIRYIADKHNMLGGCPKERAEISMLEGAVL

DIRYGVSRIAYSKDFETLKVDFLSKLPEMLKMFEDRLCHKTYLNGDHVTH

PDFMLYDALDVVLYMDPMCLDAFPKLVCFKKRIEAIPQIDKYLKSSKYIA

WPLQGWQATFGGGDHPPKSDLVPRGSCSLASGATGGRGAVENEEDLPELS

DSGDEAAWEDEDDADLPHGKQQTPCLFCNRLFTSAEETFSHCKSEHQFNI

DSMVHKHGLEFYGYIKLINFIRLKNPTVEYMNSIYNPVPWEKEEYLKPVL

EDDLLLQFDVEDLYEPVSVPFSYPNGLSENTSVVEKLKHMEARALSAEAA

LARAREDLQKMKQFAQDFVMHTDVRTCSSSTSVIADLQEDEDGVYFSSYG

HYGIHEEMLKDKIRTESYRDFIYQNPHIFKDKVVLDVGCGTGILSMFAAK

AGAKKVLGVDQSEILYQAMDIIRLNKLEDTITLIKGKIEEVHLPVEKVDV

IISEWMGYFLLFESMLDSVLYAKNKYLAKGGSVYPDICTISLVAVSDVNK

HADRIAFWDDVYGFKMSCMKKAVIPEAVVEVLDPKTLISEPCGIKHIDCH

TTSISDLEFSSDFTLKITRTSMCTAIAGYFDIYFEKNCHNRVVFSTGPQS

TKTHWKQTVFLLEKPFSVKAGEALKGKVTVHKNKKDPRSLTVTLTLNNST

QTYGLQ

General Procedure for PRMT3 Enzyme Assays on Peptide Substrates.

The assays were all performed in a buffer consisting of 20 mM Bicine (pH=7.6), 1 mM TCEP, 0.005% BSG, and 0.002% Tween 20, prepared on the day of use. Compounds in 100% DMSO (1 ul) were spotted into a polypropylene 384-well V-bottom plates (Greiner) using a Platemate Plus outfitted with a 384-channel head (Thermo Scientific). DMSO (1 ul) was added to Columns 11, 12, 23, 24, rows A-H for the maximum signal control and 1 ul of SAH, a known product and inhibitor of PRMT3, was added to columns 11, 12, 23, 24, rows I-P for the minimum signal control. A cocktail (40 ul) containing the PRMT3 enzyme was added by Multidrop Combi (Thermo-Fisher). The compounds were allowed to incubate with PRMT3 for 30 min at room temperature, then a cocktail (10 ul) containing SAM and peptide was added to initiate the reaction (final volume=51 ul). The final concentrations of the components were as follows: PRMT3 was 0.5 nM, $^3$H-SAM was 100 nM, non-radiolabeled SAM was 1.8 uM, peptide was 330 nM, SAH in the minimum signal control wells was 1 mM, and the DMSO concentration was 2%. The assays were stopped by the addition of potassium chloride (10 ul) to a final concentration of 100 mM. 50 ul of the reaction in the 384-well polypropylene plate was then transferred to a 384-well Flashplate and the biotinylated peptides were allowed to bind to the streptavidin surface for at least 1 hour before being washed once with 0.1% Tween20 in a Biotek ELx405 μlate washer. The plates were then read in a PerkinElmer TopCount plate reader to measure the quantity of $^3$H-labeled peptide bound to the Flashplate surface, measured as disintegrations per minute (dpm) or alternatively, referred to as counts per minute (cpm).

% Inhibition Calculation $$\% \: inh = 100 - \left( \frac{dpm_{cmpd} - dpm_{min}}{dpm_{max} - dpm_{min}} \right) \times 100$$

Where dpm=disintegrations per minute, cmpd=signal in assay well, and min and max are the respective minimum and maximum signal controls.

Four-Parameter IC50 Fit $$Y = \text{Bottom} + \frac{(\text{Top} - \text{Bottom})}{\left(1 + \left(\frac{X}{IC_{50}}\right)^{\text{Hill Coefficient}}\right)}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

CARM1 Biochemical Assay

General Materials.

S-adenosylmethionine (SAM), S-adenosylhomocysteine (SAH), bicine, Tween20, dimethylsulfoxide (DMSO), bovine skin gelatin (BSG), sodium butyrate and Tris(2-carboxyethyl)phosphine hydrochloride solution (TCEP) were purchased from Sigma-Aldrich at the highest level of purity possible. $^3$H-SAM was purchase from American Radiolabeled Chemicals with a specific activity of 80 Ci/mmol. 384-well streptavidin Flashplates were purchased from PerkinElmer.

Substrates.

Peptide representative of human histone H3 residues 16-30 was synthesized with an N-terminal linker-affinity tag motif and a C-terminal amide cap by 21$^{st}$ Century Biochemicals. The peptide was purified by high-performance liquid chromatography (HPLC) to greater than 95% purity and confirmed by liquid chromatography mass spectrometry (LC-MS). The sequence was Biot-Ahx-PRKQLAT-KAARKSAP-amide and contained a monomethylated arginine at position 26 (SEQ ID NO.: 14).

Molecular Biology:

Human CARM1 (PRMT4) (NM_1991 41.1) transcript clone was amplified from an HEK 293 cDNA library, incorporating a flanking 5' sequence encoding a FLAG tag (MDYKDDDDK) (SEQ ID NO.:6) fused directly to Ala 2 of CARM1 and 3' sequence encoding a hexa His sequence (EGHHHHHH) (SEQ ID NO.: 15) fused directly to Ser 608. The gene sequence encoding isoforml containing a deletion of amino acids 539-561 was amplified subsequently and subcloned into pFastBacMam (Viva Biotech).

Protein Expression.

Recombinant baculovirus were generated according to Bac-to-Bac kit instructions (Life Technologies). Protein over-expression was accomplished by infecting exponentially growing HEK 293F cell culture at 1.3×10$^6$ cell/ml with virus (MOI=10) in the presence of 8 mM sodium butyrate. Infections were carried out at 37° C. for 48 hours, harvested by centrifugation, and stored at −80° C. for purification.

Protein Purification.

Expressed full-length human Flag- and His-tagged CARM1 protein was purified from cell paste by anti-flag M2 affinity chromatography with resin equilibrated with buffer containing 20 mM Tris, 150 mM NaCl, 5% glycerol, pH 7.8. Column was washed with 500 mM NaCl in buffer A and Flag-CARM1-His was eluted with 200 ug/ml FLAG peptide in buffer A. Pooled fractions were dialyzed in 20 mM Tris, 150 mM NaCl, 5% glycerol and 1 mM DTT, pH 7.8. The purity of recovered protein was 94.

Predicted Translations:

```
Flag-CARM1-His
                                          (SEQ ID NO.: 16)
MDYKDDDDKAAAAAAVGPGAGGAGSAVPGGAGPCATVSVFPGARLLTIGD

ANGEIQRHAEQQALRLEVRAGPDSAGIALYSHEDVCVFKCSVSRETECSR

VGKQSFIITLGCNSVLIQFATPNDFCSFYNILKTCRGHTLERSVFSERTE

ESSAVQYFQFYGYLSQQQNMMQDYVRTGTYQRAILQNHTDFKDKIVLDVG

CGSGILSFFAAQAGARKIYAVEASTMAQHAEVLVKSNNLTDRIVVIPGKV

EEVSLPEQVDIIISEPMGYMLFNERMLESYLHAKKYLKPSGNMFPTIGDV

HLAPFTDEQLYMEQFTKANFWYQPSFHGVDLSALRGAAVDEYFRQPVVDT

FDIRILMAKSVKYTVNFLEAKEGDLHRIEIPFKFHMLHSGLVHGLAFWFD

VAFIGSIMTVWLSTAPTEPLTHWYQVRCLFQSPLFAKAGDTLSGTCLLIA

NKRQSYDISIVAQVDQTGSKSSNLLDLKNPFFRYTGTTPSPPPGSHYTSP

SENMWNTGSTYNLSSGMAVAGMPTAYDLSSVIASGSSVGHNNLIPLGSSG

AQGSGGGSTSAHYAVNSQFTMGGPAISMASPMSIPTNTMHYGSEGHHHHH

H
```

General Procedure for CARM1 Enzyme Assays on Peptide Substrates.

The assays were all performed in a buffer consisting of 20 mM Bicine (pH=7.6), 1 mM TCEP, 0.005% BSG, and 0.002% Tween 20, prepared on the day of use. Compounds in 100% DMSO (1 ul) were spotted into a polypropylene 384-well V-bottom plates (Greiner) using a Platemate Plus outfitted with a 384-channel head (Thermo Scientific). DMSO (1 ul) was added to Columns 11, 12, 23, 24, rows A-H for the maximum signal control and 1 ul of SAH, a known product and inhibitor of CARM1, was added to columns 11, 12, 23, 24, rows I-P for the minimum signal control. A cocktail (40 ul) containing the CARM1 enzyme was added by Multidrop Combi (Thermo-Fisher). The compounds were allowed to incubate with CARM1 for 30 min at room temperature, then a cocktail (10 ul) containing $^3$H-SAM and peptide was added to initiate the reaction (final volume=51 ul). The final concentrations of the components were as follows: CARM1 was 0.25 nM, $^3$H-SAM was 30 nM, peptide was 250 nM, SAH in the minimum signal control wells was 1 mM, and the DMSO concentration was 2%. The assays were stopped by the addition of non-radiolabeled SAM (10 ul) to a final concentration of 300 uM, which dilutes the $^3$H-SAM to a level where its incorporation into the peptide substrate is no longer detectable. 50 ul of the reaction in the 384-well polypropylene plate was then transferred to a 384-well Flashplate and the biotinylated peptides were allowed to bind to the streptavidin surface for at least 1 hour before being washed once with 0.1% Tween20 in a Biotek ELx405 μplate washer. The plates were then read in a PerkinElmer TopCount plate reader to measure the quantity of $^3$H-labeled peptide bound to the Flashplate surface, measured as disintegrations per minute (dpm) or alternatively, referred to as counts per minute (cpm).

% Inhibition Calculation $$\% \: inh = 100 - \left(\frac{dpm_{cmpd} - dpm_{min}}{dpm_{max} - dpm_{min}}\right) \times 100$$

Where dpm=disintegrations per minute, cmpd=signal in assay well, and min and max are the respective minimum and maximum signal controls.

Four-Parameter IC50 Fit $$Y = Bottom + \frac{(Top - Bottom)}{\left(1 + \left(\frac{X}{IC_{50}}\right)^{Hill \: Coefficient}\right)}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

TABLE 2

| | Biochemical IC$_{50}$ | | | | |
|---|---|---|---|---|---|
| Cmpd No. | PRMT1 | PRMT6 | PRMT8 | PRMT3 | CARM1 |
| 1 | A | A | B | D | B |
| 2 | A | A | B | C | B |
| 3 | — | A | B | D | C |
| 4 | A | A | B | E | B |
| 5 | A | A | B | C | B |
| 6 | A | A | B | D | B |
| 7 | A | A | B | D | A |
| 8 | A | A | B | D | B |
| 9 | A | A | B | D | C |
| 10 | B | B | C | E | E |
| 11 | A | A | B | C | A |
| 12 | C | C | E | E | E |
| 13 | A | A | B | D | B |
| 14 | A | B | B | D | B |
| 15 | A | A | B | C | B |
| 16 | A | B | B | D | B |
| 17 | A | A | B | C | A |
| 18 | A | A | A | C | A |
| 19 | B | B | C | D | D |
| 20 | A | A | B | C | B |
| 21 | C | B | D | E | E |
| 22 | A | A | B | D | D |
| 23 | A | A | B | D | C |
| 24 | A | B | B | E | — |
| 25 | B | B | C | — | — |
| 26 | — | B | D | — | — |
| 27 | — | C | E | — | — |
| 28 | B | A | C | — | — |
| 29 | B | B | C | — | — |
| 30 | — | B | D | — | — |
| 31 | — | D | E | — | — |
| 32 | B | A | C | — | — |
| 33 | A | A | B | — | — |
| 34 | A | A | B | — | — |
| 35 | A | A | B | — | — |
| 36 | A | A | B | — | — |
| 37 | A | A | B | — | — |
| 38 | A | A | B | — | — |
| 39 | — | A | B | — | — |
| 40 | — | A | B | — | — |
| 41 | A | A | D | — | — |
| 42 | A | A | B | — | — |
| 43 | — | A | — | — | — |
| 44 | C | B | — | — | — |
| 45 | A | A | — | — | — |
| 46 | A | A | — | — | — |
| 47 | A | A | — | — | — |

TABLE 2-continued

| Cmpd No. | Biochemical IC$_{50}$ | | | | |
|---|---|---|---|---|---|
| | PRMT1 | PRMT6 | PRMT8 | PRMT3 | CARM1 |
| 48 | A | A | — | — | — |
| 49 | A | A | — | — | — |
| 50 | A | A | — | — | — |
| 51 | A | A | — | — | — |
| 52 | A | A | — | — | — |
| 53 | A | A | — | — | — |
| 54 | A | A | — | — | — |
| 55 | A | A | — | — | — |
| 56 | A | A | — | — | — |
| 57 | A | A | — | — | — |
| 58 | A | A | — | — | — |
| 59 | A | B | — | — | — |
| 60 | A | B | — | — | — |
| 61 | A | A | — | — | — |
| 62 | A | A | A | — | — |
| 63 | A | A | A | — | — |
| 64 | — | — | — | — | — |
| 65 | A | A | A | — | — |
| 66 | — | — | — | — | — |
| 67 | A | A | A | — | — |
| 68 | — | — | — | — | — |
| 69 | — | — | — | — | — |
| 70 | A | A | A | — | — |
| 71 | — | — | — | — | — |
| 72 | — | — | — | — | — |
| 73 | — | — | — | — | — |
| 74 | — | — | — | — | — |
| 75 | — | — | — | — | — |
| 76 | — | — | — | — | — |
| 77 | — | — | — | — | — |
| 78 | — | — | — | — | — |
| 79 | — | — | — | — | — |
| 80 | — | — | — | — | — |
| 81 | — | — | — | — | — |
| 82 | — | — | — | — | — |
| 83 | — | — | — | — | — |
| 84 | — | — | — | — | — |
| 85 | — | — | — | — | — |
| 86 | C | D | D | — | — |
| 87 | B | D | C | — | — |
| 88 | — | — | — | — | — |
| 89 | — | — | — | — | — |
| 90 | A | B | B | — | — |
| 91 | A | A | A | — | — |
| 92 | A | A | A | — | — |
| 93 | A | A | A | — | — |
| 94 | — | — | — | — | — |
| 95 | A | A | A | — | — |
| 96 | — | — | — | — | — |
| 97 | — | — | — | — | — |
| 98 | — | — | — | — | — |
| 99 | — | — | — | — | — |
| 100 | — | — | — | — | — |
| 101 | — | — | — | — | — |
| 102 | — | — | — | — | — |
| 103 | — | — | — | — | — |
| 104 | A | A | A | — | — |
| 105 | — | — | — | — | — |
| 106 | A | A | A | — | — |
| 107 | A | B | A | — | — |
| 108 | A | B | B | — | — |
| 109 | A | B | A | — | — |
| 110 | A | A | A | — | — |
| 111 | A | A | A | — | — |
| 112 | A | A | A | — | — |
| 113 | A | A | B | — | — |
| 114 | B | A | B | — | — |
| 115 | A | A | B | — | — |
| 116 | A | A | A | — | — |
| 117 | A | A | B | — | — |
| 118 | C | E | E | — | — |
| 119 | B | C | B | — | — |
| 120 | A | A | A | — | — |
| 121 | A | A | A | — | — |
| 122 | B | E | D | — | — |
| 123 | A | A | A | — | — |
| 124 | A | A | A | — | — |
| 125 | A | A | A | — | — |
| 126 | A | A | A | — | — |
| 127 | A | A | A | — | — |
| 128 | A | A | A | — | — |
| 129 | A | A | A | — | — |
| 130 | A | A | A | — | — |
| 131 | B | E | C | — | — |
| 132 | B | D | D | — | — |
| 133 | A | A | A | — | — |
| 134 | A | A | A | — | — |
| 135 | A | A | A | — | — |
| 136 | A | A | A | — | — |
| 137 | A | A | A | — | — |
| 138 | B | C | C | — | — |
| 139 | A | A | B | — | — |
| 140 | A | A | A | — | — |
| 141 | A | A | A | — | — |
| 142 | A | A | A | — | — |
| 143 | A | A | A | — | — |
| 144 | A | A | A | — | — |
| 145 | A | A | — | — | — |
| 146 | A | A | — | — | — |
| 147 | A | A | — | — | — |
| 148 | A | A | — | — | — |
| 149 | A | A | — | — | — |
| 150 | A | A | — | — | — |
| 151 | A | A | — | — | — |
| 152 | A | A | — | — | — |
| 153 | A | A | — | — | — |
| 154 | A | A | — | — | — |
| 155 | A | A | — | — | — |
| 156 | A | A | — | — | — |
| 157 | A | A | — | — | — |
| 158 | A | A | — | — | — |
| 159 | A | A | — | — | — |
| 160 | A | B | — | — | — |
| 161 | A | A | A | — | — |
| 162 | A | A | A | — | — |
| 163 | A | A | A | — | — |
| 164 | A | A | A | — | — |
| 165 | A | B | A | — | — |
| 166 | A | A | A | — | — |
| 167 | A | A | A | — | — |
| 168 | A | A | A | — | — |
| 169 | A | A | A | — | — |
| 170 | A | A | A | — | — |
| 171 | A | A | — | — | — |
| 172 | A | A | — | — | — |
| 173 | A | A | — | — | — |
| 174 | A | A | — | — | — |
| 175 | A | A | A | — | — |
| 176 | A | A | A | — | — |
| 177 | A | B | B | — | — |
| 178 | A | A | A | — | — |
| 179 | A | A | A | — | — |
| 180 | A | A | — | — | — |
| 181 | A | A | — | — | — |
| 182 | A | A | A | — | — |
| 183 | A | A | A | — | — |
| 184 | A | B | A | — | — |
| 185 | A | A | A | — | — |
| 186 | B | B | A | — | — |
| 187 | B | B | B | — | — |
| 188 | B | C | C | — | — |
| 189 | B | C | B | — | — |
| 190 | B | B | B | — | — |
| 191 | A | B | B | — | — |
| 192 | B | B | B | — | — |
| 193 | A | A | A | — | — |
| 194 | A | A | A | — | — |
| 195 | A | A | A | — | — |
| 196 | B | B | B | — | — |
| 197 | A | A | A | — | — |
| 198 | D | D | D | — | — |
| 199 | A | A | A | — | — |

TABLE 2-continued

Biochemical IC$_{50}$

| Cmpd No. | PRMT1 | PRMT6 | PRMT8 | PRMT3 | CARM1 |
|---|---|---|---|---|---|
| 200 | A | A | A | — | — |
| 201 | A | B | A | — | — |
| 202 | A | A | A | — | — |
| 203 | A | A | A | — | — |
| 204 | A | A | A | — | — |
| 205 | A | A | A | — | — |
| 206 | A | B | A | — | — |
| 207 | A | A | A | — | — |
| 208 | A | A | A | — | — |
| 209 | A | A | A | — | — |
| 210 | A | A | A | — | — |
| 211 | A | A | A | — | — |
| 212 | A | A | A | — | — |
| 213 | A | A | B | — | — |
| 214 | A | A | A | — | — |
| 215 | A | A | A | — | — |
| 216 | A | A | A | — | — |
| 217 | A | A | A | — | — |
| 218 | A | A | A | — | — |
| 219 | A | A | A | — | — |
| 220 | A | A | A | — | — |
| 221 | A | A | A | — | — |
| 222 | A | A | A | — | — |
| 223 | A | A | A | — | — |
| 224 | A | A | A | — | — |
| 225 | A | A | A | — | — |
| 226 | A | A | A | — | — |
| 227 | A | A | A | — | — |
| 228 | A | A | A | — | — |
| 229 | A | A | A | — | — |
| 230 | A | A | A | — | — |
| 231 | A | A | A | — | — |
| 232 | A | A | A | — | — |
| 233 | A | A | A | — | — |
| 234 | A | A | A | — | — |
| 235 | A | A | A | — | — |
| 236 | A | A | A | — | — |
| 237 | A | A | A | — | — |
| 238 | A | A | A | — | — |
| 239 | A | A | A | — | — |
| 240 | A | A | A | — | — |
| 241 | A | A | A | — | — |
| 242 | A | A | A | — | — |
| 243 | A | A | A | — | — |
| 244 | A | A | B | — | — |
| 245 | A | A | A | — | — |
| 246 | A | A | A | — | — |
| 247 | A | A | A | — | — |
| 248 | A | A | A | — | — |
| 249 | A | A | A | — | — |
| 250 | A | A | A | — | — |
| 251 | A | A | A | — | — |
| 252 | A | A | A | — | — |
| 253 | A | A | A | — | — |
| 254 | A | A | A | — | — |
| 255 | A | A | A | — | — |
| 256 | A | A | A | — | — |
| 257 | A | B | A | — | — |
| 258 | A | A | A | — | — |
| 259 | A | A | A | — | — |
| 260 | A | A | A | — | — |
| 261 | A | A | A | — | — |
| 262 | A | A | A | — | — |
| 263 | A | A | A | — | — |
| 264 | A | B | B | — | — |
| 265 | A | B | B | — | — |
| 266 | A | A | A | — | — |
| 267 | D | D | D | — | — |
| 268 | A | B | B | — | — |
| 269 | A | B | B | — | — |
| 270 | A | B | B | — | — |
| 271 | A | B | A | — | — |
| 272 | A | A | A | — | — |
| 273 | A | A | A | — | — |
| 274 | A | B | A | — | — |
| 275 | A | A | A | — | — |

"—" indicates no data provided.
For Table 2, "A" indicates an IC$_{50}$ ≤ 0.100 μM, "B" indicates an IC$_{50}$ of 0.101-1.00 μM, "C" indicates an IC$_{50}$ of 1.01-3.00 μM, "D" indicates an IC$_{50}$ of 3.01-10 μM, and IC$_{50}$ ≥ 10.01 μM.

TABLE 2a

Biochemical IC$_{50}$ (Numerical, μM)*

| Cmpd No. | PRMT1 | PRMT6 | PRMT8 | PRMT3 | CARM1 |
|---|---|---|---|---|---|
| 1 | 0.01 | 0.07 | 0.39 | 6.83 | 0.26 |
| 2 | 0.01 | 0.04 | 0.17 | 3.00 | 0.11 |
| 3 | — | 0.02 | 0.95 | 9.40 | 1.23 |
| 4 | 0.02 | 0.02 | 0.59 | >10 | 0.50 |
| 5 | 0.01 | 0.00 | 0.42 | 1.45 | 0.31 |
| 6 | 0.04 | 0.03 | 0.24 | 3.94 | 0.57 |
| 7 | 0.01 | 0.02 | 0.52 | 5.91 | 0.09 |
| 8 | 0.02 | 0.04 | 0.36 | 5.81 | 0.37 |
| 9 | 0.01 | 0.01 | 0.76 | 8.93 | 3.00 |
| 10 | 0.39 | 0.31 | 1.92 | >10 | >10 |
| 11 | 0.01 | 0.05 | 0.25 | 1.58 | 0.05 |
| 12 | 1.58 | 1.08 | >10 | >10 | >10 |
| 13 | 0.01 | 0.01 | 0.30 | 3.62 | 0.20 |
| 14 | 0.09 | 0.93 | 0.66 | 6.77 | 0.51 |
| 15 | 0.05 | 0.04 | 0.70 | 2.34 | 0.31 |
| 16 | 0.02 | 0.15 | 0.69 | 5.79 | 0.11 |
| 17 | 0.01 | 0.05 | 0.41 | 2.36 | 0.09 |
| 18 | 0.00 | 0.01 | 0.04 | 1.75 | 0.10 |
| 19 | 0.19 | 0.17 | 2.30 | 7.74 | 3.78 |
| 20 | 0.02 | 0.02 | 0.47 | 2.34 | 0.25 |
| 21 | 1.49 | 0.67 | 9.56 | >10 | >10 |
| 22 | 0.01 | 0.02 | 0.30 | 6.46 | 3.77 |
| 23 | 0.01 | 0.01 | 0.28 | 9.65 | 2.78 |
| 24 | 0.02 | 0.18 | 0.30 | >10 | — |
| 25 | 0.25 | 0.29 | 2.86 | — | — |
| 26 | — | 0.51 | 5.63 | — | — |
| 27 | — | 2.41 | >10 | — | — |
| 28 | 0.18 | 0.08 | 1.68 | — | — |
| 29 | — | 0.29 | 3.81 | — | — |
| 30 | — | 6.59 | >10 | — | — |
| 31 | 0.11 | 0.03 | 1.15 | — | — |
| 32 | 0.02 | 0.02 | 0.77 | — | — |
| 33 | 0.02 | 0.02 | 0.50 | — | — |
| 34 | 0.02 | 0.03 | 0.44 | — | — |
| 35 | 0.00 | 0.01 | 0.14 | — | — |
| 36 | 0.00 | 0.01 | 0.28 | — | — |
| 37 | 0.01 | 0.01 | 0.13 | — | — |
| 38 | 0.00 | 0.01 | 0.26 | — | — |
| 39 | — | 0.01 | 0.36 | — | — |
| 40 | 0.02 | 0.02 | 7.01 | — | — |
| 41 | 0.01 | 0.00 | 0.35 | — | — |
| 42 | — | 0.02 | 0.0300 | — | — |
| 43 | — | 0.00 | 0.0116 | — | — |
| 44 | — | 0.02 | 0.0624 | — | — |
| 45 | 0.0028 | 0.0056 | 0.0053 | — | — |
| 46 | 0.0079 | 0.0122 | 0.0062 | — | — |
| 47 | 0.0043 | 0.0173 | 0.0125 | — | — |
| 48 | 0.0074 | 0.0178 | 0.0083 | — | — |
| 49 | 0.0043 | 0.0199 | 0.0073 | — | — |
| 50 | 0.0086 | 0.0206 | 0.0112 | — | — |
| 51 | 0.0094 | 0.0239 | 0.0214 | — | — |
| 52 | 0.0047 | 0.0243 | 0.0104 | — | — |
| 53 | 0.0105 | 0.0380 | 0.0128 | — | — |
| 54 | 0.0080 | 0.0382 | 0.0247 | — | — |
| 55 | 0.0128 | 0.0404 | 0.0247 | — | — |
| 56 | 0.0138 | 0.0618 | 0.0320 | — | — |
| 57 | 0.0186 | 0.0694 | 0.0301 | — | — |
| 58 | 0.0265 | 0.1077 | 0.0721 | — | — |
| 59 | 0.0196 | 0.1277 | 0.0484 | — | — |
| 60 | 0.0275 | 0.1549 | 0.1286 | — | — |
| 61 | 0.0205 | 0.0491 | — | — | — |

TABLE 2a-continued

Biochemical $IC_{50}$ (Numerical, μM)*

| Cmpd No. | PRMT1 | PRMT6 | PRMT8 | PRMT3 | CARM1 |
|---|---|---|---|---|---|
| 62 | 0.01187 | 0.02902 | 0.02 | — | — |
| 63 | 0.0090 | 0.0121 | 0.0120 | — | — |
| 64 | — | — | — | — | — |
| 65 | 0.00965 | 0.04193 | 0.01355 | — | — |
| 66 | — | — | — | — | — |
| 67 | 0.0078 | 0.0180 | 0.0119 | — | — |
| 68 | — | — | — | — | — |
| 69 | — | — | — | — | — |
| 70 | 0.0092 | 0.0440 | 0.0242 | — | — |
| 71 | — | — | — | — | — |
| 72 | — | — | — | — | — |
| 73 | — | — | — | — | — |
| 74 | — | — | — | — | — |
| 75 | — | — | — | — | — |
| 76 | — | — | — | — | — |
| 77 | — | — | — | — | — |
| 78 | — | — | — | — | — |
| 79 | — | — | — | — | — |
| 80 | — | — | — | — | — |
| 81 | — | — | — | — | — |
| 82 | — | — | — | — | — |
| 83 | — | — | — | — | — |
| 84 | — | — | — | — | — |
| 85 | — | — | — | — | — |
| 86 | 1.94296 | 3.40906 | 3.96737 | — | — |
| 87 | 0.56419 | 3.72633 | 1.01384 | — | — |
| 88 | — | — | — | — | — |
| 89 | — | — | — | — | — |
| 90 | 0.0344 | 0.12244 | 0.11687 | — | — |
| 91 | 0.01668 | 0.06307 | 0.02896 | — | — |
| 92 | 0.0209 | 0.04904 | 0.04206 | — | — |
| 93 | 0.03128 | 0.07193 | 0.08812 | — | — |
| 94 | — | — | — | — | — |
| 95 | 0.00935 | 0.0692 | 0.01887 | — | — |
| 96 | — | — | — | — | — |
| 97 | — | — | — | — | — |
| 98 | — | — | — | — | — |
| 99 | — | — | — | — | — |
| 100 | — | — | — | — | — |
| 101 | — | — | — | — | — |
| 102 | — | — | — | — | — |
| 103 | — | — | — | — | — |
| 104 | 0.00804 | 0.04046 | 0.01158 | — | — |
| 105 | — | — | — | — | — |
| 106 | 0.0095 | 0.01348 | 0.0145 | — | — |
| 107 | 0.0212 | 0.1296 | 0.0554 | — | — |
| 108 | 0.0610 | 0.3255 | 0.2521 | — | — |
| 109 | 0.0267 | 0.1243 | 0.0560 | — | — |
| 110 | 0.0131 | 0.0294 | 0.0429 | — | — |
| 111 | 0.0224 | 0.0455 | 0.0599 | — | — |
| 112 | 0.0189 | 0.0574 | 0.0692 | — | — |
| 113 | 0.0572 | 0.0669 | 0.1193 | — | — |
| 114 | 0.1009 | 0.0926 | 0.3400 | — | — |
| 115 | 0.0887 | 0.0627 | 0.1964 | — | — |
| 116 | 0.0098 | 0.0187 | 0.0118 | — | — |
| 117 | 0.0386 | 0.0962 | 0.1428 | — | — |
| 118 | 2.1552 | >10.0 | >10.0 | — | — |
| 119 | 0.1239 | 2.7522 | 0.7278 | — | — |
| 120 | 0.0101 | 0.0428 | 0.0251 | — | — |
| 121 | 0.0152 | 0.0977 | 0.0326 | — | — |
| 122 | 0.4207 | >10.0 | 8.3743 | — | — |
| 123 | 0.0088 | 0.0180 | 0.0247 | — | — |
| 124 | 0.0064 | 0.0262 | 0.0108 | — | — |
| 125 | 0.0053 | 0.0131 | 0.0090 | — | — |
| 126 | 0.0040 | 0.0094 | 0.0065 | — | — |
| 127 | 0.0165 | 0.0223 | 0.0478 | — | — |
| 128 | 0.0052 | 0.0131 | 0.0082 | — | — |
| 129 | 0.0236 | 0.0297 | 0.0837 | — | — |
| 130 | 0.0034 | 0.0042 | 0.0045 | — | — |
| 131 | 0.2699 | >10.0 | 1.9689 | — | — |
| 132 | 0.6264 | 5.4954 | 4.3316 | — | — |
| 133 | 0.0059 | 0.0124 | 0.0091 | — | — |
| 134 | 0.0139 | 0.0351 | 0.0248 | — | — |
| 135 | 0.0121 | 0.0349 | 0.0317 | — | — |
| 136 | 0.0029 | 0.0072 | 0.0068 | — | — |
| 137 | 0.0073 | 0.0233 | 0.0162 | — | — |
| 138 | 0.3486 | 1.2075 | 1.4305 | — | — |
| 139 | 0.0305 | 0.0226 | 0.1157 | — | — |
| 140 | 0.0156 | 0.0240 | 0.0339 | — | — |
| 141 | 0.0107 | 0.0230 | 0.0297 | — | — |
| 142 | 0.0072 | 0.0199 | 0.0159 | — | — |
| 143 | 0.0106 | 0.0220 | 0.0330 | — | — |
| 144 | 0.0216 | 0.0356 | 0.0784 | — | — |
| 145 | 0.0262 | 0.0380 | — | — | — |
| 146 | 0.0140 | 0.0217 | — | — | — |
| 147 | 0.0183 | 0.0327 | — | — | — |
| 148 | 0.0048 | 0.0081 | — | — | — |
| 149 | 0.0045 | 0.0072 | — | — | — |
| 150 | 0.0440 | 0.0556 | — | — | — |
| 151 | 0.0369 | 0.0477 | — | — | — |
| 152 | 0.0142 | 0.0352 | — | — | — |
| 153 | 0.0232 | 0.0284 | — | — | — |
| 154 | 0.0177 | 0.0443 | — | — | — |
| 155 | 0.0315 | 0.0608 | — | — | — |
| 156 | 0.0172 | 0.0578 | — | — | — |
| 157 | 0.0185 | 0.0479 | — | — | — |
| 158 | 0.0202 | 0.0910 | — | — | — |
| 159 | 0.0197 | 0.0538 | — | — | — |
| 160 | 0.0218 | 0.1121 | — | — | — |
| 161 | 0.0256 | 0.0729 | 0.0374 | — | — |
| 162 | 0.0389 | 0.0610 | 0.0927 | — | — |
| 163 | 0.0173 | 0.0657 | 0.0158 | — | — |
| 164 | 0.0197 | 0.0708 | 0.0191 | — | — |
| 165 | 0.0176 | 0.1204 | 0.0181 | — | — |
| 166 | 0.0180 | 0.0486 | 0.0230 | — | — |
| 167 | 0.0110 | 0.0315 | 0.0130 | — | — |
| 168 | 0.0198 | 0.0451 | 0.0281 | — | — |
| 169 | 0.0065 | 0.0178 | 0.0102 | — | — |
| 170 | 0.0210 | 0.0578 | 0.0237 | — | — |
| 171 | 0.0147 | 0.0411 | — | — | — |
| 172 | 0.0230 | 0.0458 | — | — | — |
| 173 | 0.0232 | 0.0899 | — | — | — |
| 174 | 0.0155 | 0.0844 | — | — | — |
| 175 | 0.0133 | 0.0376 | 0.0296 | — | — |
| 176 | 0.0102 | 0.0364 | 0.0286 | — | — |
| 177 | 0.0276 | 0.1129 | 0.1499 | — | — |
| 178 | 0.0058 | 0.0157 | 0.0205 | — | — |
| 179 | 0.0159 | 0.0629 | 0.0573 | — | — |
| 180 | 0.0049 | 0.0147 | — | — | — |
| 181 | 0.0047 | 0.0279 | — | — | — |
| 182 | 0.01161 | 0.0735 | 0.03227 | — | — |
| 183 | 0.01348 | 0.08768 | 0.03943 | — | — |
| 184 | 0.01977 | 0.10057 | 0.04732 | — | — |
| 185 | 0.01421 | 0.03518 | 0.02442 | — | — |
| 186 | 0.11047 | 0.10652 | 0.08958 | — | — |
| 187 | 0.19316 | 0.26079 | 0.18533 | — | — |
| 188 | 0.27493 | 1.23016 | 1.53507 | — | — |
| 189 | 0.10809 | 1.47313 | 0.47825 | — | — |
| 190 | 0.12394 | 0.15596 | 0.35151 | — | — |
| 191 | 0.0504 | 0.10664 | 0.15195 | — | — |
| 192 | 0.21645 | 0.17268 | 0.45873 | — | — |
| 193 | 0.0284 | 0.09512 | 0.06882 | — | — |
| 194 | 0.01446 | 0.02273 | 0.03525 | — | — |
| 195 | 0.01444 | 0.05169 | 0.0356 | — | — |
| 196 | 0.14877 | 0.11139 | 0.41502 | — | — |
| 197 | 0.00827 | 0.01065 | 0.01563 | — | — |
| 198 | 10 | 8.53693 | 10 | — | — |
| 199 | 0.01683 | 0.03653 | 0.03833 | — | — |
| 200 | 0.01152 | 0.04163 | 0.01623 | — | — |
| 201 | 0.02286 | 0.13436 | 0.03183 | — | — |
| 202 | 0.01266 | 0.06637 | 0.02686 | — | — |
| 203 | 0.02837 | 0.03683 | 0.08436 | — | — |
| 204 | 0.01837 | 0.06361 | 0.05164 | — | — |
| 205 | 0.01283 | 0.07151 | 0.01537 | — | — |
| 206 | 0.01946 | 0.2066 | 0.02894 | — | — |
| 207 | 0.00568 | 0.01846 | 0.00913 | — | — |
| 208 | 0.00694 | 0.04527 | 0.01276 | — | — |
| 209 | 0.02776 | 0.05208 | 0.04385 | — | — |
| 210 | 0.01313 | 0.03166 | 0.02286 | — | — |
| 211 | 0.00828 | 0.01138 | 0.01002 | — | — |
| 212 | 0.00557 | 0.01357 | 0.00828 | — | — |
| 213 | 0.05388 | 0.09132 | 0.16503 | — | — |

TABLE 2a-continued

Biochemical IC$_{50}$ (Numerical, µM)*

| Cmpd No. | PRMT1 | PRMT6 | PRMT8 | PRMT3 | CARM1 |
|---|---|---|---|---|---|
| 214 | 0.01978 | 0.05049 | 0.02743 | — | — |
| 215 | 0.01406 | 0.0306 | 0.02297 | — | — |
| 216 | 0.01208 | 0.0205 | 0.01779 | — | — |
| 217 | 0.03018 | 0.03404 | 0.05952 | — | — |
| 218 | 0.0417 | 0.03035 | 0.06702 | — | — |
| 219 | 0.00896 | 0.03189 | 0.01499 | — | — |
| 220 | 0.00929 | 0.01841 | 0.01294 | — | — |
| 221 | 0.00644 | 0.01915 | 0.01545 | — | — |
| 222 | 0.04299 | 0.02131 | 0.09002 | — | — |
| 223 | 0.00665 | 0.01575 | 0.00865 | — | — |
| 224 | 0.00927 | 0.01805 | 0.01018 | — | — |
| 225 | 0.00762 | 0.01164 | 0.01389 | — | — |
| 226 | 0.03311 | 0.04149 | 0.05758 | — | — |
| 227 | 0.0168 | 0.01782 | 0.03576 | — | — |
| 228 | 0.069 | 0.01848 | 0.10005 | — | — |
| 229 | 0.01084 | 0.02912 | 0.01595 | — | — |
| 230 | 0.01346 | 0.02307 | 0.02574 | — | — |
| 231 | 0.00649 | 0.01474 | 0.00932 | — | — |
| 232 | 0.00911 | 0.01937 | 0.02101 | — | — |
| 233 | 0.02075 | 0.04787 | 0.04267 | — | — |
| 234 | 0.01611 | 0.08411 | 0.04276 | — | — |
| 235 | 0.02571 | 0.03408 | 0.04404 | — | — |
| 236 | 0.02903 | 0.06239 | 0.05783 | — | — |
| 237 | 0.04219 | 0.04098 | 0.08329 | — | — |
| 238 | 0.0296 | 0.05387 | 0.08009 | — | — |
| 239 | 0.00655 | 0.00775 | 0.01319 | — | — |
| 240 | 0.0061 | 0.00672 | 0.01091 | — | — |
| 241 | 0.0224 | 0.03276 | 0.04894 | — | — |
| 242 | 0.02834 | 0.04166 | 0.08368 | — | — |
| 243 | 0.03244 | 0.01514 | 0.07082 | — | — |
| 244 | 0.03978 | 0.05482 | 0.11313 | — | — |
| 245 | 0.01854 | 0.06216 | 0.01834 | — | — |
| 246 | 0.01258 | 0.0283 | 0.02378 | — | — |
| 247 | 0.01107 | 0.02018 | 0.01644 | — | — |
| 248 | 0.01319 | 0.03262 | 0.02818 | — | — |
| 249 | 0.02419 | 0.08278 | 0.08453 | — | — |
| 250 | 0.02396 | 0.01435 | 0.04241 | — | — |
| 251 | 0.01305 | 0.01711 | 0.02073 | — | — |
| 252 | 0.03086 | 0.04826 | 0.05152 | — | — |
| 253 | 0.00715 | 0.01335 | 0.01168 | — | — |
| 254 | 0.01728 | 0.01764 | 0.044 | — | — |
| 255 | 0.01016 | 0.02765 | 0.02448 | — | — |
| 256 | 0.02367 | 0.03851 | 0.04405 | — | — |
| 257 | 0.02982 | 0.15318 | 0.03096 | — | — |
| 258 | 0.00759 | 0.01798 | 0.01083 | — | — |
| 259 | 0.01579 | 0.0331 | 0.01706 | — | — |
| 260 | 0.02021 | 0.08314 | 0.03733 | — | — |
| 261 | 0.013 | 0.03165 | 0.01668 | — | — |
| 262 | 0.03373 | 0.0812 | 0.07236 | — | — |
| 263 | 0.01915 | 0.0638 | 0.03513 | — | — |
| 264 | 0.07798 | 0.1327 | 0.18082 | — | — |
| 265 | 0.05883 | 0.17447 | 0.17058 | — | — |
| 266 | 0.0193 | 0.07899 | 0.0631 | — | — |
| 267 | 3.4983 | 10 | 5.91407 | — | — |
| 268 | 0.06863 | 0.14146 | 0.20985 | — | — |
| 269 | 0.05127 | 0.10664 | 0.15456 | — | — |
| 270 | 0.06247 | 0.14863 | 0.20383 | — | — |
| 271 | 0.03706 | 0.1208 | 0.10019 | — | — |
| 272 | 0.01236 | 0.07387 | 0.02578 | — | — |
| 273 | 0.01145 | 0.04045 | 0.02257 | — | — |
| 274 | 0.00819 | 0.10255 | 0.01193 | — | — |
| 275 | 0.00462 | 0.01859 | 0.01038 | — | — |

*For Table 2a, numerical values represent data from a single experiment or an average of multiple experiments.

RKO Methylation Assay

RKO adherent cells were purchased from ATCC (American Type Culture Collection), Manassas, Va., USA. DMEM/Glutamax medium, penicillin-streptomycin, heat inactivated fetal bovine serum, 0.05% trypsin and D-PBS were purchased from Life Technologies, Grand Island, N.Y., USA. Odyssey blocking buffer, 800CW goat anti-rabbit IgG (H+L) antibody, and Licor Odyssey infrared scanner were purchased from Licor Biosciences, Lincoln, Nebr., USA. Mono-methyl arginine antibody was purchased from Cell Signaling Technology, Danvers, Mass., USA. Methanol was purchased from VWR, Franklin, Mass., USA. 10% Tween 20 was purchased from KPL, Inc., Gaithersburg, Md., USA. DRAQ5 was purchased from Biostatus Limited, Leicestershire, UK.

RKO adherent cells were maintained in growth medium (DMEM/Glutamax medium supplemented with 10% v/v heat inactivated fetal bovine serum and 100 units/mL penicillin-streptomycin) and cultured at 37° C. under 5% $CO_2$.

Cell Treatment, in Cell Western (ICW) for Detection of Mono-Methyl Arginine and DNA Content.

RKO cells were seeded in assay medium at a concentration of 20,000 cells per mL to a poly-D-lysine coated 384 well culture plate (BD Biosciences 356697) with 50 L per well. Compound (100 nL) from a 96-well source plate was added directly to 384 well cell plate. Plates were incubated at 37° C., 5% $CO_2$ for 72 hours. After three days of incubation, plates were brought to room temperature outside of the incubator for ten minutes and blotted on paper towels to remove cell media. 50 µL of ice cold 100% methanol was added directly to each well and incubated for 30 min at room temperature. After 30 min, plates were transferred to a Biotek EL406 µlate washer and washed 2 times with 100 µL per well of wash buffer (IX PBS). Next 60 µL per well of Odyssey blocking buffer (Odyssey Buffer with 0.1% Tween 20 (v/v)) were added to each plate and incubated 1 hour at room temperature. Blocking buffer was removed and 20 µL per well of primary antibody was added (mono-methyl arginine diluted 1:200 in Odyssey buffer with 0.1% Tween 20 (v/v)) and plates were incubated overnight (16 hours) at 4° C. Plates were washed 5 times with 100 µL per well of wash buffer. Next 20 µL per well of secondary antibody was added (1:200 800CW goat anti-rabbit IgG (H+L) antibody, 1:1000 DRAQ5 (Biostatus limited) in Odyssey buffer with 0.1% Tween 20 (v/v)) and incubated for 1 hour at room temperature. The plates were washed 5 times with 100 µL per well wash buffer then 2 times with 100 µL per well of water. Plates were allowed to dry at room temperature then imaged on the Licor Odyssey machine which measures integrated intensity at 700 nm and 800 nm wavelengths. Both 700 and 800 channels were scanned.

Calculations:

First, the ratio for each well was determined by:

$$\left(\frac{\text{monomethyl Arginine 800 nm value}}{DRAQ5\ 700\ \text{nm value}}\right)$$

Each plate included fourteen control wells of DMSO only treatment (minimum activation) as well as fourteen control wells for maximum activation treated with 20 µM of a reference compound. The average of the ratio values for each control type was calculated and used to determine the percent activation for each test well in the plate. Reference compound was serially diluted three-fold in DMSO for a total of nine test concentrations, beginning at 20 µM. Percent activation was determined and $EC_{30}$ curves were generated using triplicate wells per concentration of compound.

Percent Activation =

$$100 - \left(\left(\frac{\text{(Individual Test Sample Ratio)} - \text{(Minimum Activation Ratio)}}{\text{(Maximum Activation Ratio)} - \text{(Minimum Activation Ratio)}}\right) * 100\right)$$

TABLE 3

| Cmpd No. | EC$_{30}$ |
|---|---|
| 9 | B |
| 10 | C |
| 21 | C |
| 22 | A |
| 23 | A |
| 24 | A |
| 25 | B |
| 26 | C |
| 27 | C |
| 28 | B |
| 29 | C |
| 30 | C |
| 31 | C |
| 32 | A |
| 33 | B |
| 34 | A |
| 35 | A |
| 36 | A |
| 37 | A |
| 38 | A |
| 39 | A |
| 40 | A |
| 41 | C |
| 42 | C |
| 43 | A |
| 44 | B |
| 45 | A |
| 46 | A |
| 47 | — |
| 48 | A |
| 49 | — |
| 50 | A |
| 51 | A |
| 52 | — |
| 53 | A |
| 54 | A |
| 55 | A |
| 56 | — |
| 57 | A |
| 58 | — |
| 59 | — |
| 60 | A |
| 61 | A |
| 62 | A |
| 63 | A |
| 64 | — |
| 65 | A |
| 66 | — |
| 67 | A |
| 68 | — |
| 69 | — |
| 70 | A |
| 71 | — |
| 72 | — |
| 73 | — |
| 74 | — |
| 75 | — |
| 76 | — |
| 77 | — |
| 78 | — |
| 79 | — |
| 80 | — |
| 81 | — |
| 82 | — |
| 83 | — |
| 84 | — |
| 85 | — |
| 86 | A |
| 87 | A |
| 88 | — |
| 89 | — |
| 90 | A |
| 91 | A |
| 92 | A |
| 93 | — |
| 94 | — |
| 95 | A |
| 96 | — |
| 97 | — |
| 98 | — |
| 99 | — |
| 100 | — |
| 101 | — |
| 102 | — |
| 103 | — |
| 104 | A |
| 105 | — |
| 106 | A |
| 107 | — |
| 108 | B |
| 109 | A |
| 110 | A |
| 111 | A |
| 112 | — |
| 113 | B |
| 114 | — |
| 115 | A |
| 116 | B |
| 117 | — |
| 118 | B |
| 119 | A |
| 120 | A |
| 121 | — |
| 122 | — |
| 123 | A |
| 124 | A |
| 125 | A |
| 126 | A |
| 127 | A |
| 128 | A |
| 129 | A |
| 130 | — |
| 131 | — |
| 132 | — |
| 133 | A |
| 134 | A |
| 135 | A |
| 136 | A |
| 137 | A |
| 138 | — |
| 139 | A |
| 140 | A |
| 141 | A |
| 142 | A |
| 143 | A |
| 144 | A |
| 145 | A |
| 146 | A |
| 147 | B |
| 148 | A |
| 149 | A |
| 150 | A |
| 151 | A |
| 152 | A |

TABLE 3-continued

In Cell Western

| Cmpd No. | $EC_{30}$ |
|---|---|
| 153 | A |
| 154 | A |
| 155 | B |
| 156 | A |
| 157 | A |
| 158 | A |
| 159 | A |
| 160 | A |
| 161 | B |
| 162 | B |
| 163 | A |
| 164 | A |
| 165 | A |
| 166 | A |
| 167 | A |
| 168 | A |
| 169 | A |
| 170 | — |
| 171 | A |
| 172 | B |
| 173 | A |
| 174 | A |
| 175 | C |
| 176 | A |
| 177 | A |
| 178 | A |
| 179 | A |
| 180 | A |
| 181 | A |
| 182 | A |
| 183 | A |
| 184 | A |
| 185 | A |
| 186 | — |
| 187 | B |
| 188 | — |
| 189 | B |
| 190 | B |
| 191 | B |
| 192 | B |
| 193 | A |
| 194 | A |
| 195 | B |
| 196 | B |
| 197 | A |
| 198 | A |
| 199 | A |
| 200 | A |
| 201 | A |
| 202 | A |
| 203 | A |
| 204 | A |
| 205 | A |
| 206 | A |
| 207 | A |
| 208 | A |
| 209 | A |
| 210 | A |
| 211 | A |
| 212 | A |
| 213 | A |
| 214 | A |
| 215 | A |
| 216 | A |
| 217 | A |
| 218 | |
| 219 | A |
| 220 | A |
| 221 | A |
| 222 | A |
| 223 | A |
| 224 | A |
| 225 | A |
| 226 | A |
| 227 | A |
| 228 | — |
| 229 | A |
| 230 | A |
| 231 | A |
| 232 | A |
| 233 | A |
| 234 | A |
| 235 | A |
| 236 | A |
| 237 | A |
| 238 | A |
| 239 | A |
| 240 | A |
| 241 | A |
| 242 | — |
| 243 | — |
| 244 | A |
| 245 | — |
| 246 | A |
| 247 | A |
| 248 | A |
| 249 | A |
| 250 | — |
| 251 | A |
| 252 | A |
| 253 | A |
| 254 | A |
| 255 | A |
| 256 | A |
| 257 | A |
| 258 | A |
| 259 | A |
| 260 | A |
| 261 | A |
| 262 | A |
| 263 | — |
| 264 | — |
| 265 | — |
| 266 | — |
| 267 | — |
| 268 | — |
| 269 | — |
| 270 | — |
| 271 | — |
| 272 | — |
| 273 | — |
| 274 | A |
| 275 | A |

"—" indicates no data provided.
For Table 3, "A" indicates an $EC_{30} \leq 3.00$ μM, "B" indicates an $EC_{30}$ of 3.01-12.00 μM, and "C" indicates an $EC_{30} > 12.01$ μM.

TABLE 3a

In Cell Western (Numerical, μM)*

| Cmpd No. | $EC_{30}$ |
|---|---|
| 9 | 5.61 |
| 10 | >20 |
| 21 | >20 |
| 22 | 1.24 |
| 23 | 1.61 |
| 24 | 2.40 |
| 25 | 11.83 |
| 26 | >20 |
| 27 | >20 |
| 28 | 11.10 |
| 29 | >20 |
| 30 | >20 |
| 31 | >20 |
| 32 | 2.35 |
| 33 | 3.33 |
| 34 | 1.15 |
| 35 | 0.73 |

TABLE 3a-continued

In Cell Western (Numerical, μM)*

| Cmpd No. | EC$_{30}$ |
|---|---|
| 36 | 0.63 |
| 37 | 0.26 |
| 38 | 0.13 |
| 39 | 0.50 |
| 40 | 0.87 |
| 41 | >20 |
| 42 | >20 |
| 43 | 2.60 |
| 44 | 4.57 |
| 45 | 0.0540 |
| 46 | 0.0080 |
| 47 | 0.0520 |
| 48 | 0.0140 |
| 49 | 0.0500 |
| 50 | 0.0270 |
| 51 | 0.0520 |
| 52 | 0.0410 |
| 53 | 0.0170 |
| 54 | 0.0870 |
| 55 | 0.0630 |
| 56 | 0.0960 |
| 57 | 0.0250 |
| 58 | 0.9780 |
| 59 | 0.3570 |
| 60 | 2.8410 |
| 61 | 0.1490 |
| 62 | 0.16924 |
| 63 | 1.0852 |
| 64 | — |
| 65 | 0.07752 |
| 66 | — |
| 67 | 0.0810 |
| 68 | — |
| 69 | — |
| 70 | 0.0500 |
| 71 | — |
| 72 | — |
| 73 | — |
| 74 | — |
| 75 | — |
| 76 | — |
| 77 | — |
| 78 | — |
| 79 | — |
| 80 | — |
| 81 | — |
| 82 | — |
| 83 | — |
| 84 | — |
| 85 | — |
| 86 | 0.0168 |
| 87 | 2.5254 |
| 88 | — |
| 89 | — |
| 90 | 0.3158 |
| 91 | 2.05655 |
| 92 | 2.17333 |
| 93 | — |
| 94 | — |
| 95 | 0.12166 |
| 96 | — |
| 97 | — |
| 98 | — |
| 99 | — |
| 100 | — |
| 101 | — |
| 102 | — |
| 103 | — |
| 104 | 0.01166 |
| 105 | — |
| 106 | 0.0227 |
| 107 | — |
| 108 | 8.5466 |
| 109 | 2.4785 |
| 110 | 2.5472 |
| 111 | 0.9130 |
| 112 | — |
| 113 | 7.3455 |
| 114 | — |
| 115 | 0.0189 |
| 116 | 8.8958 |
| 117 | — |
| 118 | 9.5749 |
| 119 | 0.0773 |
| 120 | 0.0098 |
| 121 | — |
| 122 | 0.3455 |
| 123 | 0.0440 |
| 124 | 0.0214 |
| 125 | 0.0876 |
| 126 | 0.6376 |
| 127 | 0.0292 |
| 128 | 1.0750 |
| 129 | 0.0045 |
| 130 | — |
| 131 | — |
| 132 | 0.0038 |
| 133 | 0.0438 |
| 134 | 0.0332 |
| 135 | 1.0140 |
| 136 | 0.0350 |
| 137 | 0.0150 |
| 138 | — |
| 139 | 0.6270 |
| 140 | 0.1640 |
| 141 | 0.1320 |
| 142 | 0.0520 |
| 143 | 0.0590 |
| 144 | 0.0630 |
| 145 | 2.3000 |
| 146 | 0.1600 |
| 147 | 8.6000 |
| 148 | 0.0160 |
| 149 | 0.1060 |
| 150 | 0.2560 |
| 151 | 0.7050 |
| 152 | 0.1190 |
| 153 | 0.1290 |
| 154 | 1.7890 |
| 155 | 4.0850 |
| 156 | 1.3570 |
| 157 | 2.4890 |
| 158 | 0.0080 |
| 159 | 0.0630 |
| 160 | 0.1660 |
| 161 | 5.0200 |
| 162 | 6.6800 |
| 163 | 0.0660 |
| 164 | 0.0780 |
| 165 | 0.5100 |
| 166 | 0.0830 |
| 167 | 0.0180 |
| 168 | 0.0850 |
| 169 | 0.0160 |
| 170 | — |
| 171 | 0.1920 |
| 172 | 4.4570 |
| 173 | 0.4080 |
| 174 | 0.0850 |
| 175 | >20 |
| 176 | 2.1420 |
| 177 | 0.5710 |
| 178 | 0.0760 |
| 179 | 0.4760 |
| 180 | 0.0190 |
| 181 | 0.1070 |
| 182 | 0.41111 |
| 183 | 0.31865 |
| 184 | 0.45829 |
| 185 | 0.45302 |
| 186 | — |
| 187 | 3.1603 |

TABLE 3a-continued

In Cell Western (Numerical, μM)*

| Cmpd No. | $EC_{30}$ |
|---|---|
| 188 | — |
| 189 | 6.62284 |
| 190 | 6.6228 |
| 191 | 9.24747 |
| 192 | 9.2475 |
| 193 | 1.43822 |
| 194 | 1.1848 |
| 195 | 4.88623 |
| 196 | 4.8862 |
| 197 | 0.40624 |
| 198 | 0.4062 |
| 199 | 0.80245 |
| 200 | 0.02034 |
| 201 | 0.15455 |
| 202 | 0.32701 |
| 203 | 0.3270 |
| 204 | 1.55419 |
| 205 | 0.01445 |
| 206 | 0.07648 |
| 207 | 0.01212 |
| 208 | 0.06719 |
| 209 | 0.91597 |
| 210 | 0.27952 |
| 211 | 0.15488 |
| 212 | 0.43283 |
| 213 | 0.4328 |
| 214 | 0.09582 |
| 215 | 0.16359 |
| 216 | 0.11104 |
| 217 | 0.1110 |
| 218 | — |
| 219 | 0.29433 |
| 220 | 0.2188 |
| 221 | 0.4903 |
| 222 | 2.60878 |
| 223 | 0.27538 |
| 224 | 0.08472 |
| 225 | 0.64935 |
| 226 | 1.53074 |
| 227 | 1.5307 |
| 228 | — |
| 229 | 0.68908 |
| 230 | 1.31527 |
| 231 | 0.09668 |
| 232 | 0.95704 |
| 233 | 1.05613 |
| 234 | 1.0561 |
| 235 | 0.81272 |
| 236 | 0.8127 |
| 237 | 1.43678 |
| 238 | 2.15067 |
| 239 | 2.1507 |
| 240 | 1.17758 |
| 241 | 1.1776 |
| 242 | — |
| 243 | — |
| 244 | 2.52536 |
| 245 | — |
| 246 | 0.0799 |
| 247 | 0.6979 |
| 248 | 1.3093 |
| 249 | 0.6585 |
| 250 | — |
| 251 | 1.4511 |
| 252 | 0.2673 |
| 253 | 0.0566 |
| 254 | 1.33631 |
| 255 | 0.21397 |
| 256 | 0.31583 |
| 257 | 0.10322 |
| 258 | 0.30272 |
| 259 | 0.40841 |
| 260 | 0.20696 |
| 261 | 0.28926 |
| 262 | 0.2893 |
| 263 | — |
| 264 | — |
| 265 | — |
| 266 | — |
| 267 | — |
| 268 | — |
| 269 | — |
| 270 | — |
| 271 | — |
| 272 | — |
| 273 | — |
| 274 | 0.01681 |
| 275 | 0.084 |

*For Table 3a, numerical values represent data from a single experiment or an average of multiple experiments.

OTHER EMBODIMENTS

The foregoing has been a description of certain non-limiting embodiments of the invention. Those of ordinary skill in the art will appreciate that various changes and modifications to this description may be made without departing from the spirit or scope of the present invention, as defined in the following claims.

---

What is claimed is:

1. A compound of formula:

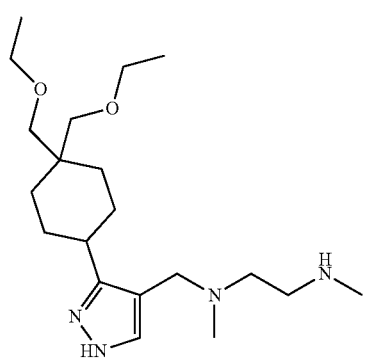 [SMILES: CCOCC1(COCC)CCC(c2n[nH]cc2CN(C)CCNC)CC1]

or a pharmaceutically acceptable salt thereof.

2. The compound of claim 1, wherein the compound is:

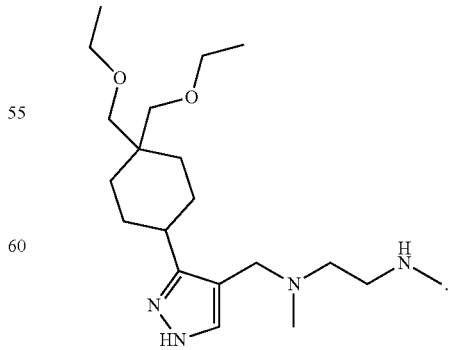

3. The compound of claim 1, wherein the compound is a pharmaceutically acceptable salt of:

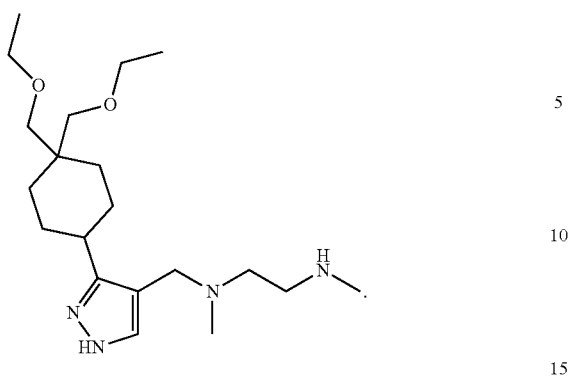

4. A pharmaceutical composition comprising a compound of claim 1, or a pharmaceutically acceptable salt thereof, and a pharmaceutically acceptable excipient.

5. A pharmaceutical composition comprising a compound of claim 2, and a pharmaceutically acceptable excipient.

6. A pharmaceutical composition comprising a compound of claim 3, and a pharmaceutically acceptable excipient.

7. A kit or packaged pharmaceutical comprising a compound of claim 1, or a pharmaceutically acceptable salt thereof, and instructions for use thereof.

8. A kit or packaged pharmaceutical comprising a compound of claim 2, and instructions for use thereof.

9. A kit or packaged pharmaceutical comprising a compound of claim 3, and instructions for use thereof.

* * * * *